US008436031B2

(12) United States Patent
Kim

(10) Patent No.: US 8,436,031 B2
(45) Date of Patent: May 7, 2013

(54) TRANSCRIPTION FACTOR MODULATING COMPOUNDS AND METHODS OF USE THEREOF

(75) Inventor: Oak K. Kim, Cambridge, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 406 days.

(21) Appl. No.: 12/462,405

(22) Filed: Aug. 3, 2009

(65) Prior Publication Data

US 2011/0306611 A1     Dec. 15, 2011

Related U.S. Application Data

(62) Division of application No. 11/115,024, filed on Apr. 25, 2005, now abandoned.

(60) Provisional application No. 60/565,047, filed on Apr. 23, 2004, provisional application No. 60/569,032, filed on May 7, 2004, provisional application No. 60/623,251, filed on Oct. 28, 2004.

(51) Int. Cl.
*A61K 31/415*     (2006.01)

(52) U.S. Cl.
USPC .................. 514/387; 514/183; 548/304.4

(58) Field of Classification Search .............. 514/183, 514/387; 548/304.4
See application file for complete search history.

(56) References Cited

U.S. PATENT DOCUMENTS

| | | | |
|---|---|---|---|
| 3,300,505 | A | 1/1967 | deStevens |
| 3,325,356 | A | 6/1967 | Di Netta et al. |
| 3,449,498 | A | 6/1969 | deStevens et al. |
| 3,516,999 | A | 6/1970 | Kano et al. |
| 3,549,754 | A | 12/1970 | Di Netta et al. |
| 3,646,049 | A | 2/1972 | Hoff et al. |
| 3,686,110 | A | 8/1972 | Fisher et al. |
| 3,743,738 | A | 7/1973 | Hoff et al. |
| 3,873,558 | A | 3/1975 | Grenda et al. |
| 4,269,846 | A | 5/1981 | Huang et al. |
| 4,859,684 | A | 8/1989 | Raeymaekers et al. |
| 4,940,742 | A | 7/1990 | Aumueller et al. |
| 4,981,975 | A | 1/1991 | Spang et al. |
| 5,008,397 | A | 4/1991 | Spang et al. |
| 5,342,957 | A | 8/1994 | Van Wauwe et al. |
| 5,552,426 | A | 9/1996 | Lunn et al. |
| 5,817,793 | A | 10/1998 | Levy |
| 5,942,532 | A | 8/1999 | Ohemeng et al. |
| 5,972,995 | A | 10/1999 | Fischer et al. |
| 6,162,393 | A | 12/2000 | De Bruiju et al. |
| 6,204,264 | B1 | 3/2001 | Kobayashi et al. |
| 6,340,697 | B1 | 1/2002 | Kobori et al. |
| 6,348,487 | B1 | 2/2002 | Connor et al. |
| 6,358,978 | B1 | 3/2002 | Ritzeler et al. |
| 7,405,235 | B2 | 7/2008 | Levy et al. |
| 2011/0230523 | A1 | 9/2011 | Levy et al. |

FOREIGN PATENT DOCUMENTS

| | | |
|---|---|---|
| BE | 674202 | 6/1966 |
| CA | 939356 | 1/1974 |
| CA | 953726 | 8/1974 |
| CA | 2496139 A1 | 3/2004 |
| DE | 1923481 | 11/1970 |
| DE | 3830697 A1 | 3/1990 |
| EP | 0254322 | 1/1988 |
| EP | 0260744 B1 | 3/1988 |
| EP | 0371559 B1 | 6/1990 |
| EP | 0609963 B1 | 8/1994 |
| EP | 0694535 A1 | 1/1996 |
| EP | 1479676 | 11/2004 |
| FR | 2047462 | 3/1971 |
| GB | 1507059 | 4/1978 |
| JP | BS453776 | 2/1970 |
| JP | 05025140 A | 2/1993 |
| JP | 08026991 | 1/1996 |
| NL | 6515833 | 6/1966 |
| WO | WO 9703070 | 1/1997 |
| WO | WO 98/06837 | 2/1998 |
| WO | WO 9817267 A1 | 4/1998 |
| WO | WO 98/37188 A1 | 8/1998 |
| WO | WO 99/17607 A2 | 4/1999 |
| WO | WO 99/61579 A2 | 12/1999 |
| WO | WO 00/12089 | 3/2000 |
| WO | WO 00/52144 A1 | 9/2000 |
| WO | WO 04/001058 A2 | 12/2003 |
| WO | WO 2004/041209 | 5/2004 |

OTHER PUBLICATIONS

Webb et al., "The Utilization of a Unified Pharmacophore Query in the Discover of New Antagonists of the Adenosine Receptor Family," *Bioorganic & Medicinal Chemistry Letters*, 10 (2000): 31-34.
Fiebich et al., "Cyclooxygenase-2 Expression in Rat Microglia is Induced by Adenosine $A_{2a}$-Receptors," *GLIA*, (1996), 18(2): 152-160.
Bouma et al., "Adenosine Inhibits Neutrophil Degranulation in Activated Human Whole Blood," *Journal of Immunology*, (1997), 158(11): 5400-5408.
Doleschall et al., "1,2,4-Triazine Und Kondensierte Derivate—Xii," *Tetrahedron*, (1973), vol. 29(4): 639-649.
Destevens et al., "Derivatives of 1-Hydroxybenzimidazoles and 1-Hydroxyindoles and Their Central Depressant Effects," *Journal of Medicinal Chemistry*, (1967), vol. 10(2):211-214.
Smirnov et al., "Structure and Reactivity of 2-Methyl-9-Sydroxy-4H-Pyrido[1,2-a]Pyrimidin-4-One," IKhimiya Geterosiklicheskikh Soedinenii, (1991): 1425-1431.

(Continued)

*Primary Examiner* — Sreeni Padmanabhan
*Assistant Examiner* — Shobha Kantamneni
(74) *Attorney, Agent, or Firm* — McCarter & English, LLP; Elizabeth A. Hanley

(57) ABSTRACT

Substituted benzoimidazole compounds useful as anti-infectives that decrease resistance, virulence, or growth of microbes are provided. Methods of making and using substituted benzoimidazole compounds, as well as pharmaceutical preparations thereof, in, e.g., reducing antibiotic resistance and inhibiting biofilms.

3 Claims, 25 Drawing Sheets

OTHER PUBLICATIONS

Rauha et al., "Antimicrobial Effects on Finnish Plan Extracts Containing Flavonoids and Other Phenolic Compounds," *International Journal of Food Microbiology*, 56 (2000): 3-12.

Basile et al., "Antibacerial Activity of Pure Flavonoids Isolated from Mosses," *Phytochemistry*, 52 (1999):1479-1482.

Martin et al., "Fis, an Accessorial Factor for Transcriptional Activation of the *mar* (Multiple Antibiotic Resistance) Promoter of *Escherichia coli* in the Presence of the Activator MarA, SoxS, or Rob," *Journal of Bacteriology*, (1997): 7410-7419.

Sharaf et al., "A Convenient Synthesis of Thiazolopyrimidines, Thiazolodipyrimidines and Heterocyclothiazolopyrimidines," *Journal of Chemical Research Synopses*, (1996) 8:354-355.

Ahn et al., "Cordycepin: Selective Growth Inhibitor Derived from Liquid Culture of *Cordyceps militaris* against *Clostridium* spp.," *Journal of Agricultural and Food Chemistry*, (2000) 48 (7): 2744-2748.

Sugar et al., "Antifungal Activity of 3'-Deoxyadenosine (Cordycepin)," *Antimicrobial Agents and Chemotherapy*, (1998) 42(7), 1424-1427.

Minisci et al., "Addition Reaction of Nitrile Oxides on Aromatic Nitrosoderivatives. A Novel Synthesis of the Benzimidazole Ring," *Tetrahedron Letters*, 12 (1963): 785-790.

Bouchet et al. *Bulletin de la Societe Chimique de France*, (1976), vol. 1-2, Pt. 2: 192-194.

Heine et al., "Aziridines XIX. The Photolysis of 1-(2,4,6-Trinitrophenyl)-2,3-Diphenylaziridine and 1-(2,4-Dinitrophenyl)-2Pheyl-3-Benzoylaziridine," *Tetrahedron Letters*, 46, (1968): 4801-4802.

Dehuri et al "Studies on Thiazolidinones. Part—XII: Synthesis and Antimicrobial Activities of Thiazolidinones and Their Derivatives from Cyclic Thioureas," *Journal of the Indian Chemical Society*, (1983), vol. LX, No. 10: 970-974.

International Search Report Application No. PCT/US03/35205, dated Aug. 10, 2004.

Supplementary Partial European Search Report for Application No. 02807554.7-1216, dated Nov. 7, 2007.

Claims 116 and 173 of co-pending U.S. Appl. No. 11/115,024 and Claim 51 of co-pending U.S. Appl. No. 10/602,562.

CAS RN: 174266-48-9, entry date Mar. 15, 1996.

Multiple sequence alignment of AraC-XylS family members.

```
AARP_PROST/22-120    SEILVWI.FGNLITNR........              LSDDIAQHSGYTKWHIQRVMFRKIVGMPLGEYTRRRRI
ADA_ECOLI/85-183     DKITHACRLLEQETp.........              VTIEALADQVAMSPFHIHRLFKATTGWPKAWQQAWRA
ADA_MYCTU/87-185     ARAMRLIADGIVDR..........              DGVSGLAAQLGYTIRQIERLQAVVGAGPLAIARACRM
ADA_SALTY/94-183     ----------LEQEt.........              pVTIAFLAQAVAMSPFHIHRLFKASIGWTPKGWQQAWRA
ADAA_BACSU/102-200   DLITEYIDKNFTEK..........              LTIIESLADICHGSPYHMHRIFKKIKGTILVEYTQQVRV
ADIY_ECOLI/149-246   DSVYQIIESDIHKD..........              WNLSWVASCLCLSPSILKKKLKSENT-SYSQIITTCRM
AGGR_ECOLI/164-261   DKVRNTIEKDLSKR..........              WTIIAITADEFNVSETTIRKRLESEYI-TFNQIIMQSRM
APPY_ECOLI/139-236   CKITGIISFNIERQ..........              WHIKDIAELIYISESIIKKKRLDEGT-SFTEIIRDIRM
ARAC_CITFR/180-279   RDACQYISDHLADSn.........              FDIASVAQHVCLSPSRISHLFRQQLGISVLSWREDQRI
ARAC_ECOLI/180-279   REFACQYISDHLADSn.........             FDIASVAQHVCLSPSRISHLFRQQLGISVLSWREDQRI
ARAC_ERWCH/186-284   IEACQFITSNLAGE..........              LRIDEVARHVCLSPSRIAHLFREQVGINILRWREDQRV
ARAC_SALTY/180-279   RDACQYISDHLADSh.........              FDIASVAQHVCLSPSRISHLFRQQLGISVLSWREDQRI
ARAL_STRAT/202-300   ASALTIFLHRDPAHS.........              WTVAEHLASAAAVSRSTIAARFKATVGQGPLEYLTRWRI
ARAL_STRLI/202-300   ATALTIGLHRDPARS.........              WTVADILADIAAVSRSTIAARFKATVGQGPLEYLTRWRI
CAFR_YERPE/8-107     NSIIQYIEENLESKf.........              INIDCIIVLYSGFSRRVIQISEFKEYVGMPIGTYTRVFRA
CELD_ECOLI/168-274   DDVPQWIKSTVEKMndkeqfseSAIENMVALSAKSQEYITRATQRYYGKTPMQIINEIRI
CFAD_ECOLI/164-261   DKVRNVIEKDLSRK..........              WIIGITADAFNVSETTIRKRLESENT-NFNQIIMQIRM
CSVR_ECOLI/166-263   DKVRGVIEKDLSRK..........              WTIIAITADVENVSETTIRKRLESEDT-NFNQIIMQSRM
ENVY_ECOLI/149-246   DSVCRIIQSDIQHY..........              WNLRIVASSLCLSPSILKKKLKNENT-SYSQIVTECRM
EUTR_ECOLI/243-344   SRAREYMLENMSEP..........              VIVLDIQNQLHVSRRILQNAFHAILGIGPNAWLKRIRL
```

| | | | | |
|---|---|---|---|---|
| ORUR_PSEAE/241-338 | TRVRRI`I`LARPGDF | ...... | PD`IE`QA`A`RELHT`S`GRS`I`RRHTSSLGT- | TYQQVLDDVRK |
| PCHR_PSEAE/201-296 | HAARDIIVGALQEP | ...... | PSIDILASRVGMNPRKLTAGFRKVFGASVFGYLQEYRL |
| PERA_ECO27/168-265 | DRVIKVIELDISKN | ...... | WKLGDVSSSMFMSDSCURKQLNKENL-TFKKIMLDIKM |
| POCR_SALTY/195-293 | KKALRYIDAHLSDD | ...... | LRLEDVASHVYLSPYYFSKLFKKYQGIGFNAWNRQRM |
| PQRA_PROVU/7-107 | NDILKWIETQLQRNe | ...... | gIKIDILANKSGYSKWHLQRIFKDFKGCIIL`GE`YVRKFRL |
| RAFR_PEDPE/176-274 | NLAVSYLQENYSIG | ...... | C`TIMDL`CHYLNLSRSMLYTLFKTHANTSPQKLITKIRL |
| RAMA_ENTCL/9-107 | DTTVEW`I`DDNLHQP | ...... | LR`IE`D`I`ARHAGYSKWHLQRLFLQYKGESLGRYIRERKL |
| RAMA_KLEPN/9-107 | DTTVEW`I`DDNLHQP | ...... | LR`ID`D`L`ARHAGYSKWHLQRLFLQYKGESLGRYIRERKL |
| RHAR_ECOLI/209-307 | DKLITRIAASLKSP | ...... | FA`I`DKF`C`DEASCSERVIRQQFRQQTGMIINQYIRQVRV |
| RHAR_SALTY/179-277 | DKLITAIANSLECP | ...... | FA`I`DAF`C`QQEQCSERVIRQQFRAQTGMIINQYIRQVFI |
| RHAS_ECOLI/174-272 | NLLLAWLEDHFADE | ...... | VNWDAVAQFSLSLRTIHRQLKQQTGLTPQRYLNRLRL |
| RHAS_SALTY/174-272 | NQLMWLEDHFAEE | ...... | VCWEFAVAEQFSLSLRTIHRQIKQHTGLTPQRYINRIRI |
| RHRA_RHIME/210-310 | ASIKMRVEQNLANGs | ...... | FSTT`D`VAEAERIIPRAIQKFFSREGT-TFSRYVLGFRL |
| RNS_ECOLI/164-261 | DKVRNLIEKDLSRK. | ...... | WIILGIIADAFNASEITIRKGIESENT-NFNQIIMQIRM |
| ROB_ECOLI/8-106 | RDLLIWIEGHLDQP | ...... | LSIDNVPAAKAGYSKWHLQRMFKDVTGHAIGAYIRAFRL |
| SOXS_ECOLI/7-105 | QDLLAWIDEHIDQP | ...... | LNIDVVAKKSGYSKWLQRMFRTVTHQ`II`GDYIRQFRI |
| SOXS_SALTY/7-105 | QTLLEWIDEHIDQP | ...... | LN`I`DVVAKKSGYSKWLQRMFRTVTHQ`II`GEYIRQFRI |
| TCPN_VIBCH/172-269 | EKISCIVKSDITRN | ...... | WRWAD`I`CGELRTNRMIIKKELESRGV-KFRELINSIRI |
| TETD_ECOLI/31-129 | KDVLLWIEHNLDQS | ...... | L`I`IDDVANKAGY`I`KWYFQRLFKKVIGV`L`ASYIRAFRI |
| THCR_RHOER/227-328 | RLAVDY`I`EAHAQQP | ...... | LTVAQVARNVGVSVRSLQVGEQNSLGTTPMRQLKIIRM |

*Fig. 1C*

| | | | | | | |
|---|---|---|---|---|---|---|
| URER_ECOLI/171-268 | QAITHLITQEPQKK.......... | ..WHDDIVAKALFTIPSTIRRHINREGV- | SFRQIILDVRM |
| URER_PROMI/171-268 | QAITHLITQDPQRK.......... | ..WHIEDVAKTLYTIPSTIRRHISKEGV- | SFCQIILDVRI |
| VIRF_SHIDY/161-258 | DQIRKIVEKNIEKR.......... | ..WRISDISNNLNLSETAVRKFLESEKL- | TFQQIILDIRM |
| VIRF_YEREN/167-265 | ERLQKFMEENYLQG.......... | ..WKLSKFAREFGVGLTIFKELFGTVGI SPRAWISERRI |
| VIRS_MYCTU/236-334 | ERVVGLARRLLPTGq.......... | CSAEAIADQLDMHPRILQRRLAAEGL-RCHDLIERERR |
| XYLR_ECOLI/288-386 | IQAMHYIRNHACKG.......... | IKVDQVLDAVGISRSNLEKRFKEEVGETTHAMIHAEKI |
| XYLR_HAEIN/288-386 | IQAMHYIRHRACHR.......... | IKVGQVLDHLETSRSNLEQRFKNEMNKTTHQVIHEEKI |
| XYLS_PSEPU/214-315 | ERVVQFIEENLKRN.......... | ISLERLAELAMMSPRSLYNLFEKHAGITPKNYIRNFKI |
| XYS1_PSEPU/214-315 | ISLERLAELAMMSPRSLYNLFEKHAGITPKNYIRNFKI |
| XYS2_PSEPU/39-140 | ERVVQFIEENLKRN.......... | ISLERLAELAINSPRSLYTMFEKHIGITPMNYIRNFKI |
| XYS3_PSEPU/214-315 | ERVVQFIEDNLKQS.......... | ISLERLAELAINSPRSLYTLFEKHAGITPKNYIRNFKI |
| XYS4_PSEPU/214-315 | ERVVQFIEENLKRN.......... | ISLERLAELAINSPRSLYTIFEKHAGITPKNYIRNFKI |
| Y4FK_RHISN/318-417 | LKAEAFMRENLINP.......... | .VTIEDIAAAARCTIPRAIQRVFRIYRGGSPMSVLCNYRI |
| YA52_HAEIN/194-295 | KRLNTAIAILQQPqm......... | .dWHIEQLAELATMSRANFIRIFQQHIGMSPGRFLIKVRI |
| YBBB_BACSU/166-264 | EKTKHYIETHADTK.......... | ITLAQISQVAGISAKHYSESFKKWIGQSVTEFITKIRI |
| YBCM_ECOLI/165-262 | SRCYNLILSEPGTK.......... | WTANKVARYLYISVSILHRRLASEGV- SFQSIIDDVRI |
| YCGK_ALTCA/67-163 | QNAMLYIENNYFND.......... | INDIVAFSVGVSRSTVKQFKLATNKTINNRIIEVRI |
| YD95_MYCTU/242-343 | RGITAIVRSKLFRDsg........ | lFPTFTDVAGELDMHPRILRRRLAEEGT-SFRAIIGEARS |
| YDEO_ECOLI/137-233 | GKVRNIMNMKPAHP.......... | .WKIKDIGDCLYISESILKKKIKQEQT- TFSQIILDARM |
| YDIP_ECOLI/183-281 | KDILFYLNNNYREK.......... | IILEQISKKFRASVSICHEFTKEYRISPDNYVIQRRM |

*Fig. 1D*

| | | | | | | |
|---|---|---|---|---|---|---|
| YEAM_ECOLI/158-258 | PKIRIMVEMAKGPve...... | wGAIGQWAGFFAMSERNIARLIVKEIGLSFRQWRQQICI |
| YFIF_BACSU/192-289 | TEVKLHKDNLSQP......... | LKLITDVASHFHISGRHISRLFAAELGVSYSEFVQNEKI |
| YHIW_ECOLI/139-236 | GKVERLISFDIAKR......... | WYIRDIAERMYTSESLIKKKIQDENT-CFSKIILASRM |
| YIDL_ECOLI/197-295 | EKLIATIIHASLQR......... | WSVADMAATIPCSEAWIRRILFLRYIGKIPKEYVLDARI |
| YIJO_ECOLI/172-270 | EAIRDYIDERYASA......... | LITRESVAQAFYISPNMLSHLFQKIGAIGFNEYINHIRI |
| YISR_BACSU/183-281 | WEAARYLQEHYKEK......... | TIIKDLSLALHYHQDVVSRQMQQVLGVIPAQYTNRVRM |
| YKGA_ECOLI/19-117 | QQLLEWIECNLEHP......... | ISIEDIAQKSGYSRRNIQLIFRNFMHVPLGEYIRKRI |
| YKGD_ECOLI/177-278 | PRLGAVIQQMLEMPgh...... | aWIVESLASIAHMSRASFAQIFRDVSGIIPLAVITKLRI |
| YMCR_STRLA/184-281 | DPLLRAVVVSLEAG......... | RSVTATADSVGLGARQIHRRSLAAFGYGPKILARVLRM |
| YPDC_ECOLI/184-282 | LITRESVAQFFNIIPNHLSKLFAQHGIMRFTEYVRWVRM | |
| YQHC_ECOLI/213-311 | SRVLKRIENKYTEN......... | LSVEQLAAFANMSVSAFHHNEKSVTSTSPLQYLKNYRI |

```
EUTR_SALTY/243-344    NAVRRELISPWSqsaTVKDAAMQGFWHLGQEATDYQQLFAEKPSLITLHQ
EXSA_PSEAE/171-269    LYAHQLILNSDM...SIVDIAMEAGFSSQSYFTQSYRRFGCIPSRSRQG
FAPR_ECOLI/154-251    NQAAKFIIRSDH...QIGMTASLVGYTSVSYFIKIEKEYYGVIPKKFEIG
FEAR_ECOLI/199-299    DFCADAIRHAADd.eKIAGIGFHWGFSDQSHFSTVEKQRFGMIPGHYRRK
GADX_ECO27/145-242    QFALQLIVIYGV...SIKRVAVSCGYHSVSYFIYVFRNYGMIPTEYQER
GADX_ECO57/145-242    QFALQLIVIHGF...SIKRVAVSCGYHSVSYFIYVFRNYGMIPTEYQER
GADX_ECOLI/145-242    QFALQLIVIHGF...SIKRVAVSCGYHSVSYFIYVFRNYGMIPTEYQER
GLXA_RHIME/223-321    RHARRILQQSPL...SIPELAYAIGFSSPAHFSNAFKRLFSCIPGSLRRR
HRPB_RALSO/375-477    EGIRSDLLDSERtpsNIIDTASRWCIRSRSALVKGYRKQFNEAPSETIWR
INVF_SALTY/112-210    AQSLINSVEGHE...NITQLAVNHGYSSPSHFSSEIKELIGVSPRKLSNI
LACR_STAXY/174-272    YFASQLIIHIST...LIISDISRQVGYKDPLIFSKNFTKHFELSASEMRHH
LCRF_YERPE/167-265    LYAHQLILNSDM...SIVDIAMEAGFSSQSYFTQSYRRFGCIPSQARLI
LUMQ_PHOLE/148-246    DIAKQLIAERQK...PLSQVAQLCGFSSQSFSQAFRRLYGMSPTFYQFF
MARA_ECOLI/14-112     TETAQKIKESNE...PIILMLAERYGFESQQTLTRIFKNYFDVPHKYRMT
MARA_SALTY/14-112     TETAQKIKESNE...PIILMLAERYGFESQQTLTRIFKNYFDVPHKYRIT
MELR_ECOLI/194-292    NHVRALLSDIDK...SILIIALTAGFRSSSRFYSIFGKYVGMSPQQYRKL
MMSR_PSEAE/201-299    EVAQQIIDSSDQ...SVARVGQAVGYDDSYFSRLFSKMGLSPSAYRQR
MSYR_STRMU/176-274    KRSQYIIENPKL...SIAELISNSVGFSDSLAFSKAFKNFGKSPSKFRKE
MXIE_SHIFL/99-199     VNGLIDVFLHNQ...TITSAAMNGYRSTSHFSNEIKTRIGFSARELSNI
MXIE_SHISO/99-199     VNGLIDVFLHNQ...TITSAAMNGYASTSHFSNEIKTRIGFSARELSNI
```

*Fig. 1G*

| | | | | | |
|---|---|---|---|---|---|
| ORUR_PSEAE/241-338 | RLALQYLTTTQL... | PLYEITALLLIGENDSSNFRRAFRKWIGKLPSDYREA |
| PCHR_PSEAE/201-296 | REAHRMLCDEEA... | NVSIVAYRVGYS-PAHFSLAFRKRYGISPSEIR-- |
| PERA_ECO27/168-265 | KHASLFLRITDK... | NIDEISCLVGENSTSYFIKVFKEYNITPKKYNGV |
| POCR_SALTY/195-293 | VSAREILCHSDW... | SIASIARNIGFSQTSYFCKVFRQTYQVTPQAYRQQ |
| PQRA_PROVU/7-107 | LEAAKSLQEKDM... | SILDIAIMGFSSQAIFTRIFKKHENITPAKFREN |
| RAFR_PEDPE/176-274 | EDAKQFLSTSNN... | SVQSIANMVGYKDSFIFSKAFKRYSGASPSYMRKS |
| RAMA_ENTCL/9-107 | LIAARDIRESDE... | RVVEICLRYGFESQQIFTRIFTRIFHQFPGAVRKE |
| RAMA_KLEPN/9-107 | LIAARDLRDTDQ... | RVMDICLKYGFDSQQIFTRVFTRIFNQPPGAVRKE |
| RHAR_ECOLI/209-307 | CHAQYLLQHSRL... | IISDISTEGFEDSNYFSVVFTRETGMFSQWRHL |
| RHAR_SALTY/179-277 | CHAQYLLQHSPL... | MISEISMQGFEDSNFFSVVFTRETGMFSQWRHL |
| RHAS_ECOLI/174-272 | MKARHILRHSEA... | SVTDIAYRCGFSDSNHFSTIFRREFNWSPRDIRQG |
| RHAS_SALTY/174-272 | IKARHILRHSDH... | SVTEIAYRCGFGDSNHFSTIFRREFNWSPRDIRQG |
| RHRA_RHIME/210-310 | SIAKSLILAEGEa. | tSISQIAYNVGENDLSYENRTFRSRYGVRPSDLRRL |
| RNS_ECOLI/164-261 | SKAALILLENSY... | QISQISNMICISSASYFIRIFNKHYGVIPKQFFTY |
| ROB_ECOLI/8-106 | SKSAVAIRLTAR... | PILDIALQYRFDSQQIFTRAFKKQFAQIPALYRRS |
| SOXS_ECOLI/7-105 | LIAAVELRITER... | PIFDIAMDIGYVSQQIFSRVFRRQFDFIPSDYRHR |
| SOXS_SALTY/7-105 | LIAAVELRITER... | PIFDIAMDIGYVSQQIFSRVFRREFDFIPSDYRHR |
| TCPN_VIBCH/172-269 | SYSISLMKIGEF... | KIKQIAYQSGFEASVSYESTVFKSTMNVAPSEYLFM |
| TEID_ECOLI/31-129 | TKAAVELRLTKK... | TLLELALKYQFDSQQSFTRFKYIFKVIPSYRRN |

*Fig. 1H*

| | | | | |
|---|---|---|---|---|
| THCR_RHOER/227-328 | QKARKDILRADPAseGVTEIAQRWGFLHVGFEAGEYKQIFGVSPSEDLRT |
| URER_ECOLI/171-268 | GVPALNYIIFSNY....SVFQISHRCGFGSNAYFCDVFKRKMMIPSQFRLQ |
| URER_PROMI/171-268 | PIPALNYIITFSNY....SVFQISHRCGFGSNAYFCDAFKRKYGMIPSQFRTQ |
| VIRF_SHIDY/161-258 | HHPAAKLILNSQS....YINDVSRLICISSPSYFITRKFNEYGITPKKFYLY |
| VIRF_YEREN/167-265 | LYPAHQIIILNGKM....SIVDIAMEAGFSSQSYFTQSYRRRFGCIPSQARLT |
| VIRS_MYCTU/236-334 | AQAARYIAQPGL....YISQIAVLIGYSFEQSAINRSCRRWFGVIPRQYRAY |
| XYLR_ECOLI/288-386 | EKARSILISITL....SINEISQMCGYPSLQYFYSVFKKAVDTIPKFYRDV |
| XYLR_HAEIN/288-386 | SRAKNILQQIDI....SIKEITEICGYPSIQYFYSVFKKEFVIPKGFRLN |
| XYLS_PSEPU/214-315 | ESIRACINDPSAnvrSITEIALDYGFLHIGRFAENYRSAFGELPSDITLRQ |
| XYLS_PSEPU/214-315 | ESIRACINDPSAnvrSITEIALDYGFLHIGRFAENYRSAFGELPSDITLRQ |
| XYS1_PSEPU/214-315 | ECVRACISNPTThirSITEVALDYGFLHIGRFAENYRSTFGELPSDITLRR |
| XYS2_PSEPU/39-140 | ECIRARISDPNAnvrSVTEVALDYGFFHIGRFAENYRSTFGELPSDITLRR |
| XYS3_PSEPU/214-315 | ECIRARISDPNAnvrSVTEVALDYGFFHIGRFAENYRSTFGELPSDITLRR |
| XYS4_PSEPU/214-315 | ECIRARISDPNAnvrSVTEVALDYGFFHIGRFAENYRSTFGELPSDITLRR |
| Y4FK_RHISN/318-417 | AAPHGAIKAGRag..SITELAINLQFSNPGRFSVIYKSAYGLSPSSALRF |
| YA52_HAEIN/194-295 | QSAAFLIKQSQQ....SVLAIAIPLEVGYQSEAHFCKVFKNYQLSPSQVRKS |
| YBBB_BACSU/166-264 | TKAKRLMAKSNC....KLKEIAHQIGYQDEFYFSRIFKKYTGCSPTSYMKK |
| YBCM_ECOLI/165-262 | NNALSAIQITVK....FISEIAPRENGYKCPSRFTERFHNRFNTIPREIRKA |
| YCGK_ALTCA/67-163 | EQAKKVILLKK--...SVTETAYEVGENNSNYFAIVEKKRTNYITPKQFKRT |
| YD95_MYCTU/242-343 | TVAVDLIRNVGL....TVCQVSTRIGYTEVSIFSHAFKRWYGVAPSEYSRR |
| YDEO_ECOLI/137-233 | QHAKNLIRVEG-...SVNKLAEQGYASTSYFIYAFRKHFGNSPKRVSKE |

*Fig. 11*

| | | | | |
|---|---|---|---|---|
| YDIP_ECOLI/183-281 | TEAKWSIINTEL... | SQAEISWRVGYENVDHFAKIFLRHVGSFSDYRRQ | | |
| YEAM_ECOLI/158-258 | IMALQGIVKGD-... | TVQKVAHTIGVDSTIPAFITVFKKGIGQTPGRYTAR | | |
| YFIF_BACSU/192-289 | NKAAEIIKSTNL... | SIKEIAEEIGFS-VHYFIRVESAKIGSSPGILFRSL | | |
| YHIW_ECOLI/139-236 | SVARRLIELRQI... | PLHTIAEKCGYSTSYFINIFRQYYGVIPHQFAQH | | |
| YIDL_ECOLI/197-295 | DIALSLIKQQGN... | SVGEVADILNFFDSFHFSKAFKHKFGYAPSAVLKN | | |
| YIJO_ECOLI/172-270 | EHAKTLIKGYDL... | KVKEVAHAGFVDSNYFCRIERKNTERSPSEYRRQ | | |
| YISR_BACSU/183-281 | TEAKRLISSTND... | KMGVTAETVGMEDPTYFSKLEKQEGISPTEYRKI | | |
| YKGA_ECOLI/19-117 | CRAAIIVRLTAK... | SMLDIALSLHEDSQQSFSREEKKLFGCSPREYRHR | | |
| YKGD_ECOLI/177-278 | QTPAAQMFSRETL... | FVVLAESVGYASESESFHKAFVREFGCIPGEYRER | | |
| YMCR_STRLA/184-281 | QRALRLARAGV-... | PFAETATLAGEADQAHLARDVREMAGSLSELVER | | |
| YPDC_ECOLI/184-282 | AKARMIIQKYHL... | SIHEVAQRGPDSDYFCRVERRQFGLTPGEYSAR | | |
| YQHC_ECOLI/213-311 | HKARMIIHDGM... | KASAAAMRVGYESASQFSREEKRYFGVIPGEDAAR | | |

*Fig. 1J*

Multiple sequence alignment of PROSITE PS00041, HTH_AraC family 1.

```
AARP_PROST/72-114    RIceaAkeIqtt...nlqVidIAlkyqFdsqqsFakaFKaylGiSP
ADA_MYCTU/137-179    RVqtARvlIett...nlpFgdVAfaaCFssiroFndtVRLacDgIP
ADAA_BACSU/152-194   RVhaAKylIqt...nkaIgdIAicvCIanapyFitlFKkktGqIP
ADIY_ECOLI/198-240   RMryAVneImmd..gkrIsqVSqscGynstsyFisvFKdfyGmIP
AGGR_ECOLI/213-255   RMskAAlllldn..syqISmmiCHsstsyFirlFVkhfGiIP
APPY_ECOLI/188-230   RMryAkllItsn..sysInvVAqkcGynstsyFicaFKdyyGvIP
ARAC_CITFR/231-273   RIsqAKllIstt...rmqIatVGrmvGFdddqlyFsrvFKkctGaSP
ARAC_ECOLI/231-273   RIsqAKllIstt...rmqIatVGrmvGFdddqlyFsrvFKkctGaSP
ARAC_ERWCH/236-278   RVirAKllIqtt...qesIarIGrvvGYddqlyFsrvFRkrvGvSP
ARAC_SALTY/231-273   RIsqAKllIstt...rmqIatVGrmvGFdddqlyFsrvFKkctGaSP
ARAL_STRAT/252-294   RIelTArqIreg...sapILaaIAhsvGYgsesaLsvaFKrvlQmNP
ARAL_STRLI/252-294   RIelAArqIreg...natLasIAhsvGYgsesaLsvaFKrvlQmFP
CELD_ECOLI/226-268   RInfAKkqIemt...nysVtdIAfeeGYsspsIFiktFKkltSfIP
CFAD_ECOLI/211-255   QlmsKaaIllle.nsyqIsqISmmiCIssasyFiirvFNkhyGvIP
CSVR_ECOLI/215-257   RMskAAllllen..syqIsqISmmiCIssasyFiriFNkhfGvIR
ENVY_ECOLI/198-240   RMryAVqmlImd..nkrItqVAqlcGYsstsyFisvFKafyGlTP
EUTR_ECOLI/293-338   RInaVRreIispwsqsmtVkdAAmqwGFwhlgqFatoYQqlfSekP
EUTR_SALTY/293-338   RInaVRreIispwsqsatVkdAAmqwGFwhlgqFatoYQqlfAekP
EXSA_PSEAE/221-263   RIlyAHqlIlns..dmsIvdIAmeaGFssasyFtqsYRrrfGcIP
FAPR_ECOLI/203-245   RMnqAkfIirs..dhqIgmIIAslvGYtsvsyFiktFKeyyGvIP
```

```
GADX_ECO27/194-236   RMvqrAlqllviy...gvsIkrVAvscGyhsvsyFiyvFRnyyGmIP
GADX_ECO57/194-236   RMvqrAlqllvih...gfsIkrVAvscGyhsvsyFiyvFRnyyGmIP
GADX_ECOLI/194-236   RMvqrAlqllvih...gfsIkrVAvscGyhsvsyFiyvFRnyyGmIP
GLXA_RHIME/273-315   RLrlrARrllqqs...plsIpeIAyatGhsspaIFsnaFKrlfSqIP
HRPB_RALSO/426-471   RLeqIRsdIldsempsrIldTAsrwcIrsrsaLvkqYRkqfNeAP
INVF_SALTY/162-204   RMvqcSLlnSveg...herItqIAvnhGysspaIFsseIKeliGvSP
LACR_STAXY/224-266   RMyfASqlIiht...stIIsdISrqvGVkdpllFskrFTkhfEiSA
LCRF_YERPE/217-259   RIlyAHqlIlng...kmsIvdIAmeaGhssqsyFtqsYRrrfGcIP
LUMQ_PHOLE/198-240   RldIAkqIlaer...qkpIsqVAqlcGhssqssFsqaFRrlyGmSP
MARA_ECOLI/64-106    KMteIAqkIkes...nepIlyIAeryGfesqqTLtrtFKmyfDvPP
MARA_SALTY/64-106    KMteIAqkIkes...nepIlyIAeryGfesqqTLtrtFKmyfDvPP
MELR_ECOLI/244-286   RImhVRallsdt...dksIIdIAltaGhrssrIFystEGkyvGmSP
MMSR_PSEAE/251-293   KIeyAcqllldss...dqsVarVGqavGyddsyyFsrlFskvmGlSP
MSMR_STRMU/226-268   RMcrSQyILemp...klsIaelSnsvGhsdslaFskaFKmyfGkSP
MXIE_SHIFL/151-193   RIvnGLldVflh...nqtItsApmmrGyrstsIFsneIIKtrlGfSA
MXIE_SHISO/151-193   RIvnGLldVflh...nqtItsApmmrGyastsIFsneIIKtrlGfSA
PCHR_PSEAE/251-292   RIlreAHrmLcde...earVstVAyrvGvsp.aFrsIaFRkryGiSP
PERA_ECO27/217-259   KMchASlfIrtt...dkrIdeISclvGhnstsyFikvFKeyyNtIP
POCR_SALTY/245-287   RMvsARellchs...dwsIasIAmlGhsqtsyFckvFRqtyQvIP
PQRA_PROVU/59-101    RIleAAksIqek...dmsIIdIAlmyGhssqatIFtrIFkhfNtIP
RAFR_PEDPE/226-268   RLedAKqrIlsts...msVqsIAmmvGykdsftFskaFKrysGaSP
```

Multiple sequence alignment PS01124, HTH_ARAC_FAMILY_2.

```
AARP_PROST/22-120     SEILVW EGNLITNR........LSTDDIPAQHSGYTKMH IQRVFRKITVGMPLGEY TRRFRI
ADA_ECOLI/85-183      DKITHACRLLEQEIp........VTHEALADQVAMSPFHIHRLFKATIGM IPKAWQQAWRA
ADA_MYCTU/87-185      ARAMRI ADGTVDR........DGVSGIAAQLGYTIRQIERUIQAVVGAGPLAIARAC RM
ADA_SALTY/94-183      ---------LEQEt........pVTLAFLAQAVAMSPFHIHRLFKASIGM IPKGWQQAWRA
ADAA_BACSU/102-200    DLITEY DKNFTEK........LITESLADICHGSPYI MRIFKKIKGI TLVEYI QQVRV
ADIY_ECOLI/149-246    DSVYQI IESDIHKD........WNLSWVASCLCLSPSII KKKI KSENT-SYSQII TTQRM
AGGR_ECOLI/164-261    DKVRNI IEKDLSKR........WTIAI IADEFNVSEI TIRKFIESEYI-TFNQII MQSRM
APPY_ECOLI/139-236    CKITGI ISFNIERQ........WHIKDIAELIYTSESLIKKGIRLRDEGT-SFTEII RDIRM
ARAC_CITFR/180-279    RDACQYISDHLADSn........FDIASVPAQHVCLSPSRISHLFRQQIGISVLSWREDQRI
ARAC_ECOLI/180-279    REACQYISDHLADSn........FDIASVPAQHVCLSPSRISHLFRQQIGISVLSWREDQRI
ARAC_ERWCH/186-284    IEACQFITSNLAGE........LRIDEVARHVCLSPSRIAHLFREQVGINTLRWREDQRV
ARAC_SALTY/180-279    RDACQYISDHLADSn........FDIASVPAQHVCLSPSRISHLFRQQIGI SVLSWREDQRI
ARAL_STRAT/202-300    ASALTFIHRDPAHS........WTVAELASAAAVSRSTIAARFKATVGQGPLEYITRWRI
ARAL_STRLI/202-300    ATALTCIHRDPARS........WTVADLADTAAVSRSTIAARFKATVGQGPLEYITRWRI
CAFR_YERPE/8-107      NSIIQYIEENLESKf........INIDCI VLYSGFSRRVLQISFKEYVGMPIGTYIRVRRA
CELD_ECOLI/168-274    DDVPQWIKSTVEKMhdkeqfseSAIENMVALSAKSQEYITTRATQRYYGK TPMQII NEIRI
CFAD_ECOLI/164-261    DKVRNV EKDLSRK........WTLGI IADAFNVSEI TIRKF ESENT-NFNQII MQIRM
```

Fig. 3A

| | | | | | |
|---|---|---|---|---|---|
| CSVR_ECOLI/166-263 | DKVRGV|IEKDLSRK....... | ......WILA|IADVFNVSEI|TIRKF|IESEDT-NFNQII|MQSRM |
| ENVY_ECOLI/149-246 | DSVCRI|IQSDIQHY....... | WNIRIVASSL|CLSPSLIKKK|TLKNENT-|SYSQIV|TECRM |
| EUTR_ECOLI/243-344 | SRAREY|VLENMSEP...... | VIVLDI|CNQLHVSRRT|LQNAFHAI|LGIPNAW|LKRIRL |
| EUTR_SALTY/243-344 | SRAREY|VLENMSEP...... | LIVLDI|CNQLHVSRRT|LQNAFHAI|LGIGPNAW|LKRIRL |
| EXSA_PSEAE/171-269 | ERLQLF|VEKHYLNE....... | WKLSDFSREFGW|GLITFKELF|GSVYGV|SPRAWI|SEFRI |
| FAPR_ECOLI/154-251 | ERIVTI|IFSDLTRK....... | WKLSDI|AEHMISEISVRKF|LEQECL-NFNQLI|LDVRM |
| FEAR_ECOLI/199-299 | QKVVTI|LIDDNIREEi..... | LRPEM|IAGEIGMSVRSI|YRMFADKGL-VVAQY|TRNFRI |
| GADX_ECO27/145-242 | TRVCIV|INNNIAHE........ | WILARI|ASELIMSPSLIKKK|IREEGT-|SYSQLI|TECRM |
| GADX_ECO57/145-242 | TRVCIV|INNNIAHE........ | WILARI|ASELIMSPSLIKKK|IREEET-|SYSQLI|TECRM |
| GADX_ECOLI/145-242 | TRVCIV|INNNIAHE........ | WILARI|ASELIMSPSLIKKK|IREEET-|SYSQLI|TECRM |
| GLXA_RHIME/223-321 | LAVLEK|METAIERP........ | LDRIAM|ARLAGVSPRH|IDRLFEHRGI|GFLDIY|REIRL |
| HRPB_RALSO/375-477 | RRAYRY|IIENIERSd..... | LITTREV|AAHINV|IERAIQLA|FKSAVG|VPSSV|IRRVRI |
| INVF_SALTY/112-210 | YWLVGI|ILAQSTSG....... | NIMRM|IGEDYGVSY|IHFRRL|CSRALGKAKSEL|RNWRM |
| LACR_STAXY/174-272 | QHAVDF|ININYQKH........ | ITVEDVAKSVNI|IRSH|IYKLF|KKNLGCSPKEY|ITY|IRVM |
| LCRF_YERPE/167-265 | ERLQKF|MEENYLQG....... | WKLSKF|AREFGW|GLITFKELF|GTVYGI|SPRAWI|SEFRI |
| LUMQ_PHOLE/148-246 | VLIDNY|IEQHLQKK....... | ISVAEI|ISSVAFLAQS|QFYAI|FKSQMG|ITPHQY|VLRKRI |
| MARA_ECOLI/14-112 | HSIILDW|IEDNLESP..... | LSIEKV|SERSGY|SKWH|LQRMFKKEI|GH|SLGQY|ITRSRKM |
| MARA_SALTY/14-112 | HSIILDW|IEDNLESP..... | LSIEKV|SERSGY|SKWH|LQRMFKKEI|GH|SLGQY|ITRSRKM |
| MELR_ECOLI/194-292 | SQMLGF|IAENYDQA....... | LIINDV|AEHVKLNANYAW|GI|FQRVWQLI|MKQY|ITAMRI |

*Fig. 3B*

```
MMSR_PSEAE/201-299   DGLHAYMREHLHAR..........LEIERLAAFQNLSKFHFVSRYKAITGTIPIQHFTLHKI
MSMR_STRMU/176-274   NQVKKIIHSQYGSS..........LRVNDIAKKLNLSRSYLYKIERKSTNLSIKEYTLQVRM
MXIE_SHIFL/99-199    YHLVLYILRTIEKEk.........eVRIKSLITEHYGVSEAYFRSLCRKALGAKVKEQINIWRI
MXIE_SHISO/99-199    YHLVLYILRTIEKEk.........eVRIKSLITEHYGVSEAYFRSLCRKALGAKVKEQINIWRI
ORUR_PSEAE/241-338   TRVVRRLLLARPGDF.........PDLEQAARELHTSGRSIRRHSSLGT-TYQQVIDDVRK
PCHR_PSEAE/201-296   HAARDLIIVGALQEP.........PSLDTILASRVGMNPRKLTAGFRKVFGASVFGYLQEMRI
PERA_ECO27/168-265   DRVIKVIELDISKN..........WKLGIVSSSMFMSDSCLRKQINKENL-IFKKIIMLDIKM
POCR_SALTY/195-293   KKALRYIDAHLSDD..........LRIEDVASHVYLSPYYEFSKLFKKYQGIGFNAWWNRQRM
PQRA_PROVU/7-107     NDILKWLETQLQRNe.........gIKIDITANKSGYSKWHIQRIFKDFKGCIILGFYVRKFRI
RAFR_PEDPE/176-274   NLAVSYLQENYSTG..........CTIMDLCHYLNLGRSYLYTLFKTHANTSPQKLITKLRI
RAMA_ENTCL/9-107     DTIVEWIDDNLHQP..........LRIEDIARHAGYSKWHIQRIFLQYKGESIGFYIREFKI
RAMA_KLEPN/9-107     DTIVEWIDDNLHQP..........LRIDDIARHAGYSKWHIQRIFLQYKGESIGFYIREFKL
RHAR_ECOLI/209-307   DKLITRIAASLKSP..........FAIDKFCDEASCSERVIRQQFRQQIGMIINQYIRQVRV
RHAR_SALTY/179-277   DKLITAIANSLECP..........FAIDAFCQQEQCSERVIRQQFRAQTGMIINQYIRQVRI
RHAS_ECOLI/174-272   NLLLAWLEDHFADE..........VNMDAVADQFSLSLRTIHRQIKQQIGLTPQFYINRURI
RHAS_SALTY/174-272   NQLMAWLEDHFAEE..........VCMWEAVAEQFSLSLRTIHRQIKQHTGLTPQFYINRURI
RHRA_RHIME/210-310   ASIKMRVEQNLANGs.........FSIIIDVAEAERIITPRAIQKFFSREGI-IFSRYVLGFRI
RNS_ECOLI/164-261    DKVRNLIIEKDLSRK..........WTIGIIADAFNASEITIRKHIESENT-NFNQIIMQIRM
ROB_ECOLI/8-106      RDLLIWLEGHLDQP..........LSIDNVAAKAGYSKWHIQRMFKDVIGHAIGAYIRARRI
SOXS_ECOLI/7-105     QDLIAWIDEHIDQP..........INIDVAKKSGYSKWYLQRMFRTVTHQIIGYIRQFRI
```

*Fig. 3C*

| | | | | | | |
|---|---|---|---|---|---|---|
| SOXS_SALTY/7-105 | QILLIEWIDEHIDQP........ | .......LNIDVVAKKSGYSKWYLQRMFRIVTHQL | GEYTRQRRL |
| TCPN_VIBCH/172-269 | EKISCIVKSDITRN........ | WRWADICGELRINRMILKKELESRGV-KFRELINSIRI |
| TEID_ECOLI/31-129 | KDVLLWIEHNLDQS........ | LIIDDVANKAGYTKWYFQRLFKKVIGVILASYIRARRL |
| THCR_RHOER/227-328 | RLAVDYLEAHAQQP........ | LITVAQVARNVGVSVRSLQVGFQNSLGTIPMRQLKIIRM |
| URER_ECOLI/171-268 | QAITHLITQEPQKK........ | WHIDDVAKALFTIPSTLRRHLNREGV-SFRQLILDVRM |
| URER_PROMI/171-268 | QAITHLITQDPQRK........ | WHIEIDVAKTLYTIPSTLRRHLSKEGV-SFCQLILDVRI |
| VIRF_SHIDY/161-258 | DQIRKLVEKNIEKR........ | WRLSDISNNLNLSEIAVRKRLESEKLTFQQIILDIRM |
| VIRF_YEREN/167-265 | ERLQKFMEENYLQG........ | WKLSKFAREFGMGLITFKELFGIVYGISPRAWISERRI |
| VIRS_MYCTU/236-334 | ERVVGLARRLLPTGq...... | .CSAEATADQLDMHPRTLQRRIAAEGL-RCHDLIERERR |
| XYLR_ECOLI/288-386 | IQAMHYIRNHACKG........ | IKVDQVLDAVGISRSNLEKRFKEEVGETIIHAMLHAEKI |
| XYLR_HAEIN/288-386 | IQAMHYIRHRACHR........ | IKVGQVLDHLETSRSNLEQRFKNEMNKTIHQVIHEEKI |
| XYLS_PSEPU/214-315 | ERVVQFIEENLKRN........ | ISLERLAELAMMSPRSLYNLFEKHAGTTPKNYIRNFKL |
| XYS1_PSEPU/214-315 | ERVVQFIEENLKRN........ | ISLERLAELAMMSPRSLYNLFEKHAGTTPKNYIRNFKL |
| XYS2_PSEPU/39-140 | ERVVQFIEENVKRS........ | ISLEQLAELAIMSPRSLYTMFEKHIGTIPMNYIRNFKL |
| XYS3_PSEPU/214-315 | ERVVQFIEDNLKQS........ | ISLERLAELAIMSPRSLYTILFEKHAGTTPKNYIRNFKL |
| XYS4_PSEPU/214-315 | ERVVQFIEENLKRN........ | ISLERLAELAIMSPRSLYTLFEKHAGTTPKNYIRNFKL |
| Y4FK_RHISN/318-417 | LKAEAFMRENLINP........ | .VTIEDLAAAARCTPRALQRMFRIYRGGSPMSVLQNYRI |
| YA52_HAEIN/194-295 | KRLNTAILTAILQQPqn..... | .dWHIEQLAELAIMSRANFIRIFCQHIGMSPGFLTKVRI |
| YBBB_BACSU/166-264 | EKTKHYIETHADIK........ | ITLAQISQWAGISAKHYSESFKKWIGQSVIEFTIKIRI |
| YBCM_ECOLI/165-262 | SRCYNILILSEPGTK........ | WTANKVARYLYISVSTLHRRLASEGV-SFQSILDDVRI |

*Fig. 3D*

| | | | | | | |
|---|---|---|---|---|---|---|
| YCGK_ALTCA/67-163 | QNAMLYIENNYFND...... | ......INIDTVAFSVGVSRSYIVKQFKLATNKTINNRIINEVRI | | | | |
| YD95_MYCTU/242-343 | RGITAIVRSKLFRDsg.... | ..lfPTFTIVAGELDMHPRTIRRFIAEEGT-SFRALIGEARS | | | | |
| YDEO_ECOLI/137-233 | GKVRNIVMKPAHP....... | .......WKLKDIQCLYISESILKKKIKQEQT-TFSQIILDARM | | | | |
| YDIP_ECOLI/183-281 | KDILFYINNNYREK...... | .......ITIEQLSKKFRASVSYICHEFTKEYRISPINYIQRRM | | | | |
| YEAM_ECOLI/158-258 | PKIRIMVEMMAKGPve.... | ....wGALGQWAGFFAMSERNIARLIVKEIGLSFRQWRQQLQI | | | | |
| YFIF_BACSU/192-289 | TEVKLHIKDNLSQP...... | ......LKLITDVASHFHISGRHLSRLFAAELGVSYSEFVQNEKI | | | | |
| YHIW_ECOLI/139-236 | GKVERLISFDIAKR...... | ......WYIRDIAERMYTSESLIKKKLQDENT-CFSKIILASRM | | | | |
| YIDL_ECOLI/197-295 | EKLIATIHASLQQR...... | ......WSVADMAATPCSEAWIRRIFLRYTGKIIPKEYLDARI | | | | |
| YLJO_ECOLI/172-270 | EAIRDYIDERVASA...... | ......LITRESVAQAFYISPNYISHIFQKIGAIGFNEYLNHIRI | | | | |
| YISR_BACSU/183-281 | WEAARYIQEHYKEK...... | ......TTIKDILSLALHYQDYVSRQVQQVLGVIPAQYINRVRM | | | | |
| YKGA_ECOLI/19-117 | QQLLEWIECNLEHP...... | ......ISIEDIAQKSGYSRRNIQLIFRNFMHVPLGEYIRKFRI | | | | |
| YKGD_ECOLI/177-278 | PRLGAVIQQMLEMPgh.... | ....aWTVESLASIAHMSRASFAQLFRDVSGTTPLAVITKLRI | | | | |
| YMCR_STRLA/184-281 | DPLIRAVVSLEAG....... | .......RSVIATADSVGLGARQIHRRSLAAFGYGPKITARVLRM | | | | |
| YPDC_ECOLI/184-282 | HSICNWVQDNYAQP...... | ......LITRESVAQFFNITPNHISKLFAQHGIMRFIEYVRWVRM | | | | |
| YQHC_ECOLI/213-311 | SRVLKIJENKYTEN...... | ......LSVEQLAAEANMSVSAFHNFKSVTSTSPLQYIKNYRI | | | | |

```
AARP_PROST/22-120     CFAAKEIQTINL...    QVIDIALKYQFDSQQSFAKFEKAYIGISESIMRLS
ADA_ECOLI/85-183      RRLRESIAKGE-...    SVITSIINAGFPDSSSYYRKADETIGMIAKQFRHG
ADA_MYCTU/87-185      QTRRVLIETINL...    SVITSIINAGFPDSSSYYRKADETIGMIAKQFRHG
ADA_SALTY/94-183      RRLREAIAKGE-...    PFGDVAFAAGHSSIRQFNDIVRLACDGIPTALRAR
ADAA_BACSU/102-200    HAPKKYLIQINK...    AIGTATCVGIANAPYFITTLFKKKTGQIPAFFRQM
ADIY_ECOLI/149-246    RYAVNEIMVDGK...    NISQVSQSCGYNSTSYFISVEKDFYGMIPLHYVSQ
AGGR_ECOLI/164-261    SKPAALILDNSY...    QISQISNMIGHSSTSYFIRLFVKHFGITPKQFLTY
APPY_ECOLI/139-236    RYAKKLITSNSY...    SINVVAQKCGYNSTSYFICAFKDYYGVIPSHYFEK
ARAC_CITFR/180-279    SQAKLIISTIRM...    FIATVGRNVGFDDQLMFSRVFKKCIGASPSEFFRAG
ARAC_ECOLI/180-279    SQAKLIISTIRM...    FIATVGRNVGFDDQLMFSRVFKKCIGASPSEFFRAG
ARAC_ERWCH/186-284    IRAKLILQTIQE...    SIANIGRVVGYDDQLMFSRVFRKRVGVSPSDFRRR
ARAC_SALTY/180-279    SQAKLIISTIRM...    FIATVGRNVGFDDQLMFSRVFKKCIGASPSEFRAG
ARAL_STRAT/202-300    ELTARQIREGSA...    FLAATAHSVGYGSESALSVAFKRVLGMPGDYRKH
ARAL_STRLI/202-300    ELPARQIREGNA...    TLASTAHSVGYGSESALSVAFKRVLGMFPGIYRKH
CAFR_YERPE/8-107      SRAAAILRLTRL...    THIEISAKLFYDSQQIFTREFKKDFGYTPRQYRMI
CELD_ECOLI/168-274    NFPAKKQLEMINY...   SVIDIAFEAGYSSPSLFIKILFKKLLTSFIPKSYRKK
CFAD_ECOLI/164-261    SKPAALILENSY...    QISQISNMICISSASYFIRVENKHYGVIPKQFFTY
CSVR_ECOLI/166-263    SKPAALILENSY...    QISQISNMICISSASYFIRIFNKHFGVIRSSFLII
ENVY_ECOLI/149-246    RYAVQMIMDNK...    NTTQVQLCGYSSTSYFISVFKAFYGLIPLNYMAK
EUTR_ECOLI/243-344    NAVRREIISPWSqsmIVKDAPMQWGFWHLGQFATTYQQIFSEKPSLTLHQ
EUTR_SALTY/243-344    NAVRREIISPWSqsaIVKDAPMQWGFWHLGQFATTYQQIFAEKPSLTLHQ
EXSA_PSEAE/171-269    LVPHQILNSDM...    SIVDIAMEAGFSSQSYFTQSYRRFGCIPSRSRQG
```

| | | | | | |
|---|---|---|---|---|---|
FAPR_ECOLI/154-251 | NQAAKFTIRSDH... | QIGMTASLMGYTSVSVFIKIEKMYGMIPKFEIG
FEAR_ECOLI/199-299 | DFCADAIRHAADd.eKIAGIGFHWGFSDQSHFSTVFKQFGMIPGEYRRK
GADX_ECO27/145-242 | QFALQLIVIYGV... | SIKRVAVSCGYHSVSVFIYVFRNYGMIPTFYQER
GADX_ECO57/145-242 | QFALQLIVIHGF... | SIKRVAVSCGYHSVSVFIYVFRNYGMIPTFYQER
GADX_ECOLI/145-242 | QFALQLIVIHGF... | SIKRVAVSCGYHSVSVFIYVFRNYGMIPTFYQER
GLXA_RHIME/223-321 | RHARRILQQSPL... | SIPELAYATGHSSPAHFSNAEKRIFSQTPGSLRRR
HRPB_RALSO/375-477 | EGIRSDLLDSERtpsNIIDTPASRWCIRSRSALVKCYRKQFNEAPSETTWR
INVF_SALTY/112-210 | AQSLLNSVEGHE... | NITQLAVNFGVSSPSHFSSEIKELIGVSPRKLSNI
LACR_STAXY/174-272 | YHFASQILHTST... | LLSDLSRQVGYKDPLLFSKNFTKHFEISASKYRHH
LCRF_YERPE/167-265 | LYAHQLILNGKM... | SIVDLAMEAGHFSSQQSYFTQSYRRFFGCIPSQARLT
LUMQ_PHOLE/148-246 | DIFAKQLIAERQK... | FLSQVAQLGHFSSQQSFSQAERRIYGMSPTRYQFF
MARA_ECOLI/14-112 | TELAQLIKESNE... | FILYLAERYGHFESQQILRIFKNMFDVPPHKVRMI
MARA_SALTY/14-112 | TELAQLIKESNE... | FILYLAERYGHFESQQILRIFKNMFDVPPHKVRII
MELR_ECOLI/194-292 | NHVRALLSDIDK... | SILDLTALTAGHRSSSRFYSIFGKYVGMSPQQYRKL
MMSR_PSEAE/201-299 | EXPACQLLDSSDQ... | SVARVGQAVGYDDSYYFSRIFSKVMGLSPSAYRQR
MSMR_STRMU/176-274 | KRSQYILENPKL... | SIAHLSNSVGHFSDSLAFSKAFKNYFGKSPSKFRKE
MXIE_SHIFL/99-199 | VNGLLDVFLHNQ... | TITTSAAMNGYRSTSHFSNEIKTRLGFSARELSNI
MXIE_SHISO/99-199 | VNGLLDVFLHNQ... | TITTSAAMNGYASTSHFSNEIKTRLGFSARELSNI
ORUR_PSEAE/241-338 | RLALQMITTQL... | FLYETALLIGFNDSSNFRRAERKWJGKLPSDYREA
PCHR_PSEAE/201-296 | REAHRMLQEEFA... | NVSTVAYRVGYS-PAHFSTAFRKRYGISPSEIR--

*Fig. 3G*

| | | | | |
|---|---|---|---|---|
| PERA_ECO27/168-265 | KFASLFIRITDK... | NIDEISCLVGFNSTSYF | IKVFKFYMNTIPKFVNGV |
| POCR_SALTY/195-293 | VSAREHICHSDW... | STASIARNIGFSQTSYF | CKVFRQIYQVIPQAYRQQ |
| PQRA_PROVU/7-107 | LEPAAKSIQEKDM... | SILDIAIMYGFSSQAIFTRI | FKKFHNTIPAKFREN |
| RAFR_PEDPE/176-274 | EDAKQRLSTSNN... | SVQSIANMVGYKDSFIF | SKAFKRYSGASPSYRKS |
| RAMA_ENTCL/9-107 | LIPAARDLRESDE... | RVYEICLRYGFESQQIFTRI | FTRIFHQPPGAYRKE |
| RAMA_KLEPN/9-107 | LIPAARDLRDTDQ... | RVYDICLKYGFDSQQIFTRV | FTRIFNQPPGAYRKE |
| RHAR_ECOLI/209-307 | CFAQYLIQHSRL... | LISDISTECGFEDSNYFSVV | FTREIGMIPSQWRHL |
| RHAR_SALTY/179-277 | CFAQYLIQHSPL... | MISEISWQCGFEDSNYFSVV | FTREIGMIPSQWRHL |
| RHAS_ECOLI/174-272 | MKARHLLRHSEA... | SVIDIAYRCGFSDSNH-FSTI | ERREFNWSPRDIRQG |
| RHAS_SALTY/174-272 | IKARHLLRHSDH... | SVTEIAYRCGFSDSNH-FSTI | ERREFNWSPRDIRQG |
| RHRA_RHIME/210-310 | SIAKSLILAEGEa.t | SISQIAYNVGFNDLSYFNRI | FERSRYGVRPSDLRRL |
| RNS_ECOLI/164-261 | SKPALILENSY... | QISQISNMICISSASYFIRI | ENKFHYGVIPKQFFTY |
| ROB_ECOLI/8-106 | SKSAVAIRLTAR... | PIILDIALQYFREDSQQIFTRA | FKKQFAQIPALYRRS |
| SOXS_ECOLI/7-105 | LIPAAVELRITER... | PIFDIAMDIGYVSQQIFSRV | FRRQFDRIPSDYRHR |
| SOXS_SALTY/7-105 | LIPAAVELRITER... | PIFDIAMDIGYVSQQIFSRV | FRREFDRIPSDYRHR |
| TCPN_VIBCH/172-269 | SYSISLMKIGEF... | KIKQIAYQGFASVSYFSIV | FKSIMNVAPSEVLFM |
| TETD_ECOLI/31-129 | TKPAAVETRLTKK... | TILETALKYGFDSQQSFTRF | FKYIFKVIPSYRRN |
| THCR_RHOER/227-328 | QKARKDLLRADPaseG | VTEIAQRWGFLHVGFFAGF | YKQIFGVSPSEDLRT |
| URER_ECOLI/171-268 | GVMAINMITFSNY... | SVFQISHRCGFGSNAYFCDV | FKRKYNMIPSQFRLQ |
| URER_PROMI/171-268 | PIAINMITFSNY... | SVFQISHRCGFGSNAYFCDA | FKRKYGMIPSQFRTQ |

| | | | | |
|---|---|---|---|---|
| YHIW_ECOLI/139-236 | SMARRIIELRQI... | PLHITAEKGYSSTSYF | INIEROMYGVIPHQFAQH | |
| YIDL_ECOLI/197-295 | DIALSLIKQQGN... | SVGEVADILNFDSFHESKAEKHFGYAPSAVLKN | | |
| YIJO_ECOLI/172-270 | EHAKTLIKGYDL... | KVKEVAHAGFVDSNYFCRLERKNTERSPSEYRRQ | | |
| YISR_BACSU/183-281 | TEAKRLISSIND... | KMGVIAETVGMEDPTYFSKLEKQIEGISPIEYRKI | | |
| YKGA_ECOLI/19-117 | CRAAIIVRLIAK... | SMLDIALSLHFDSQQSFSREFKKLFGCSPREYRHR | | |
| YKGD_ECOLI/177-278 | QIAAQMFSRETL... | FVVIAESVGYASESSFHKAFVREFGCIPGEYRER | | |
| YMCR_STRLA/184-281 | QFAIRLARAGV-... | PFAETATLAGFADQAHLARDVREMAGSSLSELVER | | |
| YPDC_ECOLI/184-282 | AKARMIIQKYHL... | SIHEVAQRCGFPDSDYFCRVERROFGLIPGEMSAR | | |
| YQHC_ECOLI/213-311 | HKARMIIHDGM... | KASAPAMRVGYESASQFSREFKRYFCVIPGEDAAR | | |

*Fig. 3J*

SEQUENCE LISTING

<160> NUMBER OF SEQ ID NOS: 450

<210> SEQ ID NO 1
<211> LENGTH: 7878
<212> TYPE: DNA
<213> ORGANISM: Echerichia coli
<220> FEATURE:
<221> NAME/KEY: CDS
<222> LOCATION: (4124)...(4843)

<400> SEQUENCE: 1

```
gttaactgtg gtggttgtca ccgcccatta cacggcatac agctatatcg agccttttgt      60
acaaaacatt gcgggattca gcgccaactt tgccacggca ttactgttat tactcggtgg     120
tgcgggcatt attggcagcg tgattttcgg taaactgggt aatcagtatg cgtctgcgtt     180
ggtgagtacg gcgattgcgc tgttgctggt gtgcctggca ttgctgttac ctgcggcgaa     240
cagtgaaata cacctcgggg tgctgagtat tttctggggg atcgcgatga tgatcatcgg     300
gcttggtatg caggttaaag tgctggcgct ggcaccagat gctaccgacg tcgcgatggc     360
gctattctcc ggcatattta atattggaat cggggcgggt gcgttggtag gtaatcaggt     420
gagtttgcac tggtcaatgt cgatgattgg ttatgtgggc gcggtgcctg cttttgccgc     480 gttaattttgg tcaatcatta tatttcgccg ctggccagtg acactcgaag aacagacgca     540
atagttgaaa ggcccattcg ggccttttttt aatggtacgt tttaatgatt tccaggatgc     600
cgttaataat aaactgcaca cccatacata ccagcaggaa tcccatcaga cgggagatcg     660
cttcaatgcc acccttgccc accagccgca taattgcgcc ggagctgcgt aggcttcccc     720
acaaaataac cgccaccagg aaaaagatca gcggcggcgc aaccatcagt acccaatcag     780
cgaaggttga actctgacgc actgtggacg ccgagctaat aatcatcgct atggttcccg     840
gaccggcagt acttggcatt gccagcggca caaaggcaat attggcactg ggttcatctt     900
ccagctcttc cgacttgctt ttcgcctccg gtgaatcaat cgctttctgt tgcggaaaga     960
gcatccgaaa accgataaac gcgacgatta agccgcctgc aattcgcaga ccgggaatcg    1020
aaatgccaaa tgtatccatc accagttgcc cggcgtaata cgccaccatc atgatggcaa    1080
atacgtacac cgaggccatc aacgactgac gattacgttc ggcactgttc atgttgcctg    1140
ccaggccaag aaataacgcg acagttgtta atgggttagc taacggcagc aacaccacca    1200
```

```
gccccaggcc aattgcttta aacaaatcta acattggtgg ttgttatcct gtgtatctgg    1260
gttatcagcg aaaagtataa ggggtaaaca aggataaagt gtcactcttt agctagcctt    1320
gcatcgcatt gaacaaaact tgaaccgatt tagcaaaacg tggcatcggt caattcattc    1380
atttgactta tacttgcctg gcaatatta tcccctgcaa ctaattactt gccagggcaa     1440
ctaatgtgaa aagtaccagc gatctgttca atgaaattat tccattgggt cgcttaatcc    1500
atatggttaa tcagaagaaa gatcgcctgc ttaacgagta tctgtctccg ctggatatta    1560
ccgcggcaca gtttaaggtg ctctgctcta tccgctgcgc ggcgtgtatt actccggttg    1620
aactgaaaaa ggtattgtcg gtcgacctgg gagcactgac ccgtatgctg gatcgcctgg    1680
tctgtaaagg ctgggtggaa aggttgccga acccgaatga caagcgcggc gtactggtaa    1740
aacttaccac cggcggcgcg gcaatatgtg aacaatgcca tcaattagtt ggccaggacc    1800
tgcaccaaga attaacaaaa aacctgacgg cggacgaagt ggcaacactt gagtatttgc    1860
ttaagaaagt cctgccgtaa acaaaaaaga ggtatgacga tgtccagacg caatactgac    1920
gctattacca ttcatagcat tttggactgg atcgaggaca acctggaatc gccactgtca    1980
ctggagaaag tgtcagagcg ttcgggttac tccaaatggc acctgcaacg gatgtttaaa    2040
aaagaaaccg gtcattcatt aggccaatac atccgcagcc gtaagatgac ggaaatcgcg    2100
caaaagctga aggaaagtaa cgagccgata ctctatctgg cagaacgata tggcttcgag    2160
tcgcaacaaa ctctgacccg aaccttcaaa aattactttg atgttccgcc gcataaatac    2220
cggatgacca atatgcaggg cgaatcgcgc tttttacatc cattaaatca ttacaacagc    2280
tagttgaaaa cgtgacaacg tcactgaggc aatcatgaaa ccactttcat ccgcaatagc    2340
agctgcgctt attctctttt ccgcgcaggg cgttgcggaa caaaccacgc agccagttgt    2400
tacttcttgt gccaatgtcg tggttgttcc cccatcgcag gaacacccac cgtttgattt    2460
aaatcacatg ggtactggca gtgataagtc ggatgcgctc ggcgtgccct attataatca    2520
acacgctatg tagtttgttc tggccccgac atctcggggc ttattaactt cccacctta    2580 ccgctttacg ccaccgcaag ccaaatacat tgatatacag cccggtcata atgagcaccg    2640
cacctaaaaa ttgcagaccc gttaagcgtt catccaacaa tagtgccgca cttgccagtc    2700
ctactacggg caccagtaac gataacggtg caacccgcca ggtttcatag cgtcccagta    2760
acgtccccca gatcccataa ccaacaattg tcgccacaaa cgccagatac atcagagaca    2820
agatggtggt catatcgata gtaaccagac tgtgaatcat ggttgcggaa ccatcgagaa    2880
tcagcgaggc aacaaagaag ggaatgattg ggattaaagc gctccagatt accagcgaca    2940
tcaccgccgg acgcgttgag tgcgacatga tcttttatt gaagatgttg ccacacgccc     3000
aactaaatgc tgccgccagg gtcaacataa agccgagcat cgccacatgc tgaccgttca    3060
gactatcttc gattaacacc agtacgccaa aaatcgctaa ggcgatcccc gccaattgtt    3120
tgccatgcag tcgctccccg aaagtaaacg cgccaagcat gatagtaaaa aacgcctgtg    3180
cctgtaacac cagcgaagcc agtccagcag gcataccgaa gttaatggca caaaaaagaa    3240
aagcaaactg cgcaaaactg atggttaatc catacccag cagcaaattc agtggtactt      3300
tcggtcgtgc gacaaaaaag atagccggaa aagcgaccag cataaagcgc aaaccggcca    3360
gcatcagcgt ggcatgttat gaagcccac tttgatgacc acaaaattta gccccatac       3420 gaccactacc agtagcgcca acaccccatc ttttcgcgac attctaccgc ctctgaattt    3480
catcttttgt aagcaatcaa cttagctgaa tttacttttc tttaacagtt gattcgttag    3540
tcgccggtta cgacggcatt aatgcgcaaa taagtcgcta tacttcggat ttttgccatg    3600
```

```
                                                         -continued ctatttctttt acatctctaa aacaaaacat aacgaaacgc actgccggac agacaaatga      3660
acttatccct acgacgctct accagcgccc ttcttgcctc gtcgttgtta ttaaccatcg      3720
gacgcggcgc taccgtgcca tttatgacca tttacttgag tcgccagtac agcctgagtg      3780
tcgatctaat cggttatgcg atgacaattg cgctcactat tggcgtcgtt tttagcctcg      3840
gttttggtat cctggcggat aagttcgaca agaaacgcta tatgttactg caattaccg      3900 ccttcgccag cggttttatt gccattactt tagtgaataa cgtgacgctg ttgtgctct      3960 tttttgccct cattaactgc gccattctg tttttgctac cgtgctgaaa gcctggtttg      4020
ccgacaatct ttcgtccacc agcaaaacga aaatcttctc aatcaactac accatgctaa      4080
acattggctg accatcggtc cgccgctcgg cacgctgttg gta atg cag agc atc      4135
                                                  Met Gln Ser Ile
                                                    1 aat ctg ccc ttc tgg ctg gca gct atc tgt tcc gcg ttt ccc atg ctt      4183
Asn Leu Pro Phe Trp Leu Ala Ala Ile Cys Ser Ala Phe Pro Met Leu
 5              10                  15                  20 ttc att caa att tgg gta aag cgc agc gag aaa atc atc gcc acg gaa      4231
Phe Ile Gln Ile Trp Val Lys Arg Ser Glu Lys Ile Ile Ala Thr Glu
             25                  30                  35 aca ggc agt gtc tgg tcg ccg aaa gtt tta tta caa gat aaa gca ctg      4279
Thr Gly Ser Val Trp Ser Pro Lys Val Leu Leu Gln Asp Lys Ala Leu
 40                  45                  50 ttg tgg ttt acc tgc tct ggt ttt ctg gct tct ttt gta agc ggc gca      4327
Leu Trp Phe Thr Cys Ser Gly Phe Leu Ala Ser Phe Val Ser Gly Ala
         55                  60                  65 ttt gct tca tgc att tca caa tat gtg atg gtg att gct gat ggg gat      4375
Phe Ala Ser Cys Ile Ser Gln Tyr Val Met Val Ile Ala Asp Gly Asp
 70                  75                  80 ttt gcc gaa aag gtg gtc gcg gtt gtt ctt ccg gtg aat gct gcc atg      4423
Phe Ala Glu Lys Val Val Ala Val Val Leu Pro Val Asn Ala Ala Met
 85                  90                  95                 100 gtg gtt acg ttg caa tat tcc gtg ggc cgc cga ctt aac ccg gct aac      4471
Val Val Thr Leu Gln Tyr Ser Val Gly Arg Arg Leu Asn Pro Ala Asn
            105                 110                 115 atc cgc gcg ctg atg aca gca ggc acc ctc tgt ttc gtc atc ggt ctg      4519
Ile Arg Ala Leu Met Thr Ala Gly Thr Leu Cys Phe Val Ile Gly Leu
        120                 125                 130 gtc ggt ttt att ttt tcc ggc aac agc ctg cta ttg tgg ggt atg tca      4567
Val Gly Phe Ile Phe Ser Gly Asn Ser Leu Leu Leu Trp Gly Met Ser
    135                 140                 145 gct gcg gta ttt act gtc ggt gaa atc att tat gcg ccg ggc gag tat      4615
Ala Ala Val Phe Thr Val Gly Glu Ile Ile Tyr Ala Pro Gly Glu Tyr
150                 155                 160 atg ttg att gac cat att gcg ccg cca gaa atg aaa gcc agc tat ttt      4663
Met Leu Ile Asp His Ile Ala Pro Pro Glu Met Lys Ala Ser Tyr Phe
165                 170                 175                 180 tcc gcc cag tct tta ggc tgg ctt ggt gcc gcg att aac cca tta gtg      4711
Ser Ala Gln Ser Leu Gly Trp Leu Gly Ala Ala Ile Asn Pro Leu Val
            185                 190                 195 agt ggc gta gtg cta acc agc ctg ccg cct tcc tcg ctg ttt gtc atc      4759
Ser Gly Val Val Leu Thr Ser Leu Pro Pro Ser Ser Leu Phe Val Ile
        200                 205                 210 tta gcg ttg gtg atc att gct gcg tgg gtg ctg atg tta aaa ggg att      4807
Leu Ala Leu Val Ile Ile Ala Ala Trp Val Leu Met Leu Lys Gly Ile
    215                 220                 225 cga gca aga ccg tgg ggg cag ccc gcg ctt tgt tga tttaagtcga          4853
Arg Ala Arg Pro Trp Gly Gln Pro Ala Leu Cys  *
230                 235
```

```
acacaataaa gatttaattc agccttcgtt taggttacct ctgctaatat ctttctcatt    4913
gagatgaaaa ttaaggtaag cgaggaaaca caccacacca taaacggagg caaataatgc    4973
tgggtaatat gaatgttttt atggccgtac tgggaataat tttattttct ggttttctgg    5033
ccgcgtattt cagccacaaa tgggatgact aatgaacgga gataatccct cacctaaccg    5093
gccccttgtt acagttgtgt acaaggggcc tgattttat dacggcgaaa aaaaaccgcc    5153
agtaaaccgg cggtgaatgc ttgcatggat agatttgtgt tttgctttta cgctaacagg    5213
cattttcctg cactgataac gaatcgttga cacagtagca tcagttttct caatgaatgt    5273
taaacggagc ttaaactcgg ttaatcacat tttgttcgtc aataaacatg cagcgatttc    5333
ttccggtttg cttaccctca tacattgccc ggtccgctct tccaatgacc acatccagag    5393
gctcttcagg aaatgcgcga ctcacacctg ctgtcacggt aatgttgata tgcccttcag    5453
aatgtgtgat ggcatggtta tcgactaact ggcaaattct gacacctgca cgacatgctt    5513
cttcatcatt agccgctttg acaataatga taaattcttc gccccgtag cgataaaccg    5573 tttcgtaatc acgcgtccaa ctggctaagt aagttgccag ggtgcgtaat actacatcgc    5633
cgattaaatg cccgtagtat cattaaccaa tttaaatcgg tcaatatcca acaacattaa    5693
ataaagattc agaggctcag cgttgcgtaa ctgatgatca aaggattcat caagaacccg    5753 acgaccggc aatcccgtca aaacatccat attgctacgg atcgtcagca aataaatttt    5813
gtaatcggtt aatgccgcag taaaagaaag caacccctcc tgaaaggcgt cgaaatgcgc    5873
gtcctgccag tgattttcaa caatagccag cattaattcc cgaccacagt tatgcatatg    5933
ttgatgggca gaatccatta gccgaacgta aggtaattca tcgttatcga gtggcccag    5993 atgatcaatc caccgaccaa actggcacag tccataagaa tggttatccg ttatttctgg    6053
cttactggca tctctcgcga ccacgctgtg aaacatactc accagccact ggtagtgggc    6113
atcgatagcc ttattgagat ttaacaagat ggcatcaatt tccgttgtct tcttgatcat    6173
tgccactcct ttttcacagt tccttgtgcg cgctattcta acgagagaaa agcaaaatta    6233
cgtcaatatt ttcatagaaa tccgaagtta tgagtcatct ctgagataac attgtgattt    6293
aaaacaaaat cagcggataa aaaagtgttt aattctgtaa attacctctg cattatcgta    6353
aataaaagga tgacaaatag cataacccaa taccctaatg gcccagtagt tcaggccatc    6413
aggctaattt attttatt ctgcaaatga gtgacccgaa cgacggccgg cgcgcttttc    6473
ttatccagac tgccactaat gttgatcatc tggtccggct gaacttctcg tccatcaaag    6533
acggccgcag gaataacgac attaatttca ccgctcttat cgcgaaaaac gtaacggtcc    6593
tctcctttgt gagaaatcaa attaccgcgt agtgaaaccg aagcgccatc gtgcatggtt    6653
tttgcgaaat caacggtcat tttttttgca tcatcggttc cgcgatagcc atcttctatt    6713
gcatgaggcg gcggtggcgc tgcatcctgt tttaaaccgc cctggtcatc tgccaacgca    6773
taaggcatga caagaaaact tgctaataca atggcctgaa atttcatact aactccttaa    6833
ttgcgtttgg tttgacttat taagtctggt tgctattttt ataattgcca aataagaata    6893
ttgccaattg ttataaggca tttaaaatca gccaactagc tgtcaaatat acagagaatt    6953
taactcacta agttaagaa gattgaaaag tcttaaacat attttcagaa taatcggatt    7013
tatatgtttg aaaattatta tattggacga gcatacagaa aaagcaaatc acctttacat    7073
ataaaagcgt ggacaaaaaa cagtgaacat taatagagat aaaattgtac aacttgtaga    7133
taccgatact attgaaaacc tgacatccgc gttgagtcaa agacttatcg cggatcaatt    7193
acgcttaact accgccgaat catgcaccgg cggtaagttg gctagcgccc tgtgtgcagc    7253
```

-continued

```
tgaagataca cccaaatttt acggtgcagg ctttgttact ttcaccgatc aggcaaagat    7313
gaaaatcctc agcgtaagcc agcaatctct tgaacgatat tctgcggtga gtgagaaagt    7373
ggcagcagaa atggcaaccg gtgccataga gcgtgcggat gctgatgtca gtattgccat    7433
taccggctac ggcggaccgg agggcggtga agatggtacg ccagcgggta ccgtctggtt    7493
tgcgtggcat attaaaggcc agaactacac tgcggttatg cattttgctg gcgactgcga    7553
aacggtatta gctttagcgg tgaggtttgc cctcgcccag ctgctgcaat tactgctata    7613
accaggctgg cctggcgata tctcaggcca gccattggtg gtgtttatat gttcaagcca    7673
cgatgttgca gcatcggcat aatcttaggt gccttaccgc gccattgtcg atacaggcgt    7733
tccagatctt cgctgttacc tctggaaagg atcgcctcgc gaaaacgcag cccattttca    7793
cgcgttaatc cgccctgctc aacaaaccac tgataaccat catcggccaa catttgcgtc    7853
cacagataag cgtaataacc tgcag                                          7878
```

<210> SEQ ID NO 2
<211> LENGTH: 239
<212> TYPE: PRT
<213> ORGANISM: Echerichia coli

<400> SEQUENCE: 2

```
Met Gln Ser Ile Asn Leu Pro Phe Trp Leu Ala Ala Ile Cys Ser Ala
 1               5                  10                  15

Phe Pro Met Leu Phe Ile Gln Ile Trp Val Lys Arg Ser Glu Lys Ile
            20                  25                  30

Ile Ala Thr Glu Thr Gly Ser Val Trp Ser Pro Lys Val Leu Leu Gln
        35                  40                  45

Asp Lys Ala Leu Leu Trp Phe Thr Cys Ser Gly Phe Leu Ala Ser Phe
    50                  55                  60

Val Ser Gly Ala Phe Ala Ser Cys Ile Ser Gln Tyr Val Met Val Ile
65                  70                  75                  80

Ala Asp Gly Asp Phe Ala Glu Lys Val Val Ala Val Val Leu Pro Val
                85                  90                  95

Asn Ala Ala Met Val Val Thr Leu Gln Tyr Ser Val Gly Arg Arg Leu
            100                 105                 110

Asn Pro Ala Asn Ile Arg Ala Leu Met Thr Ala Gly Thr Leu Cys Phe
        115                 120                 125

Val Ile Gly Leu Val Gly Phe Ile Phe Ser Gly Asn Ser Leu Leu Leu
130                 135                 140

Trp Gly Met Ser Ala Ala Val Phe Thr Val Gly Glu Ile Ile Tyr Ala
145                 150                 155                 160

Pro Gly Glu Tyr Met Leu Ile Asp His Ile Ala Pro Glu Met Lys
                165                 170                 175

Ala Ser Tyr Phe Ser Ala Gln Ser Leu Gly Trp Leu Gly Ala Ala Ile
            180                 185                 190

Asn Pro Leu Val Ser Gly Val Val Leu Thr Ser Leu Pro Pro Ser Ser
        195                 200                 205

Leu Phe Val Ile Leu Ala Leu Val Ile Ala Ala Trp Val Leu Met
    210                 215                 220

Leu Lys Gly Ile Arg Ala Arg Pro Trp Gly Gln Pro Ala Leu Cys
225                 230                 235
```

<210> SEQ ID NO 3
<211> LENGTH: 870
<212> TYPE: DNA
<213> ORGANISM: Echerichia coli

```
-continued

<220> FEATURE:
<221> NAME/KEY: CDS
<222> LOCATION: (1)...(870)

<400> SEQUENCE: 3 atg gat cag gcc ggc att att cgc gac ctt tta atc tgg ctg gaa ggt     48
Met Asp Gln Ala Gly Ile Ile Arg Asp Leu Leu Ile Trp Leu Glu Gly
 1               5                  10                  15 cat ctg gat cag ccc ctg tcg ctc gac aat gta gcg gcg aaa gca ggt     96
His Leu Asp Gln Pro Leu Ser Leu Asp Asn Val Ala Ala Lys Ala Gly
             20                  25                  30 tat tcc aag tgg cac tta cag aga atg ttt aaa gat gtc act ggc cat    144
Tyr Ser Lys Trp His Leu Gln Arg Met Phe Lys Asp Val Thr Gly His
         35                  40                  45 gct att ggc gcg tat att cgt gct cgt cgt ttg tcg aaa tcg gcg gtc    192
Ala Ile Gly Ala Tyr Ile Arg Ala Arg Arg Leu Ser Lys Ser Ala Val
     50                  55                  60 gca cta cgc ctg act gcg cgt ccg att ctg gac atc gcg ctg caa tac    240
Ala Leu Arg Leu Thr Ala Arg Pro Ile Leu Asp Ile Ala Leu Gln Tyr
 65                  70                  75                  80 cgc ttc gac tct caa cag aca ttt acc cgc gca ttc aag aag cag ttt    288
Arg Phe Asp Ser Gln Gln Thr Phe Thr Arg Ala Phe Lys Lys Gln Phe
                 85                  90                  95 gcc cag act cct gca ctt tac cgc cgt tct cct gaa tgg agc gcc ttt    336
Ala Gln Thr Pro Ala Leu Tyr Arg Arg Ser Pro Glu Trp Ser Ala Phe
            100                 105                 110 ggt att cgc ccg ccg cta cgc ctg ggt gaa ttc act atg cca gag cac    384
Gly Ile Arg Pro Pro Leu Arg Leu Gly Glu Phe Thr Met Pro Glu His
        115                 120                 125 aaa ttt gtc acc ctg gaa gat acg ccg ctg att ggt gtt acc cag agc    432
Lys Phe Val Thr Leu Glu Asp Thr Pro Leu Ile Gly Val Thr Gln Ser
    130                 135                 140 tac tcc tgt tcg ctg gag caa atc tct gat ttc cgc cat gaa atg cgt    480
Tyr Ser Cys Ser Leu Glu Gln Ile Ser Asp Phe Arg His Glu Met Arg
145                 150                 155                 160 tat cag ttc tgg cac gat ttt ctc ggc aac gcg ccg acc att ccg ccg    528
Tyr Gln Phe Trp His Asp Phe Leu Gly Asn Ala Pro Thr Ile Pro Pro
                165                 170                 175 gtg ctc tac ggc ctg aat gaa acg cgt ccg agt cag gat aaa gac gac    576
Val Leu Tyr Gly Leu Asn Glu Thr Arg Pro Ser Gln Asp Lys Asp Asp
            180                 185                 190 gag caa gag gta ttc tat acc acc gcg tta gcc cag gat cag gca gat    624
Glu Gln Glu Val Phe Tyr Thr Thr Ala Leu Ala Gln Asp Gln Ala Asp
        195                 200                 205 ggc tat gta ctg acg ggg cat ccg gtg atg ctg cag ggc ggc gaa tat    672
Gly Tyr Val Leu Thr Gly His Pro Val Met Leu Gln Gly Gly Glu Tyr
    210                 215                 220 gtg atg ttt acc tat gaa ggt ctg gga acc ggc gtg cag gag ttt atc    720
Val Met Phe Thr Tyr Glu Gly Leu Gly Thr Gly Val Gln Glu Phe Ile
225                 230                 235                 240 ctg acg gta tac gga acg tgc atg cca atg ctc aac ctg acg cgc cgt    768
Leu Thr Val Tyr Gly Thr Cys Met Pro Met Leu Asn Leu Thr Arg Arg
                245                 250                 255 aaa ggt cag gat att gag cga tac tac ccg gca gaa gat gcc aaa gcg    816
Lys Gly Gln Asp Ile Glu Arg Tyr Tyr Pro Ala Glu Asp Ala Lys Ala
            260                 265                 270 gga gat cgc cca att aat cta cgc tgt gaa ctg ctg att ccg atc cgt    864
Gly Asp Arg Pro Ile Asn Leu Arg Cys Glu Leu Leu Ile Pro Ile Arg
        275                 280                 285 cgt taa                                                             870
Arg *
```

<210> SEQ ID NO 4
<211> LENGTH: 289
<212> TYPE: PRT
<213> ORGANISM: Echerichia coli

<400> SEQUENCE: 4

Met Asp Gln Ala Gly Ile Ile Arg Asp Leu Leu Ile Trp Leu Glu Gly
 1               5                  10                  15

His Leu Asp Gln Pro Leu Ser Leu Asp Asn Val Ala Ala Lys Ala Gly
            20                  25                  30

Tyr Ser Lys Trp His Leu Gln Arg Met Phe Lys Asp Val Thr Gly His
        35                  40                  45

Ala Ile Gly Ala Tyr Ile Arg Ala Arg Arg Leu Ser Lys Ser Ala Val
    50                  55                  60

Ala Leu Arg Leu Thr Ala Arg Pro Ile Leu Asp Ile Ala Leu Gln Tyr
65                  70                  75                  80

Arg Phe Asp Ser Gln Gln Thr Phe Thr Arg Ala Phe Lys Lys Gln Phe
                85                  90                  95

Ala Gln Thr Pro Ala Leu Tyr Arg Arg Ser Pro Glu Trp Ser Ala Phe
            100                 105                 110

Gly Ile Arg Pro Pro Leu Arg Leu Gly Glu Phe Thr Met Pro Glu His
        115                 120                 125

Lys Phe Val Thr Leu Glu Asp Thr Pro Leu Ile Gly Val Thr Gln Ser
    130                 135                 140

Tyr Ser Cys Ser Leu Glu Gln Ile Ser Asp Phe Arg His Glu Met Arg
145                 150                 155                 160

Tyr Gln Phe Trp His Asp Phe Leu Gly Asn Ala Pro Thr Ile Pro Pro
                165                 170                 175

Val Leu Tyr Gly Leu Asn Glu Thr Arg Pro Ser Gln Asp Lys Asp Asp
            180                 185                 190

Glu Gln Glu Val Phe Tyr Thr Thr Ala Leu Ala Gln Asp Gln Ala Asp
        195                 200                 205

Gly Tyr Val Leu Thr Gly His Pro Val Met Leu Gln Gly Gly Glu Tyr
    210                 215                 220

Val Met Phe Thr Tyr Glu Gly Leu Gly Thr Gly Val Gln Glu Phe Ile
225                 230                 235                 240

Leu Thr Val Tyr Gly Thr Cys Met Pro Met Leu Asn Leu Thr Arg Arg
                245                 250                 255

Lys Gly Gln Asp Ile Glu Arg Tyr Tyr Pro Ala Glu Asp Ala Lys Ala
            260                 265                 270

Gly Asp Arg Pro Ile Asn Leu Arg Cys Glu Leu Leu Ile Pro Ile Arg
        275                 280                 285

Arg

<210> SEQ ID NO 5
<211> LENGTH: 52
<212> TYPE: PRT
<213> ORGANISM: Providencia Stuartii

<400> SEQUENCE: 5

Ser Glu Ile Leu Val Trp Ile Glu Gly Asn Leu Thr Asn Arg Leu Ser
 1               5                  10                  15

Leu Asp Asp Ile Ala Gln His Ser Gly Tyr Thr Lys Trp His Leu Gln
            20                  25                  30

Arg Val Phe Arg Lys Ile Val Gly Met Pro Leu Gly Glu Tyr Ile Arg

```
                35                  40                  45
Arg Arg Arg Ile
    50

<210> SEQ ID NO 6
<211> LENGTH: 53
<212> TYPE: PRT
<213> ORGANISM: Escherichia coli

<400> SEQUENCE: 6

Asp Lys Ile Thr His Ala Cys Arg Leu Leu Glu Gln Glu Thr Pro Val
1               5                   10                  15

Thr Leu Glu Ala Leu Ala Asp Gln Val Ala Met Ser Pro Phe His Leu
            20                  25                  30

His Arg Leu Phe Lys Ala Thr Thr Gly Met Thr Pro Lys Ala Trp Gln
        35                  40                  45

Gln Ala Trp Arg Ala
    50

<210> SEQ ID NO 7
<211> LENGTH: 52
<212> TYPE: PRT
<213> ORGANISM: Mycobacterium tuberculosis

<400> SEQUENCE: 7

Ala Arg Ala Met Arg Leu Ile Ala Asp Gly Thr Val Asp Arg Asp Gly
1               5                   10                  15

Val Ser Gly Leu Ala Ala Gln Leu Gly Tyr Thr Ile Arg Gln Leu Glu
            20                  25                  30

Arg Leu Leu Gln Ala Val Val Gly Ala Gly Pro Leu Ala Leu Ala Arg
        35                  40                  45

Ala Gln Arg Met
    50

<210> SEQ ID NO 8
<211> LENGTH: 44
<212> TYPE: PRT
<213> ORGANISM: Escherichia coli

<400> SEQUENCE: 8

Leu Glu Gln Glu Thr Pro Val Thr Leu Ala Phe Leu Ala Gln Ala Val
1               5                   10                  15

Ala Met Ser Pro Phe His Leu Arg Leu Phe Lys Ala Ser Thr Gly
            20                  25                  30

Met Thr Pro Lys Gly Trp Gln Gln Ala Trp Arg Ala
        35                  40

<210> SEQ ID NO 9
<211> LENGTH: 52
<212> TYPE: PRT
<213> ORGANISM: Escherichia coli

<400> SEQUENCE: 9

Asp Leu Ile Thr Glu Tyr Ile Asp Lys Asn Phe Thr Glu Lys Leu Thr
1               5                   10                  15

Leu Glu Ser Leu Ala Asp Ile Cys His Gly Ser Pro Tyr His Met His
            20                  25                  30

Arg Thr Phe Lys Lys Ile Lys Gly Ile Thr Leu Val Glu Tyr Ile Gln
        35                  40                  45

Gln Val Arg Val
```

```
<210> SEQ ID NO 10
<211> LENGTH: 51
<212> TYPE: PRT
<213> ORGANISM: Escherichia coli

<400> SEQUENCE: 10

Asp Ser Val Tyr Gln Ile Ile Glu Ser Asp Ile His Lys Asp Trp Asn
1               5                   10                  15

Leu Ser Met Val Ala Ser Cys Leu Cys Leu Ser Pro Ser Leu Leu Lys
            20                  25                  30

Lys Lys Leu Lys Ser Glu Asn Thr Ser Tyr Ser Gln Ile Ile Thr Thr
        35                  40                  45

Cys Arg Met
    50

<210> SEQ ID NO 11
<211> LENGTH: 51
<212> TYPE: PRT
<213> ORGANISM: Escherichia coli

<400> SEQUENCE: 11

Asp Lys Val Arg Asn Thr Ile Glu Lys Asp Leu Ser Lys Arg Trp Thr
1               5                   10                  15

Leu Ala Ile Ile Ala Asp Glu Phe Asn Val Ser Glu Ile Thr Ile Arg
            20                  25                  30

Lys Arg Leu Glu Ser Glu Tyr Ile Thr Phe Asn Gln Ile Leu Met Gln
        35                  40                  45

Ser Arg Met
    50

<210> SEQ ID NO 12
<211> LENGTH: 51
<212> TYPE: PRT
<213> ORGANISM: Escherichia coli

<400> SEQUENCE: 12

Cys Lys Ile Thr Gly Ile Ile Ser Phe Asn Ile Glu Arg Gln Trp His
1               5                   10                  15

Leu Lys Asp Ile Ala Glu Leu Ile Tyr Thr Ser Glu Ser Leu Ile Lys
            20                  25                  30

Lys Arg Leu Arg Asp Glu Gly Thr Ser Phe Thr Glu Ile Leu Arg Asp
        35                  40                  45

Thr Arg Met
    50

<210> SEQ ID NO 13
<211> LENGTH: 53
<212> TYPE: PRT
<213> ORGANISM: Escherichia coli

<400> SEQUENCE: 13

Arg Asp Ala Cys Gln Tyr Ile Ser Asp His Leu Ala Asp Ser Asn Phe
1               5                   10                  15

Asp Ile Ala Ser Val Ala Gln His Val Cys Leu Ser Pro Ser Arg Leu
            20                  25                  30

Ser His Leu Phe Arg Gln Gln Leu Gly Ile Ser Val Leu Ser Trp Arg
        35                  40                  45

Glu Asp Gln Arg Ile
```

<210> SEQ ID NO 14
<211> LENGTH: 53
<212> TYPE: PRT
<213> ORGANISM: Escherichia coli

<400> SEQUENCE: 14

Arg Glu Ala Cys Gln Tyr Ile Ser Asp His Leu Ala Asp Ser Asn Phe
1               5                   10                  15

Asp Ile Ala Ser Val Ala Gln His Val Cys Leu Ser Pro Ser Arg Leu
            20                  25                  30

Ser His Leu Phe Arg Gln Gln Leu Gly Ile Ser Val Leu Ser Trp Arg
        35                  40                  45

Glu Asp Gln Arg Ile
    50

<210> SEQ ID NO 15
<211> LENGTH: 52
<212> TYPE: PRT
<213> ORGANISM: Escherichia coli

<400> SEQUENCE: 15

Ile Glu Ala Cys Gln Phe Ile Thr Ser Asn Leu Ala Gly Glu Leu Arg
1               5                   10                  15

Ile Asp Glu Val Ala Arg His Val Cys Leu Ser Pro Ser Arg Leu Ala
            20                  25                  30

His Leu Phe Arg Glu Gln Val Gly Ile Asn Ile Leu Arg Trp Arg Glu
        35                  40                  45

Asp Gln Arg Val
    50

<210> SEQ ID NO 16
<211> LENGTH: 53
<212> TYPE: PRT
<213> ORGANISM: Escherichia coli

<400> SEQUENCE: 16

Arg Asp Ala Cys Gln Tyr Ile Ser Asp His Leu Ala Asp Ser His Phe
1               5                   10                  15

Asp Ile Ala Ser Val Ala Gln His Val Cys Leu Ser Pro Ser Arg Leu
            20                  25                  30

Ser His Leu Phe Arg Gln Gln Leu Gly Ile Ser Val Leu Ser Trp Arg
        35                  40                  45

Glu Asp Gln Arg Ile
    50

<210> SEQ ID NO 17
<211> LENGTH: 52
<212> TYPE: PRT
<213> ORGANISM: Escherichia coli

<400> SEQUENCE: 17

Ala Ser Ala Leu Thr Phe Leu His Arg Asp Pro Ala His Ser Trp Thr
1               5                   10                  15

Val Ala Glu Leu Ala Ser Ala Ala Val Ser Arg Ser Thr Leu Ala
            20                  25                  30

Ala Arg Phe Lys Ala Thr Val Gly Gln Gly Pro Leu Glu Tyr Leu Thr
        35                  40                  45

Arg Trp Arg Ile

<210> SEQ ID NO 18
<211> LENGTH: 52
<212> TYPE: PRT
<213> ORGANISM: Escherichia coli

<400> SEQUENCE: 18

```
Ala Thr Ala Leu Thr Cys Leu His Arg Asp Pro Ala Arg Ser Trp Thr
1               5                   10                  15

Val Ala Asp Leu Ala Asp Thr Ala Ala Val Ser Arg Ser Thr Leu Ala
            20                  25                  30

Ala Arg Phe Lys Ala Thr Val Gly Gln Gly Pro Leu Glu Tyr Leu Thr
        35                  40                  45

Arg Trp Arg Ile
    50
```

<210> SEQ ID NO 19
<211> LENGTH: 53
<212> TYPE: PRT
<213> ORGANISM: Escherichia coli

<400> SEQUENCE: 19

```
Asn Ser Ile Ile Gln Tyr Ile Glu Glu Asn Leu Glu Ser Lys Phe Ile
1               5                   10                  15

Asn Ile Asp Cys Leu Val Leu Tyr Ser Gly Phe Ser Arg Arg Tyr Leu
            20                  25                  30

Gln Ile Ser Phe Lys Glu Tyr Val Gly Met Pro Ile Gly Thr Tyr Ile
        35                  40                  45

Arg Val Arg Arg Ala
    50
```

<210> SEQ ID NO 20
<211> LENGTH: 60
<212> TYPE: PRT
<213> ORGANISM: Escherichia coli

<400> SEQUENCE: 20

```
Asp Asp Val Pro Gln Trp Leu Lys Ser Thr Val Glu Lys Met His Asp
1               5                   10                  15

Lys Glu Gln Phe Ser Glu Ser Ala Leu Glu Asn Met Val Ala Leu Ser
            20                  25                  30

Ala Lys Ser Gln Glu Tyr Leu Thr Arg Ala Thr Gln Arg Tyr Tyr Gly
        35                  40                  45

Lys Thr Pro Met Gln Ile Ile Asn Glu Ile Arg Ile
    50                  55                  60
```

<210> SEQ ID NO 21
<211> LENGTH: 51
<212> TYPE: PRT
<213> ORGANISM: Escherichia coli

<400> SEQUENCE: 21

```
Asp Lys Val Arg Asn Val Ile Glu Lys Asp Leu Ser Arg Lys Trp Thr
1               5                   10                  15

Leu Gly Ile Ile Ala Asp Ala Phe Asn Val Ser Glu Ile Thr Ile Arg
            20                  25                  30

Lys Arg Leu Glu Ser Glu Asn Thr Asn Phe Asn Gln Ile Leu Met Gln
        35                  40                  45

Leu Arg Met
```

-continued

<210> SEQ ID NO 22
<211> LENGTH: 51
<212> TYPE: PRT
<213> ORGANISM: Escherichia coli

<400> SEQUENCE: 22

```
Asp Lys Val Arg Gly Val Ile Glu Lys Asp Leu Ser Arg Lys Trp Thr
1               5                   10                  15
Leu Ala Ile Ile Ala Asp Val Phe Asn Val Ser Glu Ile Thr Ile Arg
                20                  25                  30
Lys Arg Leu Glu Ser Glu Asp Thr Asn Phe Asn Gln Ile Leu Met Gln
            35                  40                  45
Ser Arg Met
    50
```

<210> SEQ ID NO 23
<211> LENGTH: 51
<212> TYPE: PRT
<213> ORGANISM: Escherichia coli

<400> SEQUENCE: 23

```
Asp Ser Val Cys Arg Ile Ile Gln Ser Asp Ile Gln His Tyr Trp Asn
1               5                   10                  15
Leu Arg Ile Val Ala Ser Ser Leu Cys Leu Ser Pro Ser Leu Leu Lys
                20                  25                  30
Lys Lys Leu Lys Asn Glu Asn Thr Ser Tyr Ser Gln Ile Val Thr Glu
            35                  40                  45
Cys Arg Met
    50
```

<210> SEQ ID NO 24
<211> LENGTH: 52
<212> TYPE: PRT
<213> ORGANISM: Escherichia coli

<400> SEQUENCE: 24

```
Ser Arg Ala Arg Glu Tyr Val Leu Glu Asn Met Ser Glu Pro Val Thr
1               5                   10                  15
Val Leu Asp Leu Cys Asn Gln Leu His Val Ser Arg Arg Thr Leu Gln
                20                  25                  30
Asn Ala Phe His Ala Ile Leu Gly Ile Gly Pro Asn Ala Trp Leu Lys
            35                  40                  45
Arg Ile Arg Leu
    50
```

<210> SEQ ID NO 25
<211> LENGTH: 52
<212> TYPE: PRT
<213> ORGANISM: Escherichia coli

<400> SEQUENCE: 25

```
Ser Arg Ala Arg Glu Tyr Val Leu Glu Asn Met Ser Glu Pro Leu Thr
1               5                   10                  15
Val Leu Asp Leu Cys Asn Gln Leu His Val Ser Arg Arg Thr Leu Gln
                20                  25                  30
Asn Ala Phe His Ala Ile Leu Gly Ile Gly Pro Asn Ala Trp Leu Lys
            35                  40                  45
Arg Ile Arg Leu
```

<210> SEQ ID NO 26
<211> LENGTH: 52
<212> TYPE: PRT
<213> ORGANISM: Escherichia coli

<400> SEQUENCE: 26

Glu Arg Leu Gln Leu Phe Met Glu Lys His Tyr Leu Asn Glu Trp Lys
1               5                   10                  15

Leu Ser Asp Phe Ser Arg Glu Phe Gly Met Gly Leu Thr Thr Phe Lys
            20                  25                  30

Glu Leu Phe Gly Ser Val Tyr Gly Val Ser Pro Arg Ala Trp Ile Ser
        35                  40                  45

Glu Arg Arg Ile
    50

<210> SEQ ID NO 27
<211> LENGTH: 51
<212> TYPE: PRT
<213> ORGANISM: Escherichia coli

<400> SEQUENCE: 27

Glu Arg Ile Val Thr Leu Leu Phe Ser Asp Leu Thr Arg Lys Trp Lys
1               5                   10                  15

Leu Ser Asp Ile Ala Glu Glu Met His Ile Ser Glu Ile Ser Val Arg
            20                  25                  30

Lys Arg Leu Glu Gln Glu Cys Leu Asn Phe Asn Gln Leu Ile Leu Asp
        35                  40                  45

Val Arg Met
    50

<210> SEQ ID NO 28
<211> LENGTH: 52
<212> TYPE: PRT
<213> ORGANISM: Escherichia coli

<400> SEQUENCE: 28

Gln Lys Val Val Thr Leu Ile Asp Asp Asn Ile Arg Glu Glu Ile Leu
1               5                   10                  15

Arg Pro Glu Trp Ile Ala Gly Glu Thr Gly Met Ser Val Arg Ser Leu
            20                  25                  30

Tyr Arg Met Phe Ala Asp Lys Gly Leu Val Val Ala Gln Tyr Ile Arg
        35                  40                  45

Asn Arg Arg Leu
    50

<210> SEQ ID NO 29
<211> LENGTH: 51
<212> TYPE: PRT
<213> ORGANISM: Escherichia coli

<400> SEQUENCE: 29

Thr Arg Val Cys Thr Val Ile Asn Asn Asn Ile Ala His Glu Trp Thr
1               5                   10                  15

Leu Ala Arg Ile Ala Ser Glu Leu Leu Met Ser Pro Ser Leu Leu Lys
            20                  25                  30

Lys Lys Leu Arg Glu Glu Gly Thr Ser Tyr Ser Gln Leu Leu Thr Glu
        35                  40                  45

Cys Arg Met

<210> SEQ ID NO 30
<211> LENGTH: 51
<212> TYPE: PRT
<213> ORGANISM: Escherichia coli

<400> SEQUENCE: 30

Thr Arg Val Cys Thr Val Ile Asn Asn Asn Ile Ala His Glu Trp Thr
1               5                   10                  15

Leu Ala Arg Ile Ala Ser Glu Leu Leu Met Ser Pro Ser Leu Leu Lys
            20                  25                  30

Lys Lys Leu Arg Glu Glu Glu Thr Ser Tyr Ser Gln Leu Leu Thr Glu
        35                  40                  45

Cys Arg Met
    50

<210> SEQ ID NO 31
<211> LENGTH: 51
<212> TYPE: PRT
<213> ORGANISM: Escherichia coli

<400> SEQUENCE: 31

Thr Arg Val Cys Thr Val Ile Asn Asn Asn Ile Ala His Glu Trp Thr
1               5                   10                  15

Leu Ala Arg Ile Ala Ser Glu Leu Leu Met Ser Pro Ser Leu Leu Lys
            20                  25                  30

Lys Lys Leu Arg Glu Glu Glu Thr Ser Tyr Ser Gln Leu Leu Thr Glu
        35                  40                  45

Cys Arg Met
    50

<210> SEQ ID NO 32
<211> LENGTH: 52
<212> TYPE: PRT
<213> ORGANISM: Escherichia coli

<400> SEQUENCE: 32

Leu Ala Val Leu Glu Lys Met Glu Thr Ala Ile Glu Arg Pro Leu Asp
1               5                   10                  15

Arg Thr Ala Met Ala Arg Leu Ala Gly Val Ser Pro Arg His Leu Asp
            20                  25                  30

Arg Leu Phe Arg Glu His Arg Gly Thr Gly Phe Leu Asp Thr Tyr Arg
        35                  40                  45

Glu Ile Arg Leu
    50

<210> SEQ ID NO 33
<211> LENGTH: 53
<212> TYPE: PRT
<213> ORGANISM: Escherichia coli

<400> SEQUENCE: 33

Arg Arg Ala Tyr Arg Tyr Ile Ile Glu Asn Ile Glu Arg Ser Asp Leu
1               5                   10                  15

Thr Thr Arg Glu Val Ala Ala His Ile Asn Val Thr Glu Arg Ala Leu
            20                  25                  30

Gln Leu Ala Phe Lys Ser Ala Val Gly Met Ser Pro Ser Ser Val Ile
        35                  40                  45

Arg Arg Met Arg Leu

<210> SEQ ID NO 34
<211> LENGTH: 52
<212> TYPE: PRT
<213> ORGANISM: Escherichia coli

<400> SEQUENCE: 34

Tyr Trp Leu Val Gly Tyr Leu Ala Gln Ser Thr Ser Gly Asn Thr
1               5                   10                  15

Met Arg Met Leu Gly Glu Asp Tyr Gly Val Ser Tyr Thr His Phe Arg
            20                  25                  30

Arg Leu Cys Ser Arg Ala Leu Gly Gly Lys Ala Lys Ser Glu Leu Arg
        35                  40                  45

Asn Trp Arg Met
    50

<210> SEQ ID NO 35
<211> LENGTH: 52
<212> TYPE: PRT
<213> ORGANISM: Escherichia coli

<400> SEQUENCE: 35

Gln His Ala Val Asp Phe Ile Asn Thr Asn Tyr Gln Lys His Ile Thr
1               5                   10                  15

Val Glu Asp Val Ala Lys Ser Val Asn Ile Thr Arg Ser His Leu Tyr
            20                  25                  30

Lys Leu Phe Lys Lys Asn Leu Gly Cys Ser Pro Lys Glu Tyr Leu Thr
        35                  40                  45

Tyr Ile Arg Met
    50

<210> SEQ ID NO 36
<211> LENGTH: 52
<212> TYPE: PRT
<213> ORGANISM: Escherichia coli

<400> SEQUENCE: 36

Glu Arg Leu Gln Lys Phe Met Glu Asn Tyr Leu Gln Gly Trp Lys
1               5                   10                  15

Leu Ser Lys Phe Ala Arg Glu Phe Gly Met Gly Leu Thr Thr Phe Lys
            20                  25                  30

Glu Leu Phe Gly Thr Val Tyr Gly Ile Ser Pro Arg Ala Trp Ile Ser
        35                  40                  45

Glu Arg Arg Ile
    50

<210> SEQ ID NO 37
<211> LENGTH: 52
<212> TYPE: PRT
<213> ORGANISM: Escherichia coli

<400> SEQUENCE: 37

Val Leu Ile Asp Asn Tyr Ile Glu Gln His Leu Gln Lys Lys Ile Ser
1               5                   10                  15

Val Ala Glu Leu Ser Ser Val Ala Phe Leu Ala Gln Ser Gln Phe Tyr
            20                  25                  30

Ala Leu Phe Lys Ser Gln Met Gly Ile Thr Pro His Gln Tyr Val Leu
        35                  40                  45

Arg Lys Arg Leu

<210> SEQ ID NO 38
<211> LENGTH: 52
<212> TYPE: PRT
<213> ORGANISM: Escherichia coli

<400> SEQUENCE: 38

His Ser Ile Leu Asp Trp Ile Glu Asp Asn Leu Glu Ser Pro Leu Ser
1               5                   10                  15

Leu Glu Lys Val Ser Glu Arg Ser Gly Tyr Ser Lys Trp His Leu Gln
            20                  25                  30

Arg Met Phe Lys Lys Glu Thr Gly His Ser Leu Gly Gln Tyr Ile Arg
        35                  40                  45

Ser Arg Lys Met
    50

<210> SEQ ID NO 39
<211> LENGTH: 52
<212> TYPE: PRT
<213> ORGANISM: Escherichia coli

<400> SEQUENCE: 39

His Ser Ile Leu Asp Trp Ile Glu Asp Asn Leu Glu Ser Pro Leu Ser
1               5                   10                  15

Leu Glu Lys Val Ser Glu Arg Ser Gly Tyr Ser Lys Trp His Leu Gln
            20                  25                  30

Arg Met Phe Lys Lys Glu Thr Gly His Ser Leu Gly Gln Tyr Ile Arg
        35                  40                  45

Ser Arg Lys Met
    50

<210> SEQ ID NO 40
<211> LENGTH: 52
<212> TYPE: PRT
<213> ORGANISM: Escherichia coli

<400> SEQUENCE: 40

Ser Gln Met Leu Gly Phe Ile Ala Glu Asn Tyr Asp Gln Ala Leu Thr
1               5                   10                  15

Ile Asn Asp Val Ala Glu His Val Lys Leu Asn Ala Asn Tyr Ala Met
            20                  25                  30

Gly Ile Phe Gln Arg Val Met Gln Leu Thr Met Lys Gly Tyr Ile Thr
        35                  40                  45

Ala Met Arg Ile
    50

<210> SEQ ID NO 41
<211> LENGTH: 52
<212> TYPE: PRT
<213> ORGANISM: Escherichia coli

<400> SEQUENCE: 41

Asp Gly Leu His Ala Tyr Met Arg Glu His Leu His Ala Arg Leu Glu
1               5                   10                  15

Leu Glu Arg Leu Ala Ala Phe Cys Asn Leu Ser Lys Phe His Phe Val
            20                  25                  30

Ser Arg Tyr Lys Ala Ile Thr Gly Arg Thr Pro Ile Gln His Phe Leu
        35                  40                  45

His Leu Lys Ile

<210> SEQ ID NO 42
<211> LENGTH: 52
<212> TYPE: PRT
<213> ORGANISM: Escherichia coli

<400> SEQUENCE: 42

Asn Gln Val Lys Lys Ile Ile His Ser Gln Tyr Gly Ser Ser Leu Arg
1               5                   10                  15

Val Asn Asp Ile Ala Lys Lys Leu Asn Leu Ser Arg Ser Tyr Leu Tyr
            20                  25                  30

Lys Ile Phe Arg Lys Ser Thr Asn Leu Ser Ile Lys Glu Tyr Ile Leu
        35                  40                  45

Gln Val Arg Met
    50

<210> SEQ ID NO 43
<211> LENGTH: 54
<212> TYPE: PRT
<213> ORGANISM: Escherichia coli

<400> SEQUENCE: 43

Tyr His Leu Val Leu Tyr Leu Arg Thr Ile Glu Lys Glu Lys Glu
1               5                   10                  15

Val Arg Ile Lys Ser Leu Thr Glu His Tyr Gly Val Ser Glu Ala Tyr
            20                  25                  30

Phe Arg Ser Leu Cys Arg Lys Ala Leu Gly Ala Lys Val Lys Glu Gln
        35                  40                  45

Leu Asn Thr Trp Arg Leu
    50

<210> SEQ ID NO 44
<211> LENGTH: 54
<212> TYPE: PRT
<213> ORGANISM: Escherichia coli

<400> SEQUENCE: 44

Tyr His Leu Val Leu Tyr Leu Arg Thr Ile Glu Lys Glu Lys Glu
1               5                   10                  15

Val Arg Ile Lys Ser Leu Thr Glu His Tyr Gly Val Ser Glu Ala Tyr
            20                  25                  30

Phe Arg Ser Leu Cys Arg Lys Ala Leu Gly Ala Lys Val Lys Glu Gln
        35                  40                  45

Leu Asn Thr Trp Arg Leu
    50

<210> SEQ ID NO 45
<211> LENGTH: 51
<212> TYPE: PRT
<213> ORGANISM: Escherichia coli

<400> SEQUENCE: 45

Thr Arg Val Arg Arg Leu Leu Leu Ala Arg Pro Gly Asp Phe Pro Asp
1               5                   10                  15

Leu Glu Gln Ala Ala Arg Glu Leu His Thr Ser Gly Arg Ser Leu Arg
            20                  25                  30

Arg His Leu Ser Ser Leu Gly Thr Thr Tyr Gln Gln Val Leu Asp Asp
        35                  40                  45

Val Arg Lys

<210> SEQ ID NO 46
<211> LENGTH: 52
<212> TYPE: PRT
<213> ORGANISM: Escherichia coli

<400> SEQUENCE: 46

His Ala Ala Arg Asp Leu Leu Val Gly Ala Leu Gln Glu Pro Pro Ser
1               5                   10                  15

Leu Asp Thr Leu Ala Ser Arg Val Gly Met Asn Pro Arg Lys Leu Thr
            20                  25                  30

Ala Gly Phe Arg Lys Val Phe Gly Ala Ser Val Phe Gly Tyr Leu Gln
        35                  40                  45

Glu Tyr Arg Leu
    50

<210> SEQ ID NO 47
<211> LENGTH: 51
<212> TYPE: PRT
<213> ORGANISM: Escherichia coli

<400> SEQUENCE: 47

Asp Arg Val Ile Lys Val Ile Glu Leu Asp Ile Ser Lys Asn Trp Lys
1               5                   10                  15

Leu Gly Asp Val Ser Ser Ser Met Phe Met Ser Asp Ser Cys Leu Arg
            20                  25                  30

Lys Gln Leu Asn Lys Glu Asn Leu Thr Phe Lys Lys Ile Met Leu Asp
        35                  40                  45

Ile Lys Met
    50

<210> SEQ ID NO 48
<211> LENGTH: 52
<212> TYPE: PRT
<213> ORGANISM: Escherichia coli

<400> SEQUENCE: 48

Lys Lys Ala Leu Arg Tyr Ile Asp Ala His Leu Ser Asp Asp Leu Arg
1               5                   10                  15

Leu Glu Asp Val Ala Ser His Val Tyr Leu Ser Pro Tyr Tyr Phe Ser
            20                  25                  30

Lys Leu Phe Lys Lys Tyr Gln Gly Ile Gly Phe Asn Ala Trp Val Asn
        35                  40                  45

Arg Gln Arg Met
    50

<210> SEQ ID NO 49
<211> LENGTH: 54
<212> TYPE: PRT
<213> ORGANISM: Escherichia coli

<400> SEQUENCE: 49

Asn Asp Ile Leu Lys Trp Leu Glu Thr Gln Leu Gln Arg Asn Glu Gly
1               5                   10                  15

Ile Lys Ile Asp Thr Ile Ala Asn Lys Ser Gly Tyr Ser Lys Trp His
            20                  25                  30

Leu Gln Arg Ile Phe Lys Asp Phe Lys Gly Cys Thr Leu Gly Glu Tyr
        35                  40                  45

Val Arg Lys Arg Arg Leu

<210> SEQ ID NO 50
<211> LENGTH: 52
<212> TYPE: PRT
<213> ORGANISM: Escherichia coli

<400> SEQUENCE: 50

Asn Leu Ala Val Ser Tyr Leu Gln Glu Asn Tyr Ser Thr Gly Cys Thr
1               5                   10                  15

Ile Met Asp Leu Cys His Tyr Leu Asn Leu Ser Arg Ser Tyr Leu Tyr
            20                  25                  30

Thr Leu Phe Lys Thr His Ala Asn Thr Ser Pro Gln Lys Leu Leu Thr
        35                  40                  45

Lys Leu Arg Leu
    50

<210> SEQ ID NO 51
<211> LENGTH: 52
<212> TYPE: PRT
<213> ORGANISM: Escherichia coli

<400> SEQUENCE: 51

Asp Thr Ile Val Glu Trp Ile Asp Asn Leu His Gln Pro Leu Arg
1               5                   10                  15

Ile Glu Asp Ile Ala Arg His Ala Gly Tyr Ser Lys Trp His Leu Gln
            20                  25                  30

Arg Leu Phe Leu Gln Tyr Lys Gly Glu Ser Leu Gly Arg Tyr Ile Arg
        35                  40                  45

Glu Arg Lys Leu
    50

<210> SEQ ID NO 52
<211> LENGTH: 52
<212> TYPE: PRT
<213> ORGANISM: Escherichia coli

<400> SEQUENCE: 52

Asp Thr Ile Val Glu Trp Ile Asp Asp Asn Leu His Gln Pro Leu Arg
1               5                   10                  15

Ile Asp Asp Ile Ala Arg His Ala Gly Tyr Ser Lys Trp His Leu Gln
            20                  25                  30

Arg Leu Phe Leu Gln Tyr Lys Gly Glu Ser Leu Gly Arg Tyr Ile Arg
        35                  40                  45

Glu Arg Lys Leu
    50

<210> SEQ ID NO 53
<211> LENGTH: 52
<212> TYPE: PRT
<213> ORGANISM: Escherichia coli

<400> SEQUENCE: 53

Asp Lys Leu Ile Thr Arg Leu Ala Ala Ser Leu Lys Ser Pro Phe Ala
1               5                   10                  15

Leu Asp Lys Phe Cys Asp Glu Ala Ser Cys Ser Glu Arg Val Leu Arg
            20                  25                  30

Gln Gln Phe Arg Gln Gln Thr Gly Met Thr Ile Asn Gln Tyr Leu Arg
        35                  40                  45

Gln Val Arg Val

-continued

<210> SEQ ID NO 54
<211> LENGTH: 52
<212> TYPE: PRT
<213> ORGANISM: Escherichia coli

<400> SEQUENCE: 54

Asp Lys Leu Ile Thr Ala Leu Ala Asn Ser Leu Glu Cys Pro Phe Ala
1               5                   10                  15

Leu Asp Ala Phe Cys Gln Gln Glu Gln Cys Ser Glu Arg Val Leu Arg
            20                  25                  30

Gln Gln Phe Arg Ala Gln Thr Gly Met Thr Ile Asn Gln Tyr Leu Arg
        35                  40                  45

Gln Val Arg Ile
    50

<210> SEQ ID NO 55
<211> LENGTH: 52
<212> TYPE: PRT
<213> ORGANISM: Escherichia coli

<400> SEQUENCE: 55

Asn Leu Leu Leu Ala Trp Leu Glu Asp His Phe Ala Asp Glu Val Asn
1               5                   10                  15

Trp Asp Ala Val Ala Asp Gln Phe Ser Leu Ser Leu Arg Thr Leu His
            20                  25                  30

Arg Gln Leu Lys Gln Gln Thr Gly Leu Thr Pro Gln Arg Tyr Leu Asn
        35                  40                  45

Arg Leu Arg Leu
    50

<210> SEQ ID NO 56
<211> LENGTH: 52
<212> TYPE: PRT
<213> ORGANISM: Escherichia coli

<400> SEQUENCE: 56

Asn Gln Leu Met Ala Trp Leu Glu Asp His Phe Ala Glu Glu Val Cys
1               5                   10                  15

Trp Glu Ala Val Ala Glu Gln Phe Ser Leu Ser Leu Arg Thr Leu His
            20                  25                  30

Arg Gln Leu Lys Gln His Thr Gly Leu Thr Pro Gln Arg Tyr Leu Asn
        35                  40                  45

Arg Leu Arg Leu
    50

<210> SEQ ID NO 57
<211> LENGTH: 52
<212> TYPE: PRT
<213> ORGANISM: Escherichia coli

<400> SEQUENCE: 57

Ala Ser Ile Lys Met Arg Val Glu Gln Asn Leu Ala Asn Gly Ser Phe
1               5                   10                  15

Ser Ile Thr Asp Val Ala Glu Ala Glu Arg Ile Thr Pro Arg Ala Ile
            20                  25                  30

Gln Lys Phe Phe Ser Arg Glu Gly Thr Thr Phe Ser Arg Tyr Val Leu
        35                  40                  45

Gly Arg Arg Leu

<210> SEQ ID NO 58
<211> LENGTH: 51
<212> TYPE: PRT
<213> ORGANISM: Escherichia coli

<400> SEQUENCE: 58

Asp Lys Val Arg Asn Leu Ile Glu Lys Asp Leu Ser Arg Lys Trp Thr
1               5                   10                  15

Leu Gly Ile Ile Ala Asp Ala Phe Asn Ala Ser Glu Ile Thr Ile Arg
            20                  25                  30

Lys Arg Leu Glu Ser Glu Asn Thr Asn Phe Asn Gln Ile Leu Met Gln
        35                  40                  45

Leu Arg Met
    50

<210> SEQ ID NO 59
<211> LENGTH: 52
<212> TYPE: PRT
<213> ORGANISM: Escherichia coli

<400> SEQUENCE: 59

Arg Asp Leu Leu Ile Trp Leu Glu Gly His Leu Asp Gln Pro Leu Ser
1               5                   10                  15

Leu Asp Asn Val Ala Ala Lys Ala Gly Tyr Ser Lys Trp His Leu Gln
            20                  25                  30

Arg Met Phe Lys Asp Val Thr Gly His Ala Ile Gly Ala Tyr Ile Arg
        35                  40                  45

Ala Arg Arg Leu
    50

<210> SEQ ID NO 60
<211> LENGTH: 52
<212> TYPE: PRT
<213> ORGANISM: Escherichia coli

<400> SEQUENCE: 60

Gln Asp Leu Ile Ala Trp Ile Asp Glu His Ile Asp Gln Pro Leu Asn
1               5                   10                  15

Ile Asp Val Val Ala Lys Lys Ser Gly Tyr Ser Lys Trp Tyr Leu Gln
            20                  25                  30

Arg Met Phe Arg Thr Val Thr His Gln Thr Leu Gly Asp Tyr Ile Arg
        35                  40                  45

Gln Arg Arg Leu
    50

<210> SEQ ID NO 61
<211> LENGTH: 52
<212> TYPE: PRT
<213> ORGANISM: Escherichia coli

<400> SEQUENCE: 61

Gln Thr Leu Ile Glu Trp Ile Asp Glu His Ile Asp Gln Pro Leu Asn
1               5                   10                  15

Ile Asp Val Val Ala Lys Lys Ser Gly Tyr Ser Lys Trp Tyr Leu Gln
            20                  25                  30

Arg Met Phe Arg Thr Val Thr His Gln Thr Leu Gly Glu Tyr Ile Arg
        35                  40                  45

Gln Arg Arg Leu

-continued

<210> SEQ ID NO 62
<211> LENGTH: 51
<212> TYPE: PRT
<213> ORGANISM: Escherichia coli

<400> SEQUENCE: 62

Glu Lys Ile Ser Cys Leu Val Lys Ser Asp Ile Thr Arg Asn Trp Arg
1               5                   10                  15

Trp Ala Asp Ile Cys Gly Glu Leu Arg Thr Asn Arg Met Ile Leu Lys
            20                  25                  30

Lys Glu Leu Glu Ser Arg Gly Val Lys Phe Arg Glu Leu Ile Asn Ser
        35                  40                  45

Ile Arg Ile
    50

<210> SEQ ID NO 63
<211> LENGTH: 52
<212> TYPE: PRT
<213> ORGANISM: Escherichia coli

<400> SEQUENCE: 63

Lys Asp Val Leu Leu Trp Ile Glu His Asn Leu Asp Gln Ser Leu Leu
1               5                   10                  15

Leu Asp Asp Val Ala Asn Lys Ala Gly Tyr Thr Lys Trp Tyr Phe Gln
            20                  25                  30

Arg Leu Phe Lys Lys Val Thr Gly Val Thr Leu Ala Ser Tyr Ile Arg
        35                  40                  45

Ala Arg Arg Leu
    50

<210> SEQ ID NO 64
<211> LENGTH: 52
<212> TYPE: PRT
<213> ORGANISM: Escherichia coli

<400> SEQUENCE: 64

Arg Leu Ala Val Asp Tyr Leu Glu Ala His Ala Gln Gln Pro Leu Thr
1               5                   10                  15

Val Ala Gln Val Ala Arg Asn Val Gly Val Ser Val Arg Ser Leu Gln
            20                  25                  30

Val Gly Phe Gln Asn Ser Leu Gly Thr Thr Pro Met Arg Gln Leu Lys
        35                  40                  45

Ile Ile Arg Met
    50

<210> SEQ ID NO 65
<211> LENGTH: 51
<212> TYPE: PRT
<213> ORGANISM: Escherichia coli

<400> SEQUENCE: 65

Gln Ala Ile Thr His Leu Ile Thr Gln Glu Pro Gln Lys Lys Trp His
1               5                   10                  15

Leu Asp Asp Val Ala Lys Ala Leu Phe Thr Thr Pro Ser Thr Leu Arg
            20                  25                  30

Arg His Leu Asn Arg Glu Gly Val Ser Phe Arg Gln Leu Leu Leu Asp
        35                  40                  45

Val Arg Met

<210> SEQ ID NO 66
<211> LENGTH: 51
<212> TYPE: PRT
<213> ORGANISM: Escherichia coli

<400> SEQUENCE: 66

Gln Ala Ile Thr His Leu Ile Thr Gln Asp Pro Gln Arg Lys Trp His
1               5                   10                  15

Leu Glu Asp Val Ala Lys Thr Leu Tyr Thr Thr Pro Ser Thr Leu Arg
            20                  25                  30

Arg His Leu Ser Lys Glu Gly Val Ser Phe Cys Gln Leu Leu Leu Asp
        35                  40                  45

Val Arg Ile
    50

<210> SEQ ID NO 67
<211> LENGTH: 51
<212> TYPE: PRT
<213> ORGANISM: Escherichia coli

<400> SEQUENCE: 67

Asp Gln Ile Arg Lys Ile Val Glu Lys Asn Ile Glu Lys Arg Trp Arg
1               5                   10                  15

Leu Ser Asp Ile Ser Asn Asn Leu Asn Leu Ser Glu Ile Ala Val Arg
            20                  25                  30

Lys Arg Leu Glu Ser Gly Lys Leu Thr Phe Gln Gln Ile Leu Leu Asp
        35                  40                  45

Ile Arg Met
    50

<210> SEQ ID NO 68
<211> LENGTH: 52
<212> TYPE: PRT
<213> ORGANISM: Escherichia coli

<400> SEQUENCE: 68

Glu Arg Leu Gln Lys Phe Met Glu Glu Asn Tyr Leu Gln Gly Trp Lys
1               5                   10                  15

Leu Ser Lys Phe Ala Arg Glu Phe Gly Met Gly Leu Thr Thr Phe Lys
            20                  25                  30

Glu Leu Phe Gly Thr Val Tyr Gly Ile Ser Pro Arg Ala Trp Ile Ser
        35                  40                  45

Glu Arg Arg Ile
    50

<210> SEQ ID NO 69
<211> LENGTH: 52
<212> TYPE: PRT
<213> ORGANISM: Mycobacterium tuberculosis

<400> SEQUENCE: 69

Glu Arg Val Val Gly Leu Ala Arg Arg Leu Leu Pro Thr Gly Gln Cys
1               5                   10                  15

Ser Ala Glu Ala Ile Ala Asp Gln Leu Asp Met His Pro Arg Thr Leu
            20                  25                  30

Gln Arg Arg Leu Ala Ala Glu Gly Leu Arg Cys His Asp Leu Ile Glu
        35                  40                  45

Arg Glu Arg Arg

<210> SEQ ID NO 70
<211> LENGTH: 52
<212> TYPE: PRT
<213> ORGANISM: Escherichia coli

<400> SEQUENCE: 70

Ile Gln Ala Met His Tyr Ile Arg Asn His Ala Cys Lys Gly Ile Lys
1               5                   10                  15

Val Asp Gln Val Leu Asp Ala Val Gly Ile Ser Arg Ser Asn Leu Glu
            20                  25                  30

Lys Arg Phe Lys Glu Glu Val Gly Glu Thr Ile His Ala Met Ile His
        35                  40                  45

Ala Glu Lys Leu
    50

<210> SEQ ID NO 71
<211> LENGTH: 52
<212> TYPE: PRT
<213> ORGANISM: Escherichia coli

<400> SEQUENCE: 71

Ile Gln Ala Met His Tyr Ile Arg His Arg Ala Cys His Arg Ile Lys
1               5                   10                  15

Val Gly Gln Val Leu Asp His Leu Glu Thr Ser Arg Ser Asn Leu Glu
            20                  25                  30

Gln Arg Phe Lys Asn Glu Met Asn Lys Thr Ile His Gln Val Ile His
        35                  40                  45

Glu Glu Lys Ile
    50

<210> SEQ ID NO 72
<211> LENGTH: 52
<212> TYPE: PRT
<213> ORGANISM: Escherichia coli

<400> SEQUENCE: 72

Glu Arg Val Val Gln Phe Ile Glu Glu Asn Leu Lys Arg Asn Ile Ser
1               5                   10                  15

Leu Glu Arg Leu Ala Glu Leu Ala Met Met Ser Pro Arg Ser Leu Tyr
            20                  25                  30

Asn Leu Phe Glu Lys His Ala Gly Thr Thr Pro Lys Asn Tyr Ile Arg
        35                  40                  45

Asn Arg Lys Leu
    50

<210> SEQ ID NO 73
<211> LENGTH: 52
<212> TYPE: PRT
<213> ORGANISM: Escherichia coli

<400> SEQUENCE: 73

Glu Arg Val Val Gln Phe Ile Glu Glu Asn Leu Lys Arg Asn Ile Ser
1               5                   10                  15

Leu Glu Arg Leu Ala Glu Leu Ala Met Met Ser Pro Arg Ser Leu Tyr
            20                  25                  30

Asn Leu Phe Glu Lys His Ala Gly Thr Thr Pro Lys Asn Tyr Ile Arg
        35                  40                  45

Asn Arg Lys Leu

-continued

<210> SEQ ID NO 74
<211> LENGTH: 52
<212> TYPE: PRT
<213> ORGANISM: Escherichia coli

<400> SEQUENCE: 74

Glu Arg Val Val Gln Phe Ile Glu Glu Asn Val Lys Arg Ser Ile Ser
1               5                   10                  15

Leu Glu Gln Leu Ala Glu Leu Ala Leu Met Ser Pro Arg Ser Leu Tyr
            20                  25                  30

Thr Met Phe Glu Lys His Thr Gly Thr Thr Pro Met Asn Tyr Ile Arg
        35                  40                  45

Asn Arg Lys Leu
    50

<210> SEQ ID NO 75
<211> LENGTH: 52
<212> TYPE: PRT
<213> ORGANISM: Escherichia coli

<400> SEQUENCE: 75

Glu Arg Val Val Gln Phe Ile Glu Asp Asn Leu Lys Gln Ser Ile Ser
1               5                   10                  15

Leu Glu Arg Leu Ala Glu Leu Ala Leu Met Ser Pro Arg Ser Leu Tyr
            20                  25                  30

Thr Leu Phe Glu Lys His Ala Gly Thr Thr Pro Lys Asn Tyr Ile Arg
        35                  40                  45

Asn Arg Lys Leu
    50

<210> SEQ ID NO 76
<211> LENGTH: 52
<212> TYPE: PRT
<213> ORGANISM: Escherichia coli

<400> SEQUENCE: 76

Glu Arg Val Val Gln Phe Ile Glu Glu Asn Leu Lys Arg Asn Ile Ser
1               5                   10                  15

Leu Glu Arg Leu Ala Glu Leu Ala Leu Met Ser Pro Arg Ser Leu Tyr
            20                  25                  30

Thr Leu Phe Glu Lys His Ala Gly Thr Thr Pro Lys Asn Tyr Ile Arg
        35                  40                  45

Asn Arg Lys Leu
    50

<210> SEQ ID NO 77
<211> LENGTH: 52
<212> TYPE: PRT
<213> ORGANISM: Escherichia coli

<400> SEQUENCE: 77

Leu Lys Ala Glu Ala Phe Met Arg Glu Asn Leu Thr Asn Pro Val Thr
1               5                   10                  15

Ile Glu Asp Leu Ala Ala Ala Arg Cys Thr Pro Arg Ala Leu Gln
            20                  25                  30

Arg Met Phe Arg Thr Tyr Arg Gly Gly Ser Pro Met Ser Val Leu Cys
        35                  40                  45

Asn Tyr Arg Leu

<210> SEQ ID NO 78
<211> LENGTH: 55
<212> TYPE: PRT
<213> ORGANISM: Escherichia coli

<400> SEQUENCE: 78

Lys Arg Leu Asn Thr Ala Leu Ile Ala Ile Leu Gln Gln Pro Gln Asn
1               5                   10                  15

Asp Trp His Ile Glu Gln Leu Ala Glu Leu Ala Thr Met Ser Arg Ala
            20                  25                  30

Asn Phe Ile Arg Ile Phe Gln Gln His Ile Gly Met Ser Pro Gly Arg
        35                  40                  45

Phe Leu Thr Lys Val Arg Leu
    50                  55

<210> SEQ ID NO 79
<211> LENGTH: 52
<212> TYPE: PRT
<213> ORGANISM: Escherichia coli

<400> SEQUENCE: 79

Glu Lys Thr Lys His Tyr Ile Glu Thr His Ala Asp Thr Lys Ile Thr
1               5                   10                  15

Leu Ala Gln Leu Ser Gln Met Ala Gly Ile Ser Ala Lys His Tyr Ser
            20                  25                  30

Glu Ser Phe Lys Lys Trp Thr Gly Gln Ser Val Thr Glu Phe Ile Thr
        35                  40                  45

Lys Thr Arg Ile
    50

<210> SEQ ID NO 80
<211> LENGTH: 51
<212> TYPE: PRT
<213> ORGANISM: Escherichia coli

<400> SEQUENCE: 80

Ser Arg Cys Tyr Asn Leu Leu Ser Glu Pro Gly Thr Lys Trp Thr
1               5                   10                  15

Ala Asn Lys Val Ala Arg Tyr Leu Tyr Ile Ser Val Ser Thr Leu His
            20                  25                  30

Arg Arg Leu Ala Ser Glu Gly Val Ser Phe Gln Ser Ile Leu Asp Asp
        35                  40                  45

Val Arg Leu
    50

<210> SEQ ID NO 81
<211> LENGTH: 52
<212> TYPE: PRT
<213> ORGANISM: Escherichia coli

<400> SEQUENCE: 81

Gln Asn Ala Met Leu Tyr Ile Glu Asn Asn Tyr Phe Asn Asp Ile Asn
1               5                   10                  15

Ile Asp Thr Val Ala Phe Ser Val Gly Val Ser Arg Ser Tyr Leu Val
            20                  25                  30

Lys Gln Phe Lys Leu Ala Thr Asn Lys Thr Ile Asn Asn Arg Ile Ile
        35                  40                  45

Glu Val Arg Ile

<210> SEQ ID NO 82
<211> LENGTH: 55
<212> TYPE: PRT
<213> ORGANISM: Mycobacterium tuberculosis

<400> SEQUENCE: 82

Arg Gly Ile Thr Ala Leu Val Arg Ser Lys Leu Phe Arg Asp Ser Gly
1               5                   10                  15

Leu Phe Pro Thr Phe Thr Asp Val Ala Gly Glu Leu Asp Met His Pro
            20                  25                  30

Arg Thr Leu Arg Arg Leu Ala Glu Glu Gly Thr Ser Phe Arg Ala
        35                  40                  45

Leu Leu Gly Glu Ala Arg Ser
    50                  55

<210> SEQ ID NO 83
<211> LENGTH: 51
<212> TYPE: PRT
<213> ORGANISM: Escherichia coli

<400> SEQUENCE: 83

Gly Lys Val Arg Asn Ile Val Asn Met Lys Pro Ala His Pro Trp Lys
1               5                   10                  15

Leu Lys Asp Ile Cys Asp Cys Leu Tyr Ile Ser Glu Ser Leu Leu Lys
            20                  25                  30

Lys Lys Leu Lys Gln Glu Gln Thr Thr Phe Ser Gln Ile Leu Leu Asp
        35                  40                  45

Ala Arg Met
    50

<210> SEQ ID NO 84
<211> LENGTH: 52
<212> TYPE: PRT
<213> ORGANISM: Escherichia coli

<400> SEQUENCE: 84

Lys Asp Ile Leu Phe Tyr Leu Asn Asn Asn Tyr Arg Glu Lys Ile Thr
1               5                   10                  15

Leu Glu Gln Leu Ser Lys Lys Phe Arg Ala Ser Val Ser Tyr Ile Cys
            20                  25                  30

His Glu Phe Thr Lys Glu Tyr Arg Ile Ser Pro Ile Asn Tyr Val Ile
        35                  40                  45

Gln Arg Arg Met
    50

<210> SEQ ID NO 85
<211> LENGTH: 55
<212> TYPE: PRT
<213> ORGANISM: Escherichia coli

<400> SEQUENCE: 85

Pro Lys Ile Arg Thr Met Val Glu Met Met Ala Lys Gly Pro Val Glu
1               5                   10                  15

Trp Gly Ala Leu Gly Gln Trp Ala Gly Phe Phe Ala Met Ser Glu Arg
            20                  25                  30

Asn Leu Ala Arg Leu Ile Val Lys Glu Thr Gly Leu Ser Phe Arg Gln
        35                  40                  45

Trp Arg Gln Gln Leu Gln Leu

```
                50                  55

<210> SEQ ID NO 86
<211> LENGTH: 52
<212> TYPE: PRT
<213> ORGANISM: Escherichia coli

<400> SEQUENCE: 86

Thr Glu Val Lys Leu His Ile Lys Asp Asn Leu Ser Gln Pro Leu Lys
1               5                   10                  15

Leu Thr Asp Val Ala Ser His Phe His Ile Ser Gly Arg His Leu Ser
            20                  25                  30

Arg Leu Phe Ala Ala Glu Leu Gly Val Ser Tyr Ser Glu Phe Val Gln
        35                  40                  45

Asn Glu Lys Ile
    50

<210> SEQ ID NO 87
<211> LENGTH: 51
<212> TYPE: PRT
<213> ORGANISM: Escherichia coli

<400> SEQUENCE: 87

Gly Lys Val Glu Arg Leu Ile Ser Phe Asp Ile Ala Lys Arg Trp Tyr
1               5                   10                  15

Leu Arg Asp Ile Ala Glu Arg Met Tyr Thr Ser Glu Ser Leu Ile Lys
            20                  25                  30

Lys Lys Leu Gln Asp Glu Asn Thr Cys Phe Ser Lys Ile Leu Leu Ala
        35                  40                  45

Ser Arg Met
    50

<210> SEQ ID NO 88
<211> LENGTH: 52
<212> TYPE: PRT
<213> ORGANISM: Escherichia coli

<400> SEQUENCE: 88

Glu Lys Leu Ile Ala Thr Leu His Ala Ser Leu Gln Gln Arg Trp Ser
1               5                   10                  15

Val Ala Asp Met Ala Ala Thr Ile Pro Cys Ser Glu Ala Trp Leu Arg
            20                  25                  30

Arg Leu Phe Leu Arg Tyr Thr Gly Lys Thr Pro Lys Glu Tyr Tyr Leu
        35                  40                  45

Asp Ala Arg Leu
    50

<210> SEQ ID NO 89
<211> LENGTH: 52
<212> TYPE: PRT
<213> ORGANISM: Escherichia coli

<400> SEQUENCE: 89

Glu Ala Ile Arg Asp Tyr Ile Asp Glu Arg Tyr Ala Ser Ala Leu Thr
1               5                   10                  15

Arg Glu Ser Val Ala Gln Ala Phe Tyr Ile Ser Pro Asn Tyr Leu Ser
            20                  25                  30

His Leu Phe Gln Lys Thr Gly Ala Ile Gly Phe Asn Glu Tyr Leu Asn
        35                  40                  45

His Thr Arg Leu
```

-continued

<210> SEQ ID NO 90
<211> LENGTH: 52
<212> TYPE: PRT
<213> ORGANISM: Escherichia coli

<400> SEQUENCE: 90

Trp Glu Ala Ala Arg Tyr Leu Gln Glu His Tyr Lys Glu Lys Thr Thr
1               5                   10                  15

Ile Lys Asp Leu Ser Leu Ala Leu His Tyr His Gln Asp Tyr Val Ser
            20                  25                  30

Arg Cys Met Gln Gln Val Leu Gly Val Thr Pro Ala Gln Tyr Thr Asn
        35                  40                  45

Arg Val Arg Met
    50

<210> SEQ ID NO 91
<211> LENGTH: 52
<212> TYPE: PRT
<213> ORGANISM: Escherichia coli

<400> SEQUENCE: 91

Gln Gln Leu Leu Glu Trp Ile Glu Cys Asn Leu Glu His Pro Ile Ser
1               5                   10                  15

Ile Glu Asp Ile Ala Gln Lys Ser Gly Tyr Ser Arg Arg Asn Ile Gln
            20                  25                  30

Leu Leu Phe Arg Asn Phe Met His Val Pro Leu Gly Glu Tyr Ile Arg
        35                  40                  45

Lys Arg Arg Leu
    50

<210> SEQ ID NO 92
<211> LENGTH: 55
<212> TYPE: PRT
<213> ORGANISM: Escherichia coli

<400> SEQUENCE: 92

Pro Arg Leu Gly Ala Val Ile Gln Gln Met Leu Glu Met Pro Gly His
1               5                   10                  15

Ala Trp Thr Val Glu Ser Leu Ala Ser Ile Ala His Met Ser Arg Ala
            20                  25                  30

Ser Phe Ala Gln Leu Phe Arg Asp Val Ser Gly Thr Thr Pro Leu Ala
        35                  40                  45

Val Leu Thr Lys Leu Arg Leu
    50              55

<210> SEQ ID NO 93
<211> LENGTH: 52
<212> TYPE: PRT
<213> ORGANISM: Escherichia coli

<400> SEQUENCE: 93

Asp Pro Leu Leu Arg Ala Val Val Ser Leu Glu Ala Gly Arg Ser
1               5                   10                  15

Val Thr Ala Thr Ala Asp Ser Val Gly Leu Gly Ala Arg Gln Leu His
            20                  25                  30

Arg Arg Ser Leu Ala Ala Phe Gly Tyr Gly Pro Lys Thr Leu Ala Arg
        35                  40                  45

Val Leu Arg Met

-continued

<210> SEQ ID NO 94
<211> LENGTH: 52
<212> TYPE: PRT
<213> ORGANISM: Escherichia coli

<400> SEQUENCE: 94

His Ser Ile Cys Asn Trp Val Gln Asp Asn Tyr Ala Gln Pro Leu Thr
1               5                   10                  15

Arg Glu Ser Val Ala Gln Phe Phe Asn Ile Thr Pro Asn His Leu Ser
            20                  25                  30

Lys Leu Phe Ala Gln His Gly Thr Met Arg Phe Ile Glu Tyr Val Arg
        35                  40                  45

Trp Val Arg Met
    50

<210> SEQ ID NO 95
<211> LENGTH: 52
<212> TYPE: PRT
<213> ORGANISM: Escherichia coli

<400> SEQUENCE: 95

Ser Arg Val Leu Lys Arg Ile Glu Asn Lys Tyr Thr Glu Asn Leu Ser
1               5                   10                  15

Val Glu Gln Leu Ala Ala Glu Ala Asn Met Ser Val Ser Ala Phe His
            20                  25                  30

His Asn Phe Lys Ser Val Thr Ser Thr Ser Pro Leu Gln Tyr Leu Lys
        35                  40                  45

Asn Tyr Arg Leu
    50

<210> SEQ ID NO 96
<211> LENGTH: 47
<212> TYPE: PRT
<213> ORGANISM: Providencia Stuartii

<400> SEQUENCE: 96

Cys Glu Ala Ala Lys Glu Leu Gln Thr Thr Asn Leu Gln Val Ile Asp
1               5                   10                  15

Ile Ala Leu Lys Tyr Gln Phe Asp Ser Gln Gln Ser Phe Ala Lys Arg
            20                  25                  30

Phe Lys Ala Tyr Leu Gly Ile Ser Pro Ser Leu Tyr Arg Leu Ser
        35                  40                  45

<210> SEQ ID NO 97
<211> LENGTH: 46
<212> TYPE: PRT
<213> ORGANISM: Escherichia coli

<400> SEQUENCE: 97

Arg Arg Leu Arg Glu Ser Leu Ala Lys Gly Glu Ser Val Thr Thr Ser
1               5                   10                  15

Ile Leu Asn Ala Gly Phe Pro Asp Ser Ser Ser Tyr Tyr Arg Lys Ala
            20                  25                  30

Asp Glu Thr Leu Gly Met Thr Ala Lys Gln Phe Arg His Gly
        35                  40                  45

<210> SEQ ID NO 98
<211> LENGTH: 47
<212> TYPE: PRT

<213> ORGANISM: Mycobacterium tuberculosis

<400> SEQUENCE: 98

```
Gln Thr Ala Arg Val Leu Ile Glu Thr Thr Asn Leu Pro Phe Gly Asp
 1               5                  10                  15

Val Ala Phe Ala Ala Gly Phe Ser Ser Ile Arg Gln Phe Asn Asp Thr
            20                  25                  30

Val Arg Leu Ala Cys Asp Gly Thr Pro Thr Ala Leu Arg Ala Arg
        35                  40                  45
```

<210> SEQ ID NO 99
<211> LENGTH: 46
<212> TYPE: PRT
<213> ORGANISM: Escherichia coli

<400> SEQUENCE: 99

```
Arg Arg Leu Arg Glu Ala Leu Ala Lys Gly Glu Pro Ile Thr Ala Ala
 1               5                  10                  15

Ile Tyr Arg Ala Gly Phe Pro Asp Ser Ser Ser Tyr Tyr Arg His Ala
            20                  25                  30

Asp Gln Thr Leu Gly Met Thr Ala Lys Gln Phe Arg Lys Gly
        35                  40                  45
```

<210> SEQ ID NO 100
<211> LENGTH: 47
<212> TYPE: PRT
<213> ORGANISM: Escherichia coli

<400> SEQUENCE: 100

```
His Ala Ala Lys Lys Tyr Leu Ile Gln Thr Asn Lys Ala Ile Gly Asp
 1               5                  10                  15

Ile Ala Ile Cys Val Gly Ile Ala Asn Ala Pro Tyr Phe Ile Thr Leu
            20                  25                  30

Phe Lys Lys Lys Thr Gly Gln Thr Pro Ala Arg Phe Arg Gln Met
        35                  40                  45
```

<210> SEQ ID NO 101
<211> LENGTH: 47
<212> TYPE: PRT
<213> ORGANISM: Escherichia coli

<400> SEQUENCE: 101

```
Arg Tyr Ala Val Asn Glu Leu Met Met Asp Gly Lys Asn Ile Ser Gln
 1               5                  10                  15

Val Ser Gln Ser Cys Gly Tyr Asn Ser Thr Ser Tyr Phe Ile Ser Val
            20                  25                  30

Phe Lys Asp Phe Tyr Gly Met Thr Pro Leu His Tyr Val Ser Gln
        35                  40                  45
```

<210> SEQ ID NO 102
<211> LENGTH: 47
<212> TYPE: PRT
<213> ORGANISM: Escherichia coli

<400> SEQUENCE: 102

```
Ser Lys Ala Ala Leu Leu Leu Leu Asp Asn Ser Tyr Gln Ile Ser Gln
 1               5                  10                  15

Ile Ser Asn Met Ile Gly Phe Ser Ser Thr Ser Tyr Phe Ile Arg Leu
            20                  25                  30

Phe Val Lys His Phe Gly Ile Thr Pro Lys Gln Phe Leu Thr Tyr
        35                  40                  45
```

<210> SEQ ID NO 103
<211> LENGTH: 47
<212> TYPE: PRT
<213> ORGANISM: Escherichia coli

<400> SEQUENCE: 103

Arg Tyr Ala Lys Lys Leu Ile Thr Ser Asn Ser Tyr Ser Ile Asn Val
1               5                   10                  15

Val Ala Gln Lys Cys Gly Tyr Asn Ser Thr Ser Tyr Phe Ile Cys Ala
            20                  25                  30

Phe Lys Asp Tyr Tyr Gly Val Thr Pro Ser His Tyr Phe Glu Lys
        35                  40                  45

<210> SEQ ID NO 104
<211> LENGTH: 47
<212> TYPE: PRT
<213> ORGANISM: Escherichia coli

<400> SEQUENCE: 104

Ser Gln Ala Lys Leu Leu Leu Ser Thr Thr Arg Met Pro Ile Ala Thr
1               5                   10                  15

Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
        35                  40                  45

<210> SEQ ID NO 105
<211> LENGTH: 47
<212> TYPE: PRT
<213> ORGANISM: Escherichia coli

<400> SEQUENCE: 105

Ser Gln Ala Lys Leu Leu Leu Ser Thr Thr Arg Met Pro Ile Ala Thr
1               5                   10                  15

Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
        35                  40                  45

<210> SEQ ID NO 106
<211> LENGTH: 47
<212> TYPE: PRT
<213> ORGANISM: Escherichia coli

<400> SEQUENCE: 106

Ile Arg Ala Lys Leu Leu Leu Gln Thr Thr Gln Glu Ser Ile Ala Asn
1               5                   10                  15

Ile Gly Arg Val Val Gly Tyr Asp Asp Gln Leu Tyr Phe Ser Arg Val
            20                  25                  30

Phe Arg Lys Arg Val Gly Val Ser Pro Ser Asp Phe Arg Arg Arg
        35                  40                  45

<210> SEQ ID NO 107
<211> LENGTH: 47
<212> TYPE: PRT
<213> ORGANISM: Escherichia coli

<400> SEQUENCE: 107

Ser Gln Ala Lys Leu Leu Leu Ser Thr Thr Arg Met Pro Ile Ala Thr
1               5                   10                  15

```
Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
            35                  40                  45
```

<210> SEQ ID NO 108
<211> LENGTH: 47
<212> TYPE: PRT
<213> ORGANISM: Escherichia coli

<400> SEQUENCE: 108

```
Glu Leu Thr Ala Arg Gln Leu Arg Glu Gly Ser Ala Pro Leu Ala Ala
1               5                   10                  15

Ile Ala His Ser Val Gly Tyr Gly Ser Glu Ser Ala Leu Ser Val Ala
            20                  25                  30

Phe Lys Arg Val Leu Gly Met Asn Pro Gly Asp Tyr Arg Lys His
            35                  40                  45
```

<210> SEQ ID NO 109
<211> LENGTH: 47
<212> TYPE: PRT
<213> ORGANISM: Escherichia coli

<400> SEQUENCE: 109

```
Glu Leu Ala Ala Arg Gln Leu Arg Glu Gly Asn Ala Thr Leu Ala Ser
1               5                   10                  15

Ile Ala His Ser Val Gly Tyr Gly Ser Glu Ser Ala Leu Ser Val Ala
            20                  25                  30

Phe Lys Arg Val Leu Gly Met Pro Pro Gly Asp Tyr Arg Lys His
            35                  40                  45
```

<210> SEQ ID NO 110
<211> LENGTH: 47
<212> TYPE: PRT
<213> ORGANISM: Escherichia coli

<400> SEQUENCE: 110

```
Ser Arg Ala Ala Ala Leu Leu Arg Leu Thr Arg Leu Thr Ile Ile Glu
1               5                   10                  15

Ile Ser Ala Lys Leu Phe Tyr Asp Ser Gln Gln Thr Phe Thr Arg Glu
            20                  25                  30

Phe Lys Lys Ile Phe Gly Tyr Thr Pro Arg Gln Tyr Arg Met Ile
            35                  40                  45
```

<210> SEQ ID NO 111
<211> LENGTH: 47
<212> TYPE: PRT
<213> ORGANISM: Escherichia coli

<400> SEQUENCE: 111

```
Asn Phe Ala Lys Lys Gln Leu Glu Met Thr Asn Tyr Ser Val Thr Asp
1               5                   10                  15

Ile Ala Phe Glu Ala Gly Tyr Ser Ser Pro Ser Leu Phe Ile Lys Thr
            20                  25                  30

Phe Lys Lys Leu Thr Ser Phe Thr Pro Lys Ser Tyr Arg Lys Lys
            35                  40                  45
```

<210> SEQ ID NO 112
<211> LENGTH: 47
<212> TYPE: PRT
<213> ORGANISM: Escherichia coli

<400> SEQUENCE: 112

Ser Lys Ala Ala Leu Leu Leu Glu Asn Ser Tyr Gln Ile Ser Gln
1               5                   10                  15

Ile Ser Asn Met Ile Gly Ile Ser Ser Ala Ser Tyr Phe Ile Arg Val
            20                  25                  30

Phe Asn Lys His Tyr Gly Val Thr Pro Lys Gln Phe Phe Thr Tyr
        35                  40                  45

<210> SEQ ID NO 113
<211> LENGTH: 47
<212> TYPE: PRT
<213> ORGANISM: Escherichia coli

<400> SEQUENCE: 113

Ser Lys Ala Ala Leu Leu Leu Glu Asn Ser Tyr Gln Ile Ser Gln
1               5                   10                  15

Ile Ser Asn Met Ile Gly Ile Ser Ser Ala Ser Tyr Phe Ile Arg Ile
            20                  25                  30

Phe Asn Lys His Phe Gly Val Thr Arg Ser Ser Phe Leu Ile Ile
        35                  40                  45

<210> SEQ ID NO 114
<211> LENGTH: 47
<212> TYPE: PRT
<213> ORGANISM: Escherichia coli

<400> SEQUENCE: 114

Arg Tyr Ala Val Gln Met Leu Leu Met Asp Asn Lys Asn Ile Thr Gln
1               5                   10                  15

Val Ala Gln Leu Cys Gly Tyr Ser Ser Thr Ser Tyr Phe Ile Ser Val
            20                  25                  30

Phe Lys Ala Phe Tyr Gly Leu Thr Pro Leu Asn Tyr Leu Ala Lys
        35                  40                  45

<210> SEQ ID NO 115
<211> LENGTH: 50
<212> TYPE: PRT
<213> ORGANISM: Escherichia coli

<400> SEQUENCE: 115

Asn Ala Val Arg Arg Glu Leu Ile Ser Pro Trp Ser Gln Ser Met Thr
1               5                   10                  15

Val Lys Asp Ala Ala Met Gln Trp Gly Phe Trp His Leu Gly Gln Phe
            20                  25                  30

Ala Thr Asp Tyr Gln Gln Leu Phe Ser Glu Lys Pro Ser Leu Thr Leu
        35                  40                  45

His Gln
    50

<210> SEQ ID NO 116
<211> LENGTH: 50
<212> TYPE: PRT
<213> ORGANISM: Escherichia coli

<400> SEQUENCE: 116

Asn Ala Val Arg Arg Glu Leu Ile Ser Pro Trp Ser Gln Ser Ala Thr
1               5                   10                  15

Val Lys Asp Ala Ala Met Gln Trp Gly Phe Trp His Leu Gly Gln Phe
            20                  25                  30

Ala Thr Asp Tyr Gln Gln Leu Phe Ala Glu Lys Pro Ser Leu Thr Leu

His Gln
    50

<210> SEQ ID NO 117
<211> LENGTH: 47
<212> TYPE: PRT
<213> ORGANISM: Escherichia coli

<400> SEQUENCE: 117

Leu Tyr Ala His Gln Leu Leu Asn Ser Asp Met Ser Ile Val Asp
1               5                   10                  15

Ile Ala Met Glu Ala Gly Phe Ser Ser Gln Ser Tyr Phe Thr Gln Ser
                20                  25                  30

Tyr Arg Arg Arg Phe Gly Cys Thr Pro Ser Arg Ser Arg Gln Gly
        35                  40                  45

<210> SEQ ID NO 118
<211> LENGTH: 47
<212> TYPE: PRT
<213> ORGANISM: Escherichia coli

<400> SEQUENCE: 118

Asn Gln Ala Ala Lys Phe Ile Ile Arg Ser Asp His Gln Ile Gly Met
1               5                   10                  15

Ile Ala Ser Leu Val Gly Tyr Thr Ser Val Ser Tyr Phe Ile Lys Thr
                20                  25                  30

Phe Lys Glu Tyr Tyr Gly Val Thr Pro Lys Lys Phe Glu Ile Gly
        35                  40                  45

<210> SEQ ID NO 119
<211> LENGTH: 49
<212> TYPE: PRT
<213> ORGANISM: Escherichia coli

<400> SEQUENCE: 119

Asp Phe Cys Ala Asp Ala Ile Arg His Ala Ala Asp Asp Glu Lys Leu
1               5                   10                  15

Ala Gly Ile Gly Phe His Trp Gly Phe Ser Asp Gln Ser His Phe Ser
                20                  25                  30

Thr Val Phe Lys Gln Arg Phe Gly Met Thr Pro Gly Tyr Arg Arg
        35                  40                  45

Lys

<210> SEQ ID NO 120
<211> LENGTH: 47
<212> TYPE: PRT
<213> ORGANISM: Escherichia coli

<400> SEQUENCE: 120

Gln Arg Ala Leu Gln Leu Ile Val Ile Tyr Gly Val Ser Ile Lys Arg
1               5                   10                  15

Val Ala Val Ser Cys Gly Tyr His Ser Val Ser Tyr Phe Ile Tyr Val
                20                  25                  30

Phe Arg Asn Tyr Tyr Gly Met Thr Pro Thr Glu Tyr Gln Glu Arg
        35                  40                  45

<210> SEQ ID NO 121
<211> LENGTH: 47
<212> TYPE: PRT
<213> ORGANISM: Escherichia coli

<400> SEQUENCE: 121

Gln Arg Ala Leu Gln Leu Ile Val Ile His Gly Phe Ser Ile Lys Arg
1               5                   10                  15
Val Ala Val Ser Cys Gly Tyr His Ser Val Ser Tyr Phe Ile Tyr Val
                20                  25                  30
Phe Arg Asn Tyr Tyr Gly Met Thr Pro Thr Glu Tyr Gln Glu Arg
            35                  40                  45

<210> SEQ ID NO 122
<211> LENGTH: 47
<212> TYPE: PRT
<213> ORGANISM: Escherichia coli

<400> SEQUENCE: 122

Gln Arg Ala Leu Gln Leu Ile Val Ile His Gly Phe Ser Ile Lys Arg
1               5                   10                  15
Val Ala Val Ser Cys Gly Tyr His Ser Val Ser Tyr Phe Ile Tyr Val
                20                  25                  30
Phe Arg Asn Tyr Tyr Gly Met Thr Pro Thr Glu Tyr Gln Glu Arg
            35                  40                  45

<210> SEQ ID NO 123
<211> LENGTH: 47
<212> TYPE: PRT
<213> ORGANISM: Escherichia coli

<400> SEQUENCE: 123

Arg His Ala Arg Arg Leu Leu Gln Gln Ser Pro Leu Ser Ile Pro Glu
1               5                   10                  15
Ile Ala Tyr Ala Thr Gly Phe Ser Ser Pro Ala His Phe Ser Asn Ala
                20                  25                  30
Phe Lys Arg Leu Phe Ser Gln Thr Pro Gly Ser Leu Arg Arg Arg
            35                  40                  45

<210> SEQ ID NO 124
<211> LENGTH: 50
<212> TYPE: PRT
<213> ORGANISM: Escherichia coli

<400> SEQUENCE: 124

Glu Gly Ile Arg Ser Asp Leu Leu Asp Ser Glu Arg Asn Pro Ser Asn
1               5                   10                  15
Ile Ile Asp Thr Ala Ser Arg Trp Gly Ile Arg Ser Arg Ser Ala Leu
                20                  25                  30
Val Lys Gly Tyr Arg Lys Gln Phe Asn Glu Ala Pro Ser Glu Thr Ile
            35                  40                  45
Trp Arg
    50

<210> SEQ ID NO 125
<211> LENGTH: 47
<212> TYPE: PRT
<213> ORGANISM: Escherichia coli

<400> SEQUENCE: 125

Ala Gln Ser Leu Leu Asn Ser Val Glu Gly His Glu Asn Ile Thr Gln
1               5                   10                  15
Leu Ala Val Asn His Gly Tyr Ser Ser Pro Ser His Phe Ser Ser Glu
                20                  25                  30

```
Ile Lys Glu Leu Ile Gly Val Ser Pro Arg Lys Leu Ser Asn Ile
        35                  40                  45
```

<210> SEQ ID NO 126
<211> LENGTH: 47
<212> TYPE: PRT
<213> ORGANISM: Escherichia coli

<400> SEQUENCE: 126

```
Tyr His Ala Ser Gln Leu Leu Ile His Thr Ser Thr Leu Ile Ser Asp
 1               5                   10                  15

Ile Ser Arg Gln Val Gly Tyr Lys Asp Pro Leu Leu Phe Ser Lys Asn
            20                  25                  30

Phe Thr Lys His Phe Glu Ile Ser Ala Ser Glu Tyr Arg His His
        35                  40                  45
```

<210> SEQ ID NO 127
<211> LENGTH: 47
<212> TYPE: PRT
<213> ORGANISM: Escherichia coli

<400> SEQUENCE: 127

```
Leu Tyr Ala His Gln Leu Leu Leu Asn Gly Lys Met Ser Ile Val Asp
 1               5                   10                  15

Ile Ala Met Glu Ala Gly Phe Ser Ser Gln Ser Tyr Phe Thr Gln Ser
            20                  25                  30

Tyr Arg Arg Arg Phe Gly Cys Thr Pro Ser Gln Ala Arg Leu Thr
        35                  40                  45
```

<210> SEQ ID NO 128
<211> LENGTH: 47
<212> TYPE: PRT
<213> ORGANISM: Escherichia coli

<400> SEQUENCE: 128

```
Asp Leu Ala Lys Gln Leu Ile Ala Glu Arg Gln Lys Pro Leu Ser Gln
 1               5                   10                  15

Val Ala Gln Leu Cys Gly Phe Ser Ser Gln Ser Ser Phe Ser Gln Ala
            20                  25                  30

Phe Arg Arg Leu Tyr Gly Met Ser Pro Thr Arg Tyr Gln Phe Phe
        35                  40                  45
```

<210> SEQ ID NO 129
<211> LENGTH: 47
<212> TYPE: PRT
<213> ORGANISM: Escherichia coli

<400> SEQUENCE: 129

```
Thr Glu Ile Ala Gln Lys Leu Lys Glu Ser Asn Glu Pro Ile Leu Tyr
 1               5                   10                  15

Leu Ala Glu Arg Tyr Gly Phe Asp Ser Gln Gln Thr Leu Thr Arg Thr
            20                  25                  30

Phe Lys Asn Tyr Phe Asp Val Pro Pro His Lys Tyr Arg Met Thr
        35                  40                  45
```

<210> SEQ ID NO 130
<211> LENGTH: 47
<212> TYPE: PRT
<213> ORGANISM: Escherichia coli

<400> SEQUENCE: 130

```
Thr Glu Ile Ala Gln Lys Leu Lys Glu Ser Asn Glu Pro Ile Leu Tyr
```

```
                1               5                  10                 15
Leu Ala Glu Arg Tyr Gly Phe Glu Ser Gln Gln Thr Leu Thr Arg Thr
                20                 25                 30

Phe Lys Asn Tyr Phe Asp Val Pro Pro His Lys Tyr Arg Ile Thr
        35                 40                 45

<210> SEQ ID NO 131
<211> LENGTH: 47
<212> TYPE: PRT
<213> ORGANISM: Escherichia coli

<400> SEQUENCE: 131

Asn His Val Arg Ala Leu Leu Ser Asp Thr Asp Lys Ser Ile Leu Asp
 1               5                  10                 15

Ile Ala Leu Thr Ala Gly Phe Arg Ser Ser Arg Phe Tyr Ser Thr
                20                 25                 30

Phe Gly Lys Tyr Val Gly Met Ser Pro Gln Gln Tyr Arg Lys Leu
        35                 40                 45

<210> SEQ ID NO 132
<211> LENGTH: 47
<212> TYPE: PRT
<213> ORGANISM: Escherichia coli

<400> SEQUENCE: 132

Glu Tyr Ala Cys Gln Leu Leu Asp Ser Ser Asp Gln Ser Val Ala Arg
 1               5                  10                 15

Val Gly Gln Ala Val Gly Tyr Asp Asp Ser Tyr Tyr Phe Ser Arg Leu
                20                 25                 30

Phe Ser Lys Val Met Gly Leu Ser Pro Ser Ala Tyr Arg Gln Arg
        35                 40                 45

<210> SEQ ID NO 133
<211> LENGTH: 47
<212> TYPE: PRT
<213> ORGANISM: Escherichia coli

<400> SEQUENCE: 133

Lys Arg Ser Gln Tyr Leu Leu Glu Asn Pro Lys Leu Ser Ile Ala Glu
 1               5                  10                 15

Ile Ser Asn Ser Val Gly Phe Ser Asp Ser Leu Ala Phe Ser Lys Ala
                20                 25                 30

Phe Lys Asn Tyr Phe Gly Lys Ser Pro Ser Lys Phe Arg Lys Glu
        35                 40                 45

<210> SEQ ID NO 134
<211> LENGTH: 47
<212> TYPE: PRT
<213> ORGANISM: Escherichia coli

<400> SEQUENCE: 134

Val Asn Gly Leu Leu Asp Val Phe Leu His Asn Gln Thr Ile Thr Ser
 1               5                  10                 15

Ala Ala Met Asn Asn Gly Tyr Arg Ser Thr Ser His Phe Ser Asn Glu
                20                 25                 30

Ile Lys Thr Arg Leu Gly Phe Ser Ala Arg Glu Leu Ser Asn Ile
        35                 40                 45

<210> SEQ ID NO 135
<211> LENGTH: 47
<212> TYPE: PRT
```

<213> ORGANISM: Escherichia coli

<400> SEQUENCE: 135

Val Asn Gly Leu Leu Asp Val Phe Leu His Asn Gln Thr Ile Thr Ser
1               5                   10                  15

Ala Ala Met Asn Asn Gly Tyr Ala Ser Thr Ser His Phe Ser Asn Glu
            20                  25                  30

Ile Lys Thr Arg Leu Gly Phe Ser Ala Arg Glu Leu Ser Asn Ile
        35                  40                  45

<210> SEQ ID NO 136
<211> LENGTH: 47
<212> TYPE: PRT
<213> ORGANISM: Escherichia coli

<400> SEQUENCE: 136

Arg Leu Ala Leu Gln Tyr Leu Thr Thr Thr Gln Leu Pro Leu Tyr Glu
1               5                   10                  15

Ile Ala Leu Leu Leu Gly Phe Asn Asp Ser Ser Asn Phe Arg Arg Ala
            20                  25                  30

Phe Arg Lys Trp Thr Gly Lys Leu Pro Ser Asp Tyr Arg Glu Ala
        35                  40                  45

<210> SEQ ID NO 137
<211> LENGTH: 44
<212> TYPE: PRT
<213> ORGANISM: Escherichia coli

<400> SEQUENCE: 137

Arg Glu Ala His Arg Met Leu Cys Asp Glu Ala Asn Val Ser Thr
1               5                   10                  15

Val Ala Tyr Arg Val Gly Tyr Ser Pro Ala His Phe Ser Ile Ala Phe
            20                  25                  30

Arg Lys Arg Tyr Gly Ile Ser Pro Ser Glu Ile Arg
        35                  40

<210> SEQ ID NO 138
<211> LENGTH: 47
<212> TYPE: PRT
<213> ORGANISM: Escherichia coli

<400> SEQUENCE: 138

Lys His Ala Ser Leu Phe Leu Arg Thr Thr Asp Lys Asn Ile Asp Glu
1               5                   10                  15

Ile Ser Cys Leu Val Gly Phe Asn Ser Thr Ser Tyr Phe Ile Lys Val
            20                  25                  30

Phe Lys Glu Tyr Tyr Asn Thr Thr Pro Lys Lys Tyr Asn Gly Val
        35                  40                  45

<210> SEQ ID NO 139
<211> LENGTH: 47
<212> TYPE: PRT
<213> ORGANISM: Escherichia coli

<400> SEQUENCE: 139

Val Ser Ala Arg Glu Leu Leu Cys His Ser Asp Trp Ser Ile Ala Ser
1               5                   10                  15

Ile Ala Arg Asn Leu Gly Phe Ser Gln Thr Ser Tyr Phe Cys Lys Val
            20                  25                  30

Phe Arg Gln Thr Tyr Gln Val Thr Pro Gln Ala Tyr Arg Gln Gln
        35                  40                  45

<210> SEQ ID NO 140
<211> LENGTH: 47
<212> TYPE: PRT
<213> ORGANISM: Escherichia coli

<400> SEQUENCE: 140

Leu Glu Ala Ala Lys Ser Leu Gln Glu Lys Asp Met Ser Ile Leu Asp
1               5                   10                  15

Ile Ala Leu Met Tyr Gly Phe Ser Gln Ala Thr Phe Thr Arg Ile
            20                  25                  30

Phe Lys Lys His Phe Asn Thr Thr Pro Ala Lys Phe Arg Glu Asn
        35                  40                  45

<210> SEQ ID NO 141
<211> LENGTH: 47
<212> TYPE: PRT
<213> ORGANISM: Escherichia coli

<400> SEQUENCE: 141

Glu Asp Ala Lys Gln Arg Leu Ser Thr Ser Asn Asn Ser Val Gln Ser
1               5                   10                  15

Ile Ala Asn Met Val Gly Tyr Lys Asp Ser Phe Thr Phe Ser Lys Ala
            20                  25                  30

Phe Lys Arg Tyr Ser Gly Ala Ser Pro Ser Tyr Tyr Arg Lys Ser
        35                  40                  45

<210> SEQ ID NO 142
<211> LENGTH: 47
<212> TYPE: PRT
<213> ORGANISM: Escherichia coli

<400> SEQUENCE: 142

Leu Leu Ala Ala Arg Asp Leu Arg Glu Ser Asp Glu Arg Val Tyr Glu
1               5                   10                  15

Ile Cys Leu Arg Tyr Gly Phe Glu Ser Gln Gln Thr Phe Thr Arg Ile
            20                  25                  30

Phe Thr Arg Thr Phe His Gln Pro Pro Gly Ala Tyr Arg Lys Glu
        35                  40                  45

<210> SEQ ID NO 143
<211> LENGTH: 47
<212> TYPE: PRT
<213> ORGANISM: Escherichia coli

<400> SEQUENCE: 143

Leu Leu Ala Ala Arg Asp Leu Arg Asp Thr Asp Gln Arg Val Tyr Asp
1               5                   10                  15

Ile Cys Leu Lys Tyr Gly Phe Asp Ser Gln Gln Thr Phe Thr Arg Val
            20                  25                  30

Phe Thr Arg Thr Phe Asn Gln Pro Pro Gly Ala Tyr Arg Lys Glu
        35                  40                  45

<210> SEQ ID NO 144
<211> LENGTH: 47
<212> TYPE: PRT
<213> ORGANISM: Escherichia coli

<400> SEQUENCE: 144

Cys His Ala Gln Tyr Leu Leu Gln His Ser Arg Leu Leu Ile Ser Asp
1               5                   10                  15

Ile Ser Thr Glu Cys Gly Phe Glu Asp Ser Asn Tyr Phe Ser Val Val
            20                  25                  30

Phe Thr Arg Glu Thr Gly Met Thr Pro Ser Gln Trp Arg His Leu
        35                  40                  45

<210> SEQ ID NO 145
<211> LENGTH: 47
<212> TYPE: PRT
<213> ORGANISM: Escherichia coli

<400> SEQUENCE: 145

Cys His Ala Gln Tyr Leu Leu Gln His Ser Pro Leu Met Ile Ser Glu
1               5                   10                  15

Ile Ser Met Gln Cys Gly Phe Glu Asp Ser Asn Tyr Phe Ser Val Val
            20                  25                  30

Phe Thr Arg Glu Thr Gly Met Thr Pro Ser Gln Trp Arg His Leu
        35                  40                  45

<210> SEQ ID NO 146
<211> LENGTH: 47
<212> TYPE: PRT
<213> ORGANISM: Escherichia coli

<400> SEQUENCE: 146

Met Lys Ala Arg His Leu Leu Arg His Ser Glu Ala Ser Val Thr Asp
1               5                   10                  15

Ile Ala Tyr Arg Cys Gly Phe Ser Asp Ser Asn His Phe Ser Thr Leu
            20                  25                  30

Phe Arg Arg Glu Phe Asn Trp Ser Pro Arg Asp Ile Arg Gln Gly
        35                  40                  45

<210> SEQ ID NO 147
<211> LENGTH: 47
<212> TYPE: PRT
<213> ORGANISM: Escherichia coli

<400> SEQUENCE: 147

Ile Lys Ala Arg His Leu Leu Arg His Ser Asp His Ser Val Thr Glu
1               5                   10                  15

Ile Ala Tyr Arg Cys Gly Phe Gly Asp Ser Asn His Phe Ser Thr Leu
            20                  25                  30

Phe Arg Arg Glu Phe Asn Trp Ser Pro Arg Asp Ile Arg Gln Gly
        35                  40                  45

<210> SEQ ID NO 148
<211> LENGTH: 49
<212> TYPE: PRT
<213> ORGANISM: Escherichia coli

<400> SEQUENCE: 148

Ser Leu Ala Lys Ser Leu Ile Leu Ala Glu Gly Glu Ala Thr Ser Ile
1               5                   10                  15

Ser Gln Ile Ala Tyr Asn Val Gly Phe Asn Asp Leu Ser Tyr Phe Asn
            20                  25                  30

Arg Thr Phe Arg Ser Arg Tyr Gly Val Arg Pro Ser Asp Leu Arg Arg
        35                  40                  45

Leu

<210> SEQ ID NO 149
<211> LENGTH: 47
<212> TYPE: PRT

<213> ORGANISM: Escherichia coli

<400> SEQUENCE: 149

Ser Lys Ala Ala Leu Leu Leu Glu Asn Ser Tyr Gln Ile Ser Gln
1               5                   10                  15

Ile Ser Asn Met Ile Gly Ile Ser Ala Ser Tyr Phe Ile Arg Ile
            20                  25                  30

Phe Asn Lys His Tyr Gly Val Thr Pro Lys Gln Phe Phe Thr Tyr
        35                  40                  45

<210> SEQ ID NO 150
<211> LENGTH: 47
<212> TYPE: PRT
<213> ORGANISM: Escherichia coli

<400> SEQUENCE: 150

Ser Lys Ser Ala Val Ala Leu Arg Leu Thr Ala Arg Pro Ile Leu Asp
1               5                   10                  15

Ile Ala Leu Gln Tyr Arg Phe Asp Ser Gln Gln Thr Phe Thr Arg Ala
            20                  25                  30

Phe Lys Lys Gln Phe Ala Gln Thr Pro Ala Leu Tyr Arg Arg Ser
        35                  40                  45

<210> SEQ ID NO 151
<211> LENGTH: 47
<212> TYPE: PRT
<213> ORGANISM: Escherichia coli

<400> SEQUENCE: 151

Leu Leu Ala Ala Val Glu Leu Arg Thr Thr Glu Arg Pro Ile Phe Asp
1               5                   10                  15

Ile Ala Met Asp Leu Gly Tyr Val Ser Gln Gln Thr Phe Ser Arg Val
            20                  25                  30

Phe Arg Arg Gln Phe Asp Arg Thr Pro Ser Asp Tyr Arg His Arg
        35                  40                  45

<210> SEQ ID NO 152
<211> LENGTH: 47
<212> TYPE: PRT
<213> ORGANISM: Escherichia coli

<400> SEQUENCE: 152

Leu Leu Ala Ala Val Glu Leu Arg Thr Thr Glu Arg Pro Ile Phe Asp
1               5                   10                  15

Ile Ala Met Asp Leu Gly Tyr Val Ser Gln Gln Thr Phe Ser Arg Val
            20                  25                  30

Phe Arg Arg Glu Phe Asp Arg Thr Pro Ser Asp Tyr Arg His Arg
        35                  40                  45

<210> SEQ ID NO 153
<211> LENGTH: 47
<212> TYPE: PRT
<213> ORGANISM: Escherichia coli

<400> SEQUENCE: 153

Ser Tyr Ser Ile Ser Leu Met Lys Thr Gly Glu Phe Lys Ile Lys Gln
1               5                   10                  15

Ile Ala Tyr Gln Ser Gly Phe Ala Ser Val Ser Tyr Phe Ser Thr Val
            20                  25                  30

Phe Lys Ser Thr Met Asn Val Ala Pro Ser Glu Tyr Leu Phe Met
        35                  40                  45

<210> SEQ ID NO 154
<211> LENGTH: 47
<212> TYPE: PRT
<213> ORGANISM: Escherichia coli

<400> SEQUENCE: 154

Thr Lys Ala Ala Val Glu Leu Arg Leu Thr Lys Lys Thr Ile Leu Glu
1               5                   10                  15

Ile Ala Leu Lys Tyr Gln Phe Asp Ser Gln Gln Ser Phe Thr Arg Arg
            20                  25                  30

Phe Lys Tyr Ile Phe Lys Val Thr Pro Ser Tyr Tyr Arg Arg Asn
        35                  40                  45

<210> SEQ ID NO 155
<211> LENGTH: 50
<212> TYPE: PRT
<213> ORGANISM: Escherichia coli

<400> SEQUENCE: 155

Gln Lys Ala Arg Lys Asp Leu Leu Arg Ala Asp Pro Ala Ser Glu Gly
1               5                   10                  15

Val Thr Glu Ile Ala Gln Arg Trp Gly Phe Leu His Val Gly Arg Phe
            20                  25                  30

Ala Gly Glu Tyr Lys Gln Thr Phe Gly Val Ser Pro Ser Glu Asp Leu
        35                  40                  45

Arg Thr
    50

<210> SEQ ID NO 156
<211> LENGTH: 47
<212> TYPE: PRT
<213> ORGANISM: Escherichia coli

<400> SEQUENCE: 156

Gly Met Ala Leu Asn Tyr Leu Thr Phe Ser Asn Tyr Ser Val Phe Gln
1               5                   10                  15

Ile Ser His Arg Cys Gly Phe Gly Ser Asn Ala Tyr Phe Cys Asp Val
            20                  25                  30

Phe Lys Arg Lys Tyr Asn Met Thr Pro Ser Gln Phe Arg Leu Gln
        35                  40                  45

<210> SEQ ID NO 157
<211> LENGTH: 47
<212> TYPE: PRT
<213> ORGANISM: Escherichia coli

<400> SEQUENCE: 157

Pro Ile Ala Leu Asn Tyr Leu Thr Phe Ser Asn Tyr Ser Val Phe Gln
1               5                   10                  15

Ile Ser His Arg Cys Gly Phe Gly Ser Asn Ala Tyr Phe Cys Asp Ala
            20                  25                  30

Phe Lys Arg Lys Tyr Gly Met Thr Pro Ser Gln Phe Arg Thr Gln
        35                  40                  45

<210> SEQ ID NO 158
<211> LENGTH: 47
<212> TYPE: PRT
<213> ORGANISM: Escherichia coli

<400> SEQUENCE: 158

```
His His Ala Ala Lys Leu Leu Asn Ser Gln Ser Tyr Ile Asn Asp
1               5                   10                  15

Val Ser Arg Leu Ile Gly Ile Ser Pro Ser Tyr Phe Ile Arg Lys
                20                  25                  30

Phe Asn Glu Tyr Tyr Gly Ile Thr Pro Lys Lys Phe Tyr Leu Tyr
            35                  40                  45
```

<210> SEQ ID NO 159
<211> LENGTH: 47
<212> TYPE: PRT
<213> ORGANISM: Escherichia coli

<400> SEQUENCE: 159

```
Leu Tyr Ala His Gln Leu Leu Asn Gly Lys Met Ser Ile Val Asp
1               5                   10                  15

Ile Ala Met Glu Ala Gly Phe Ser Gln Ser Tyr Phe Thr Gln Ser
                20                  25                  30

Tyr Arg Arg Arg Phe Gly Cys Thr Pro Ser Gln Ala Arg Leu Thr
            35                  40                  45
```

<210> SEQ ID NO 160
<211> LENGTH: 47
<212> TYPE: PRT
<213> ORGANISM: Mycobacterium tuberculosis

<400> SEQUENCE: 160

```
Ala Gln Ala Ala Arg Tyr Leu Ala Gln Pro Gly Leu Tyr Leu Ser Gln
1               5                   10                  15

Ile Ala Val Leu Leu Gly Tyr Ser Glu Gln Ser Ala Leu Asn Arg Ser
                20                  25                  30

Cys Arg Arg Trp Phe Gly Met Thr Pro Arg Gln Tyr Arg Ala Tyr
            35                  40                  45
```

<210> SEQ ID NO 161
<211> LENGTH: 47
<212> TYPE: PRT
<213> ORGANISM: Escherichia coli

<400> SEQUENCE: 161

```
Glu Lys Ala Arg Ser Leu Leu Ile Ser Thr Thr Leu Ser Ile Asn Glu
1               5                   10                  15

Ile Ser Gln Met Cys Gly Tyr Pro Ser Leu Gln Tyr Phe Tyr Ser Val
                20                  25                  30

Phe Lys Lys Ala Tyr Asp Thr Thr Pro Lys Glu Tyr Arg Asp Val
            35                  40                  45
```

<210> SEQ ID NO 162
<211> LENGTH: 47
<212> TYPE: PRT
<213> ORGANISM: Escherichia coli

<400> SEQUENCE: 162

```
Ser Arg Ala Lys Asn Leu Leu Gln Gln Thr Asp Ile Ser Ile Lys Glu
1               5                   10                  15

Ile Thr Glu Ile Cys Gly Tyr Pro Ser Ile Gln Tyr Phe Tyr Ser Val
                20                  25                  30

Phe Lys Lys Glu Phe Glu Met Thr Pro Lys Glu Phe Arg Leu Asn
            35                  40                  45
```

<210> SEQ ID NO 163
<211> LENGTH: 50

```
<212> TYPE: PRT
<213> ORGANISM: Escherichia coli

<400> SEQUENCE: 163

Glu Ser Ile Arg Ala Cys Leu Asn Asp Pro Ser Ala Asn Val Arg Ser
1               5                   10                  15

Ile Thr Glu Ile Ala Leu Asp Tyr Gly Phe Leu His Leu Gly Arg Phe
            20                  25                  30

Ala Glu Asn Tyr Arg Ser Ala Phe Gly Glu Leu Pro Ser Asp Thr Leu
        35                  40                  45

Arg Gln
    50

<210> SEQ ID NO 164
<211> LENGTH: 50
<212> TYPE: PRT
<213> ORGANISM: Escherichia coli

<400> SEQUENCE: 164

Glu Ser Ile Arg Ala Cys Leu Asn Asp Pro Ser Ala Asn Val Arg Ser
1               5                   10                  15

Ile Thr Glu Ile Ala Leu Asp Tyr Gly Phe Leu His Leu Gly Arg Phe
            20                  25                  30

Ala Glu Asn Tyr Arg Ser Ala Phe Gly Glu Leu Pro Ser Asp Thr Leu
        35                  40                  45

Arg Gln
    50

<210> SEQ ID NO 165
<211> LENGTH: 50
<212> TYPE: PRT
<213> ORGANISM: Escherichia coli

<400> SEQUENCE: 165

Glu Cys Val Arg Ala Cys Leu Ser Asn Pro Thr Thr Asn Ile Arg Ser
1               5                   10                  15

Ile Thr Glu Val Ala Leu Asp Tyr Gly Phe Leu His Leu Gly Arg Phe
            20                  25                  30

Ala Glu Lys Tyr Arg Ser Thr Phe Gly Glu Leu Pro Ser Asp Thr Leu
        35                  40                  45

Ser Leu
    50

<210> SEQ ID NO 166
<211> LENGTH: 50
<212> TYPE: PRT
<213> ORGANISM: Escherichia coli

<400> SEQUENCE: 166

Glu Cys Ile Arg Ala Arg Leu Ser Asp Pro Asn Ala Asn Val Arg Ser
1               5                   10                  15

Val Thr Glu Met Ala Leu Asp Tyr Gly Phe Phe His Thr Gly Arg Phe
            20                  25                  30

Ala Glu Asn Tyr Arg Ser Thr Phe Gly Glu Leu Pro Ser Asp Thr Leu
        35                  40                  45

Arg Arg
    50

<210> SEQ ID NO 167
<211> LENGTH: 50
```

```
<212> TYPE: PRT
<213> ORGANISM: Escherichia coli

<400> SEQUENCE: 167

Glu Cys Ile Arg Ala Arg Leu Ser Asp Pro Asn Ala Asn Val Arg Ser
1               5                   10                  15

Val Thr Glu Met Ala Leu Asp Tyr Gly Phe Phe His Thr Gly Arg Phe
            20                  25                  30

Ala Glu Asn Tyr Arg Ser Thr Phe Gly Glu Leu Pro Ser Asp Thr Leu
        35                  40                  45

Arg Arg
    50

<210> SEQ ID NO 168
<211> LENGTH: 48
<212> TYPE: PRT
<213> ORGANISM: Escherichia coli

<400> SEQUENCE: 168

Ala Ala Ala His Gly Ala Ile Lys Ala Gly Arg Ala Gly Ser Ile Thr
1               5                   10                  15

Glu Leu Ala Leu Asn Leu Gln Phe Ser Asn Pro Gly Arg Phe Ser Val
            20                  25                  30

Leu Tyr Lys Ser Ala Tyr Gly Leu Ser Pro Ser Ser Ala Leu Arg Phe
        35                  40                  45

<210> SEQ ID NO 169
<211> LENGTH: 47
<212> TYPE: PRT
<213> ORGANISM: Escherichia coli

<400> SEQUENCE: 169

Gln Ser Ala Ala Phe Leu Leu Lys Gln Ser Gln Gln Ser Val Leu Ala
1               5                   10                  15

Ile Ala Leu Glu Val Gly Tyr Gln Ser Glu Ala His Phe Cys Lys Val
            20                  25                  30

Phe Lys Asn Tyr Tyr Gln Leu Ser Pro Ser Gln Tyr Arg Lys Ser
        35                  40                  45

<210> SEQ ID NO 170
<211> LENGTH: 47
<212> TYPE: PRT
<213> ORGANISM: Escherichia coli

<400> SEQUENCE: 170

Thr Lys Ala Lys Arg Leu Met Ala Lys Ser Asn Cys Lys Leu Lys Glu
1               5                   10                  15

Ile Ala His Gln Thr Gly Tyr Gln Asp Glu Phe Tyr Phe Ser Arg Ile
            20                  25                  30

Phe Lys Lys Tyr Thr Gly Cys Ser Pro Thr Ser Tyr Met Lys Lys
        35                  40                  45

<210> SEQ ID NO 171
<211> LENGTH: 47
<212> TYPE: PRT
<213> ORGANISM: Escherichia coli

<400> SEQUENCE: 171

Asn Asn Ala Leu Ser Ala Ile Gln Thr Thr Val Lys Pro Ile Ser Glu
1               5                   10                  15

Ile Ala Arg Glu Asn Gly Tyr Lys Cys Pro Ser Arg Phe Thr Glu Arg
```

```
                  20                  25                  30

Phe His Asn Arg Phe Asn Ile Thr Pro Arg Glu Ile Arg Lys Ala
              35                  40                  45

<210> SEQ ID NO 172
<211> LENGTH: 45
<212> TYPE: PRT
<213> ORGANISM: Escherichia coli

<400> SEQUENCE: 172

Glu Gln Ala Lys Lys Val Leu Leu Lys Ser Val Thr Glu Thr Ala
1               5                   10                  15

Tyr Glu Val Gly Phe Asn Asn Ser Asn Tyr Phe Ala Thr Val Phe Lys
                20                  25                  30

Lys Arg Thr Asn Tyr Thr Pro Lys Gln Phe Lys Arg Thr
              35                  40                  45

<210> SEQ ID NO 173
<211> LENGTH: 47
<212> TYPE: PRT
<213> ORGANISM: Mycobacterium tuberculosis

<400> SEQUENCE: 173

Thr Val Ala Val Asp Leu Leu Arg Asn Val Gly Leu Thr Val Gln Gln
1               5                   10                  15

Val Ser Thr Arg Leu Gly Tyr Thr Glu Val Ser Thr Phe Ser His Ala
                20                  25                  30

Phe Lys Arg Trp Tyr Gly Val Ala Pro Ser Glu Tyr Ser Arg Arg
              35                  40                  45

<210> SEQ ID NO 174
<211> LENGTH: 46
<212> TYPE: PRT
<213> ORGANISM: Escherichia coli

<400> SEQUENCE: 174

Gln His Ala Lys Asn Leu Ile Arg Val Glu Gly Ser Val Asn Lys Ile
1               5                   10                  15

Ala Glu Gln Cys Gly Tyr Ala Ser Thr Ser Tyr Phe Ile Tyr Ala Phe
                20                  25                  30

Arg Lys His Phe Gly Asn Ser Pro Lys Arg Val Ser Lys Glu
              35                  40                  45

<210> SEQ ID NO 175
<211> LENGTH: 47
<212> TYPE: PRT
<213> ORGANISM: Escherichia coli

<400> SEQUENCE: 175

Thr Glu Ala Lys Trp Ser Leu Thr Asn Thr Glu Leu Ser Gln Ala Glu
1               5                   10                  15

Ile Ser Trp Arg Val Gly Tyr Glu Asn Val Asp His Phe Ala Lys Leu
                20                  25                  30

Phe Leu Arg His Val Gly Cys Ser Pro Ser Asp Tyr Arg Arg Gln
              35                  40                  45

<210> SEQ ID NO 176
<211> LENGTH: 46
<212> TYPE: PRT
<213> ORGANISM: Escherichia coli

<400> SEQUENCE: 176
```

```
Ile Met Ala Leu Gln Gly Leu Val Lys Gly Asp Thr Val Gln Lys Val
1               5                   10                  15

Ala His Thr Leu Gly Tyr Asp Ser Thr Thr Ala Phe Ile Thr Met Phe
            20                  25                  30

Lys Lys Gly Leu Gly Gln Thr Pro Gly Arg Tyr Ile Ala Arg
            35                  40                  45
```

<210> SEQ ID NO 177
<211> LENGTH: 46
<212> TYPE: PRT
<213> ORGANISM: Escherichia coli

<400> SEQUENCE: 177

```
Asn Lys Ala Ala Glu Leu Leu Lys Ser Thr Asn Leu Ser Ile Lys Glu
1               5                   10                  15

Ile Ala Glu Glu Ile Gly Phe Ser Val His Tyr Phe Thr Arg Val Phe
            20                  25                  30

Ser Ala Lys Ile Gly Ser Ser Pro Gly Leu Phe Arg Ser Leu
            35                  40                  45
```

<210> SEQ ID NO 178
<211> LENGTH: 47
<212> TYPE: PRT
<213> ORGANISM: Escherichia coli

<400> SEQUENCE: 178

```
Ser Met Ala Arg Arg Leu Leu Glu Leu Arg Gln Ile Pro Leu His Thr
1               5                   10                  15

Ile Ala Glu Lys Cys Gly Tyr Ser Ser Thr Ser Tyr Phe Ile Asn Thr
            20                  25                  30

Phe Arg Gln Tyr Tyr Gly Val Thr Pro His Gln Phe Ala Gln His
            35                  40                  45
```

<210> SEQ ID NO 179
<211> LENGTH: 47
<212> TYPE: PRT
<213> ORGANISM: Escherichia coli

<400> SEQUENCE: 179

```
Asp Leu Ala Leu Ser Leu Leu Lys Gln Gln Gly Asn Ser Val Gly Glu
1               5                   10                  15

Val Ala Asp Thr Leu Asn Phe Phe Asp Ser Phe His Phe Ser Lys Ala
            20                  25                  30

Phe Lys His Lys Phe Gly Tyr Ala Pro Ser Ala Val Leu Lys Asn
            35                  40                  45
```

<210> SEQ ID NO 180
<211> LENGTH: 47
<212> TYPE: PRT
<213> ORGANISM: Escherichia coli

<400> SEQUENCE: 180

```
Glu His Ala Lys Thr Leu Leu Lys Gly Tyr Asp Leu Val Lys Val Glu
1               5                   10                  15

Val Ala His Ala Cys Gly Phe Val Asp Ser Asn Tyr Phe Cys Arg Leu
            20                  25                  30

Phe Arg Lys Asn Thr Glu Arg Ser Pro Ser Glu Tyr Arg Arg Gln
            35                  40                  45
```

<210> SEQ ID NO 181

```
<211> LENGTH: 47
<212> TYPE: PRT
<213> ORGANISM: Escherichia coli

<400> SEQUENCE: 181

Thr Glu Ala Lys Arg Leu Leu Ser Ser Thr Asn Asp Lys Met Gly Val
1               5                   10                  15

Ile Ala Glu Thr Val Gly Met Glu Asp Pro Thr Tyr Phe Ser Lys Leu
            20                  25                  30

Phe Lys Gln Ile Glu Gly Ile Ser Pro Ile Glu Tyr Arg Lys Ile
        35                  40                  45

<210> SEQ ID NO 182
<211> LENGTH: 47
<212> TYPE: PRT
<213> ORGANISM: Escherichia coli

<400> SEQUENCE: 182

Cys Arg Ala Ala Ile Leu Val Arg Leu Thr Ala Lys Ser Met Leu Asp
1               5                   10                  15

Ile Ala Leu Ser Leu His Phe Asp Ser Gln Gln Ser Phe Ser Arg Glu
            20                  25                  30

Phe Lys Lys Leu Phe Gly Cys Ser Pro Arg Glu Tyr Arg His Arg
        35                  40                  45

<210> SEQ ID NO 183
<211> LENGTH: 47
<212> TYPE: PRT
<213> ORGANISM: Escherichia coli

<400> SEQUENCE: 183

Gln Ile Ala Ala Gln Met Phe Ser Arg Glu Thr Leu Pro Val Val Val
1               5                   10                  15

Ile Ala Glu Ser Val Gly Tyr Ala Ser Glu Ser Ser Phe His Lys Ala
            20                  25                  30

Phe Val Arg Glu Phe Gly Cys Thr Pro Gly Glu Tyr Arg Glu Arg
        35                  40                  45

<210> SEQ ID NO 184
<211> LENGTH: 46
<212> TYPE: PRT
<213> ORGANISM: Escherichia coli

<400> SEQUENCE: 184

Gln Arg Ala Leu Arg Leu Ala Arg Ala Gly Val Pro Phe Ala Glu Thr
1               5                   10                  15

Ala Thr Leu Ala Gly Phe Ala Asp Gln Ala His Leu Ala Arg Asp Val
            20                  25                  30

Arg Glu Met Ala Gly Ser Ser Leu Ser Glu Leu Val Glu Arg
        35                  40                  45

<210> SEQ ID NO 185
<211> LENGTH: 47
<212> TYPE: PRT
<213> ORGANISM: Escherichia coli

<400> SEQUENCE: 185

Ala Lys Ala Arg Met Ile Leu Gln Lys Tyr His Leu Ser Ile His Glu
1               5                   10                  15

Val Ala Gln Arg Cys Gly Phe Pro Asp Ser Asp Tyr Phe Cys Arg Val
            20                  25                  30
```

```
Phe Arg Arg Gln Phe Gly Leu Thr Pro Gly Glu Tyr Ser Ala Arg
        35                  40                  45
```

<210> SEQ ID NO 186
<211> LENGTH: 47
<212> TYPE: PRT
<213> ORGANISM: Escherichia coli

<400> SEQUENCE: 186

```
His Lys Ala Arg Met Met Ile Ile His Asp Gly Met Lys Ala Ser Ala
 1               5                  10                  15

Ala Ala Met Arg Val Gly Tyr Glu Ser Ala Ser Gln Phe Ser Arg Glu
            20                  25                  30

Phe Lys Arg Tyr Phe Gly Val Thr Pro Gly Glu Asp Ala Ala Arg
        35                  40                  45
```

<210> SEQ ID NO 187
<211> LENGTH: 43
<212> TYPE: PRT
<213> ORGANISM: Providencia Stuartii

<400> SEQUENCE: 187

```
Arg Ile Cys Glu Ala Ala Lys Glu Leu Gln Thr Thr Asn Leu Gln Val
 1               5                  10                  15

Ile Asp Ile Ala Leu Lys Tyr Gln Phe Asp Ser Gln Gln Ser Phe Ala
            20                  25                  30

Lys Arg Phe Lys Ala Tyr Leu Gly Ile Ser Pro
        35                  40
```

<210> SEQ ID NO 188
<211> LENGTH: 43
<212> TYPE: PRT
<213> ORGANISM: Mycobacterium tuberculosis

<400> SEQUENCE: 188

```
Arg Met Gln Thr Ala Arg Val Leu Ile Glu Thr Thr Asn Leu Pro Phe
 1               5                  10                  15

Gly Asp Val Ala Phe Ala Ala Gly Phe Ser Ser Ile Arg Gln Phe Asn
            20                  25                  30

Asp Thr Val Arg Leu Ala Cys Asp Gly Thr Pro
        35                  40
```

<210> SEQ ID NO 189
<211> LENGTH: 43
<212> TYPE: PRT
<213> ORGANISM: Escherichia coli

<400> SEQUENCE: 189

```
Arg Val His Ala Ala Lys Lys Tyr Leu Ile Gln Thr Asn Lys Ala Ile
 1               5                  10                  15

Gly Asp Ile Ala Ile Cys Val Gly Ile Ala Asn Ala Pro Tyr Phe Ile
            20                  25                  30

Thr Leu Phe Lys Lys Lys Thr Gly Gln Thr Pro
        35                  40
```

<210> SEQ ID NO 190
<211> LENGTH: 43
<212> TYPE: PRT
<213> ORGANISM: Escherichia coli

<400> SEQUENCE: 190

```
Arg Met Arg Tyr Ala Val Asn Glu Leu Met Met Asp Gly Lys Asn Ile
 1               5                  10                  15
```

```
                 1               5                  10                 15
Ser Gln Val Ser Gln Ser Cys Gly Tyr Asn Ser Thr Tyr Phe Ile
                20                  25                 30

Ser Val Phe Lys Asp Phe Tyr Gly Met Thr Pro
        35                  40

<210> SEQ ID NO 191
<211> LENGTH: 43
<212> TYPE: PRT
<213> ORGANISM: Escherichia coli

<400> SEQUENCE: 191

Arg Met Ser Lys Ala Ala Leu Leu Leu Asp Asn Ser Tyr Gln Ile
 1               5                  10                 15

Ser Gln Ile Ser Asn Met Ile Gly Phe Ser Ser Thr Ser Tyr Phe Ile
                20                  25                 30

Arg Leu Phe Val Lys His Phe Gly Ile Thr Pro
        35                  40

<210> SEQ ID NO 192
<211> LENGTH: 43
<212> TYPE: PRT
<213> ORGANISM: Escherichia coli

<400> SEQUENCE: 192

Arg Met Arg Tyr Ala Lys Lys Leu Ile Thr Ser Asn Ser Tyr Ser Ile
 1               5                  10                 15

Asn Val Val Ala Gln Lys Cys Gly Tyr Asn Ser Thr Tyr Phe Ile
                20                  25                 30

Cys Ala Phe Lys Asp Tyr Tyr Gly Val Thr Pro
        35                  40

<210> SEQ ID NO 193
<211> LENGTH: 43
<212> TYPE: PRT
<213> ORGANISM: Escherichia coli

<400> SEQUENCE: 193

Arg Ile Ser Gln Ala Lys Leu Leu Leu Ser Thr Thr Arg Met Pro Ile
 1               5                  10                 15

Ala Thr Val Gly Arg Asn Val Gly Phe Asp Asp Gln Leu Tyr Phe Ser
                20                  25                 30

Arg Val Phe Lys Lys Cys Thr Gly Ala Ser Pro
        35                  40

<210> SEQ ID NO 194
<211> LENGTH: 43
<212> TYPE: PRT
<213> ORGANISM: Escherichia coli

<400> SEQUENCE: 194

Arg Ile Ser Gln Ala Lys Leu Leu Leu Ser Thr Thr Arg Met Pro Ile
 1               5                  10                 15

Ala Thr Val Gly Arg Asn Val Gly Phe Asp Asp Gln Leu Tyr Phe Ser
                20                  25                 30

Arg Val Phe Lys Lys Cys Thr Gly Ala Ser Pro
        35                  40

<210> SEQ ID NO 195
<211> LENGTH: 43
<212> TYPE: PRT
```

<213> ORGANISM: Escherichia coli

<400> SEQUENCE: 195

Arg Val Ile Arg Ala Lys Leu Leu Gln Thr Thr Gln Glu Ser Ile
1               5                   10                  15

Ala Asn Ile Gly Arg Val Val Gly Tyr Asp Asp Gln Leu Tyr Phe Ser
            20                  25                  30

Arg Val Phe Arg Lys Arg Val Gly Val Ser Pro
        35                  40

<210> SEQ ID NO 196
<211> LENGTH: 43
<212> TYPE: PRT
<213> ORGANISM: Escherichia coli

<400> SEQUENCE: 196

Arg Ile Ser Gln Ala Lys Leu Leu Ser Thr Thr Arg Met Pro Ile
1               5                   10                  15

Ala Thr Val Gly Arg Asn Val Gly Phe Asp Asp Gln Leu Tyr Phe Ser
            20                  25                  30

Arg Val Phe Lys Lys Cys Thr Gly Ala Ser Pro
        35                  40

<210> SEQ ID NO 197
<211> LENGTH: 43
<212> TYPE: PRT
<213> ORGANISM: Escherichia coli

<400> SEQUENCE: 197

Arg Ile Glu Leu Thr Ala Arg Gln Leu Arg Glu Gly Ser Ala Pro Leu
1               5                   10                  15

Ala Ala Ile Ala His Ser Val Gly Tyr Gly Ser Glu Ser Ala Leu Ser
            20                  25                  30

Val Ala Phe Lys Arg Val Leu Gly Met Asn Pro
        35                  40

<210> SEQ ID NO 198
<211> LENGTH: 43
<212> TYPE: PRT
<213> ORGANISM: Escherichia coli

<400> SEQUENCE: 198

Arg Ile Glu Leu Ala Ala Arg Gln Leu Arg Glu Gly Asn Ala Thr Leu
1               5                   10                  15

Ala Ser Ile Ala His Ser Val Gly Tyr Gly Ser Glu Ser Ala Leu Ser
            20                  25                  30

Val Ala Phe Lys Arg Val Leu Gly Met Pro Pro
        35                  40

<210> SEQ ID NO 199
<211> LENGTH: 43
<212> TYPE: PRT
<213> ORGANISM: Escherichia coli

<400> SEQUENCE: 199

Arg Ile Asn Phe Ala Lys Lys Gln Leu Glu Met Thr Asn Tyr Ser Val
1               5                   10                  15

Thr Asp Ile Ala Phe Glu Ala Gly Tyr Ser Ser Pro Ser Leu Phe Ile
            20                  25                  30

Lys Thr Phe Lys Lys Leu Thr Ser Phe Thr Pro
        35                  40

<210> SEQ ID NO 200
<211> LENGTH: 45
<212> TYPE: PRT
<213> ORGANISM: Escherichia coli

<400> SEQUENCE: 200

Gln Leu Arg Met Ser Lys Ala Ala Leu Leu Leu Glu Asn Ser Tyr
1               5                   10                  15
Gln Ile Ser Gln Ile Ser Asn Met Ile Gly Ile Ser Ser Ala Ser Tyr
            20                  25                  30
Phe Ile Arg Val Phe Asn Lys His Tyr Gly Val Thr Pro
        35                  40                  45

<210> SEQ ID NO 201
<211> LENGTH: 43
<212> TYPE: PRT
<213> ORGANISM: Escherichia coli

<400> SEQUENCE: 201

Arg Met Ser Lys Ala Ala Leu Leu Leu Glu Asn Ser Tyr Gln Ile
1               5                   10                  15
Ser Gln Ile Ser Asn Met Ile Gly Ile Ser Ser Ala Ser Tyr Phe Ile
            20                  25                  30
Arg Ile Phe Asn Lys His Phe Gly Val Thr Arg
        35                  40

<210> SEQ ID NO 202
<211> LENGTH: 43
<212> TYPE: PRT
<213> ORGANISM: Escherichia coli

<400> SEQUENCE: 202

Arg Met Arg Tyr Ala Val Gln Met Leu Leu Met Asp Asn Lys Asn Ile
1               5                   10                  15
Thr Gln Val Ala Gln Leu Cys Gly Tyr Ser Ser Thr Ser Tyr Phe Ile
            20                  25                  30
Ser Val Phe Lys Ala Phe Tyr Gly Leu Thr Pro
        35                  40

<210> SEQ ID NO 203
<211> LENGTH: 46
<212> TYPE: PRT
<213> ORGANISM: Escherichia coli

<400> SEQUENCE: 203

Arg Leu Asn Ala Val Arg Arg Glu Leu Ile Ser Pro Trp Ser Gln Ser
1               5                   10                  15
Met Thr Val Lys Asp Ala Ala Met Gln Trp Gly Phe Trp His Leu Gly
            20                  25                  30
Gln Phe Ala Thr Asp Tyr Gln Gln Leu Phe Ser Glu Lys Pro
        35                  40                  45

<210> SEQ ID NO 204
<211> LENGTH: 46
<212> TYPE: PRT
<213> ORGANISM: Escherichia coli

<400> SEQUENCE: 204

Arg Leu Asn Ala Val Arg Arg Glu Leu Ile Ser Pro Trp Ser Gln Ser
1               5                   10                  15

-continued

Ala Thr Val Lys Asp Ala Ala Met Gln Trp Gly Phe Trp His Leu Gly
            20                  25                  30

Gln Phe Ala Thr Asp Tyr Gln Leu Phe Ala Glu Lys Pro
        35                  40                  45

<210> SEQ ID NO 205
<211> LENGTH: 43
<212> TYPE: PRT
<213> ORGANISM: Escherichia coli

<400> SEQUENCE: 205

Arg Ile Leu Tyr Ala His Gln Leu Leu Leu Asn Ser Asp Met Ser Ile
1               5                   10                  15

Val Asp Ile Ala Met Glu Ala Gly Phe Ser Ser Gln Ser Tyr Phe Thr
            20                  25                  30

Gln Ser Tyr Arg Arg Arg Phe Gly Cys Thr Pro
        35                  40

<210> SEQ ID NO 206
<211> LENGTH: 43
<212> TYPE: PRT
<213> ORGANISM: Escherichia coli

<400> SEQUENCE: 206

Arg Met Asn Gln Ala Ala Lys Phe Ile Ile Arg Ser Asp His Gln Ile
1               5                   10                  15

Gly Met Ile Ala Ser Leu Val Gly Tyr Thr Ser Val Ser Tyr Phe Ile
            20                  25                  30

Lys Thr Phe Lys Glu Tyr Tyr Gly Val Thr Pro
        35                  40

<210> SEQ ID NO 207
<211> LENGTH: 43
<212> TYPE: PRT
<213> ORGANISM: Escherichia coli

<400> SEQUENCE: 207

Arg Met Gln Arg Ala Leu Gln Leu Ile Val Ile Tyr Gly Val Ser Ile
1               5                   10                  15

Lys Arg Val Ala Val Ser Cys Gly Tyr His Ser Val Ser Tyr Phe Ile
            20                  25                  30

Tyr Val Phe Arg Asn Tyr Tyr Gly Met Thr Pro
        35                  40

<210> SEQ ID NO 208
<211> LENGTH: 43
<212> TYPE: PRT
<213> ORGANISM: Escherichia coli

<400> SEQUENCE: 208

Arg Met Gln Arg Ala Leu Gln Leu Ile Val Ile His Gly Phe Ser Ile
1               5                   10                  15

Lys Arg Val Ala Val Ser Cys Gly Tyr His Ser Val Ser Tyr Phe Ile
            20                  25                  30

Tyr Val Phe Arg Asn Tyr Tyr Gly Met Thr Pro
        35                  40

<210> SEQ ID NO 209
<211> LENGTH: 43
<212> TYPE: PRT
<213> ORGANISM: Escherichia coli

<400> SEQUENCE: 209

Arg Met Gln Arg Ala Leu Gln Leu Ile Val Ile His Gly Phe Ser Ile
1               5                   10                  15

Lys Arg Val Ala Val Ser Cys Gly Tyr His Ser Val Ser Tyr Phe Ile
                20                  25                  30

Tyr Val Phe Arg Asn Tyr Tyr Gly Met Thr Pro
            35                  40

<210> SEQ ID NO 210
<211> LENGTH: 43
<212> TYPE: PRT
<213> ORGANISM: Escherichia coli

<400> SEQUENCE: 210

Arg Leu Arg His Ala Arg Arg Leu Leu Gln Gln Ser Pro Leu Ser Ile
1               5                   10                  15

Pro Glu Ile Ala Tyr Ala Thr Gly Phe Ser Ser Pro Ala His Phe Ser
                20                  25                  30

Asn Ala Phe Lys Arg Leu Phe Ser Gln Thr Pro
            35                  40

<210> SEQ ID NO 211
<211> LENGTH: 46
<212> TYPE: PRT
<213> ORGANISM: Escherichia coli

<400> SEQUENCE: 211

Arg Leu Glu Gly Ile Arg Ser Asp Leu Leu Asp Ser Glu Arg Asn Pro
1               5                   10                  15

Ser Asn Ile Ile Asp Thr Ala Ser Arg Trp Gly Ile Arg Ser Arg Ser
                20                  25                  30

Ala Leu Val Lys Gly Tyr Arg Lys Gln Phe Asn Glu Ala Pro
            35                  40                  45

<210> SEQ ID NO 212
<211> LENGTH: 43
<212> TYPE: PRT
<213> ORGANISM: Escherichia coli

<400> SEQUENCE: 212

Arg Met Ala Gln Ser Leu Leu Asn Ser Val Glu Gly His Glu Asn Ile
1               5                   10                  15

Thr Gln Leu Ala Val Asn His Gly Tyr Ser Ser Pro Ser His Phe Ser
                20                  25                  30

Ser Glu Ile Lys Glu Leu Ile Gly Val Ser Pro
            35                  40

<210> SEQ ID NO 213
<211> LENGTH: 43
<212> TYPE: PRT
<213> ORGANISM: Escherichia coli

<400> SEQUENCE: 213

Arg Met Tyr His Ala Ser Gln Leu Leu Ile His Thr Ser Thr Leu Ile
1               5                   10                  15

Ser Asp Ile Ser Arg Gln Val Gly Tyr Lys Asp Pro Leu Leu Phe Ser
                20                  25                  30

Lys Asn Phe Thr Lys His Phe Glu Ile Ser Ala
            35                  40

<210> SEQ ID NO 214
<211> LENGTH: 43
<212> TYPE: PRT
<213> ORGANISM: Escherichia coli

<400> SEQUENCE: 214

Arg Ile Leu Tyr Ala His Gln Leu Leu Asn Gly Lys Met Ser Ile
1               5                   10                  15

Val Asp Ile Ala Met Glu Ala Gly Phe Ser Ser Gln Ser Tyr Phe Thr
            20                  25                  30

Gln Ser Tyr Arg Arg Arg Phe Gly Cys Thr Pro
        35                  40

<210> SEQ ID NO 215
<211> LENGTH: 43
<212> TYPE: PRT
<213> ORGANISM: Escherichia coli

<400> SEQUENCE: 215

Arg Leu Asp Leu Ala Lys Gln Leu Ile Ala Glu Arg Gln Lys Pro Leu
1               5                   10                  15

Ser Gln Val Ala Gln Leu Cys Gly Phe Ser Ser Gln Ser Phe Ser
            20                  25                  30

Gln Ala Phe Arg Arg Leu Tyr Gly Met Ser Pro
        35                  40

<210> SEQ ID NO 216
<211> LENGTH: 43
<212> TYPE: PRT
<213> ORGANISM: Escherichia coli

<400> SEQUENCE: 216

Lys Met Thr Glu Ile Ala Gln Lys Leu Lys Glu Ser Asn Glu Pro Ile
1               5                   10                  15

Leu Tyr Leu Ala Glu Arg Tyr Gly Phe Glu Ser Gln Gln Thr Leu Thr
            20                  25                  30

Arg Thr Phe Lys Asn Tyr Phe Asp Val Pro Pro
        35                  40

<210> SEQ ID NO 217
<211> LENGTH: 43
<212> TYPE: PRT
<213> ORGANISM: Escherichia coli

<400> SEQUENCE: 217

Lys Met Thr Glu Ile Ala Gln Lys Leu Lys Glu Ser Asn Glu Pro Ile
1               5                   10                  15

Leu Tyr Leu Ala Glu Arg Tyr Gly Phe Glu Ser Gln Gln Thr Leu Thr
            20                  25                  30

Arg Thr Phe Lys Asn Tyr Phe Asp Val Pro Pro
        35                  40

<210> SEQ ID NO 218
<211> LENGTH: 43
<212> TYPE: PRT
<213> ORGANISM: Escherichia coli

<400> SEQUENCE: 218

Arg Ile Asn His Val Arg Ala Leu Leu Ser Asp Thr Asp Lys Ser Ile
1               5                   10                  15

Leu Asp Ile Ala Leu Thr Ala Gly Phe Arg Ser Ser Ser Arg Phe Tyr
            20                  25                  30

Ser Thr Phe Gly Lys Tyr Val Gly Met Ser Pro
            35                  40

<210> SEQ ID NO 219
<211> LENGTH: 43
<212> TYPE: PRT
<213> ORGANISM: Escherichia coli

<400> SEQUENCE: 219

Lys Ile Glu Tyr Ala Cys Gln Leu Leu Asp Ser Ser Asp Gln Ser Val
 1               5                  10                  15

Ala Arg Val Gly Gln Ala Val Gly Tyr Asp Asp Ser Tyr Tyr Phe Ser
            20                  25                  30

Arg Leu Phe Ser Lys Val Met Gly Leu Ser Pro
            35                  40

<210> SEQ ID NO 220
<211> LENGTH: 43
<212> TYPE: PRT
<213> ORGANISM: Escherichia coli

<400> SEQUENCE: 220

Arg Met Lys Arg Ser Gln Tyr Leu Leu Glu Asn Pro Lys Leu Ser Ile
 1               5                  10                  15

Ala Glu Ile Ser Asn Ser Val Gly Phe Ser Asp Ser Leu Ala Phe Ser
            20                  25                  30

Lys Ala Phe Lys Asn Tyr Phe Gly Lys Ser Pro
            35                  40

<210> SEQ ID NO 221
<211> LENGTH: 43
<212> TYPE: PRT
<213> ORGANISM: Escherichia coli

<400> SEQUENCE: 221

Arg Leu Val Asn Gly Leu Leu Asp Val Phe Leu His Asn Gln Thr Ile
 1               5                  10                  15

Thr Ser Ala Ala Met Asn Asn Gly Tyr Arg Ser Thr Ser His Phe Ser
            20                  25                  30

Asn Glu Ile Lys Thr Arg Leu Gly Phe Ser Ala
            35                  40

<210> SEQ ID NO 222
<211> LENGTH: 43
<212> TYPE: PRT
<213> ORGANISM: Escherichia coli

<400> SEQUENCE: 222

Arg Leu Val Asn Gly Leu Leu Asp Val Phe Leu His Asn Gln Thr Ile
 1               5                  10                  15

Thr Ser Ala Ala Met Asn Asn Gly Tyr Ala Ser Thr Ser His Phe Ser
            20                  25                  30

Asn Glu Ile Lys Thr Arg Leu Gly Phe Ser Ala
            35                  40

<210> SEQ ID NO 223
<211> LENGTH: 42
<212> TYPE: PRT
<213> ORGANISM: Escherichia coli

<400> SEQUENCE: 223

Arg Leu Arg Glu Ala His Arg Met Leu Cys Asp Glu Glu Ala Asn Val
1               5                   10                  15

Ser Thr Val Ala Tyr Arg Val Gly Tyr Ser Pro Ala His Phe Ser Ile
            20                  25                  30

Ala Phe Arg Lys Arg Tyr Gly Ile Ser Pro
        35                  40

<210> SEQ ID NO 224
<211> LENGTH: 43
<212> TYPE: PRT
<213> ORGANISM: Escherichia coli

<400> SEQUENCE: 224

Lys Met Lys His Ala Ser Leu Phe Leu Arg Thr Thr Asp Lys Asn Ile
1               5                   10                  15

Asp Glu Ile Ser Cys Leu Val Gly Phe Asn Ser Thr Ser Tyr Phe Ile
            20                  25                  30

Lys Val Phe Lys Glu Tyr Tyr Asn Thr Thr Pro
        35                  40

<210> SEQ ID NO 225
<211> LENGTH: 43
<212> TYPE: PRT
<213> ORGANISM: Escherichia coli

<400> SEQUENCE: 225

Arg Met Val Ser Ala Arg Glu Leu Leu Cys His Ser Asp Trp Ser Ile
1               5                   10                  15

Ala Ser Ile Ala Arg Asn Leu Gly Phe Ser Gln Thr Ser Tyr Phe Cys
            20                  25                  30

Lys Val Phe Arg Gln Thr Tyr Gln Val Thr Pro
        35                  40

<210> SEQ ID NO 226
<211> LENGTH: 43
<212> TYPE: PRT
<213> ORGANISM: Escherichia coli

<400> SEQUENCE: 226

Arg Leu Leu Glu Ala Ala Lys Ser Leu Gln Glu Lys Asp Met Ser Ile
1               5                   10                  15

Leu Asp Ile Ala Leu Met Tyr Gly Phe Ser Ser Gln Ala Thr Phe Thr
            20                  25                  30

Arg Ile Phe Lys Lys His Phe Asn Thr Thr Pro
        35                  40

<210> SEQ ID NO 227
<211> LENGTH: 43
<212> TYPE: PRT
<213> ORGANISM: Escherichia coli

<400> SEQUENCE: 227

Arg Leu Glu Asp Ala Lys Gln Arg Leu Ser Thr Ser Asn Asn Ser Val
1               5                   10                  15

Gln Ser Ile Ala Asn Met Val Gly Tyr Lys Asp Ser Phe Thr Phe Ser
            20                  25                  30

Lys Ala Phe Lys Arg Tyr Ser Gly Ala Ser Pro
        35                  40

<210> SEQ ID NO 228
<211> LENGTH: 43

```
<212> TYPE: PRT
<213> ORGANISM: Escherichia coli

<400> SEQUENCE: 228

Lys Leu Leu Leu Ala Ala Arg Asp Leu Arg Asp Thr Asp Gln Arg Val
 1               5                  10                  15

Tyr Asp Ile Cys Leu Lys Tyr Gly Phe Asp Ser Gln Gln Thr Phe Thr
            20                  25                  30

Arg Val Phe Thr Arg Thr Phe Asn Gln Pro Pro
        35                  40

<210> SEQ ID NO 229
<211> LENGTH: 43
<212> TYPE: PRT
<213> ORGANISM: Escherichia coli

<400> SEQUENCE: 229

Arg Val Cys His Ala Gln Tyr Leu Leu Gln His Ser Arg Leu Leu Ile
 1               5                  10                  15

Ser Asp Ile Ser Thr Glu Cys Gly Phe Glu Asp Ser Asn Tyr Phe Ser
            20                  25                  30

Val Val Phe Thr Arg Glu Thr Gly Met Thr Pro
        35                  40

<210> SEQ ID NO 230
<211> LENGTH: 43
<212> TYPE: PRT
<213> ORGANISM: Escherichia coli

<400> SEQUENCE: 230

Arg Ile Cys His Ala Gln Tyr Leu Leu Gln His Ser Pro Leu Met Ile
 1               5                  10                  15

Ser Glu Ile Ser Met Gln Cys Gly Phe Glu Asp Ser Asn Tyr Phe Ser
            20                  25                  30

Val Val Phe Thr Arg Glu Thr Gly Met Thr Pro
        35                  40

<210> SEQ ID NO 231
<211> LENGTH: 43
<212> TYPE: PRT
<213> ORGANISM: Escherichia coli

<400> SEQUENCE: 231

Arg Leu Met Lys Ala Arg His Leu Leu Arg His Ser Glu Ala Ser Val
 1               5                  10                  15

Thr Asp Ile Ala Tyr Arg Cys Gly Phe Ser Asp Ser Asn His Phe Ser
            20                  25                  30

Thr Leu Phe Arg Arg Glu Phe Asn Trp Ser Pro
        35                  40

<210> SEQ ID NO 232
<211> LENGTH: 43
<212> TYPE: PRT
<213> ORGANISM: Escherichia coli

<400> SEQUENCE: 232

Arg Leu Ile Lys Ala Arg His Leu Leu Arg His Ser Asp His Ser Val
 1               5                  10                  15

Thr Glu Ile Ala Tyr Arg Cys Gly Phe Gly Asp Ser Asn His Phe Ser
            20                  25                  30

Thr Leu Phe Arg Arg Glu Phe Asn Trp Ser Pro
```

<210> SEQ ID NO 233
<211> LENGTH: 45
<212> TYPE: PRT
<213> ORGANISM: Escherichia coli

<400> SEQUENCE: 233

Gln Leu Arg Met Ser Lys Ala Ala Leu Leu Leu Glu Asn Ser Tyr
1               5                   10                  15

Gln Ile Ser Gln Ile Ser Asn Met Ile Gly Ile Ser Ser Ala Ser Tyr
            20                  25                  30

Phe Ile Arg Ile Phe Asn Lys His Tyr Gly Val Thr Pro
        35                  40                  45

<210> SEQ ID NO 234
<211> LENGTH: 43
<212> TYPE: PRT
<213> ORGANISM: Escherichia coli

<400> SEQUENCE: 234

Arg Leu Leu Leu Ala Ala Val Glu Leu Arg Thr Thr Glu Arg Pro Ile
1               5                   10                  15

Phe Asp Ile Ala Met Asp Leu Gly Tyr Val Ser Gln Gln Thr Phe Ser
            20                  25                  30

Arg Val Phe Arg Arg Gln Phe Asp Arg Thr Pro
        35                  40

<210> SEQ ID NO 235
<211> LENGTH: 43
<212> TYPE: PRT
<213> ORGANISM: Escherichia coli

<400> SEQUENCE: 235

Arg Leu Leu Leu Ala Ala Val Glu Leu Arg Thr Thr Glu Arg Pro Ile
1               5                   10                  15

Phe Asp Ile Ala Met Asp Leu Gly Tyr Val Ser Gln Gln Thr Phe Ser
            20                  25                  30

Arg Val Phe Arg Arg Glu Phe Asp Arg Thr Pro
        35                  40

<210> SEQ ID NO 236
<211> LENGTH: 43
<212> TYPE: PRT
<213> ORGANISM: Escherichia coli

<400> SEQUENCE: 236

Arg Ile Ser Tyr Ser Ile Ser Leu Met Lys Thr Gly Glu Phe Lys Ile
1               5                   10                  15

Lys Gln Ile Ala Tyr Gln Ser Gly Phe Ala Ser Val Ser Tyr Phe Ser
            20                  25                  30

Thr Val Phe Lys Ser Thr Met Asn Val Ala Pro
        35                  40

<210> SEQ ID NO 237
<211> LENGTH: 46
<212> TYPE: PRT
<213> ORGANISM: Escherichia coli

<400> SEQUENCE: 237

Arg Met Gln Lys Ala Arg Lys Asp Leu Leu Arg Ala Asp Pro Ala Ser
1               5                   10                  15

```
Glu Gly Val Thr Glu Ile Ala Gln Arg Trp Gly Phe Leu His Val Gly
            20                  25                  30

Arg Phe Ala Gly Glu Tyr Lys Gln Thr Phe Gly Val Ser Pro
            35                  40                  45

<210> SEQ ID NO 238
<211> LENGTH: 43
<212> TYPE: PRT
<213> ORGANISM: Escherichia coli

<400> SEQUENCE: 238

Arg Met Gly Met Ala Leu Asn Tyr Leu Thr Phe Ser Asn Tyr Ser Val
 1               5                  10                  15

Phe Gln Ile Ser His Arg Cys Gly Phe Gly Ser Asn Ala Tyr Phe Cys
            20                  25                  30

Asp Val Phe Lys Arg Lys Tyr Asn Met Thr Pro
            35                  40

<210> SEQ ID NO 239
<211> LENGTH: 43
<212> TYPE: PRT
<213> ORGANISM: Escherichia coli

<400> SEQUENCE: 239

Arg Ile Pro Ile Ala Leu Asn Tyr Leu Thr Phe Ser Asn Tyr Ser Val
 1               5                  10                  15

Phe Gln Ile Ser His Arg Cys Gly Phe Gly Ser Asn Ala Tyr Phe Cys
            20                  25                  30

Asp Ala Phe Lys Arg Lys Tyr Gly Met Thr Pro
            35                  40

<210> SEQ ID NO 240
<211> LENGTH: 43
<212> TYPE: PRT
<213> ORGANISM: Escherichia coli

<400> SEQUENCE: 240

Arg Met His His Ala Ala Lys Leu Leu Leu Asn Ser Gln Ser Tyr Ile
 1               5                  10                  15

Asn Asp Val Ser Arg Leu Ile Gly Ile Ser Ser Pro Ser Tyr Phe Ile
            20                  25                  30

Arg Lys Phe Asn Glu Tyr Tyr Gly Ile Thr Pro
            35                  40

<210> SEQ ID NO 241
<211> LENGTH: 43
<212> TYPE: PRT
<213> ORGANISM: Escherichia coli

<400> SEQUENCE: 241

Arg Ile Leu Tyr Ala His Gln Leu Leu Leu Asn Gly Lys Met Ser Ile
 1               5                  10                  15

Val Asp Ile Ala Met Glu Ala Gly Phe Ser Ser Gln Ser Tyr Phe Thr
            20                  25                  30

Gln Ser Tyr Arg Arg Arg Phe Gly Cys Thr Pro
            35                  40

<210> SEQ ID NO 242
<211> LENGTH: 43
<212> TYPE: PRT
<213> ORGANISM: Escherichia coli
```

<400> SEQUENCE: 242

Lys Leu Glu Lys Ala Arg Ser Leu Leu Ile Ser Thr Thr Leu Ser Ile
1               5                   10                  15

Asn Glu Ile Ser Gln Met Cys Gly Tyr Pro Ser Leu Gln Tyr Phe Tyr
            20                  25                  30

Ser Val Phe Lys Lys Ala Tyr Asp Thr Thr Pro
        35                  40

<210> SEQ ID NO 243
<211> LENGTH: 43
<212> TYPE: PRT
<213> ORGANISM: Escherichia coli

<400> SEQUENCE: 243

Lys Ile Ser Arg Ala Lys Asn Leu Leu Gln Gln Thr Asp Ile Ser Ile
1               5                   10                  15

Lys Glu Ile Thr Glu Ile Cys Gly Tyr Pro Ser Ile Gln Tyr Phe Tyr
            20                  25                  30

Ser Val Phe Lys Lys Glu Phe Glu Met Thr Pro
        35                  40

<210> SEQ ID NO 244
<211> LENGTH: 46
<212> TYPE: PRT
<213> ORGANISM: Escherichia coli

<400> SEQUENCE: 244

Lys Leu Glu Ser Ile Arg Ala Cys Leu Asn Asp Pro Ser Ala Asn Val
1               5                   10                  15

Arg Ser Ile Thr Glu Ile Ala Leu Asp Tyr Gly Phe Leu His Leu Gly
            20                  25                  30

Arg Phe Ala Glu Asn Tyr Arg Ser Ala Phe Gly Glu Leu Pro
        35                  40                  45

<210> SEQ ID NO 245
<211> LENGTH: 46
<212> TYPE: PRT
<213> ORGANISM: Escherichia coli

<400> SEQUENCE: 245

Lys Leu Glu Ser Ile Arg Ala Cys Leu Asn Asp Pro Ser Ala Asn Val
1               5                   10                  15

Arg Ser Ile Thr Glu Ile Ala Leu Asp Tyr Gly Phe Leu His Leu Gly
            20                  25                  30

Arg Phe Ala Glu Asn Tyr Arg Ser Ala Phe Gly Glu Leu Pro
        35                  40                  45

<210> SEQ ID NO 246
<211> LENGTH: 46
<212> TYPE: PRT
<213> ORGANISM: Escherichia coli

<400> SEQUENCE: 246

Lys Leu Glu Cys Val Arg Ala Cys Leu Ser Asn Pro Thr Thr Asn Ile
1               5                   10                  15

Arg Ser Ile Thr Glu Val Ala Leu Asp Tyr Gly Phe Leu His Leu Gly
            20                  25                  30

Arg Phe Ala Glu Lys Tyr Arg Ser Thr Phe Gly Glu Leu Pro
        35                  40                  45

<210> SEQ ID NO 247
<211> LENGTH: 46
<212> TYPE: PRT
<213> ORGANISM: Escherichia coli

<400> SEQUENCE: 247

Lys Leu Glu Cys Ile Arg Ala Arg Leu Ser Asp Pro Asn Ala Asn Val
1               5                   10                  15

Arg Ser Val Thr Glu Met Ala Leu Asp Tyr Gly Phe Phe His Thr Gly
            20                  25                  30

Arg Phe Ala Glu Asn Tyr Arg Ser Thr Phe Gly Glu Leu Pro
        35                  40                  45

<210> SEQ ID NO 248
<211> LENGTH: 46
<212> TYPE: PRT
<213> ORGANISM: Escherichia coli

<400> SEQUENCE: 248

Lys Leu Glu Cys Ile Arg Ala Arg Leu Ser Asp Pro Asn Ala Asn Val
1               5                   10                  15

Arg Ser Val Thr Glu Met Ala Leu Asp Tyr Gly Phe Phe His Thr Gly
            20                  25                  30

Arg Phe Ala Glu Asn Tyr Arg Ser Thr Phe Gly Glu Leu Pro
        35                  40                  45

<210> SEQ ID NO 249
<211> LENGTH: 44
<212> TYPE: PRT
<213> ORGANISM: Escherichia coli

<400> SEQUENCE: 249

Arg Leu Ala Ala Ala His Gly Ala Ile Lys Ala Gly Arg Ala Gly Ser
1               5                   10                  15

Ile Thr Glu Leu Ala Leu Asn Leu Gln Phe Ser Asn Pro Gly Arg Phe
            20                  25                  30

Ser Val Leu Tyr Lys Ser Ala Tyr Gly Leu Ser Pro
        35                  40

<210> SEQ ID NO 250
<211> LENGTH: 43
<212> TYPE: PRT
<213> ORGANISM: Escherichia coli

<400> SEQUENCE: 250

Arg Leu Gln Ser Ala Ala Phe Leu Leu Lys Gln Ser Gln Gln Ser Val
1               5                   10                  15

Leu Ala Ile Ala Leu Glu Val Gly Tyr Gln Ser Glu Ala His Phe Cys
            20                  25                  30

Lys Val Phe Lys Asn Tyr Tyr Gln Leu Ser Pro
        35                  40

<210> SEQ ID NO 251
<211> LENGTH: 43
<212> TYPE: PRT
<213> ORGANISM: Escherichia coli

<400> SEQUENCE: 251

Arg Ile Thr Lys Ala Lys Arg Leu Met Ala Lys Ser Asn Cys Lys Leu
1               5                   10                  15

Lys Glu Ile Ala His Gln Thr Gly Tyr Gln Asp Glu Phe Tyr Phe Ser

```
            20                  25                  30

Arg Ile Phe Lys Lys Tyr Thr Gly Cys Ser Pro
        35                  40

<210> SEQ ID NO 252
<211> LENGTH: 41
<212> TYPE: PRT
<213> ORGANISM: Escherichia coli

<400> SEQUENCE: 252

Arg Ile Glu Gln Ala Lys Lys Val Leu Leu Lys Ser Val Thr Glu
 1               5                  10                  15

Thr Ala Tyr Glu Val Gly Phe Asn Asn Ser Asn Tyr Phe Ala Thr Val
            20                  25                  30

Phe Lys Lys Arg Thr Asn Tyr Thr Pro
        35                  40

<210> SEQ ID NO 253
<211> LENGTH: 42
<212> TYPE: PRT
<213> ORGANISM: Escherichia coli

<400> SEQUENCE: 253

Arg Met Gln His Ala Lys Asn Leu Ile Arg Val Glu Gly Ser Val Asn
 1               5                  10                  15

Lys Ile Ala Glu Gln Cys Gly Tyr Ala Ser Thr Ser Tyr Phe Ile Tyr
            20                  25                  30

Ala Phe Arg Lys His Phe Gly Asn Ser Pro
        35                  40

<210> SEQ ID NO 254
<211> LENGTH: 42
<212> TYPE: PRT
<213> ORGANISM: Escherichia coli

<400> SEQUENCE: 254

Gln Leu Ile Met Ala Leu Gln Gly Leu Val Lys Gly Asp Thr Val Gln
 1               5                  10                  15

Lys Val Ala His Thr Leu Gly Tyr Asp Ser Thr Thr Ala Phe Ile Thr
            20                  25                  30

Met Phe Lys Lys Gly Leu Gly Gln Thr Pro
        35                  40

<210> SEQ ID NO 255
<211> LENGTH: 42
<212> TYPE: PRT
<213> ORGANISM: Escherichia coli

<400> SEQUENCE: 255

Lys Ile Asn Lys Ala Ala Glu Leu Leu Lys Ser Thr Asn Leu Ser Ile
 1               5                  10                  15

Lys Glu Ile Ala Glu Glu Ile Gly Phe Ser Val His Tyr Phe Thr Arg
            20                  25                  30

Val Phe Ser Ala Lys Ile Gly Ser Ser Pro
        35                  40

<210> SEQ ID NO 256
<211> LENGTH: 43
<212> TYPE: PRT
<213> ORGANISM: Escherichia coli

<400> SEQUENCE: 256
```

Arg Met Ser Met Ala Arg Arg Leu Leu Glu Leu Arg Gln Ile Pro Leu
1               5                   10                  15

His Thr Ile Ala Glu Lys Cys Gly Tyr Ser Ser Thr Ser Tyr Phe Ile
                20                  25                  30

Asn Thr Phe Arg Gln Tyr Tyr Gly Val Thr Pro
                35                  40

<210> SEQ ID NO 257
<211> LENGTH: 43
<212> TYPE: PRT
<213> ORGANISM: Escherichia coli

<400> SEQUENCE: 257

Arg Leu Asp Leu Ala Leu Ser Leu Leu Lys Gln Gln Gly Asn Ser Val
1               5                   10                  15

Gly Glu Val Ala Asp Thr Leu Asn Phe Phe Asp Ser Phe His Phe Ser
                20                  25                  30

Lys Ala Phe Lys His Lys Phe Gly Tyr Ala Pro
                35                  40

<210> SEQ ID NO 258
<211> LENGTH: 43
<212> TYPE: PRT
<213> ORGANISM: Escherichia coli

<400> SEQUENCE: 258

Arg Leu Glu His Ala Lys Thr Leu Leu Lys Gly Tyr Asp Leu Lys Val
1               5                   10                  15

Lys Glu Val Ala His Ala Cys Gly Phe Val Asp Ser Asn Tyr Phe Cys
                20                  25                  30

Arg Leu Phe Arg Lys Asn Thr Glu Arg Ser Pro
                35                  40

<210> SEQ ID NO 259
<211> LENGTH: 43
<212> TYPE: PRT
<213> ORGANISM: Escherichia coli

<400> SEQUENCE: 259

Arg Met Thr Glu Ala Lys Arg Leu Leu Ser Ser Thr Asn Asp Lys Met
1               5                   10                  15

Gly Val Ile Ala Glu Thr Val Gly Met Glu Asp Pro Thr Tyr Phe Ser
                20                  25                  30

Lys Leu Phe Lys Gln Ile Glu Gly Ile Ser Pro
                35                  40

<210> SEQ ID NO 260
<211> LENGTH: 42
<212> TYPE: PRT
<213> ORGANISM: Escherichia coli

<400> SEQUENCE: 260

Arg Met Gln Arg Ala Leu Arg Leu Ala Arg Ala Gly Val Pro Phe Ala
1               5                   10                  15

Glu Thr Ala Thr Leu Ala Gly Phe Ala Asp Gln Ala His Leu Ala Arg
                20                  25                  30

Asp Val Arg Glu Met Ala Gly Ser Ser Leu
                35                  40

<210> SEQ ID NO 261

```
<211> LENGTH: 43
<212> TYPE: PRT
<213> ORGANISM: Escherichia coli

<400> SEQUENCE: 261

Arg Met Ala Lys Ala Arg Met Ile Leu Gln Lys Tyr His Leu Ser Ile
1               5                   10                  15

His Glu Val Ala Gln Arg Cys Gly Phe Pro Asp Ser Asp Tyr Phe Cys
            20                  25                  30

Arg Val Phe Arg Arg Gln Phe Gly Leu Thr Pro
        35                  40

<210> SEQ ID NO 262
<211> LENGTH: 43
<212> TYPE: PRT
<213> ORGANISM: Escherichia coli

<400> SEQUENCE: 262

Lys Ile Thr His Ala Cys Arg Leu Leu Glu Gln Glu Thr Pro Val Thr
1               5                   10                  15

Leu Glu Ala Leu Ala Asp Gln Val Ala Met Ser Pro Phe His Leu His
            20                  25                  30

Arg Leu Phe Lys Ala Thr Thr Gly Met Thr Pro
        35                  40

<210> SEQ ID NO 263
<211> LENGTH: 42
<212> TYPE: PRT
<213> ORGANISM: Escherichia coli

<400> SEQUENCE: 263

Arg Ala Arg Arg Leu Arg Glu Ser Leu Ala Lys Gly Glu Ser Val Thr
1               5                   10                  15

Thr Ser Ile Leu Asn Ala Gly Phe Pro Asp Ser Ser Tyr Tyr Arg
            20                  25                  30

Lys Ala Asp Glu Thr Leu Gly Met Thr Ala
        35                  40

<210> SEQ ID NO 264
<211> LENGTH: 43
<212> TYPE: PRT
<213> ORGANISM: Escherichia coli

<400> SEQUENCE: 264

Lys Ile Ala Cys Ala Cys Arg Leu Leu Glu Gln Glu Thr Pro Val Thr
1               5                   10                  15

Leu Ala Phe Leu Ala Gln Ala Val Ala Met Ser Pro Phe His Leu His
            20                  25                  30

Arg Leu Phe Lys Ala Ser Thr Gly Met Thr Pro
        35                  40

<210> SEQ ID NO 265
<211> LENGTH: 42
<212> TYPE: PRT
<213> ORGANISM: Escherichia coli

<400> SEQUENCE: 265

Arg Ala Arg Arg Leu Arg Glu Ala Leu Ala Lys Gly Glu Pro Ile Thr
1               5                   10                  15

Ala Ala Ile Tyr Arg Ala Gly Phe Pro Asp Ser Ser Tyr Tyr Arg
            20                  25                  30
```

His Ala Asp Gln Thr Leu Gly Met Thr Ala
          35                  40

<210> SEQ ID NO 266
<211> LENGTH: 46
<212> TYPE: PRT
<213> ORGANISM: Escherichia coli

<400> SEQUENCE: 266

Arg Val Arg Arg Ala Ser Arg Ala Ala Leu Leu Arg Leu Thr Arg
 1               5                  10                  15

Leu Thr Ile Ile Glu Ile Ser Ala Lys Leu Phe Tyr Asp Ser Gln Gln
              20                  25                  30

Thr Phe Thr Arg Glu Phe Lys Lys Ile Phe Gly Tyr Thr Pro
          35                  40                  45

<210> SEQ ID NO 267
<211> LENGTH: 46
<212> TYPE: PRT
<213> ORGANISM: Escherichia coli

<400> SEQUENCE: 267

Arg Ala Arg Arg Leu Ser Lys Ser Ala Val Ala Leu Arg Leu Thr Ala
 1               5                  10                  15

Arg Pro Ile Leu Asp Ile Ala Leu Gln Tyr Arg Phe Asp Ser Gln Gln
              20                  25                  30

Thr Phe Thr Arg Ala Phe Lys Lys Gln Phe Ala Gln Thr Pro
          35                  40                  45

<210> SEQ ID NO 268
<211> LENGTH: 46
<212> TYPE: PRT
<213> ORGANISM: Escherichia coli

<400> SEQUENCE: 268

Arg Ala Arg Arg Leu Thr Lys Ala Ala Val Glu Leu Arg Leu Thr Lys
 1               5                  10                  15

Lys Thr Ile Leu Glu Ile Ala Leu Lys Tyr Gln Phe Ser Gln Gln
              20                  25                  30

Ser Phe Thr Arg Arg Phe Lys Tyr Ile Phe Lys Val Thr Pro
          35                  40                  45

<210> SEQ ID NO 269
<211> LENGTH: 52
<212> TYPE: PRT
<213> ORGANISM: Providencia Stuartii

<400> SEQUENCE: 269

Ser Glu Ile Leu Val Trp Ile Glu Gly Asn Leu Thr Asn Arg Leu Ser
 1               5                  10                  15

Leu Asp Asp Ile Ala Gln His Ser Gly Tyr Thr Lys Trp His Leu Gln
              20                  25                  30

Arg Val Phe Arg Lys Ile Val Gly Met Pro Leu Gly Glu Tyr Ile Arg
          35                  40                  45

Arg Arg Arg Ile
     50

<210> SEQ ID NO 270
<211> LENGTH: 53
<212> TYPE: PRT
<213> ORGANISM: Escherichia coli

```
<400> SEQUENCE: 270

Asp Lys Ile Thr His Ala Cys Arg Leu Glu Gln Glu Thr Pro Val
1               5                   10                  15

Thr Leu Glu Ala Leu Ala Asp Gln Val Ala Met Ser Pro Phe His Leu
            20                  25                  30

His Arg Leu Phe Lys Ala Thr Thr Gly Met Thr Pro Lys Ala Trp Gln
        35                  40                  45

Gln Ala Trp Arg Ala
    50

<210> SEQ ID NO 271
<211> LENGTH: 52
<212> TYPE: PRT
<213> ORGANISM: Mycobacterium tuberculosis

<400> SEQUENCE: 271

Ala Arg Ala Met Arg Leu Ile Ala Asp Gly Thr Val Asp Arg Asp Gly
1               5                   10                  15

Val Ser Gly Leu Ala Ala Gln Leu Gly Tyr Thr Ile Arg Gln Leu Glu
            20                  25                  30

Arg Leu Leu Gln Ala Val Val Gly Ala Gly Pro Leu Ala Leu Ala Arg
        35                  40                  45

Ala Gln Arg Met
    50

<210> SEQ ID NO 272
<211> LENGTH: 44
<212> TYPE: PRT
<213> ORGANISM: Escherichia coli

<400> SEQUENCE: 272

Leu Glu Gln Glu Thr Pro Val Thr Leu Ala Phe Leu Ala Gln Ala Val
1               5                   10                  15

Ala Met Ser Pro Phe His Leu His Arg Leu Phe Lys Ala Ser Thr Gly
            20                  25                  30

Met Thr Pro Lys Gly Trp Gln Gln Ala Trp Arg Ala
        35                  40

<210> SEQ ID NO 273
<211> LENGTH: 52
<212> TYPE: PRT
<213> ORGANISM: Escherichia coli

<400> SEQUENCE: 273

Asp Leu Ile Thr Glu Tyr Ile Asp Lys Asn Phe Thr Glu Lys Leu Thr
1               5                   10                  15

Leu Glu Ser Leu Ala Asp Ile Cys His Gly Ser Pro Tyr His Met His
            20                  25                  30

Arg Thr Phe Lys Lys Ile Lys Gly Ile Thr Leu Val Gly Tyr Ile Gln
        35                  40                  45

Gln Val Arg Val
    50

<210> SEQ ID NO 274
<211> LENGTH: 51
<212> TYPE: PRT
<213> ORGANISM: Escherichia coli

<400> SEQUENCE: 274

Asp Ser Val Tyr Gln Ile Ile Glu Ser Asp Ile His Lys Asp Trp Asn
```

-continued

```
                1               5                  10                 15
Leu Ser Met Val Ala Ser Cys Leu Cys Leu Ser Pro Ser Leu Leu Lys
                20                  25                 30

Lys Lys Leu Lys Ser Glu Asn Thr Ser Tyr Ser Gln Ile Ile Thr Thr
            35                  40                  45

Cys Arg Met
        50
```

<210> SEQ ID NO 275
<211> LENGTH: 51
<212> TYPE: PRT
<213> ORGANISM: Escherichia coli

<400> SEQUENCE: 275

```
Asp Lys Val Arg Asn Thr Ile Glu Lys Asp Leu Ser Lys Arg Trp Thr
 1               5                  10                 15

Leu Ala Ile Ile Ala Asp Glu Phe Asn Val Ser Glu Ile Thr Ile Arg
                20                  25                 30

Lys Arg Leu Glu Ser Glu Tyr Ile Thr Phe Asn Gln Ile Leu Met Gln
            35                  40                  45

Ser Arg Met
        50
```

<210> SEQ ID NO 276
<211> LENGTH: 51
<212> TYPE: PRT
<213> ORGANISM: Escherichia coli

<400> SEQUENCE: 276

```
Cys Lys Ile Thr Gly Ile Ile Ser Phe Asn Ile Glu Arg Gln Trp His
 1               5                  10                 15

Leu Lys Asp Ile Ala Glu Leu Ile Tyr Thr Ser Glu Ser Leu Ile Lys
                20                  25                 30

Lys Arg Leu Arg Asp Glu Gly Thr Ser Phe Thr Glu Ile Leu Arg Asp
            35                  40                  45

Thr Arg Met
        50
```

<210> SEQ ID NO 277
<211> LENGTH: 53
<212> TYPE: PRT
<213> ORGANISM: Escherichia coli

<400> SEQUENCE: 277

```
Arg Asp Ala Cys Gln Tyr Ile Ser Asp His Leu Ala Asp Ser Asn Phe
 1               5                  10                 15

Asp Ile Ala Ser Val Ala Gln His Val Cys Leu Ser Pro Ser Arg Leu
                20                  25                 30

Ser His Leu Phe Arg Gln Gln Leu Gly Ile Ser Val Leu Ser Trp Arg
            35                  40                  45

Glu Asp Gln Arg Ile
        50
```

<210> SEQ ID NO 278
<211> LENGTH: 53
<212> TYPE: PRT
<213> ORGANISM: Escherichia coli

<400> SEQUENCE: 278

Arg Glu Ala Cys Gln Tyr Ile Ser Asp His Leu Ala Asp Ser Asn Phe

```
                1               5                  10                  15
Asp Ile Ala Ser Val Ala Gln His Val Cys Leu Ser Pro Ser Arg Leu
                20                      25                  30

Ser His Leu Phe Arg Gln Gln Leu Gly Ile Ser Val Leu Ser Trp Arg
            35                      40                  45

Glu Asp Gln Arg Ile
        50

<210> SEQ ID NO 279
<211> LENGTH: 52
<212> TYPE: PRT
<213> ORGANISM: Escherichia coli

<400> SEQUENCE: 279

Ile Glu Ala Cys Gln Phe Ile Thr Ser Asn Leu Ala Gly Glu Leu Arg
1               5                   10                  15

Ile Asp Glu Val Ala Arg His Val Cys Leu Ser Pro Ser Arg Leu Ala
                20                      25                  30

His Leu Phe Arg Glu Gln Val Gly Ile Asn Ile Leu Arg Trp Arg Glu
            35                      40                  45

Asp Gln Arg Val
        50

<210> SEQ ID NO 280
<211> LENGTH: 53
<212> TYPE: PRT
<213> ORGANISM: Escherichia coli

<400> SEQUENCE: 280

Arg Asp Ala Cys Gln Tyr Ile Ser Asp His Leu Ala Asp Ser His Phe
1               5                   10                  15

Asp Ile Ala Ser Val Ala Gln His Val Cys Leu Ser Pro Ser Arg Leu
                20                      25                  30

Ser His Leu Phe Arg Gln Gln Leu Gly Ile Ser Val Leu Ser Trp Arg
            35                      40                  45

Glu Asp Gln Arg Ile
        50

<210> SEQ ID NO 281
<211> LENGTH: 52
<212> TYPE: PRT
<213> ORGANISM: Escherichia coli

<400> SEQUENCE: 281

Ala Ser Ala Leu Thr Phe Leu His Arg Asp Pro Ala His Ser Trp Thr
1               5                   10                  15

Val Ala Glu Leu Ala Ser Ala Ala Val Ser Arg Ser Thr Leu Ala
                20                      25                  30

Ala Arg Phe Lys Ala Thr Val Gly Gln Gly Pro Leu Glu Tyr Leu Thr
            35                      40                  45

Arg Trp Arg Ile
        50

<210> SEQ ID NO 282
<211> LENGTH: 52
<212> TYPE: PRT
<213> ORGANISM: Escherichia coli

<400> SEQUENCE: 282

Ala Thr Ala Leu Thr Cys Leu His Arg Asp Pro Ala Arg Ser Trp Thr
```

-continued

```
                1               5                  10                 15
Val Ala Asp Leu Ala Asp Thr Ala Ala Val Ser Arg Ser Thr Leu Ala
                    20                  25                  30

Ala Arg Phe Lys Ala Thr Val Gly Gln Gly Pro Leu Glu Tyr Leu Thr
            35                  40                  45

Arg Trp Arg Ile
    50

<210> SEQ ID NO 283
<211> LENGTH: 53
<212> TYPE: PRT
<213> ORGANISM: Escherichia coli

<400> SEQUENCE: 283

Asn Ser Ile Ile Gln Tyr Ile Glu Glu Asn Leu Glu Ser Lys Phe Ile
1               5                   10                  15

Asn Ile Asp Cys Leu Val Leu Tyr Ser Gly Phe Ser Arg Arg Tyr Leu
            20                  25                  30

Gln Ile Ser Phe Lys Glu Tyr Val Gly Met Pro Ile Gly Thr Tyr Ile
        35                  40                  45

Arg Val Arg Arg Ala
    50

<210> SEQ ID NO 284
<211> LENGTH: 60
<212> TYPE: PRT
<213> ORGANISM: Escherichia coli

<400> SEQUENCE: 284

Asp Asp Val Pro Gln Trp Leu Lys Ser Thr Val Glu Lys Met His Asp
1               5                   10                  15

Lys Glu Gln Phe Ser Glu Ser Ala Leu Glu Asn Met Val Ala Leu Ser
            20                  25                  30

Ala Lys Ser Gln Glu Tyr Leu Thr Arg Ala Thr Gln Arg Tyr Tyr Gly
        35                  40                  45

Lys Thr Pro Met Gln Ile Ile Asn Glu Ile Arg Ile
    50                  55                  60

<210> SEQ ID NO 285
<211> LENGTH: 51
<212> TYPE: PRT
<213> ORGANISM: Escherichia coli

<400> SEQUENCE: 285

Asp Lys Val Arg Asn Val Ile Glu Lys Asp Leu Ser Arg Lys Trp Thr
1               5                   10                  15

Leu Gly Ile Ile Ala Asp Ala Phe Asn Val Ser Glu Ile Thr Ile Arg
            20                  25                  30

Lys Arg Leu Glu Ser Glu Asn Thr Asn Phe Asn Gln Ile Leu Met Gln
        35                  40                  45

Leu Arg Met
    50

<210> SEQ ID NO 286
<211> LENGTH: 51
<212> TYPE: PRT
<213> ORGANISM: Escherichia coli

<400> SEQUENCE: 286

Asp Lys Val Arg Gly Val Ile Glu Lys Asp Leu Ser Arg Lys Trp Thr
```

```
                1               5                  10                 15
Leu Ala Ile Ile Ala Asp Val Phe Asn Val Ser Glu Ile Thr Ile Arg
                    20                 25                 30

Lys Arg Leu Glu Ser Glu Asp Thr Asn Phe Asn Gln Ile Leu Met Gln
            35                 40                 45

Ser Arg Met
        50

<210> SEQ ID NO 287
<211> LENGTH: 51
<212> TYPE: PRT
<213> ORGANISM: Escherichia coli

<400> SEQUENCE: 287

Asp Ser Val Cys Arg Ile Ile Gln Ser Asp Ile Gln His Tyr Trp Asn
  1               5                  10                 15

Leu Arg Ile Val Ala Ser Ser Leu Cys Leu Ser Pro Ser Leu Leu Lys
                    20                 25                 30

Lys Lys Leu Lys Asn Glu Asn Thr Ser Tyr Ser Gln Ile Val Thr Glu
            35                 40                 45

Cys Arg Met
        50

<210> SEQ ID NO 288
<211> LENGTH: 52
<212> TYPE: PRT
<213> ORGANISM: Escherichia coli

<400> SEQUENCE: 288

Ser Arg Ala Arg Glu Tyr Val Leu Glu Asn Met Ser Glu Pro Val Thr
  1               5                  10                 15

Val Leu Asp Leu Cys Asn Gln Leu His Val Ser Arg Arg Thr Leu Gln
                    20                 25                 30

Asn Ala Phe His Ala Ile Leu Gly Ile Gly Pro Asn Ala Trp Leu Lys
            35                 40                 45

Arg Ile Arg Leu
        50

<210> SEQ ID NO 289
<211> LENGTH: 52
<212> TYPE: PRT
<213> ORGANISM: Escherichia coli

<400> SEQUENCE: 289

Ser Arg Ala Arg Glu Tyr Val Leu Glu Asn Met Ser Glu Pro Leu Thr
  1               5                  10                 15

Val Leu Asp Leu Cys Asn Gln Leu His Val Ser Arg Arg Thr Leu Gln
                    20                 25                 30

Asn Ala Phe His Ala Ile Leu Gly Ile Gly Pro Asn Ala Trp Leu Lys
            35                 40                 45

Arg Ile Arg Leu
        50

<210> SEQ ID NO 290
<211> LENGTH: 52
<212> TYPE: PRT
<213> ORGANISM: Escherichia coli

<400> SEQUENCE: 290

Glu Arg Leu Gln Leu Phe Met Glu Lys His Tyr Leu Asn Glu Trp Lys
```

```
                1               5                   10                  15
Leu Ser Asp Phe Ser Arg Glu Phe Gly Met Gly Leu Thr Thr Phe Lys
                20                  25                  30

Glu Leu Phe Gly Ser Val Tyr Gly Val Ser Pro Arg Ala Trp Ile Ser
                35                  40                  45

Glu Arg Arg Ile
            50
```

<210> SEQ ID NO 291
<211> LENGTH: 51
<212> TYPE: PRT
<213> ORGANISM: Escherichia coli

<400> SEQUENCE: 291

```
Glu Arg Ile Val Thr Leu Leu Phe Ser Asp Leu Thr Arg Lys Trp Lys
 1               5                  10                  15

Leu Ser Asp Ile Ala Glu Glu Met His Ile Ser Glu Ile Ser Val Arg
                20                  25                  30

Lys Arg Leu Glu Gln Glu Cys Leu Asn Phe Asn Gln Leu Ile Leu Asp
                35                  40                  45

Val Arg Met
        50
```

<210> SEQ ID NO 292
<211> LENGTH: 52
<212> TYPE: PRT
<213> ORGANISM: Escherichia coli

<400> SEQUENCE: 292

```
Gln Lys Val Val Thr Leu Ile Asp Asp Asn Ile Arg Glu Glu Ile Leu
 1               5                  10                  15

Arg Pro Glu Trp Ile Ala Gly Glu Thr Gly Met Ser Val Arg Ser Leu
                20                  25                  30

Tyr Arg Met Phe Ala Asp Lys Gly Leu Val Val Ala Gln Tyr Ile Arg
                35                  40                  45

Asn Arg Arg Leu
        50
```

<210> SEQ ID NO 293
<211> LENGTH: 51
<212> TYPE: PRT
<213> ORGANISM: Escherichia coli

<400> SEQUENCE: 293

```
Thr Arg Val Cys Thr Val Ile Asn Asn Asn Ile Ala His Glu Trp Thr
 1               5                  10                  15

Leu Ala Arg Ile Ala Ser Glu Leu Leu Met Ser Pro Ser Leu Leu Lys
                20                  25                  30

Lys Lys Leu Arg Glu Glu Gly Thr Ser Tyr Ser Gln Leu Leu Thr Glu
                35                  40                  45

Cys Arg Met
        50
```

<210> SEQ ID NO 294
<211> LENGTH: 51
<212> TYPE: PRT
<213> ORGANISM: Escherichia coli

<400> SEQUENCE: 294

```
Thr Arg Val Cys Thr Val Ile Asn Asn Asn Ile Ala His Glu Trp Thr
 1               5                  10                  15
```

```
                1               5                  10                 15
Leu Ala Arg Ile Ala Ser Glu Leu Leu Met Ser Pro Ser Leu Leu Lys
                20                 25                 30

Lys Lys Leu Arg Glu Glu Glu Thr Ser Tyr Ser Gln Leu Leu Thr Glu
        35                 40                 45

Cys Arg Met
    50
```

<210> SEQ ID NO 295
<211> LENGTH: 51
<212> TYPE: PRT
<213> ORGANISM: Escherichia coli

<400> SEQUENCE: 295

```
Thr Arg Val Cys Thr Val Ile Asn Asn Asn Ile Ala His Glu Trp Thr
  1               5                  10                 15

Leu Ala Arg Ile Ala Ser Glu Leu Leu Met Ser Pro Ser Leu Leu Lys
                20                 25                 30

Lys Lys Leu Arg Glu Glu Glu Thr Ser Tyr Ser Gln Leu Leu Thr Glu
        35                 40                 45

Cys Arg Met
    50
```

<210> SEQ ID NO 296
<211> LENGTH: 52
<212> TYPE: PRT
<213> ORGANISM: Escherichia coli

<400> SEQUENCE: 296

```
Leu Ala Val Leu Glu Lys Met Glu Thr Ala Ile Glu Arg Pro Leu Asp
  1               5                  10                 15

Arg Thr Ala Met Ala Arg Leu Ala Gly Val Ser Pro Arg His Leu Asp
                20                 25                 30

Arg Leu Phe Arg Glu His Arg Gly Thr Gly Phe Leu Asp Thr Tyr Arg
        35                 40                 45

Glu Ile Arg Leu
    50
```

<210> SEQ ID NO 297
<211> LENGTH: 53
<212> TYPE: PRT
<213> ORGANISM: Escherichia coli

<400> SEQUENCE: 297

```
Arg Arg Ala Tyr Arg Tyr Ile Ile Glu Asn Ile Glu Arg Ser Asp Leu
  1               5                  10                 15

Thr Thr Arg Glu Val Ala Ala His Ile Asn Val Thr Glu Arg Ala Leu
                20                 25                 30

Gln Leu Ala Phe Lys Ser Ala Val Gly Met Ser Pro Ser Ser Val Ile
        35                 40                 45

Arg Arg Met Arg Leu
    50
```

<210> SEQ ID NO 298
<211> LENGTH: 52
<212> TYPE: PRT
<213> ORGANISM: Escherichia coli

<400> SEQUENCE: 298

```
Tyr Trp Leu Val Gly Tyr Leu Leu Ala Gln Ser Thr Ser Gly Asn Thr
```

-continued

```
                1               5                  10                  15
Met Arg Met Leu Gly Glu Asp Tyr Gly Val Ser Tyr Thr His Phe Arg
                    20                  25                  30

Arg Leu Cys Ser Arg Ala Leu Gly Gly Lys Ala Lys Ser Glu Leu Arg
            35                  40                  45

Asn Trp Arg Met
        50
```

<210> SEQ ID NO 299
<211> LENGTH: 52
<212> TYPE: PRT
<213> ORGANISM: Escherichia coli

<400> SEQUENCE: 299

```
Gln His Ala Val Asp Phe Ile Asn Thr Asn Tyr Gln Lys His Ile Thr
  1               5                  10                  15

Val Glu Asp Val Ala Lys Ser Val Asn Ile Thr Arg Ser His Leu Tyr
            20                  25                  30

Lys Leu Phe Lys Lys Asn Leu Gly Cys Ser Pro Lys Glu Tyr Leu Thr
            35                  40                  45

Tyr Ile Arg Met
        50
```

<210> SEQ ID NO 300
<211> LENGTH: 52
<212> TYPE: PRT
<213> ORGANISM: Escherichia coli

<400> SEQUENCE: 300

```
Glu Arg Leu Gln Lys Phe Met Glu Glu Asn Tyr Leu Gln Gly Trp Lys
  1               5                  10                  15

Leu Ser Lys Phe Ala Arg Glu Phe Gly Met Gly Leu Thr Thr Phe Lys
            20                  25                  30

Glu Leu Phe Gly Thr Val Tyr Gly Ile Ser Pro Arg Ala Trp Ile Ser
            35                  40                  45

Glu Arg Arg Ile
        50
```

<210> SEQ ID NO 301
<211> LENGTH: 52
<212> TYPE: PRT
<213> ORGANISM: Escherichia coli

<400> SEQUENCE: 301

```
Val Leu Ile Asp Asn Tyr Ile Glu Gln His Leu Gln Lys Lys Ile Ser
  1               5                  10                  15

Val Ala Glu Leu Ser Ser Val Ala Phe Leu Ala Gln Ser Gln Phe Tyr
            20                  25                  30

Ala Leu Phe Lys Ser Gln Met Gly Ile Thr Pro His Gln Tyr Val Leu
            35                  40                  45

Arg Lys Arg Leu
        50
```

<210> SEQ ID NO 302
<211> LENGTH: 52
<212> TYPE: PRT
<213> ORGANISM: Escherichia coli

<400> SEQUENCE: 302

```
His Ser Ile Leu Asp Trp Ile Glu Asp Asn Leu Glu Ser Pro Leu Ser
```

```
                1               5                  10                 15
Leu Glu Lys Val Ser Glu Arg Ser Gly Tyr Ser Lys Trp His Leu Gln
                        20                 25                 30

Arg Met Phe Lys Lys Glu Thr Gly His Ser Leu Gly Gln Tyr Ile Arg
            35                 40                 45

Ser Arg Lys Met
    50

<210> SEQ ID NO 303
<211> LENGTH: 52
<212> TYPE: PRT
<213> ORGANISM: Escherichia coli

<400> SEQUENCE: 303

His Ser Ile Leu Asp Trp Ile Glu Asp Asn Leu Glu Ser Pro Leu Ser
1               5                  10                 15

Leu Glu Lys Val Ser Glu Arg Ser Gly Tyr Ser Lys Trp His Leu Gln
                        20                 25                 30

Arg Met Phe Lys Lys Glu Thr Gly His Ser Leu Gly Gln Tyr Ile Arg
            35                 40                 45

Ser Arg Lys Met
    50

<210> SEQ ID NO 304
<211> LENGTH: 52
<212> TYPE: PRT
<213> ORGANISM: Escherichia coli

<400> SEQUENCE: 304

Ser Gln Met Leu Gly Phe Ile Ala Glu Asn Tyr Asp Gln Ala Leu Thr
1               5                  10                 15

Ile Asn Asp Val Ala Glu His Val Lys Leu Asn Ala Asn Tyr Ala Met
                        20                 25                 30

Gly Ile Phe Gln Arg Val Met Gln Leu Thr Met Lys Gln Tyr Ile Thr
            35                 40                 45

Ala Met Arg Ile
    50

<210> SEQ ID NO 305
<211> LENGTH: 52
<212> TYPE: PRT
<213> ORGANISM: Escherichia coli

<400> SEQUENCE: 305

Asp Gly Leu His Ala Tyr Met Arg Glu His Leu His Ala Arg Leu Glu
1               5                  10                 15

Leu Glu Arg Leu Ala Ala Phe Cys Asn Leu Ser Lys Phe His Phe Val
                        20                 25                 30

Ser Arg Tyr Lys Ala Ile Thr Gly Arg Thr Pro Ile Gln His Phe Leu
            35                 40                 45

His Leu Lys Ile
    50

<210> SEQ ID NO 306
<211> LENGTH: 52
<212> TYPE: PRT
<213> ORGANISM: Escherichia coli

<400> SEQUENCE: 306

Asn Gln Val Lys Lys Ile Ile His Ser Gln Tyr Gly Ser Ser Leu Arg
```

```
                1               5                   10                  15
Val Asn Asp Ile Ala Lys Lys Leu Asn Leu Ser Arg Ser Tyr Leu Tyr
                    20                  25                  30

Lys Ile Phe Arg Lys Ser Thr Asn Leu Ser Ile Lys Glu Tyr Ile Leu
            35                  40                  45

Gln Val Arg Met
    50

<210> SEQ ID NO 307
<211> LENGTH: 54
<212> TYPE: PRT
<213> ORGANISM: Escherichia coli

<400> SEQUENCE: 307

Tyr His Leu Val Leu Tyr Leu Leu Arg Thr Ile Glu Lys Glu Lys Glu
 1               5                  10                  15

Val Arg Ile Lys Ser Leu Thr Glu His Tyr Gly Val Ser Glu Ala Tyr
                    20                  25                  30

Phe Arg Ser Leu Cys Arg Lys Ala Leu Gly Ala Lys Val Lys Glu Gln
            35                  40                  45

Leu Asn Thr Trp Arg Leu
    50

<210> SEQ ID NO 308
<211> LENGTH: 54
<212> TYPE: PRT
<213> ORGANISM: Escherichia coli

<400> SEQUENCE: 308

Tyr His Leu Val Leu Tyr Leu Leu Arg Thr Ile Glu Lys Glu Lys Glu
 1               5                  10                  15

Val Arg Ile Lys Ser Leu Thr Glu His Tyr Gly Val Ser Glu Ala Tyr
                    20                  25                  30

Phe Arg Ser Leu Cys Arg Lys Ala Leu Gly Ala Lys Val Lys Glu Gln
            35                  40                  45

Leu Asn Thr Trp Arg Leu
    50

<210> SEQ ID NO 309
<211> LENGTH: 51
<212> TYPE: PRT
<213> ORGANISM: Escherichia coli

<400> SEQUENCE: 309

Thr Arg Val Arg Arg Leu Leu Leu Ala Arg Pro Gly Asp Phe Pro Asp
 1               5                  10                  15

Leu Glu Gln Ala Ala Arg Glu Leu His Thr Ser Gly Arg Ser Leu Arg
                    20                  25                  30

Arg His Leu Ser Ser Leu Gly Thr Thr Tyr Gln Gln Val Leu Asp Asp
            35                  40                  45

Val Arg Lys
    50

<210> SEQ ID NO 310
<211> LENGTH: 52
<212> TYPE: PRT
<213> ORGANISM: Escherichia coli

<400> SEQUENCE: 310

His Ala Ala Arg Asp Leu Leu Val Gly Ala Leu Gln Glu Pro Pro Ser
```

```
                1               5                  10                 15
Leu Asp Thr Leu Ala Ser Arg Val Gly Met Asn Pro Arg Lys Leu Thr
                    20                 25                 30

Ala Gly Phe Arg Lys Val Phe Gly Ala Ser Val Phe Gly Tyr Leu Gln
            35                 40                 45

Glu Tyr Arg Leu
        50

<210> SEQ ID NO 311
<211> LENGTH: 51
<212> TYPE: PRT
<213> ORGANISM: Escherichia coli

<400> SEQUENCE: 311

Asp Arg Val Ile Lys Val Ile Glu Leu Asp Ile Ser Lys Asn Trp Lys
 1               5                  10                 15

Leu Gly Asp Val Ser Ser Ser Met Phe Met Ser Asp Ser Cys Leu Arg
                    20                 25                 30

Lys Gln Leu Asn Lys Glu Asn Leu Thr Phe Lys Lys Ile Met Leu Asp
            35                 40                 45

Ile Lys Met
        50

<210> SEQ ID NO 312
<211> LENGTH: 52
<212> TYPE: PRT
<213> ORGANISM: Escherichia coli

<400> SEQUENCE: 312

Lys Lys Ala Leu Arg Tyr Ile Asp Ala His Leu Ser Asp Asp Leu Arg
 1               5                  10                 15

Leu Glu Asp Val Ala Ser His Val Tyr Leu Ser Pro Tyr Tyr Phe Ser
                    20                 25                 30

Lys Leu Phe Lys Lys Tyr Gln Gly Ile Gly Phe Asn Ala Trp Val Asn
            35                 40                 45

Arg Gln Arg Met
        50

<210> SEQ ID NO 313
<211> LENGTH: 54
<212> TYPE: PRT
<213> ORGANISM: Escherichia coli

<400> SEQUENCE: 313

Asn Asp Ile Leu Lys Trp Leu Glu Thr Gln Leu Gln Arg Asn Glu Gly
 1               5                  10                 15

Ile Lys Ile Asp Thr Ile Ala Asn Lys Ser Gly Tyr Ser Lys Trp His
                    20                 25                 30

Leu Gln Arg Ile Phe Lys Asp Phe Lys Gly Cys Thr Leu Gly Glu Tyr
            35                 40                 45

Val Arg Lys Arg Arg Leu
        50

<210> SEQ ID NO 314
<211> LENGTH: 52
<212> TYPE: PRT
<213> ORGANISM: Escherichia coli

<400> SEQUENCE: 314

Asn Leu Ala Val Ser Tyr Leu Gln Glu Asn Tyr Ser Thr Gly Cys Thr
```

```
            1               5                  10                  15
Ile Met Asp Leu Cys His Tyr Leu Asn Leu Ser Arg Ser Tyr Leu Tyr
              20                  25                  30

Thr Leu Phe Lys Thr His Ala Asn Thr Ser Pro Gln Lys Leu Leu Thr
              35                  40                  45

Lys Leu Arg Leu
        50
```

<210> SEQ ID NO 315
<211> LENGTH: 52
<212> TYPE: PRT
<213> ORGANISM: Escherichia coli

<400> SEQUENCE: 315

```
Asp Thr Ile Val Glu Trp Ile Asp Asp Asn Leu His Gln Pro Leu Arg
 1               5                  10                  15

Ile Glu Asp Ile Ala Arg His Ala Gly Tyr Ser Lys Trp His Leu Gln
              20                  25                  30

Arg Leu Phe Leu Gln Tyr Lys Gly Glu Ser Leu Gly Arg Tyr Ile Arg
              35                  40                  45

Glu Arg Lys Leu
        50
```

<210> SEQ ID NO 316
<211> LENGTH: 52
<212> TYPE: PRT
<213> ORGANISM: Escherichia coli

<400> SEQUENCE: 316

```
Asp Thr Ile Val Glu Trp Ile Asp Asp Asn Leu His Gln Pro Leu Arg
 1               5                  10                  15

Ile Asp Asp Ile Ala Arg His Ala Gly Tyr Ser Lys Trp His Leu Gln
              20                  25                  30

Arg Leu Phe Leu Gln Tyr Lys Gly Glu Ser Leu Gly Arg Tyr Ile Arg
              35                  40                  45

Glu Arg Lys Leu
        50
```

<210> SEQ ID NO 317
<211> LENGTH: 52
<212> TYPE: PRT
<213> ORGANISM: Escherichia coli

<400> SEQUENCE: 317

```
Asp Lys Leu Ile Thr Arg Leu Ala Ala Ser Leu Lys Ser Pro Phe Ala
 1               5                  10                  15

Leu Asp Lys Phe Cys Asp Glu Ala Ser Cys Ser Glu Arg Val Leu Arg
              20                  25                  30

Gln Gln Phe Arg Gln Gln Thr Gly Met Thr Ile Asn Gln Tyr Leu Arg
              35                  40                  45

Gln Val Arg Val
        50
```

<210> SEQ ID NO 318
<211> LENGTH: 52
<212> TYPE: PRT
<213> ORGANISM: Escherichia coli

<400> SEQUENCE: 318

```
Asp Lys Leu Ile Thr Ala Leu Ala Asn Ser Leu Glu Cys Pro Phe Ala
```

```
                1               5                  10                 15
Leu Asp Ala Phe Cys Gln Gln Glu Gln Cys Ser Glu Arg Val Leu Arg
                20                 25                 30

Gln Gln Phe Arg Ala Gln Thr Gly Met Thr Ile Asn Gln Tyr Leu Arg
        35                 40                 45

Gln Val Arg Ile
    50

<210> SEQ ID NO 319
<211> LENGTH: 52
<212> TYPE: PRT
<213> ORGANISM: Escherichia coli

<400> SEQUENCE: 319

Asn Leu Leu Leu Ala Trp Leu Glu Asp His Phe Ala Asp Glu Val Asn
1               5                   10                  15

Trp Asp Ala Val Ala Asp Gln Phe Ser Leu Ser Leu Arg Thr Leu His
                20                  25                  30

Arg Gln Leu Lys Gln Gln Thr Gly Leu Thr Pro Gln Arg Tyr Leu Asn
        35                  40                  45

Arg Leu Arg Leu
    50

<210> SEQ ID NO 320
<211> LENGTH: 52
<212> TYPE: PRT
<213> ORGANISM: Escherichia coli

<400> SEQUENCE: 320

Asn Gln Leu Met Ala Trp Leu Glu Asp His Phe Ala Glu Glu Val Cys
1               5                   10                  15

Trp Glu Ala Val Ala Glu Gln Phe Ser Leu Ser Leu Arg Thr Leu His
                20                  25                  30

Arg Gln Leu Lys Gln His Thr Gly Leu Thr Pro Gln Arg Tyr Leu Asn
        35                  40                  45

Arg Leu Arg Leu
    50

<210> SEQ ID NO 321
<211> LENGTH: 52
<212> TYPE: PRT
<213> ORGANISM: Escherichia coli

<400> SEQUENCE: 321

Ala Ser Ile Lys Met Arg Val Glu Gln Asn Leu Ala Asn Gly Ser Phe
1               5                   10                  15

Ser Ile Thr Asp Val Ala Glu Ala Glu Arg Ile Thr Pro Arg Ala Ile
                20                  25                  30

Gln Lys Phe Phe Ser Arg Glu Gly Thr Thr Phe Ser Arg Tyr Val Leu
        35                  40                  45

Gly Arg Arg Leu
    50

<210> SEQ ID NO 322
<211> LENGTH: 51
<212> TYPE: PRT
<213> ORGANISM: Escherichia coli

<400> SEQUENCE: 322

Asp Lys Val Arg Asn Leu Ile Glu Lys Asp Leu Ser Arg Lys Trp Thr
```

```
                1               5                  10                  15
Leu Gly Ile Ile Ala Asp Ala Phe Asn Ala Ser Glu Ile Thr Ile Arg
                    20                  25                  30

Lys Arg Leu Glu Ser Glu Asn Thr Asn Phe Asn Gln Ile Leu Met Gln
        35                  40                  45

Leu Arg Met
    50

<210> SEQ ID NO 323
<211> LENGTH: 52
<212> TYPE: PRT
<213> ORGANISM: Escherichia coli

<400> SEQUENCE: 323

Arg Asp Leu Leu Ile Trp Leu Glu Gly His Leu Asp Gln Pro Leu Ser
 1               5                  10                  15

Leu Asp Asn Val Ala Ala Lys Ala Gly Tyr Ser Lys Trp His Leu Gln
                20                  25                  30

Arg Met Phe Lys Asp Val Thr Gly His Ala Ile Gly Ala Tyr Ile Arg
            35                  40                  45

Ala Arg Arg Leu
    50

<210> SEQ ID NO 324
<211> LENGTH: 52
<212> TYPE: PRT
<213> ORGANISM: Escherichia coli

<400> SEQUENCE: 324

Gln Asp Leu Ile Ala Trp Ile Asp Glu His Ile Asp Gln Pro Leu Asn
 1               5                  10                  15

Ile Asp Val Val Ala Lys Lys Ser Gly Tyr Ser Lys Trp Tyr Leu Gln
                20                  25                  30

Arg Met Phe Arg Thr Val Thr His Gln Thr Leu Gly Asp Tyr Ile Arg
            35                  40                  45

Gln Arg Arg Leu
    50

<210> SEQ ID NO 325
<211> LENGTH: 52
<212> TYPE: PRT
<213> ORGANISM: Escherichia coli

<400> SEQUENCE: 325

Gln Thr Leu Ile Glu Trp Ile Asp Glu His Ile Asp Gln Pro Leu Asn
 1               5                  10                  15

Ile Asp Val Val Ala Lys Lys Ser Gly Tyr Ser Lys Trp Tyr Leu Gln
                20                  25                  30

Arg Met Phe Arg Thr Val Thr His Gln Thr Leu Gly Gly Tyr Ile Arg
            35                  40                  45

Gln Arg Arg Leu
    50

<210> SEQ ID NO 326
<211> LENGTH: 51
<212> TYPE: PRT
<213> ORGANISM: Escherichia coli

<400> SEQUENCE: 326

Glu Lys Ile Ser Cys Leu Val Lys Ser Asp Ile Thr Arg Asn Trp Arg
```

```
                1               5                  10                 15
Trp Ala Asp Ile Cys Gly Glu Leu Arg Thr Asn Arg Met Ile Leu Lys
                20                 25                 30

Lys Glu Leu Glu Ser Arg Gly Val Lys Phe Arg Glu Leu Ile Asn Ser
        35                 40                 45

Ile Arg Ile
    50

<210> SEQ ID NO 327
<211> LENGTH: 52
<212> TYPE: PRT
<213> ORGANISM: Escherichia coli

<400> SEQUENCE: 327

Lys Asp Val Leu Leu Trp Ile Glu His Asn Leu Asp Gln Ser Leu Leu
1               5                  10                 15

Leu Asp Asp Val Ala Asn Lys Ala Gly Tyr Thr Lys Trp Tyr Phe Gln
                20                 25                 30

Arg Leu Phe Lys Lys Val Thr Gly Val Thr Leu Ala Ser Tyr Ile Arg
        35                 40                 45

Ala Arg Arg Leu
    50

<210> SEQ ID NO 328
<211> LENGTH: 52
<212> TYPE: PRT
<213> ORGANISM: Escherichia coli

<400> SEQUENCE: 328

Arg Leu Ala Val Asp Tyr Leu Glu Ala His Ala Gln Gln Pro Leu Thr
1               5                  10                 15

Val Ala Gln Val Ala Arg Asn Val Gly Val Ser Val Arg Ser Leu Gln
                20                 25                 30

Val Gly Phe Gln Asn Ser Leu Gly Thr Thr Pro Met Arg Gln Leu Lys
        35                 40                 45

Ile Ile Arg Met
    50

<210> SEQ ID NO 329
<211> LENGTH: 51
<212> TYPE: PRT
<213> ORGANISM: Escherichia coli

<400> SEQUENCE: 329

Gln Ala Ile Thr His Leu Ile Thr Gln Glu Pro Gln Lys Lys Trp His
1               5                  10                 15

Leu Asp Asp Val Ala Lys Ala Leu Phe Thr Thr Pro Ser Thr Leu Arg
                20                 25                 30

Arg His Leu Asn Arg Glu Gly Val Ser Phe Arg Gln Leu Leu Leu Asp
        35                 40                 45

Val Arg Met
    50

<210> SEQ ID NO 330
<211> LENGTH: 51
<212> TYPE: PRT
<213> ORGANISM: Escherichia coli

<400> SEQUENCE: 330

Gln Ala Ile Thr His Leu Ile Thr Gln Asp Pro Gln Arg Lys Trp His
```

```
                 1               5                   10                  15
Leu Glu Asp Val Ala Lys Thr Leu Tyr Thr Thr Pro Ser Thr Leu Arg
                    20                  25                  30

Arg His Leu Ser Lys Glu Gly Val Ser Phe Cys Gln Leu Leu Asp
            35                  40                  45

Val Arg Ile
        50

<210> SEQ ID NO 331
<211> LENGTH: 51
<212> TYPE: PRT
<213> ORGANISM: Escherichia coli

<400> SEQUENCE: 331

Asp Gln Ile Arg Lys Ile Val Glu Lys Asn Ile Glu Lys Arg Trp Arg
 1               5                   10                  15

Leu Ser Asp Ile Ser Asn Asn Leu Asn Leu Ser Glu Ile Ala Val Arg
                20                  25                  30

Lys Arg Leu Glu Ser Glu Lys Leu Thr Phe Gln Gln Ile Leu Leu Asp
            35                  40                  45

Ile Arg Met
        50

<210> SEQ ID NO 332
<211> LENGTH: 52
<212> TYPE: PRT
<213> ORGANISM: Escherichia coli

<400> SEQUENCE: 332

Glu Arg Leu Gln Lys Phe Met Glu Glu Asn Tyr Leu Gln Gly Trp Lys
 1               5                   10                  15

Leu Ser Lys Phe Ala Arg Glu Phe Gly Met Gly Leu Thr Thr Phe Lys
                20                  25                  30

Glu Leu Phe Gly Thr Val Tyr Gly Ile Ser Pro Arg Ala Trp Ile Ser
            35                  40                  45

Glu Arg Arg Ile
        50

<210> SEQ ID NO 333
<211> LENGTH: 52
<212> TYPE: PRT
<213> ORGANISM: Mycobacterium tuberculosis

<400> SEQUENCE: 333

Glu Arg Val Val Gly Leu Ala Arg Arg Leu Leu Pro Thr Gly Gln Cys
 1               5                   10                  15

Ser Ala Glu Ala Ile Ala Asp Gln Leu Asp Met His Pro Arg Thr Leu
                20                  25                  30

Gln Arg Arg Leu Ala Ala Glu Gly Leu Arg Cys His Asp Leu Ile Glu
            35                  40                  45

Arg Glu Arg Arg
        50

<210> SEQ ID NO 334
<211> LENGTH: 52
<212> TYPE: PRT
<213> ORGANISM: Escherichia coli

<400> SEQUENCE: 334

Ile Gln Ala Met His Tyr Ile Arg Asn His Ala Cys Lys Gly Ile Lys
```

```
                 1               5                  10                 15
Val Asp Gln Val Leu Asp Ala Val Gly Ile Ser Arg Ser Asn Leu Glu
                       20                 25                 30

Lys Arg Phe Lys Glu Glu Val Gly Glu Thr Ile His Ala Met Ile His
            35                 40                 45

Ala Glu Lys Leu
        50

<210> SEQ ID NO 335
<211> LENGTH: 52
<212> TYPE: PRT
<213> ORGANISM: Escherichia coli

<400> SEQUENCE: 335

Ile Gln Ala Met His Tyr Ile Arg His Arg Ala Cys His Arg Ile Lys
 1               5                  10                 15

Val Gly Gln Val Leu Asp His Leu Glu Thr Ser Arg Ser Asn Leu Glu
                       20                 25                 30

Gln Arg Phe Lys Asn Glu Met Asn Lys Thr Ile His Gln Val Ile His
            35                 40                 45

Glu Glu Lys Ile
        50

<210> SEQ ID NO 336
<211> LENGTH: 52
<212> TYPE: PRT
<213> ORGANISM: Escherichia coli

<400> SEQUENCE: 336

Glu Arg Val Val Gln Phe Ile Glu Glu Asn Leu Lys Arg Asn Ile Ser
 1               5                  10                 15

Leu Glu Arg Leu Ala Glu Leu Ala Met Met Ser Pro Arg Ser Leu Tyr
                       20                 25                 30

Asn Leu Phe Glu Lys His Ala Gly Thr Thr Pro Lys Asn Tyr Ile Arg
            35                 40                 45

Asn Arg Lys Leu
        50

<210> SEQ ID NO 337
<211> LENGTH: 52
<212> TYPE: PRT
<213> ORGANISM: Escherichia coli

<400> SEQUENCE: 337

Glu Arg Val Val Gln Phe Ile Glu Glu Asn Leu Lys Arg Asn Ile Ser
 1               5                  10                 15

Leu Glu Arg Leu Ala Glu Leu Ala Met Met Ser Pro Arg Ser Leu Tyr
                       20                 25                 30

Asn Leu Phe Glu Lys His Ala Gly Thr Thr Pro Lys Asn Tyr Ile Arg
            35                 40                 45

Asn Arg Lys Leu
        50

<210> SEQ ID NO 338
<211> LENGTH: 52
<212> TYPE: PRT
<213> ORGANISM: Escherichia coli

<400> SEQUENCE: 338

Glu Arg Val Val Gln Phe Ile Glu Glu Asn Val Lys Arg Ser Ile Ser
```

```
                1               5                   10                  15
Leu Glu Gln Leu Ala Glu Leu Ala Leu Met Ser Pro Arg Ser Leu Tyr
                    20                  25                  30

Thr Met Phe Glu Lys His Thr Gly Thr Thr Pro Met Asn Tyr Ile Arg
            35                  40                  45

Asn Arg Lys Leu
    50

<210> SEQ ID NO 339
<211> LENGTH: 52
<212> TYPE: PRT
<213> ORGANISM: Escherichia coli

<400> SEQUENCE: 339

Glu Arg Val Val Gln Phe Ile Glu Asp Asn Leu Lys Gln Ser Ile Ser
1               5                   10                  15

Leu Glu Arg Leu Ala Glu Leu Ala Leu Met Ser Pro Arg Ser Leu Tyr
                    20                  25                  30

Thr Leu Phe Glu Lys His Ala Gly Thr Thr Pro Lys Asn Tyr Ile Arg
            35                  40                  45

Asn Arg Lys Leu
    50

<210> SEQ ID NO 340
<211> LENGTH: 52
<212> TYPE: PRT
<213> ORGANISM: Escherichia coli

<400> SEQUENCE: 340

Glu Arg Val Val Gln Phe Ile Glu Glu Asn Leu Lys Arg Asn Ile Ser
1               5                   10                  15

Leu Glu Arg Leu Ala Glu Leu Ala Leu Met Ser Pro Arg Ser Leu Tyr
                    20                  25                  30

Thr Leu Phe Glu Lys His Ala Gly Thr Thr Pro Lys Asn Tyr Ile Arg
            35                  40                  45

Asn Arg Lys Leu
    50

<210> SEQ ID NO 341
<211> LENGTH: 52
<212> TYPE: PRT
<213> ORGANISM: Escherichia coli

<400> SEQUENCE: 341

Leu Lys Ala Glu Ala Phe Met Arg Glu Asn Leu Thr Asn Pro Val Thr
1               5                   10                  15

Ile Glu Asp Leu Ala Ala Ala Ala Arg Cys Thr Pro Arg Ala Leu Gln
                    20                  25                  30

Arg Met Phe Arg Thr Tyr Arg Gly Gly Ser Pro Met Ser Val Leu Cys
            35                  40                  45

Asn Tyr Arg Leu
    50

<210> SEQ ID NO 342
<211> LENGTH: 55
<212> TYPE: PRT
<213> ORGANISM: Escherichia coli

<400> SEQUENCE: 342

Lys Arg Leu Asn Thr Ala Leu Ile Ala Ile Leu Gln Gln Pro Gln Asn
```

```
                1               5                  10                 15
Asp Trp His Ile Glu Gln Leu Ala Glu Leu Ala Thr Met Ser Arg Ala
                    20                 25                 30

Asn Phe Ile Arg Ile Phe Gln Gln His Ile Gly Met Ser Pro Gly Arg
                    35                 40                 45

Phe Leu Thr Lys Val Arg Leu
            50                 55

<210> SEQ ID NO 343
<211> LENGTH: 52
<212> TYPE: PRT
<213> ORGANISM: Escherichia coli

<400> SEQUENCE: 343

Glu Lys Thr Lys His Tyr Ile Glu Thr His Ala Asp Thr Lys Ile Thr
 1               5                  10                 15

Leu Ala Gln Leu Ser Gln Met Ala Gly Ile Ser Ala Lys His Tyr Ser
                20                 25                 30

Glu Ser Phe Lys Lys Trp Thr Gly Gln Ser Val Thr Glu Phe Ile Thr
                35                 40                 45

Lys Thr Arg Ile
       50

<210> SEQ ID NO 344
<211> LENGTH: 51
<212> TYPE: PRT
<213> ORGANISM: Escherichia coli

<400> SEQUENCE: 344

Ser Arg Cys Tyr Asn Leu Leu Ser Glu Pro Gly Thr Lys Trp Thr
 1               5                  10                 15

Ala Asn Lys Val Ala Arg Tyr Leu Tyr Ile Ser Val Ser Thr Leu His
                20                 25                 30

Arg Arg Leu Ala Ser Glu Gly Val Ser Phe Gln Ser Ile Leu Asp Asp
                35                 40                 45

Val Arg Leu
       50

<210> SEQ ID NO 345
<211> LENGTH: 52
<212> TYPE: PRT
<213> ORGANISM: Escherichia coli

<400> SEQUENCE: 345

Gln Asn Ala Met Leu Tyr Ile Glu Asn Asn Tyr Phe Asn Asp Ile Asn
 1               5                  10                 15

Ile Asp Thr Val Ala Phe Ser Val Gly Val Ser Arg Ser Tyr Leu Val
                20                 25                 30

Lys Gln Phe Lys Leu Ala Thr Asn Lys Thr Ile Asn Asn Arg Ile Ile
                35                 40                 45

Glu Val Arg Ile
       50

<210> SEQ ID NO 346
<211> LENGTH: 55
<212> TYPE: PRT
<213> ORGANISM: Mycobacterium tuberculosis

<400> SEQUENCE: 346

Arg Gly Ile Thr Ala Leu Val Arg Ser Lys Leu Phe Arg Asp Ser Gly
```

```
                1               5                  10                 15
Leu Phe Pro Thr Phe Thr Asp Val Ala Gly Glu Leu Asp Met His Pro
                        20                 25                 30

Arg Thr Leu Arg Arg Arg Leu Ala Glu Glu Gly Thr Ser Phe Arg Ala
            35                 40                 45

Leu Leu Gly Glu Ala Arg Ser
    50                 55

<210> SEQ ID NO 347
<211> LENGTH: 51
<212> TYPE: PRT
<213> ORGANISM: Escherichia coli

<400> SEQUENCE: 347

Gly Lys Val Arg Asn Ile Val Asn Met Lys Pro Ala His Pro Trp Lys
 1               5                  10                 15

Leu Lys Asp Ile Cys Asp Cys Leu Tyr Ile Ser Glu Ser Leu Leu Lys
                20                 25                 30

Lys Lys Leu Lys Gln Glu Gln Thr Thr Phe Ser Gln Ile Leu Leu Asp
            35                 40                 45

Ala Arg Met
    50

<210> SEQ ID NO 348
<211> LENGTH: 52
<212> TYPE: PRT
<213> ORGANISM: Escherichia coli

<400> SEQUENCE: 348

Lys Asp Ile Leu Phe Tyr Leu Asn Asn Tyr Arg Glu Lys Ile Thr
 1               5                  10                 15

Leu Glu Gln Leu Ser Lys Lys Phe Arg Ala Ser Val Ser Tyr Ile Cys
                20                 25                 30

His Glu Phe Thr Lys Glu Tyr Arg Ile Ser Pro Ile Asn Tyr Val Ile
            35                 40                 45

Gln Arg Arg Met
    50

<210> SEQ ID NO 349
<211> LENGTH: 55
<212> TYPE: PRT
<213> ORGANISM: Escherichia coli

<400> SEQUENCE: 349

Pro Lys Ile Arg Thr Met Val Glu Met Met Ala Lys Gly Pro Val Glu
 1               5                  10                 15

Trp Gly Ala Leu Gly Gln Trp Ala Gly Phe Phe Ala Met Ser Glu Arg
                20                 25                 30

Asn Leu Ala Arg Leu Ile Val Lys Glu Thr Gly Leu Ser Phe Arg Gln
            35                 40                 45

Trp Arg Gln Gln Leu Gln Leu
    50                 55

<210> SEQ ID NO 350
<211> LENGTH: 52
<212> TYPE: PRT
<213> ORGANISM: Escherichia coli

<400> SEQUENCE: 350

Thr Glu Val Lys Leu His Ile Lys Asp Asn Leu Ser Gln Pro Leu Lys
```

```
                1               5                   10                  15
Leu Thr Asp Val Ala Ser His Phe His Ile Ser Gly Arg His Leu Ser
            20                  25                  30

Arg Leu Phe Ala Ala Glu Leu Gly Val Ser Tyr Ser Glu Phe Val Gln
            35                  40                  45

Asn Glu Lys Ile
    50

<210> SEQ ID NO 351
<211> LENGTH: 51
<212> TYPE: PRT
<213> ORGANISM: Escherichia coli

<400> SEQUENCE: 351

Gly Lys Val Glu Arg Leu Ile Ser Phe Asp Ile Ala Lys Arg Trp Tyr
  1               5                  10                  15

Leu Arg Asp Ile Ala Glu Arg Met Tyr Thr Ser Glu Ser Leu Ile Lys
            20                  25                  30

Lys Lys Leu Gln Asp Glu Asn Thr Cys Phe Ser Lys Ile Leu Leu Ala
            35                  40                  45

Ser Arg Met
    50

<210> SEQ ID NO 352
<211> LENGTH: 52
<212> TYPE: PRT
<213> ORGANISM: Escherichia coli

<400> SEQUENCE: 352

Glu Lys Leu Ile Ala Thr Leu His Ala Ser Leu Gln Gln Arg Trp Ser
  1               5                  10                  15

Val Ala Asp Met Ala Ala Thr Ile Pro Cys Ser Glu Ala Trp Leu Arg
            20                  25                  30

Arg Leu Phe Leu Arg Tyr Thr Gly Lys Thr Pro Lys Glu Tyr Tyr Leu
            35                  40                  45

Asp Ala Arg Leu
    50

<210> SEQ ID NO 353
<211> LENGTH: 52
<212> TYPE: PRT
<213> ORGANISM: Escherichia coli

<400> SEQUENCE: 353

Glu Ala Ile Arg Asp Tyr Ile Asp Glu Arg Tyr Ala Ser Ala Leu Thr
  1               5                  10                  15

Arg Glu Ser Val Ala Gln Ala Phe Tyr Ile Ser Pro Asn Tyr Leu Ser
            20                  25                  30

His Leu Phe Gln Lys Thr Gly Ala Ile Gly Phe Asn Gly Tyr Leu Asn
            35                  40                  45

His Thr Arg Leu
    50

<210> SEQ ID NO 354
<211> LENGTH: 52
<212> TYPE: PRT
<213> ORGANISM: Escherichia coli

<400> SEQUENCE: 354

Trp Glu Ala Ala Arg Tyr Leu Gln Glu His Tyr Lys Glu Lys Thr Thr
```

```
                1               5                  10                 15
Ile Lys Asp Leu Ser Leu Ala Leu His Tyr His Gln Asp Tyr Val Ser
                    20                  25                 30

Arg Cys Met Gln Gln Val Leu Gly Val Thr Pro Ala Gln Tyr Thr Asn
                    35                  40                 45

Arg Val Arg Met
        50

<210> SEQ ID NO 355
<211> LENGTH: 52
<212> TYPE: PRT
<213> ORGANISM: Escherichia coli

<400> SEQUENCE: 355

Gln Gln Leu Leu Glu Trp Ile Glu Cys Asn Leu Glu His Pro Ile Ser
 1               5                  10                 15

Ile Glu Asp Ile Ala Gln Lys Ser Gly Tyr Ser Arg Arg Asn Ile Gln
                    20                  25                 30

Leu Leu Phe Arg Asn Phe Met His Val Pro Leu Gly Glu Tyr Ile Arg
                    35                  40                 45

Lys Arg Arg Leu
        50

<210> SEQ ID NO 356
<211> LENGTH: 55
<212> TYPE: PRT
<213> ORGANISM: Escherichia coli

<400> SEQUENCE: 356

Pro Arg Leu Gly Ala Val Ile Gln Gln Met Leu Glu Met Pro Gly His
 1               5                  10                 15

Ala Trp Thr Val Glu Ser Leu Ala Ser Ile Ala His Met Ser Arg Ala
                    20                  25                 30

Ser Phe Ala Gln Leu Phe Arg Asp Val Ser Gly Thr Thr Pro Leu Ala
                    35                  40                 45

Val Leu Thr Lys Leu Arg Leu
        50                  55

<210> SEQ ID NO 357
<211> LENGTH: 52
<212> TYPE: PRT
<213> ORGANISM: Escherichia coli

<400> SEQUENCE: 357

Asp Pro Leu Leu Arg Ala Val Val Ser Leu Glu Ala Gly Arg Ser
 1               5                  10                 15

Val Thr Ala Thr Ala Asp Ser Val Gly Leu Gly Ala Arg Gln Leu His
                    20                  25                 30

Arg Arg Ser Leu Ala Ala Phe Gly Tyr Gly Pro Lys Thr Leu Ala Arg
                    35                  40                 45

Val Leu Arg Met
        50

<210> SEQ ID NO 358
<211> LENGTH: 52
<212> TYPE: PRT
<213> ORGANISM: Escherichia coli

<400> SEQUENCE: 358

His Ser Ile Cys Asn Trp Val Gln Asp Asn Tyr Ala Gln Pro Leu Thr
```

```
                1               5                  10                 15
Arg Glu Ser Val Ala Gln Phe Phe Asn Ile Thr Pro Asn His Leu Ser
                                20                 25                 30

Lys Leu Phe Ala Gln His Gly Thr Met Arg Phe Ile Glu Tyr Val Arg
            35                 40                 45

Trp Val Arg Met
        50

<210> SEQ ID NO 359
<211> LENGTH: 52
<212> TYPE: PRT
<213> ORGANISM: Escherichia coli

<400> SEQUENCE: 359

Ser Arg Val Leu Lys Arg Ile Glu Asn Lys Tyr Thr Glu Asn Leu Ser
1               5                  10                 15

Val Glu Gln Leu Ala Ala Glu Ala Asn Met Ser Val Ser Ala Phe His
                20                 25                 30

His Asn Phe Lys Ser Val Thr Ser Thr Ser Pro Leu Gln Tyr Leu Lys
            35                 40                 45

Asn Tyr Arg Leu
        50

<210> SEQ ID NO 360
<211> LENGTH: 47
<212> TYPE: PRT
<213> ORGANISM: Providencia Stuartii

<400> SEQUENCE: 360

Cys Glu Ala Ala Lys Glu Leu Gln Thr Thr Asn Leu Gln Val Ile Asp
1               5                  10                 15

Ile Ala Leu Lys Tyr Gln Phe Asp Ser Gln Gln Ser Phe Ala Lys Arg
                20                 25                 30

Phe Lys Ala Tyr Leu Gly Ile Ser Pro Ser Leu Tyr Arg Leu Ser
            35                 40                 45

<210> SEQ ID NO 361
<211> LENGTH: 46
<212> TYPE: PRT
<213> ORGANISM: Escherichia coli

<400> SEQUENCE: 361

Arg Arg Leu Arg Glu Ser Leu Ala Lys Gly Glu Ser Val Thr Thr Ser
1               5                  10                 15

Ile Leu Asn Ala Gly Phe Pro Asp Ser Ser Tyr Tyr Arg Lys Ala
                20                 25                 30

Asp Glu Thr Leu Gly Met Thr Ala Lys Gln Phe Arg His Gly
            35                 40                 45

<210> SEQ ID NO 362
<211> LENGTH: 47
<212> TYPE: PRT
<213> ORGANISM: Mycobacterium tuberculosis

<400> SEQUENCE: 362

Gln Thr Ala Arg Val Leu Ile Glu Thr Thr Asn Leu Pro Phe Gly Asp
1               5                  10                 15

Val Ala Phe Ala Ala Gly Phe Ser Ser Ile Arg Gln Phe Asn Asp Thr
                20                 25                 30

Val Arg Leu Ala Cys Asp Gly Thr Pro Thr Ala Leu Arg Ala Arg
```

```
               35                  40                  45
```

<210> SEQ ID NO 363
<211> LENGTH: 46
<212> TYPE: PRT
<213> ORGANISM: Escherichia coli

<400> SEQUENCE: 363

```
Arg Arg Leu Arg Glu Ala Leu Ala Lys Gly Glu Pro Ile Thr Ala Ala
  1               5                  10                  15

Ile Tyr Arg Ala Gly Phe Pro Asp Ser Ser Tyr Tyr Arg His Ala
                 20                  25                  30

Asp Gln Thr Leu Gly Met Thr Ala Lys Gln Phe Arg Lys Gly
               35                  40                  45
```

<210> SEQ ID NO 364
<211> LENGTH: 47
<212> TYPE: PRT
<213> ORGANISM: Escherichia coli

<400> SEQUENCE: 364

```
His Ala Ala Lys Lys Tyr Leu Ile Gln Thr Asn Lys Ala Ile Gly Asp
  1               5                  10                  15

Ile Ala Ile Cys Val Gly Ile Ala Asn Ala Pro Tyr Phe Ile Thr Leu
                 20                  25                  30

Phe Lys Lys Lys Thr Gly Gln Thr Pro Ala Arg Phe Arg Gln Met
               35                  40                  45
```

<210> SEQ ID NO 365
<211> LENGTH: 47
<212> TYPE: PRT
<213> ORGANISM: Escherichia coli

<400> SEQUENCE: 365

```
Arg Tyr Ala Val Asn Glu Leu Met Met Asp Gly Lys Asn Ile Ser Gln
  1               5                  10                  15

Val Ser Gln Ser Cys Gly Tyr Asn Ser Thr Ser Tyr Phe Ile Ser Val
                 20                  25                  30

Phe Lys Asp Phe Tyr Gly Met Thr Pro Leu His Tyr Val Ser Gln
               35                  40                  45
```

<210> SEQ ID NO 366
<211> LENGTH: 47
<212> TYPE: PRT
<213> ORGANISM: Escherichia coli

<400> SEQUENCE: 366

```
Ser Lys Ala Ala Leu Leu Leu Asp Asn Ser Tyr Gln Ile Ser Gln
  1               5                  10                  15

Ile Ser Asn Met Ile Gly Phe Ser Ser Thr Ser Tyr Phe Ile Arg Leu
                 20                  25                  30

Phe Val Lys His Phe Gly Ile Thr Pro Lys Gln Phe Leu Thr Tyr
               35                  40                  45
```

<210> SEQ ID NO 367
<211> LENGTH: 47
<212> TYPE: PRT
<213> ORGANISM: Escherichia coli

<400> SEQUENCE: 367

```
Arg Tyr Ala Lys Lys Leu Ile Thr Ser Asn Ser Tyr Ser Ile Asn Val
  1               5                  10                  15
```

-continued

Val Ala Gln Lys Cys Gly Tyr Asn Ser Thr Ser Tyr Phe Ile Cys Ala
            20                  25                  30

Phe Lys Asp Tyr Tyr Gly Val Thr Pro Ser His Tyr Phe Glu Lys
        35                  40                  45

<210> SEQ ID NO 368
<211> LENGTH: 47
<212> TYPE: PRT
<213> ORGANISM: Escherichia coli

<400> SEQUENCE: 368

Ser Gln Ala Lys Leu Leu Leu Ser Thr Thr Arg Met Pro Ile Ala Thr
1               5                   10                  15

Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
        35                  40                  45

<210> SEQ ID NO 369
<211> LENGTH: 47
<212> TYPE: PRT
<213> ORGANISM: Escherichia coli

<400> SEQUENCE: 369

Ser Gln Ala Lys Leu Leu Leu Ser Thr Thr Arg Met Pro Ile Ala Thr
1               5                   10                  15

Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
        35                  40                  45

<210> SEQ ID NO 370
<211> LENGTH: 47
<212> TYPE: PRT
<213> ORGANISM: Escherichia coli

<400> SEQUENCE: 370

Ile Arg Ala Lys Leu Leu Leu Gln Thr Thr Gln Glu Ser Ile Ala Asn
1               5                   10                  15

Ile Gly Arg Val Val Gly Tyr Asp Asp Gln Leu Tyr Phe Ser Arg Val
            20                  25                  30

Phe Arg Lys Arg Val Gly Val Ser Pro Ser Asp Phe Arg Arg Arg
        35                  40                  45

<210> SEQ ID NO 371
<211> LENGTH: 47
<212> TYPE: PRT
<213> ORGANISM: Escherichia coli

<400> SEQUENCE: 371

Ser Gln Ala Lys Leu Leu Leu Ser Thr Thr Arg Met Pro Ile Ala Thr
1               5                   10                  15

Val Gly Arg Asn Val Gly Phe Asp Asp Gln Leu Tyr Phe Ser Arg Val
            20                  25                  30

Phe Lys Lys Cys Thr Gly Ala Ser Pro Ser Glu Phe Arg Ala Gly
        35                  40                  45

<210> SEQ ID NO 372
<211> LENGTH: 47
<212> TYPE: PRT
<213> ORGANISM: Escherichia coli

<400> SEQUENCE: 372

Glu Leu Thr Ala Arg Gln Leu Arg Glu Gly Ser Ala Pro Leu Ala Ala
1               5                   10                  15

Ile Ala His Ser Val Gly Tyr Gly Ser Glu Ser Ala Leu Ser Val Ala
                20                  25                  30

Phe Lys Arg Val Leu Gly Met Asn Pro Gly Asp Tyr Arg Lys His
            35                  40                  45

<210> SEQ ID NO 373
<211> LENGTH: 47
<212> TYPE: PRT
<213> ORGANISM: Escherichia coli

<400> SEQUENCE: 373

Glu Leu Ala Ala Arg Gln Leu Arg Glu Gly Asn Ala Thr Leu Ala Ser
1               5                   10                  15

Ile Ala His Ser Val Gly Tyr Gly Ser Glu Ser Ala Leu Ser Val Ala
                20                  25                  30

Phe Lys Arg Val Leu Gly Met Pro Pro Gly Asp Tyr Arg Lys His
            35                  40                  45

<210> SEQ ID NO 374
<211> LENGTH: 47
<212> TYPE: PRT
<213> ORGANISM: Escherichia coli

<400> SEQUENCE: 374

Ser Arg Ala Ala Ala Leu Leu Arg Leu Thr Arg Leu Thr Ile Ile Glu
1               5                   10                  15

Ile Ser Ala Lys Leu Phe Tyr Asp Ser Gln Gln Thr Phe Thr Arg Glu
                20                  25                  30

Phe Lys Lys Ile Phe Gly Tyr Thr Pro Arg Gln Tyr Arg Met Ile
            35                  40                  45

<210> SEQ ID NO 375
<211> LENGTH: 47
<212> TYPE: PRT
<213> ORGANISM: Escherichia coli

<400> SEQUENCE: 375

Asn Phe Ala Lys Lys Gln Leu Glu Met Thr Asn Tyr Ser Val Thr Asp
1               5                   10                  15

Ile Ala Phe Glu Ala Gly Tyr Ser Ser Pro Ser Leu Phe Ile Lys Thr
                20                  25                  30

Phe Lys Lys Leu Thr Ser Phe Thr Pro Lys Ser Tyr Arg Lys Lys
            35                  40                  45

<210> SEQ ID NO 376
<211> LENGTH: 47
<212> TYPE: PRT
<213> ORGANISM: Escherichia coli

<400> SEQUENCE: 376

Ser Lys Ala Ala Leu Leu Leu Glu Asn Ser Tyr Gln Ile Ser Gln
1               5                   10                  15

Ile Ser Asn Met Ile Gly Ile Ser Ser Ala Ser Tyr Phe Ile Arg Val
                20                  25                  30

Phe Asn Lys His Tyr Gly Val Thr Pro Lys Gln Phe Phe Thr Tyr
            35                  40                  45

<210> SEQ ID NO 377
<211> LENGTH: 47
<212> TYPE: PRT
<213> ORGANISM: Escherichia coli

<400> SEQUENCE: 377

Ser Lys Ala Ala Leu Leu Leu Glu Asn Ser Tyr Gln Ile Ser Gln
1               5                   10                  15
Ile Ser Asn Met Ile Gly Ile Ser Ala Ser Tyr Phe Ile Arg Ile
            20                  25                  30
Phe Asn Lys His Phe Gly Val Thr Arg Ser Ser Phe Leu Ile Ile
        35                  40                  45

<210> SEQ ID NO 378
<211> LENGTH: 47
<212> TYPE: PRT
<213> ORGANISM: Escherichia coli

<400> SEQUENCE: 378

Arg Tyr Ala Val Gln Met Leu Leu Met Asp Asn Lys Asn Ile Thr Gln
1               5                   10                  15
Val Ala Gln Leu Cys Gly Tyr Ser Ser Thr Ser Tyr Phe Ile Ser Val
            20                  25                  30
Phe Lys Ala Phe Tyr Gly Leu Thr Pro Leu Asn Tyr Leu Ala Lys
        35                  40                  45

<210> SEQ ID NO 379
<211> LENGTH: 50
<212> TYPE: PRT
<213> ORGANISM: Escherichia coli

<400> SEQUENCE: 379

Asn Ala Val Arg Arg Glu Leu Ile Ser Pro Trp Ser Gln Ser Met Thr
1               5                   10                  15
Val Lys Asp Ala Ala Met Gln Trp Gly Phe Trp His Leu Gly Gln Phe
            20                  25                  30
Ala Thr Asp Tyr Gln Gln Leu Phe Ser Glu Lys Pro Ser Leu Thr Leu
        35                  40                  45
His Gln
    50

<210> SEQ ID NO 380
<211> LENGTH: 50
<212> TYPE: PRT
<213> ORGANISM: Escherichia coli

<400> SEQUENCE: 380

Asn Ala Val Arg Arg Glu Leu Ile Ser Pro Trp Ser Gln Ser Ala Thr
1               5                   10                  15
Val Lys Asp Ala Ala Met Gln Trp Gly Phe Trp His Leu Gly Gln Phe
            20                  25                  30
Ala Thr Asp Tyr Gln Gln Leu Phe Ala Glu Lys Pro Ser Leu Thr Leu
        35                  40                  45
His Gln
    50

<210> SEQ ID NO 381
<211> LENGTH: 47
<212> TYPE: PRT
<213> ORGANISM: Escherichia coli

<400> SEQUENCE: 381

Leu Tyr Ala His Gln Leu Leu Asn Ser Asp Met Ser Ile Val Asp
1               5                   10                  15

Ile Ala Met Glu Ala Gly Phe Ser Ser Gln Ser Tyr Phe Thr Gln Ser
                20                  25                  30

Tyr Arg Arg Arg Phe Gly Cys Thr Pro Ser Arg Ser Arg Gln Gly
            35                  40                  45

<210> SEQ ID NO 382
<211> LENGTH: 47
<212> TYPE: PRT
<213> ORGANISM: Escherichia coli

<400> SEQUENCE: 382

Asn Gln Ala Ala Lys Phe Ile Ile Arg Ser Asp His Gln Ile Gly Met
1               5                   10                  15

Ile Ala Ser Leu Val Gly Tyr Thr Ser Val Ser Tyr Phe Ile Lys Thr
                20                  25                  30

Phe Lys Glu Tyr Tyr Gly Val Thr Pro Lys Lys Phe Glu Ile Gly
            35                  40                  45

<210> SEQ ID NO 383
<211> LENGTH: 49
<212> TYPE: PRT
<213> ORGANISM: Escherichia coli

<400> SEQUENCE: 383

Asp Phe Cys Ala Asp Ala Ile Arg His Ala Ala Asp Asp Glu Lys Leu
1               5                   10                  15

Ala Gly Ile Gly Phe His Trp Gly Phe Ser Asp Gln Ser His Phe Ser
                20                  25                  30

Thr Val Phe Lys Gln Arg Phe Gly Met Thr Pro Gly Glu Tyr Arg Arg
            35                  40                  45

Lys

<210> SEQ ID NO 384
<211> LENGTH: 47
<212> TYPE: PRT
<213> ORGANISM: Escherichia coli

<400> SEQUENCE: 384

Gln Arg Ala Leu Gln Leu Ile Val Ile Tyr Gly Val Ser Ile Lys Arg
1               5                   10                  15

Val Ala Val Ser Cys Gly Tyr His Ser Val Ser Tyr Phe Ile Tyr Val
                20                  25                  30

Phe Arg Asn Tyr Tyr Gly Met Thr Pro Thr Glu Tyr Gln Glu Arg
            35                  40                  45

<210> SEQ ID NO 385
<211> LENGTH: 47
<212> TYPE: PRT
<213> ORGANISM: Escherichia coli

<400> SEQUENCE: 385

Gln Arg Ala Leu Gln Leu Ile Val Ile His Gly Phe Ser Ile Lys Arg
1               5                   10                  15

Val Ala Val Ser Cys Gly Tyr His Ser Val Ser Tyr Phe Ile Tyr Val
                20                  25                  30

Phe Arg Asn Tyr Tyr Gly Met Thr Pro Thr Glu Tyr Gln Glu Arg
            35                  40                  45

<210> SEQ ID NO 386
<211> LENGTH: 47
<212> TYPE: PRT
<213> ORGANISM: Escherichia coli

<400> SEQUENCE: 386

Gln Arg Ala Leu Gln Leu Ile Val Ile His Gly Phe Ser Ile Lys Arg
1               5                   10                  15

Val Ala Val Ser Cys Gly Tyr His Ser Val Ser Tyr Phe Ile Tyr Val
            20                  25                  30

Phe Arg Asn Tyr Tyr Gly Met Thr Pro Thr Glu Tyr Gln Glu Arg
        35                  40                  45

<210> SEQ ID NO 387
<211> LENGTH: 47
<212> TYPE: PRT
<213> ORGANISM: Escherichia coli

<400> SEQUENCE: 387

Arg His Ala Arg Arg Leu Leu Gln Gln Ser Pro Leu Ser Ile Pro Glu
1               5                   10                  15

Ile Ala Tyr Ala Thr Gly Phe Ser Ser Pro Ala His Phe Ser Asn Ala
            20                  25                  30

Phe Lys Arg Leu Phe Ser Gln Thr Pro Gly Ser Leu Arg Arg
        35                  40                  45

<210> SEQ ID NO 388
<211> LENGTH: 50
<212> TYPE: PRT
<213> ORGANISM: Escherichia coli

<400> SEQUENCE: 388

Glu Gly Ile Arg Ser Asp Leu Leu Asp Ser Glu Arg Asn Pro Ser Asn
1               5                   10                  15

Ile Ile Asp Thr Ala Ser Arg Trp Gly Ile Arg Ser Arg Ser Ala Leu
            20                  25                  30

Val Lys Gly Tyr Arg Lys Gln Phe Asn Glu Ala Pro Ser Glu Thr Ile
        35                  40                  45

Trp Arg
   50

<210> SEQ ID NO 389
<211> LENGTH: 47
<212> TYPE: PRT
<213> ORGANISM: Escherichia coli

<400> SEQUENCE: 389

Ala Gln Ser Leu Leu Asn Ser Val Glu Gly His Glu Asn Ile Thr Gln
1               5                   10                  15

Leu Ala Val Asn His Gly Tyr Ser Ser Pro Ser His Phe Ser Ser Glu
            20                  25                  30

Ile Lys Glu Leu Ile Gly Val Ser Pro Arg Lys Leu Ser Asn Ile
        35                  40                  45

<210> SEQ ID NO 390
<211> LENGTH: 47
<212> TYPE: PRT
<213> ORGANISM: Escherichia coli

<400> SEQUENCE: 390

Tyr His Ala Ser Gln Leu Leu Ile His Thr Ser Thr Leu Ile Ser Asp
1               5                   10                  15

Ile Ser Arg Gln Val Gly Tyr Lys Asp Pro Leu Leu Phe Ser Lys Asn
            20                  25                  30

Phe Thr Lys His Phe Glu Ile Ser Ala Ser Glu Tyr Arg His His
            35                  40                  45

<210> SEQ ID NO 391
<211> LENGTH: 47
<212> TYPE: PRT
<213> ORGANISM: Escherichia coli

<400> SEQUENCE: 391

Leu Tyr Ala His Gln Leu Leu Leu Asn Gly Lys Met Ser Ile Val Asp
1               5                   10                  15

Ile Ala Met Glu Ala Gly Phe Ser Ser Gln Ser Tyr Phe Thr Gln Ser
            20                  25                  30

Tyr Arg Arg Arg Phe Gly Cys Thr Pro Ser Gln Ala Arg Leu Thr
            35                  40                  45

<210> SEQ ID NO 392
<211> LENGTH: 47
<212> TYPE: PRT
<213> ORGANISM: Escherichia coli

<400> SEQUENCE: 392

Asp Leu Ala Lys Gln Leu Ile Ala Glu Arg Gln Lys Pro Leu Ser Gln
1               5                   10                  15

Val Ala Gln Leu Cys Gly Phe Ser Ser Gln Ser Ser Phe Ser Gln Ala
            20                  25                  30

Phe Arg Arg Leu Tyr Gly Met Ser Pro Thr Arg Tyr Gln Phe Phe
            35                  40                  45

<210> SEQ ID NO 393
<211> LENGTH: 47
<212> TYPE: PRT
<213> ORGANISM: Escherichia coli

<400> SEQUENCE: 393

Thr Glu Ile Ala Gln Lys Leu Lys Glu Ser Asn Glu Pro Ile Leu Tyr
1               5                   10                  15

Leu Ala Glu Arg Tyr Gly Phe Glu Ser Gln Gln Thr Leu Thr Arg Thr
            20                  25                  30

Phe Lys Asn Tyr Phe Asp Val Pro Pro His Lys Tyr Arg Met Thr
            35                  40                  45

<210> SEQ ID NO 394
<211> LENGTH: 47
<212> TYPE: PRT
<213> ORGANISM: Escherichia coli

<400> SEQUENCE: 394

Thr Glu Ile Ala Gln Lys Leu Lys Glu Ser Asn Glu Pro Ile Leu Tyr
1               5                   10                  15

Leu Ala Glu Arg Tyr Gly Phe Glu Ser Gln Gln Thr Leu Thr Arg Thr
            20                  25                  30

Phe Lys Asn Tyr Phe Asp Val Pro Pro His Lys Tyr Arg Ile Thr
            35                  40                  45

<210> SEQ ID NO 395
<211> LENGTH: 47

```
<212> TYPE: PRT
<213> ORGANISM: Escherichia coli

<400> SEQUENCE: 395

Asn His Val Arg Ala Leu Leu Ser Asp Thr Asp Lys Ser Ile Leu Asp
 1               5                  10                  15

Ile Ala Leu Thr Ala Gly Phe Arg Ser Ser Arg Phe Tyr Ser Thr
                20                  25                  30

Phe Gly Lys Tyr Val Gly Met Ser Pro Gln Gln Tyr Arg Lys Leu
            35                  40                  45

<210> SEQ ID NO 396
<211> LENGTH: 47
<212> TYPE: PRT
<213> ORGANISM: Escherichia coli

<400> SEQUENCE: 396

Glu Tyr Ala Cys Gln Leu Leu Asp Ser Ser Asp Gln Ser Val Ala Arg
 1               5                  10                  15

Val Gly Gln Ala Val Gly Tyr Asp Asp Ser Tyr Tyr Phe Ser Arg Leu
                20                  25                  30

Phe Ser Lys Val Met Gly Leu Ser Pro Ser Ala Tyr Arg Gln Arg
            35                  40                  45

<210> SEQ ID NO 397
<211> LENGTH: 47
<212> TYPE: PRT
<213> ORGANISM: Escherichia coli

<400> SEQUENCE: 397

Lys Arg Ser Gln Tyr Leu Leu Glu Asn Pro Lys Leu Ser Ile Ala Glu
 1               5                  10                  15

Ile Ser Asn Ser Val Gly Phe Ser Asp Ser Leu Ala Phe Ser Lys Ala
                20                  25                  30

Phe Lys Asn Tyr Phe Gly Lys Ser Pro Ser Lys Phe Arg Lys Glu
            35                  40                  45

<210> SEQ ID NO 398
<211> LENGTH: 47
<212> TYPE: PRT
<213> ORGANISM: Escherichia coli

<400> SEQUENCE: 398

Val Asn Gly Leu Leu Asp Val Phe Leu His Asn Gln Thr Ile Thr Ser
 1               5                  10                  15

Ala Ala Met Asn Asn Gly Tyr Arg Ser Thr Ser His Phe Ser Asn Glu
                20                  25                  30

Ile Lys Thr Arg Leu Gly Phe Ser Ala Arg Glu Leu Ser Asn Ile
            35                  40                  45

<210> SEQ ID NO 399
<211> LENGTH: 47
<212> TYPE: PRT
<213> ORGANISM: Escherichia coli

<400> SEQUENCE: 399

Val Asn Gly Leu Leu Asp Val Phe Leu His Asn Gln Thr Ile Thr Ser
 1               5                  10                  15

Ala Ala Met Asn Asn Gly Tyr Ala Ser Thr Ser His Phe Ser Asn Glu
                20                  25                  30

Ile Lys Thr Arg Leu Gly Phe Ser Ala Arg Glu Leu Ser Asn Ile
```

-continued

<210> SEQ ID NO 400
<211> LENGTH: 47
<212> TYPE: PRT
<213> ORGANISM: Escherichia coli

<400> SEQUENCE: 400

Arg Leu Ala Leu Gln Tyr Leu Thr Thr Thr Gln Leu Pro Leu Tyr Glu
1               5                   10                  15

Ile Ala Leu Leu Leu Gly Phe Asn Asp Ser Ser Asn Phe Arg Arg Ala
            20                  25                  30

Phe Arg Lys Trp Thr Gly Lys Leu Pro Ser Asp Tyr Arg Glu Ala
        35                  40                  45

<210> SEQ ID NO 401
<211> LENGTH: 44
<212> TYPE: PRT
<213> ORGANISM: Escherichia coli

<400> SEQUENCE: 401

Arg Glu Ala His Arg Met Leu Cys Asp Glu Glu Ala Asn Val Ser Thr
1               5                   10                  15

Val Ala Tyr Arg Val Gly Tyr Ser Pro Ala His Phe Ser Ile Ala Phe
            20                  25                  30

Arg Lys Arg Tyr Gly Ile Ser Pro Ser Glu Ile Arg
        35                  40

<210> SEQ ID NO 402
<211> LENGTH: 47
<212> TYPE: PRT
<213> ORGANISM: Escherichia coli

<400> SEQUENCE: 402

Lys His Ala Ser Leu Phe Leu Arg Thr Thr Asp Lys Asn Ile Asp Glu
1               5                   10                  15

Ile Ser Cys Leu Val Gly Phe Asn Ser Thr Ser Tyr Phe Ile Lys Val
            20                  25                  30

Phe Lys Glu Tyr Tyr Asn Thr Thr Pro Lys Lys Tyr Asn Gly Val
        35                  40                  45

<210> SEQ ID NO 403
<211> LENGTH: 47
<212> TYPE: PRT
<213> ORGANISM: Escherichia coli

<400> SEQUENCE: 403

Val Ser Ala Arg Glu Leu Leu Cys His Ser Asp Trp Ser Ile Ala Ser
1               5                   10                  15

Ile Ala Arg Asn Leu Gly Phe Ser Gln Thr Ser Tyr Phe Cys Lys Val
            20                  25                  30

Phe Arg Gln Thr Tyr Gln Val Thr Pro Gln Ala Tyr Arg Gln Gln
        35                  40                  45

<210> SEQ ID NO 404
<211> LENGTH: 47
<212> TYPE: PRT
<213> ORGANISM: Escherichia coli

<400> SEQUENCE: 404

Leu Glu Ala Ala Lys Ser Leu Gln Glu Lys Asp Met Ser Ile Leu Asp
1               5                   10                  15

```
Ile Ala Leu Met Tyr Gly Phe Ser Ser Gln Ala Thr Phe Thr Arg Ile
            20                  25                  30

Phe Lys Lys His Phe Asn Thr Thr Pro Ala Lys Phe Arg Glu Asn
    35                  40                  45
```

<210> SEQ ID NO 405
<211> LENGTH: 47
<212> TYPE: PRT
<213> ORGANISM: Escherichia coli

<400> SEQUENCE: 405

```
Glu Asp Ala Lys Gln Arg Leu Ser Thr Ser Asn Asn Ser Val Gln Ser
 1               5                  10                  15

Ile Ala Asn Met Val Gly Tyr Lys Asp Ser Phe Thr Phe Ser Lys Ala
            20                  25                  30

Phe Lys Arg Tyr Ser Gly Ala Ser Pro Ser Tyr Tyr Arg Lys Ser
    35                  40                  45
```

<210> SEQ ID NO 406
<211> LENGTH: 47
<212> TYPE: PRT
<213> ORGANISM: Escherichia coli

<400> SEQUENCE: 406

```
Leu Leu Ala Ala Arg Asp Leu Arg Glu Ser Asp Glu Arg Val Tyr Glu
 1               5                  10                  15

Ile Cys Leu Arg Tyr Gly Phe Glu Ser Gln Gln Thr Phe Thr Arg Ile
            20                  25                  30

Phe Thr Arg Thr Phe His Gln Pro Pro Gly Ala Tyr Arg Lys Glu
    35                  40                  45
```

<210> SEQ ID NO 407
<211> LENGTH: 47
<212> TYPE: PRT
<213> ORGANISM: Escherichia coli

<400> SEQUENCE: 407

```
Leu Leu Ala Ala Arg Asp Leu Arg Asp Thr Asp Gln Arg Val Tyr Asp
 1               5                  10                  15

Ile Cys Leu Lys Tyr Gly Phe Asp Ser Gln Gln Thr Phe Thr Arg Val
            20                  25                  30

Phe Thr Arg Thr Phe Asn Gln Pro Pro Gly Ala Tyr Arg Lys Glu
    35                  40                  45
```

<210> SEQ ID NO 408
<211> LENGTH: 47
<212> TYPE: PRT
<213> ORGANISM: Escherichia coli

<400> SEQUENCE: 408

```
Cys His Ala Gln Tyr Leu Leu Gln His Ser Arg Leu Leu Ile Ser Asp
 1               5                  10                  15

Ile Ser Thr Glu Cys Gly Phe Glu Asp Ser Asn Tyr Phe Ser Val Val
            20                  25                  30

Phe Thr Arg Glu Thr Gly Met Thr Pro Ser Gln Trp Arg His Leu
    35                  40                  45
```

<210> SEQ ID NO 409
<211> LENGTH: 47
<212> TYPE: PRT
<213> ORGANISM: Escherichia coli

<400> SEQUENCE: 409

Cys His Ala Gln Tyr Leu Leu Gln His Ser Pro Leu Met Ile Ser Glu
1               5                   10                  15

Ile Ser Met Gln Cys Gly Phe Glu Asp Ser Asn Tyr Phe Ser Val Val
            20                  25                  30

Phe Thr Arg Glu Thr Gly Met Thr Pro Ser Gln Trp Arg His Leu
        35                  40                  45

<210> SEQ ID NO 410
<211> LENGTH: 47
<212> TYPE: PRT
<213> ORGANISM: Escherichia coli

<400> SEQUENCE: 410

Met Lys Ala Arg His Leu Leu Arg His Ser Glu Ala Ser Val Thr Asp
1               5                   10                  15

Ile Ala Tyr Arg Cys Gly Phe Ser Asp Ser Asn His Phe Ser Thr Leu
            20                  25                  30

Phe Arg Arg Glu Phe Asn Trp Ser Pro Arg Asp Ile Arg Gln Gly
        35                  40                  45

<210> SEQ ID NO 411
<211> LENGTH: 47
<212> TYPE: PRT
<213> ORGANISM: Escherichia coli

<400> SEQUENCE: 411

Ile Lys Ala Arg His Leu Leu Arg His Ser Asp His Ser Val Thr Glu
1               5                   10                  15

Ile Ala Tyr Arg Cys Gly Phe Gly Asp Ser Asn His Phe Ser Thr Leu
            20                  25                  30

Phe Arg Arg Glu Phe Asn Trp Ser Pro Arg Asp Ile Arg Gln Gly
        35                  40                  45

<210> SEQ ID NO 412
<211> LENGTH: 49
<212> TYPE: PRT
<213> ORGANISM: Escherichia coli

<400> SEQUENCE: 412

Ser Leu Ala Lys Ser Leu Ile Leu Ala Glu Gly Glu Ala Thr Ser Ile
1               5                   10                  15

Ser Gln Ile Ala Tyr Asn Val Gly Phe Asn Asp Leu Ser Tyr Phe Asn
            20                  25                  30

Arg Thr Phe Arg Ser Arg Tyr Gly Val Arg Pro Ser Asp Leu Arg Arg
        35                  40                  45

Leu

<210> SEQ ID NO 413
<211> LENGTH: 47
<212> TYPE: PRT
<213> ORGANISM: Escherichia coli

<400> SEQUENCE: 413

Ser Lys Ala Ala Leu Leu Leu Leu Glu Asn Ser Tyr Gln Ile Ser Gln
1               5                   10                  15

Ile Ser Asn Met Ile Gly Ile Ser Ser Ala Ser Tyr Phe Ile Arg Ile
            20                  25                  30

Phe Asn Lys His Tyr Gly Val Thr Pro Lys Gln Phe Phe Thr Tyr

```
                35                  40                  45
```

<210> SEQ ID NO 414
<211> LENGTH: 47
<212> TYPE: PRT
<213> ORGANISM: Escherichia coli

<400> SEQUENCE: 414

```
Ser Lys Ser Ala Val Ala Leu Arg Leu Thr Ala Arg Pro Ile Leu Asp
  1               5                  10                  15

Ile Ala Leu Gln Tyr Arg Phe Asp Ser Gln Gln Thr Phe Thr Arg Ala
                 20                  25                  30

Phe Lys Lys Gln Phe Ala Gln Thr Pro Ala Leu Tyr Arg Arg Ser
                 35                  40                  45
```

<210> SEQ ID NO 415
<211> LENGTH: 47
<212> TYPE: PRT
<213> ORGANISM: Escherichia coli

<400> SEQUENCE: 415

```
Leu Leu Ala Ala Val Glu Leu Arg Thr Thr Glu Arg Pro Ile Phe Asp
  1               5                  10                  15

Ile Ala Met Asp Leu Gly Tyr Val Ser Gln Gln Thr Phe Ser Arg Val
                 20                  25                  30

Phe Arg Arg Gln Phe Asp Arg Thr Pro Ser Asp Tyr Arg His Arg
                 35                  40                  45
```

<210> SEQ ID NO 416
<211> LENGTH: 47
<212> TYPE: PRT
<213> ORGANISM: Escherichia coli

<400> SEQUENCE: 416

```
Leu Leu Ala Ala Val Glu Leu Arg Thr Thr Glu Arg Pro Ile Phe Asp
  1               5                  10                  15

Ile Ala Met Asp Leu Gly Tyr Val Ser Gln Gln Thr Phe Ser Arg Val
                 20                  25                  30

Phe Arg Arg Glu Phe Asp Arg Thr Pro Ser Asp Tyr Arg His Arg
                 35                  40                  45
```

<210> SEQ ID NO 417
<211> LENGTH: 47
<212> TYPE: PRT
<213> ORGANISM: Escherichia coli

<400> SEQUENCE: 417

```
Ser Tyr Ser Ile Ser Leu Met Lys Thr Gly Glu Phe Lys Ile Lys Gln
  1               5                  10                  15

Ile Ala Tyr Gln Ser Gly Phe Ala Ser Val Ser Tyr Phe Ser Thr Val
                 20                  25                  30

Phe Lys Ser Thr Met Asn Val Ala Pro Ser Glu Tyr Leu Phe Met
                 35                  40                  45
```

<210> SEQ ID NO 418
<211> LENGTH: 47
<212> TYPE: PRT
<213> ORGANISM: Escherichia coli

<400> SEQUENCE: 418

```
Thr Lys Ala Ala Val Glu Leu Arg Leu Thr Lys Lys Thr Ile Leu Glu
  1               5                  10                  15
```

Ile Ala Leu Lys Tyr Gln Phe Asp Ser Gln Gln Ser Phe Thr Arg Arg
            20                  25                  30

Phe Lys Tyr Ile Phe Lys Val Thr Pro Ser Tyr Tyr Arg Arg Asn
        35                  40                  45

<210> SEQ ID NO 419
<211> LENGTH: 50
<212> TYPE: PRT
<213> ORGANISM: Escherichia coli

<400> SEQUENCE: 419

Gln Lys Ala Arg Lys Asp Leu Leu Arg Ala Asp Pro Ala Ser Glu Gly
1               5                   10                  15

Val Thr Glu Ile Ala Gln Arg Trp Gly Phe Leu His Val Gly Arg Phe
            20                  25                  30

Ala Gly Glu Tyr Lys Gln Thr Phe Gly Val Ser Pro Ser Glu Asp Leu
        35                  40                  45

Arg Thr
    50

<210> SEQ ID NO 420
<211> LENGTH: 47
<212> TYPE: PRT
<213> ORGANISM: Escherichia coli

<400> SEQUENCE: 420

Gly Met Ala Leu Asn Tyr Leu Thr Phe Ser Asn Tyr Ser Val Phe Gln
1               5                   10                  15

Ile Ser His Arg Cys Gly Phe Gly Ser Asn Ala Tyr Phe Cys Asp Val
            20                  25                  30

Phe Lys Arg Lys Tyr Asn Met Thr Pro Ser Gln Phe Arg Leu Gln
        35                  40                  45

<210> SEQ ID NO 421
<211> LENGTH: 47
<212> TYPE: PRT
<213> ORGANISM: Escherichia coli

<400> SEQUENCE: 421

Pro Ile Ala Leu Asn Tyr Leu Thr Phe Ser Asn Tyr Ser Val Phe Gln
1               5                   10                  15

Ile Ser His Arg Cys Gly Phe Gly Ser Asn Ala Tyr Phe Cys Asp Ala
            20                  25                  30

Phe Lys Arg Lys Tyr Gly Met Thr Pro Ser Gln Phe Arg Thr Gln
        35                  40                  45

<210> SEQ ID NO 422
<211> LENGTH: 47
<212> TYPE: PRT
<213> ORGANISM: Escherichia coli

<400> SEQUENCE: 422

His His Ala Ala Lys Leu Leu Leu Asn Ser Gln Ser Tyr Ile Asn Asp
1               5                   10                  15

Val Ser Arg Leu Ile Gly Ile Ser Ser Pro Ser Tyr Phe Ile Arg Lys
            20                  25                  30

Phe Asn Glu Tyr Tyr Gly Ile Thr Pro Lys Lys Phe Tyr Leu Tyr
        35                  40                  45

<210> SEQ ID NO 423

```
<211> LENGTH: 47
<212> TYPE: PRT
<213> ORGANISM: Escherichia coli

<400> SEQUENCE: 423
```

Leu Tyr Ala His Gln Leu Leu Leu Asn Gly Lys Met Ser Ile Val Asp
 1               5                  10                  15

Ile Ala Met Glu Ala Gly Phe Ser Ser Gln Ser Tyr Phe Thr Gln Ser
            20                  25                  30

Tyr Arg Arg Arg Phe Gly Cys Thr Pro Ser Gln Ala Arg Leu Thr
        35                  40                  45

```
<210> SEQ ID NO 424
<211> LENGTH: 47
<212> TYPE: PRT
<213> ORGANISM: Escherichia coli

<400> SEQUENCE: 424
```

Ala Gln Ala Ala Arg Tyr Leu Ala Gln Pro Gly Leu Tyr Leu Ser Gln
 1               5                  10                  15

Ile Ala Val Leu Leu Gly Tyr Ser Glu Gln Ser Ala Leu Asn Arg Ser
            20                  25                  30

Cys Arg Arg Trp Phe Gly Met Thr Pro Arg Gln Tyr Arg Ala Tyr
        35                  40                  45

```
<210> SEQ ID NO 425
<211> LENGTH: 47
<212> TYPE: PRT
<213> ORGANISM: Escherichia coli

<400> SEQUENCE: 425
```

Glu Lys Ala Arg Ser Leu Leu Ile Ser Thr Thr Leu Ser Ile Asn Glu
 1               5                  10                  15

Ile Ser Gln Met Cys Gly Tyr Pro Ser Leu Gln Tyr Phe Tyr Ser Val
            20                  25                  30

Phe Lys Lys Ala Tyr Asp Thr Thr Pro Lys Glu Tyr Arg Asp Val
        35                  40                  45

```
<210> SEQ ID NO 426
<211> LENGTH: 47
<212> TYPE: PRT
<213> ORGANISM: Escherichia coli

<400> SEQUENCE: 426
```

Ser Arg Ala Lys Asn Leu Leu Gln Gln Thr Asp Ile Ser Ile Lys Glu
 1               5                  10                  15

Ile Thr Glu Ile Cys Gly Tyr Pro Ser Ile Gln Tyr Phe Tyr Ser Val
            20                  25                  30

Phe Lys Lys Glu Phe Glu Met Thr Pro Lys Glu Phe Arg Leu Asn
        35                  40                  45

```
<210> SEQ ID NO 427
<211> LENGTH: 50
<212> TYPE: PRT
<213> ORGANISM: Escherichia coli

<400> SEQUENCE: 427
```

Glu Ser Ile Arg Ala Cys Leu Asn Asp Pro Ser Ala Asn Val Arg Ser
 1               5                  10                  15

Ile Thr Glu Ile Ala Leu Asp Tyr Gly Phe Leu His Leu Gly Arg Phe
            20                  25                  30

-continued

Ala Glu Asn Tyr Arg Ser Ala Phe Gly Glu Leu Pro Ser Asp Thr Leu
        35                  40                  45

Arg Gln
    50

<210> SEQ ID NO 428
<211> LENGTH: 50
<212> TYPE: PRT
<213> ORGANISM: Escherichia coli

<400> SEQUENCE: 428

Glu Ser Ile Arg Ala Cys Leu Asn Asp Pro Ser Ala Asn Val Arg Ser
1               5                   10                  15

Ile Thr Glu Ile Ala Leu Asp Tyr Gly Phe Leu His Leu Gly Arg Phe
            20                  25                  30

Ala Glu Asn Tyr Arg Ser Ala Phe Gly Glu Leu Pro Ser Asp Thr Leu
        35                  40                  45

Arg Gln
    50

<210> SEQ ID NO 429
<211> LENGTH: 50
<212> TYPE: PRT
<213> ORGANISM: Escherichia coli

<400> SEQUENCE: 429

Glu Cys Val Arg Ala Cys Leu Ser Asn Pro Thr Thr Asn Ile Arg Ser
1               5                   10                  15

Ile Thr Glu Val Ala Leu Asp Tyr Gly Phe Leu His Leu Gly Arg Phe
            20                  25                  30

Ala Glu Lys Tyr Arg Ser Thr Phe Gly Glu Leu Pro Ser Asp Thr Leu
        35                  40                  45

Ser Leu
    50

<210> SEQ ID NO 430
<211> LENGTH: 50
<212> TYPE: PRT
<213> ORGANISM: Escherichia coli

<400> SEQUENCE: 430

Glu Cys Ile Arg Ala Arg Leu Ser Asp Pro Asn Ala Asn Val Arg Ser
1               5                   10                  15

Val Thr Glu Met Ala Leu Asp Tyr Gly Phe Phe His Thr Gly Arg Phe
            20                  25                  30

Ala Glu Asn Tyr Arg Ser Thr Phe Gly Glu Leu Pro Ser Asp Thr Leu
        35                  40                  45

Arg Arg
    50

<210> SEQ ID NO 431
<211> LENGTH: 50
<212> TYPE: PRT
<213> ORGANISM: Escherichia coli

<400> SEQUENCE: 431

Glu Cys Ile Arg Ala Arg Leu Ser Asp Pro Asn Ala Asn Val Arg Ser
1               5                   10                  15

Val Thr Glu Met Ala Leu Asp Tyr Gly Phe Phe His Thr Gly Arg Phe
            20                  25                  30

```
Ala Glu Asn Tyr Arg Ser Thr Phe Gly Glu Leu Pro Ser Asp Thr Leu
        35                  40                  45

Arg Arg
    50

<210> SEQ ID NO 432
<211> LENGTH: 48
<212> TYPE: PRT
<213> ORGANISM: Escherichia coli

<400> SEQUENCE: 432

Ala Ala Ala His Gly Ala Ile Lys Ala Gly Arg Ala Gly Ser Ile Thr
 1               5                  10                  15

Glu Leu Ala Leu Asn Leu Gln Phe Ser Asn Pro Gly Arg Phe Ser Val
            20                  25                  30

Leu Tyr Lys Ser Ala Tyr Gly Leu Ser Pro Ser Ser Ala Leu Arg Phe
        35                  40                  45

<210> SEQ ID NO 433
<211> LENGTH: 47
<212> TYPE: PRT
<213> ORGANISM: Escherichia coli

<400> SEQUENCE: 433

Gln Ser Ala Ala Phe Leu Leu Lys Gln Ser Gln Gln Ser Val Leu Ala
 1               5                  10                  15

Ile Ala Leu Glu Val Gly Tyr Gln Ser Glu Ala His Phe Cys Lys Val
            20                  25                  30

Phe Lys Asn Tyr Tyr Gln Leu Ser Pro Ser Gln Tyr Arg Lys Ser
        35                  40                  45

<210> SEQ ID NO 434
<211> LENGTH: 47
<212> TYPE: PRT
<213> ORGANISM: Escherichia coli

<400> SEQUENCE: 434

Thr Lys Ala Lys Arg Leu Met Ala Lys Ser Asn Cys Lys Leu Lys Glu
 1               5                  10                  15

Ile Ala His Gln Thr Gly Tyr Gln Asp Glu Phe Tyr Phe Ser Arg Ile
            20                  25                  30

Phe Lys Lys Tyr Thr Gly Cys Ser Pro Thr Ser Tyr Met Lys Lys
        35                  40                  45

<210> SEQ ID NO 435
<211> LENGTH: 47
<212> TYPE: PRT
<213> ORGANISM: Escherichia coli

<400> SEQUENCE: 435

Asn Asn Ala Leu Ser Ala Ile Gln Thr Thr Val Lys Pro Ile Ser Glu
 1               5                  10                  15

Ile Ala Arg Glu Asn Gly Tyr Lys Cys Pro Ser Arg Phe Thr Glu Arg
            20                  25                  30

Phe His Asn Arg Phe Asn Ile Thr Pro Arg Glu Ile Arg Lys Ala
        35                  40                  45

<210> SEQ ID NO 436
<211> LENGTH: 45
<212> TYPE: PRT
<213> ORGANISM: Escherichia coli
```

-continued

<400> SEQUENCE: 436

Glu Gln Ala Lys Lys Val Leu Leu Lys Ser Val Thr Glu Thr Ala
1               5                   10                  15

Tyr Glu Val Gly Phe Asn Asn Ser Asn Tyr Phe Ala Thr Val Phe Lys
                20                  25                  30

Lys Arg Thr Asn Tyr Thr Pro Lys Gln Phe Lys Arg Thr
            35                  40                  45

<210> SEQ ID NO 437
<211> LENGTH: 47
<212> TYPE: PRT
<213> ORGANISM: Escherichia coli

<400> SEQUENCE: 437

Thr Val Ala Val Asp Leu Leu Arg Asn Val Gly Leu Thr Val Gln Gln
1               5                   10                  15

Val Ser Thr Arg Leu Gly Tyr Thr Glu Val Ser Thr Phe Ser His Ala
                20                  25                  30

Phe Lys Arg Trp Tyr Gly Val Ala Pro Ser Glu Tyr Ser Arg Arg
            35                  40                  45

<210> SEQ ID NO 438
<211> LENGTH: 46
<212> TYPE: PRT
<213> ORGANISM: Escherichia coli

<400> SEQUENCE: 438

Gln His Ala Lys Asn Leu Ile Arg Val Glu Gly Ser Val Asn Lys Ile
1               5                   10                  15

Ala Glu Gln Cys Gly Tyr Ala Ser Thr Ser Tyr Phe Ile Tyr Ala Phe
                20                  25                  30

Arg Lys His Phe Gly Asn Ser Pro Lys Arg Val Ser Lys Glu
            35                  40                  45

<210> SEQ ID NO 439
<211> LENGTH: 47
<212> TYPE: PRT
<213> ORGANISM: Escherichia coli

<400> SEQUENCE: 439

Thr Glu Ala Lys Trp Ser Leu Thr Asn Thr Glu Leu Ser Gln Ala Glu
1               5                   10                  15

Ile Ser Trp Arg Val Gly Tyr Glu Asn Val Asp His Phe Ala Lys Leu
                20                  25                  30

Phe Leu Arg His Val Gly Cys Ser Pro Ser Asp Tyr Arg Arg Gln
            35                  40                  45

<210> SEQ ID NO 440
<211> LENGTH: 46
<212> TYPE: PRT
<213> ORGANISM: Escherichia coli

<400> SEQUENCE: 440

Ile Met Ala Leu Gln Gly Leu Val Lys Gly Asp Thr Val Gln Lys Val
1               5                   10                  15

Ala His Thr Leu Gly Tyr Asp Ser Thr Thr Ala Phe Ile Thr Met Phe
                20                  25                  30

Lys Lys Gly Leu Gly Gln Thr Pro Gly Arg Tyr Ile Ala Arg
            35                  40                  45

-continued

<210> SEQ ID NO 441
<211> LENGTH: 46
<212> TYPE: PRT
<213> ORGANISM: Escherichia coli

<400> SEQUENCE: 441

Asn Lys Ala Ala Glu Leu Leu Lys Ser Thr Asn Leu Ser Ile Lys Glu
1               5                   10                  15

Ile Ala Glu Glu Ile Gly Phe Ser Val His Tyr Phe Thr Arg Val Phe
            20                  25                  30

Ser Ala Lys Ile Gly Ser Ser Pro Gly Leu Phe Arg Ser Leu
        35                  40                  45

<210> SEQ ID NO 442
<211> LENGTH: 47
<212> TYPE: PRT
<213> ORGANISM: Escherichia coli

<400> SEQUENCE: 442

Ser Met Ala Arg Arg Leu Leu Glu Leu Arg Gln Ile Pro Leu His Thr
1               5                   10                  15

Ile Ala Glu Lys Cys Gly Tyr Ser Ser Thr Ser Tyr Phe Ile Asn Thr
            20                  25                  30

Phe Arg Gln Tyr Tyr Gly Val Thr Pro His Gln Phe Ala Gln His
        35                  40                  45

<210> SEQ ID NO 443
<211> LENGTH: 47
<212> TYPE: PRT
<213> ORGANISM: Escherichia coli

<400> SEQUENCE: 443

Asp Leu Ala Leu Ser Leu Leu Lys Gln Gln Gly Asn Ser Val Gly Glu
1               5                   10                  15

Val Ala Asp Thr Leu Asn Phe Phe Asp Ser Phe His Phe Ser Lys Ala
            20                  25                  30

Phe Lys His Lys Phe Gly Tyr Ala Pro Ser Ala Val Leu Lys Asn
        35                  40                  45

<210> SEQ ID NO 444
<211> LENGTH: 47
<212> TYPE: PRT
<213> ORGANISM: Escherichia coli

<400> SEQUENCE: 444

Glu His Ala Lys Thr Leu Leu Lys Gly Tyr Asp Leu Lys Val Lys Glu
1               5                   10                  15

Val Ala His Ala Cys Gly Phe Val Asp Ser Asn Tyr Phe Cys Arg Leu
            20                  25                  30

Phe Arg Lys Asn Thr Glu Arg Ser Pro Ser Glu Tyr Arg Arg Gln
        35                  40                  45

<210> SEQ ID NO 445
<211> LENGTH: 47
<212> TYPE: PRT
<213> ORGANISM: Escherichia coli

<400> SEQUENCE: 445

Thr Glu Ala Lys Arg Leu Leu Ser Ser Thr Asn Asp Lys Met Gly Val
1               5                   10                  15

Ile Ala Glu Thr Val Gly Met Glu Asp Pro Thr Tyr Phe Ser Lys Leu
            20                  25                  30

```
Phe Lys Gln Ile Glu Gly Ile Ser Pro Ile Glu Tyr Arg Lys Ile
        35                  40                  45
```

<210> SEQ ID NO 446
<211> LENGTH: 47
<212> TYPE: PRT
<213> ORGANISM: Escherichia coli

<400> SEQUENCE: 446

```
Cys Arg Ala Ala Ile Leu Val Arg Leu Thr Ala Lys Ser Met Leu Asp
 1               5                  10                  15

Ile Ala Leu Ser Leu His Phe Asp Ser Gln Ser Phe Ser Arg Glu
            20                  25                  30

Phe Lys Lys Leu Phe Gly Cys Ser Pro Arg Glu Tyr Arg His Arg
        35                  40                  45
```

<210> SEQ ID NO 447
<211> LENGTH: 47
<212> TYPE: PRT
<213> ORGANISM: Escherichia coli

<400> SEQUENCE: 447

```
Gln Ile Ala Ala Gln Met Phe Ser Arg Glu Thr Leu Pro Val Val Val
 1               5                  10                  15

Ile Ala Glu Ser Val Gly Tyr Ala Ser Glu Ser Ser Phe His Lys Ala
            20                  25                  30

Phe Val Arg Glu Phe Gly Cys Thr Pro Gly Glu Tyr Arg Glu Arg
        35                  40                  45
```

<210> SEQ ID NO 448
<211> LENGTH: 46
<212> TYPE: PRT
<213> ORGANISM: Escherichia coli

<400> SEQUENCE: 448

```
Gln Arg Ala Leu Arg Leu Ala Arg Ala Gly Val Pro Phe Ala Glu Thr
 1               5                  10                  15

Ala Thr Leu Ala Gly Phe Ala Asp Gln Ala His Leu Ala Arg Asp Val
            20                  25                  30

Arg Glu Met Ala Gly Ser Ser Leu Ser Glu Leu Val Glu Arg
        35                  40                  45
```

<210> SEQ ID NO 449
<211> LENGTH: 47
<212> TYPE: PRT
<213> ORGANISM: Escherichia coli

<400> SEQUENCE: 449

```
Ala Lys Ala Arg Met Ile Leu Gln Lys Tyr His Leu Ser Ile His Glu
 1               5                  10                  15

Val Ala Gln Arg Cys Gly Phe Pro Asp Ser Asp Tyr Phe Cys Arg Val
            20                  25                  30

Phe Arg Arg Gln Phe Gly Leu Thr Pro Gly Glu Tyr Ser Ala Arg
        35                  40                  45
```

<210> SEQ ID NO 450
<211> LENGTH: 47
<212> TYPE: PRT
<213> ORGANISM: Escherichia coli

<400> SEQUENCE: 450

-continued

```
His Lys Ala Arg Met Met Ile Ile His Asp Gly Met Lys Ala Ser Ala
 1               5                  10                  15

Ala Ala Met Arg Val Gly Tyr Glu Ser Ala Ser Gln Phe Ser Arg Glu
            20                  25                  30

Phe Lys Arg Tyr Phe Gly Val Thr Pro Gly Glu Asp Ala Ala Arg
        35                  40                  45
```

TRANSCRIPTION FACTOR MODULATING COMPOUNDS AND METHODS OF USE THEREOF

RELATED APPLICATIONS

This application is a division of U.S. patent application Ser. No. 11/115,024, filed Apr. 25, 2005 now abandoned, which claims priority to U.S. Provisional Patent Application 60/623,251, filed Oct. 28, 2004, U.S. Provisional Patent Application 60/569,032, filed May 7, 2004, and U.S. Provisional Patent Application 60/565,047, filed Apr. 23, 2004. This application is related to U.S. patent application Ser. No. 10/700,661, filed Nov. 3, 2003, which claims priority to U.S. Provisional Patent Application No. 60/425,916, filed Nov. 13, 2002; and U.S. Provisional Patent Application No. 60/423,319, filed Nov. 1, 2002, and which is a continuation-in-part of U.S. application Ser. No. 10/139,591, filed on May 6, 2002, which claims priority to U.S. Provisional Patent Application Ser. No. 60/288,660, entitled "Helix-Turn-Helix Protein Modulating Compounds and Methods of Use Thereof," filed on May 4, 2001. The entire contents of each of the aforementioned applications are hereby incorporated herein by reference.

BACKGROUND OF THE INVENTION

Most antibiotics currently used and in development to treat bacterial infections impose selective pressure on microorganisms and have led to the development of widespread antibiotic resistance. Therefore, the development of an alternative approach to treating microbial infections would be of great benefit.

Multidrug resistance in bacteria is generally attributed to the acquisition of multiple transposons and plasmids bearing genetic determinants for different mechanisms of resistance (Gold et al. 1996. *N. Engl. J. Med.* 335:1445). However, descriptions of intrinsic mechanisms that confer multidrug resistance have begun to emerge. The first of these was a chromosomally encoded multiple antibiotic resistance (mar) locus in *Escherichia coli* (George and Levy, 1983. *J. Bacteriol.* 155:531; George and Levy 1983 *J. Bacteriol.* 155:541). Mar mutants of *E. coli* arose at a frequency of $10^{-6}$ to $10^{-7}$ and were selected by growth on subinhibitory levels of tetracycline or chloramphenicol (George and Levy, supra). These mutants exhibited resistance to tetracyclines, chloramphenicol, penicillins, cephalosporins, puromycin, nalidixic acid, and rifampin (George and Levy, supra). Later, the resistance phenotype was extended to include fluoroquinolones (Cohen et al. 1989. *Antimicrob. Agents Chemother.* 33:1318), oxidative stress agents (Ariza et al. 1994. *J. Bacteriol.* 176:143; Greenberg et al. 1991. *J. Bacteriol.* 73:4433), and more recently, organic solvents (White et al. 1997. *J. of Bacteriology* 179:6122; Asako, et al. 1997. *J. Bacteriol.* 176:143) and household disinfectants, e.g., pine oil and/or TRICLOSAN® (McMurry et al. 1998. *FEMS Microbiology Letters* 166:305; Moken et al. 1997. *Antimicrobial Agents and Chemotherapy* 41:2770).

The mar locus consists of two divergently positioned transcriptional units that flank a common promoter/operator region in *E. coli*, *Salmonella typhimurium*, and other Entrobacteriacae (Alekshun and Levy. 1997, *Antimicrobial Agents and Chemother.* 41: 2067). One operon encodes MarC, a putative integral inner membrane protein without any yet apparent function, but which appears to contribute to the Mar phenotype in some strains. The other operon comprises marRAB, encoding the Mar repressor (MarR), which binds marO and negatively regulates expression of marRAB (Cohen et al. 1994. *J. Bacteriol.* 175:1484; Martin and Rosner 1995. *PNAS* 92:5456; Seoane and Levy. 1995 *J. Bacteriol.* 177:530), an activator (MarA), which controls expression of other genes on the chromosome, e.g., the mar regulon (Cohen et al. 1994 *J. Bacteriol.* 175:1484; Gambino et. al. 1993. *J. Bacteriol.* 175:2888; Seoane and Levy, 1995 *J. Bacteriol.* 177:530), and a putative small protein (MarB) of unknown function.

Exposure of *E. coli* to several chemicals, including tetracycline and chloramphenicol (Hachler et al. 1991 *J Bacteriol* 173(17):5532-8; Ariza, 1994, *J Bacteriol;* 176(1):143-8), sodium salicylate and its derivatives (Cohen, 1993, *J Bacteriol;* 175(24):7856-62) and oxidative stress agents (Seoane et al. 1995. *J Bacteriol;* 177(12):3414-9) induces the Mar phenotype. Some of these chemicals act directly at the level of MarR by interacting with the repressor and inactivating its function (Alekshun. 1999. *J. Bacteriol.* 181:3303-3306) while others (antibiotics such as tetracycline and chloramphenicol) appear to induce mar expression by an alternative mechanism (Alekshun. 1999. *J. Bacteriol.* 181:3303-3306) e.g., through a signal transduction pathway.

Once expressed, MarA activates the transcription of several genes that constitute the *E. coli* mar regulon (Alekshun, 1997, *Antimicrob. Agents Chemother.* 41:2067-2075; Alekshun, 1999, *J. Bacteriol.* 181:3303-3306). With respect to decreased antibiotic susceptibility, the increased expression of the AcrAB/TolC multidrug efflux system (Fralick, 1996, *J Bacteriol.* 178(19):5803-5; Okusu, 1996 J Bacteriol; 178(1): 306-8) and decreased synthesis of OmpF (Cohen, 1988, *J Bacteriol.;* 170(12):5416-22) an outer membrane protein, play major roles. Organic solvent tolerance, however, is attributed to MarA mediating increased expression of AcrAB, TolC, OmpX, and a 77 kDa protein (Aono, 1998, *Extremophiles;* 2(3):239-48; Aono, 1998 *J Bacteriol;* 180(4):938-44.) but is independent of OmpF levels (Asako, 1999, *Appl Environ Microbiol;* 65(1):294-6).

MarA is a member of the XylS/AraC family of transcriptional activators (Gallegos et al. 1993. *Nucleic Acids Res.* 21:807). There are more than 100 proteins within the XylS/AraC family and a defining characteristic of this group of proteins is the presence of two helix-turn-helix (HTH) DNA binding motifs. Proteins within this family activate many different genes, some of which produce antibiotic and oxidative stress resistance or control microbial metabolism and virulence (Gallegos et al. supra).

SUMMARY OF THE INVENTION

The instant invention identifies microbial transcription factors, e.g., transcription factors of the AraC-XylS family, as virulence factors in microbes and shows that inhibition of these factors reduces the virulence of microbial cells. Because these transcription factors control virulence, rather than essential cellular processes, the development of resistance is much less likely. Accordingly, in one aspect, the invention is directed to a method for preventing infection of a subject by a microbe comprising: administering a compound that modulates the expression or activity of a microbial transcription factor to a subject at risk of developing an infection such that infection of the subject is prevented.

In one embodiment, the invention pertains to a method for reducing antibiotic resistance of a microbial cell. The method includes contacting the cell with a transcription factor modulating compound of the formula (XI):

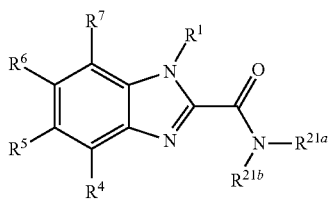

(XI)

wherein
R¹ is OH, OCOCO₂H, a substituted or unsubstituted straight or branched $C_1$-$C_5$ alkyloxy group, or a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), $CO_2$($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen; and $R^{21a}$ and $R^{21b}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof; such that the antibiotic resistance of said cell is reduced.

In another embodiment, the invention pertains, at least in part, to a method for reducing antibiotic resistance of a microbial cell, comprising contacting the cell with a transcription factor modulating compound of the formula (XII):

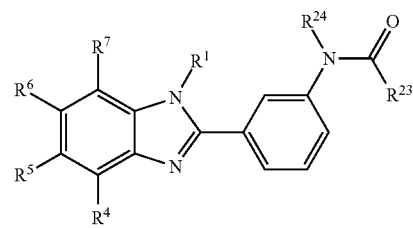

(XII)

wherein
R¹ is OH, OCOCO₂H, a substituted or unsubstituted straight or branched $C_1$-$C_5$ alkyloxy group, or a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), $CO_2$($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen; and $R^{22}$ is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof; such that the antibiotic resistance of said cell is reduced.

In another embodiment, the invention includes a method for reducing antibiotic resistance of a microbial cell. The method includes contacting the cell with a transcription factor modulating compound of the formula (XIII):

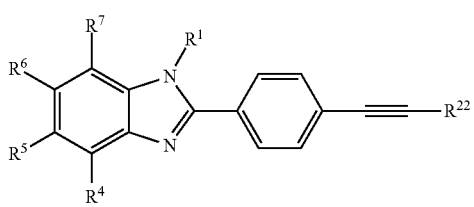

(XIII)

wherein R¹ is OH, OCOCO₂H, a substituted or unsubstituted straight or branched $C_1$-$C_5$ alkyloxy group, a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), $CO_2$($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen; and $R^{23}$ and $R^{24}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof;

provided that when R¹ is OH, R⁴, R⁵, and R⁷ are H, and R⁶ is $NO_2$, then $R^{23}$ is not methyl, unsubstituted phenyl, or unsubstituted furanyl; such that the antibiotic resistance of said cell is reduced.

In another embodiment, the invention pertains to a method for reducing antibiotic resistance of a microbial cell, comprising contacting the cell with a transcription factor modulating compound of the formula (XIV):

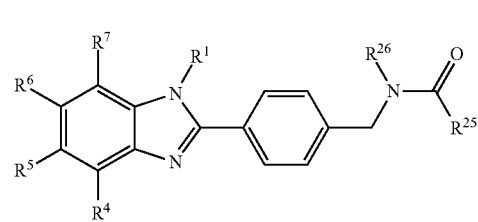

(XIV)

wherein
R¹ is OH, OCOCO₂H, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$, and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), $O$($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen; and $R^{25}$ and $R^{26}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof;

provided that when $R^1$ is OH, $R^4$, $R^5$, and $R^7$ are H, and $R^6$ is $NO_2$, then $R^{25}$ is not unsubstituted phenyl or O-tert-butyl; such that the antibiotic resistance of said cell is reduced.

In yet another embodiment, the invention pertains to a method for reducing antibiotic resistance of a microbial cell. The method includes contacting a cell with a transcription factor modulating compound of the formula (XV):

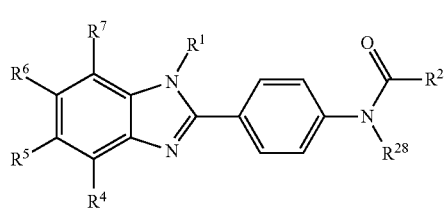

(XV)

wherein $R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), $O$($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen;

$R^{27}$ is selected from the group consisting of substituted heteroaryl; substituted alkyl; substituted or unsubstituted alkenyl; alkynyl; alkylcarbonyl, arylcarbonyl; heteroarylcarbonyl; sulfonyl; alkylamino; arylamino; heteroarylamino; alkoxy, aryloxy, heteroaryloxy; substituted straight chain $C_1$-$C_5$ alkyl or alkenyl; substituted or unsubstituted isoxazole, thiazolidine, imidazole, quinoline, pyrrole, triazole, or pyrazine; 2-fluorophenyl, 2-methylphenyl, 2-cyanophenyl, 1-methylphenyl, and 1-fluorophenyl; and $R^{28}$ is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof; such that the antibiotic resistance of said cell is reduced.

A method for reducing antibiotic resistance of a microbial cell, comprising contacting the cell with a transcription factor modulating compound of the formula (XVI):

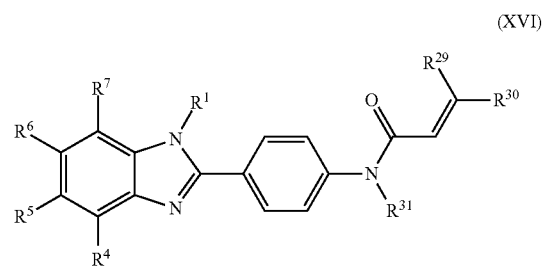

(XVI)

wherein $R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), $O$($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen;

$R^{29}$, $R^{30}$ and $R^{31}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, and aroyl, and pharmaceutically acceptable salts, esters and prodrugs thereof; such that the antibiotic resistance of said cell is reduced.

In yet another embodiment, the invention pertains to a method for reducing antibiotic resistance of a microbial cell. The method includes contacting the cell with a transcription factor modulating compound of the formula (XVII):

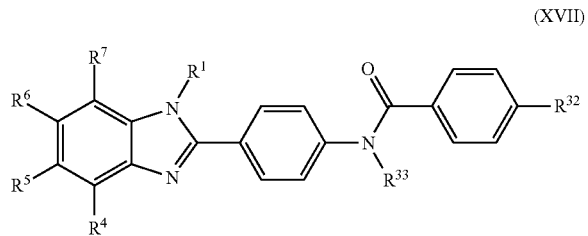

(XVII)

wherein $R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(N-HOH), and halogen;

$R^{32}$ is selected from the group consisting of OH, Br, CN, $CO_2H$, morpholinyl, substituted aryl, substituted or unsubstituted alkenyl, alkynyl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, dialkylamino, arylamino, heteroarylamino, aroyl;

$R^{33}$ is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, dialkylamino, arylamino, heteroarylamino, aroyl and pharmaceutically acceptable salts, esters and prodrugs thereof;

provided that when $R^1$ is OH, $R^4$, $R^5$, $R^7$ and $R^{33}$ are H, $R^6$ is $NO_2$, then $R^{32}$ is not dimethylamino; and provided that when $R^1$ is OH, $R^4$, $R^5$, $R^7$ and $R^{33}$ are H, $R^6$ is Br, then $R^{32}$ is not dimethylamino; such that the antibiotic resistance of said cell is reduced.

In another embodiment, the invention pertains to a method for modulating transcription, by contacting a transcription factor with a transcription factor modulating compound of formula (XI), (XII), (XIII), (XIV), (XV), (XVI), or (XVII).

In one embodiment, the transcription factor is a member of the AraC-XylS family of transcription factors.

In one embodiment, the transcription factor is a member of the MarA family of transcription factors.

In another embodiment, the method further comprises administering an antibiotic.

In another aspect, the invention pertains to a method for preventing urinary tract infection of a subject by a microbe comprising: administering a compound that modulates the expression or activity of a microbial transcription factor to a subject at risk of developing a urinary tract infection such that infection of the subject is prevented.

In yet another aspect, the invention pertains to a method for reducing virulence of a microbe comprising: administering a compound that modulates the expression or activity of a microbial transcription factor to a subject at risk of developing an infection with the microbe such that virulence of the microbe is reduced.

In one embodiment, the transcription factor is a member of the AraC-XylS family of transcription factors.

In another embodiment, the transcription factor is a member of the MarA family of transcription factors.

In yet another embodiment, the method further comprises administering an antibiotic.

In another aspect, the invention pertains to a method for treating a microbial infection in a subject comprising: administering a compound that modulates the expression or activity of a transcription factor to a subject having a microbial infection such that infection of the subject is treated.

In one embodiment, the transcription factor is a member of the AraC-XylS family of transcription factors.

In another embodiment, the transcription factor is a member of the MarA family of transcription factors.

In still another embodiment, the invention further comprises administering an antibiotic.

In another aspect, the invention pertains to a method for treating a urinary tract infection in a subject comprising: administering a compound that modulates the expression or activity of a transcription factor to a subject having a urinary tract infection such that infection of the subject is treated.

In one embodiment, the transcription factor is a member of the AraC-XylS family of transcription factors.

In one embodiment, the transcription factor is a member of the MarA family of transcription factors.

In another embodiment, the method further comprises administering an antibiotic.

In another aspect, the invention pertains to a method for reducing virulence in a microbe comprising: administering a compound that inhibits the expression or activity of a transcription factor to a subject having a microbial infection such that virulence of the microbe is reduced.

In one embodiment, the transcription factor is a member of the AraC-XylS family of transcription factors.

In another embodiment, the transcription factor is a member of the MarA family of transcription factors.

In yet another embodiment, the method further comprises administering an antibiotic.

In another aspect, the invention pertains to a method for evaluating the effectiveness of a compound that modulates the expression or activity of a microbial transcription factor at inhibiting microbial virulence comprising: infecting a non-human animal with a microbe, wherein the ability of the microbe to establish an infection in the non-human animal requires that the microbe colonize the animal; administering the compound that modulates the expression or activity of the microbial transcription factor to the non-human animal; and determining the level of infection of the non-human animal, wherein the ability of the compound to reduce the level of infection of the animal indicates that the compound is effective at inhibiting microbial virulence.

In one embodiment, the transcription factor is a member of the AraC-XylS family of transcription factors.

In another embodiment, the transcription factor is a member of the MarA family of transcription factors.

In yet another embodiment, the method further comprises administering an antibiotic.

In still another embodiment, the level of infection of the non-human animal is determined by measuring the ability of the microbe to colonize the tissue of the non-human animal.

In another embodiment, the level of infection of the non-human animal is determined by enumerating the number of microbes present in the tissue of the non-human animal.

In another aspect, the invention pertains to a method for identifying a compound for treating microbial infection, comprising: innoculating a non-human animal with a microbe, wherein the ability of the microbe to establish an infection in the non-human animal requires that the microbe colonize the animal; administering a compound which reduces the expression or activity of a microbial transcription factor to the animal, and determining the effect of the test compound on the ability of the microbe to colonize the animal, such that a compound for treating microbial infection is identified.

In one embodiment, the transcription factor is a member of the AraC-XylS family of transcription factors.

In another embodiment, the transcription factor is a member of the MarA family of transcription factors.

In still another embodiment, the level of infection of the non-human animal is determined by measuring the ability of the microbe to colonize the tissue of the non-human animal.

In another embodiment, the level of infection of the non-human animal is determined by enumerating the number of microbes present in the tissue of the non-human animal.

In another aspect, method for identifying a compound for reducing microbial virulence, comprising: inoculating a non-human animal with a microbe, wherein the ability of the microbe to establish an infection in the non-human animal requires that the microbe colonize the animal; administering a compound which reduces the expression or activity of a microbial transcription factor to the animal, and determining the effect of the test compound on the ability of the microbe to colonize the animal, such that a compound for reducing microbial virulence is identified.

In another embodiment, the transcription factor is a member of the AraC-XylS family of transcription factors.

In still another embodiment, the transcription factor is a member of the MarA family of transcription factors.

In yet another embodiment, the level of infection of the non-human animal is determined by measuring the ability of the microbe to colonize the tissue of the non-human animal.

In another embodiment, the level of infection of the non-human animal is determined by enumerating the number of microbes present in the tissue of the non-human animal.

In another aspect, the invention pertains to a method for identifying transcription factors which promote microbial virulence comprising: creating a microbe in which a transcription factor to be tested is misexpressed; introducing the microbe into a non-human animal; wherein the ability of the microbe to establish an infection in the non-human animal requires that the microbe colonize the animal; and determining the ability of the microbe to colonize the animal, wherein a reduced ability of the microbe to colonize the animal as compared to a wild-type microbial cell identifies the transcription factor as a transcription factor which promotes microbial virulence.

In another embodiment, the transcription factor is a member of the AraC-XylS family of transcription factors.

In another embodiment, the transcription factor is a member of the MarA family of transcription factors.

In another embodiment, the level of infection of the non-human animal is determined by measuring the ability of the microbe to colonize the tissue of the non-human animal.

In another embodiment, the level of infection of the non-human animal is determined by enumerating the number of microbes present in the tissue of the non-human animal.

In another aspect, the invention pertains to a method for reducing the ability of a microbe to adhere to an abiotic surface comprising: contacting the abiotic surface or the microbe with a compound that modulates the activity of a transcription factor such that the ability of the microbe to adhere to the abiotic surface is reduced.

In one embodiment, the transcription factor is a member of the AraC-XylS family of transcription factors.

In another embodiment, the transcription factor is a member of the MarA family of transcription factors.

In yet another embodiment, the method further comprises contacting the abiotic surface or the microbe with a second agent that is effective at controlling the growth of the microbe.

In still another embodiment, the abiotic surface is selected from the group consisting of: stents, catheters, and prosthetic devices.

In one aspect, the invention pertains to a pharmaceutical composition comprising a compound that modulates the activity or expression of a microbial transcription factor and a pharmaceutically acceptable carrier, wherein the compound reduces microbial virulence.

In another aspect, the invention pertains to a pharmaceutical composition comprising a compound that modulates the activity or expression of a microbial transcription factor and an antibiotic in a pharmaceutically acceptable carrier.

The present invention represents an advance over the prior art by identifying transcription factor modulating compounds, such as, but not limited to helix-turn-helix protein modulating compounds, and providing novel assays that can be used to identify compounds which modulate microbial transcription factors, such as MarA family polypeptides and AraC family polypeptides. Modulation of gene transcription brought about by the modulation of transcription factors, such as helix-turn-helix domain containing proteins, can control a wide variety of cellular processes. For example, in prokaryotic cells processes such as metabolism, resistance, and virulence can be controlled.

Assays to identify compounds that are capable of modulating bacterial transcription factors would be of great benefit in the identification of agonists and antagonists that can be used to control gene transcription in both prokaryotic and eukaryotic cells.

In one embodiment, the invention pertains to a method for reducing antibiotic resistance of a cell, e.g., a eukaryotic or prokaryotic cell. In a preferred embodiment, the cell is a microbial cell. In one embodiment, the invention pertains to a method for reducing antibiotic resistance in a microbial cell, by contacting a cell with a transcription factor modulating compound, such that the antibiotic resistance of the cell is reduced. In an embodiment, the transcription factor modulating compound is of the formula (I):

A-E　　　　　　　　　　　　　　　　　　(I)

wherein A is a polar moiety; E is a hydrophobic moiety, and pharmaceutically acceptable salts thereof.

In another embodiment, the invention pertains to a method for modulating transcription. The method includes contacting a transcription factor with a transcription factor modulating compound, such that the transcription factor is modulated. The transcription factor modulating compound is of the formula (I):

A-E　　　　　　　　　　　　　　　　　　(I)

wherein A is a polar moiety; and E is a hydrophobic moiety, and pharmaceutically acceptable salts thereof.

In another embodiment, the invention also includes methods for identifying transcription factor modulating compounds. The method includes contacting a microbial cell with a test compound under conditions which allow interaction of the compound with the microbial cell and measuring the ability of the test compound to affect the cell. The microbial cell includes a selective marker under the direct control of a transcription factor responsive element and a transcription factor.

In yet another embodiment, the invention includes methods for identifying a transcription factor modulating compound. The method includes contacting a microbial cell comprising: 1) a selective marker under the control of a transcription factor responsive element and 2) a transcription factor, with a test compound under conditions which allow interaction of the compound with the microbial cell, and measuring the ability of the test compound to affect the growth (e.g., in vitro or in vivo) or survival of the microbial cell, wherein the inactivation of the transcription factor leads to a decrease in in vitro or in vivo cell survival. The invention also pertains to similar methods where the inactivation of the transcription factor leads to an increase in cell survival, as well as methods wherein the activation of the transcription factor leads to increased or, alternatively, decreased cell survival.

In another embodiment, the invention also pertains to methods for identifying a transcription factor modulating compound, by contacting a microbial cell comprising: 1) a chromosomal deletion in a guaB or purA gene, 2) heterologous guaB or purA gene under the control of its transcription factor responsive promoter, and 3) a transcription factor, with a test compound under conditions which allow interaction of the compound with the microbial cell. The method further includes the steps of measuring the ability of the compound to affect gene expression of the reporter or the growth or survival of the microbial cell as an indication of whether the compound modulates the activity of a transcription factor. The ability of the compound to modulate the activity of a transcription factor leads to an alteration in gene expression may effect cell growth or survival.

The invention pertains to transcription factor modulating compounds, HTH protein modulating compounds, and MarA family modulating compounds identified by the methods of the invention, methods of using these compounds and pharmaceutical compositions comprising these compounds. The transcription factor modulating compounds of the invention include, but are not limited to, compounds of formulae (I)-(XVII) and Tables 4 and 5.

The invention also pertains to methods using computer modeling programs to identify transcription factor modulating compounds. For example, the invention pertains to a method of identifying transcription factor modulating compounds. The method includes obtaining the structure of the transcription factor modulating compound, and using or identifying a scaffold which has an interaction energy score of −20 or less with a portion of the transcription factor, thus identifying potential transcription factor modulating scaffolds.

The invention also pertains, at least in part, to a kit for identifying a transcription factor modulating compound which modulates the activity of a transcription factor polypeptide comprising a microbial cell. The kit includes 1) a selective marker under the control of a transcription factor responsive element and 2) a transcription factor.

The invention also pertains, at least in part, to pharmaceutical compositions which contain an effective amount of a transcription factor modulating compound, and, optionally, a pharmaceutically acceptable carrier.

The invention also pertains to a method of inhibiting a biofilm, by administering a composition comprising a transcription factor modulating compound such that the biofilm is inhibited.

In a further embodiment, the invention pertains to a pharmaceutical composition comprising an effective amount of a transcription factor modulating compound, and a pharmaceutically acceptable carrier. The transcription factor modulating compound is of the formula (II):

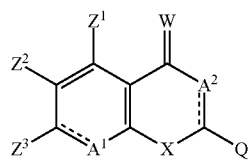

(II)

wherein
W is O or S;
X is O, S, or C, optionally linked to Q;
$A^1$ is C—$Z^4$, O, or S;
$A^2$ is C—$Z^5$, or N—$Z^5$;
$Z^1$, $Z^2$, $Z^3$, $Z^4$ and $Z^5$ are each independently hydrogen, alkoxy, hydroxy, halogen, alkyl, alkenyl, alkynyl, aryl, heterocyclic, amino, or cyano;

$Z^3$ is hydrogen, alkoxy, hydroxy, halogen, alkyl, alkenyl, alkynyl, aryl, heterocyclic, amino, nitro, cyano, carbonyl, or thiocarbonyl;

Q is an aromatic or heterocyclic moiety, and pharmaceutically acceptable salts thereof.

In another further embodiment, the invention pertains to a pharmaceutical composition comprising an effective amount of a transcription factor modulating compound, and a pharmaceutically acceptable carrier. The compound is of the formula (III):

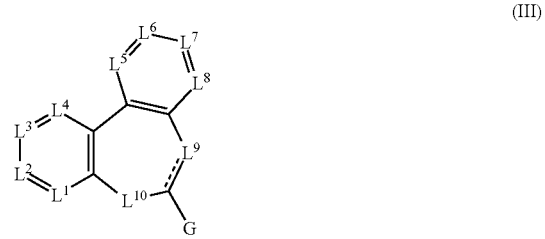

(III)

wherein

G is substituted or unsubstituted aromatic moiety, heterocyclic, alkyl, alkenyl, alkynyl, hydroxy, cyano, nitro, amino, carbonyl, or hydrogen; and $L^1$, $L^2$, $L^3$, $L^4$, $L^5$, $L^6$, $L^7$, $L^8$, $L^9$, and $L^{10}$ are each independently oxygen, substituted or unsubstituted nitrogen, sulfur and or substituted or unsubstituted carbon, and pharmaceutically acceptable salts thereof.

In yet another embodiment, the invention pertains to a pharmaceutical composition comprising an effective amount of a transcription factor modulating compound and a pharmaceutically acceptable carrier. The transcription factor modulating compound is of the formula (IV):

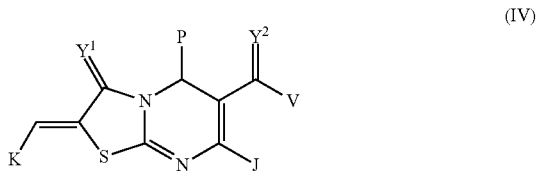

(IV)

wherein $Y^1$ and $Y^2$ are each oxygen or sulfur;

J is hydrogen, substituted or unsubstituted alkyl, alkenyl, alkynyl, cyano, nitro, amino, or halogen;

V is substituted or unsubstituted alkyl, alkenyl, alkynyl, alkoxy, alkylamino, or alkylthio;

P and K are each independently substituted or unsubstituted aryl, and pharmaceutically acceptable salts thereof.

In another embodiment, the invention pertains to a pharmaceutical composition comprising a pharmaceutically acceptable carrier and a transcription factor modulating compound. The transcription factor modulating compound is of the formula (V):

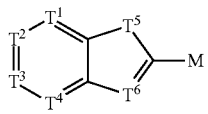

(V)

wherein $T^1$, $T^2$, $T^3$, $T^4$, $T^5$, and $T^6$ are each independently substituted or unsubstituted carbon, oxygen, substituted or unsubstituted nitrogen, or sulfur;

M is hydrogen, alkyl, alkenyl, heterocyclic, alkynyl, or aryl, or pharmaceutically acceptable salts thereof.

In yet another embodiment, the invention pertains to a pharmaceutical composition comprising a pharmaceutically acceptable carrier and a transcription factor modulating compound. The transcription factor modulating compound is of the formula (Va):

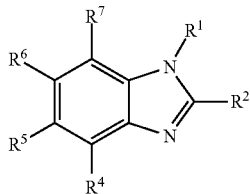

(Va)

wherein $R^1$ is OH, $OCOCO_2H$, or a substituted or unsubstituted straight or branched $C_1$-$C_5$ alkyloxy group;

$R^2$ is H, $CO_2(C_1$-$C_5$ substituted or unsubstituted, straight or branched alkyl), or a substituted or unsubstituted aryl group; and $R^4$, $R^5$, $R^6$, and $R^7$ are independently selected from the group consisting of H, ($C_1$-$C_5$ substituted or unsubstituted, straight or branched alkyl), $CO_2(C_1$-$C_5$ substituted or unsubstituted, straight or branched alkyl), $CO(C_1$-$C_5$ substituted or unsubstituted, straight or branched alkyl), CO(substituted or unsubstituted aryl or heteroaryl), $CO(C_3$-$C_6$ substituted or unsubstituted cycloalkyl), $O(C_1$-$C_5$ substituted or unsubstituted, straight or branched alkyl), $C(NOH)(C_1$-$C_5$ substituted or unsubstituted, straight or branched alkyl), substituted or unsubstituted amino, $CO_2H$, CN, $NO_2$, $CONH_2$, (CO)(NHOH), and halogen.

In certain embodiments of formula Va, those compounds disclosed in U.S. Ser. No. 10/139,591, filed May 6, 2002, are excluded from the scope of the present invention.

In other embodiments of formula Va, when $R^6$ is $NO_2$ and $R^2$ is unsubstituted phenyl, then $R^1$ is not $O(CHCH_3)(CO_2)CH_2CH_3$ or $OCH_2CO_2H$. Also, in another embodiment, when $R^6$ is H or $NO_2$, then $R^1$ is not a phenyl-substituted alkyloxy group. In yet another embodiment, when $R^4$, $R^5$, $R^6$, and $R^7$ are all H and $R^2$ is para-methoxyphenyl, then $R^1$ is not OH. And in another embodiment, when $R^4$, $R^5$, $R^6$, and $R^7$ are all H and $R^2$ is unsubstituted phenyl, then $R^1$ is not $OCH_2CO_2CH_2CH_3$;

In certain aspects of formula Va, $R^4$, $R^5$, and $R^7$ are all H.

Similarly, $R^1$ of formula Va may be selected from the group consisting of OH, $O(CR'R'')_{1-3}H$, $O(CR'R'')_{1-3}OH$, $O(CR'R'')_{1-3}CO_2H$, $O(CR'R'')_{1-3}CO_2(CR'R'')_{1-3}H$, $O(CR'R'')_{1-3}(CO)NH_2$, $O(CR'R'')_{1-3}(CNH)NH_2$, $OCOCO_2H$, $O(CR'R'')_{1-3}SO_3H$, $O(CR'R'')_{1-3}OSO_3H$, $O(CR'R'')_{1-3}PO_3H$, $O(CR'R'')_{1-3}OPO_3H$, $O(CR'R'')_{1-3}N[(CR'R'')_{0-3}H]_2$, $O(CR'R'')_{1-3}(CO)(NHOH)$, and $O(CR'R'')_{1-3}(heteroaryl)$;

wherein R' and R" are each independently H, a $C_1$-$C_3$ alkyl, $C_2$-$C_3$ alkenyl, or $C_2$-$C_3$ alkynyl group. Each R' and R" is preferably H or $CH_3$.

When $R^1$ of formula Va is $O(CR'R'')_{1-3}$(heteroaryl), the heteroaryl group may be a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

Similarly, when $R^2$ of formula Va may be a substituted or unsubstituted phenyl, pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In a more particular embodiment, $R^6$ of formula Va is H, $(CR'R'')_{1-3}H$, $(CR'R'')_{1-3}OH$, $(CR'R'')_{1-3}NH_2$, (NOH)$(CR'R'')_{1-3}H$, $CO(CR'R'')_{0-3}NH_2$, $CO(CR'R'')_{1-3}H$, $CO(CR'R'')_{1-3}OH$, $CO(CR'R'')_{0-3}CF_3$, $(CR'R'')_{0-3}N[(CR'R'')_{0-3}H]_2$, CO(substituted or unsubstituted heteroaryl), $CO(C_3$-$C_6$ substituted or unsubstituted cycloalkyl), $O(CR'R'')_{1-3}H$, CO(substituted or unsubstituted phenyl), $CO_2(CR'R'')_{0-3}H$, CN, $NO_2$, F, Cl, Br, or I, wherein R' and R" are each independently H, a $C_1$-$C_3$ alkyl, $C_2$-$C_3$ alkenyl, or $C_2$-$C_3$ alkynyl group. Preferably each R' and R" is independently H or $CH_3$.

In yet another embodiment, $R^6$ of formula Va is CO(substituted or unsubstituted heteroaryl), wherein said heteroaryl group is a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In another embodiment, $R^6$ of formula Va is an electron withdrawing substituent, selected from the group consisting of F, $CF_3$, $NO_2$, C(NOH)(CR'R''), wherein each R' and R" are each independently H or $CH_3$.

In another embodiment, the invention pertains to a pharmaceutical composition comprising a pharmaceutically acceptable carrier and a transcription factor modulating compound. The transcription factor modulating compound may be of the formula (VI):

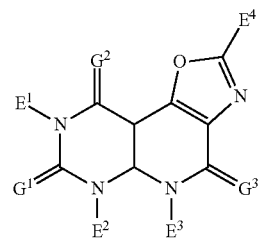

(VI)

wherein $G^1$, $G^2$, and $G^3$ are each independently O, S, substituted or unsubstituted nitrogen, or substituted or unsubstituted carbon;

$E^1$, $E^2$, and $E^3$ are each independently hydrogen, alkyl, alkenyl, alkynyl, aryl, aralkyl, or acyl; and $E^4$ is alkyl, alkenyl, alkynyl, aryl, halogen, cyano, amino, nitro, or acyl, and pharmaceutically acceptable salts thereof.

BRIEF DESCRIPTION OF THE DRAWINGS

FIG. 1 is a multiple sequence alignment of AraC-XylS family polypeptides.

FIG. 2 is a multiple sequence alignment of PROSITE PS00041 and AraC family polypeptides.

FIG. 3 is a multiple sequence alignment of PROSITE PS01124 and AraC family polypeptides.

DETAILED DESCRIPTION OF THE INVENTION

Figure 4:
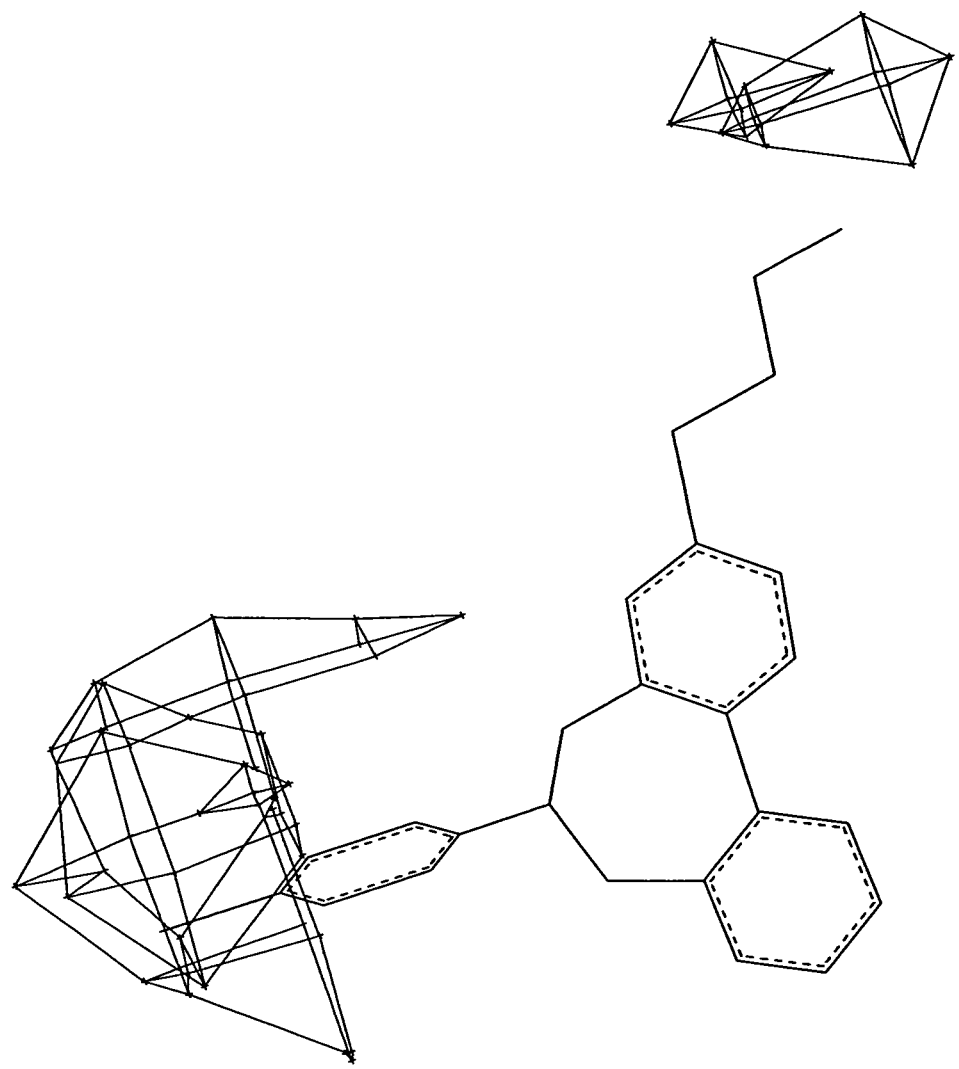
FIG. 4 is a CoMFA contour map for a representative triazinoxazepine.

The instant invention identifies microbial transcription factors, e.g., transcription factors of the AraC-XylS family, as virulence factors in microbes and shows that inhibition of these factors reduces the virulence of microbial cells. Because these transcription factors control virulence, rather than essential cellular processes, modulation of these factors should not promote resistance.

Some major families of transcription factors found in bacteria include the helix-turn-helix transcription factors (HTH) (Harrison, S. C., and A. K. Aggarwal 1990. *Annual Review of Biochemistry*. 59:933-969) such as AraC, MarA, Rob, SoxS and LysR; winged helix transcription factors (Gajiwala, K. S., and S. K. Burley 2000. 10:110-116), e.g., MarR, Sar/Rot family, and OmpR (Huffman, J. L., and R. G. Brennan 2002. *Curr Opin Struct Biol*. 12:98-106, Martínez-Hackert, E., and A. M. Stock 1997. *Structure*. 5:109-124); and looped-hinge helix transcription factors (Huffman, J. L., and R. G. Brennan 2002 *Curr Opin Struct Biol*. 12:98-106), e.g. the AbrB protein family.

The AraC-XylS family of transcription factors comprises many members. MarA, SoxS, Rma, and Rob are examples of proteins within the AraC-XylS family of transcription factors. These factors belong to a subset of the AraC-XylS family that have historically been considered to play roles in promoting resistance to multiple antibiotics and have not been considered to be virulence factors. In fact, the role of marA in virulence has been tested using a marA null mutant of *Salmonella enterica* serovar *Typhimurium* (*S. typhimurium*) in a mouse infection model (Sulavik et al. 1997. *J. Bacteriology* 179:1857) and no such role has been found. In another model (using co-infection experiments or crude statistics) only a weak effect of a marA null mutant in chickens has been demonstrated (Randall et al. 2001. J. Med. Microbiol. 50:770). In contrast to this earlier work, this invention is based, at least in part, on the finding that the ability of microbes to cause infection in a host can be inhibited by inhibiting the expression and/or activity of microbial transcription factors. Thus, the instant invention validates the use of microbial transcription factors as therapeutic targets.

The invention pertains, at least in part, to compounds which modulate transcription factors (e.g., helix-turn-helix (HTH) proteins, AraC family polypeptides, MarA family polypeptides, etc.), methods of identifying the transcription factor modulating compounds (e.g., HTH protein modulating compounds, AraC family polypeptide modulating compounds, MarA family polypeptide modulating compounds, etc.), and methods of using the compounds.

1. Transcription Factors

The term "transcription factor" includes proteins that are involved in gene regulation in both prokaryotic and eukaryotic organisms. In one embodiment, transcription factors can have a positive effect on gene expression and, thus, may be referred to as an "activator" or a "transcriptional activation factor." In another embodiment, a transcription factor can negatively effect gene expression and, thus, may be referred to as "repressors" or a "transcription repression factor." Activators and repressors are generally used terms and their functions are discerned by those skilled in the art.

As used herein, the term "infectivity" or "virulence" includes the ability of a pathogenic microbe to colonize a host, a first step required in order to establish growth in a host. Infectivity or virulence is required for a microbe to be a pathogen. In addition, a virulent microbe is one which can cause a severe infection. As used herein, the term "pathogen" includes both obligate and opportunistic organisms. The ability of a microbe to resist antibiotics is also important in promoting growth in a host, however, in one embodiment, antibiotic resistance is not included in the terms "infectivity" or "virulence" as used herein. Accordingly, in one embodiment, the instant invention pertains to methods of reducing the infectivity or virulence of a microbe without affecting (e.g., increasing or decreasing) antibiotic resistance. Preferably, as used herein, the term "infectivity or virulence" includes the ability of an organism to establish itself in a host by evading the host's barriers and immunologic defenses.

Figure 1B:
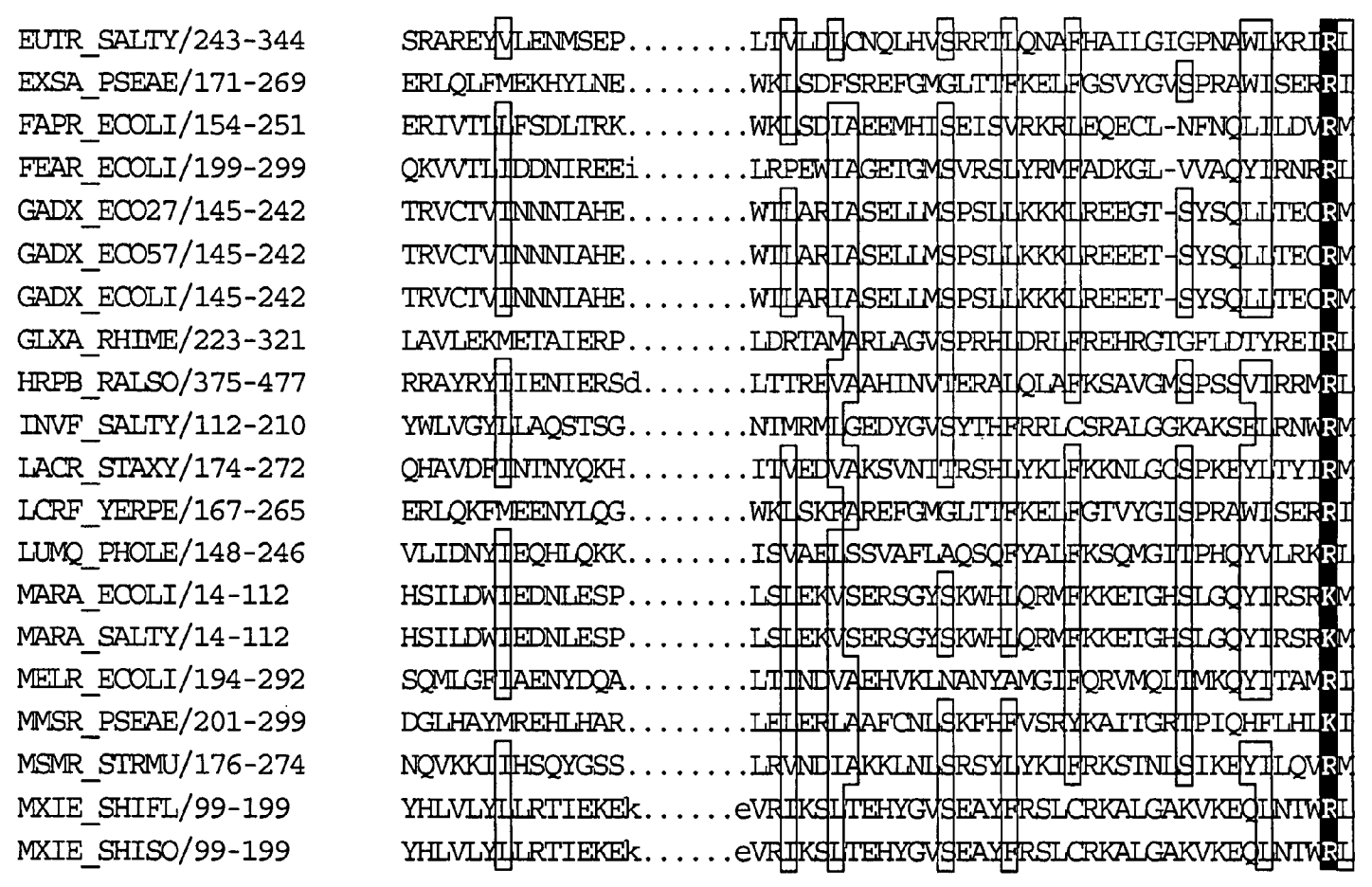
Figure 1F:
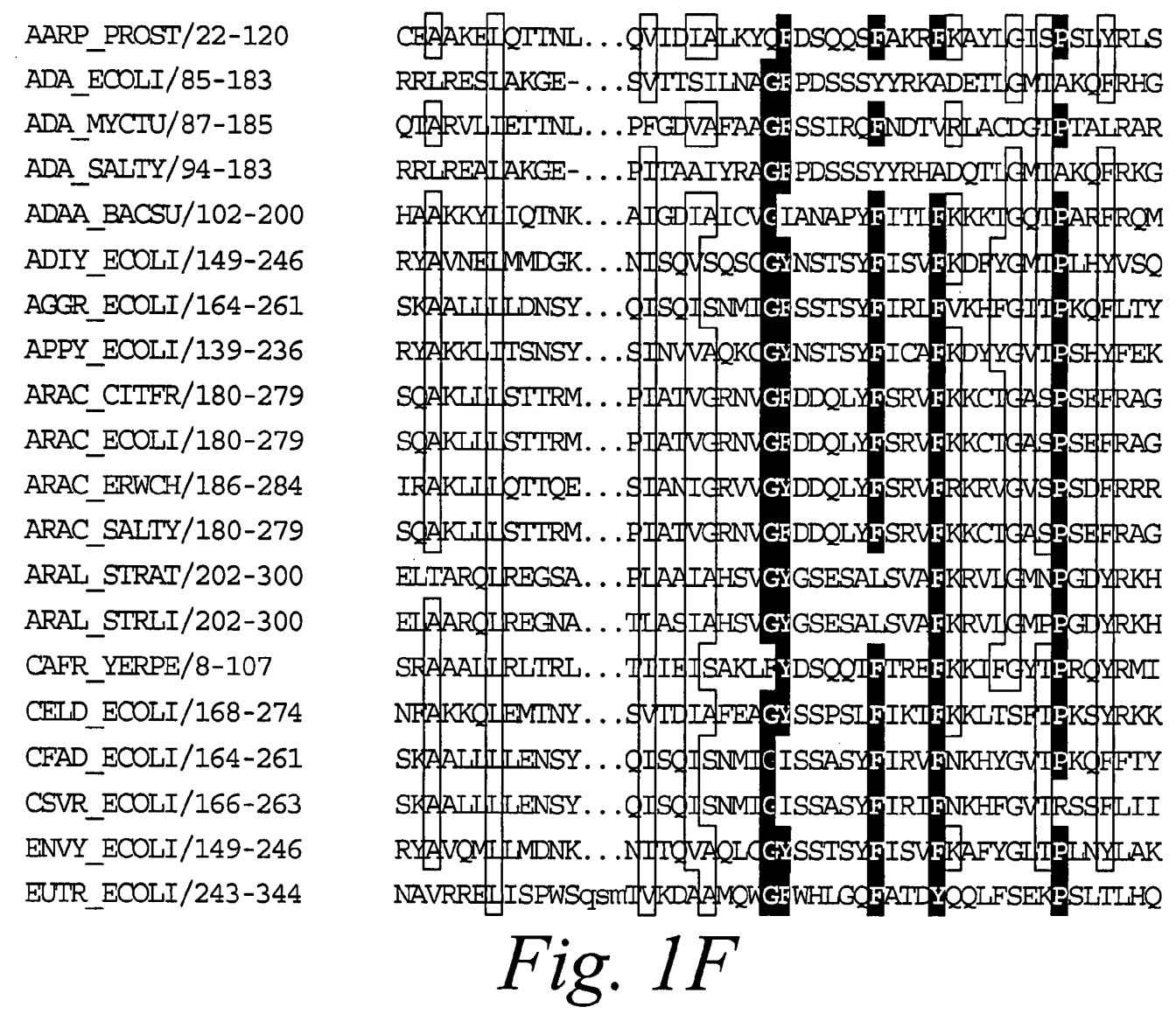
Figure 2C:
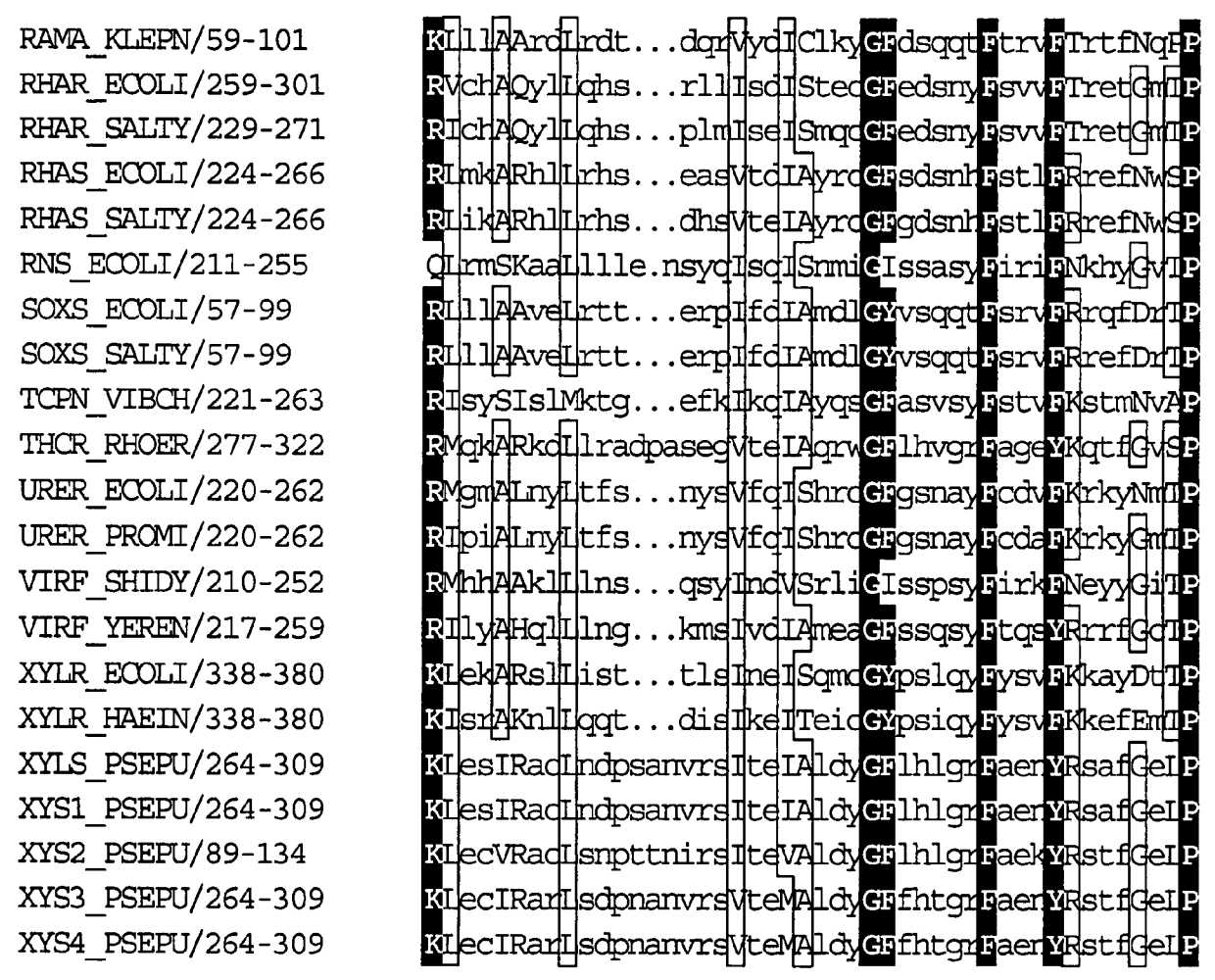
Figure 2D:
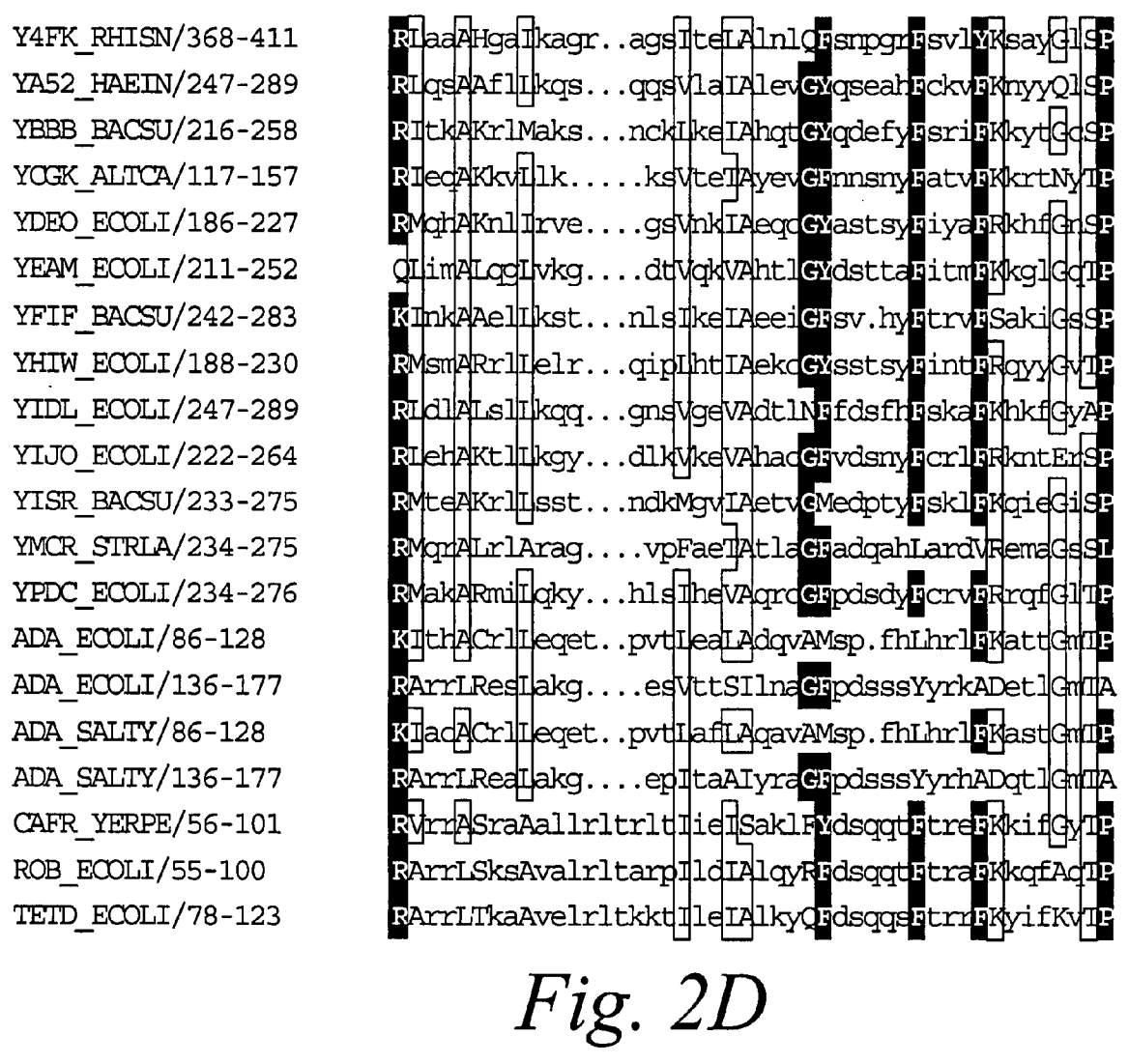

The term "AraC family polypeptide," "AraC-XylS family polypeptide" or "AraC-XylS family peptide" include an art recognized group of prokaryotic transcription factors which contains more than 100 different proteins (Gallegos et al., (1997) *Micro. Mol. Biol. Rev.* 61: 393; Martin and Rosner, (2001) *Curr. Opin. Microbiol.* 4:132). AraC family polypeptides include proteins defined in the PROSITE (PS) database (http://www.expasy.ch/prosite/) as profile PS01124. The AraC family polypeptides also include polypeptides described in PS0041, HTH AraC Family 1, and PS01124, and HTH AraC Family 2. Multiple sequence alignments for the AraC-XylS family polypeptides, HTH AraC family 1, and HTH AraC family 2 are shown in FIGS. 1-3, respectively. In an embodiment, the AraC family polypeptides are generally comprised of, at the level of primary sequence, by a conserved stretch of about 100 amino acids, which are believed to be responsible for the DNA binding activity of this protein (Gallegos et al., (1997) *Micro. Mol. Biol. Rev.* 61: 393; Martin and Rosner, (2001) *Curr. Opin. Microbiol.* 4: 132). AraC family polypeptides also may include two helix turn helix DNA binding motifs (Martin and Rosner, (2001) *Curr. Opin. Microbiol.* 4: 132; Gallegos et al., (1997) *Micro. Mol. Biol. Rev.* 61: 393; Kwon et al., (2000) *Nat. Struct. Biol.* 7: 424; Rhee et al., (1998) *Proc. Natl. Acad. Sci. U.S.A.* 95: 10413). The term includes MarA family polypeptides and HTH proteins. In one embodiment, the invention pertains to a method for modulating an AraC family polypeptide, by contacting the AraC family polypeptide with a test compound which interacts with a portion of the polypeptide involved in DNA binding. In a further embodiment, the test compound interacts with a conserved aminoacid residue (capitalized) of the HTH AraC family 1 protein indicated in FIG. 2.

The term "helix-turn-helix protein," "HTH protein," "helix-turn-helix polypeptides," and "HTH polypeptides," includes proteins comprising one or more helix-turn-helix domains. Helix-turn-helix domains are known in the art and have been implicated in DNA binding (*Ann Rev. of Biochem.* 1984. 53:293). An example of the consensus sequence for a helix-turn domain can be found in Brunelle and Schleif (1989. *J. Mol. Biol.* 209:607). The domain has been illustrated by the sequence XXXPhoAlaXXPhoGlyPhoXXXX-PhoXXPhoXX, where X is any amino acid and Pho is a hydrophobic amino acid.

The helix-turn-helix domain was the first DNA-binding protein motif to be recognized. Although originally the HTH domain was identified in bacterial proteins, the HTH domain has since been found in hundreds of DNA-binding proteins from both eukaryotes and prokaryotes. It is constructed from two alpha helices connected by a short extended chain of amino acids, which constitutes the "turn."

In one embodiment, a helix-turn-helix domain containing protein is a Mar A family polypeptide. The language "MarA family polypeptide" includes the many naturally occurring HTH proteins, such as transcription regulation proteins which have sequence similarities to MarA and which contain the MarA family signature pattern, which can also be referred to as an XylS/AraC signature pattern. An exemplary signature pattern which defines MarA family polypeptides is shown, e.g., on PROSITE and is represented by the sequence: [KRQ]-[LIVMA]-X(2)-[GSTALIV]-{FYWPGDN}X(2)-

[LIVMSA]-X(4,9)-[LIVMF]-X(2)-[LIVMSTA]-X(2)-[GSTACIL]-X(3)-[GANQRF]-[LIVMFY]-X(4,5)-[LFY]-X(3)-[FYIVA]-{FYWHCM}-X(3)-[GSADENQKR]-X-[NSTAPKL]-[PARL], where X is any amino acid. MarA family polypeptides have two "helix-turn-helix" domains. This signature pattern was derived from the region that follows the first, most amino terminal, helix-turn-helix domain (HTH1) and includes the totality of the second, most carboxy terminal helix-turn-helix domain (HTH2). (See PROSITE PS00041).

The MarA family of proteins ("MarA family polypeptides") represent one subset of AraC-XylS family polypeptides and include proteins like MarA, SoxS, Rob, Rma, AarP, PqrA, etc. The MarA family polypeptides, generally, are involved in regulating resistance to antibiotics, organic solvents, and oxidative stress agents (Alekshun and Levy, (1997) *Antimicrob. Agents. Chemother.* 41: 2067). Like other AraC-XylS family polypeptides, MarA-like proteins also generally contain two HTH motifs as exemplified by the MarA and Rob crystal structures (Kwon et al., (2000) *Nat. Struct. Biol.* 7: 424; Rhee et al., (1998) *Proc. Natl. Acad. Sci. U.S.A.* 95: 10413). Members of the MarA family can be identified by those skilled in the art and will generally be represented by proteins with homology to amino acids 30-76 and 77-106 of MarA (SEQ ID. NO. 1).

Preferably, a MarA family polypeptide or portion thereof comprises the first MarA family HTH domain (HTH1) (Brunelle, 1989, *J Mol Biol;* 209(4):607-22). In another embodiment, a MarA polypeptide comprises the second MarA family HTH domain (HTH2) (Caswell, 1992, *Biochem J.;* 287:493-509.). In a preferred embodiment, a MarA polypeptide comprises both the first and second MarA family HTH domains.

MarA family polypeptide sequences are "structurally related" to one or more known MarA family members, preferably to MarA. This relatedness can be shown by sequence or structural similarity between two MarA family polypeptide sequences or between two MarA family nucleotide sequences that specify such polypeptides. Sequence similarity can be shown, e.g., by optimally aligning MarA family member sequences using an alignment program for purposes of comparison and comparing corresponding positions. To determine the degree of similarity between sequences, they will be aligned for optimal comparison purposes (e.g., gaps may be introduced in the sequence of one protein for nucleic acid molecule for optimal alignment with the other protein or nucleic acid molecules). The amino acid residues or bases and corresponding amino acid positions or bases are then compared. When a position in one sequence is occupied by the same amino acid residue or by the same base as the corresponding position in the other sequence, then the molecules are identical at that position. If amino acid residues are not identical, they may be similar. As used herein, an amino acid residue is "similar" to another amino acid residue if the two amino acid residues are members of the same family of residues having similar side chains. Families of amino acid residues having similar side chains have been defined in the art (see, for example, Altschul et al. 1990. *J. Mol. Biol.* 215:403) including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). The degree (percentage) of similarity between sequences, therefore, is a function of the number of identical or similar positions shared by two sequences (i.e., % homology=# of identical or similar positions/total # of positions×100). Alignment strategies are well known in the art; see, for example, Altschul et al. supra for optimal sequence alignment.

MarA family polypeptides may share some amino acid sequence similarity with MarA. The nucleic acid and amino acid sequences of MarA as well as other MarA family polypeptides are available in the art. For example, the nucleic acid and amino acid sequence of MarA can be found, e.g., on GeneBank (accession number M96235 or in Cohen et al. 1993. *J. Bacteriol.* 175:1484, or in SEQ ID NO:1 and SEQ ID NO:2.

The nucleic acid and/or amino acid sequences of MarA can be used as "query sequences" to perform a search against databases (e.g., either public or private) to, for example, identify other MarA family members having related sequences. Such searches can be performed, e.g., using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to MarA family nucleic acid molecules. BLAST protein searches can be performed with the XBLAST program, score=50, wordlength=3 to obtain amino acid sequences homologous to MarA protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

MarA family members can also be identified as being similar based on their ability to specifically hybridize to nucleic acid sequences specifying MarA. Such stringent conditions are known to those skilled in the art and can be found e.g., in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Conditions for hybridizations are largely dependent on the melting temperature Tm that is observed for half of the molecules of a substantially pure population of a double-stranded nucleic acid. Tm is the temperature in ° C. at which half the molecules of a given sequence are melted or single-stranded. For nucleic acids of sequence 11 to 23 bases, the Tm can be estimated in degrees C. as 2(number of A+T residues)+4(number of C+G residues). Hybridization or annealing of nucleic acid molecules should be conducted at a temperature lower than the Tm, e.g., 15° C., 20° C., 25° C. or 30° C. lower than the Tm. The effect of salt concentration (in M of NaCl) can also be calculated, see for example, Brown, A., "Hybridization" pp. 503-506, in *The Encyclopedia of Molec. Biol.*, J. Kendrew, Ed., Blackwell, Oxford (1994).

Preferably, the nucleic acid sequence of a MarA family member identified in this way is at least about 10%, 20%, more preferably at least about 30%, more preferably at least about 40% identical and preferably at least about 50%, or 60% identical to a MarA nucleotide sequence. In preferred embodiments, the nucleic acid sequence of a MarA family member is at least about 70%, 80%, preferably at least about 90%, more preferably at least about 95% identical with a MarA nucleotide sequence. Preferably, MarA family members have an amino acid sequence at least about 20%, preferably at least about 30%, more preferably at least about 40% identical and preferably at least about 50%, or 60% or more identical with a MarA amino acid sequence. In preferred embodiments, the nucleic acid sequence of a MarA family member is at least about 70%, 80%, more preferably at least about 90%, or more preferably at least about 95% identical with a MarA nucleotide sequence. However, it will be understood that the level of sequence similarity among microbial regulators of gene transcription, even though members of the same family, is not necessarily high. This is particularly true in the case of divergent genomes where the level of sequence identity may be low, e.g., less than 20% (e.g., *B. burgdorferi* as compared e.g., to *B. subtilis*). Accordingly, structural similarity among MarA family members can also be determined based on "three-dimensional correspondence" of amino acid residues. As used herein, the language "three-dimensional correspondence" is meant to includes residues which spatially correspond, e.g., are in the same position of a MarA family polypeptide member as determined, e.g., by x-ray crystallography, but which may not correspond when aligned using a linear alignment program. The language "three-dimensional correspondence" also includes residues which perform the same function, e.g., bind to DNA or bind the same cofactor, as determined, e.g., by mutational analysis.

Exemplary MarA family polypeptides are shown in Table 1, FIGS. 1-3, and at Prosite (PS00041) and include: AarP, Ada, AdaA, AdiY, AfrR, AggR, AppY, AraC, CafR, CelD, CfaD, CsvR, D90812, EnvY, ExsA, FapR, HrpB, InF, InvF, LcrF, LumQ, MarA, MelR, MixE, MmsR, MsmR, OrfR, Orf_f375, PchR, PerA, PocR, PqrA, RafR, RamA, RhaR, RhaS, Rns, Rob, SoxS, S52856, TetD, TcpN, ThcR, TmbS, U73857, U34257, U21191, UreR, VirF, XylR, XylS, Xys1, 2, 3, 4, Ya52, YbbB, YfiF, YisR, YzbC, and YijO. The nucleotide and amino acid sequences of the *E. coli* Rob molecule are shown in SEQ ID NO:3 and 4, respectively.

TABLE 1

Some Bacterial MarA homologs[a]

Gram-negative bacteria

*Escherichia coli*
MarA (1)
OrfR (2, 3)
SoxS (4, 5)
AfrR (6)
AraC (7)
CelD (8)
D90812 (9)
FapR (10, 11)
MelR (12)
ORF f375 (13, 14)
RhaR (15, 16, 17)
RhaS (18)
Rob (19)
U73857 (20)
XylR (21)
YijO (22)
*Proteus vulgaris*
PqrA (23)
*Salmonella typhimurium*
MarA (24)
InvF (25)
PocR (26)
*Kiebsiella pneumoniae*
RamA (27)
*Haemophilus influenzae*
Ya52 (28)
*Yersinia* spp.
CafR (29)
LcrF (30) or VirF (30)
*Providencia stuartii*
AarP (31)
*Pseudomonas* spp.
MmsR (32)
TmbS (33)
XylS (34)
Xys1, 2, 3, 4 (35, 36)
Cyanobacteria
*Synechocystis* spp.
LumQ (37)
PchR (37)

TABLE 1-continued

Some Bacterial MarA homologs[a]

Gram-positive bacteria

*Lactobacillus helveticus*
U34257 (38)
*Azorhizobium caulinodans*
S52856 (39)
*Streptomyces* spp.
U21191 (40)
AraL (41)
*Streptococcus mutans*
MsmR (42)
*Pediococcus pentosaceus*
RafR (43)
*Photobacterium leiognathi*
LumQ (44)
*Bacillus subtilis*
AdaA (45)
YbbB (46)
YfiF (47)
YisR (48)
YzbC (49)

[a]The smaller MarA homologs, ranging in size from 87 (U34257) to 138 (OrfR) amino acid residues, are represented in boldface. References are given in parentheses and are listed below.
References for Table 1:
(1) S. P. Cohen, et al. 1993. *J. Bacteriol* 175: 1484-1492
(2) G. M. Braus, et al. 1984. *J. Bacteriol.* 160: 504-509
(3) K. Schollmeier, et al., 1984. *J. Bacteriol.* 160: 499-503
(4) C. F. Amabile-Cuevas, et al., 1991. *Nucleic Acids Res.* 19: 4479-4484
(5) J. Wu, et al., 1991. *J. Bacteriol.* 173: 2864-2871
(6) M. K. Wolf, et al., 1990. *Infect. Immun.* 58: 1124-1128
(7) C. M. Stoner, et al. 1982. *J. Mol. Biol.* 153: 649-652
(8) L. L. Parker, et al., 1990. *Genetics* 123: 455-471
(9) H. Mori, 1996. Unpublished data taken from the NCBI databases
(10) P. Klaasen, et al., 1990. *Mol. Microbiol.* 4: 1779-1783
(11) M. Ahmed, et al., 1994. *J. Biol. Chem* 269-28506-28513
(12) C. Webster, et al., 1989. *Gene* 83: 207-213
(13) G. Plunkett, III. 1995. Unpublished
(14) C Garcia-Martin, et al., 1992. *J. Gen. Microbiol.* 138: 1109-1116
(15) G. Plunkett, III., et al. 1993. *Nucleic Acids Res.* 21: 3391-3398
(16) C. G. Tate, et al. 1992. *J. Biol. Chem.* 267: 6923-6932
(17) J. F. Tobin et al., 1987. *J. Mol. Biol.* 196: 789-799
(18) J. Nishitani, 1991. *Gene* 105: 37-42
(19) R. E. Benz, et al., 1993. *Zentralbl. Bakteriol. Parasitenkd. Infektionskr. Hyg. Abt. 1 Orig.* 278: 187-196
(20) M. Duncan, et al., 1996. Unpublished data
(21) H. J. Sofia, et al., 1994. *Nucleic Acids Res.* 22: 2576-2586
(22) F. R. Blattner, et al., 1993. *Nucleic Acids Res.* 21: 5408-5417
(23) H. Ishida, et al., 1995. *Antimicrob. Agents Chemother.* 39: 453-457
(24) M. C. Sulavik, et al., 1997. *J. Bacteriol.* 179: 1857-1866
(25) K. Kaniga, et al., 1994. *Mol. Microbiol.* 13: 555-568
(26) J. R. Roth, et al. 1993. *J. Bacteriol.* 175: 3303-3316
(27) A. M. George, et al., 1983. *J. Bacteriol.* 155: 541-548
(28) R. D. Fleischmann, et al., 1995. *Science* 269: 469-512
(29) E. E. Galyov, et al., 1991. *FEBS Lett.* 286: 79-82
(30) N. P. Hoe, et al., 1992. *J. Bacteriol.* 174: 4275-4286
(31) G. Cornelis, et al., 1989. *J. Bacteriol.* 171: 254-262
(32) D. R. Macinga, et al., 1995. *J. Bacteriol.* 177: 3407-3413
(33) M. I. Steele, et al., 1992. *J. Biol. Chem.* 267: 13585-13592
(34) G. Deho, et al., 1995. Unpublished data
(35) N. Mermod, et al., 1984. *EMBO J.* 3: 2461-2466
(36) S. J. Assinder, et al., 1992. *Nucleic Acids Res.* 20: 5476
(37) S. J. Assinder, et al., 1993. *J. Gen. Microbiol.* 139: 557-568
(38) E. G. Dudley, et al., 1996. *J. Bacteriol.* 178: 701-704
(39) D. Geelen, et al., 1995. Unpublished data
(40) J. Kormanec, et al., 1995. *Gene* 165: 77-80
(41) C. W. Chen, et al., 1992. *J. Bacteriol.* 174: 7762-7769
(42) R. R. Russell, et al., 1992. *J. Biol. Chem,* 267: 4631-4637
(43) K. K. Leenhouts, et al., 1995. Unpublished data
(44) J. W. Lin, et al., 1995. *Biochem. Biophys. Res. Commun.* 217: 684-695
(45) F. Morohoshi, et al. 1990. *Nucleic Acids Res.* 18: 5473-5480
(46) M. Rosenberg, et al., 1979. *Annu. Rev. Genet.* 13: 319-353
(47) H. Yamamoto, et al., 1996. *Microbiology* 142: 1417-1421
(48) L. B. Bussey, et al., 1993. *J. Bacteriol.* 175: 6348-6353
(49) P. G. Quirk, et al., 1994. *Biochim. Biophys. Acta* 1186: 27-34

The term "transcription factor modulating compound" or transcription factor modulator" includes HTH protein modulating compounds, HTH protein modulators. Transcription factor modulating compounds include compounds which interact with one or more transcription factors, such that the activity of the transcription factor is modulated, e.g., enhanced or inhibited. The term also includes both AraC family modulating compounds and MarA family modulating compounds. In one embodiment, the transcription factor modulating compound is an inhibiting compound of a transcription factor, e.g., a prokaryotic transcription factor or a eukaryotic transcription activation factor. In one embodiment, the transcription factor modulating compounds modulate the activity of a transcription factor as measured by assays known in the art or LANCE assays such as those described in Example 8. In one embodiment, the transcription factor modulating compound inhibits a particular transcription factor by about 10% or greater, about 40% or greater, about 50% or greater, about 60% or greater, about 70% or greater, about 80% or greater, about 90% or greater, about 95% or greater, or about 100% as compared to the activity of the transcription factor with out the transcription factor modulating compound. In another embodiment, the transcription factor modulating compound inhibits biofilm formation. In one embodiment, the transcription factor modulating compound inhibits biofilm formation as measured by assays known in the art or the Crystal Violet assay described in Example 7. In one embodiment, the transcription factor of the invention inhibits the formation of a biofilm by about 25% or more, 50% or more, 75% or more, 80% or more, 90% or more, 95% or more, 96% or more, 97% or more, 98% or more, 99% or more, 99.9% or more, 99.99% or more, or by 100%, as compared to the formation of a biofilm without the transcription factor modulating compound.

The term "HTH protein modulating compound" or "HTH protein modulator" includes compounds which interact with one or more HTH proteins such that the activity of the HTH protein is modulated, e.g., enhanced or, inhibited. In one embodiment, the HTH protein modulating compound is a MarA family polypeptide modulating compound. In one embodiment, the activity of the HTH protein is enhanced when it interacts with the HTH protein modulating compound. For example, the activity of the HTH protein may be increased by greater than 10%, greater the 20%, greater than 50%, greater than 75%, greater than 80%, greater than 90%, or 100% of the activity of the HTH protein in the absence of the HTH modulating compound. In another embodiment, the activity of the HTH protein is decreased upon an interaction with the HTH protein modulating compound. In an embodiment, the activity of the HTH protein is decreased by about 25% or more, 50% or more, 75% or more, 80% or more, 90% or more, 95% or more, 96% or more, 97% or more, 98% or more, 99% or more, 99.9% or more, 99.99% or more, or by 100%, as compared to the activity of the protein of a HTH protein when not contacted with an HTH modulating compound of the invention using techniques and assays described herein. Values and ranges included and/or intermediate of the values set forth herein are also intended to be within the scope of the present invention.

The term "MarA family polypeptide modulating compound" or "MarA family modulating compound" include compounds which interact with one or more MarA family polypeptides such that the activity of the MarA family peptide is enhanced or inhibited. In an embodiment, the MarA family polypeptide modulating compound is an inhibiting compound. In a further embodiment, the MarA family inhibiting compound is an inhibitor of MarA, Rob, and/or SoxS. In another embodiment, the MarA family polypeptide modulating compound modulates the expression of luciferase in the Luciferase Assay described in Example 9. In one embodiment, the MarA family polypeptide modulating compound decreases luciferase expression by greater than 10%, greater than 20%, greater than 30%, greater than 40%, greater than 50%, greater than 60%, greater than 70%, greater than 80%, greater than 90% or about 100%.

The term "polypeptide(s)" refers to a peptide or protein comprising two or more amino acids joined to each other by peptide bonds or modified peptide bonds. "Polypeptide(s)" includes both short chains, commonly referred to as peptides, oligopeptides and oligomers and longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, $2^{nd}$ Ed., T. E. Creighton, W. H. Freeman and Company, New York (1993) and Wold, F., Posttranslational Protein Modifications Perspectives and Prospects, pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

As used herein, the term "winged helix" includes dimeric transcription factors in which each monomer comprises a helix-turn-helix motif followed by one or two β-hairpin wings (Brennan. 1993. *Cell.* 74:773; Gajiwala and Burley. 2000. *Curr. Opin. Struct. Biol.* 10:110). The classic winged helix motif comprises two wings, three α helices, and three β strands in the sequence H1-B1-H2-T-H3-B2-W1-B3-W2 (where H is a helix, B is a β strand, T is a turn, and W is a wing), although some variation in structure has been demonstrated (Huffman and Brennan. 2002. *Current Opinion in Structural Biology.* 12:98).

As used herein the term "looped-hinge helix" included transcription factors, such as AbrB which, in the absence of DNA, have revealed a dimeric N-terminal region consisting of a four-stranded β sheet and a C-terminal DNA-binding region comprising one α helix and a "looped hinge" (see, e.g., Huffman and Brennan. 2002 *Current Opinion in Structural Biology* 12:98). Residues corresponding to R23 and R24 of AbrB are critical for DNA recognition and contribute to the electropositive nature of the DNA-binding region.

Preferred polypeptides (and the nucleic acid molecules that encode them) are "naturally occurring." As used herein, a "naturally-occurring" molecule refers to a molecule having an amino acid or a nucleotide sequence that occurs in nature (e.g., a natural polypeptide). In addition, naturally or non-naturally occurring variants of the polypeptides and nucleic acid molecules which retain the same functional activity, (such as, the ability to bind to target nucleic acid molecules (e.g., comprising a marbox) or to polypeptides (e.g. RNA polymerase) with a naturally occurring polypeptide are provided for. Such immunologic cross-reactivity can be demonstrated, e.g., by the ability of a variant to bind to a MarA family polypeptide responsive element. Such variants can be made, e.g., by mutation using techniques that are known in the art. Alternatively, variants can be chemically synthesized.

As used herein the term "variant(s)" includes nucleic acid molecules or polypeptides that differ in sequence from a reference nucleic acid molecule or polypeptide, but retain its essential properties. Changes in the nucleotide sequence of the variant may, or may not, alter the amino acid sequence of a polypeptide encoded by the reference nucleic acid molecule. Nucleotide or amino acid changes may result in amino acid substitutions, additions, deletions, fusions and truncations in the polypeptide encoded by a naturally occurring reference sequence. A typical variant of a polypeptide differs in amino acid sequence from a reference polypeptide. Generally, differences are limited so that the sequences of the reference polypeptide and the variant are closely similar overall and, in many regions, identical. A variant and reference polypeptide may differ in amino acid sequence by one or more substitutions, additions, and/or deletions in any combination.

A variant of a nucleic acid molecule or polypeptide may be naturally occurring, such as an allelic variant, or it may be a variant that is not known to occur naturally. Non-naturally occurring variants of nucleic acid molecules and polypeptides may be made from a reference nucleic acid molecule or polypeptide by mutagenesis techniques, by direct synthesis, and by other recombinant methods known to skilled artisans. Alternatively, variants can be chemically synthesized. For instance, artificial or mutant forms of autologous polypeptides which are functionally equivalent, (e.g., have the ability to interact with a MarA family polypeptide responsive element) can be made using techniques which are well known in the art.

Mutations can include, e.g., at least one discrete point mutation which can give rise to a substitution, or by at least one deletion or insertion. For example, mutations can also be made by random mutagenesis or using cassette mutagenesis. For the former, the entire coding region of a molecule is mutagenized by one of several methods (chemical, PCR, doped oligonucleotide synthesis) and that collection of randomly mutated molecules is subjected to selection or screening procedures. In the latter, discrete regions of a polypeptide, corresponding either to defined structural or functional determinants are subjected to saturating or semi-random mutagenesis and these mutagenized cassettes are re-introduced into the context of the otherwise wild type allele. In one embodiment, PCR mutagenesis can be used. For example, Megaprimer PCR can be used (O. H. Landt, 1990. Gene 96:125-128).

In preferred embodiments, a MarA family polypeptide excludes one or more of XylS, AraC, and MelR. In other preferred embodiments, a MarA family polypeptide is involved in antibiotic resistance. In particularly preferred embodiments, a MarA family polypeptide is selected from the group consisting of: MarA, RamA, AarP, Rob, SoxS, and PqrA.

The language "activity of a transcription factor" includes the ability of a transcription factor to interact with DNA, e.g., to bind to a transcription factor responsive promoter, or to initiate transcription from such a promoter. The language expressly includes the activities of AraC family polypeptides, HTH proteins and MarA family polypeptides.

The language "activity of a MarA family polypeptide" includes the ability of the MarA family polypeptide to interact with DNA, e.g., to bind to a MarA family polypeptide responsive promoter, or to initiate transcription from such a promoter. MarA functions both as a transcriptional activator (e.g., upregulating genes such as inaA, galT, micF, etc.) and as a repressor (e.g., downregulating genes such as fecA, purA, guaB, etc.) (Alekshun, 1997, *Antimicrob. Agents Chemother.* 41:2067-2075; Barbosa & Levy, *J. Bact.* 2000, Vol. 182, p. 3467-3474; Pomposiello et al. *J. Bact.* 2001, Vol 183, p. 3890-3902).

The language "transcription factor responsive element" includes a nucleic acid sequence which can interact with a transcription factor (e.g., promoters or enhancers or operators) which are involved in initiating transcription of an operon in a microbe. Transcription factor responsive elements responsive to various transcription factors are known in the art and additional responsive elements can be identified by one of ordinary skill in the art. For example, microarray analysis can be used to identify genes that are regulated by a transcription factor of interest. For interest, genes regulated by a transcription factor would be expressed at higher levels in wild type cells than in cells which are deleted for the transcription factor. In addition, genes responsive to a given transcription factor would comprise one or more target sequences responsive to the transcription factor in their promoter regions (Lyons et al. 2000. PNAS 97:7957). Exemplary responsive elements include: araBAD, araE, araFGH (responsive to AraC); melBAD (responsive to MelR); rhaSR (responsive to RhaR); rahBAD, rhaT (responsive to RhaS); Pm (responsive to XylS); fumC, inaA, micF, nfo, pai5, sodA, tolC, acrAB, fldA, fpr, mar, poxB, ribA, and zwf (responsive to MarA, SoxS, Rob); and coo, rns (responsive to Rns).

The language "marA family polypeptide responsive element" includes a nucleic acid sequence which can interact with marA, e.g., promoters or enhancers which are involved in regulating transcription of a nucleic acid sequence in a microbe. MarA responsive elements comprise approximately 16 base pair marbox sequence, the sequence critical for the binding of MarA to its target. In addition, a secondary site, the accessory marbox, upstream of the primary marbox contributes to basal and derepressed mar transcription. A marbox may be situated in either the forward or backward orientation. (Martin, 1999, *Mol. Microbiol.* 34:431-441). In the marRAB operon, the marbox is in the backward orientation and is thus located on the sense strand with respect to marRAB (Martin, 1999, *Mol. Microbiol.* 34:431-441). Subtle differences within the marbox sequence of particular promoters may account for differential regulation by MarA and other related, e.g., SoxS and Rob, transcription factors (Martin, 2000, *Mol Microbiol;* 35(3):623-34). In one embodiment, MarA family responsive elements are promoters that are structurally or functionally related to a marA promoter, e.g., interact with MarA or a protein related to MarA. Preferably, the marA family polypeptide responsive element is a marRAB promoter. For example, in the mar operon, several promoters are marA family polypeptide responsive promoters as defined herein, e.g., the 405-bp ThaI fragment from the marO region is a marA family responsive promoter (Cohen et al. 1993. *J. Bact.* 175:7856). In addition, MarA has been shown to bind to a 16 bp MarA binding site (referred to as the "marbox" within marO (Martin et al. 1996. *J. Bacteriol.* 178:2216). MarA also affects transcription from the acrAB; micF; mlr 1, 2, 3; slp; nfo; inaA; fpr; sodA; soi-17, 19; zwf; fumC; or rpsF promoters (Alekshun and Levy. 1997. *Antimicrobial Agents and Chemother.* 41:2067). Other marA family responsive promoters are known in the art and include: araBAD, araE, araFGH and araC, which are activated by AraC; Pm, which is activated by XylS; melAB which is activated by MelR; and oriC which is bound by Rob.

The language "MarA family polypeptide responsive promoter" also includes portions of the above promoters which are sufficient to activate transcription upon interaction with a MarA family member protein. The portions of any of the MarA family polypeptide-responsive promoters which are minimally required for their activity can be easily determined by one of ordinary skill in the art, e.g., using mutagenesis. Exemplary techniques are described by Gallegos et al. (1996, *J. Bacteriol.* 178:6427). A "MarA family polypeptide responsive promoter" also includes non-naturally occurring variants of MarA family polypeptide responsive promoters which have the same function as naturally occurring MarA family promoters. Preferably such variants have at least 30% or greater, 40% or greater, or 50% or greater, nucleotide sequence identity with a naturally occurring MarA family polypeptide responsive promoter. In preferred embodiments, such variants have at least about 70% nucleotide sequence identity with a naturally occurring MarA family polypeptide responsive promoter. In more preferred embodiments, such variants have at least about 80% nucleotide sequence identity with a naturally occurring MarA family polypeptide responsive promoter. In particularly preferred embodiments, such variants have at least about 90% nucleotide sequence identity and preferably at least about 95% nucleotide sequence identity with a naturally occurring MarA family polypeptide responsive promoter. In yet other embodiments nucleic acid molecules encoding variants of MarA family polypeptide responsive promoters are capable of hybridizing under stringent conditions to nucleic acid molecules encoding naturally occurring MarA family polypeptide responsive promoters.

In one embodiment, the methods described herein can employ molecules identified as responding to the transcription factors of the invention, i.e., molecules in a regulon whose expression is controlled by the transcription factor. For example, compounds that modulate transcription of genes that are directly modulated by a microbial transcription factor (e.g., a marA family transcription factor) can be used to modulate virulence of a microbe or modulate infection by a microbe. In another embodiment, such genes can be identified as important in controlling virulence using the methods described herein. As used herein, the term "regulon" includes two or more loci in two or more different operons whose expression is regulated by a common repressor or activator protein.

The term "interact" includes close contact between molecules that results in a measurable effect, e.g., the binding of one molecule with another. For example, a MarA family polypeptide can interact with a MarA family polypeptide responsive element and alter the level of transcription of DNA. Likewise, compounds can interact with a MarA family polypeptide and alter the activity of a MarA family polypeptide.

The term "inducible promoter" includes promoters that are activated to induce the synthesis of the genes they control. As used herein, the term "constitutive promoter" includes promoters that do not require the presence of an inducer, e.g., are continuously active.

The terms "heterologous DNA" or "heterologous nucleic acid" includes DNA that does not occur naturally in the cell (e.g., as part of the genome) in which it is present or which is found in a location or locations in the genome that differ from that in which it occurs in nature or which is operatively linked to DNA to which it is not normally linked in nature (i.e., a gene that has been operatively linked to a heterologous promoter). Heterologous DNA is 1) not naturally occurring in a particular position (e.g., at a particular position in the genome) or 2) is not endogenous to the cell into which it is introduced, but has been obtained from another cell. Heterologous DNA can be from the same species or from a different species. Any DNA that one of skill in the art would recognize or consider as heterologous or foreign to the cell in which is expressed is herein encompassed by the term heterologous DNA.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid molecule.

The term "microbe" includes microorganisms expressing or made to express a transcription factor, araC family polypeptide, HTH protein, or a marA family polypeptide. "Microbes" are of some economic importance, e.g., are environmentally important or are important as human pathogens. For example, in one embodiment microbes cause environmental problems, e.g., fouling or spoilage, or perform useful functions such as breakdown of plant matter. In another embodiment, microbes are organisms that live in or on mammals and are medically important. Preferably microbes are unicellular and include bacteria, fungi, or protozoa. In another embodiment, microbes suitable for use in the invention are multicellular, e.g., parasites or fungi. In preferred embodiments, microbes are pathogenic for humans, animals, or plants. Microbes may be used as intact cells or as sources of materials for cell-free assays. In one embodiment, the microbes include prokaryotic organisms. In other embodiments, the microbes include eukaryotic organisms. Exemplary bacteria that comprise MarA homologs include the following:

| MarA |
| --- |
| *E. coli* |
| UPEC (uropathogenic) |
| EPEC (enteropathogenic) |
| *Salmonella enterica* |
| Cholerasuis (septicemia) |
| Enteritidis enteritis |
| Typhimurium enteritis |
| Typhimurium (multi-drug resistant) |
| *Yersinia enterocolitica* |
| *Yersinia pestis* |
| *Pseudomonas aeruginosa* |
| *Enterobacter* spp. |

-continued

| MarA |
|---|
| *Klebsiella* sp. |
| *Proteus* spp. |
| *Vibrio cholerae* |
| *Shigella* sp. |
| *Providencia stuartii* |
| *Neisseria meningitidis* |
| *Mycobacterium tuberculosis* |
| *Mycobacterium leprae* |
| *Staphylococcus aureus* |
| *Streptococcus pyogenes* |
| *Enterococcus faecalis* |
| *Bordetella pertussis* |
| *Bordetella bronchiseptica* |

The term selective marker includes polypeptides that serve as indicators, e.g., provide a selectable or screenable trait when expressed by a cell. The term "selective marker" includes both selectable markers and counterselectable markers. As used herein the term "selectable marker" includes markers that result in a growth advantage when a compound or molecule that fulfills the test parameter of the assay is present. The term "counterselectable marker" includes markers that result in a growth disadvantage unless a compound or molecule is present which disrupts a condition giving rise to expression of the counterselectable marker. Exemplary selective markers include cytotoxic gene products, gene products that confer antibiotic resistance, gene products that are essential for growth, gene products that confer a selective growth disadvantage when expressed in the presence of a particular metabolic substrate (e.g., the expression of the URA3 gene confers a growth disadvantage in the presence of 5-fluoro-orotic acid).

As used herein the term "reporter gene" includes any gene which encodes an easily detectable product which is operably linked to a regulatory sequence, e.g., to a transcription factor responsive promoter. By operably linked it is meant that under appropriate conditions an RNA polymerase may bind to the promoter of the regulatory region and proceed to transcribe the nucleotide sequence such that the reporter gene is transcribed. In preferred embodiments, a reporter gene consists of the transcription factor responsive promoter linked in frame to the reporter gene. In certain embodiments, however, it may be desirable to include other sequences, e.g, transcriptional regulatory sequences, in the reporter gene construct. For example, modulation of the activity of the promoter may be effected by altering the RNA polymerase binding to the promoter region, or, alternatively, by interfering with initiation of transcription or elongation of the mRNA. Thus, sequences which are herein collectively referred to as transcriptional regulatory elements or sequences may also be included in the reporter gene construct. In addition, the construct may include sequences of nucleotides that alter translation of the resulting mRNA, thereby altering the amount of reporter gene product.

Examples of reporter genes include, but are not limited to CAT (chloramphenicol acetyl transferase) (Alton and Vapnek (1979), *Nature* 282: 864-869) luciferase, and other enzyme detection systems, such as beta-galactosidase; firefly luciferase (deWet et al. (1987), *Mol. Cell. Biol.* 7:725-737); bacterial luciferase (Engebrecht and Silverman (1984), PNAS 1: 4154-4158; Baldwin et al. (1984), *Biochemistry* 23: 3663-3667); PhoA, alkaline phosphatase (Toh et al. (1989) *Eur. J. Biochem.* 182: 231-238, Hall et al. (1983) J. Mol. Appl. Gen. 2: 101), human placental secreted alkaline phosphatase (Cullen and Malim (1992) *Methods in Enzymol.* 216:362-368) and green fluorescent protein (U.S. Pat. No. 5,491,084; WO96/23898).

In certain embodiments of the invention it will be desirable to obtain "isolated or recombinant" nucleic acid molecules transcription factors or mutant forms thereof. The term "isolated or recombinant" includes nucleic acid molecules which have been, e.g., (1) amplified in vitro by, for example, polymerase chain reaction (PCR); (2) recombinantly produced by cloning, or (3) purified, as by cleavage and gel separation; or (4) synthesized by, for example, chemical synthesis. Such a nucleic acid molecule is isolated from the sequences which naturally flank it in the genome and from cellular components.

In yet other embodiments of the invention, it will be desirable to obtain a substantially purified or recombinant transcription factor. Such polypeptides, for example, can be purified from cells which have been engineered to express an isolated or recombinant nucleic acid molecule which encodes a transcription factor. For example, as described in more detail below, a bacterial cell can be transformed with a plasmid which encodes a transcription factor. The transcription factor can then be purified from the bacterial cells and used, for example, in the cell-free assays described herein or known in the art.

As used herein, the term "antibiotic" includes antimicrobial agents isolated from natural sources or chemically synthesized. The term "antibiotic" refers to antimicrobial agents for use in human therapy. Preferred antibiotics include: tetracycline, fluoroquinolones, chloramphenicol, penicillins, cephalosporins, puromycin, nalidixic acid, and rifampin.

The term "test compound" includes any reagent or test agent which is employed in the assays of the invention and assayed for its ability to influence the activity of a transcription factor, e.g., an AraC family polypeptide, an HTH protein, or a MarA family polypeptide, e.g., by binding to the polypeptide or to a molecule with which it interacts. More than one compound, e.g., a plurality of compounds, can be tested at the same time for their ability to modulate the activity of a transcription factor, e.g., an AraC family polypeptide, an HTH protein, or a MarA family polypeptide, activity in a screening assay. In an advantageous embodiment, the test compound is a MarA family modulating compound.

Test compounds that can be tested in the subject assays include antibiotic and non-antibiotic compounds. In one embodiment, test compounds include candidate detergent or disinfectant compounds. Exemplary test compounds which can be screened for activity include, but are not limited to, peptides, non-peptidic compounds, nucleic acids, carbohydrates, small organic molecules (e.g., polyketides), and natural product extract libraries. The term "non-peptidic test compound" includes compounds that are comprised, at least in part, of molecular structures different from naturally-occurring L-amino acid residues linked by natural peptide bonds. However, "non-peptidic test compounds" also include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic test compounds" also are intended to include natural products.

In one embodiment, small molecules can be used as test compounds. The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "antagonist" includes transcription factor modulating compounds (e.g., AraC family polypeptide modulating compounds, HTH protein modulating compounds, MarA family polypeptide modulating compounds, etc.) which inhibit the activity of a transcription factor by binding to and inactivating the transcription factor (e.g., an AraC family modulating compound, an MarA family polypeptide modulating compound, etc.), by binding to a nucleic acid target with which the transcription factor interacts (e.g., for MarA, a marbox), by disrupting a signal transduction pathway responsible for activation of a particular regulon (e.g., for Mar, the inactivation of MarR or activation of MarA synthesis), and/or by disrupting a critical protein-protein interaction (e.g., MarA-RNA polymerase interactions that are required for MarA to function as a transcription factor.) Antagonists may include, for example, naturally or chemically synthesized compounds such as small cell permeable organic molecules, nucleic acid interchelators, peptides, etc.

The term "agonist" includes transcription factor modulating compounds (e.g., AraC family polypeptide modulating compounds, HTH protein modulating compounds, MarA family polypeptide modulating compounds, etc.) which promote the activity of a transcription factor by binding to and activating the transcription factor (e.g., an AraC family modulating compound, an MarA family polypeptide modulating compound, etc.), by binding to a nucleic acid target with which the transcription factor interacts (e.g., for MarA, a marbox), by facilitating a signal transduction pathway responsible for activation of a particular regulon (e.g., for Mar, the inactivation of MarR or activation of MarA synthesis), and/or by facilitating a critical protein-protein interaction (e.g., MarA-RNA polymerase interactions that are required for MarA to function as a transcription factor.) Agonists may include, for example, naturally or chemically synthesized compounds such as small cell permeable organic molecules, nucleic acid interchelators, peptides, etc.

II. MarA Family Polypeptide Helix-Turn-Helix Domains

Helix-turn-helix domains are known in the art and have been implicated in DNA binding (*Ann Rev. of Biochem.* 1984. 53:293). An example of the consensus sequence for a helix-turn domain can be found in Brunelle and Schleif (1989, *J. Mol. Biol.* 209:607). The domain has been illustrated by the sequence XXXPhoAlaXXPhoGlyPhoXXXX-PhoXXPhoXX, where X is any amino acid and Pho is a hydrophobic amino acid.

The crystal structure of MarA has been determined and the first (most amino terminal) HTH domain of MarA has been identified as comprising from about amino acid 31 to about amino acid 52 and the second HTH domain of MarA has been identified as comprising from about amino acid 79 to about amino acid 102 (Rhee et al. 1998. *Proc. Natl. Acad. Sci. USA.* 95:10413).

Locations of the helix-turn-helix domains in other MarA family members as well as other HTH proteins can easily be found by one of skill in the art. For example using the MarA protein sequence and an alignment program, e.g., the Pro-Dom program or other programs known in the art, a portion of the MarA amino acid sequence e.g., comprising one or both HTH domains of MarA (such as from about amino acid 30 to about amino acid 107 of MarA) to produce an alignment. Using such an alignment, the amino acid sequences corresponding to the HTH domains of MarA can be identified in other MarA family member proteins. An exemplary consensus sequence for the first helix-turn-helix domain of a MarA family polypeptide can be illustrated as XXXXAXXXXX-SXXXLXXXFX, where X is any amino acid. An exemplary consensus sequence for the second helix-turn-helix domain of a MarA family polypeptide is illustrated as XXIXX-IAXXXGFXSXXXFXXX[F/Y], where X is any amino acid. Preferably, a MarA family polypeptide first helix-turn-helix domain comprises the consensus sequence E/D-X-V/L-A-D/E-X-A/S-G-X-S-X3-L-Q-X2-F-K/R/E-X2-T/I. Preferably, a MarA family polypeptide second helix-turn-helix domain comprises the consensus sequence 1-X-D-1-A-X3-G-F-X-S-X2-F-X3-F-X4.

In an embodiment, a MarA family member HTH domain is a MarA HTH domain. The first and second helix-turn-helix domains of MarA are, respectively, EKVSERS-GYSKWHLQRMFKKET and ILYLAERYGFESQQTL-TRTFKNYF. Other exemplary MarA family helix-turn-helix domains include: about amino acid 210 to about amino acid 229 and about amino acid 259 to about amino acid 278 of MelR; about amino acid 196 to about amino acid 215 and about amino acid 245 to about amino acid 264 of AraC; and about amino acid 230 to about amino acid 249 (or 233-253) and about amino acid 281 to about amino acid 301 (or 282-302) of XylS (see e.g., Brunelle et al. 1989. *J. Mol. Biol.* 209:607; Niland et al. 1996. *J. Mol. Biol.* 264:667; Gallegos et al. 1997. *Microbiology and Molecular Biology Reviews.* 61:393).

"MarA family polypeptide helix-turn-helix domains" are derived from or are homologous to the helix-turn-helix domains found in the MarA family polypeptides as described supra. In preferred embodiments, a MarA family polypeptide excludes one or more of XylS, AraC, and MelR. In particularly preferred embodiments, a MarA family polypeptide is selected from the group consisting of: MarA, RamA, AarP, Rob, SoxS, and PqrA.

Both of the helix-turn-helix domains present in MarA family polypeptides are in the carboxy terminal end of the protein. Proteins or portions thereof comprising either or both of these domains can be used in the instant methods. In certain embodiments, a polypeptide which is used in screening for compounds comprises the helix-turn-helix domain most proximal to the carboxy terminus (HTH2) of the MarA family polypeptide from which it is derived. In other embodiments, such a polypeptide comprises the helix-turn-helix domain most proximal to the amino terminus (HTH1) of the MarA family polypeptide from which it is derived. In one embodiment, other polypeptide sequences may also be present, e.g., sequences that might facilitate immobilizing the domain on a support, or, alternatively, might facilitate the purification of the domain.

In an embodiment, such a polypeptide consists essentially of the helix-turn-helix domain most proximal to the carboxy terminus of the MarA family polypeptide from which it is derived. In other preferred embodiments, such a polypeptide consists essentially of the helix-turn-helix domain most proximal to the amino terminus of the MarA family polypeptide from which it is derived.

In an embodiment, such a polypeptide consists of the helix-turn-helix domain most proximal to the carboxy terminus of the AraC family polypeptide or MarA family polypeptide from which it is derived. In other preferred embodiments, such a polypeptide consists of the helix-turn-helix domain most proximal to the amino terminus of the AraC family polypeptide or MarA family polypeptide from which it is derived.

MarA family polypeptide or AraC family polypeptide helix-turn-helix domains can be made using techniques which are known in the art. The nucleic acid and amino acid sequences of transcription factors, such as MarA family polypeptides, are available, for example, from GenBank. Using this information, the helix-turn-helix consensus motif and mutational analysis provided herein, one of ordinary skill in the art can identify MarA family or AraC family polypeptide helix-turn-helix domains.

In certain embodiments of the invention it will be desirable to obtain "isolated or recombinant" nucleic acid molecules encoding transcription factors or portions thereof (e.g., HTH protein helix-turn-helix domains, AraC family helix-turn-helix domains, MarA family helix-turn-helix domains or mutant forms thereof). By "isolated or recombinant" is meant a nucleic acid molecule which has been (1) amplified in vitro by, for example, polymerase chain reaction (PCR); (2) recombinantly produced by cloning, or (3) purified, as by cleavage and gel separation; or (4) synthesized by, for example, chemical synthesis. Such a nucleic acid molecule is isolated from the sequences which naturally flank it in the genome and from cellular components.

The isolated or recombinant nucleic acid molecules encoding transcription factors (e.g., HTH protein helix-turn-helix domains, AraC family helix-turn-helix domains, MarA family helix-turn-helix domains or mutant forms thereof) can then, for example, be utilized in binding assays, can be expressed in a cell, or can be expressed on the surface of phage, as discussed further below.

In yet other embodiments of the invention, it will be desirable to obtain a substantially purified or recombinant HTH protein helix-turn-helix domains (e.g., MarA family helix-turn-helix domains or mutant forms thereof). Such polypeptides, for example, can be purified from cells which have been engineered to express an isolated or recombinant nucleic acid molecule which encodes a HTH protein helix-turn-helix domain (e.g., MarA family helix-turn-helix domain or mutant forms thereof). For example, as described in more detail below, a bacterial cell can be transformed with a plasmid which encodes a MarA family helix-turn-helix domain. The MarA family helix-turn-helix protein can then be purified from the bacterial cells and used, for example, in the cell-free assays described herein.

Purification of a HTH protein helix-turn-helix domain (e.g., MarA family helix-turn-helix domain) can be accomplished using techniques known in the art. For example, column chromatography could be used, or antibodies specific for the domain or for a polypeptide fused to the domain can be employed, for example on a column or in a panning assay.

In preferred embodiments, cells used to express HTH protein helix-turn-helix domains (e.g., MarA family helix-turn-helix domains or mutant forms thereof) for purification, e.g., host cells, comprise a mutation which renders any endogenous HTH proteins nonfunctional or causes the endogenous protein to not be expressed. In other embodiments, mutations may also be made in MarR or related genes of the host cell, such that repressor proteins which bind to the same promoter as a MarA family polypeptide are not expressed by the host cell.

In certain embodiments of the invention, it will be desirable to use a mutant form of a HTH protein helix-turn helix domain, e.g., a non-naturally occurring form of a MarA family helix-turn-helix domain which has altered activity, e.g., does not retain wild type MarA family polypeptide helix-turn-helix domain activity, or which has reduced activity or which is more active when compared to a wild-type MarA family polypeptide helix-turn-helix domain.

Such mutant forms can be made using techniques which are well known in the art. For example, random mutagenesis can be used. Using random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. In the second approach, discrete regions of a protein, corresponding either to defined structural or functional determinants (e.g., the first or second alpha helix of a helix-turn-helix domain) are subjected to saturating or semi-random mutagenesis and these mutagenized cassettes are re-introduced into the context of the otherwise wild type allele.

In a preferred embodiment, PCR mutagenesis is used. For example, Example 2 describes the use of Megaprimer PCR (O. H. Landt, Gene 96:125-128) used to introduce an NheI restriction site into the centers of both the helix A (position 1989) and helix B (position 2016) regions of the marA gene.

In one embodiment, such mutant helix-turn-helix domains comprise one or more mutations in the helix-turn-helix domain most proximal to the carboxy terminus (HTH2) of the MarA family polypeptide molecule. In a preferred embodiment, the mutation comprises an insertion into helix A and helix B of the helix-turn-helix domain most proximal to the carboxy terminus of the MarA family polypeptide. In one embodiment, such mutant helix-turn-helix domains comprise one or more mutations in the helix-turn-helix domain most proximal to the amino terminus (HTH1) of the MarA family polypeptide molecule. In a preferred embodiment, the mutation comprises an insertion into helix A and helix B of the helix-turn-helix domain most proximal to the amino terminus of the MarA family polypeptide. In particularly preferred embodiments, the mutation is selected from the group consisting of: an insertion at an amino acid corresponding to about position 33 of MarA and an insertion at an amino acid position corresponding to about position 42 of MarA. "Corresponding" amino acids can be determined, e.g., using an alignment of the helix-turn-helix domains.

Such mutant forms of MarA family helix-turn-helix motifs are useful as controls to verify the specificity of antiinfective compounds for a MarA family helix-turn-helix domain or as controls for the identification of genetic loci which affect resistance to antiinfectives. For example, the mutant MarA family helix-turn-helix domains described in the appended Examples demonstrate that insertional inactivation of MarA at either helix A or helix B in the first HTH domain abolished the multidrug resistance phenotype in both *E. coli* and *M. smegmatis*. By the use of an assay system such as that described in Example 2, which demonstrates the ability of MarA family polypeptide helix-turn-helix domains to increase antibiotic resistance and that mutant forms of these domains do not have the same effect, one can clearly show that the response of any genetic loci identified is specific to a MarA family helix-turn-helix domain.

III. Expression of Polypeptide or Portions Thereof

Nucleic acids encoding transcription factors, such as AraC family polypeptides, HTH proteins, e.g., MarA family polypeptides or selectable markers (or portions thereof that retain an activity of the full-length polypeptide, e.g., are capable of binding to a transcription factor responsive element or retain their indicator function) can be expressed in cells using vectors. Almost any conventional delivery vector can be used. Such vectors are widely available commercially and it is within the knowledge and discretion of one of ordinary skill in the art to choose a vector which is appropriate for use with a given microbial cell. The sequences encoding these domains can be introduced into a cell on a self-replicating vector or may be introduced into the chromosome of a microbe using homologous recombination or by an insertion element such as a transposon.

These nucleic acids can be introduced into microbial cells using standard techniques, for example, by transformation using calcium chloride or electroporation. Such techniques for the introduction of DNA into microbes are well known in the art. In one embodiment, a nucleic acid molecule which has been amplified in vitro by, for example, polymerase chain reaction (PCR); recombinantly produced by cloning, or) purified, as by cleavage and gel separation; or synthesized by, for example, chemical synthesis can be used to produce MarA family polypeptides (George, A. M. & Levy, S. B. (1983) *J. Bacteriol.* 155, 541-548; Cohen, S. P. et al. (1993) J *Infect. Dis.* 168, 484-488; Cohen, S. P et al. (1993) J *Bacteriol.* 175, 1484-1492; Sulavick, M. C. et al. (1997) J. *Bacteriol.* 179, 1857-1866).

Host cells can be genetically engineered to incorporate nucleic acid molecules of the invention. In one embodiment nucleic acid molecules specifying transcription factors can be placed in a vector. The term "vector" refers to a nucleic acid molecule capable of transporting another nucleic acid molecule to which it has been linked. The term "expression vector" or "expression system" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions. A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

Appropriate vectors are widely available commercially and it is within the knowledge and discretion of one of ordinary skill in the art to choose a vector which is appropriate for use with a given host cell. The sequences encoding a transcription factor, such as, for example, MarA family polypeptides, can be introduced into a cell on a self-replicating vector or may be introduced into the chromosome of a microbe using homologous recombination or by an insertion element such as a transposon.

The expression system constructs may contain control regions that regulate expression. "Transcriptional regulatory sequence" is a generic term to refer to DNA sequences, such as initiation signals, enhancers, operators, and promoters, which induce or control transcription of polypeptide coding sequences with which they are operably linked. It will also be understood that a recombinant gene encoding a transcription factor gene, e.g., an HTH protein gene or an AraC family polypeptide, e.g., MarA family polypeptide, can be under the control of transcriptional regulatory sequences which are the same or which are different from those sequences which control transcription of the naturally-occurring transcription factor gene. Exemplary regulatory sequences are described in Goeddel; *Gene Expression Technology: Methods in Enzymology* 185, Academic Press, San Diego, Calif. (1990). For instance, any of a wide variety of expression control sequences, that control the expression of a DNA sequence when operatively linked to it, may be used in these vectors to express DNA sequences encoding the polypeptide.

Generally, any system or vector suitable to maintain, propagate or express nucleic acid molecules and/or to express a polypeptide in a host may be used for expression in this regard. The appropriate DNA sequence may be inserted into the expression system by any of a variety of well-known and routine techniques, such as, for example, those set forth in Sambrook et al., Molecular Cloning, A Laboratory Manual, (supra).

Exemplary expression vectors for expression of a gene encoding a polypeptide and capable of replication in a bacterium, e.g., a gram positive, gram negative, or in a cell of a simple eukaryotic fungus such as a *Saccharomyces* or, *Pichia*, or in a cell of a eukaryotic organism such as an insect, a bird, a mammal, or a plant, are known in the art. Such vectors may carry functional replication-specifying sequences (replicons) both for a host for expression, for example a *Streptomyces*, and for a host, for example, *E. coli*, for genetic manipulations and vector construction. See, e.g., U.S. Pat. No. 4,745,056. Suitable vectors for a variety of organisms are described in Ausubel, F. et al., *Short Protocols in Molecular Biology*, Wiley, New York (1995), and for example, for *Pichia*, can be obtained from Invitrogen (Carlsbad, Calif.).

Useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat polypeptide, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. A useful translational enhancer sequence is described in U.S. Pat. No. 4,820,639.

In one embodiment, an inducible promoter will be employed to express a polypeptide of the invention. For example, in one embodiment, trp (induced by tryptophan), tac (induced by lactose), or tet (induced by tetracycline) can be used in bacterial cells, or GAL1 (induced by galactose) can be used in yeast cell.

In another embodiment, a constitutive promoter can be used to express a polypeptide of the invention.

It should be understood that the design of the expression vector may depend on such factors as the choice of the host cell to be transformed and/or the type of polypeptide desired to be expressed. Representative examples of appropriate hosts include bacterial cells, such as gram positive, gram negative cells; fungal cells, such as yeast cells and *Aspergillus* cells; insect cells such as *Drosophila* S2 and *Spodoplera* Sf9 cells; animal cells such as CHO, COS, HeLa, C127, 3T3, BHK, 293 and Bowes melanoma cells; and plant cells.

In one embodiment, cells used to express heterologous polypeptides of the invention, comprise a mutation which renders one or more endogenous transcription factors, such as a AraC family polypeptide or a MarA family polypeptide, nonfunctional or causes one or more endogenous polypeptide to not be expressed. Manipulation of the genetic background in this manner allows for screening for compounds that modulate specific transcription factors, such as MarA family members or AraC family members, or more than one transcription factors.

In other embodiments, mutations may also be made in other related genes of the host cell, such that there will be no interference from the endogenous host loci. In yet another embodiment, a mutation may be made in a chromosomal gene to create a heterotroph.

Introduction of a nucleic acid molecule into the host cell ("transformation") can be effected by methods described in many standard laboratory manuals, such as Davis et al., Basic Methods In Molecular Biology, (1986) and Sambrook et al., Molecular Cloning: A Laboratory Manual, 2nd Ed., Cold Spring Harbor Laboratory Press, Cold Spring Harbor, N.Y. (1989). Examples include calcium phosphate transfection, DEAE-dextran mediated transfection, transvection, microinjection, cationic lipid-mediated transfection, electroporation, transduction, scrape loading, ballistic introduction and infection.

Purification of polypeptides, e.g., recombinantly expressed polypeptides, can be accomplished using techniques known in the art. For example, if the polypeptide is expressed in a form that is secreted from cells, the medium can be collected. Alternatively, if the polypeptide is expressed in a form that is retained by cells, the host cells can be lysed to release the polypeptide. Such spent medium or cell lysate can be used to concentrate and purify the polypeptide. For example, the medium or lysate can be passed over a column, e.g., a column to which antibodies specific for the polypeptide have been bound. Alternatively, such antibodies can be specific for a second polypeptide which has been fused to the first polypeptide (e.g., as a tag) to facilitate purification of the first polypeptide. Other means of purifying polypeptides are known in the art.

IV. Methods for Identifying Antiinfective Compounds which Modulate an Activity of a Transcription Factor Transcription factor agonists and antagonists can be assayed in a variety of ways. For example, in one embodiment, the invention provides for methods for identifying a compound which modulates an transcription factor, e.g., by measuring the ability of the compound to interact with an transcription factor nucleic acid molecule or an transcription factor polypeptide or the ability of a compound to modulate the activity or expression of an transcription factor polypeptide. Furthermore, the ability of a compound to modulate the binding of an transcription factor polypeptide or transcription factor nucleic acid molecule to a molecule to which they normally bind, e.g., a nucleic acid or protein molecule can be tested.

In one embodiment, a transcription factor and its cognate DNA sequence can be present in a cell free system, e.g., a cell lysate and the effect of the compound on that interaction can be measured using techniques known in the art.

In a preferred embodiment, the assay system is a cell-based system. Compounds identified using the subject methods are useful, e.g., to interfere with the ability of a microbe to grow in a host and/or in reducing microbial virulence and, thereby, and in reducing the ability of the microbe to cause infection in a host.

The ability of the test compound to modulate the expression and/or activity of a transcription factor can be determined in a variety of ways. Exemplary methods which can be used in the instant assays are known in the art and are described, e.g., in U.S. Pat. No. 5,817,793 and WO 99/61579. Other exemplary methods are described in more detail below.

In one embodiment, the invention provides for methods of identifying a test compound which modulates the expression and/or activity of a transcription factor, (e.g., an HTH protein, a MarA family polypeptide, an AraC family polypeptide, etc.) by contacting a cell expressing a transcription factor (or portion thereof) with a test compound under conditions which allow interaction of the test compound with the cell.

Assays

In one embodiment, the expression of a selectable marker that confers a selective growth disadvantage or lethality is placed under the direct control of a MarA responsive element in a cell expressing marA.

In one embodiment, marA is plasmid encoded. In one embodiment, the genetic background of the host organism is manipulated, e.g., to delete one or more chromosomal marA genes or marA homolog genes.

In one embodiment, expression of marA is controlled by a highly regulated and inducible promoter. For example, in one embodiment, a promoter selected from the group consisting of trp, tac, or tet in bacterial cells or GAL1 in yeast cells can be used.

In another embodiment, expression of marA is constitutive.

In one embodiment, a selective marker is a cytotoxic gene product (e.g., ccdB).

In another embodiment, a selective marker is a gene that confers antibiotic resistance (e.g., kan, cat, or bla).

In another embodiment, a selective marker is an essential gene (e.g., purA or guaB in a purine or guanine heterotroph).

In still another embodiment, a selective marker is a gene that confers a selective growth disadvantage in the presence of a particular metabolic substrate (e.g., the expression of URA3 in the presence of 5-fluoroorotic acid [5-FOA] in yeast).

In one embodiment, compounds that modulate transcription factors (e.g., HTH proteins, AraC family polypeptides, or MarA family polypeptides) are identified using a one-hybrid screening assay. As used herein, the term "one-hybrid screen" as used herein includes assays that detect the disruption of protein-nucleic acid interactions. These assays will identify agents that interfere with the binding of a transcription factor (e.g., an HTH protein, a AraC family polypeptide, or a MarA family polypeptide) to a particular target, e.g., DNA containing, for MarA, a marbox, at the level of the target itself, e.g., by binding to the target and preventing the transcriptional activation factor from interacting with or binding to this site.

In another embodiment, compounds of the invention are identified using a two-hybrid screening assay. As used herein the term "two-hybrid screen" as used herein includes assays that detect the disruption of protein-protein interactions. Such two hybrid assays can be used to interfere with crucial protein-transcription factor interactions (e.g., HTH protein interactions, AraC family polypeptide interactions, MarA family polypeptide interactions). One example would be to prevent RNA polymerase-MarA family polypeptide contacts, that are necessary for the MarA family polypeptide to function as a transcription factor (either positive acting or negative acting).

In yet another embodiment, compounds of the invention are identified using a three-hybrid screening assay. As used herein the term "three-hybrid screen" as used herein includes assays that will detect the disruption of a signal transduction pathway(s) required for the activation of a particular regulon of interest. In one embodiment, the three-hybrid screen is used to detect disruption of a signal transduction pathway(s) required for the activation of the Mar regulon, i.e., synthesis of MarA. (Li and Park. *J. Bact.* 181:4824). The assay can be used to identify compounds that may be responsible for activating transcription factor expression, e.g., Mar induction by antibiotics may proceed in this manner.

In one embodiment of the assay, the expression of a selective marker (e.g., ccdB, cat, bla, kan, guaB, URA3) is put under the direct control of an activatable MarA responsive activatable promoter (e.g., inaA, galT, micF). In the absence of Mar A, the expression of the selective marker would be silent. For example, in the case of regulation of the cytotoxic gene ccdB, the gene would be silent and the cells would survive. Synthesis of MarA from an inducible plasmid in a suitable host would result in the activation of the MarA responsive activatable promoter and expression of the selective marker. In the case of ccdB, the gene would be expressed and result in cell death. Compounds that inhibit MarA would be identified as those that permit cell survival under conditions of MarA expression.

In another embodiment, e.g., where the expression of the MarA responsive activatable promoter regulates a gene such as URA3, a different result could be obtained. In this case, in the absence of MarA and thus, in the absence of URA3 expression, cells would grow in the presence of a 5-FOA. Upon activation of MarA expression and thus synthesis of URA3, cells would die following the conversion of 5-FOA to a toxic metabolite by URA3.

In another embodiment, a selectable marker is put under the direct control of a repressible MarA responsive promoter (e.g., fecA). In this example, under conditions of constitutive MarA synthesis, e.g., in a constitutive mar (marc) mutant the expression of the selectable marker would be silent. In the case of ccdB, this would mean that cells would remain viable. Following inactivation of MarA, the selectable marker would be turned on, resulting in cell death.

In another embodiment, a purine or guanine heterotroph can be constructed by the inactivation of the chromosomal guaB or purA genes in *E. coli*. The guaB or purA gene would then be cloned into a suitable vector, under the control of its natural promoter. This construct would then be transformed into the heterotrophic host. The heterotroph will not grow if MarA expression is constitutive and if cells are grown on media lacking purines or guanine. This can be attributed to MarA mediated repression of guaB or purA synthesis. Candidate inhibiting compounds of MarA can be identified as compounds that restored growth, i.e., relieved MarA mediated repression of guaB and purA expression. In another embodiment, genes that are required for growth in vivo, for example in an animal model of infection.

In preferred embodiments, controls may be included to ensure that any compounds which are identified using the subject assays do not merely appear to modulate the activity of a transcription factor, because they inhibit protein synthesis. For example, if a compound appears to inhibit the synthesis of a protein being translated from RNA which is transcribed upon activation of a MarA family responsive element, it may be desirable to show that the synthesis of a control, e.g., a protein which is being translated from RNA which is not transcribed upon activation of a MarA family responsive element, is not affected by the addition of the same compound. For example, the amount of the MarA family polypeptide being made and compared to the amount of an endogenous protein being made. In another embodiment the microbe could be transformed with another plasmid comprising a promoter which is not a MarA family responsive promoter and a protein operably linked to that promoter. The expression of the control protein could be used to normalize the amount of protein produced in the presence and absence of compound.

V. Microbes Suitable for Testing

Numerous different microbes are suitable for testing in the instant assays. As such, they may be used as intact cells or as sources of material, e.g., nucleic acid molecules or polypeptides as described herein.

In preferred embodiments, microbes for use in the claimed methods are bacteria, either Gram negative or Gram positive bacteria. More specifically, any bacteria that are shown to become resistant to antibiotics, e.g., to display a Mar phenotype are preferred for use in the claimed methods, or that are infectious or potentially infectious.

Examples of microbes suitable for testing include, but are not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Yibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*.

In one embodiment, microbes suitable for testing are bacteria from the family Enterobacteriaceae. In preferred embodiments, the compound is effective against a bacteria of a genus selected from the group consisting of: *Escherichia, Proteus, Salmonella, Klebsiella, Providencia, Enterobacter, Burkholderia, Pseudomonas, Aeromonas, Haemophilus, Yersinia, Neisseria*, and *Mycobacteria*.

In yet other embodiments, the microbes to be tested are Gram positive bacteria and are from a genus selected from the group consisting of: *Lactobacillus, Azorhizobium, Streptomyces, Pediococcus, Photobacterium, Bacillus, Enterococcus, Staphylococcus, Clostridium*, and *Streptococcus*.

In other embodiments, the microbes to be tested are fungi. In a preferred embodiment the fungus is from the genus *Mucor* or *Candida*, e.g., *Mucor racmeosus* or *Candida albicans*.

In yet other embodiments, the microbes to be tested are protozoa. In a preferred embodiment the microbe is a malaria or cryptosporidium parasite.

VI. Transcription Factor Modulating Compounds and Test Compounds

Compounds for testing in the instant methods can be derived from a variety of different sources and can be known or can be novel. In one embodiment, libraries of compounds are tested in the instant methods to identify transcriptional activation factor modulating compounds, e.g., HTH protein modulating compounds, AraC family polypeptide modulating compounds, MarA family polypeptide modulating compounds, etc. In another embodiment, known compounds are tested in the instant methods to identify transcription factor modulating compounds (such as, for example, HTH protein modulating compounds, AraC family polypeptide modulating compounds, MarA family polypeptide modulating compounds, etc.). In an embodiment, compounds among the list of compounds generally regarded as safe (GRAS) by the Environmental Protection Agency are tested in the instant methods. In another embodiment, the transcription factors which are modulated by the modulating compounds are of prokaryotic microbes.

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. *J. Am. Chem. Soc.* 114:10987; DeWitt et al. 1993. Proc. Natl. Acad. Sci. USA 90:6909) peptoids (Zuckermann. 1994. *J. Med. Chem.* 37:2678) oligocarbamates (Cho et al. 1993. Science. 261:1303), and hydantoins (DeWitt et al. supra). Rebek et al. have described an approach for the synthesis of molecular libraries of small organic molecules with a diversity of 104-105 (Carell et al. 1994. *Angew. Chem. Int. Ed. Engl.* 33:2059; Carell et al. *Angew. Chem. Int. Ed. Engl.* 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. *Anticancer Drug Des.* 1997. 12:145).

Exemplary compounds which can be screened for activity include, but are not limited to, peptides, nucleic acids, carbohydrates, small organic molecules, and natural product extract libraries. In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. *Proc. Natl. Acad. Sci. USA* 91:11422; Horwell et al. 1996 *Immunopharmacology* 33:68; and in Gallop et al. 1994. *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.). Other types of peptide libraries may also be expressed, see, for example, U.S. Pat. Nos. 5,270,181 and 5,292,646). In still another embodiment, combinatorial polypeptides can be produced from a cDNA library.

In other embodiments, the compounds can be nucleic acid molecules. In preferred embodiments, nucleic acid molecules for testing are small oligonucleotides. Such oligonucleotides can be randomly generated libraries of oligonucleotides or can be specifically designed to reduce the activity of a transcription factor, e.g., a HTH protein, a MarA family polypeptide, or an AraC family polypeptide. For example, in one embodiment, these oligonucleotides are sense or antisense oligonucleotides. In an embodiments, oligonucleotides for testing are sense to the binding site of a particular transcription factor, e.g., a MarA family polypeptide helix-turn-helix domain. Methods of designing such oligonucleotides given the sequences of a particular transcription factor polypeptide, such as a MarA family polypeptide, is within the skill of the art.

In yet another embodiment, computer programs can be used to identify individual compounds or classes of compounds with an increased likelihood of modulating a transcription factor activity, e.g., an HTH protein, a AraC family polypeptide, or a MarA family polypeptide activity. Such programs can screen for compounds with the proper molecular and chemical complementarities with a chosen transcription factor. In this manner, the efficiency of screening for transcription factor modulating compounds in the assays described above can be enhanced.

VII. Computer Modeling Techniques for Identifying Transcription Factor Modulating Compounds The invention also pertains to the use of molecular design techniques to design transcription factor modulating compounds, e.g., HTH protein modulating compounds, AraC family modulating compounds, MarA family modulating compounds, or MarA modulating compounds, which are capable of binding or interacting with one or more transcription factors (e.g., of a prokaryotic or eukaryotic organism). The invention pertains to both the transcription factor modulating compounds identified by the methods as well as the modeling methods, and compositions comprising the compounds identified by the methods.

In an embodiment, the invention pertains to a method of identifying transcription factor modulating compounds. The method includes obtaining the structure of a transcription factor of interest, and using GLIDE to identify a scaffold which has an interaction energy score of −20 or less (e.g., −40 or less, e.g., −60 or less) with a portion of the transcription factor.

The invention pertains, at least in part, to a computational screening of small molecule databases for chemical entities or compounds that can bind in whole, or in part, to a transcription factor, such as a HTH protein, an AraC family polypeptide, a MarA family polypeptide, e.g., MarA. In this screening, the quality of fit of such entities or compounds to the binding site may be judged either by shape complementarity or by estimated interaction energy (Meng, E. C. et al., 1992, *J. Coma. Chem.*, 13:505-524). Such a procedure allows for the screening of a very large library of potential transcription factor modulating compounds for the proper molecular and chemical complementarities with a selected protein or class or proteins. Transcription factor modulating compounds identified through computational screening can later be passed through the in vivo assays described herein as further screens. For example, a MarA inhibiting compound identified through computational screening could be tested for its ability to promote cell survival in a cell system containing a counterselectable marker under the control a MarA activated promoter. The promotion of cell survival in the foregoing assay would be indicative of a compound that inhibits MarA's activity as a transcriptional activator. Other suitable assays are described in the Examples and through the specification.

The crystal structures of both MarA (PDB ID code 1BL0) and its homolog Rob (PDB ID code 1DY5) are available in the Protein Data Bank (http://www.rcsb.org/pdb/). These structures were used to identify sites on the proteins that could be targeted by small molecule chemical inhibiting compounds. A total of at least eight potential small molecule binding sites on MarA (Table 2) and four sites on Rob (Table 3) were identified as potential small molecule binding sites. The invention pertains, at least in part, to MarA modulating compounds which interact with any one of the following sites of MarA (based on the sequence given in SEQ ID NO. 2).

TABLE 2

| Site Number | Residues (based on full length MarA) | Site Label |
|---|---|---|
| 1 | 42 to 50 | R46 Major Groove |
| 2 | 54 to 62 | L56 HTH core |
| 3 | 55 to 65 | R61 Minor Groove |
| 4 | 15 to 25 | W19 |
| 5 | 14 to 25 | E21 |
| 6 | 24 to 35 | L28 |
| 7 | 76 to 83 | P78 |
| 8 | 106 to 112 | R110 |

The GLIDE docking method was then used to fit combinatorial chemistry scaffolds into these sites and an interaction energy was calculated for each. Eight scaffolds were predicted to bind to site 1, encompassing amino acids tryptophan 42 to lysine 50, with an interaction energy score of −60 or less. These scaffolds are shown below:

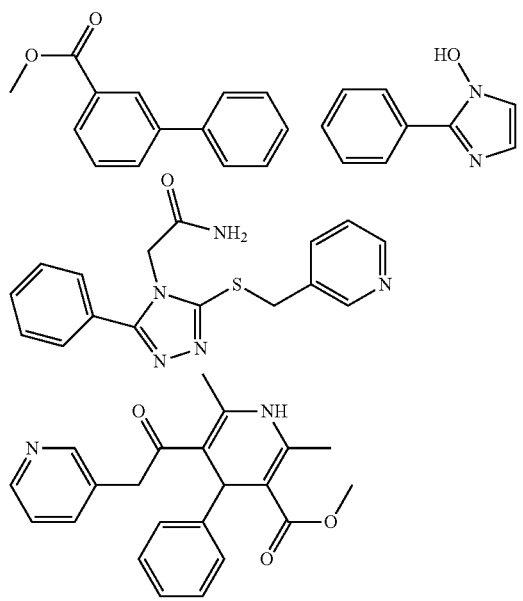

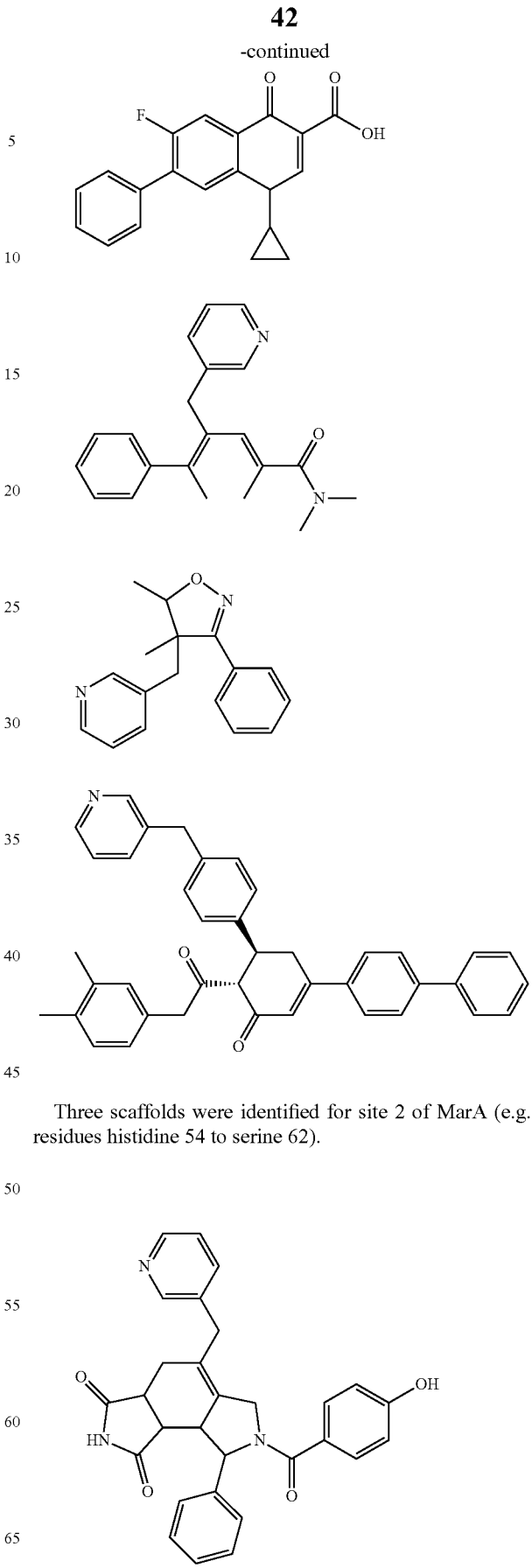

Three scaffolds were identified for site 2 of MarA (e.g., residues histidine 54 to serine 62).

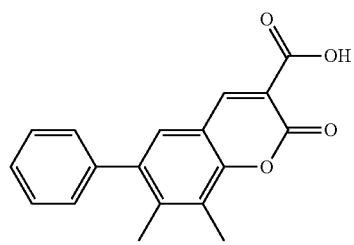
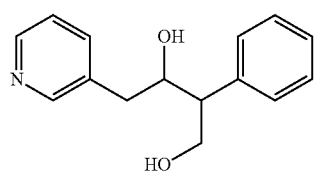
Four scaffolds were identified for MarA site 3, (e.g., residues serine 55 to methionine 65):
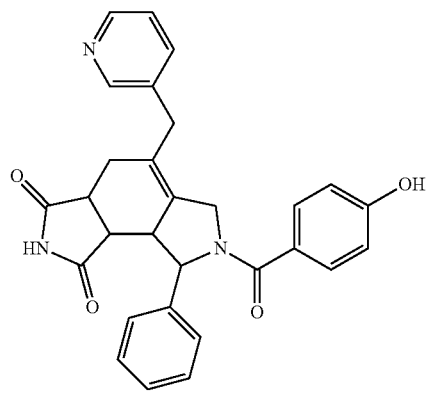
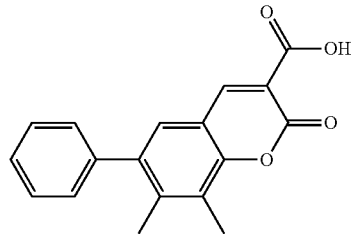
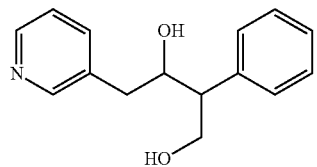
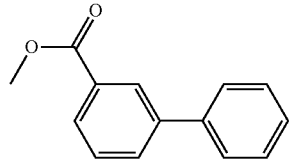
Six scaffolds were identified for site 6 (e.g., residues leucine 24 to glutamate 35).
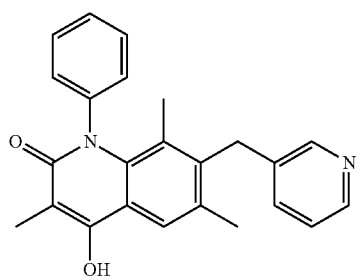
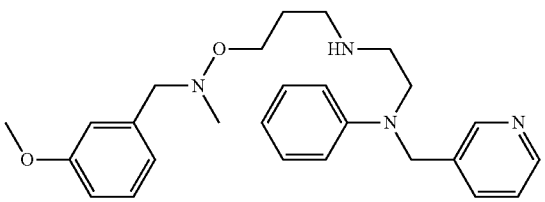
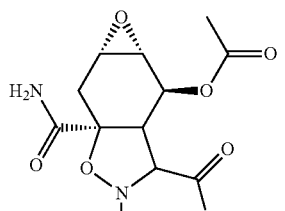
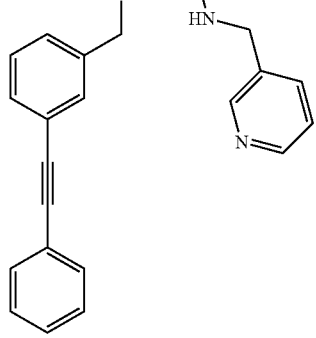
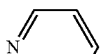
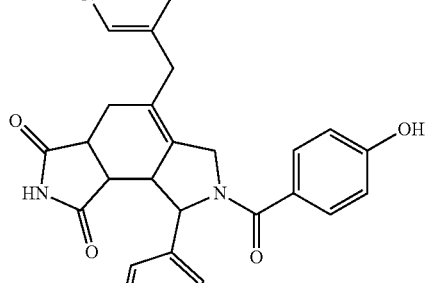
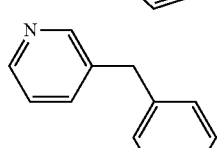
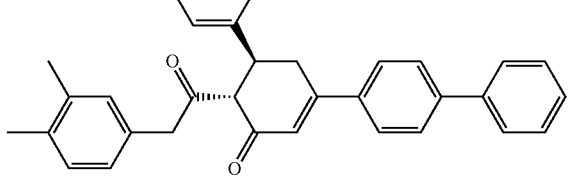

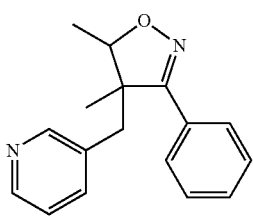 [SMILES: CC1ON=C(c2ccccc2)C1(C)Cc1cccnc1]

These scaffolds were then used to search the CambridgeSoft ACX-SC database of over 600,000 non-proprietary chemical structures and the number of chemicals similar to the scaffolds was determined.

The term "scaffold" includes the compounds identified by the computer modeling program. These compounds may or may not be themselves transcription factor modulating compounds. An ordinarily skilled artisan will be able to analyze a scaffold obtained from the computer modeling program and modify the scaffold such that the resulting compounds have enhanced chemical properties over the initial scaffold compound, e.g., are more stable for administration, less toxic, have enhanced affinity for a particular transcription factor, etc. The invention pertains not only to the scaffolds identified, but also the transcription factor modulating compounds which are developed using the scaffolds.

Table 3 lists portions of Rob which were identified as possible interaction sites for a modulating compound. The invention pertains, at least in part, to any compounds modeled to bind to these regions of Rob. The numbering corresponds to that given in SEQ ID NO. 4.

TABLE 3

| Site Number | Residues (based on full length Rob) | Site Label |
|---|---|---|
| 1 | 37 to 45 | R40 Major Groove |
| 2 | 43 to 54 | I50 HTH Core |
| 3 | 51 to 60 | R55 Minor Groove |
| 4 | 10 to 20 | W13 |

These scaffolds were identified as possible modulating compounds which with site 1 of Rob (residues 37-45), a MarA family polypeptide.

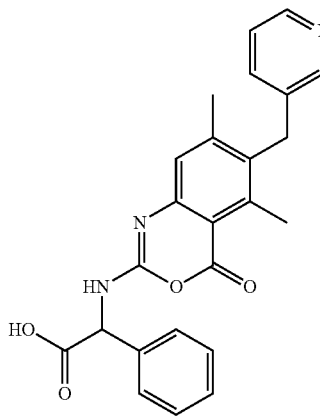

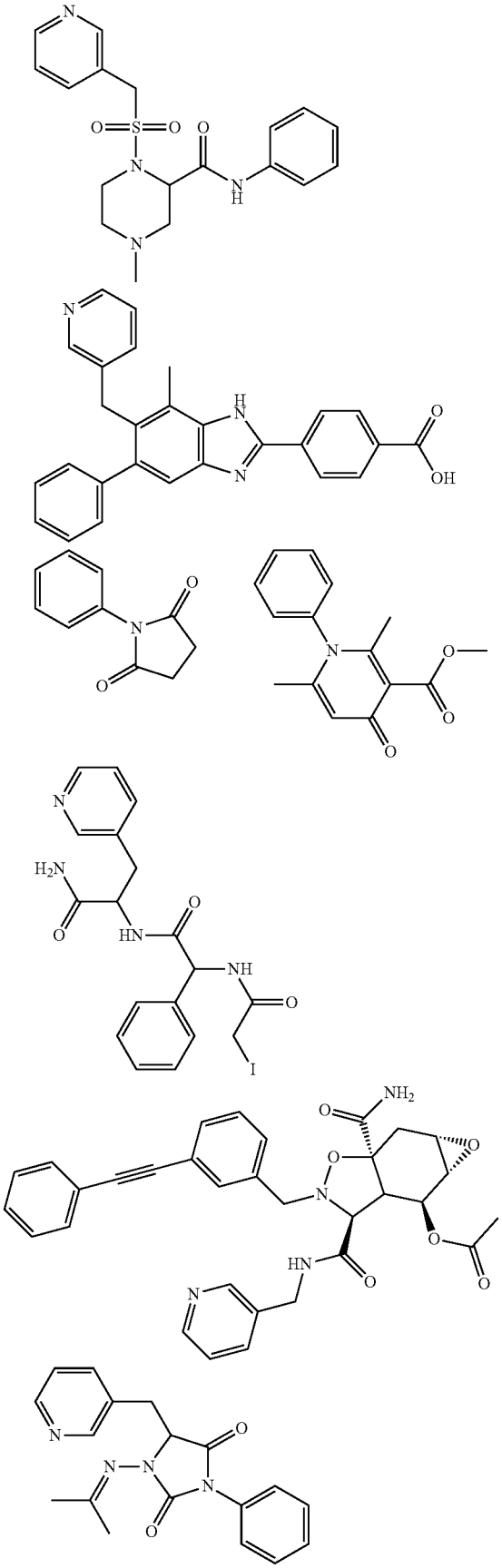

47
-continued
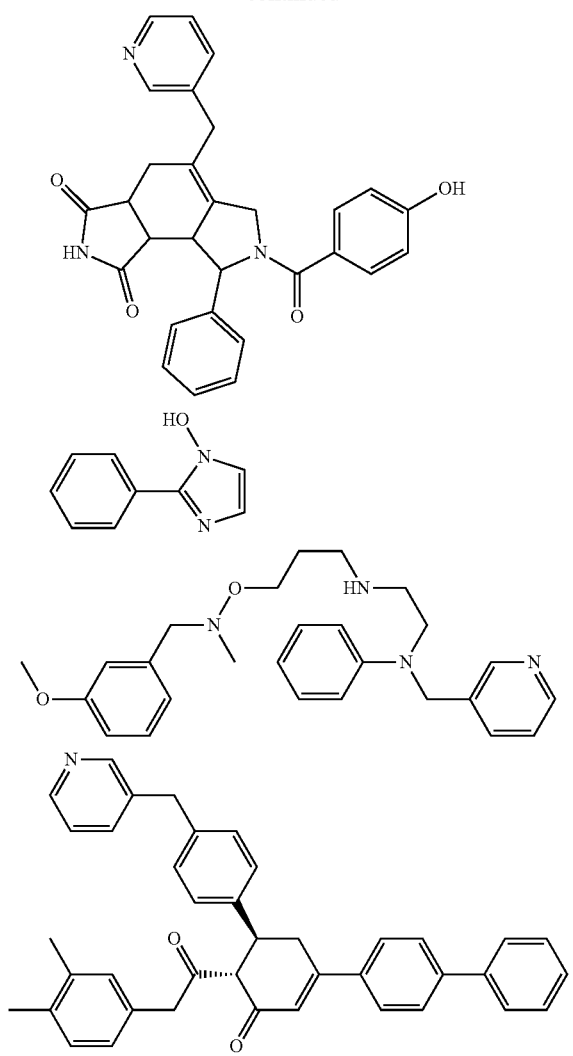
These scaffolds were identified as small molecules that may interact with site 2 of Rob (residues 43-52), a MarA family polypeptide.
48
-continued
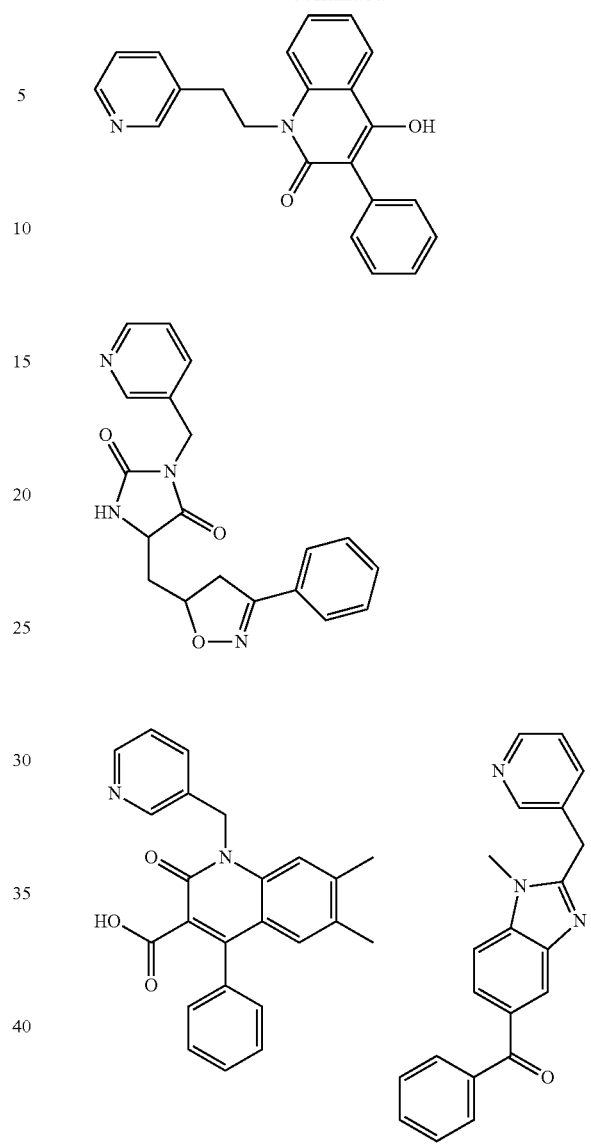
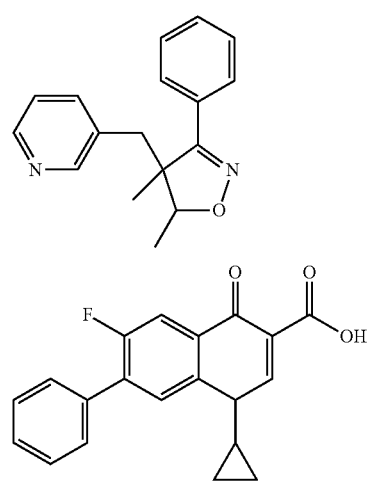
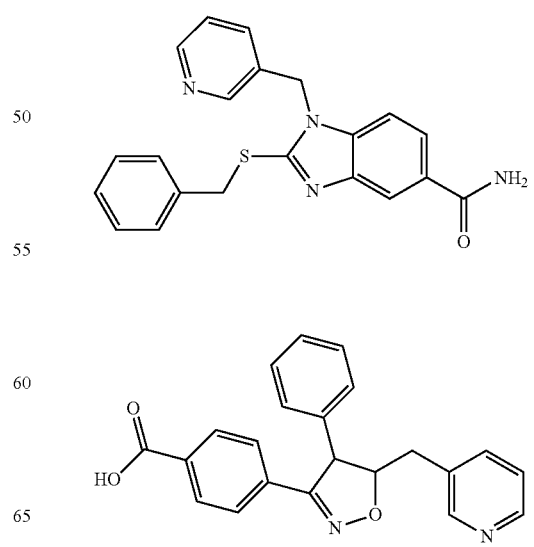

49
-continued
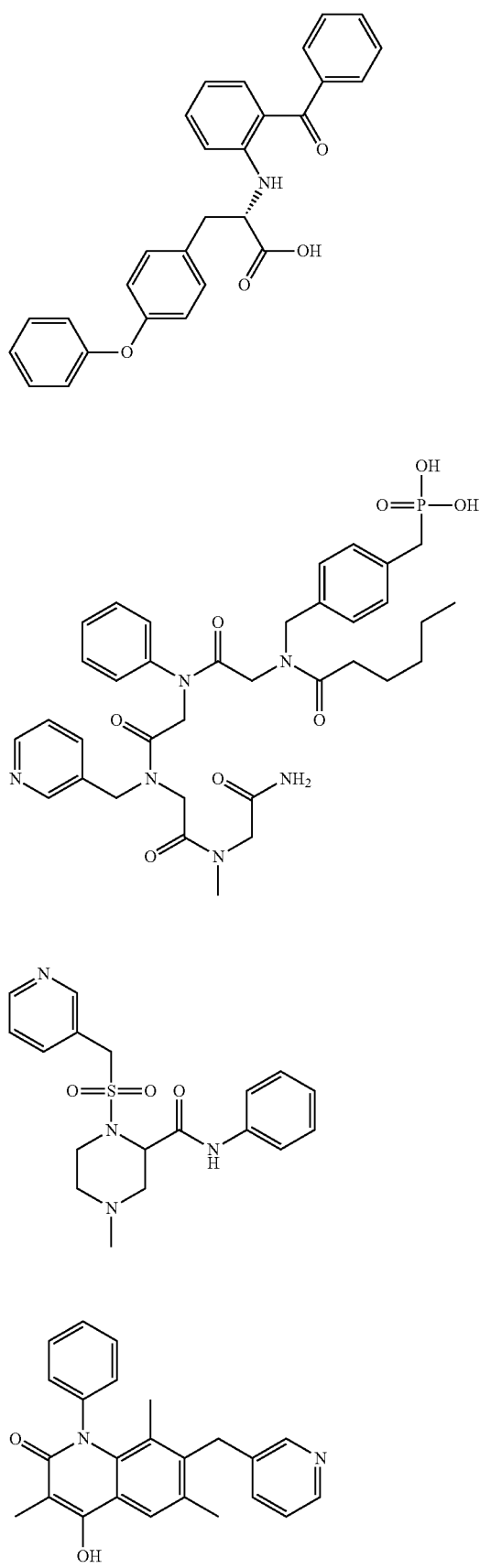
50
-continued
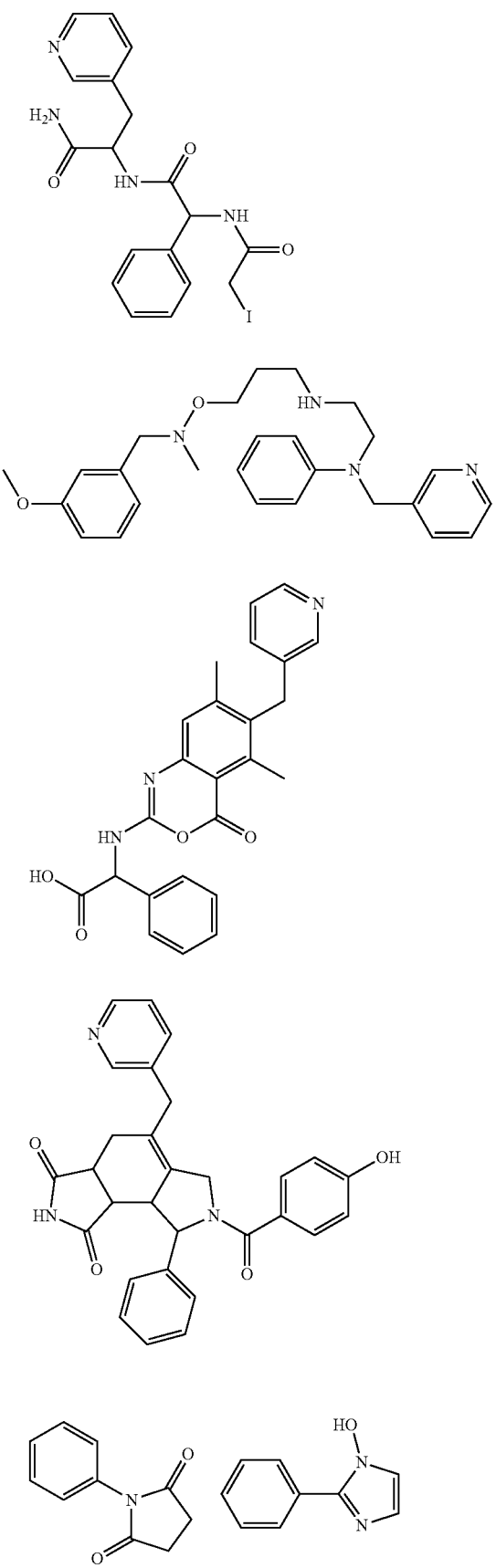

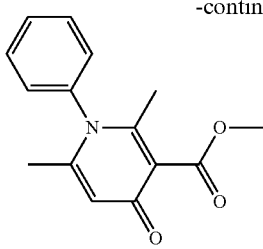

The design of compounds that bind to, modulate, or inhibit transcription factors, generally involves consideration of two factors. First, the compound must be capable of physically and structurally associating with a particular transcription factor. Non-covalent molecular interactions important in the association of a transcription factor with a modulating compound include hydrogen bonding, van der Waals and hydrophobic interactions.

Second, the modulating compound must be able to assume a conformation that allows it to associate with the selected transcription factor. Although certain portions of the inhibiting compound will not directly participate in this association with the transcription factor, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of a particular transcription factor such as MarA, or the spacing between functional groups of a compound comprising several chemical entities that directly interact with the particular transcription factor.

In a further embodiment, the potential modulating effect of a chemical compound on a selected transcription factor (e.g., a HTH protein, a AraC family polypeptide, a MarA family polypeptide, e.g., MarA) is analyzed prior to its actual synthesis and testing by the use of computer modeling techniques. If the theoretical structure of the given compound suggests insufficient interaction and association between it and the selected transcription factor, synthesis and testing of the compound is avoided. However, if computer modeling indicates a strong interaction, the molecule may then be synthesized and tested for its ability to bind to the selected transcription factor and modulate the transcription factor's activity.

A transcription factor modulating compound or other binding compound (e.g., an HTH protein modulating compound, an AraC family polypeptide modulating compound, or a MarA family inhibiting compound, e.g., a MarA inhibiting compound) may be computationally evaluated and designed by screening and selecting chemical entities or fragments for their ability to associate with the individual small molecule binding sites or other areas of a transcription factor.

One skilled in the art may use one of several methods to screen chemical entities or fragments for their ability to associate with a selected transcription factor and more particularly with the individual small molecule binding sites of the particular transcription activation factor. This process may begin by visually inspecting the structure of the transcription factor on a computer screen based on the atomic coordinates of the transcription factor crystals. Selected chemical entities may then be positioned in a variety of orientations, or docked, within an individual binding site of the transcription factor. Docking may be performed using software such as Quanta and Sybyl, followed by energy minimization with standard molecular mechanics forcefields or dynamics with programs such as CHARMM (Brooks, B. R. et al., 1983, *J. Comp. Chem.*, 4:187-217) or AMBER (Weiner, S. J. et al., 1984, *J. Am. Chem. Soc.*, 106:765-784).

Specialized computer programs may also assist in the process of selecting molecules that bind to a selected transcription factor, (e.g., an HTH protein, an AraC family polypeptide, or a MarA family polypeptide, e.g., MarA). The programs include, but are not limited to:

1. GRID (Goodford, P. J., 1985, "A Computational Procedure for Determining Energetically Favorable Binding Sites on Biologically Important Macromolecules" *J. Med. Chem.*, 28:849-857 GRID is available from Oxford University, Oxford, UK.
2. AUTODOCK (Goodsell, D. S, and A. J. Olsen, 1990, "Automated Docking of Substrates to Proteins by Simulated Annealing" Proteins: Structure. *Function, and Genetics*, 8:195-202. AUTODOCK is available from Scripps Research Institute, La Jolla, Calif. AUTODOCK helps in docking inhibiting compounds to a selected transcription factor in a flexible manner using a Monte Carlo simulated annealing approach. The procedure enables a search without bias introduced by the researcher.
3. MCSS (Miranker, A. and M. Karplus, 1991, "Functionality Maps of Binding Sites: A Multiple Copy Simultaneous Search Method." Proteins: Structure, Function and Genetics, 11:29-34). MCSS is available from Molecular Simulations, Burlington, Mass.
4. MACCS-3D (Martin, Y. C., 1992, J. Med. Chem., 35:2145-2154) is a 3D database system available from MDL Information Systems, San Leandro, Calif.
5. DOCK (Kuntz, I. D. et al., 1982, "A Geometric Approach to Macromolecule-Ligand Interactions" *J. Mol. Biol.*, 161: 269-288). DOCK is available from University of California, San Francisco, Calif.
   DOCK is based on a description of the negative image of a space-filling representation of the molecule (i.e. the selected transcription factor) that should be filled by the inhibiting compound. DOCK includes a force-field for energy evaluation, limited conformational flexibility and consideration of hydrophobicity in the energy evaluation.
6. MCDLNG (Monte Carlo De Novo Ligand Generator) (D. K. Gehlhaar, et al. 1995. *J. Med. Chem.* 38:466-472). MCDLNG starts with a structure (i.e. an X-ray crystal structure) and fills the binding site with a close packed array of generic atoms. A Monte Carlo procedure is then used to randomly: rotate, move, change bond type, change atom type, make atoms appear, make bonds appear, make atoms disappear, make bonds disappear, etc. The energy function used by MCDLNG favors the formation of rings and certain bonding arrangements. Desolvation penalties are given for heteroatoms, but heteroatoms can benefit from hydrogen bonding with the binding site.

In an embodiment of the invention, docking is performed by using the Affinity program within InsightII (Molecular Simulations Inc., 1996, San Diego, Calif., now Accelrys Inc.). Affinity is a suite of programs for automatically docking a ligand (i.e. a transcription factor modulating compound) to a receptor (i.e. a transcription factor). Commands in Affinity automatically find the best binding structures of the ligand to the receptor based on the energy of the ligand/receptor complex. As described below, Affinity allows for the simulation of flexible-flexible docking.

Affinity consists of two commands, GridDocking and fixedDocking, under the new pulldown Affinity in the Docking module of the Insight II program. Both commands use the same, Monte Carlo type procedure to dock a guest molecule (i.e. HTH protein modulating compound) to a host (i.e., a transcription factor). They also share the feature that the "bulk" of the receptor (i.e. transcription factor), defined as atoms not in the binding (active) site specified, is held rigid during the docking process, while the binding site atoms and ligand atoms are movable. The commands differ, however, in their treatment of nonbond interactions. In GridDocking, interactions between hulk and movable atoms are approximated by the very accurate and efficient molecular mechanical/grid (MM/Grid) method developed by Luty et al. 1995. *J. Comp. Chem.* 16:454, while interactions among movable atoms are treated exactly. GridDocking also includes the solvation method of Stouten et al. 1993. Molecular Simulation 10:97. On the other hand, the fixedDocking command computes nonbond interactions using methods in the Discover program (cutoff methods and the cell multipole method) and it does not include any solvation terms.

Affinity does not, generally, require any intervention from the user during the docking. It automatically moves the ligand (i.e. modulating compound), evaluates energies, and checks if the structure is acceptable. Moreover, the ligand and the binding site of the receptor (i.e. the selected transcription modulator) are flexible during the search.

Most of the docking methods in the literature are based on descriptors or empirical rules (for a review see Kuntz et al. 1994. *Acc. Chem. Res.* 27:117. These include DOCK (Kuntz et al. 1982. *J. Mol. Biol.* 161:269., Shoichet et al. 1992. *J. Compt. Chem.* 13:380., Oshiro et al. 1995. *J. Comp. Aided Molec. Design* 9:113.), CAVEAT (Bartlett et al. 1989. "Chemical and Biological Problems in Molecular Recognition" Royal Society of Chemistry: Cambridge, pp. 182-196., Lauri & Bartlett. 1994. *J. Comput. Aided Mol. Design* 8:51), FLOG (Miller et al. 1994. *J. Comp. Aided Molec. Design* 8:153), and PRO_LIGAND (Clark et al. 1995. *J. Comp. Aided Molec. Design* 9:13), to name a few. Affinity differs from these methods in several aspects.

First, it uses full molecular mechanics in searching for and evaluating docked structures. In contrast descriptor-based methods use empirical rules which usually take into account only hydrogen bonding, hydrophobic interactions, and steric effects. This simplified description of ligand/receptor interaction is insufficient in some cases. For example, Meng et al. 1992. *J. Compt. Chem.* 13:505 studied three scoring methods in evaluating docked structures generated by DOCK. They found that only the forcefield scores from molecular mechanics correctly identify structures closest to experimental binding geometry, while scoring functions that consider only steric factors or only electrostatic factors are less successful. Note that in the study by Meng et al. 1992. *J. Comm. Chem.* 13:505, docking was still performed using descriptors. Affinity, on the other hand, uses molecular mechanics in both docking and scoring and is therefore more consistent.

Second, in Affinity, while the bulk of the receptor is fixed, the defined binding site is free to move, thereby allowing the receptor to adjust to the binding of different ligands or different binding modes of the same ligand. By contrast, almost all of the descriptor-based methods fix the entire receptor.

Third, the ligand itself is flexible in Affinity which permits different conformations of a ligand (i.e. transcription factor modulating compound) to be docked to a receptor (i.e. transcription factor). Recently Oshiro et al. (1995 *J. Comp. Aided Molec. Design* 9; 113) extended DOCK to handle flexible ligands. FLOG is also able to treat flexible ligand by including different conformations for each structure in the database (Miller et al. 1995. *J. Comp. Aided Molec. Design.* 8:153). Most other methods are limited to rigid ligands.

There are also a few energy based docking methods (Kuntz et al. 1994. *Acc. Chem Res.* 27:117). These methods use either molecular dynamics (notably simulated annealing) or Monte Carlo methods. For example, Caflisch et al. 1992. *Proteins: Struct. Funct. and Genetics* 13:223) developed a two step procedure for docking flexible ligands. In their procedure, ligand is first docked using a special energy function designed to remove bad contact between the ligand and the receptor efficiently. Then Monte Carlo minimization (Li & Scheraga. 1987. *Proc. Natl. Acad. Sci. U.S.A.* 84:6611) is carried out to refine the docked structures using molecular mechanics. Hart and Read. 1992. *Proteins: Struct. Funct. and Genetics* 13:206 also employ two steps to dock ligands. They use a score function based on receptor geometry to approximately dock ligands in the first step, and then use Monte Carlo minimization similar to that of Caflisch et al. 1992. *Proteins: Struct. Funct. and Genetics* 13:223 for the second step. The method by Mizutani et al. (1994. *J. Mol. Biol.* 243:310) is another variation of this two step method.

Affinity uses a Monte Carlo procedure in docking ligands, but there are important distinctions over the prior art methods. First, the Monte Carlo procedure in Affinity can be used in conjunction either with energy minimization (to mimic the Monte Carlo minimization method of Li & Scheraga. 1987. *Proc. Natl. Acad. Sci. U.S.A.* 84:6611) or with molecular dynamics (to mimic the hybrid Monte Carlo method, Clamp et al. 1994. *J. Comput. Chem.* 15:838, or the smart Monte Carlo method, Senderowitz et al. 1995. *J. Am. Chem. Soc.* 117:8211). This flexibility allows Affinity to be applied to a variety of docking problems. Second, in the initial screening of docked structures, Affinity employs energy differences obtained from molecular mechanics, while the methods discussed above use empirical rules or descriptors. Therefore, Affinity is more consistent in that it uses molecular mechanics in both initial screening and final refinement of docked structures. Third, Affinity allows the binding site of the receptor to relax, while the methods discussed above fix the entire receptor. Fourth, Affinity employs two new nonbond techniques which are both accurate and efficient to make docking practical. One is the Grid/MM method of Luty et al. which represents the bulk of the receptor by grids (Luty et al. 1995. *J. Comp. Chem.* 16:454). This method is 10-20 times faster than the no-cutoff method with almost no loss in accuracy. It also incorporates the solvation method of Stouten et al. (1993. *Molecular Simulation* 10:97). The other is the cell multipole method. This method is about 50% slower than the Grid/MM method, but it does not require grid setup. Thus, a typical docking calculation takes about 1-3 hours of CPU time on an Indigo R4400 workstation.

Once suitable chemical fragments have been selected, they can be assembled into a single compound or inhibiting compound. Assembly may be proceed by visual inspection of the relationship of the fragments to each other on a three-dimensional image display on a computer screen in relation to the structure coordinates of a particular transcription factor, e.g., MarA. This may be followed by manual model building using software such as Quanta or Sybyl.

Useful programs to aid one of skill in the art in connecting the individual chemical fragments include:

1. 3D Database systems such as MACCS-3D (MDL Information Systems, San Leandro, Calif. This area is reviewed in Martin, Y. C., 1992, "3D Database Searching in Drug Design", *J. Med. Chem.*, 35, pp. 2145-2154).
2. CAVEAT (Bartlett, P. A. et al, 1989, "CAVEAT: A Program to Facilitate the Structure-Derived Design of Biologically Active Molecules". In Molecular Recognition in Chemical and Biological Problems", Special Pub., Royal Chem.

Soc., 78, pp. 182-196). CAVEAT is available from the University of California, Berkeley, Calif. CAVEAT suggests inhibiting compounds to MarA based on desired bond vectors.

3. HOOK (available from Molecular Simulations, Burlington, Mass.). HOOK proposes docking sites by using multiple copies of functional groups in simultaneous searches.

In another embodiment, transcription factor modulating compounds may be designed as a whole or "de novo" using either an empty active site or optionally including some portion(s) of a known inhibiting compound(s). These methods include:

1. LUDI (Bohm, H.-J., "The Computer Program LUDI: A New Method for the De Novo Design of Enzyme Inhibiting compounds", J. ComR. Aid. Molec. Design, 6, pp. 61-78 (1992)). LUDI is available from Biosym Technologies, San Diego, Calif. LUDI is a program based on fragments rather than on descriptors. LUDI proposes somewhat larger fragments to match with the interaction sites of a macromolecule and scores its hits based on geometric criteria taken from the Cambridge Structural Database (CSD), the Protein Data Bank (PDB) and on criteria based on binding data. LUDI is a library based method for docking fragments onto a binding site. Fragments are aligned with 4 directional interaction sites (lipophilic-aliphatic, lipophilic-aromatic, hydrogen donor, and hydrogen acceptor) and scored for their degree of overlap. Fragments are then connected (i.e. a linker of the proper length is attached to each terminal atom in the fragments). Note that conformational flexibility can be accounted for only by including multiple conformations of a particular fragment in the library.

2. LEGEND (Nishibata, Y. and A. Itai, Tetrahedron, 47, p. 8985 (1991)). LEGEND is available from Molecular Simulations, Burlington, Mass.

3. CoMFA (Conformational Molecular Field Analysis) (J. J. Kaminski. 1994. Adv. Drug Delivery Reviews 14:331-337.) CoMFA defines 3-dimensional molecular shape descriptors to represent properties such as hydrophobic regions, sterics, and electrostatics. Compounds from a database are then overlaid on the 3D pharmacophore model and rated for their degree of overlap. Small molecule databased that be searched include: ACD (over 1,000,000 compounds), Maybridge (about 500,000 compounds), NCI (about 500,000 compounds), and CCSD. In measuring the goodness of the fit, molecules can either be fit to the 3D molecular shape descriptors or to the active conformation of a known inhibiting compound.

4. LeapFrog (available from Tripos Associates, St. Louis, Mo.).

FlexX (© 1993-2002 GMD German National Research Center for Information Technology; Rarey, M. et al *J. Mol. Biol.*, 261:407-489) is a fast, flexible docking method that uses an incremental construction algorithm to place ligands into and active site of the transcription factor. Ligands (e.g., transcription factor modulating compounds) that are capable of "fitting" into the active site are then scored according to any number of available scoring schemes to determine the quality of the complimentarity between the active site and ligand.

Other molecular modeling techniques may also be employed in accordance with this invention. See, e.g., Cohen, N. C. et al., "Molecular Modeling Software and Methods for Medicinal Chemistry, J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Candidate transcription factor modulating compounds can be evaluated for their modulating, e.g., inhibitory, activity using conventional techniques which may involve determining the location and binding proximity of a given moiety, the occupied space of a bound inhibiting compound, the deformation energy of binding of a given compound and electrostatic interaction energies. Examples of conventional techniques useful in the above evaluations include, but are not limited to, quantum mechanics, molecular dynamics, Monte Carlo sampling, systematic searches and distance geometry methods (Marshall, G. R., 1987, *Ann. Ref. Pharmacol. Toxicol.*, 27:193). Examples of computer programs for such uses include, but are not limited to, Gaussian 92, revision E2 (Gaussian, Inc. Pittsburgh, Pa.), AMBER version 4.0 (University of California, San Francisco), QUANTA/CHARMM (Molecular Simulations, Inc., Burlington, Mass.), and Insight II/Discover (Biosym Technologies Inc., San Diego, Calif.). These programs may be implemented, for example, using a Silicon Graphics Indigo2 workstation or IBM RISC/6000 workstation model 550. Other hardware systems and software packages will be known and of evident applicability to those skilled in the art.

Once a compound has been designed and selected by the above methods, the efficiency with which that compound may bind to a particular transcription factor may be tested and optimized by computational evaluation. An effective transcription factor modulating compound should demonstrate a relatively small difference in energy between its bound and free states (i.e., a small deformation energy of binding). Transcription factor modulating compounds may interact with the selected transcription factor in more than one conformation that is similar in overall binding energy. In those cases, the deformation energy of binding may be taken to be the difference between the energy of the free compound and the average energy of the conformations observed when the inhibiting compound binds to the enzyme.

A compound designed or selected as interacting with a selected transcription factor, e.g., a MarA family polypeptide, e.g., MarA, may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the modulating compound and the enzyme when the modulating compound is bound to the selected transcription factor, preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A. Kollman, University of California at San Francisco, ©1994]; QUANTA/CHARMM [Molecular Simulations, Inc., Burlington, Mass. ©1994]; and Insight II/Discover (Biosysm Technologies Inc., San Diego, Calif. ©1994). These programs may be implemented, for instance, using a Silicon Graphics workstation, IRIS 4D/35 or IBM RISC/6000 workstation model 550. Other hardware systems and software packages will be known to those skilled in the art.

Once a transcription factor modulating compound has been optimally selected or designed, as described above, substitutions may then be made in some of its atoms or side groups in order to improve or modify its binding properties. Initial substitutions are preferable conservative, i.e., the replacement group will have approximately the same size, shape, hydrophobicity and charge as the original group. Substitutions known in the art to alter conformation should be avoided. Such substituted chemical compounds may then be analyzed for efficiency of fit to the selected transcription factor by the same computer methods described above.

Computer programs can be used to identify unoccupied (aqueous) space between the van der Waals surface of a compound and the surface defined by residues in the binding site. These gaps in atom-atom contact represent volume that could be occupied by new functional groups on a modified version of the lead compound. More efficient use of the unoccupied space in the binding site could lead to a stronger binding compound if the overall energy of such a change is favorable. A region of the binding pocket which has unoccupied volume large enough to accommodate the volume of a group equal to or larger than a covalently bonded carbon atom can be identified as a promising position for functional group substitution. Functional group substitution at this region can constitute substituting something other than a carbon atom, such as oxygen. If the volume is large enough to accommodate a group larger than a carbon atom, a different functional group which would have a high likelihood of interacting with protein residues in this region may be chosen. Features which contribute to interaction with protein residues and identification of promising substitutions include hydrophobicity, size, rigidity and polarity. The combination of docking, $K_i$ estimation, and visual representation of sterically allowed room for improvement permits prediction of potent derivatives.

Similarity Screening

Once a transcription factor modulating compound has been selected or designed, computational methods to assess its overall likeness or similarity to other molecules can be used to search for additional compounds with similar biochemical behavior. In such a way, for instance, HTS derived hits can be tested to assure that they are bona fide ligands against a particular active site, and to eliminate the possibility that a particular hit is an artifact of the screening process. There are currently several methods and approaches to determine a particular compound's similarity to members of a virtual database of compounds. One example is the OPTISIM methodology that is distributed in the Tripos package, SYBYL (© 1991-2002 Tripos, Inc., St. Louis, Mo.). OPTISIM exploits the fact that each 3-dimensional representation of a molecule can be broken down into a set of 2-dimensional fragments and encoded into a pre-defined binary string. The result is that each compound within a particular set is represented by a unique numerical code or fingerprint that is amenable to mathematical manipulations such as sorting and comparison. OPTISIM is automated to calculate and report the percent difference in the fingerprints of the respective compounds for instance according to the using a formalism known as the Tanimoto coefficient. For instance, a compound that is similar in structure to another will share a high coefficient. Large virtual databases of commercially available compounds or of hypothetical compounds can be quickly screened to identify compounds with high Tanimoto coefficient.

CoMFA/QSAR

Once a series of similar transcription factor modulating compounds has been identified and expanded by the methods described, their experimentally determined biological activities can be correlated with their structural features using a number of available statistical packages. In a typical project within the industry, the CoMFA (COmparative Molecular Field Analysis) and QSAR (Quantitative Structure Activity Relationship) packages within the SYBYL suite of programs (Tripos Associates, St. Louis, Mo.) are utilized. In CoMFA, a particular series of compounds with measured activities are co-aligned in a manner that is believed to emulate their arrangement as they interact with the active site. A 3-dimensional lattice, or grid is then constructed to encompass the collection of the so-aligned compounds. At each point on the lattice, an evaluation of the potential energy is determined and tabulated-typically potentials that simulate the electronic and steric fields are determined, but other potential functions are available. Using the statistical methods such as PLS (Partial Least Squares), correlation between the measured activities and the potential energy values at the grid-points can be determined and summed in a linear equation to produce the overall molecular correlation or QSAR model. A particularly useful feature in CoMFA is that the individual contribution for each grid-point is known; the importance of the grid points upon the overall correlation can be visualized graphically in what is referred to as a CoMFA field. When this field is combined with the original compound alignment, it becomes a powerful tool to rationalize the activities of the individual compounds from whence the model was derived, and to predict how chemical modification of a reference compound would be effected. As an example, a QSAR model was developed for a set of 92 benzodiazepines using the method described above. A representative CoMFA field is shown in FIG. 4; the region delineated by wire mesh (adjacent to the referenced triazinoxazepine) is the region where chemical modification characterized by increasing steric bulk would lead to favorable effects in transcription factor modulation.

The invention pertains, per se, to not only the methods for identifying the transcription factor modulating compounds, but to the compounds identified by the methods of the invention as well as methods for using the identified compounds.

VIII. MarA Family Modulating Compounds, and Methods of Use Thereof

In an embodiment, the invention pertains to methods for modulating a transcription factor, e.g., an HTH protein, an AraC family polypeptide, or a MarA family polypeptide. The method includes contacting the transcription factor, e.g., a MarA family polypeptide, with a transcription factor modulutating compound of the formula (I):

$$A\text{-}E \qquad\qquad (I)$$

wherein A is a polar moiety, E is a hydrophobic moiety, and pharmaceutically acceptable salts thereof. The transcription factor modulating compound, e.g., a MarA family modulating compound, may comprise one or more polar moieties and/or one or more hydrophobic moieties.

In another embodiment, the invention pertains to methods for reducing antibiotic resistance of a microbial cell. The method includes contacting the cell with a transcription factor modulating compound, e.g., a MarA family modulating compound, such that the antibiotic resistance of the cell is reduced.

In another embodiment, the invention pertains to inhibiting transcription, comprising contacting a transcription factor with a transcription factor modulating compound, such that transcription is inhibited. In a further embodiment, the transcription of a prokaryotic cell is inhibited. In another further embodiment, the transcription factor modulating compound is a compound of anyone of formulae (I)-(XVII).

The term "antibiotic resistance" includes resistance of a microbial cell to a antibiotic compound, especially an antibiotic compound which had been previously used to treat similar microbial organisms successfully.

The term "polar moiety" includes moieties with at least one heterocycle. It also includes moieties such as, but not limited to, hydroxyl, halogens, thioethers, carboxylic acids, metals (e.g. alkali, alkaline, Au, Hg, Ag, Mn, Co, Cu, Zn, etc.), nitro, amino, alkoxy, and other moieties which allow the compound to perform its intended function. The term "polar moiety" includes moieties which allow the transcription factor modulating compound to perform its intended function, e.g., modulate a transcription factor, e.g., an AraC family polypeptide or a MarA family polypeptide. A heterocyclic polar moiety may comprise one or more rings, one or more of which may be aromatic. In an embodiment, one or more rings of the polar moiety are fused. The heterocyclic polar moiety may also be bicyclic.

The heterocyclic polar moiety may comprise one or more nitrogen, sulfur, or oxygen atoms. Examples of heterocycles include benzodioxazole, benzofuran, benzoimidazole, benzoxazole, benzothiazole, benzothiophene, chromenone, deazapurine, furan, imidazole, imidazopyridine, indole, indolizine, isooxazole, isothiaozole, isoquinoline, methylenedioxyphenyl, napthridine, oxazole, purine, pyrazine, pyrazole, pyridazine, pyridine, pyrimidine, pyrrole, pyrollidine, quinoline, tetrazole, thiazole, thiophene, triazole, and triazoletetrazole.

Furthermore, the polar moiety may be substituted when chemically feasible. For example, the polar moiety may be substituted with one or more substituents such as alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Examples of substituents also include nitro, alkoxy, aryl, amidyl, ester, thioester, alkyl (e.g., methyl, ethyl, propyl, butyl, pentyl, etc.), araalkyl (e.g., substituted or unsubstituted benzyl), hydroxy, halogen (e.g., fluorine, bromine, chlorine, iodine, etc.).

The term "hydrophobic moiety" includes moieties such as which allow the transcription factor modulating compound (e.g., an HTH protein modulating compound, an AraC family polypeptide modulating compound, a MarA family polypeptide modulating compound, etc.) to perform its intended function, e.g., modulate a transcription factor. Examples of hydrophobic moieties include, for example, hydrogen, alkyl, alkenyl, alkynyl, and aryl moieties. The hydrophobic moieties may be unsubstituted or substituted, if chemically feasible (e.g., not hydrogen). In an embodiment, the hydrophobic moiety is substituted or unsubstituted phenyl. Examples of substituents include alkyl, alkenyl, alkynyl, alkoxy, halogen, amino, thiol, hydroxy, nitro, aryl, and heteroaryl. The substituents can be substituted or unsubstituted. In an embodiment, the phenyl hydrophobic moiety is para-substituted, e.g., alkyl (methyl, ethyl, propyl, butyl, pentyl, etc.), halogen (e.g., fluorine, bromine, chlorine, iodine, etc.), hydroxy, substituted.

In another embodiment, the hydrophobic moiety is heterocyclic. Examples of heterocyclic hydrophobic moieties include imidazopyridine, quinolinyl, pyridinyl, etc.

In one embodiment, the transcription factor modulating compound (e.g., MarA family polypeptide modulating compound, AraC family polypeptide modulating compound, etc.) is of the formula (VII):

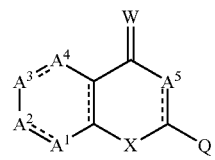

(VII)

wherein
W is NH, O or S;
X is O, S, or C, optionally linked to Q;
$A^1$ is C—$Z^1$, O, or S;
$A^2$ is C—$Z^2$, O, or S;
$A^3$ is C—$Z^3$, O, or S;
$A^4$ is C—$Z^4$, O, or S;
$A^5$ is C—$Z^5$, or N—$Z^5$;
$Z^1$, $Z^2$, $Z^3$, and $Z^4$ are each independently selected from the group consisting of hydrogen, alkoxy, hydroxy, halogen, and alkyl;
$Z^5$ is hydrogen, alkoxy, hydroxy, halogen, alkyl, or carbonyl;
Q is hydrogen, alkyl, alkenyl, alkynyl, halogen, hydroxy, aryl, and pharmaceutically acceptable salts thereof.

In yet another embodiment, the transcription factor modulating compound (e.g., the MarA family polypeptide modulating compound, AraC family polypeptide modulating compound, etc.) is of the formula (II):

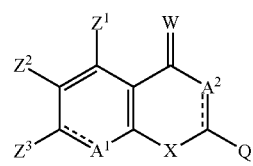

(II)

wherein
W is O or S;
X is O, S, or C, optionally linked to Q;
$A^1$ is C—$Z^4$, O, or S;
$A^2$ is C—$Z^5$, or N—$Z^5$;
$Z^1$, $Z^2$, $Z^3$, $Z^4$ and $Z^5$ are each independently hydrogen, alkoxy, hydroxy, halogen, alkyl, alkenyl, alkynyl, aryl, heterocyclic, amino, or cyano;
$Z^3$ is hydrogen, alkoxy, hydroxy, halogen, alkyl, alkenyl, alkynyl, aryl, heterocyclic, amino, nitro, cyano, carbonyl, or thiocarbonyl;
Q is an aromatic or heterocyclic moiety, and pharmaceutically acceptable salts thereof.

In a further embodiment, W may be oxygen and X may be oxygen. Furthermore, $A^1$ and $A^2$ may be C—$Z^4$ and C—$Z^5$, respectively. Examples of $Z^4$ and $Z^5$ include hydrogen and hydroxy. Examples of $Z^1$ and $Z^2$ include hydrogen and hydroxy. Other examples of $Z^2$ also include halogen, e.g., fluorine, chlorine, bromine, and iodine. Examples of $Z^3$ include, for example, hydrogen, alkoxy and hydroxy. Examples of Q include substituted and unsubstituted phenyl. The phenyl may be para-substituted. Examples of substituents include hydroxyl, halogen (e.g., fluorine, bromine, chlorine, iodine, etc.), amino, alkyl (e.g., methyl, ethyl, propyl, butyl, pentyl, etc.), nitro, cyano, etc. In an embodiment, the transcription factor modulating compound is a MarA modulating compound, and in a further embodiment, a MarA inhibiting compound.

In another embodiment, the transcription factor modulating compound (e.g., an AraC family polypeptide modulating compound, a MarA family polypeptide modulating compound, etc.) is of the formula (VIII):

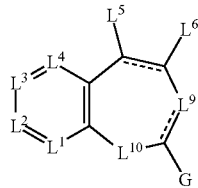
(VIII)

wherein:

G is a substituted or unsubstituted aromatic moiety, heterocyclic, alkyl, alkenyl, alkynyl, hydroxy, cyano, nitro, amino, carbonyl, or hydrogen;

$L^1$, $L^2$, $L^3$, $L^4$, $L^9$ and $L^{10}$ are each independently oxygen, sulfur, substituted or unsubstituted nitrogen, and substituted or unsubstituted carbon; and $L^5$ and $L^6$ are each independently hydrogen, substituted or unsubstituted alkyl, alkenyl, alkynyl, acyl, heterocyclic, amino, nitro, hydroxy, cyano, alkoxy, or aryl, and $L^5$ and $L^6$ may optionally be linked with a chain of one to six atoms to form a fused ring, and pharmaceutically acceptable salts thereof.

In another embodiment, the transcription factor modulating compound (e.g., an AraC family polypeptide modulating compound, a MarA family polypeptide modulating compound, etc.) is of the formula (IX):

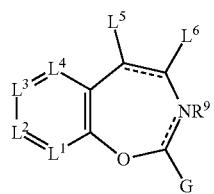
(IX)

wherein:

G is substituted or unsubstituted aromatic moiety, heterocyclic, alkyl, alkenyl, alkynyl, hydroxy, cyano, nitro, amino, carbonyl, or hydrogen;

$L^1$, $L^2$, $L^3$, and $L^4$ are each independently oxygen, sulfur, substituted or unsubstituted nitrogen, and substituted or unsubstituted carbon; and $R^9$, $L^5$ and $L^6$ are each independently hydrogen, substituted or unsubstituted alkyl, alkenyl, alkynyl, acyl, heterocyclic, amino, nitro, hydroxy, cyano, alkoxy, or aryl, and $L_5$ and $L_6$ may optionally be linked with a chain of one to six atoms to form a fused ring, and pharmaceutically acceptable salts thereof.

In another embodiment, the transcription factor modulating compound (e.g., an AraC family polypeptide modulating compound, a MarA family polypeptide modulating compound, etc.) is of the formula (III):

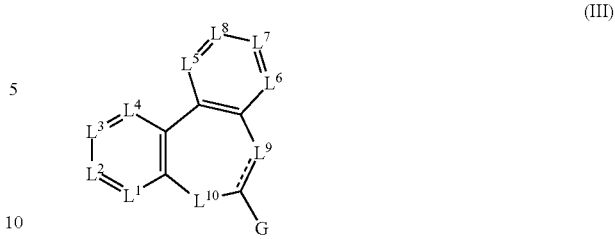
(III)

wherein

G is substituted or unsubstituted aromatic moiety, heterocyclic, alkyl, alkenyl, alkynyl, hydroxy, cyano, nitro, amino, carbonyl, or hydrogen; and $L^1$, $L^2$, $L^3$, $L^4$, $L^5$, $L^6$, $L^7$, $L^8$, $L^9$, and $L^{10}$ are each independently oxygen, substituted or unsubstituted nitrogen, sulfur and or substituted or unsubstituted carbon, and pharmaceutically acceptable salts thereof.

In a further embodiment, $L^9$ is N—$R^9$, wherein $R^9$ is hydrogen, substituted or unsubstituted alkyl, alkenyl, alkynyl, acyl, or aryl. In another, $L^{10}$ is oxygen. In an embodiment, $R^9$ is hydrogen. In another, G is substituted or unsubstituted phenyl or heteroaryl. In a further embodiment, G is cycloalkenyl, e.g., cyclohexenyl. In one embodiment, $L^1$, $L^2$, $L^3$, and $L^4$ are each substituted or unsubstituted carbon and $L^5$, $L^6$, and $L^8$ are each nitrogen. $L^7$ may be substituted carbon, e.g., substituted with a thioether moiety. In another embodiment, $L^9$ and $L^{10}$ are each nitrogen. In another embodiment, the invention pertains to compounds of formula (III), wherein $L^9$ is nitrogen, $L^{10}$ is oxygen, $L^1$-$L^8$ are each C—H, the dotted line represents a double bond and where G is not hydrogen or methyl.

In another embodiment, the transcription factor modulating compound (e.g., an AraC family polypeptide modulating compound, a MarA family polypeptide modulating compound, etc.) is of the formula (X):

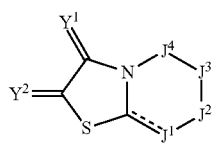
(X)

wherein $Y^1$ and $Y^2$ are each oxygen, sulfur, or substituted or unsubstituted carbon;

$J^1$, $J^2$, $J^3$, and $J^4$ are each oxygen, nitrogen, or optionally substituted carbon, and pharmaceutically acceptable salts thereof.

In another embodiment, the transcription factor modulating compound (e.g., an AraC family polypeptide modulating compound, a MarA family polypeptide modulating compound, etc.) is of the formula (IV):

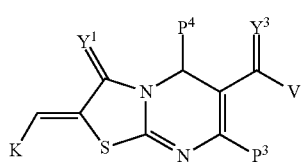
(IV)

wherein $Y^1$ and $Y^2$ are each oxygen or sulfur;

J is hydrogen, substituted or unsubstituted alkyl, alkenyl, alkynyl, cyano, nitro, amino, or halogen;

V is substituted or unsubstituted alkyl, alkenyl, alkynyl, alkoxy, alkylamino, or alkylthio;

P and K are each independently substituted or unsubstituted aryl, and pharmaceutically acceptable salts thereof.

In a further embodiment, $Y^1$ and $Y^3$ are each oxygen, V is alkoxy and J is lower alkyl. In another embodiment, P is substituted or unsubstituted phenyl. K may be substituted or unsubstituted heteroaryl.

In another embodiment, the transcription factor modulating compound (e.g., an AraC family polypeptide modulating compound, a MarA family polypeptide modulating compound, etc.) is of the formula (V):

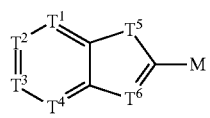

(V)

wherein $T^1$, $T^2$, $T^3$, $T^4$, $T^5$, and $T^6$ are each independently substituted or unsubstituted carbon, oxygen, substituted or unsubstituted nitrogen, or sulfur;

M is hydrogen, alkyl, alkenyl, alkynyl, heterocyclic or aryl, or pharmaceutically acceptable salts thereof.

In a further embodiment, $T^5$ is N—W or C—W, wherein W is alkyl, alkenyl, alkynyl, aryl, heterocyclic, acyl, hydroxy, alkoxy, alkthio, amino, nitro, halogen, or hydrogen. In another further embodiment, $T^6$ is N.

In a further embodiment, M is substituted or unsubstituted aryl. W may be substituted or unsubstituted alkyl. In another embodiment, $T^1$, $T^2$, $T^3$ and $T^4$ are each substituted or unsubstituted carbon. In a further embodiment, at least one of $T^1$, $T^2$, $T^3$, and $T^4$ is nitrogen, and the remaining T moieties are substituted or unsubstituted carbon.

In another embodiment, the transcription factor modulating compound (e.g., an AraC family polypeptide modulating compound, a MarA family polypeptide modulating compound, etc.) is of the formula (Va):

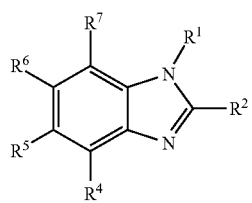

(Va)

wherein $R^1$ is OH, $OCOCO_2H$, or a substituted or unsubstituted straight or branched $C_1$-$C_5$ alkyloxy group;

$R^2$ is H, $CO_2$($C_1$-$C_5$ substituted or unsubstituted, straight or branched alkyl), or a substituted or unsubstituted aryl group; and $R^4$, $R^5$, $R^6$, and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), $O$($C_1$-$C_5$ substituted or unsubstituted, straight or branched alkyl), $C(NOH)$($C_1$-$C_5$ substituted or unsubstituted, straight or branched alkyl), substituted or unsubstituted amino, $CO_2H$, CN, $NO_2$, $CONH_2$, (CO)(NHOH), and halogen.

In certain embodiments of formula Va, those compounds disclosed in U.S. Ser. No. 10/139,591, filed May 6, 2002, are excluded from the scope of the present invention.

In other embodiments of formula Va, when $R^6$ is $NO_2$ and $R^2$ is unsubstituted phenyl, then $R^1$ is not $O(CHCH_3)(CO_2)CH_2CH_3$ or $OCH_2CO_2H$. Also, in another embodiment, when $R^6$ is H or $NO_2$, then $R^1$ is not a phenyl-substituted alkyloxy group. In yet another embodiment, when $R^4$, $R^5$, $R^6$, and $R^7$ are all H and $R^2$ is para-methoxyphenyl, then $R^1$ is not OH. And in another embodiment, when $R^4$, $R^5$, $R^6$, and $R^7$ are all H and $R^2$ is unsubstituted phenyl, then $R^1$ is not $OCH_2CO_2CH_2CH_3$;

In certain aspects of formula Va, $R^4$, $R^5$, and $R^7$ are all H.

Similarly, $R^1$ of formula Va may be selected from the group consisting of OH, $O(CR'R'')_{1-3}H$, $O(CR'R'')_{1-3}OH$, $O(CR'R'')_{1-3}CO_2H$, $O(CR'R'')_{1-3}CO_2(CR'R'')_{1-3}H$, $O(CR'R'')_{1-3}(CO)NH_2$, $O(CR'R'')_{1-3}(CNH)NH_2$, $OCOCO_2H$, $O(CR'R'')_{1-3}SO_3H$, $O(CR'R'')_{1-3}OSO_3H$, $O(CR'R'')_{1-3}PO_3H$, $O(CR'R'')_{1-3}OPO_3H$, $O(CR'R'')_{1-3}N[(CR'R'')_{0-3}H]_2$, $O(CR'R'')_{1-3}(CO)(NHOH)$, and $O(CR'R'')_{1-3}$(heteroaryl); wherein R' and R'' are each independently H, a $C_1$-$C_3$ alkyl, $C_2$-$C_3$ alkenyl, or $C_2$-$C_3$ alkynyl group. Each R' and R'' is preferably H or $CH_3$.

When $R^1$ of formula Va is $O(CR'R'')_{1-3}$(heteroaryl), the heteroaryl group may be a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

Similarly, when $R^2$ of formula Va may be a substituted or unsubstituted phenyl, pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In a more particular embodiment, $R^6$ of formula Va is H, $(CR'R'')_{1-3}H$, $(CR'R'')_{1-3}OH$, $(CR'R'')_{1-3}NH_2$, (NOH)$(CR'R'')_{1-3}H$, $CO(CR'R'')_{0-3}NH_2$, $CO(CR'R'')_{1-3}H$, $CO(CR'R'')_{1-3}OH$, $CO(CR'R'')_{0-3}CF_3$, $(CR'R'')_{0-3}N[(CR'R'')_{0-3}H]_2$, CO(substituted or unsubstituted heteroaryl), $CO$($C_3$-$C_6$ substituted or unsubstituted cycloalkyl), $O(CR'R'')_{1-3}H$, CO(substituted or unsubstituted phenyl), $CO_2(CR'R'')_{0-3}H$, CN, $NO_2$, F, Cl, Br, or I, wherein R' and R'' are each independently H, a $C_1$-$C_3$ alkyl, $C_2$-$C_3$ alkenyl, or $C_2$-$C_3$ alkynyl group. Preferably each R' and R'' is independently H or $CH_3$.

In yet another embodiment, $R^6$ of formula Va is CO(substituted or unsubstituted heteroaryl), wherein said heteroaryl group is a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In another embodiment, $R^4$, $R^5$, and $R^7$ are each hydrogen; $R^6$ is $NO_2$, and $R^1$ is hydroxyl. In a further embodiment, $R^2$ is substituted aryl, e.g., substituted phenyl, substituted furanyl, or substituted benzoimidazole. In a further embodiment, when $R^2$ is substituted phenyl, $R^2$ is substituted with an optionally substituted arylcarbonylamino group, an amino group, a dialkyl amino group, or a carboxylate group. The aryl carbonylamino group may be substituted with dialkyl amino, alkyl, or halogens. In a further embodiment, when $R^2$ is a substituted furanyl group, $R^2$ is substituted with an aryl group, e.g., phenyl. In another embodiment, when R² is an optionally substituted benzoimidazole, it is substituted with an alkyl group.

In another embodiment, the transcription factor modulating compound is of the formula (XI):

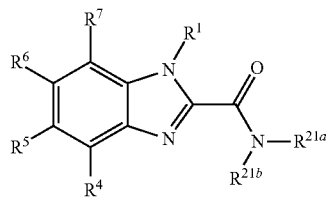

(XI)

wherein

R¹ is OH, OCOCO₂H, a substituted or unsubstituted straight or branched $C_1$-$C_5$ alkyloxy group, or a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), CO₂($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, CO₂H, CN, NO₂, CONH₂, (CO)(N-HOH), and halogen; and R²¹ᵃ and R²¹ᵇ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof.

In one embodiment, R¹ may be OH. In another embodiment, R⁴, R⁵, R⁷ and R²⁶ can be H. In yet another embodiment, R⁶ may be NO₂. In yet another embodiment, R²⁵ can be a substituted alkenyl group, wherein said substituted alkenyl group is substituted with substituted or unsubstituted phenyl. Suitable substituted phenyl groups include, for example, para-halogenated phenyl groups, such as para-fluoro phenyl.

In another embodiment, the invention provides transcription factor modulating compounds of the formula (XII):

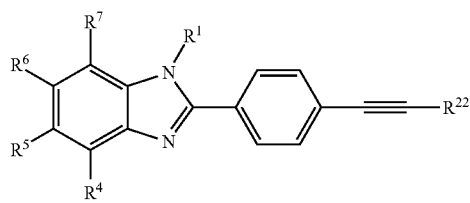

(XII)

wherein

R¹ is OH, OCOCO₂H, a substituted or unsubstituted straight or branched $C_1$-$C_5$ alkyloxy group, or a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), CO₂($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, CO₂H, CN, NO₂, CONH₂, (CO)(N-HOH), and halogen; and R²² is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof.

In one embodiment, R¹ may be OH. In another embodiment, R⁴, R⁵, R⁷ and R²⁶ can be H. In yet another embodiment, R⁶ may be NO₂. In yet another embodiment, R²⁵ can be a substituted alkenyl group, wherein said substituted alkenyl group is substituted with substituted or unsubstituted phenyl. Suitable substituted phenyl groups include, for example, para-halogenated phenyl groups, such as para-fluoro phenyl.

In another embodiment, the invention provides transcription factor modulating compounds of the formula (XIII):

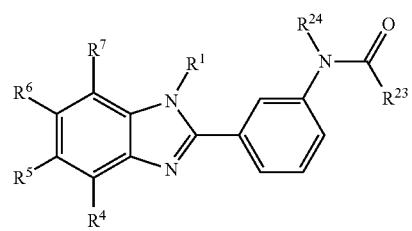

(XIII)

wherein

R¹ is OH, OCOCO₂H, a substituted or unsubstituted straight or branched $C_1$-$C_5$ alkyloxy group, a substituted or unsubstituted straight or branched $C_1$-$C_5$ alkyl group;

R⁴, R⁵, R⁶, and R⁷ are independently selected from the group consisting of H, ($C_1$-$C_5$ substituted or unsubstituted, straight or branched alkyl), CO₂($C_1$-$C_5$ substituted or unsubstituted, straight or branched alkyl), CO($C_1$-$C_5$ substituted or unsubstituted, straight or branched alkyl), CO(substituted or unsubstituted aryl or heteroaryl), CO($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, CO₂H, CN, NO₂, CONH₂, (CO)(N-HOH), and halogen; and R²³ and R²⁴ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof;

provided that when R¹ is OH, R⁴, R⁵, and R⁷ are H, and R⁶ is NO₂, then R²³ is not methyl, unsubstituted phenyl, or unsubstituted furanyl.

In one embodiment, R¹ may be OH. In another embodiment, R⁴, R⁵, R⁷ and R²⁶ can be H. In yet another embodiment, R⁶ may be NO₂. In yet another embodiment, R²⁵ can be a substituted alkenyl group, wherein said substituted alkenyl group is substituted with substituted or unsubstituted phenyl.

Suitable substituted phenyl groups include, for example, para-halogenated phenyl groups, such as para-fluoro phenyl.

In another embodiment, the invention provides a method for reducing antibiotic resistance of a microbial cell, comprising contacting said cell with a transcription factor modulating compound of the formula (XIV):

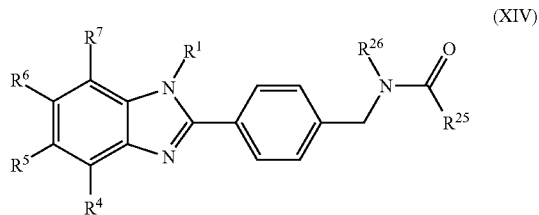

(XIV)

wherein
$R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$, and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(NHOH), and halogen; and $R^{25}$ and $R^{26}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof;
provided that when $R^1$ is OH, $R^4$, $R^5$, and $R^7$ are H, and $R^6$ is $NO_2$, then $R^{25}$ is not unsubstituted phenyl or O-tert-butyl.

In one embodiment, $R^1$ may be OH. In another embodiment, $R^4$, $R^5$, $R^7$ and $R^{26}$ can be H. In yet another embodiment, $R^6$ may be $NO_2$. In yet another embodiment, $R^{25}$ can be a substituted alkenyl group, wherein said substituted alkenyl group is substituted with substituted or unsubstituted phenyl. Suitable substituted phenyl groups include, for example, para-halogenated phenyl groups, such as para-fluoro phenyl.

In another embodiment, the invention provides a transcription factor modulating compound of the formula (XV):

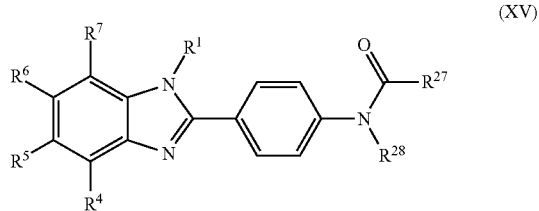

(XV)

wherein
$R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(NHOH), and halogen;

$R^{27}$ is selected from the group consisting of substituted heteroaryl; substituted alkyl; substituted or unsubstituted alkenyl; alkynyl; alkylcarbonyl, arylcarbonyl; heteroarylcarbonyl; sulfonyl; alkylamino; arylamino; heteroarylamino; alkoxy, aryloxy, heteroaryloxy; substituted straight chain $C_1$-$C_5$ alkyl or alkenyl; substituted or unsubstituted isoxazole, thiazolidine, imidazole, quinoline, pyrrole, triazole, or pyrazine; 2-fluorophenyl, 2-methylphenyl, 2-cyanophenyl, 1-methylphenyl, and 1-fluorophenyl; and $R^{28}$ is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, aroyl and pharmaceutically acceptable salts, esters and prodrugs thereof.

In one embodiment, $R^1$ may be OH. In another embodiment, $R^4$, $R^5$, $R^7$ and $R^{28}$ may each be H. In a further embodiment, $R^6$ can be $NO_2$.

In one embodiment, $R^{27}$ may be substituted alkyl which can be substituted with, for example, substituted or unsubstituted phenyl. In another embodiment, said substituted phenyl may be substituted with alkoxy, such as para-alkoxy phenyl. In a particular embodiment, the para-alkoxy phenyl can be para-methoxy phenyl.

In another embodiment, $R^{27}$ may be a meta-substituted phenyl, wherein said meta-substituted phenyl can be alkyl substituted. In a particular embodiment, the meta-substituted phenyl can be meta-methyl phenyl. In another particular embodiment, meta-substituted phenyl may be meta-cyano phenyl. In a further embodiment, the meta-substituted phenyl can be substituted with a halogen. Furthermore, the meta-substituted phenyl may be, for example, meta-fluoro phenyl.

In yet another embodiment, $R^{27}$ can be a heteroaryl group. Suitable heteroaryl groups include, for example, methyl-pyrrolyl and furanyl.

In another embodiment, the invention provides a transcription factor modulating compound of the formula (XVI):

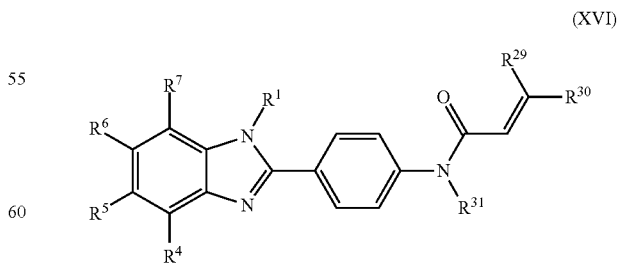

(XVI)

wherein
$R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(NHOH), and halogen;

$R^{29}$, $R^{30}$ and $R^{31}$ are independently selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, arylamino, heteroarylamino, and aroyl, and pharmaceutically acceptable salts, esters and prodrugs thereof.

In one embodiment, $R^1$ may be OH. In another embodiment, $R^4$, $R^5$, $R^7$ and $R^{31}$ may each be H. In a further embodiment, $R^6$ may be $NO_2$.

In another embodiment, $R^{30}$ can be H. In a further embodiment, $R^{29}$ may be substituted or unsubstituted phenyl, wherein said substituted phenyl can be substituted with alkoxy. In a particular embodiment, said substituted phenyl can be, for example, ortho-alkoxy substituted phenyl. Furthermore, said substituted phenyl can be ortho-methoxy phenyl.

In yet another embodiment, $R^{29}$ may be H. In a further embodiment, $R^{30}$ may be substituted alkenyl, wherein said substituted alkenyl can be substituted with a substituted or unsubstituted phenyl. Furthermore, the substituted phenyl can be para-alkyl phenyl, para-alkoxy phenyl, ortho-alkoxy phenyl or a halogenated phenyl. In addition, the substituted phenyl group can be, for example, para-methyl phenyl, para-methoxy phenyl, ortho-methoxy phenyl, para-cyano phenyl, para-trifluoromethyl phenyl, para-fluoro phenyl, ortho, para-difluoro phenyl or meta, para-difluoro phenyl.

In yet a further embodiment, $R^{30}$ can be a heteroaryl group, wherein said heteroaryl group can be furanyl.

The invention also includes a transcription factor modulating compound of the formula (XVII):

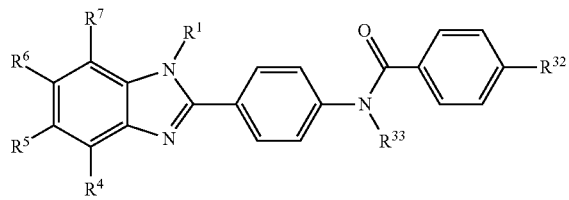

(XVII)

wherein $R^1$ is OH, $OCOCO_2H$, a substituted or unsubstituted straight or branched $C_1$-$C_5$ alkyloxy group, or a substituted or unsubstituted straight or branched $C_1$-$C_5$ alkyl group;

$R^4$, $R^5$, $R^6$ and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(NHOH), and halogen;

$R^{32}$ is selected from the group consisting of OH, Br, CN, $CO_2H$, morpholinyl, substituted aryl, substituted or unsubstituted alkenyl, alkynyl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, dialkylamino, arylamino, heteroarylamino, aroyl;

$R^{33}$ is selected from the group consisting of H, substituted or unsubstituted alkyl, alkenyl, alkynyl, aryl, heteroaryl, alkoxy, aryloxy, heteroaryloxy, alkylsulfonyl, arylsulfonyl, aminosulfonyl, alkylcarbonyl, arylcarbonyl, heteroarylcarbonyl, acyl, acylamino, alkylamino, dialkylamino, arylamino, heteroarylamino, aroyl and pharmaceutically acceptable salts, esters and prodrugs thereof;

provided that when $R^1$ is OH, $R^4$, $R^5$, $R^7$ and $R^{33}$ are H, $R^6$ is $NO_2$, then $R^{32}$ is not dimethylamino;

provided that when $R^1$ is OH, $R^4$, $R^5$, $R^7$ and $R^{33}$ are H, $R^6$ is Br, then $R^{32}$ is not dimethylamino.

In one embodiment, $R^1$ may be OH. In another embodiment, $R^4$, $R^7$ and $R^{33}$ may each be H. In a further embodiment, $R^5$ can be H. In yet another embodiment, $R^6$ can be $NO_2$. In another embodiment, $R^{32}$ can be a carbonyl group, such as an aldehyde or an acylcarbonyl. In a further embodiment, $R^{32}$ may be CN. In a further embodiment, $R^{32}$ can be a heteroaryl group, wherein said heteroaryl group may be oxazolyl or triazolyl. In another embodiment, $R^6$ may be CN or dialkylamino and $R^{32}$ may be dialkylamino. In a further embodiment, $R^6$ can be H, $R^5$ can be CN and $R^{32}$ can be dialkylamino.

In a further embodiment, the transcription factor modulating compound is of the formula (Va):

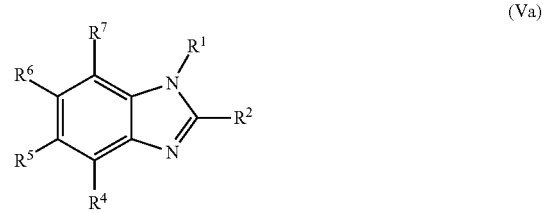

(Va)

wherein $R^1$ is OH, or a substituted or unsubstituted straight or branched alkyloxy group;

$R^2$ is a substituted or unsubstituted aryl or heteroaryl group;

$R^4$, $R^5$, and $R^7$ are independently selected from the group consisting of H, ($C_1$-$C_5$ substituted or unsubstituted, straight or branched alkyl), $CO_2$($C_1$-$C_5$ substituted or unsubstituted, straight or branched alkyl), $CO$($C_1$-$C_5$ substituted or unsubstituted, straight or branched alkyl), CO(substituted or unsubstituted aryl or heteroaryl), $CO$($C_3$-$C_6$ substituted or unsubstituted cycloalkyl), O($C_1$-$C_5$ substituted or unsubstituted, straight or branched alkyl), C(NOH)($C_1$-$C_5$ substituted or unsubstituted, straight or branched alkyl), substituted or unsubstituted amino, $CO_2H$, CN, $NO_2$, $CONH_2$, (CO)(NHOH), and halogen; and $R^6$ is an electron withdrawing substitutent;

provided that when $R^6$ is $NO_2$ and $R^2$ is unsubstituted phenyl, then $R^1$ is not $O(CHCH_3)(CO_2)CH_2CH_3$ or $OCH_2CO_2H$;

provided that when $R^6$ is H or $NO_2$, then $R^1$ is not a phenyl-substituted alkyloxy group, and pharmaceutically acceptable salts, esters, and prodrugs thereof.

In another embodiment, $R^6$ is an electron withdrawing substituent. Examples of electron withdrawing substituted include halogens (e.g., F, Cl, Br, etc.), halogenated alkyls (e.g., $CF_3$, $CF_2CF_3$, etc.), $NO_2$, C(NOH)(CR'R"), wherein each R' and R" are each independently H or lower alkyl (e.g., $CH_3$, ethyl, propyl, butyl, etc.).

In a further embodiment, $R^4$, $R^5$, and $R^7$ are each H.

Examples of $R^1$ include OH, substituted or unsubstituted alkoxy (e.g., $OCH_3$, $OCH_2CN$).

In another embodiment, $R^2$ is substituted or unsubstituted aryl. Examples include phenyl, furanyl, or benzimidazolyl. In a further embodiment, wherein $R^2$ substituted phenyl which is substituted by arylcarbonylamino, heteroarylcarbonylamino, alkylcarbonyl, alkyloxy, amino or dialkylamino. In a further embodiment, $R^2$ is para-arylcarbonylamino phenyl, ortho-heteroarylcarbonylamino phenyl, para-alkylcarbonylamino phenyl, para- and ortho-alkyloxy phenyl, para-amino phenyl, meta-amino phenyl, para-dialkylamino phenyl, or meta-dialkylamino phenyl.

In a further embodiment, $R^2$ is substituted furanyl (e.g., substituted aryl 2-furanyl, alkyl 2-furanyl). In a further embodiment, $R^2$ is a substituted benzimidazolyl, e.g., 1-benzimidazolyl substituted by $CH_2CO_2H$.

In a further embodiment, the transcription factor modulating compound is:

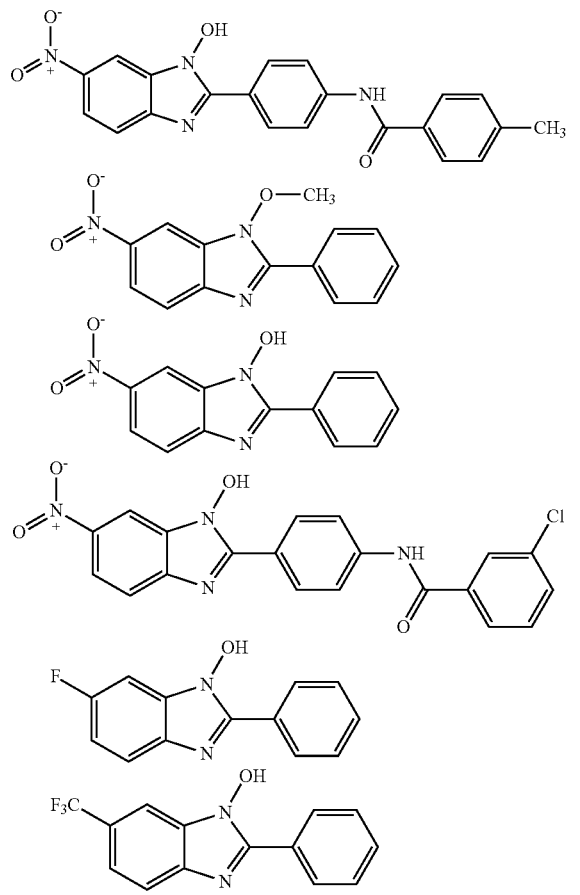

-continued

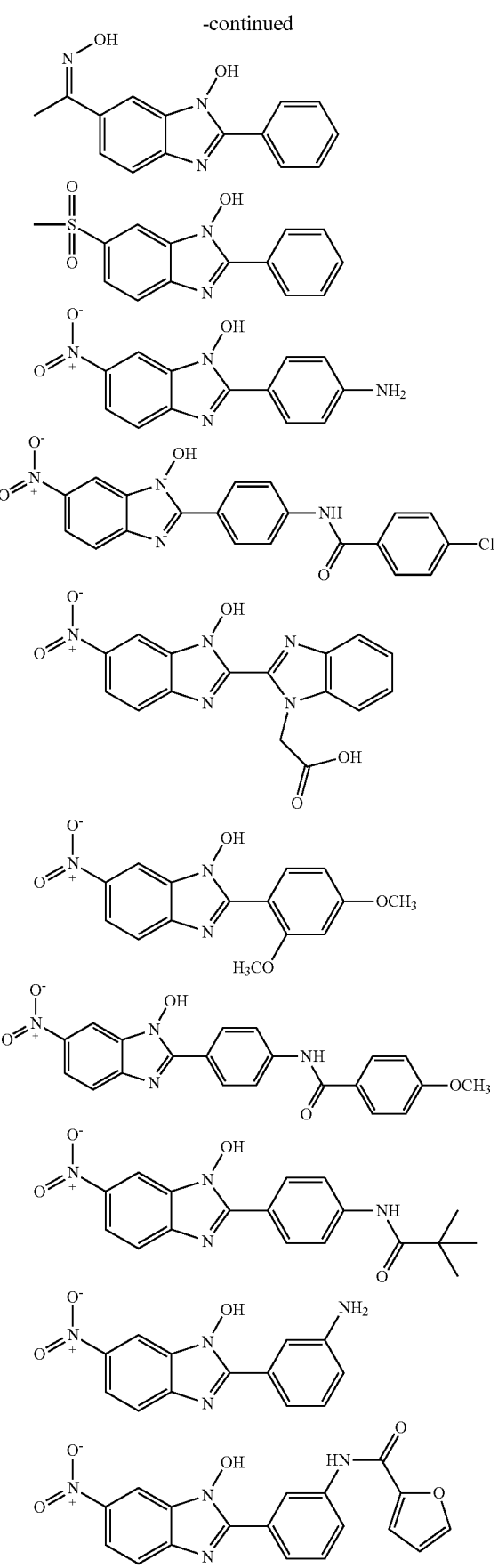

73
-continued
74
-continued
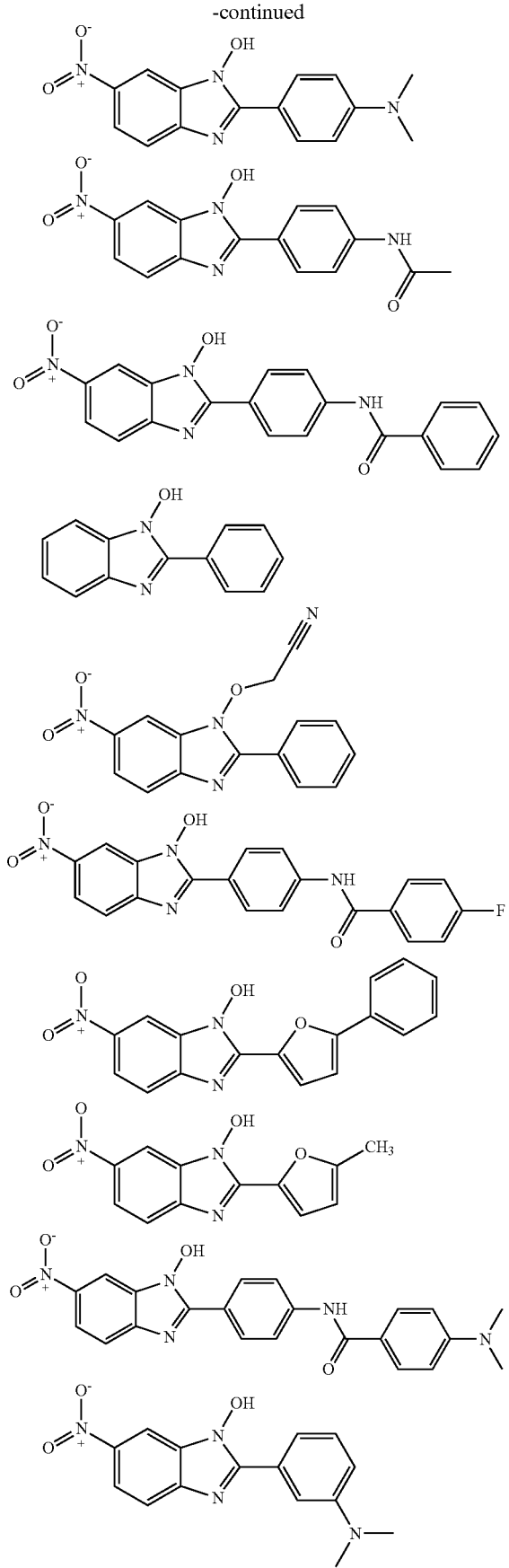
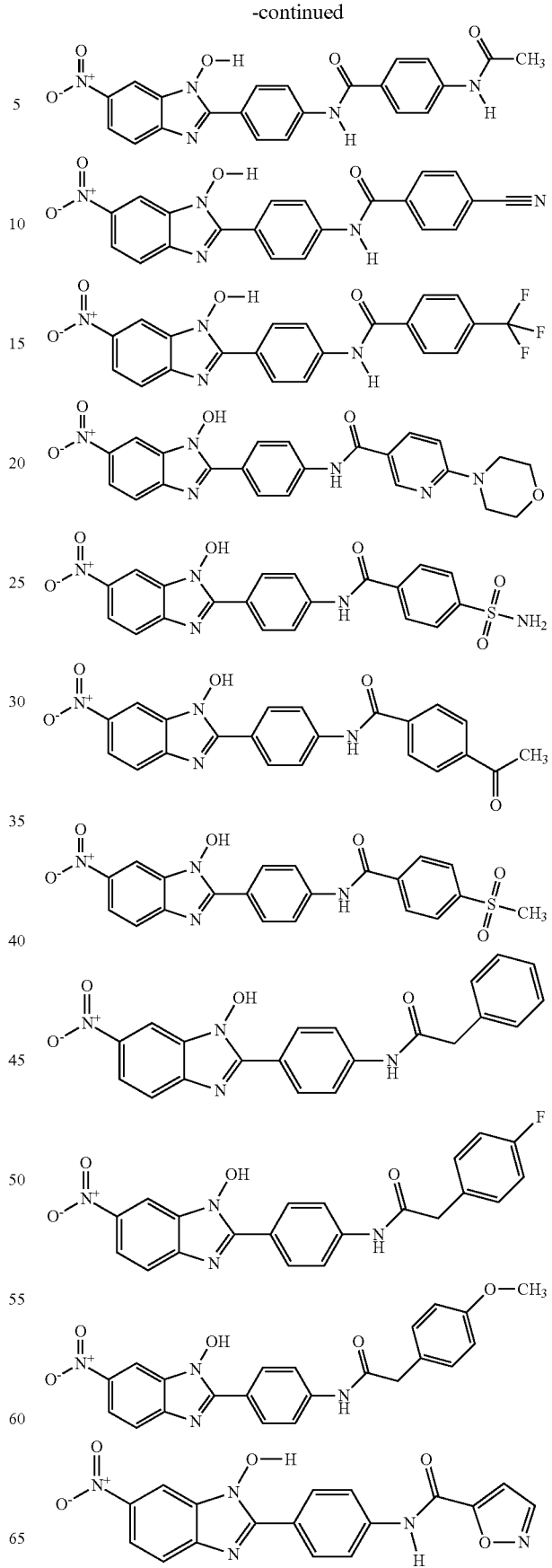

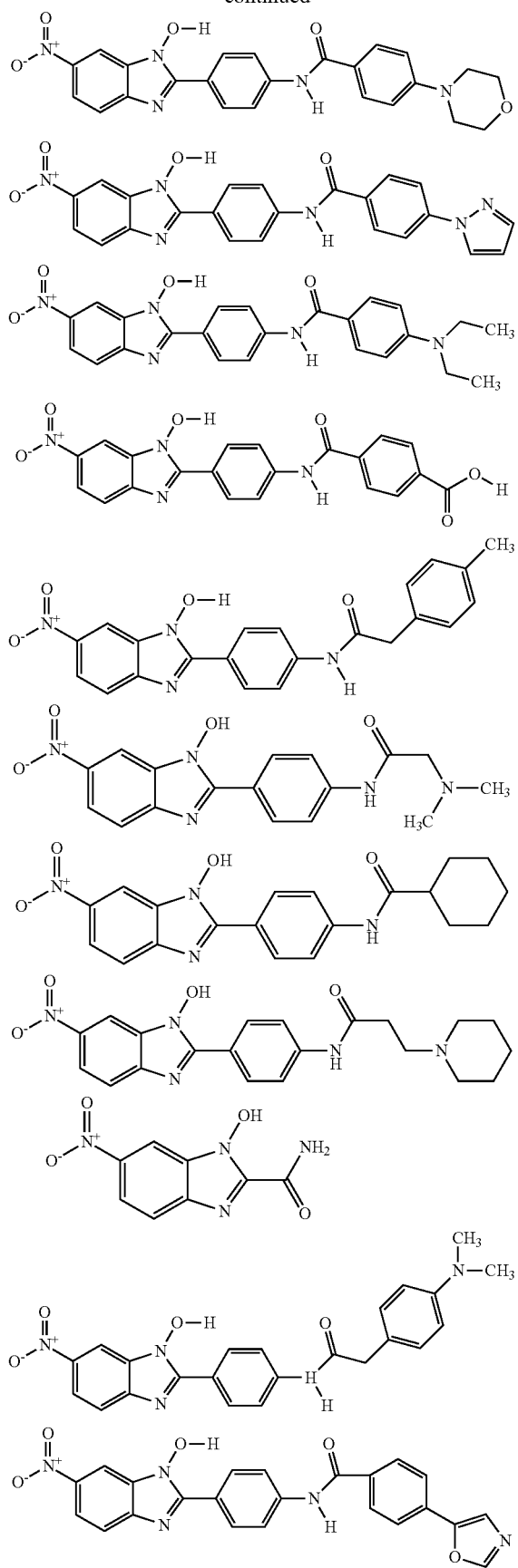
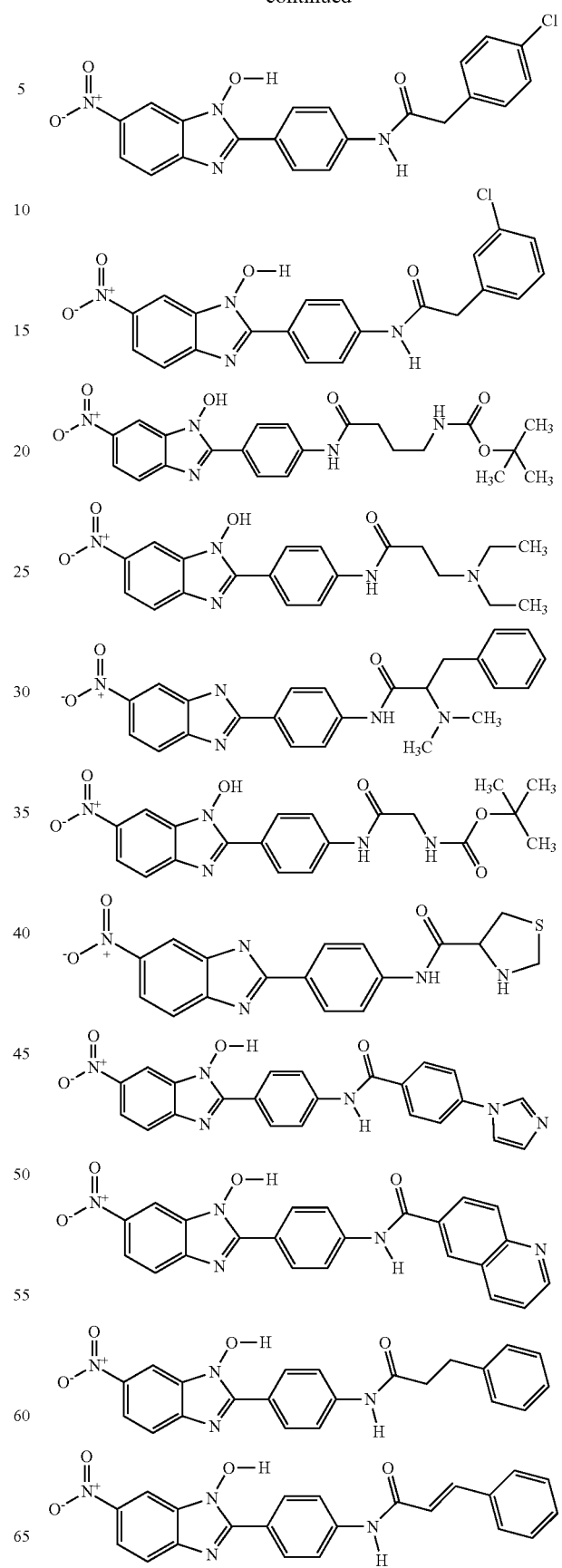

77
-continued
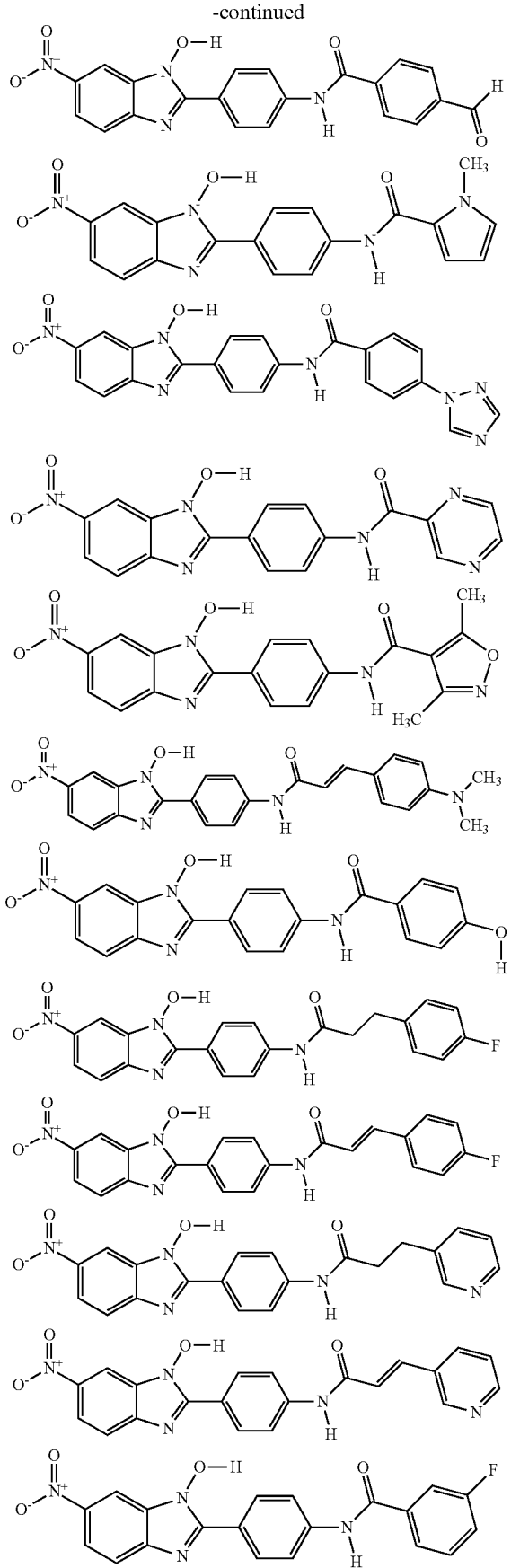
78
-continued
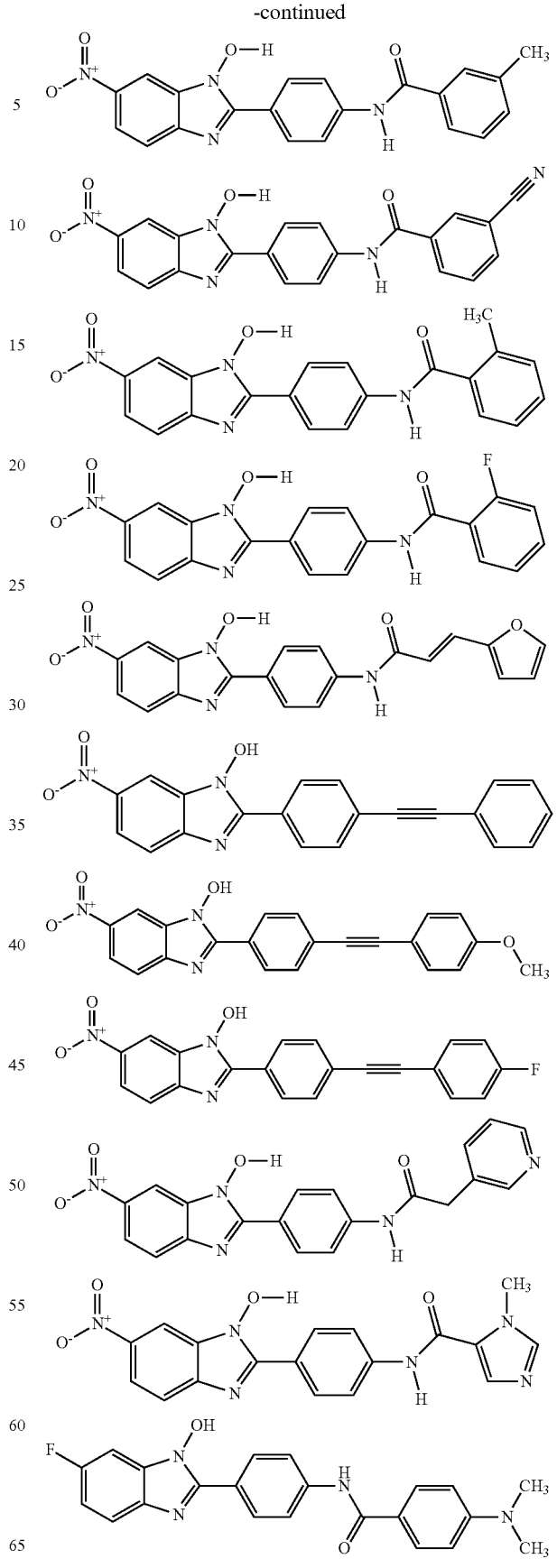

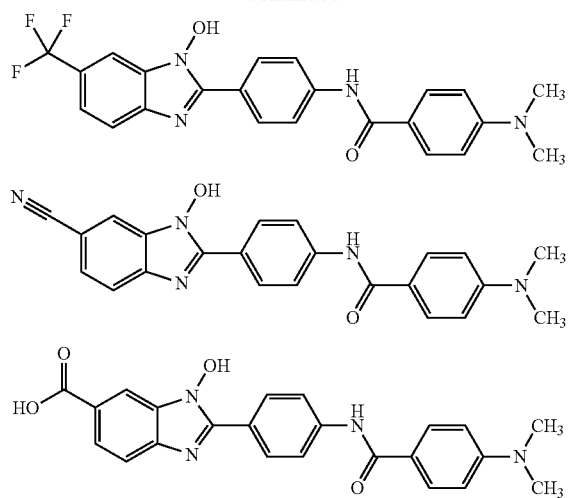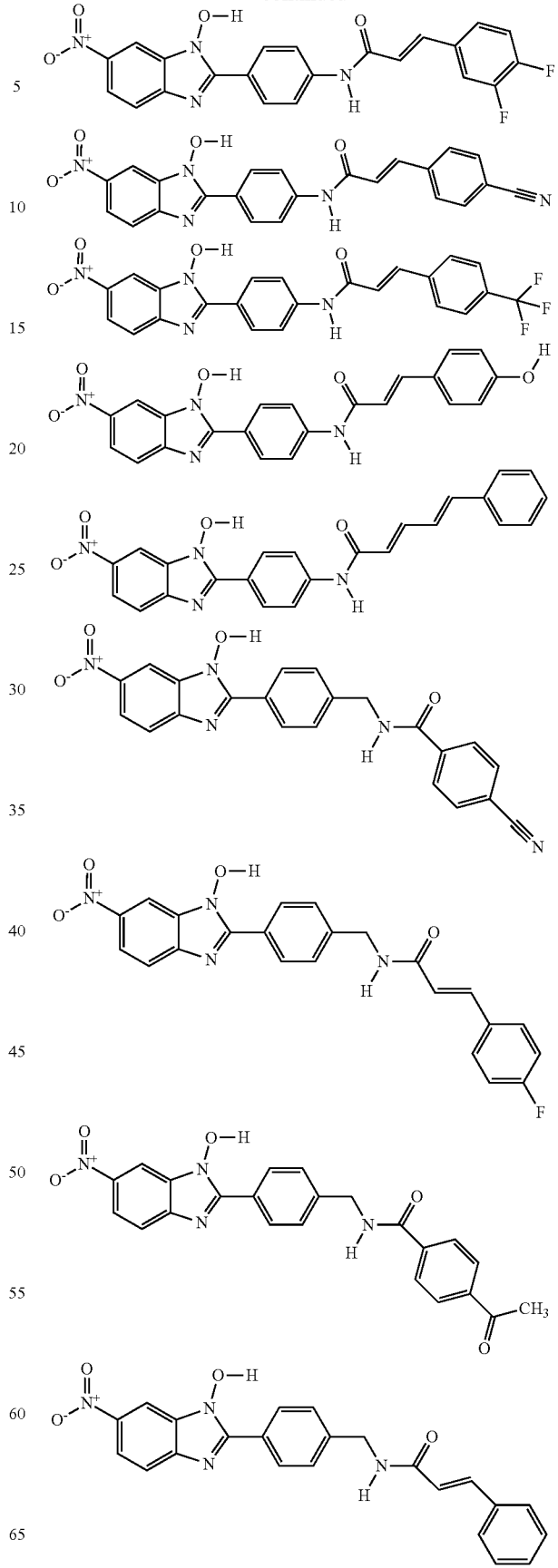

-continued

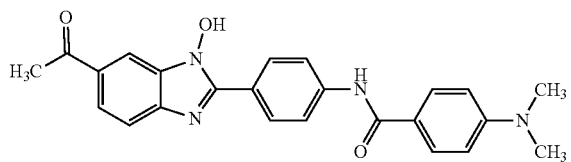

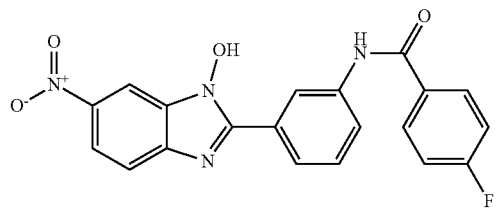

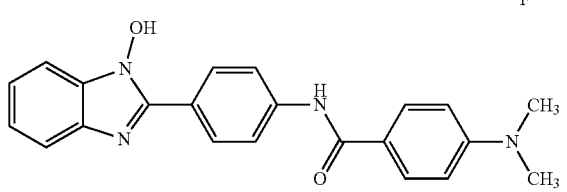

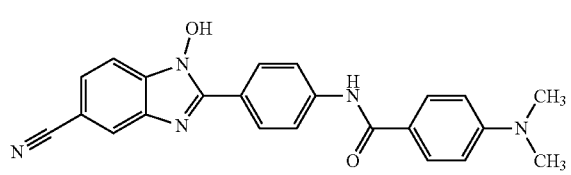

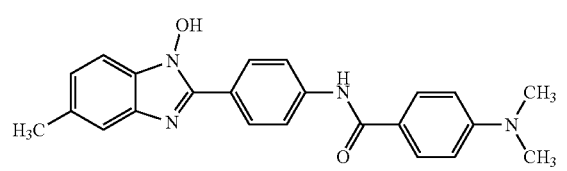

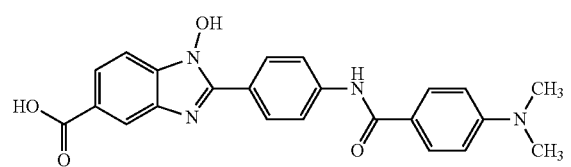

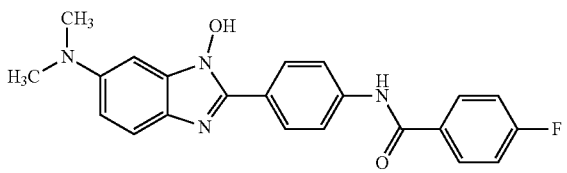

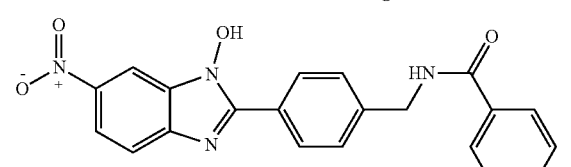

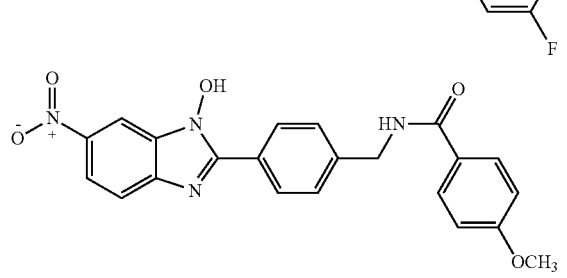

-continued

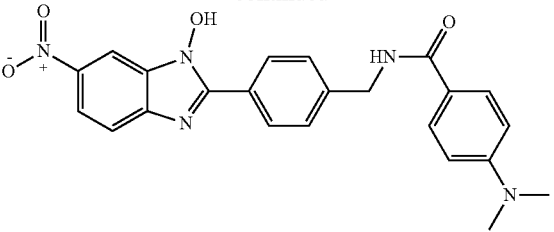

The $EC_{50}$, of a transcription factor modulating compound can be measured using the assay described in Example 12. In a further embodiment, the transcription factor modulating compound has an $EC_{50}$ activity against SoxS of less than about 10 µM, less than about 5 µM, or less than about 1 µM. In a further embodiment, the transcription factor modulating compound can have an $EC_{50}$, activity against MarA of less than about 10 µM, less than about 5 µM, or less than about 1 µM. In yet another embodiment, the transcription factor modulating compound can have an $EC_{50}$, against LcrF (VirF) of less than about 10 µM, less than about 5 µM, or less than about 1 µM.

In another further embodiment, the transcription factor modulating causes a log decrease in CFU/g of kidney tissue. This can be measured using the assay described Example 13. In one embodiment, the transcription factor modulating compound cause a log decrease in CFU/g of kidney tissue of greater than 1.0 CFU/g. In a further embodiment, the compound causes a log decrease in CFU/g of kidney tissue greater than 2.5 CFU/g.

In another embodiment, the transcription factor modulating compound (e.g., an AraC family polypeptide modulating compound, a MarA family polypeptide modulating compound, etc.) is of the formula (VI):

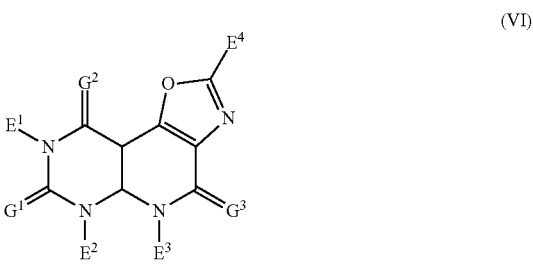

(VI)

wherein $G^1$, $G^2$, and $G^3$ are each independently O, S, substituted or unsubstituted nitrogen, or substituted or unsubstituted carbon;

$E^1$, $E^2$, and $E^3$ are each independently hydrogen, alkyl, alkenyl, alkynyl, aryl, aralkyl, or acyl; and $E^4$ is alkyl, alkenyl, alkynyl, aryl, halogen, cyano, amino, nitro, or acyl, and pharmaceutically acceptable salts thereof.

In a further embodiment, $G^1$, $G^2$ and $G^3$ are each oxygen.

Other transcription factor modulating compounds are shown in Table 3. The invention pertains to each of these compounds, methods (both therapeutic and otherwise) using each of the compounds, and compositions comprising at least one of the compounds of Table 4, Table 5, Table 6, Table 7, Table 8, Table 9, Table 10, or Table 11 or of formulae (I), (II), (III), (IV), (V), (Va), (VI), (VII), (VIII), (IX), (X), (XI), (XII), (XIII), (XIV), (XV), (XVI), (XVII).

The invention also pertains to each of the following compounds: 2-(4-isopropylphenyl)-4H-chromen-4-one; 2-(3,4-Dihydroxy-phenyl)-3,5,7-trihydroxy-chromen-4-one; N-isopropyl-2-[(4-methyl-5-quinolin-6-yl-4H-1,2,4-triazol-3-yl)thio]acetamide; 4-hydroxy-6-methyl-5,6-dihydro-2H-pyrano[3,2-c]quinoline-2,5-dione; 5,7-Dihydroxy-2-(4-hydroxy-phenyl)-chromen-4-one; 2-[4-(dimethylamino) phenyl]-4H-chromen-4-one; 1-(benzyloxy)-2-phenyl-1H-imidazo[4,5-b]pyridine; 2-(benzylthio)-4-phenyl-5-(1-phenyl-1H-1,2,3,4-tetraazol-5-yl)pyrimidine; 6-fluoro-2-phenyl-4H-chromen-4-one; 7-methoxy-2-phenyl-4H-chromen-4-one; 4-(1,3-dioxo-1,3-dihydro-2H-inden-2-yliden)-2-phenyl-6-(2-pyridinyl)tetrahydropyrrolo[3,4-c]pyrrole-1,3(2H,3aH)-dione; 2-(2-Hydroxy-3-oxo-5-p-tolyl-2,3-dihydro-furan-2-yl)-malonamic acid ethyl ester; 2-[(6-nitro-2-phenyl-1H-1,3-benzimidazol-1-yl)oxy]acetic acid; 2-(4-fluorophenyl)-4H-chromen-4-one; 1-methoxy-2-(4-methylphenyl)-1H-imidazo[4,5-b]pyridine; 6-(5-Iodo-furan-2-yl)-3-methylsulfanyl-6,7-dihydro-5-oxa-1,2,4,7-tetraaza-dibenzo[a,c]cycloheptene; 6-(4-Ethoxy-phenyl)-3-methylsulfanyl-6,7-dihydro-5-oxa-1,2,4,7-tetraaza-dibenzo[a,c]cycloheptene; 3-Methylsulfanyl-6-(5-nitro-furan-2-yl)-6,7-dihydro-5-oxa-1,2,4,7-tetraaza-dibenzo[a,c]cycloheptene; 3-Methylsulfanyl-6-[5-(4-nitro-phenyl)-furan-2-yl]-6,7-dihydro-5-oxa-1,2,4,7-tetraaza-dibenzo[a,c]cycloheptene; 4-(3-Ethylsulfanyl-6,7-dihydro-5-oxa-1,2,4,7-tetraaza-dibenzo[a,c]cyclohepten-6-yl)-benzene-1,2-diol; 6-(4-Benzyloxy-phenyl)-3-propylsulfanyl-6,7-dihydro-5-oxa-1,2,4,7-tetraaza-dibenzo[a,c]cycloheptene; 6-Benzo[1,3]dioxol-5-yl-3-methylsulfanyl-6,7-dihydro-5-oxa-1,2,4,7-tetraaza-dibenzo[a,c]cycloheptene; 3-Butylsulfanyl-6-(2,4-dimethoxy-phenyl)-6,7-dihydro-5-oxa-1,2,4,7-tetraaza-dibenzo[a,c]cycloheptene; 6-(4-Allyloxy-phenyl)-3-butylsulfanyl-6,7-dihydro-5-oxa-1,2,4,7-tetraaza-dibenzo[a,c]cycloheptene; 3-Butylsulfanyl-6-(4-ethoxy-phenyl)-6,7-dihydro-5-oxa-1,2,4,7-tetraaza-dibenzo[a,c]cycloheptene; 6-(4-Methoxy-phenyl)-3-propylsulfanyl-6,7-dihydro-5-oxa-1,2,4,7-tetraaza-dibenzo[a,c]cycloheptene; 6-[5-(3-Nitro-phenyl)-furan-2-yl]-3-propylsulfanyl-6,7-dihydro-5-oxa-1,2,4,7-tetraaza-dibenzo[a,c]cycloheptene; 2-(3-Phenyl-1H-pyrazol-4-ylmethylene)-benzo[4,5]imidazo[2,1-b]thiazol-3-one; 2-[5-(3-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester; 5-(4-Dimethylamino-phenyl)-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 5-Benzo[1,3]dioxol-5-yl-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 5-(3,4-Dimethoxy-phenyl)-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 7-Methyl-2-[5-(2-methyl-4-nitro-phenyl)-furan-2-ylmethylene]-5-(4-methyl sulfanyl-phenyl)-3-oxo-2,3-dihydro-5H-thiazolo[3,2-a]pyrimidine-6-carboxylic acid ethyl ester; 2-[5-(4-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester; 5-Benzo[1,3]dioxol-5-yl-2-[5-(4-ethoxycarbonyl-phenyl)-furan-2-ylmethylene]-7-methyl-3-oxo-2,3-dihydro-5H-thiazolo[3,2-a]pyrimidine-6-carboxylic acid ethyl ester; 7-Methyl-3-oxo-5-phenyl-2-[5-(3-trifluoromethyl-phenyl)-furan-2-ylmethylene]-2,3-dihydro-5H-thiazolo[3,2-a]pyrimidine-6-carboxylic acid ethyl ester; 7-Methyl-2-[5-(2-methyl-4-nitro-phenyl)-furan-2-yl methylene]-3-oxo-5-phenyl-2,3-dihydro-5H-thiazolo[3,2-a]pyrimidine-6-carboxylic acid ethyl ester; 2-[5-(3-Carboxy-phenyl)-furan-2-ylmethylene]-5-(4-dimethylamino-phenyl)-7-methyl-3-oxo-2,3-dihydro-5H-thiazolo[3,2-a]pyrimidine-6-carboxylic acid ethyl ester; 5-(4-Dimethylamino-phenyl)-7-methyl-2-[5-(4-methyl-3-nitro-phenyl)-furan-2-yl methylene]-3-oxo-2,3-dihydro-5H-thiazolo[3,2-a]pyrimidine-6-carboxylic acid ethyl ester; 2-[5-(3-Carboxy-phenyl)-furan-2-ylmethylene]-7-methyl-5-(4-methylsulfanyl-phenyl)-3-oxo-2,3-dihydro-5H-thiazolo [3,2-a]pyrimidine-6-carboxylic acid ethyl ester; [1,2]Naphthoquinone 1-[O-(6-oxo-6H-anthra[1,9-cd]isoxazol-5-yl)-oxime]; 3-Acetyl-2,5,7-triphenyl-1H-1,3a,4,8-tetraaza-7a-azonia-cyclopenta[a]indene; 1-Amino-3-benzo[1,3]dioxol-5-yl-benzo[4,5]imidazo[1,2-a]pyridine-2,4-dicarbonitrile; 2-[2-(5-Furan-2-yl-4-phenyl-4H-[1,2,4]triazol-3-yl sulfanyl)-acetylamino]-benzoic acid methyl ester; 6,7-Dimethyl-2-(3-phenyl-1H-pyrazol-4-ylmethylene)-benzo[4,5]imidazo[2,1-b]thiazol-3-one; 2-(5-Benzo[1,2,5]oxadiazol-5-yl-4-methyl-4H-[1,2,4]triazol-3-ylsulfanyl)-N-(3-methylsulfanyl-phenyl)-acetamide; 4-(1,3-Dioxo-indan-2-ylidene)-2-phenyl-6-pyridin-2-yl-tetrahydro-pyrrolo[3,4-c]pyrrole-1,3-dione; 6-Nitro-2-phenyl-1-(3-trifluoromethyl-benzyloxy)-1H-benzoimidazole; (6-Nitro-2-phenyl-benzoimidazol-1-yloxy)-acetic acid; 1-Benzyloxy-6-nitro-2-phenyl-1H-benzoimidazole; 1-(4-Methyl-benzyloxy)-6-nitro-2-phenyl-1H-benzoimidazole; 6,8-Dimethyl-2-(4-nitro-phenyl)-5-phenyl-5H,6H-1-oxa-3,5,6,8-tetraaza-cyclopenta[a]naphthalene-4,7,9-trione; 6,8-Dimethyl-5-phenyl-2-p-tolyl-5H,6H-1-oxa-3,5,6,8-tetraaza-cyclopenta[a]naphthalene-4,7,9-trione; 2-[3-(4-Fluoro-phenyl)-1-phenyl-1H-pyrazol-4-yl methylene]-benzo[4,5]imidazo[2,1-b]thiazol-3-one; Cobalt 5,10,15,20-Tetra-pyridin-4-yl-porphyrine; 2-[3-(4-Fluoro-phenyl)-1-phenyl-1H-pyrazol-4-ylmethylene]-5-methyl-6-vinyl-imidazo[2,1-b]thiazol-3-one; Cobalt 5,10,15,20-Tetra-pyridin-3-yl-porphyrine; Zinc 5,10,15,20-Tetra-pyridin-4-yl-porphyrine; 2-(4-hydroxyphenyl)-4H-chromen-4-one, and pharmaceutically acceptable salts thereof.

In a further embodiment, the transcription factor modulating compound is not apigenin.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). The term "aryl" also includes multicyclic aryl groups such as porphrins, phthalocyanines, etc.

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO-$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "electron withdrawing substituent" includes, but is not limited to, ammonium (including alkylammonium, arylammonium, and heteroarylammonium), solfonyl including alkylsulfonyl, arylsulfonyl, and heteroarylsulfonyl), halogen, perhalogenated alkyl, cyano, oxime, carbonyl (including alkylcarbonyl, arylcarbonyl, and heteroarylcarbonyl), and nitro.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Bonds represented by "=====" in a structural formula mean that the bond may be either a single or a double bond.

IX. Formulations Comprising Transcription Factor Modulating Compounds

The invention provides compositions which include a therapeutically-effective amount or dose of a transcription factor modulating compound and/or a compound identified in any of the instant assays and one or more carriers (e.g., pharmaceutically acceptable additives and/or diluents). The pharmaceutical compositions of the invention may comprise any compound described in this application as a transcription factor modulating compound, an AraC family polypeptide modulating compound, a MarA family polypeptide modulating compound, a MarA family inhibiting compound, a MarA inhibiting compound, compounds of formulae (I), (II), (III), (IV), (V), (VI), (VII), (VIII), (IX), (X), (XI), (XII), (XIII), (XIV), (XV), (XVI), (XVI), (XVIII) Table 4, Table 5, Table 6, Table 7, Table 8, Table 9, Table 10, Table 11 scaffold, etc. Each of these compounds may be used alone of in combination as a part of a pharmaceutical composition of the invention. Furthermore, a composition can also include a second antimicrobial agent, e.g., an antibiotic.

The invention pertains to pharmaceutical compositions comprising an effective amount of a transcription factor modulating compound (e.g., a MarA family polypeptide modulating compound or an AraC family polypeptide modulating compound), and a pharmaceutically acceptable carrier. In one embodiment, the transcription factor modulating compound is of the formula (II):

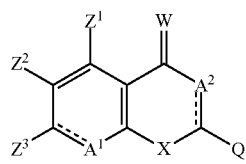

(II)

wherein
W is O or S;
X is O, S, or C, optionally linked to Q;
$A^1$ is C—$Z^4$, O, or S;
$A^2$ is C—$Z^5$, or N—$Z^5$;
$Z^1$, $Z^2$, $Z^3$, $Z^4$ and $Z^5$ are each independently hydrogen, alkoxy, hydroxy, halogen, alkyl, alkenyl, alkynyl, aryl, heterocyclic, amino, or cyano;
$Z^3$ is hydrogen, alkoxy, hydroxy, halogen, alkyl, alkenyl, alkynyl, aryl, heterocyclic, amino, nitro, cyano, carbonyl, or thiocarbonyl;
Q is an aromatic or heterocyclic moiety, and pharmaceutically acceptable salts thereof.

In another embodiment, the pharmaceutical compositions of the invention include an effective amount of a transcription factor modulating compound of the formula (III):

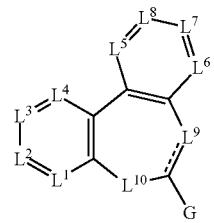

(III)

wherein
G is substituted or unsubstituted aromatic moiety, heterocyclic, alkyl, alkenyl, alkynyl, hydroxy, cyano, nitro, amino, carbonyl, or hydrogen; and
$L^1$, $L^2$, $L^3$, $L^4$, $L^5$, $L^6$, $L^7$, $L^8$, $L^9$, and $L^{10}$ are each independently oxygen, substituted or unsubstituted nitrogen, sulfur and or substituted or unsubstituted carbon, and pharmaceutically acceptable salts thereof.

In yet another embodiment, the pharmaceutical compositions of the invention include a pharmaceutically acceptable carrier (optional) and an effective amount of a transcription factor modulating compound of the formula (IV):

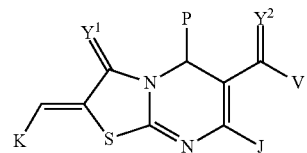

(IV)

wherein
$Y^1$ and $Y^2$ are each oxygen or sulfur;
J is hydrogen, substituted or unsubstituted alkyl, alkenyl, alkynyl, cyano, nitro, amino, or halogen;
V is substituted or unsubstituted alkyl, alkenyl, alkynyl, alkoxy, alkylamino, or alkylthio;
P and K are each independently substituted or unsubstituted aryl, and pharmaceutically acceptable salts thereof.

In yet another embodiment, the pharmaceutical compositions of the invention include a pharmaceutically acceptable carrier (optional) and an effective amount of a transcription factor modulating compound of the formula (V):

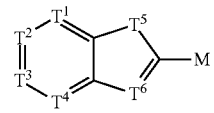

(V)

wherein
$T^1$, $T^2$, $T^3$, $T^4$, $T^5$, and $T^6$ are each independently substituted or unsubstituted carbon, oxygen, substituted or unsubstituted nitrogen, or sulfur;
M is hydrogen, alkyl, alkenyl, alkynyl, or aryl, or pharmaceutically acceptable salts thereof.

In yet another embodiment, the pharmaceutical compositions of the invention include a pharmaceutically acceptable carrier (optional) and an effective amount of a transcription factor modulating compound of the formula (Va):

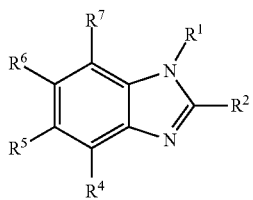

(Va)

wherein $R^1$ is OH, OCOCO$_2$H, or a substituted or unsubstituted straight or branched C$_1$-C$_5$ alkyloxy group;

$R^2$ is H, CO$_2$(C$_1$-C$_5$ substituted or unsubstituted, straight or branched alkyl), or a substituted or unsubstituted aryl group; and $R^4$, $R^5$, $R^6$, and $R^7$ are independently selected from the group consisting of H, (C$_1$-C$_5$ substituted or unsubstituted, straight or branched alkyl), CO$_2$(C$_1$-C$_5$ substituted or unsubstituted, straight or branched alkyl), CO(C$_1$-C$_5$ substituted or unsubstituted, straight or branched alkyl), CO(substituted or unsubstituted aryl or heteroaryl), CO(C$_3$-C$_6$ substituted or unsubstituted cycloalkyl), O(C$_1$-C$_5$ substituted or unsubstituted, straight or branched alkyl), C(NOH)(C$_1$-C$_5$ substituted or unsubstituted, straight or branched alkyl), substituted or unsubstituted amino, CO$_2$H, CN, NO$_2$, CONH$_2$, (CO)(NHOH), and halogen.

In certain embodiments of formula Va, those compounds disclosed in U.S. Ser. No. 10/139,591, filed May 6, 2002, are excluded from the scope of the present invention.

In other embodiments of formula Va, when $R^6$ is NO$_2$ and $R^2$ is unsubstituted phenyl, then $R^1$ is not O(CHCH$_3$)(CO$_2$)CH$_2$CH$_3$ or OCH$_2$CO$_2$H. Also, in another embodiment, when $R^6$ is H or NO$_2$, then $R^1$ is not a phenyl-substituted alkyloxy group. In yet another embodiment, when $R^4$, $R^5$, $R^6$, and $R^7$ are all H and $R^2$ is para-methoxyphenyl, then $R^1$ is not OH. And in another embodiment, when $R^4$, $R^5$, $R^6$, and $R^7$ are all H and $R^2$ is unsubstituted phenyl, then $R^1$ is not OCH$_2$CO$_2$CH$_2$CH$_3$;

In certain aspects of formula Va, $R^4$, $R^5$, and $R^7$ are all H. Similarly, $R^1$ of formula Va may be selected from the group consisting of OH, O(CR'R")$_{1-3}$H, O(CR'R")$_{1-3}$OH, O(CR'R")$_{1-3}$CO$_2$H, O(CR'R")$_{1-3}$CO$_2$(CR'R")$_{1-3}$H, O(CR'R")$_{1-3}$(CO)NH$_2$, O(CR'R")$_{1-3}$(CNH)NH$_2$, OCOCO$_2$H, O(CR'R")$_{1-3}$SO$_3$H, O(CR'R")$_{1-3}$OSO$_3$H, O(CR'R")$_{1-3}$PO$_3$H, O(CR'R")$_{1-3}$OPO$_3$H, O(CR'R")$_{1-3}$N[(CR'R")$_{0-3}$H]$_2$, O(CR'R")$_{1-3}$(CO)(NHOH), and O(CR'R")$_{1-3}$(heteroaryl); wherein R' and R" are each independently H, a C$_1$-C$_3$ alkyl, C$_2$-C$_3$ alkenyl, or C$_2$-C$_3$ alkynyl group. Each R' and R" is preferably H or CH$_3$.

When $R^1$ of formula Va is O(CR'R")$_{1-3}$(heteroaryl), the heteroaryl group may be a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

Similarly, when $R^2$ of formula Va may be a substituted or unsubstituted phenyl, pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In a more particular embodiment, $R^6$ of formula Va is H, (CR'R")$_{1-3}$H, (CR'R")$_{1-3}$OH, (CR'R")$_{1-3}$NH$_2$, (NOH)(CR'R")$_{1-3}$H, CO(CR'R")$_{0-3}$NH$_2$, CO(CR'R")$_{1-3}$H, CO(CR'R")$_{1-3}$OH, CO(CR'R")$_{0-3}$CF$_3$, (CR'R")$_{0-3}$N[(CR'R")$_{0-3}$H]$_2$, CO(substituted or unsubstituted heteroaryl), CO(C$_3$-C$_6$ substituted or unsubstituted cycloalkyl), O(CR'R")$_{1-3}$H, CO(substituted or unsubstituted phenyl), CO$_2$(CR'R")$_{0-3}$H, CN, NO$_2$, F, Cl, Br, or I, wherein R' and R" are each independently H, a C$_1$-C$_3$ alkyl, C$_2$-C$_3$ alkenyl, or C$_2$-C$_3$ alkynyl group. Preferably each R' and R" is independently H or CH$_3$.

In yet another embodiment, $R^6$ of formula Va is CO(substituted or unsubstituted heteroaryl), wherein said heteroaryl group is a pyrrolyl, furanyl, thiophenyl, thiazolyl, isothiaozolyl, imidazolyl, triazolyl, tetrazolyl, pyrazolyl, oxazolyl, isooxazolyl, pyridinyl, pyrazinyl, pyridazinyl, or pyrimidinyl group.

In still another embodiment of formula Va, $R^1$ is OH, OCOCO$_2$H, or a substituted straight or branched C$_1$-C$_5$ alkyloxy group, provided that $R^1$ is not a 2-amino-substituted ethoxy group or a substituted or unsubstituted benzyloxy group; $R^2$ is H, CO$_2$(C$_1$-C$_5$ substituted or unsubstituted, straight or branched alkyl), or a substituted or unsubstituted aryl group, provided that said aryl group is not a thiazolyl or isothiazolyl group; and $R^4$, $R^5$, $R^6$, and $R^7$ are independently selected from the group consisting of H, (C$_1$-C$_5$ substituted or unsubstituted, straight or branched alkyl), CO$_2$(C$_1$-C$_5$ substituted or unsubstituted, straight or branched alkyl), CO(C$_1$-C$_5$ substituted or unsubstituted, straight or branched alkyl), CO(substituted or unsubstituted aryl or heteroaryl), CO(C$_3$-C$_6$ substituted or unsubstituted cycloalkyl), O(C$_1$-C$_5$ substituted or unsubstituted, straight or branched alkyl), C(NOH)(C$_1$-C$_5$ substituted or unsubstituted, straight or branched alkyl), substituted or unsubstituted amino, CO$_2$H, CN, NO$_2$, CONH$_2$, (CO)(NHOH), and halogen; provided that when $R^6$ is NO$_2$ and $R^2$ is unsubstituted phenyl, then $R^1$ is not O(CHCH$_3$)(CO$_2$)CH$_2$CH$_3$ or OCH$_2$CO$_2$H; provided that when $R^6$ is or NO$_2$, then $R^1$ is not a phenyl-substituted alkyloxy group; provided that when $R^4$, $R^5$, $R^6$, and $R^7$ are all H and $R^2$ is para-methoxyphenyl, then $R^1$ is not OH; and provided that when $R^4$, $R^5$, $R^6$, and $R^7$ are all H and $R^2$ is unsubstituted phenyl, or when $R^4$, $R^5$, and $R^7$ are all H, $R^6$ is Cl, and $R^2$ is para-methyl-phenyl, then $R^1$ is not OCH$_2$CO$_2$CH$_2$CH$_3$.

In another embodiment, $R^6$ of formula Va is an electron withdrawing substituent, selected from the group consisting of F, CF$_3$, NO$_2$, C(NOH)(CR'R"), wherein each R' and R" are each independently H or CH$_3$.

In yet another embodiment, the pharmaceutical compositions of the invention include a pharmaceutically acceptable carrier (optional) and an effective amount of a transcription factor modulating compound of the formula (VI):

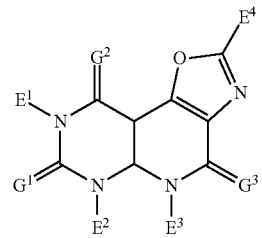

(VI)

wherein $G^1$, $G^2$, and $G^3$ are each independently O, S, substituted or unsubstituted nitrogen, or substituted or unsubstituted carbon;

$E^1$, $E^2$, and $E^3$ are each independently hydrogen, alkyl, alkenyl, alkynyl, aryl, aralkyl, or acyl; and $E^4$ is alkyl, alkenyl, alkynyl, aryl, halogen, cyano, amino, nitro, or acyl, and pharmaceutically acceptable salts thereof.

In yet another further embodiment, the pharmaceutical compositions of the invention comprise an effective amount of a transcription factor modulating compound listed below or found in Table 4, Table 5, Table 6, Table 7, Table 8, Table 9, Table 10, Table 11:

2-(4-isopropylphenyl)-4H-chromen-4-one; 2-(3,4-Dihydroxy-phenyl)-3,5,7-trihydroxy-chromen-4-one, N-isopropyl-2-[(4-methyl-5-quinolin-6-yl-4H-1,2,4-triazol-3-yl)thio]acetamide; 4-hydroxy-6-methyl-5,6-dihydro-2H-pyrano[3,2-c]quinoline-2,5-dione; 5,7-Dihydroxy-2-(4-hydroxy-phenyl)-chromen-4-one; 2-[4-(dimethylamino)phenyl]-4H-chromen-4-one; 1-(benzyloxy)-2-phenyl-1H-imidazo[4,5-b]pyridine; 2-(benzylthio)-4-phenyl-5-(1-phenyl-1H-1,2,3,4-tetraazol-5-yl)pyrimidine; 6-fluoro-2-phenyl-4H-chromen-4-one; 7-methoxy-2-phenyl-4H-chromen-4-one; 4-(1,3-dioxo-1,3-dihydro-2H-inden-2-yliden)-2-phenyl-6-(2-pyridinyl)tetrahydropyrrolo[3,4-c]pyrrole-1,3(2H,3aH)-dione; 2-(2-Hydroxy-3-oxo-5-p-tolyl-2,3-dihydro-furan-2-yl)-malonamic acid ethyl ester; 2-[(6-nitro-2-phenyl-1H-1,3-benzimidazol-1-yl)oxy]acetic acid; 2-(4-fluorophenyl)-4H-chromen-4-one; 1-methoxy-2-(4-methylphenyl)-1H-imidazo[4,5-b]pyridine; 6-(5-Iodo-furan-2-yl)-3-methylsulfanyl-6,7-dihydro-5-oxa-1,2,4,7-tetraaza-dibenzo[a,c]cycloheptene; 6-(4-Ethoxy-phenyl)-3-methylsulfanyl-6,7-dihydro-5-oxa-1,2,4,7-tetraaza-dibenzo[a,c]cycloheptene; 3-Methylsulfanyl-6-(5-nitro-furan-2-yl)-6,7-dihydro-5-oxa-1,2,4,7-tetraaza-dibenzo[a,c]cycloheptene; 3-Methylsulfanyl-6-[5-(4-nitro-phenyl)-furan-2-yl]-6,7-dihydro-5-oxa-1,2,4,7-tetraaza-dibenzo[a,c]cycloheptene; 4-(3-Ethylsulfanyl-6,7-dihydro-5-oxa-1,2,4,7-tetraaza-dibenzo[a,c]cyclohepten-6-yl)-benzene-1,2-diol; 6-(4-Benzyloxy-phenyl)-3-propylsulfanyl-6,7-dihydro-5-oxa-1,2,4,7-tetraaza-dibenzo[a,c]cycloheptene; 6-Benzo[1,3]dioxol-5-yl-3-methylsulfanyl-6,7-dihydro-5-oxa-1,2,4,7-tetraaza-dibenzo[a,c]cycloheptene; 3-Butylsulfanyl-6-(2,4-dimethoxy-phenyl)-6,7-dihydro-5-oxa-1,2,4,7-tetraaza-dibenzo[a,c]cycloheptene; 6-(4-Allyloxy-phenyl)-3-butylsulfanyl-6,7-dihydro-5-oxa-1,2,4,7-tetraaza-dibenzo[a,c]cycloheptene; 3-Butylsulfanyl-6-(4-ethoxy-phenyl)-6,7-dihydro-5-oxa-1,2,4,7-tetraaza-dibenzo[a,c]cycloheptene; 6-(4-Methoxy-phenyl)-3-propylsulfanyl-6,7-dihydro-5-oxa-1,2,4,7-tetraaza-dibenzo[a,c]cycloheptene; 6-[5-(3-Nitro-phenyl)-furan-2-yl]-3-propylsulfanyl-6,7-dihydro-5-oxa-1,2,4,7-tetraaza-dibenzo[a,c]cycloheptene; 2-(3-Phenyl-1H-pyrazol-4-ylmethylene)-benzo[4,5]imidazo[2,1-b]thiazol-3-one; 2-[5-(3-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester; 5-(4-Dimethylamino-phenyl)-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 5-Benzo[1,3]dioxol-5-yl-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 5-(3,4-Dimethoxy-phenyl)-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester; 7-Methyl-2-[5-(2-methyl-4-nitro-phenyl)-furan-2-ylmethylene]-5-(4-methylsulfanyl-phenyl)-3-oxo-2,3-dihydro-5H-thiazolo[3,2-a]pyrimidine-6-carboxylic acid ethyl ester; 2-[5-(4-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester; 5-Benzo[1,3]dioxol-5-yl-2-[5-(4-ethoxycarbonyl-phenyl)-furan-2-ylmethylene]-7-methyl-3-oxo-2,3-dihydro-5H-thiazolo[3,2-a]pyrimidine-6-carboxylic acid ethyl ester; 7-Methyl-3-oxo-5-phenyl-2-[5-(3-trifluoromethyl-phenyl)-furan-2-ylmethylene]-2,3-dihydro-5H-thiazolo[3,2-a]pyrimidine-6-carboxylic acid ethyl ester; 7-Methyl-2-[5-(2-methyl-4-nitro-phenyl)-furan-2-ylmethylene]-3-oxo-5-phenyl-2,3-dihydro-5H-thiazolo[3,2-a]pyrimidine-6-carboxylic acid ethyl ester; 2-[5-(3-Carboxy-phenyl)-furan-2-ylmethylene]-5-(4-dimethylamino-phenyl)-7-methyl-3-oxo-2,3-dihydro-5H-thiazolo[3,2-a]pyrimidine-6-carboxylic acid ethyl ester; 5-(4-Dimethylamino-phenyl)-7-methyl-2-[5-(4-methyl-3-nitro-phenyl)-furan-2-yl methylene]-3-oxo-2,3-dihydro-5H-thiazolo[3,2-a]pyrimidine-6-carboxylic acid ethyl ester; 2-[5-(3-Carboxy-phenyl)-furan-2-ylmethylene]-7-methyl-5-(4-methylsulfanyl-phenyl)-3-oxo-2,3-dihydro-5H-thiazolo[3,2-a]pyrimidine-6-carboxylic acid ethyl ester; [1,2]Naphthoquinone 1-[O-(6-oxo-6H-anthra[1,9-cd]isoxazol-5-yl)-oxime]; 3-Acetyl-2,5,7-triphenyl-1H-1,3a,4,8-tetraaza-7a-azonia-cyclopenta[a]indene; 1-Amino-3-benzo[1,3]dioxol-5-yl-benzo[4,5]imidazo[1,2-a]pyridine-2,4-dicarbonitrile; 2-[2-(5-Furan-2-yl-4-phenyl-4H-[1,2,4]-triazol-3-yl sulfanyl)-acetylamino]-benzoic acid methyl ester; 6,7-Dimethyl-2-(3-phenyl-1H-pyrazol-4-ylmethylene)-benzo[4,5]imidazo[2,1-b]thiazol-3-one; 2-(5-Benzo[1,2,5]oxadiazol-5-yl-4-methyl-4H-[1,2,4]triazol-3-ylsulfanyl)-N-(3-methylsulfanyl-phenyl)-acetamide; 4-(1,3-Dioxo-indan-2-ylidene)-2-phenyl-6-pyridin-2-yl-tetrahydro-pyrrolo[3,4-c]pyrrole-1,3-dione; 6-Nitro-2-phenyl-1-(3-trifluoromethyl-benzyloxy)-1H-benzoimidazole; (6-Nitro-2-phenyl-benzoimidazol-1-yloxy)-acetic acid; 1-Benzyloxy-6-nitro-2-phenyl-1H-benzoimidazole; 1-(4-Methyl-benzyloxy)-6-nitro-2-phenyl-1H-benzoimidazole; 6,8-Dimethyl-2-(4-nitro-phenyl)-5-phenyl-5H,6H-1-oxa-3,5,6,8-tetraaza-cyclopenta[a]naphthalene-4,7,9-trione; 6,8-Dimethyl-5-phenyl-2-p-tolyl-5H,6H-1-oxa-3,5,6,8-tetraaza-cyclopenta[a]naphthalene-4,7,9-trione; 2-[3-(4-Fluoro-phenyl)-1-phenyl-1H-pyrazol-4-ylmethylene]-benzo[4,5]imidazo[2,1-b]thiazol-3-one; Cobalt 5,10,15,20-Tetra-pyridin-4-yl-porphyrine; 2-[3-(4-Fluoro-phenyl)-1-phenyl-1H-pyrazol-4-ylmethylene]-5-methyl-6-vinyl-imidazo[2,1-b]thiazol-3-one; Cobalt 5,10,15,20-Tetra-pyridin-3-yl-porphyrine; Zinc 5,10,15,20-Tetra-pyridin-4-yl-porphyrine; 2-(4-hydroxyphenyl)-4H-chromen-4-one, and pharmaceutically acceptable salts thereof.

In one embodiment, the present invention provides a pharmaceutical composition comprising a pharmaceutically acceptable carrier and a transcription factor modulating compound, wherein said compound is of the formula (XI), (XII), (XIII), (XIV), (XV), (XVI), or (XVII). In another embodiment, the pharmaceutical composition can further comprise an antibiotic. In a further embodiment, the effective amount of the pharmaceutical composition can be effective for treating a biofilm associated state in a subject. The biofilm associated states can include, for example, middle ear infections, cystic fibrosis, osteomyelitis, acne, dental cavities, endocarditis, and prostatitis.

In another embodiment, the method for preventing a bacterial associated state in a subject, comprising administering to the subject an effective amount of a transcription factor modulating compound, such that the bacterial associated state is prevented. In a further embodiment, the transcription factor modulating compound is of the formula (XI), (XII), (XIII), (XIV), (XV), (XVI), or (XVII). In a further embodiment, the transcription factor modulating compound can include, for example, a MarA family polypeptide inhibitor and an AraC family polypeptide inhibitor.

The term "subject" includes plants and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans) which are capable of suffering from a bacterial associated disorder. The term "subject" also comprises immunocompromised subjects, who may be at a higher risk for infection.

The term "preventing" the administration of an effective amount of the transcription factor modulating compound to prevent a bacterial associated state from occurring.

The term "bacterial associated state" includes states characterized by the presence of bacteria which can be prevented by administering the transcription factor modulating compounds of the invention. The term includes biofilm associated states and other infections or the undesirable presence of a bacteria on or in a subject.

As described in detail below, the pharmaceutical compositions can be formulated for administration in solid or liquid form, including those adapted for the following: (1) oral administration, for example, aqueous or non-aqueous solutions or suspensions, tablets, boluses, powders, granules, pastes; (2) parental administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream, foam, or suppository; or (5) aerosol, for example, as an aqueous aerosol, liposomal preparation or solid particles containing the compound.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the antiinfective agents or compounds of the invention from one organ, or portion of the body, to another organ, or portion of the body without affecting its biological effect. Each carrier should be "acceptable" in the sense of being compatible with the other ingredients of the composition and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microbes may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions of the present invention may be administered to epithelial surfaces of the body orally, parenterally, topically, rectally, nasally, intravaginally, intracisternally. They are of course given by forms suitable for each administration route. For example, they are administered in tablets or capsule form, by injection, inhalation, eye lotion, ointment, etc., administration by injection, infusion or inhalation; topical by lotion or ointment; and rectal or vaginal suppositories.

The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a sucrose octasulfate and/or an antibacterial, drug or other material other than directly into the central nervous system, such that it enters the subject's system and, thus, is subject to metabolism and other like processes, for example, subcutaneous administration.

In some methods, the compositions of the invention can be topically administered to any epithelial surface. An "epithelial surface" according to this invention is defined as an area of tissue that covers external surfaces of a body, or which lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, suppositories, douches, enemas, gels, creams, emulsions, lotions, slurries, powders, sprays, lipsticks, foams, pastes, toothpastes, ointments, salves, balms, douches, drops, troches, chewing gums, lozenges, mouthwashes, rinses.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinypyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Such compositions can be particularly useful, for example, for treatment or prevention of an unwanted cell, e.g., vaginal *Neisseria gonorrhoeae*, or infections of the oral cavity, including cold sores, infections of eye, the skin, or the lower intestinal tract. Standard composition strategies for topical agents can be applied to the antiinfective compounds or a pharmaceutically acceptable salt thereof in order to enhance the persistence and residence time of the drug, and to improve the prophylactic efficacy achieved.

For topical application to be used in the lower intestinal tract or vaginally, a rectal suppository, a suitable enema, a gel, an ointment, a solution, a suspension or an insert can be used. Topical transdermal patches may also be used. Transdermal patches have the added advantage of providing controlled delivery of the compositions of the invention to the body. Such dosage forms can be made by dissolving or dispersing the agent in the proper medium.

Compositions of the invention can be administered in the form of suppositories for rectal or vaginal administration. These can be prepared by mixing the agent with a suitable non-irritating carrier which is solid at room temperature but liquid at rectal temperature and therefore will melt in the rectum or vagina to release the drug. Such materials include cocoa butter, beeswax, polyethylene glycols, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams, films, or spray compositions containing such carriers as are known in the art to be appropriate. The carrier employed in the sucrose octasulfate/contraceptive agent should be compatible with vaginal administration and/or coating of contraceptive devices. Combinations can be in solid, semi-solid and liquid dosage forms, such as diaphragm, jelly, douches, foams, films, ointments, creams, balms, gels, salves, pastes, slurries, vaginal suppositories, sexual lubricants, and coatings for devices, such as condoms, contraceptive sponges, cervical caps and diaphragms.

For ophthalmic applications, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolatum. Exemplary ophthalmic compositions include eye ointments, powders, solutions and the like.

Powders and sprays can contain, in addition to sucrose octasulfate and/or antibiotic or contraceptive agent(s), carriers such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), proteins like serum albumin, sorbitan esters, oleic acid, lecithin, amino acids such as glycine, buffers, salts, sugars or sugar alcohols. Aerosols generally are prepared from isotonic solutions.

Compositions of the invention can also be orally administered in any orally-acceptable dosage form including, but not limited to, capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of sucrose octasulfate and/or antibiotic or contraceptive agent(s) as an active ingredient. A compound may also be administered as a bolus, electuary or paste. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Tablets, and other solid dosage forms, such as dragees, capsules, pills and granules, may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the antiinfective agent(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Sterile injectable forms of the compositions of this invention can be aqueous or oleaginous suspension. These suspensions may be formulated according to techniques known in the art using suitable dispersing or wetting agents and suspending agents. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The antiinfective agent or a pharmaceutically acceptable salt thereof will represent some percentage of the total dose in other dosage forms in a material forming a combination product, including liquid solutions or suspensions, suppositories, douches, enemas, gels, creams, emulsions, lotions slurries, soaps, shampoos, detergents, powders, sprays, lipsticks, foams, pastes, toothpastes, ointments, salves, balms, douches, drops, troches, lozenges, mouthwashes, rinses and others. Creams and gels for example, are typically limited by the physical chemical properties of the delivery medium to concentrations less than 20% (e.g., 200 mg/gm). For special uses, far less concentrated preparations can be prepared, (e.g., lower percent formulations for pediatric applications). For example, the pharmaceutical composition of the invention can comprise sucrose octasulfate in an amount of 0.001-99%, typically 0.01-75%, more typically 0.1-20%, especially 1-10% by weight of the total preparation. In particular, a preferred concentration thereof in the preparation is 0.5-50%, especially 0.5-25%, such as 1-10%. It can be suitably applied 1-10 times a day, depending on the type and severity of the condition to be treated or prevented.

Given the low toxicity of an antiinfective agent or a pharmaceutically acceptable salt thereof over many decades of clinical use as an anti-ulcerant [W. R. Garnett, *Clin. Pharm.* 1:307-314 (1982); R. N. Brogden et al., *Drugs* 27:194-209 (1984); D. M. McCarthy, *New Eng J Med.*, 325:1017-1025 (1991), an upper limit for the therapeutically effective dose is not a critical issue.

For prophylactic applications, the pharmaceutical composition of the invention can be applied prior to potential infection. The timing of application prior to potential infection can be optimized to maximize the prophylactic effectiveness of the compound. The timing of application will vary depending on the mode of administration, the epithelial surface to which it is applied, the surface area, doses, the stability and effectiveness of composition under the pH of the epithelial surface, the frequency of application, e.g., single application or multiple applications. One skilled in the art will be able to determine the most appropriate time interval required to maximize prophylactic effectiveness of the compound.

The practice of the present invention will employ, unless otherwise indicated, conventional techniques of cell biology, cell culture, molecular biology, genetics, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *DNA Cloning*, Volumes I and II (D. N. Glover ed., 1985); Oligonucleotide Synthesis (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

X. The Role of Transcription Activation Factor Polypeptides in Biofilms

In one embodiment, the invention pertains to a method for dispersing or preventing the formation of a biofilm on a surface or in an area, by administering an effective amount of a transcription factor modulating compound, e.g., a HTH protein modulating compound, an AraC family polypeptide modulating compound, a MarA family polypeptide modulating compound, or a MarA inhibiting compound.

It has been discovered that the absence of MarA and its homologs has a negative effect on biofilm formation in *E. coli*. In order to confirm this finding genetically, plasmid encoded marA was transformed into an *E. coli* strain deleted of marA, soxS, and rob (triple knockout). The expression of MarA in this triple knockout restored biofilm formation in this host to a level that was comparable to that of the wild type host.

The term "biofilm" includes biological films that develop and persist at interfaces in aqueous and other environments. Biofilms are composed of microorganisms embedded in an organic gelatinous structure composed of one or more matrix polymers which are secreted by the resident microorganisms. The term "biofilm" also includes bacteria that are attached to a surface in sufficient numbers to be detected or communities of microorganisms attached to a surface (Costerton, J. W., et al. (1987) *Ann. Rev. Microbiol.* 41:435-464; Shapiro, J. A. (1988) *Sci Am.* 256:82-89; O'Toole, G. et al. (2000) *Annu Rev Microbiol.* 54:49-79).

In another embodiment, the invention pertains to methods of treating biofilm associated states in a subject, by administering to said subject an effective amount of a transcription factor modulating compound, e.g., a MarA family inhibiting compound, such that the biofilm associated state is treated.

The term "biofilm associated states" includes disorders which are characterized by the presence or potential presence of a bacterial biofilm. Many medically important pathogens form biofilms and biofilm formation is often one component of the infectious process (Costerton, J. W. et al. (1999) *Science* 284:1318-1322). Examples of biofilm associated states include, but are not limited to, middle ear infections, cystic fibrosis, osteomyelitis, acne, dental cavities, and prostatitis. Biofilm associated states also include infection of the subject by one or more bacteria, e.g., *Pseudomonas aeruginosa*. One consequence of biofilm formation is that bacteria within biofilms are generally less susceptible to a range of different antibiotics relative to their planktonic counterparts.

Furthermore, the invention also pertains to methods for preventing the formation of biofilms on surfaces or in areas, by contacting the area with an effective amount of a transcription factor modulating compound, e.g., a MarA family inhibiting compound, etc.

Industrial facilities employ many methods of preventing biofouling of industrial water systems. Many microbial organisms are involved in biofilm formation in industrial waters. Growth of slime-producing bacteria in industrial water systems causes problems including decreased heat transfer, fouling and blockage of lines and valves, and corrosion or degradation of surfaces. Control of bacterial growth in the past has been accomplished with biocides. Many biocides and biocide formulations are known in the art. However, many of these contain components which may be environmentally deleterious or toxic, and are often resistant to breakdown.

The transcription factor inhibiting compounds, such as but not limited to AraC family inhibiting compounds and MarA family inhibiting compounds, of the present invention are useful in a variety of environments including industrial, clinical, the household, and personal care. The compositions of the invention may comprise one or more compounds of the invention as an active ingredient acting alone, additively, or synergistically against the target organism.

The MarA family inhibiting compounds and modulating compounds of the invention may be formulated in a composition suitable for use in environments including industry, pharmaceutics, household, and personal care. In an embodiment, the compounds of the invention are soluble in water. The modulating compounds may be applied or delivered with an acceptable carrier system. The composition may be applied or delivered with a suitable carrier system such that the active ingredient (e.g., transcription factor modulating compound of the invention such as a MarA family modulating compound, e.g., a MarA family polypeptide inhibiting compound) may be dispersed or dissolved in a stable manner so that the active ingredient, when it is administered directly or indirectly, is present in a form in which it is available in a advantageous way.

Also, the separate components of the compositions of the invention may be preblended or each component may be added separately to the same environment according to a predetermined dosage for the purpose of achieving the desired concentration level of the treatment components and so long as the components eventually come into intimate admixture with each other. Further, the present invention may be administered or delivered on a continuous or intermittent basis.

A transcription factor modulating compound of the present invention, e.g., a MarA family modulating compound of the present invention, when present in a composition will generally be present in an amount from about 0.000001% to about 100%, more preferably from about 0.001% to about 50%, and most preferably from about 0.01% to about 25%.

For compositions of the present invention comprising a carrier, the composition comprises, for example, from about 1% to about 99%, preferably from about 50% to about 99%, and most preferably from about 75% to about 99% by weight of at least one carrier.

The transcription factor modulating compound, e.g., the MarA family polypeptide inhibiting compound, of the invention may be formulated with any suitable carrier and prepared for delivery in forms, such as, solutions, microemulsions, suspensions or aerosols. Generation of the aerosol or any other means of delivery of the present invention may be accomplished by any of the methods known in the art. For example, in the case of aerosol delivery, the compound is supplied in a finely divided form along with any suitable carrier with a propellant. Liquefied propellants are typically gases at ambient conditions and are condensed under pressure. The propellant may be any acceptable and known in the art including propane and butane, or other lower alkanes, such as those of up to 5 carbons. The composition is held within a container with an appropriate propellant and valve, and maintained at elevated pressure until released by action of the valve.

The compositions of the invention may be prepared in a conventional form suitable for, but not limited to topical or local application such as an ointment, paste, gel, spray and liquid, by including stabilizers, penetrants and the carrier or diluent with the compound according to a known technique in the art. These preparations may be prepared in a conventional form suitable for enteral, parenteral, topical or inhalational applications.

The present invention may be used in compositions suitable for household use. For example, compounds of the present invention are also useful as active antimicrobial ingredients in household products such as cleansers, detergents, disinfectants, dishwashing liquids, soaps and detergents. In an embodiment, the transcription factor modulating compound of the present invention may be delivered in an amount and form effective for the prevention, removal or termination of microbes.

The compositions of the invention for household use comprise, for example, at least one transcription factor modulating compound of the invention and at least one suitable carrier. For example, the composition may comprise from about 0.00001% to about 50%, preferably from about 0.0001% to about 25%, most preferably from about 0.0005% to about 10% by weight of the modulating compound based on the weight percentage of the total composition.

The transcription factor modulating compound of the present invention may also be used in hygiene compositions for personal care. For instance, compounds of the invention can be used as an active ingredient in personal care products such as facial cleansers, astringents, body wash, shampoos, conditioners, cosmetics and other hygiene products. The hygiene composition may comprise any carrier or vehicle known in the art to obtain the desired form (such as solid, liquid, semisolid or aerosol) as long as the effects of the compound of the present invention are not impaired. Methods of preparation of hygiene compositions are not described herein in detail, but are known in the art. For its discussion of such methods, *The CTFA Cosmetic Ingredient Handbook*, Second Edition, 1992, and pages 5-484 of *A Formulary of Cosmetic Preparations* (Vol. 2, Chapters 7-16) are incorporated herein by reference.

The hygiene composition for use in personal care comprise generally at least one modulating compound of the present application and at least one suitable carrier. For example, the composition may comprise from about 0.00001% to about 50%, preferably from about 0.0001% to about 25%, more preferably from about 0.0005% to about 10% by weight of the transcription factor modulating compound of the invention based on the weight percentage of the total composition.

The transcription factor modulating compound of the present invention may be used in industry. In the industrial setting, the presence of microbes can be problematic, as microbes are often responsible for industrial contamination and biofouling. Compositions of the invention for industrial applications may comprise an effective amount of the compound of the present invention in a composition for industrial use with at least one acceptable carrier or vehicle known in the art to be useful in the treatment of such systems. Such carriers or vehicles may include diluents, deflocculating agents, penetrants, spreading agents, surfactants, suspending agents, wetting agents, stabilizing agents, compatibility agents, sticking agents, waxes, oils, co-solvents, coupling agents, foams, antifoaming agents, natural or synthetic polymers, elastomers and synergists. Methods of preparation, delivery systems and carriers for such compositions are not described here in detail, but are known in the art. For its discussion of such methods, U.S. Pat. No. 5,939,086 is herein incorporated by reference. Furthermore, the preferred amount of the composition to be used may vary according to the active ingredient(s) and situation in which the composition is being applied.

The transcription factor modulating compounds, e.g., MarA family polypeptide inhibiting compounds, and compositions of the present invention may be useful in nonaqueous environments. Such nonaqueous environments may include, but are not limited to, terrestrial environments, dry surfaces or semi-dry surfaces in which the compound or composition is applied in a manner and amount suitable for the situation.

The transcription factor modulating compounds, e.g., MarA family polypeptide modulating compounds, e.g., MarA inhibiting compounds, of the present invention may be used to form contact-killing coatings or layers on a variety of substrates including personal care products (such as toothbrushes, contact lens cases and dental equipment), healthcare products, household products, food preparation surfaces and packaging, and laboratory and scientific equipment. Further, other substrates include medical devices such as catheters, urological devices, blood collection and transfer devices, tracheotomy devices, intraocular lenses, wound dressings, sutures, surgical staples, membranes, shunts, gloves, tissue patches, prosthetic devices (e.g., heart valves) and wound drainage tubes. Still further, other substrates include textile products such as carpets and fabrics, paints and joint cement. A further use is as an antimicrobial soil fumigant.

The transcription factor modulating compounds of the invention may also be incorporated into polymers, such as polysaccharides (cellulose, cellulose derivatives, starch, pectins, alginate, chitin, guar, carrageenan), glycol polymers, polyesters, polyurethanes, polyacrylates, polyacrylonitrile, polyamides (e.g., nylons), polyolefins, polystyrenes, vinyl polymers, polypropylene, silks or biopolymers. The modulating compounds may be conjugated to any polymeric material such as those with the following specified functionality: 1) carboxy acid, 2) amino group, 3) hydroxyl group and/or 4) haloalkyl group.

The composition for treatment of nonaqueous environments may be comprise at least one transcription factor modulating compound of the present application and at least one suitable carrier. In an embodiment, the composition comprises from about 0.001% to about 75%, advantageously from about 0.01% to about 50%, and preferably from about 0.1% to about 25% by weight of a transcription factor modulating compound of the invention based on the weight percentage of the total composition.

The transcription factor modulating compounds and compositions of the invention may also be useful in aqueous environments. "Aqueous environments" include any type of system containing water, including, but not limited to, natural bodies of water such as lakes or ponds; artificial, recreational bodies of water such as swimming pools and hot tubs; and drinking reservoirs such as wells. The compositions of the present invention may be useful in treating microbial growth in these aqueous environments and may be applied, for example, at or near the surface of water.

The compositions of the invention for treatment of aqueous environments may comprise at least one transcription factor modulating compound of the present invention and at least one suitable carrier. In an embodiment, the composition comprises from about 0.001% to about 50%, advantageously from about 0.003% to about 15%, preferably from about 0.01% to about 5% by weight of the compound of the invention based on the weight percentage of the total composition.

The present invention also provides a process for the production of an antibiofouling composition for industrial use. Such process comprises bringing at least one of any industrially acceptable carrier known in the art into intimate admixture with a transcription factor modulating compound of the present invention. The carrier may be any suitable carrier discussed above or known in the art.

The suitable antibiofouling compositions may be in any acceptable form for delivery of the composition to a site potentially having, or having at least one living microbe. The antibiofouling compositions may be delivered with at least one suitably selected carrier as hereinbefore discussed using standard formulations. The mode of delivery may be such as to have a binding inhibiting effective amount of the antibiofouling composition at a site potentially having, or having at least one living microbe. The antibiofouling compositions of the present invention are useful in treating microbial growth that contributes to biofouling, such as scum or slime formation, in these aqueous environments. Examples of industrial processes in which these compounds might be effective include cooling water systems, reverse osmosis membranes, pulp and paper systems, air washer systems and the food processing industry. The antibiofouling composition may be delivered in an amount and form effective for the prevention, removal or termination of microbes.

The antibiofouling composition of the present invention generally comprise at least one compound of the invention. The composition may comprise from about 0.001% to about 50%, more preferably from about 0.003% to about 15%, most preferably from about 0.01% to about 5% by weight of the compound of the invention based on the weight percentage of the total composition.

The amount of antibiofouling composition may be delivered in an amount of about 1 mg/l to about 1000 mg/l, advantageously from about 2 mg/l to about 500 mg/l, and preferably from about 20 mg/l to about 140 mg/l.

Antibiofouling compositions for water treatment generally comprise transcription factor modulating compounds of the invention in amounts from about 0.001% to about 50% by weight of the total composition. Other components in the antibiofouling compositions (used at 0.1% to 50%) may include, for example, 2-bromo-2-nitropropane-1,3-diol (BNPD), β-nitrostyrene (BNS), dodecylguanidine hydrochloride, 2,2-dibromo-3-nitrilopropionamide (DBNPA), glutaraldehyde, isothiazolin, methylene bis(thiocyanate), triazines, n-alkyl dimethylbenzylammonium chloride, trisodium phosphate-based, antimicrobials, tributyltin oxide, oxazolidines, tetrakis (hydroxymethyl)phosphonium sulfate (THPS), phenols, chromated copper arsenate, zinc or copper pyrithione, carbamates, sodium or calcium hypochlorite, sodium bromide, halohydantoins (Br, Cl), or mixtures thereof.

Other possible components in the compositions of the invention include biodispersants (about 0.1% to about 15% by weight of the total composition), water, glycols (about 20-30%) or Pluronic (at approximately 7% by weight of the total composition). The concentration of antibiofouling composition for continuous or semi-continuous use is about 5 to about 70 mg/l.

Antibiofouling compositions for industrial water treatment may comprise compounds of the invention in amounts from about 0.001% to about 50% based on the weight of the total composition. The amount of compound of the invention in antibiofouling compositions for aqueous water treatment may be adjusted depending on the particular environment.

Shock dose ranges are generally about 20 to about 140 mg/l; the concentration for semi-continuous use is about 0.5× of these concentrations.

The invention also pertains, at least in part, to a method of regulating biofilm development. The method includes administering a composition which contains a transcription factor modulating compound of the invention. The composition can also include other components which enhance the ability of the composition to degrade biofilms.

The composition can be formulated as a cleaning product, e.g., a household or an industrial cleaner to remove, prevent, inhibit, or modulate biofilm development. Advantageously, the biofilm is adversely affected by the administration of the compound of the invention, e.g., biofilm development is diminished. These compositions may include compounds such as disinfectants, soaps, detergents, as well as other surfactants. Examples of surfactants include, for example, sodium dodecyl sulfate; quaternary ammonium compounds; alkyl pyridinium iodides; TWEEN 80, TWEEN 85, TRITON X-100; BRIJ 56; biological surfactants; rhamnolipid, surfactin, visconsin, and sulfonates. The composition of the invention may be applied in known areas and surfaces where disinfection is required, including but not limited to drains, shower curtains, grout, toilets and flooring. A particular application is on hospital surfaces and medical instruments. The disinfectant of the invention may be useful as a disinfectant for bacteria such as, but not limited to, Pseudomonadaceae, Azatobacteraceae, Rhizabiaceae, Mthylococcaceae, Halobacteriaceae, Acetobacteraceae, Legionellaceae, Neisseriaceae, and other genera.

The invention also pertains to a method for cleaning and disinfecting contact lenses. The method includes contacting the contact lenses with a solution of at least one compound of the invention in an acceptable carrier. The invention also pertains to the solution comprising the compound, packaged with directions for using the solution to clean contact lenses.

The invention also includes a method of treating medical indwelling devices. The method includes contacting at least one compound of the invention with a medical indwelling device, such as to prevent or substantially inhibit the formation of a biofilm. Examples of medical indwelling devices include catheters, orthopedic devices and implants.

A dentifrice or mouthwash containing the compounds of the invention may be formulated by adding the compounds of the invention to dentifrice and mouthwash formulations, e.g., as set forth in *Remington's Pharmaceutical Sciences,* 18th Ed., Mack Publishing Co., 1990, Chapter 109 (incorporated herein by reference in its entirety). The dentifrice may be formulated as a gel, paste, powder or slurry. The dentifrice may include binders, abrasives, flavoring agents, foaming agents and humectants. Mouthwash formulations are known in the art, and the compounds of the invention may be advantageously added to them.

In one embodiment, the invention pertains to each of the transcription factor modulating compounds described herein in Table 4, Table 5, Table 6, Table 7, Table 8, Table 9, Table 10, Table 11, and in Formulae (I)-(XVII).

The contents of all references, patent applications and patents, cited throughout this application are hereby expressly incorporated by reference. Each reference disclosed herein is incorporated by reference herein in its entirety. Any patent application to which this application claims priority is also incorporated by reference herein in its entirety.

The invention is further illustrated by the following examples, which should not be construed as further limiting.

EXEMPLIFICATION OF THE INVENTION

Example 1

Synthesis of Test Compounds

The transcriptional modulating compounds described in this application can be synthesized by art recognized techniques or using the methods described herein.

6-(2-Amino-phenyl)-3-thioxo-3,4-dihydro-2H-[1,2,4]triazin-5-one

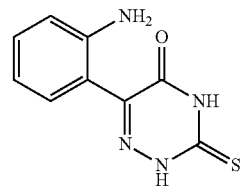 [SMILES: Nc1ccccc1-c1n[nH]c(=S)[nH]c1=O]

This was prepared by a modified literature procedure (Doleschall, G.; Lempert, K. *Tetrahedron* 1973, 29, 639-649). Isatin (10 g, 67.96 mmol) was dissolved in ca. 10% aqueous KOH (9.9 g in 100 mL of water) and then treated with thiosemicarbazide (6.28 g; 68.90 mmol). After 1 hour of heating at 115° C. (bath temperature), the reaction mixture was poured over ice and treated with glacial acetic acid dropwise, till the pH was ca. 5. The yellow fluffy precipitate was filtered, washed copiously with water (8×50 mL) and dried first in air and then under high vacuum to afford 12.9 g of yellow solid.

6-(2-Amino-phenyl)-3-butylsulfanyl-2H-[1,2,4]triazin-5-one

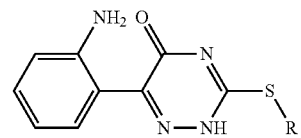

This was prepared by a modified literature procedure (Doleschall, G.; Lempert, K. *Tetrahedron* 1973, 29, 639-649). The product from the previous experiment (8.0 g, 36.3 mmol) was dissolved in ca. 10% aq. KOH (10.3 g in 100 mL of water) and treated with "BuI (7 mL). Ethanol (70 mL) was added to it and the reaction mixture was allowed to stir overnight. The reaction mixture was diluted with ether (100 mL) and water (70 mL). The ether layer was separated and the aqueous layer washed further with ether (3×100 mL) and then poured over ice. Upon careful, drop-wise addition of glacial acetic acid with vigorous stirring at 0-4° C., yellow precipitate was obtained which was filtered, washed with water (4×20 mL) and then with ether (2×10 mL) and dried. Yield: 5.12 g.

Other alkyl or substituted alkyl halides were used instead of n-butyliodide following the similar method.

3-Methylsulfanyl-6-(G)-6,7-dihydro-5-oxa-1,2,4,7-tetraaza-dibenzo[a,c]cycloheptene

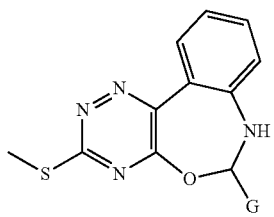

This was prepared by a modified literature procedure (Doleschall, G.; Lempert, K. *Tetrahedron* 1973, 29, 639-649). To a suspension of compound 2 (or analogs of 2) (ca. 0.384 mmol, 1 equiv) in dry ethanol (3-4 mL), 25 µL of glacial acetic acid was added, followed by ca. 1.1 equiv of the corresponding aldehyde (G-CHO, where, G=substituted or unsubstituted aliphatic, aromatic, or heterocyclic groups). The reaction mixture was refluxed for ca. 5-7 min resulting in a dark red—dark-reddish orange solution. Upon cooling to room temperature orange-orange-yellow solid crashed out of solution, which was filtered, washed with cold (ca. −30° C.) methanol (2×1 mL), and/or ether and dried. In some cases, the crude products were recrystallized from DMF/ether or methanol/ether; in most of the cases, the crude products, prepared as above, were >95% pure. Various ketones (GCOG') were reacted with 2 (or analogs of 2) in a similar way to afford compounds of structural type 4. All the final compounds were characterized by means of $^1$H NMR, LC-MS, HPLC ($C_{18}$ columns, acetonitrile/water with 0.01% triethylamine as mobile phase), and CHN analyses.

General Synthesis of Orthoesters, GC(OR)$_3$; R=Me

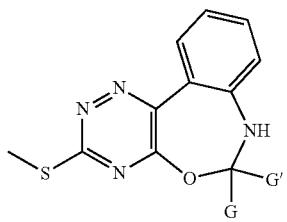

The syntheses of the desired orthoesters were accomplished by a modified literature procedure in multiple steps (McClelland, R. A. et al. *J. Org. Chem.* 1981, 46, 1011-1012). Several novel orthoesters were prepared by this method. To a solution of an acid chloride in dichloromethane, N-methylaniline was added slowly, followed by triethylamine and catalytic amount of 4-dimethylaminopyridine. After stirring it for ca. 12 h, the reaction mixture was diluted with ether, the precipitate was filtered, washed with ether and dried. The amide, thus prepared, was then stirred overnight with methyl triflate in dichloromethane, diluted with ether, and the precipitate was filtered, washed, and dried to obtain an imidatonium triflate salt. This salt was dissolved in dichloromethane, cooled to 0° C., and added slowly, with stirring, to a cold (0° C.) solution of sodium methoxide in dry methanol over a period of ca. 30-60 min. The solvent was evaporated to dryness and the residue was extracted in n-hexane. Upon evaporation of hexane, the white solid was obtained, which was dissolved in dry methanol and treated with glacial acetic acid. After 10 minutes of stirring, the excess acid was neutralized with potassium carbonate (solid), and the solvent removed under vacuum. The residue was extracted in ether, washed with water, and dried over potassium carbonate. The crude material was obtained by evaporation of ether, and further purified either by flash chromatography or fractional distillation.

3-Methylsulfanyl-6-(G)-5-oxa-1,2,4,7-tetraaza-dibenzo[a,c]cycloheptene

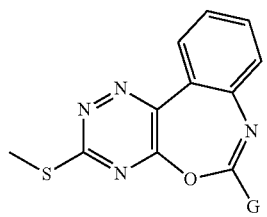

Compound of the type 2 (0.384 mmol, 1 equiv) was suspended in ethanol (2-3 mL), treated with glacial acetic acid (100 µL), followed by an orthoester (2 equiv) of the general formula G-C(OR)$_3$, where G=substituted or unsubstituted aliphatic, aromatic, or heterocyclic group, R=H, substituted or unsubstituted aliphatic, aromatic, or heterocyclic group. The reaction mixture was refluxed for 70-180 minutes, cooled to room temperature. In some cases, the product crashed out of solution, in others, the crude reaction mixture was evaporated to dryness, re-dissolved in a minimum amount of methanol and diluted with ether. The solid was washed with ether (cold, 0-4° C.; 1×1 mL) and dried under vacuum.

4-Iodo-3-nitrothioanisole

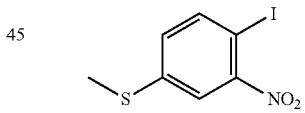

A flask was charged with 10 g of 4-iodothioanisole and 5.5 mL of dimethylsulfate and warmed to ca. 90° C. for 10 min. The resulting solution was dissolved in conc. sulfuric acid (30 mL) and cooled to ca. 0-4° C., whereupon it was treated, with extreme caution, slowly with conc. HNO$_3$ (ca. 2 mL) while maintaining the reaction temperature below 4° C. After stirring it for ca. 10 min, the reaction mixture was stirred at ca. 90° C. for ca. 3 d. The reaction was monitored with HPLC, TLC, and LC-MS, and if needed, smaller portions of nitric acid were added to the reaction mixture to force it to completion. Use of fuming sulfuric acid is also helpful. After the complete consumption of the aromatic starting material, the reaction mixture was cooled, poured over crushed ice, treated with 30% aq. perchloric acid at 4° C. The light colored precipitate was filtered, washed thoroughly with water, and dried under vacuum. The perchlorate salt was stirred with saturated aq. NaCl solution at 95° C. for 3-6 h. Upon cooling to room temperature, the precipitate was filtered, washed thoroughly with water to get rid of any inorganic salts, and dried under vacuum to obtain 4-iodo-3-nitrothioanisole in >80% yield.

4-Iodo-3-aminothioanisole

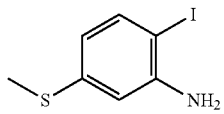

Ca. 7 g of 4-iodo-3-nitrothioanisole was dissolved in absolute ethanol and treated slowly with a solution of $SnCl_2 \cdot 2H_2O$ in 12% aq. HCl. The reaction mixture was stirred at 50° C. for 25-30 min., when the HPLC monitoring indicated that the reaction was complete. The reaction mixture was poured over crushed ice, and treated with aq. NaOH solution to pH 8. The precipitate was filtered, washed with water and dried in air. The crude material was crystallized by overnight cooling (4° C.) of its ethanol (minimum amount) solution treated with 10% aq. HCl. The crystalline material was further dried under high vacuum to afford the desired amine as its hydrochloride salt in >70% yield.

4-Methylsulfanyl-2'-nitro-biphenyl-2-ylamine

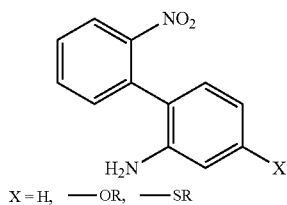

X = H, —OR, —SR

A methanol/dioxane (20 mL/5 mL of methanol/dioxane) solution/suspension of 4-iodo-3-nitrothioanisole (1 mmol), $Pd(OAc)_2$ (0.01 mmol) was purged with argon for ~5 min. To this solution $Et_3N$ (3 mmol), and 5 mL of water were added and purged with argon for another 5 min. To the above solution, 2-aminophenyl boronic acid (2 mmol, solution in 5 ml, of DMF, purged with argon), was added and the reaction mixture was heated at 70° C. (oil bath temperature) for 2 h. The reaction was monitored by HPLC and LC-MS to follow the product formation. The reaction mixture was then cooled down to room temperature and filtered through diatomaceous earth. The filtrate was concentrated and purified using preparative HPLC.

4-Methylsulfanyl-2'-amino-biphenyl-2-ylamine

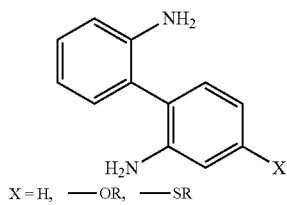

X = H, —OR, —SR

A flask was charged with ca. 1 mmol of 4-Methylsulfanyl-2'-nitro-biphenyl-2-ylamine, 15 mL of ethanol, and 0.1 mmol of $PtO_2$, and stirred under hydrogen atmosphere at 40 psi for 10 minutes. The reaction mixture was filtered through diatomaceous earth, washed with ethanol, and the combined organic layer was evaporated to dryness. The crude material was purified by preparative HPLC. The same material can also be prepared by the previous method, (Suzuki coupling conditions) starting from 4-iodo-3-aminothioanisole, and purified by preparative HPLC.

6-(G)-3-methylsulfanyl-5H-dibenzo[d,f][1,3]diazepine

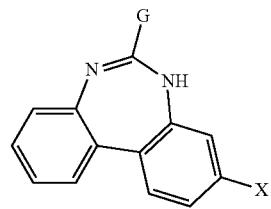

X = H, —OR, —SR

To a solution of the 2,2'-biphenyldiamine (0.093 g; 0.51 mmol) in ethanol (2 mL), were added glacial acetic acid (50 μL) and 2 equiv of an orthoester of the general formula $GC(OR)_3$. In case of TFA salt of the diamine, there was no need of adding acetic acid to the reaction mixture. The reaction mixture was refluxed for 3 h, cooled to room temperature, and evaporated to dryness. The residue was suspended in methanol saturated with dry HCl, stirred for a few minutes, filtered, washed with methanol, and finally with ether. The hydrochloride salt of the diazepine was dried under vacuum to afford a light yellow solid. In order to obtain a free base of the diazepine, the above hydrochloride salt was suspended in methanol, and treated with 10% aq. NaOH solution. After stirring at room temperature for ca. 10 min, the precipitate was filtered, washed with water, and dried under vacuum.

3-(6-Nitro-2-phenyl-benzoimidazol-1-yl)-propionitrile and 3-(5-Nitro-2-phenyl-benzoimidazol-1-yl)-propionitrile

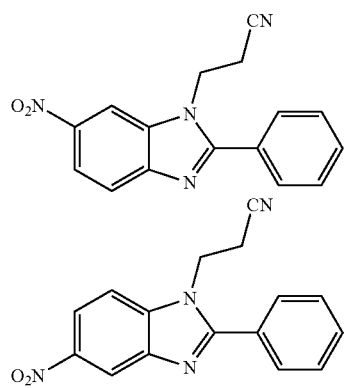

A mixture of 5-nitro-2-phenylbenzimidazole (1 g, 4.2 mmol), acrylonitrile (50 mL) and N,N-dimethylpiridine (25 mg) was heated at 70° C. for 4 hr. The excess of acrylonitrile was evaporated and oily residue was subjected to the flash chromatography on silica gel using hexane-ethyl acetate (75: 25 v/v) as an eluent. Structure of the regioisomers was determined using $^1$H NOESY studies. 0.25 g (20%) of the 6-nitro isomer and 0.23 g (18.9%) of the 5-nitro isomer were obtained.

3-(6-Nitro-2-phenyl-benzoimidazol-1-yl)-propionic acid and 3-(5-Nitro-2-phenyl-benzoimidazol-1-yl)-propionic acid

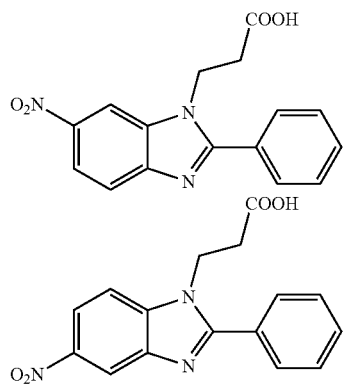

To the 6-nitro nitrile (0.15 g, 0.51 mmol) concentrated HCl (5 mL) was added and resulting mixture was heated at 50° C. for 0.5 hours. The acid was evaporated in vacuo and product was purified by HPLC. Yield 34 mg (21%). An identical procedure was used starting from the 5-nitro nitrile yielding the product (22 mg, 13.8%).

Example 2

In this example, the expression of a selective marker (e.g., ccdB) is put under the direct control of a promoter activated by MarA (e.g., inaA, galT, or micF). In the absence of MarA, the expression of the selective marker is silent and cells survive. Synthesis of MarA from an inducible plasmid in a bacterial or yeast cell leads to the activation of the inaA promoter, expression of ccdB, and subsequently results in cell death. Compounds that inhibit MarA are those that permit cell survival under conditions of MarA expression. The results of this assay are given in Table 4. In Table 4, * indicates good inhibition of MarA and ** indicates very good inhibition of MarA.

Example 3

In this example, the expression of luciferase is put under the direct control of a promoter activated by MarA (e.g., inaA, galT, or micF) in a cell constitutively expressing MarA. In the absence of MarA, cells luminesce. Upon modulating of MarA activity, the expression of the reporter is altered.

TABLE 4

| ID | Structure | Name | Affinity |
|---|---|---|---|
| A | 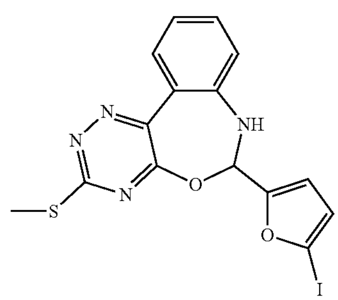 [SMILES: CSc1nnc2c(n1)OC(c1ccc(I)o1)Nc1ccccc1-2] | 6-(5-Iodo-furan-2-yl)-3-methylsulfanyl-6,7-dihydro-5-oxa-1,2,4,7-tetraaza-dibenzo[a,c]cycloheptene | ** |
| B | 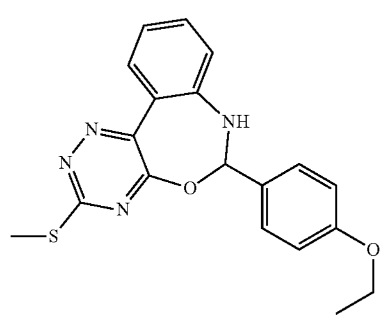 [SMILES: CCOc1ccc(C2Nc3ccccc3-c3nnc(SC)nc3O2)cc1] | 6-(4-Ethoxy-phenyl)-3-methylsulfanyl-6,7-dihydro-5-oxa-1,2,4,7-tetraaza-dibenzo[a,c]cycloheptene | * |

TABLE 4-continued

| ID | Structure | Name | Affinity |
|---|---|---|---|
| C | 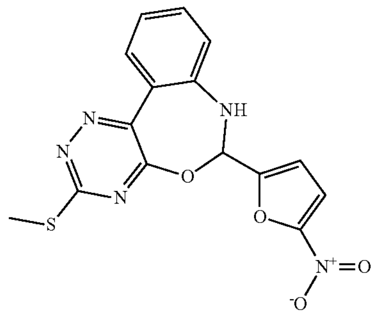 | 3-Methylsulfanyl-6-(5-nitro-furan-2-yl)-6,7-dihydro-5-oxa-1,2,4,7-tetraaza-dibenzo[a,c]cycloheptene | * |
| D | 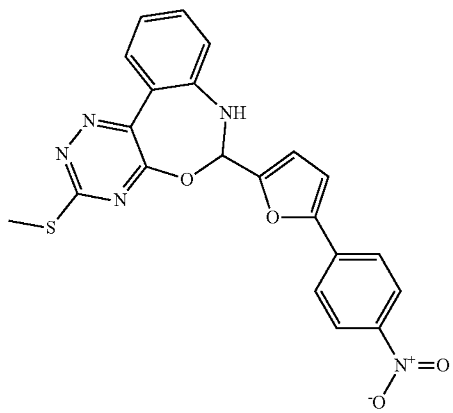 | 3-Methylsulfanyl-6-[5-(4-nitro-phenyl)-furan-2-yl]-6,7-dihydro-5-oxa-1,2,4,7-tetraaza-dibenzo[a,c]cycloheptene | * |
| E | 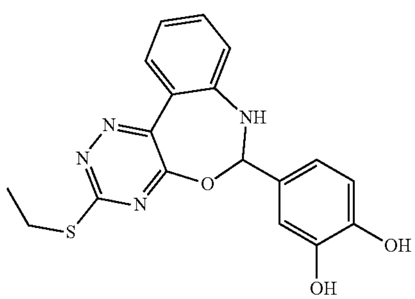 [SMILES: CCSc1nnc2c(n1)OC(c1ccc(O)c(O)c1)Nc1ccccc1-2] | 4-(3-Ethylsulfanyl-6,7-dihydro-5-oxa-1,2,4,7-tetraaza-dibenzo[a,c]cyclohepten-6-yl)-benzene-1,2-diol | * |
| F | 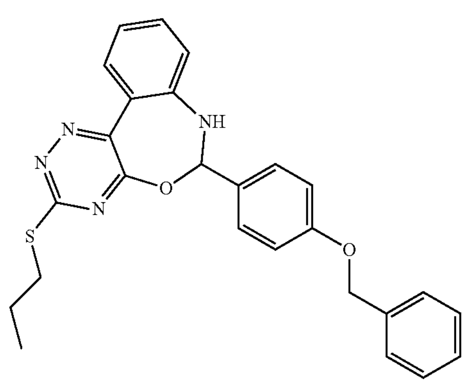 [SMILES: CCCSc1nnc2c(n1)OC(c1ccc(OCc3ccccc3)cc1)Nc1ccccc1-2] | 6-(4-Benzyloxy-phenyl)-3-propylsulfanyl-6,7-dihydro-5-oxa-1,2,4,7-tetraaza-dibenzo[a,c]cycloheptene | ** |

TABLE 4-continued

| ID | Structure | Name | Affinity |
|---|---|---|---|
| G | 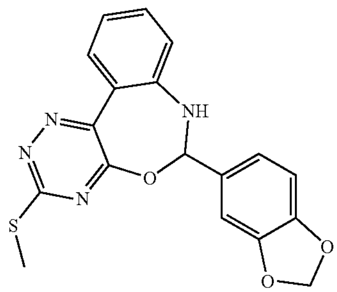 [SMILES: CSc1nnc2c(n1)OC(c1ccc3c(c1)OCO3)Nc1ccccc1-2] | 6-Benzo[1,3]dioxol-5-yl-3-methylsulfanyl-6,7-dihydro-5-oxa-1,2,4,7-tetraaza-dibenzo[a,c]cycloheptene | ??? |
| H | 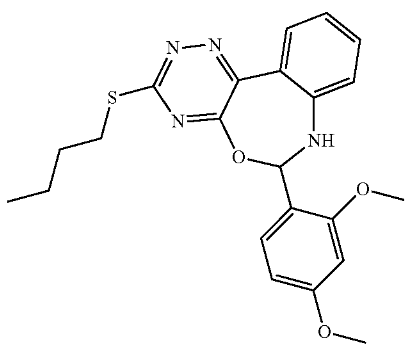 [SMILES: CCCCSc1nnc2c(n1)OC(c1ccc(OC)cc1OC)Nc1ccccc1-2] | 3-Butylsulfanyl-6-(2,4-dimethoxy-phenyl)-6,7-dihydro-5-oxa-1,2,4,7-tetraaza-dibenzo[a,c]cycloheptene | * |
| I | 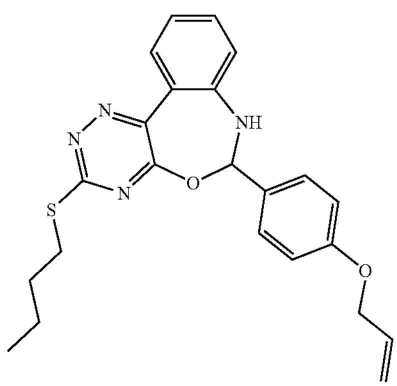 [SMILES: C=CCOc1ccc(C2Nc3ccccc3-c3nnc(SCCCC)nc3O2)cc1] | 6-(4-Allyloxy-phenyl)-3-butylsulfanyl-6,7-dihydro-5-oxa-1,2,4,7-tetraaza-dibenzo[a,c]cycloheptene | ** |
| J | 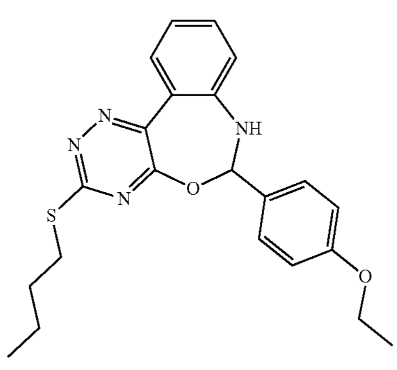 [SMILES: CCCCSc1nnc2c(n1)OC(c1ccc(OCC)cc1)Nc1ccccc1-2] | 3-Butylsulfanyl-6-(4-ethoxy-phenyl)-6,7-dihydro-5-oxa-1,2,4,7-tetraaza-dibenzo[a,c]cycloheptene | * |

TABLE 4-continued

| ID | Structure | Name | Affinity |
|---|---|---|---|
| K | 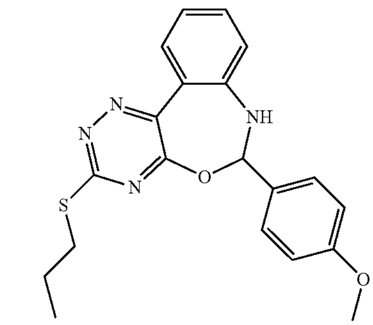 [SMILES: CCCSc1nnc2c(n1)OC(c1ccc(OC)cc1)Nc1ccccc1-2] | 6-(4-Methoxy-phenyl)-3-propylsulfanyl-6,7-dihydro-5-oxa-1,2,4,7-tetraaza-dibenzo[a,c]cycloheptene | * |
| L | 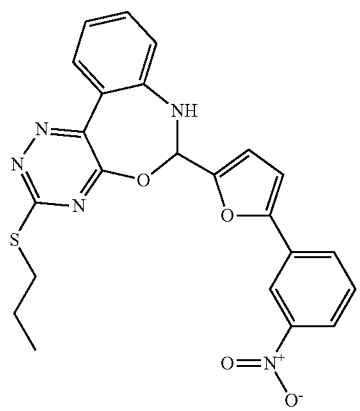 [SMILES: CCCSc1nnc2c(n1)OC(c1ccc(-c3cccc([N+](=O)[O-])c3)o1)Nc1ccccc1-2] | 6-[5-(3-Nitro-phenyl)-furan-2-yl]-3-propylsulfanyl-6,7-dihydro-5-oxa-1,2,4,7-tetraaza-dibenzo[a,c]cycloheptene | ** |
| M | 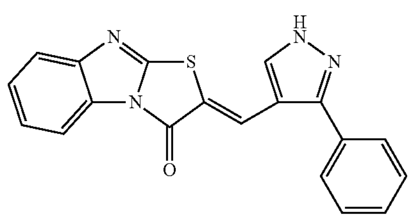 [SMILES: O=c1/c(=C/c2c[nH]nc2-c2ccccc2)sc2nc3ccccc3n12] | 2-(3-Phenyl-1H-pyrazol-4-ylmethylene)-benzo[4,5]imidazo[2,1-b]thiazol-3-one | ** |
| N | 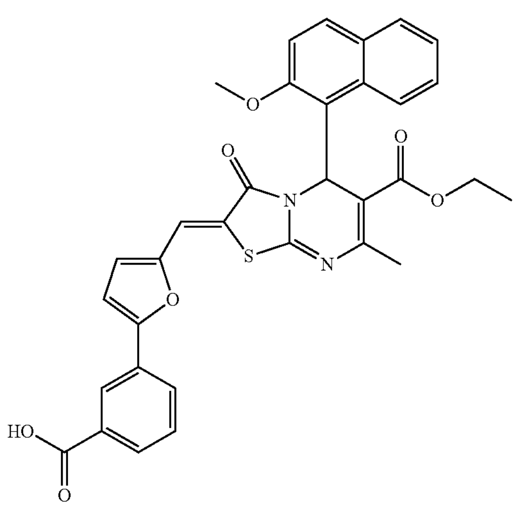 [SMILES: CCOC(=O)C1=C(C)N=c2s/c(=C\c3ccc(-c4cccc(C(=O)O)c4)o3)c(=O)n2C1c1c(OC)ccc2ccccc12] | 2-[5-(3-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester | ** |

TABLE 4-continued

| ID | Structure | Name | Affinity |
|---|---|---|---|
| O | 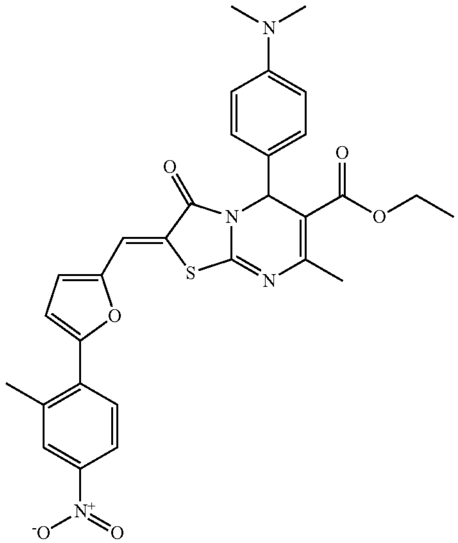 | 5-(4-Dimethylamino-phenyl)-7-methyl-2-[5-(2-methyl-4-nitro-phenyl)-furan-2-ylmethylene]-3-oxo-2,3-dihydro-5H-thiazolo[3,2-a]pyrimidine-6-carboxylic acid ethyl ester | *** |
| P | 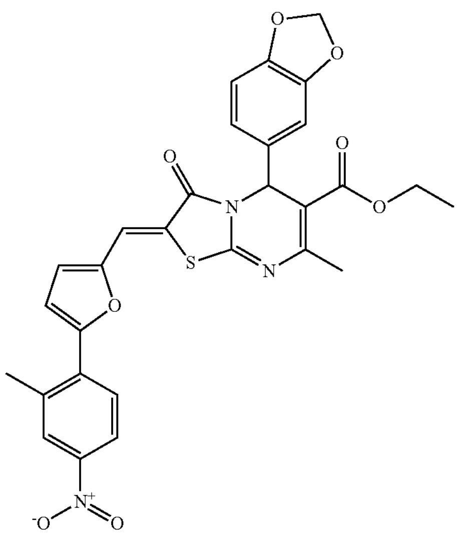 | 5-Benzo[1,3]dioxol-5-yl-7-methyl-2-[5-(2-methyl-4-nitro-phenyl)-furan-2-ylmethylene]-3-oxo-2,3-dihydro-5H-thiazolo[3,2-a]pyrimidine-6-carboxylic acid ethyl ester | * |
| Q | 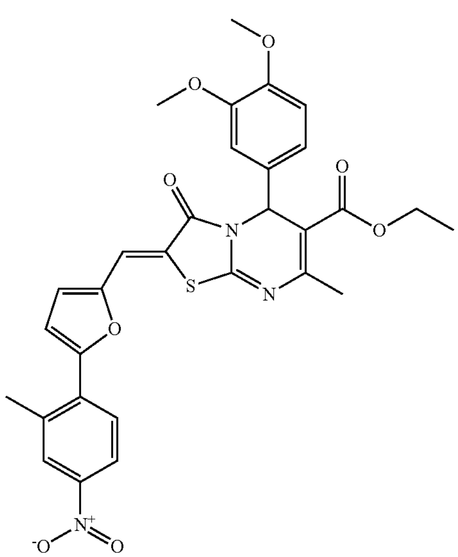 | 5-(3,4-Dimethoxy-phenyl)-7-methyl-2-[5-(2-methyl-4-nitro-phenyl)-furan-2-yl methylene]-3-oxo-2,3-dihydro-5H-thiazolo[3,2-a]pyrimidine-6-carboxylic acid ethyl ester | *** |

TABLE 4-continued

| ID | Structure | Name | Affinity |
|---|---|---|---|
| R | 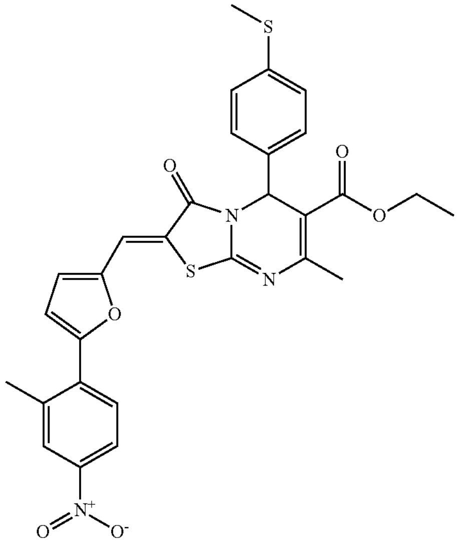 | 7-Methyl-2-[5-(2-methyl-4-nitro-phenyl)-furan-2-ylmethylene]-5-(4-methylsulfanyl-phenyl)-3-oxo-2,3-dihydro-5H-thiazolo[3,2-a]pyrimidine-6-carboxylic acid ethyl ester | *** |
| S | 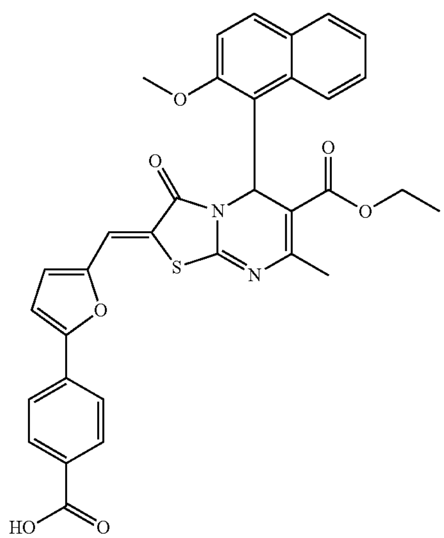 [SMILES: CCOC(=O)C1=C(C)N=c2s/c(=C\c3ccc(-c4ccc(C(=O)O)cc4)o3)c(=O)n2C1c1c(OC)ccc2ccccc12] | 2-[5-(4-Carboxy-phenyl)-furan-2-ylmethylene]-5-(2-methoxy-naphthalen-1-yl)-7-methyl-3-oxo-2,3-dihydro-5H-thiazolo[3,2-a]pyrimidine-6-carboxylic acid ethyl ester | *** |
| T | 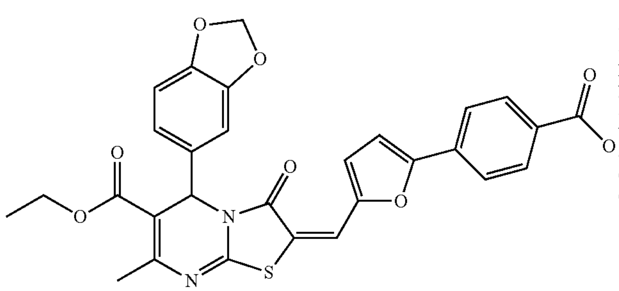 [SMILES: CCOC(=O)C1=C(C)N=c2s/c(=C/c3ccc(-c4ccc(C(=O)O)cc4)o3)c(=O)n2C1c1ccc2c(c1)OCO2] | 5-Benzo[1,3]dioxol-5-yl-2-[5-(4-ethoxycarbonyl-phenyl)-furan-2-ylmethylene]-7-methyl-3-oxo-2,3-dihydro-5H-thiazolo[3,2-a]pyrimidine-6-carboxylic acid ethyl ester | *** |
| U | 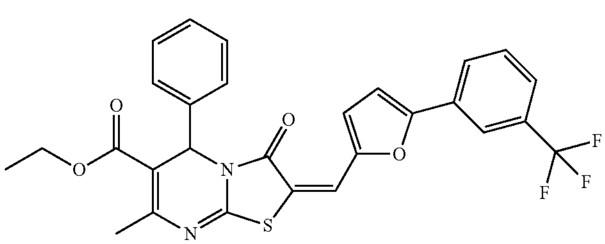 [SMILES: CCOC(=O)C1=C(C)N=c2s/c(=C/c3ccc(-c4cccc(C(F)(F)F)c4)o3)c(=O)n2C1c1ccccc1] | 7-Methyl-3-oxo-5-phenyl-2-[5-(3-trifluoromethyl-phenyl)-furan-2-ylmethylene]-2,3-dihydro-5H-thiazolo[3,2-a]pyrimidine-6-carboxylic acid ethyl ester | ** |

TABLE 4-continued

| ID | Structure | Name | Affinity |
|---|---|---|---|
| V | 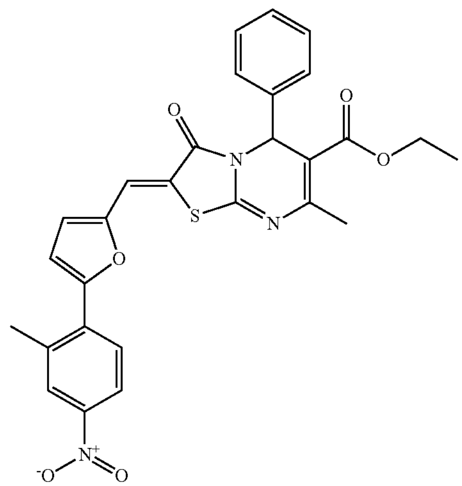 | 7-Methyl-2-[5-(2-methyl-4-nitro-phenyl)-furan-2-ylmethylene]-3-oxo-5-phenyl-2,3-dihydro-5H-thiazolo[3,2-a]pyrimidine-6-carboxylic acid ethyl ester | *** |
| W | 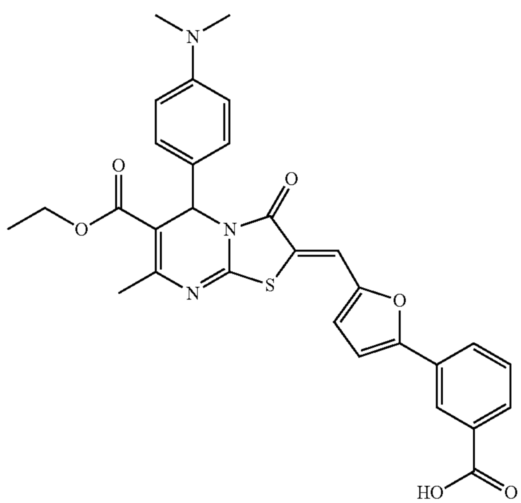 [SMILES: CCOC(=O)C1=C(C)N=c2s/c(=C\c3ccc(-c4cccc(C(=O)O)c4)o3)c(=O)n2C1c1ccc(N(C)C)cc1] | 2-[5-(3-Carboxy-phenyl)-furan-2-ylmethylene]-5-(4-dimethylamino-phenyl)-7-methyl-3-oxo-2,3-dihydro-5H-thiazolo[3,2-a]pyrimidine-6-carboxylic acid ethyl ester | ** |
| X | 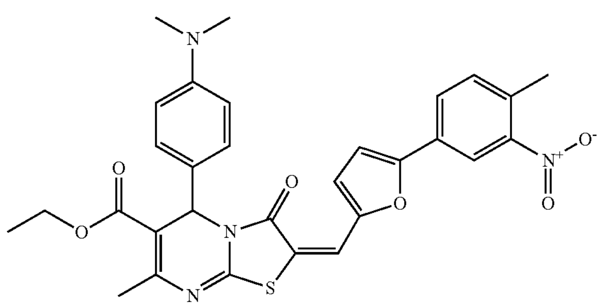 [SMILES: CCOC(=O)C1=C(C)N=c2s/c(=C/c3ccc(-c4ccc(C)c([N+](=O)[O-])c4)o3)c(=O)n2C1c1ccc(N(C)C)cc1] | 5-(4-Dimethylamino-phenyl)-7-methyl-2-[5-(4-methyl-3-nitro-phenyl)-furan-2-ylmethylene]-3-oxo-2,3-dihydro-5H-thiazolo[3,2-a]pyrimidine-6-carboxylic acid ethyl ester | ** |

TABLE 4-continued
| ID | Structure | Name | Affinity |
|---|---|---|---|
| Y | 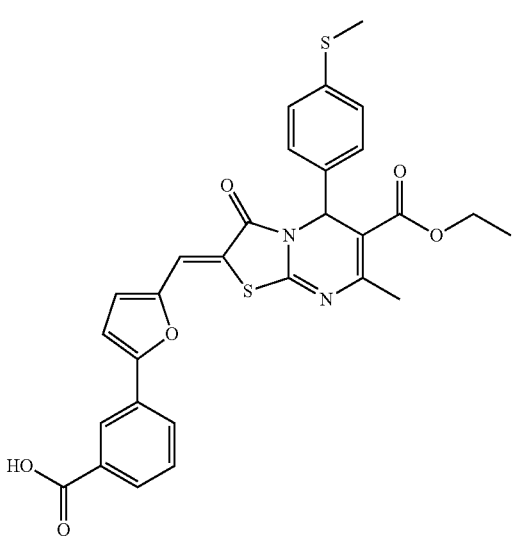 [SMILES: CCOC(=O)C1=C(C)N=c2s/c(=C\c3ccc(-c4cccc(C(=O)O)c4)o3)c(=O)n2C1c1ccc(SC)cc1] | 2-[5-(3-Carboxy-phenyl)-furan-2-ylmethylene]-7-methyl-5-(4-methylsulfanyl-phenyl)-3-oxo-2,3-dihydro-5H-thiazolo[3,2-a]pyrimidine-6-carboxylic acid ethyl ester | *** |
| Z | 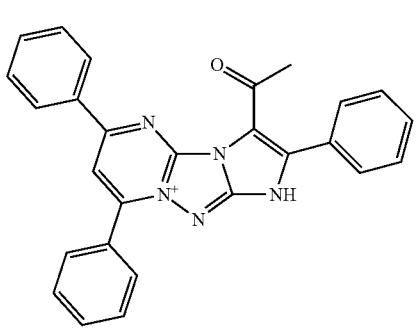 [SMILES: CC(=O)c1c(-c2ccccc2)[nH]c2n[n+]3c(-c4ccccc4)cc(-c4ccccc4)nc3n12] | [1,2]Naphthoquinone 1-[O-(6-oxo-6H-anthra[1,9-cd]isoxazol-5-yl)-oxime] | * |
| AA | 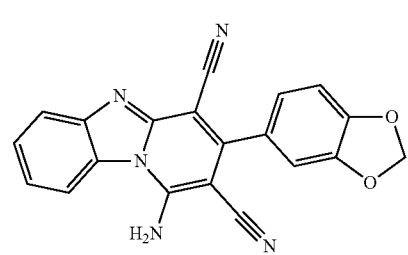 | 3-Acetyl-2,5,7-triphenyl-1H-1,3a,4,8-tetraaza-7a-azonia-cyclopenta[a]indene | *** |
| AB | 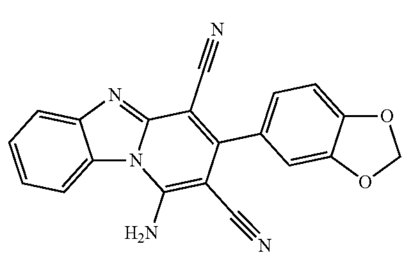 [SMILES: N#Cc1c(-c2ccc3c(c2)OCO3)c(C#N)c2nc3ccccc3n2c1N] | 1-Amino-3-benzo[1,3]dioxol-5-yl-benzo[4,5]imidazo[1,2-a]pyridine-2,4-dicarbonitrile | ** |

TABLE 4-continued

| ID | Structure | Name | Affinity |
|---|---|---|---|
| AC | 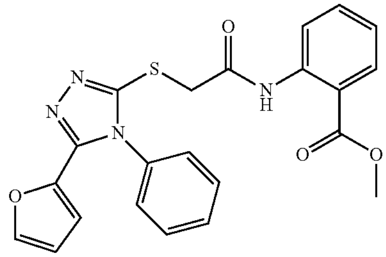 [SMILES: COC(=O)c1ccccc1NC(=O)CSc1nnc(-c2ccco2)n1-c1ccccc1] | 2-[2-(5-Furan-2-yl-4-phenyl-4H-[1,2,4]triazol-3-ylsulfanyl)-acetylamino]-benzoic acid methyl ester | * |
| AD | 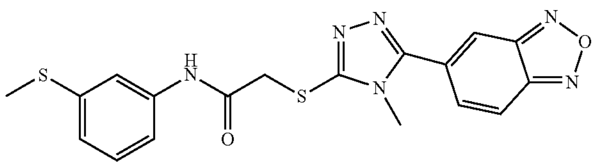 [SMILES: CSc1cccc(NC(=O)CSc2nnc(-c3ccc4nonc4c3)n2C)c1] | 6,7-Dimethyl-2-(3-phenyl-1H-pyrazol-4-ylmethylene)-benzo[4,5]imidazo[2,1-b]thiazol-3-one | * |
| AE | 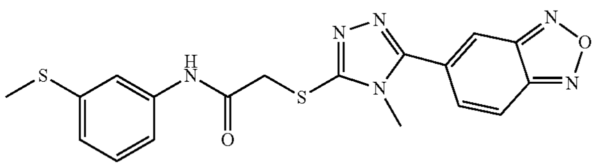 [SMILES: CSc1cccc(NC(=O)CSc2nnc(-c3ccc4nonc4c3)n2C)c1] | 2-(5-Benzo[1,2,5]oxadiazol-5-yl-4-methyl-4H-[1,2,4]triazol-3-ylsulfanyl)-N-(3-methylsulfanyl-phenyl)-acetamide | * |
| AF | 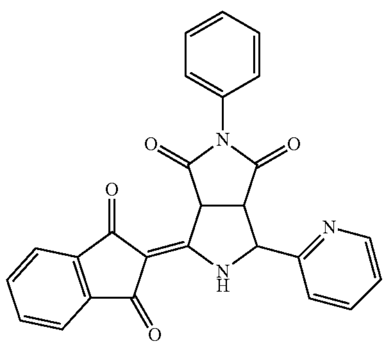 [SMILES: O=C1C(=C2NC(c3ccccn3)C3C(=O)N(c4ccccc4)C(=O)C23)C(=O)c2ccccc21] | 4-(1,3-Dioxo-indan-2-ylidene)-2-phenyl-6-pyridin-2-yl-tetrahydro-pyrrolo[3,4-c]pyrrole-1,3-dione | ** |
| AG | 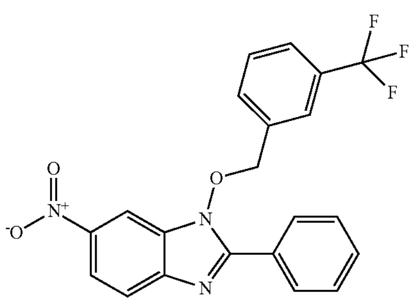 | 6-Nitro-2-phenyl-1-(3-trifluoromethyl-benzyloxy)-1H-benzoimidazole | ** |
| AH | 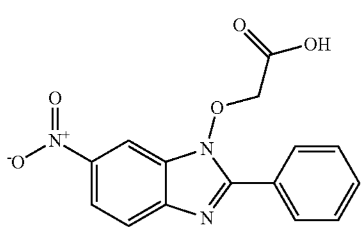 | (6-Nitro-2-phenyl-benzoimidazol-1-yloxy)-acetic acid | ** |

TABLE 4-continued

| ID | Structure | Name | Affinity |
|----|-----------|------|----------|
| AI | 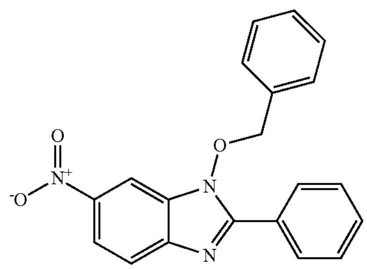 | 1-Benzyloxy-6-nitro-2-phenyl-1H-benzoimidazole | ** |
| AJ | 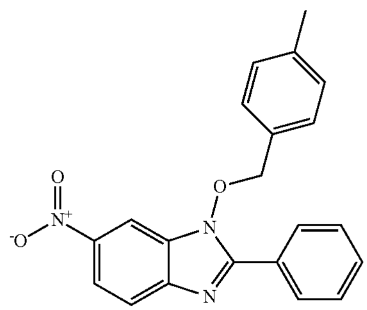 | 1-(4-Methyl-benzyloxy)-6-nitro-2-phenyl-1H-benzoimidazole | * |
| AK | 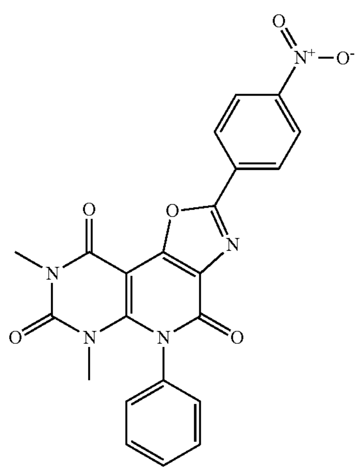 [SMILES: Cn1c(=O)c2c3oc(-c4ccc([N+](=O)[O-])cc4)nc3c(=O)n(-c3ccccc3)c2n(C)c1=O] | 6,8-Dimethyl-2-(4-nitro-phenyl)-5-phenyl-5H,6H-1-oxa-3,5,6,8-tetraaza-cyclopenta[a]naphthalene-4,7,9-trione | ** |
| AL | 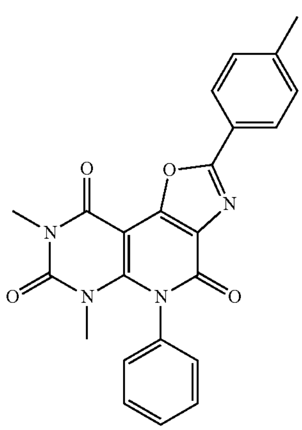 | 6,8-Dimethyl-5-phenyl-2-p-tolyl-5H,6H-1-oxa-3,5,6,8-tetraaza-cyclopenta[a]naphthalene-4,7,9-trione | * |

| ID | Structure | Name | Affinity |
| --- | --- | --- | --- |
| AM | 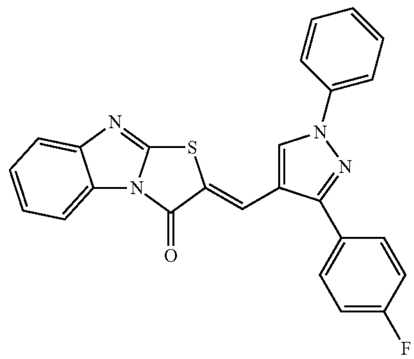 [SMILES: O=c1/c(=C/c2cn(-c3ccccc3)nc2-c2ccc(F)cc2)sc2nc3ccccc3n12] | 2-[3-(4-Fluoro-phenyl)-1-phenyl-1H-pyrazol-4-ylmethylene]-benzo[4,5]imidazo[2,1-b]thiazol-3-one | ** |
| AN | 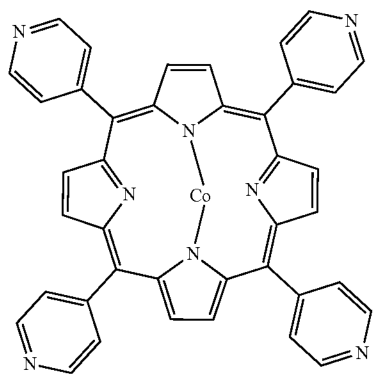 | Cobalt 5,10,15,20-Tetra-pyridin-4-yl-porphyrine | *** |
| AO | 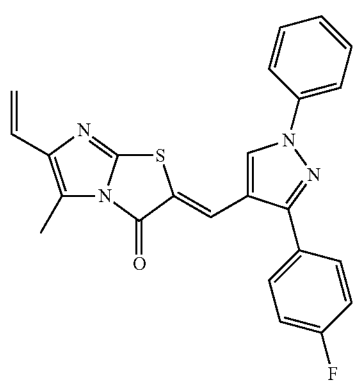 [SMILES: C=Cc1nc2s/c(=C\c3cn(-c4ccccc4)nc3-c3ccc(F)cc3)c(=O)n2c1C] | 2-[3-(4-Fluoro-phenyl)-1-phenyl-1H-pyrazol-4-ylmethylene]-5-methyl-6-vinyl-imidazo[2,1-b]thiazol-3-one | ** |
| AP | 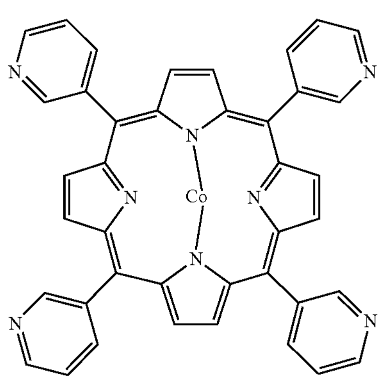 | Cobalt 5,10,15,20-Tetra-pyridin-3-yl-porphyrine | *** |

TABLE 4-continued
| ID | Structure | Name | Affinity |
|---|---|---|---|
| AQ | 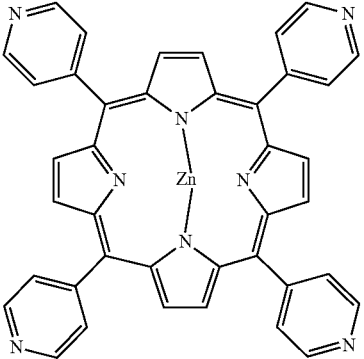 | Zinc 5,10,15,20-Tetra-pyridin-4-yl-porphyrine | *** |
| AR | 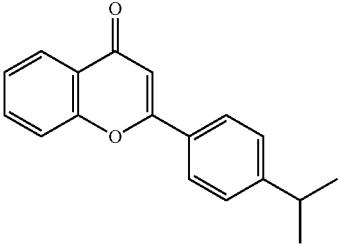 [SMILES: CC(C)c1ccc(-c2cc(=O)c3ccccc3o2)cc1] | 2-(4-isopropylphenyl)-4H-chromen-4-one | *** |
| AS | 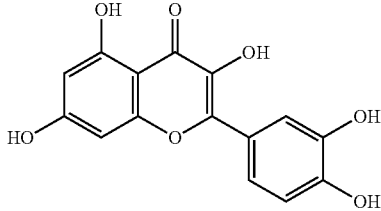 [SMILES: O=c1c(O)c(-c2ccc(O)c(O)c2)oc2cc(O)cc(O)c12] | 2-(3,4-Dihydroxy-phenyl)-3,5,7-trihydroxy-chromen-4-one (luteolin) | *** |
| AT | 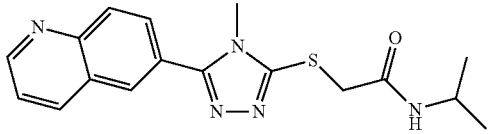 [SMILES: CC(C)NC(=O)CSc1nnc(-c2ccc3ncccc3c2)n1C] | N-isopropyl-2-[(4-methyl-5-quinolin-6-yl-4H-1,2,4-triazol-3-yl)thio]acetamide | *** |
| AU | 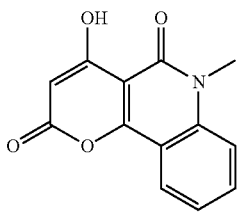 [SMILES: Cn1c(=O)c2c(O)cc(=O)oc2c2ccccc21] | 4-hydroxy-6-methyl-5,6-dihydro-2H-pyrano[3,2-c]quinoline-2,5-dione | *** |
| AV | 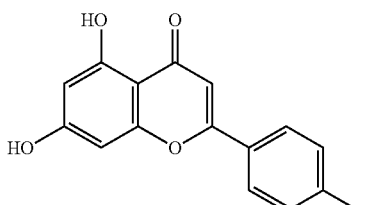 | 5,7-Dihydroxy-2-(4-hydroxy-phenyl)-chromen-4-one | *** |

TABLE 4-continued

| ID | Structure | Name | Affinity |
| --- | --- | --- | --- |
| AW | 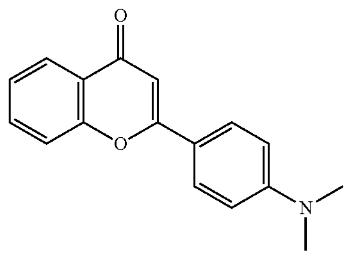 [SMILES: CN(C)c1ccc(-c2cc(=O)c3ccccc3o2)cc1] | 2-[4-(dimethylamino)phenyl]-4H-chromen-4-one | ** |
| AX | 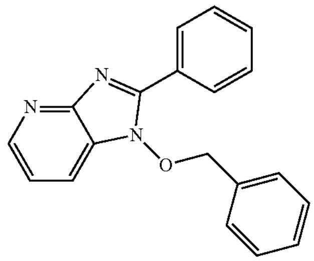 [SMILES: c1ccc(COn2c(-c3ccccc3)nc3ncccc32)cc1] | 1-(benzyloxy)-2-phenyl-1H-imidazo[4,5-b]pyridine | ** |
| AY | 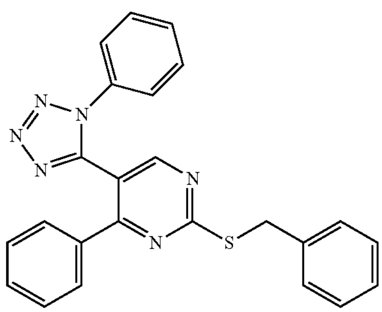 [SMILES: c1ccc(CSc2ncc(-c3nnnn3-c3ccccc3)c(-c3ccccc3)n2)cc1] | 2-(benzylthio)-4-phenyl-5-(1-phenyl-1H-1,2,3,4-tetraazol-5-yl)pyrimidine | ** |
| AZ | 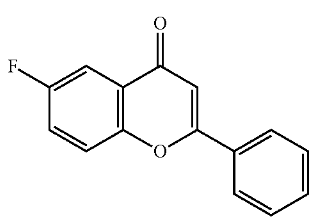 [SMILES: O=c1cc(-c2ccccc2)oc2ccc(F)cc12] | 6-fluoro-2-phenyl-4H-chromen-4-one | ** |
| BA | 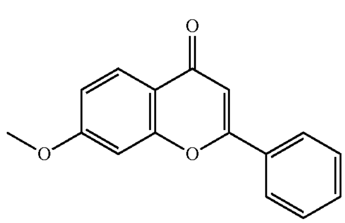 [SMILES: COc1ccc2c(=O)cc(-c3ccccc3)oc2c1] | 7-methoxy-2-phenyl-4H-chromen-4-o | |

TABLE 4-continued

| ID | Structure | Name | Affinity |
|---|---|---|---|
| BB | 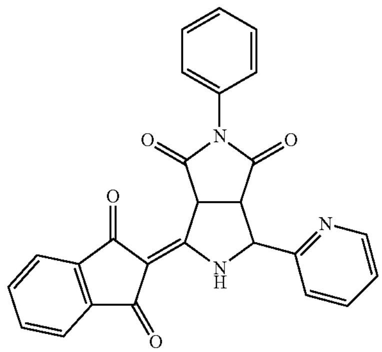 [SMILES: O=C1C(=C2NC(c3ccccn3)C3C(=O)N(c4ccccc4)C(=O)C23)C(=O)c2ccccc21] | 4-(1,3-dioxo-1,3-dihydro-2H-inden-2-yliden)-2-phenyl-6-(2-pyridinyl)tetrahydro pyrrolo[3,4-c]pyrrole-1,3(2H,3aH)-dione | * |
| BC | 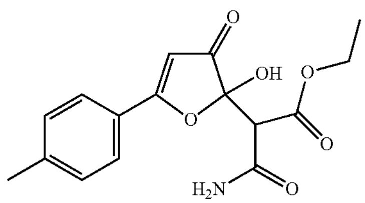 [SMILES: CCOC(=O)C(C(N)=O)C1(O)OC(c2ccc(C)cc2)=CC1=O] | 2-(2-Hydroxy-3-oxo-5-p-tolyl-2,3-dihydro-furan-2-yl)-malonamic acid ethyl ester | * |
| BD | 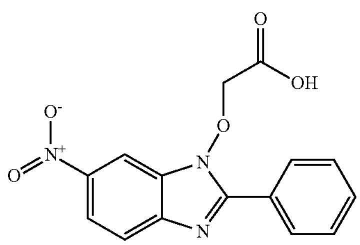 [SMILES: O=C(O)COn1c(-c2ccccc2)nc2ccc([N+](=O)[O-])cc21] | 2-[(6-nitro-2-phenyl-1H-1,3-benzimidazol-1-yl)oxy]acetic acid | * |
| BE | 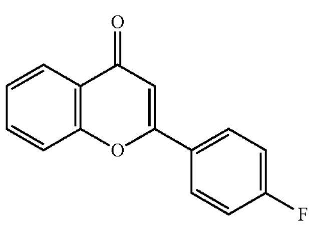 [SMILES: O=c1cc(-c2ccc(F)cc2)oc2ccccc12] | 2-(4-fluorophenyl)-4H-chromen-4-one | * |
| BF | 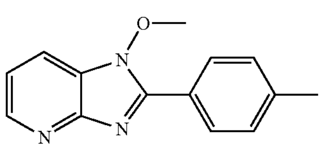 [SMILES: COn1c(-c2ccc(C)cc2)nc2ncccc21] | 1-methoxy-2-(4-methyl phenyl)-1H-imidazo[4,5-b]pyridine | * |
| BG | 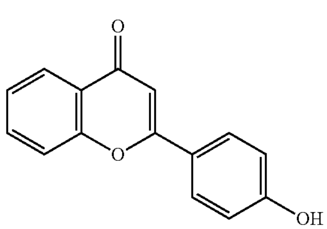 [SMILES: O=c1cc(-c2ccc(O)cc2)oc2ccccc12] | 2-(4-hydroxyphenyl)-4H-chromen-4-one | * |

Example 4

In this example, the expression of a selective marker (e.g., ccdB) is put under the direct control of a promoter repressed by MarA (e.g., fecA, purA, guaB). Under conditions of constitutive MarA synthesis (e.g., using a constitutive mar (mar$^c$) mutant), the expression of ccdB is silent. Following inactivation of MarA, the synthesis of ccdB results in cell death.

Example 5

In this example, the expression of a selective marker (e.g., URA3) is put under the direct control of a promoter repressed by MarA (e.g., fecA, purA, guaB). Under conditions of constitutive MarA synthesis (e.g., using a constitutive mar (mar$^c$) mutant), the expression of URA3 is silent. Following inactivation of MarA, and in the presence of 5-FOA the synthesis of URA3 results in cell death.

Example 6

In this example, a purine or guanine heterotroph is constructed by inactivation of either of the chromosomal guaB or purA genes in E. coli. The guaB or purA gene is then placed into a suitable vector under the control of its natural promoter and transformed into the heterotrophic host.

Example 7

E. coli Biofilm Assay

The biofilm assay screens test compounds for their ability to inhibit bacteria from forming a biofilm.
Materials:
The M9 media ("M9") contained M9, casamino acids, and glucose. The test compound was dissolved in 10 mg/mL DMSO stock solution.
Method:
Preparation of Inoculum
Inoculum was started the day of the experiment by adding a colony or glycerol stock stab to 2 mL M9. The tube was placed in the 37° C. shaker incubator for approximately 4-6 hours. This inoculum was referred to as the "Starter inoculum." The inoculum was then removed from the shaker incubator and diluted to $1 \times 10^6$ cells/mL in M9.
Preparation of Controls
Typically, there were eight of each control, including a positive and negative control. For both the positive and negative controls, 2.5 µL of DMSO was added to 200 µL of M9. 25 µL of the diluted DMSO was added to 50 µL of M9 in the assay plate.
Preparation of Test Compounds
The test compounds were screened at 20 µg/mL. 2.5 µL of the test compound were taken from a plate containing 10 mg/mL stock and added to 200 µL of M9 and mixed. 25 µL of the diluted test compound was added to 50 µL of M9 in the assay plate. The resulting concentration of the test compound was 40 µg/mL
Preparation of Plate
75 µL of the inoculum at $1 \times 10^6$ cells/mL was added to each well containing compound and the positive controls. 75 µL M9 was added to the negative controls. The final concentration of the test compound was 20 µg/mL and the final concentration of the inoculum was $2 \times 10^5$ cells/mL. The plates were then placed in a microplate reader (Wallac Victor$^2$V) and read OD$_{535}$ ("Initial growth reading"). The plates were then placed in an incubator overnight at 35° C. In the morning, the plates were read in a microplate reader at OD$_{535}$ ("Final growth reading.")
Addition of Crystal Violet
The inoculum was then removed from the wells and the plates were washed several times with tap water. 150 µL of Crystal Violet (0.02% Crystal Violet dissolved in water) was then added to each well.
Addition of Ethanol
The crystal violet was then removed and the plates were washed several times with tap water. 150 µL of ethanol were then added to each well, after mixing. The plates were then placed in a microplate reader and read the OD$_{535}$. This was referred to as the "Crystal Violet" reading.

Data Analysis
To determine whether a test compound inhibited growth, the Initial growth reading was subtracted from the Final growth reading ("Subtracted Growth"). The same was done for the positive controls and averaged. The % inhibition of growth was determined by the following formula:

100−(100*Subtracted growth of sample/Average growth of Pos Controls)

To determine whether a test compound inhibited Biofilm formation, the % Inhibition of Biofilm Formation was determined using the following formula:

100−(100*Crystal Violet read of sample/Average crystal violet read of Pos Controls)

The results from the Crystal Violet assay are summarized in Table 5. In Table 5, ND indicates that a given compound did not inhibit biofilm formation in the CV assay. * indicates that the test compound inhibited some biofilm formation and ** indicates that the compound inhibited the formation of a biofilm well.

Example 8

LANCE Screening Assay for Inhibitors of MarA, SoxS, or Rob DNA-Binding

This example describes a method for the identification of test compounds that inhibit the interactions of purified transcription factor such as MarA, SoxS and/or Rob with a target DNA sequence in an in vitro system. Such molecules will hopefully be able to inhibit this interaction in vivo, leading to inhibition of transcriptional regulation by these factors and ultimately in inhibition of the drug resistance and/or virulence phenotypes associated with MarA, SoxS and Rob.
Materials
The 6His-tagged MarA, SoxS and Rob purified according to respective protocol. The N-term-biotinylated double-stranded DNA has a sequence of CCG ATT TAG CAA AAC GTG GCA TCG GTC (SEQ ID NO. 5). The antibody used was the LANCE Eu-labeled anti-6×His Antibody (Eu-αHis) (Perkin Elmer cat # AD0110) which had at least 6 Europium molecules per antibody. Streptavidin conjugated to SureLight™-Allophycocyanin (SA-APC) was obtained from Perkin Elmer (cat # CR130-100). The Assay buffer contained 20 mM Hepes pH 7.6, 1 mM EDTA, 10 mM (NH$_4$)$_2$SO$_4$, and 30 mM KCl, and 0.2% Tween-20.
Method
The plates or vials of the compounds to be tested were thawed. These stocks were at a concentration of 10 mg/ml in DMSO. The solutions were allowed to thaw completely, and the plates were briefly shaken on the Titermix to redissolve any precipitated compound. Thawed aliquots of MarA, SoxS and Rob protein from the stock stored at −80° C. and 1M stock of dithiothreitol stored at −20° C. were then placed on ice.

Dilutions at 1:100 of the compounds were made into a fresh 96-well polystyrene plate. The dilutions were prepared with 100% DMSO to give a final concentration of 100 µg/ml solutions. The dilutions were vortexed on a Titermix.

Fresh DTT was added to 25-50 mL of assay buffer to produce a 1 mM final concentration. Next, 90 µl of assay buffer was added to each of the 10 µl protein aliquots, and the solution was mixed by pipetting. These proteins were diluted to give the required amount of each of the diluted proteins, resulting in 20 µl of diluted protein per well. In preparing the solutions, 20% excess was made to allow enough for control wells. Typically, depending on the protein preps and the initial binding curves that were performed, 1000-2000 fmoles of each protein was required per well. The diluted protein solutions were the placed on ice.

Three tests plates per plate of compound (for MarA, SoxS and Rob) were prepared. Using a multichannel pipet, 5 μl of the compound was added to each well. 5 μl of DMSO was added to the blank and control wells, and 5 μl of the control inhibitor was added to the respective wells.

Using the multichannel pipet, 20 μl of protein was added to all wells except those designated "blank". To these blank wells, 20 μl of assay buffer was added. The plates were covered with a plate sealer and incubated at room temperature, shaking on the Titermix, for 30 minutes.

Next, the DNA solution was prepared, with enough for at least 20% more wells than were tested. 15 μl (0.4 fmoles) was added per well. Then the DNA was diluted in assay buffer, and vortexed briefly to mix. The plate sealer was removed, and 15 μl of DNA solution was added to all of the wells. the plates were then resealed, and returned to the Titermix for a further 30 minutes.

After 25 minutes, the antibody solution was prepared. 0.4 fmoles of SA-APC and 0.125 fmoles of Eu-αHis were added per well in a total volume of 10 μl. Amounts were prepared sufficient for at least 20% excess. The plate sealer was the removed and 10 μl of antibody solution was added to every well. The plates were subsequently resealed, placed on the Titermix, and covered with aluminum foil. The plates were mixed for 1 hour. The plates were then read on the Wallac Victor V, using the LANCE 615/665 protocol.

Data Processing

For each plate, the mean control (i.e. signal from protein and DNA without inhibition), mean blank (background signal without protein) and mean inhibitor (P001407) $LANCE_{665}$ counts were determined. The percentage inhibition by each molecule (each test well) was then determined according to the following equation:

$$\% \text{ Inhibition} = 100 - (((\text{test} - \text{mean blank})/(\text{mean control} - \text{mean blank})) * 100)$$

Compounds that gave 40% or greater inhibition were identified as hits and screened again for IC50.

$IC_{50}$ Screening

The protocol used was identical to that outlined above, except that only 10 compounds were assayed per plate. The testing concentrations started at 10 μg/ml and were diluted two-fold from 10 to 0.078 μg/ml.

$IC_{50}$ Data Processing

Percent inhibition was calculated as shown above. Percent inhibition was then plotted vs. log (conc. Inhibitor) using Graph pad Prism software. The $IC_{50}$ concentration was determined as the concentration that gives 50% inhibition.

The data from this example is also summarized in Table 5. * indicates that a particular test compound inhibited the particular bacteria very well,  indicates that the particular test compound inhibited the particular bacteria well, and * indicates that the particular test compound inhibited the particular bacteria to some extent.

TABLE 5

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| BH | 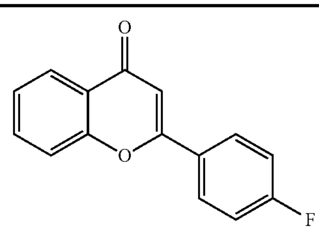 | * |  |  | * | * |  |  |  |  |
| BI | 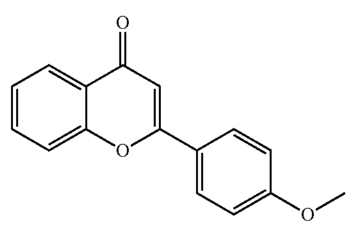 [SMILES: COc1ccc(-c2cc(=O)c3ccccc3o2)cc1] |  |  | ** | NT | * | NT |  |  | ND |
| BJ | 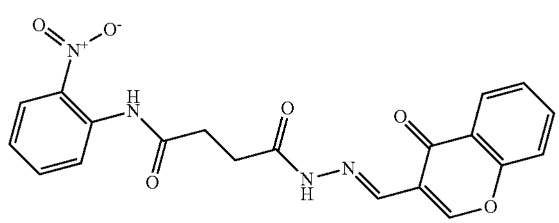 [SMILES: O=C(CCC(=O)Nc1ccccc1[N+](=O)[O-])N/N=C/c1coc2ccccc2c1=O] | * | * |  | * | *** | * |  | ND |  |
| BK | 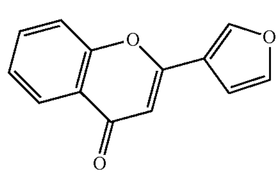 [SMILES: O=c1cc(-c2ccoc2)oc2ccccc12] | * | * | ** | * | * |  | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| BL | 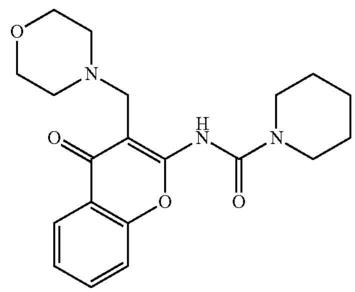 [SMILES: O=C(Nc1oc2ccccc2c(=O)c1CN1CCOCC1)N1CCCCC1] | * | * |  |  | * | * |  |  | ND |
| BN | 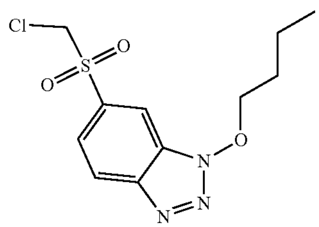 [SMILES: CCCCOn1nnc2ccc(S(=O)(=O)CCl)cc21] | NT | * | *** | * | * | * |  |  | ND |
| BO | 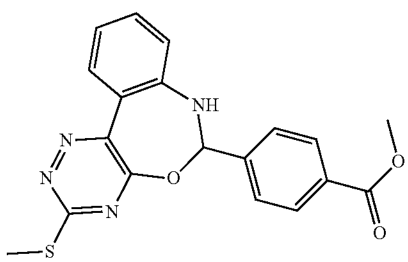 [SMILES: COC(=O)c1ccc(C2Nc3ccccc3-c3nnc(SC)nc3O2)cc1] | * | * |  |  | * | * |  |  | ND |
| BP | 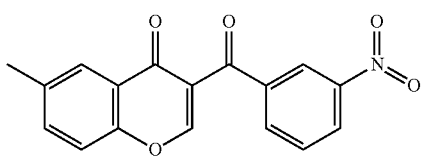 [SMILES: Cc1ccc2occ(C(=O)c3cccc([N+](=O)[O-])c3)c(=O)c2c1] | * | * | ** | NT | * | NT | ** | * | ** |
| BQ | 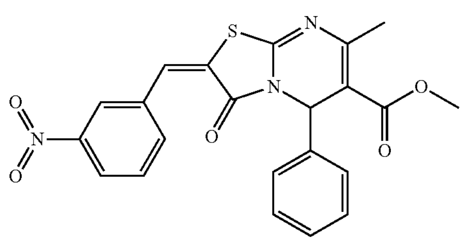 [SMILES: COC(=O)C1=C(C)N=c2s/c(=C/c3cccc([N+](=O)[O-])c3)c(=O)n2C1c1ccccc1] | ** | * | * | * |  | * |  | ND |  |
| BR | 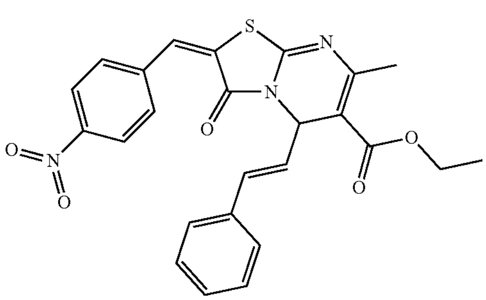 [SMILES: CCOC(=O)C1=C(C)N=c2s/c(=C/c3ccc([N+](=O)[O-])cc3)c(=O)n2C1/C=C/c1ccccc1] | * | * | * | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| BS | 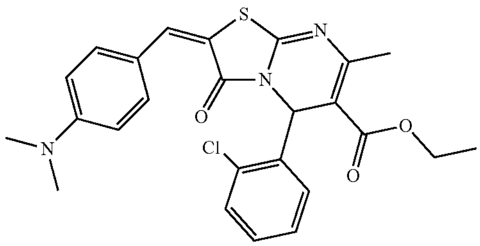 [SMILES: CCOC(=O)C1=C(C)N=c2s/c(=C/c3ccc(N(C)C)cc3)c(=O)n2C1c1ccccc1Cl] | NT | * | NT | * | NT | * |  |  | ** |
| BT | 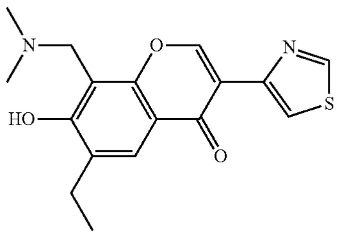 [SMILES: CCc1cc2c(=O)c(-c3cscn3)coc2c(CN(C)C)c1O] | NT | * |  |  | ** | * | ** | * | * |
| BU | 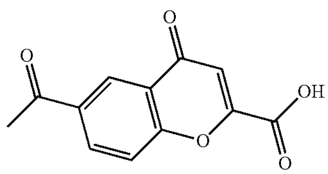 [SMILES: CC(=O)c1ccc2oc(C(=O)O)cc(=O)c2c1] | * | * | ** | NT | * | NT | ** | ND | ND |
| BV | 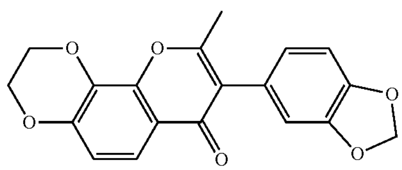 [SMILES: Cc1oc2c3c(ccc2c(=O)c1-c1ccc2c(c1)OCO2)OCCO3] | * | * | ** | NT | * | NT |  |  | ** |
| BW | 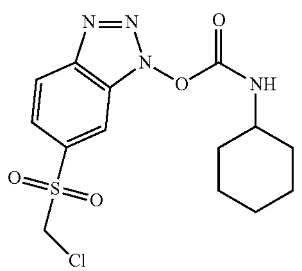 [SMILES: O=C(NC1CCCCC1)On1nnc2ccc(S(=O)(=O)CCl)cc21] | * | NT |  | * |  |  | ** | ND | ND |
| BX | 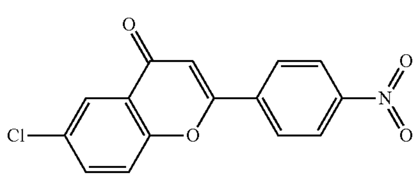 [SMILES: O=c1cc(-c2ccc([N+](=O)[O-])cc2)oc2ccc(Cl)cc12] | * | * | * | NT |  | NT |  | ND | ND |
| BY | 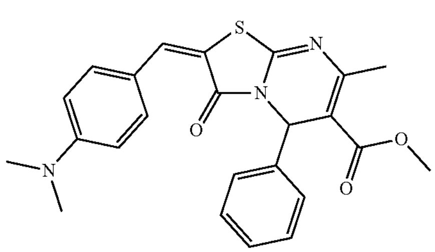 | ** | * | * | * | * | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| BZ | 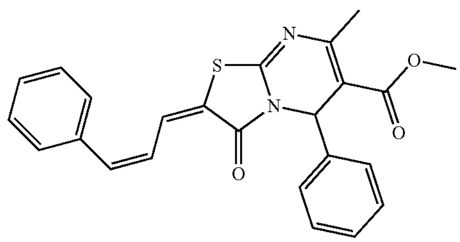 [SMILES: COC(=O)C1=C(C)N=c2s/c(=C/C=C\c3ccccc3)c(=O)n2C1c1ccccc1] | * | * | ** | * |  |  | ** | ND | ND |
| CA | 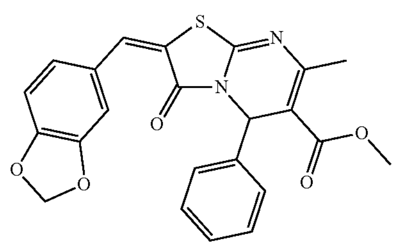 [SMILES: COC(=O)C1=C(C)N=c2s/c(=C/c3ccc4c(c3)OCO4)c(=O)n2C1c1ccccc1] | * | * |  | ** | * | NT |  | ND |  |
| CB | 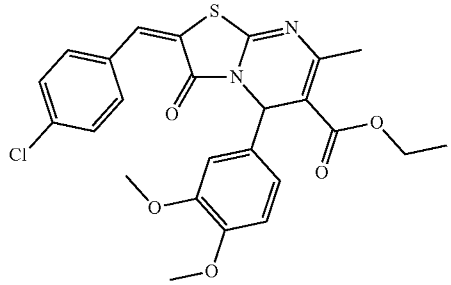 [SMILES: CCOC(=O)C1=C(C)N=c2s/c(=C/c3ccc(Cl)cc3)c(=O)n2C1c1ccc(OC)c(OC)c1] | * | * | ** | * | ** | * |  | ND |  |
| CC | 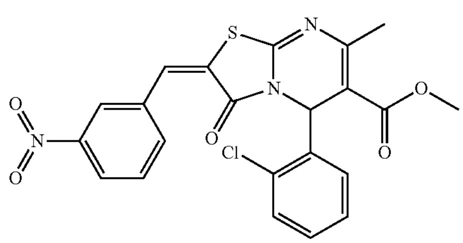 [SMILES: COC(=O)C1=C(C)N=c2s/c(=C/c3cccc([N+](=O)[O-])c3)c(=O)n2C1c1ccccc1Cl] | * | * | ** | * |  |  | ** | * D | |
| CD | 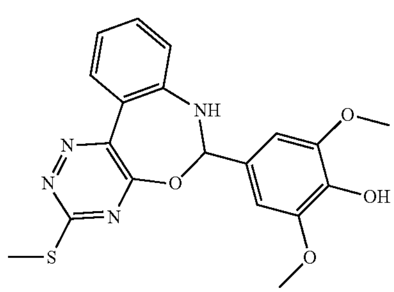 | * | NT |  | * | * | * |  | ND | ** |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| CE | 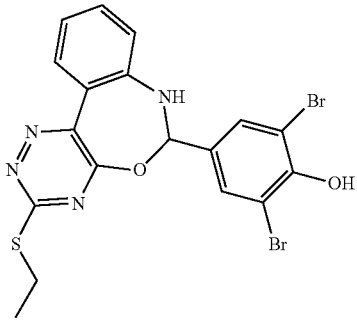 [SMILES: CCSc1nnc2c(n1)OC(c1cc(Br)c(O)c(Br)c1)Nc1ccccc1-2] | NT |  | NT |  | NT | * | ** | * | ND |
| CF | 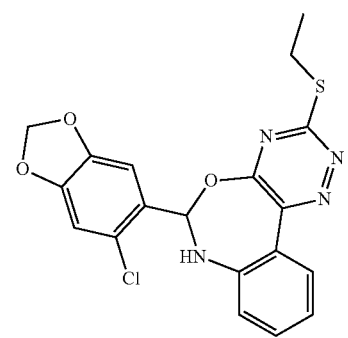 [SMILES: CCSc1nnc2c(n1)OC(c1cc3c(cc1Cl)OCO3)Nc1ccccc1-2] | * | * |  | NT |  | NT |  | ND |  |
| CG | 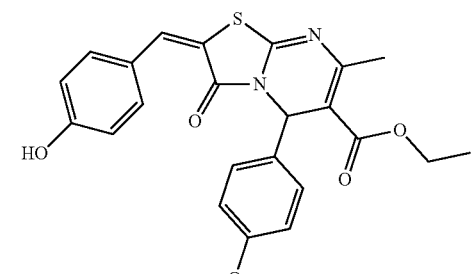 | * | * |  | NT |  | NT |  | ND |  |
| CH | 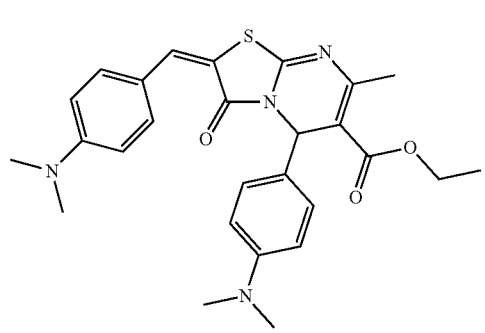 [SMILES: CCOC(=O)C1=C(C)N=c2s/c(=C/c3ccc(N(C)C)cc3)c(=O)n2C1c1ccc(N(C)C)cc1] | * | * | * | NT | * | NT | ** | ND | ND |
| CI | 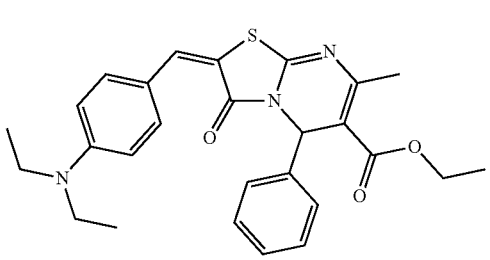 [SMILES: CCOC(=O)C1=C(C)N=c2s/c(=C/c3ccc(N(CC)CC)cc3)c(=O)n2C1c1ccccc1] | * | * |  | NT |  | NT |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| CJ | 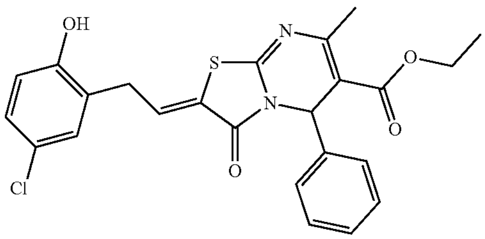 [SMILES: CCOC(=O)C1=C(C)N=c2s/c(=C\Cc3cc(Cl)ccc3O)c(=O)n2C1c1ccccc1] |  |  | * | * | * | * | ** | ND | ND |
| CK | 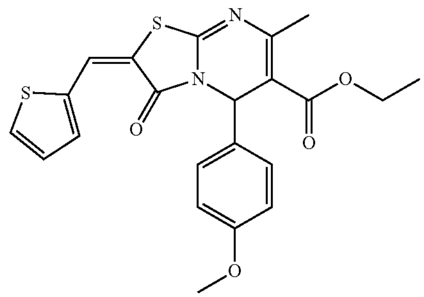 [SMILES: CCOC(=O)C1=C(C)N=c2s/c(=C/c3cccs3)c(=O)n2C1c1ccc(OC)cc1] |  |  | * | * | * |  |  | ND | ND |
| CL | 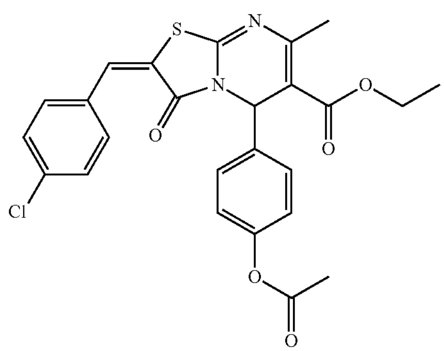 [SMILES: CCOC(=O)C1=C(C)N=c2s/c(=C/c3ccc(Cl)cc3)c(=O)n2C1c1ccc(OC(C)=O)cc1] | * |  |  | * | ** | * | ** | ND | ND |
| CM | 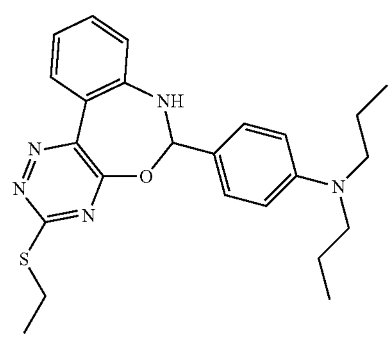 [SMILES: CCCN(CCC)c1ccc(C2Nc3ccccc3-c3nnc(SCC)nc3O2)cc1] | * | * | ** | * | * | * |  |  | ** |
| CN | 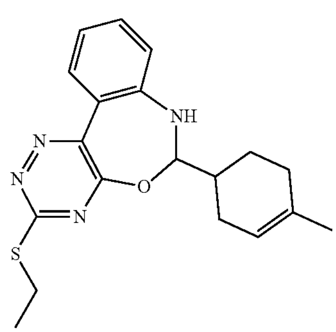 [SMILES: CCSc1nnc2c(n1)OC(C1CC=C(C)CC1)Nc1ccccc1-2] | * | * | * | * | ** | * |  |  | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| CO | 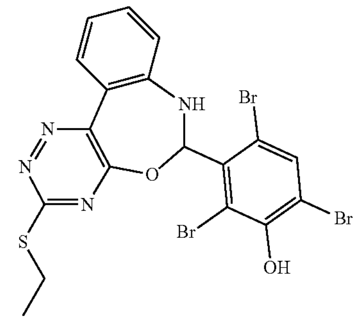 [SMILES: CCSc1nnc2c(n1)OC(c1c(Br)cc(Br)c(O)c1Br)Nc1ccccc1-2] | * | * | ** | * | * |  |  | ** | * |
| CP | 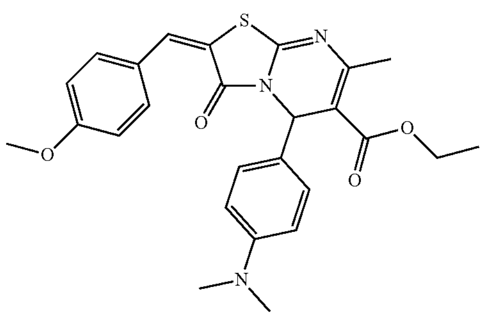 [SMILES: CCOC(=O)C1=C(C)N=c2s/c(=C/c3ccc(OC)cc3)c(=O)n2C1c1ccc(N(C)C)cc1] | ** | * | *** | * | *** | * |  |  | * |
| CQ | 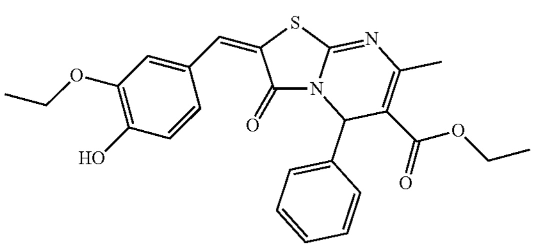 [SMILES: CCOC(=O)C1=C(C)N=c2s/c(=C/c3ccc(O)c(OCC)c3)c(=O)n2C1c1ccccc1] | NT | * | ** | * | * | * |  |  | * |
| CR | 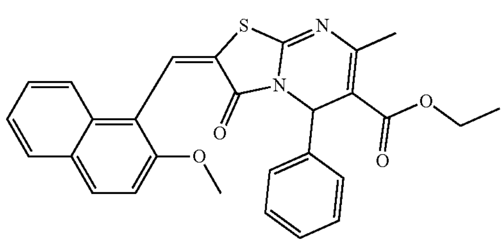 [SMILES: CCOC(=O)C1=C(C)N=c2s/c(=C/c3c(OC)ccc4ccccc34)c(=O)n2C1c1ccccc1] | NT | * | NT |  | NT | * |  |  | ND |
| CS | 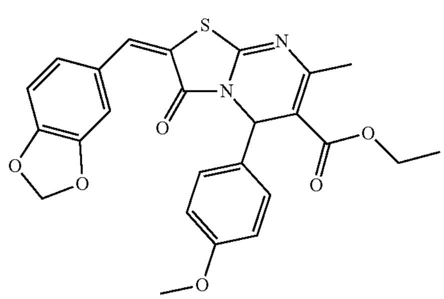 [SMILES: CCOC(=O)C1=C(C)N=c2s/c(=C/c3ccc4c(c3)OCO4)c(=O)n2C1c1ccc(OC)cc1] | NT | * | NT | * | NT | * |  |  | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| CT | 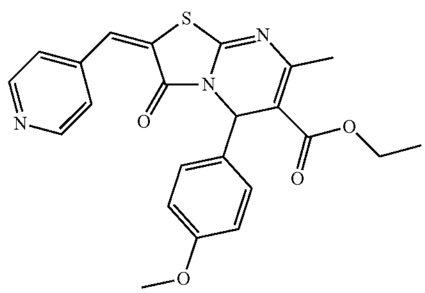 [SMILES: CCOC(=O)C1=C(C)N=c2s/c(=C/c3ccncc3)c(=O)n2C1c1ccc(OC)cc1] |  | NT | * | * |  | * |  | ND | * |
| CU | 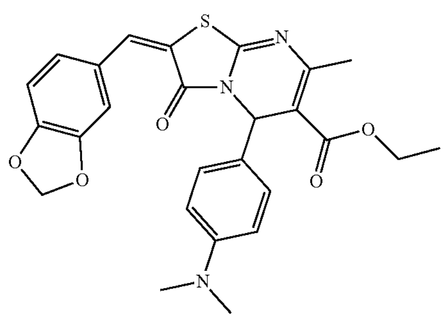 [SMILES: CCOC(=O)C1=C(C)N=c2s/c(=C/c3ccc4c(c3)OCO4)c(=O)n2C1c1ccc(N(C)C)cc1] | NT | NT |  |  | * | * | ** | ND | ND |
| CV | 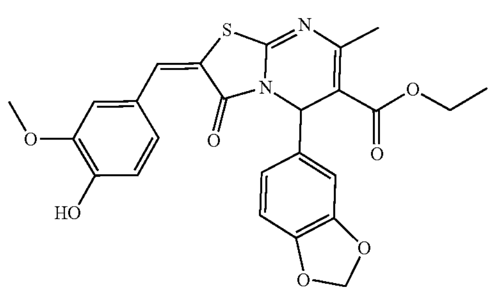 [SMILES: CCOC(=O)C1=C(C)N=c2s/c(=C/c3ccc(O)c(OC)c3)c(=O)n2C1c1ccc2c(c1)OCO2] | NT | * | * | NT |  | NT |  | ND | ND |
| CW | 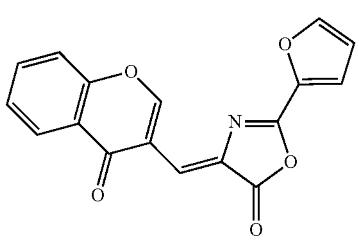 [SMILES: O=C1OC(c2ccco2)=N/C1=C\c1coc2ccccc2c1=O] | *** | * | ** | * | * | * |  | ND |  |
| CX | 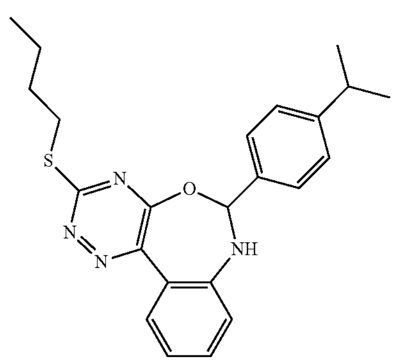 [SMILES: CCCCSc1nnc2c(n1)OC(c1ccc(C(C)C)cc1)Nc1ccccc1-2] | * | * |  | * |  | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| CY | 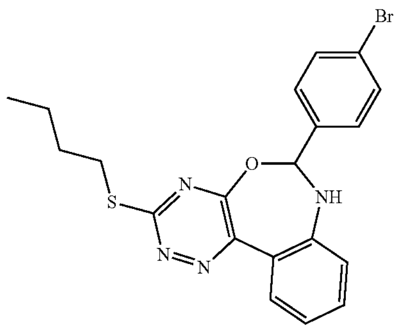 [SMILES: CCCCSc1nnc2c(n1)OC(c1ccc(Br)cc1)Nc1ccccc1-2] | *** | * | * | * | ** | * | ** | ND | ND |
| CZ | 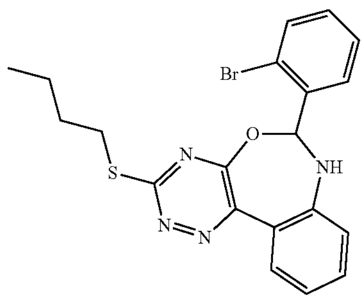 [SMILES: CCCCSc1nnc2c(n1)OC(c1ccccc1Br)Nc1ccccc1-2] | ** | * | * | * | * |  |  | ND | ND |
| DA | 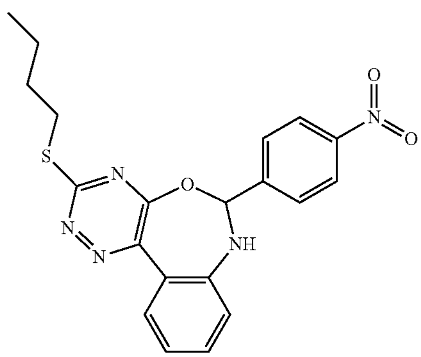 [SMILES: CCCCSc1nnc2c(n1)OC(c1ccc([N+](=O)[O-])cc1)Nc1ccccc1-2] | *** | * | * | * | * | * | ** | ND | ND |
| DB | 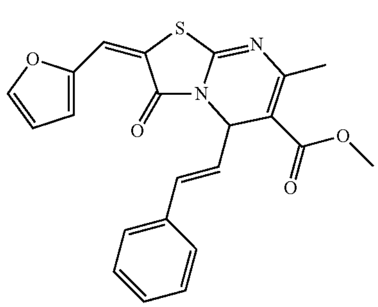 [SMILES: COC(=O)C1=C(C)N=c2s/c(=C/c3ccco3)c(=O)n2C1/C=C/c1ccccc1] | * |  | * | * | * | * | ** | ND | ND |
| DC | 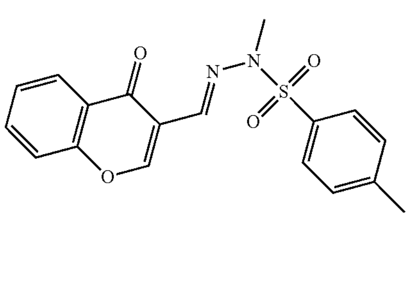 [SMILES: Cc1ccc(S(=O)(=O)N(C)/N=C/c2coc3ccccc3c2=O)cc1] | ** | * | ** | * | ** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| DD | 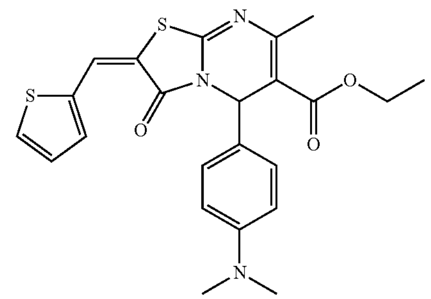 [SMILES: CCOC(=O)C1=C(C)N=c2s/c(=C/c3cccs3)c(=O)n2C1c1ccc(N(C)C)cc1] | ** | * | * | * | * | * | ** | ND | * |
| DE | 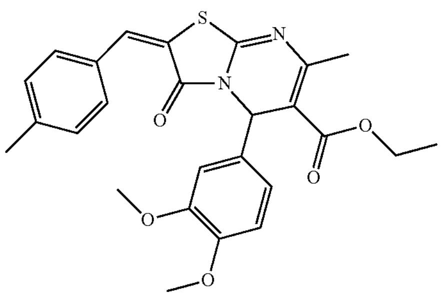 [SMILES: CCOC(=O)C1=C(C)N=c2s/c(=C/c3ccc(C)cc3)c(=O)n2C1c1ccc(OC)c(OC)c1] | NT | * | NT | * | NT |  |  | ** | ND |
| DF | 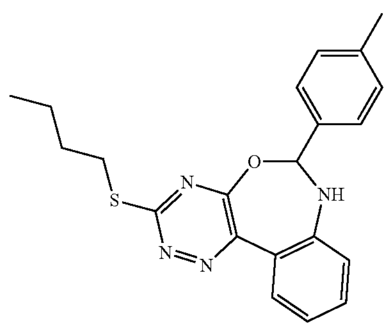 [SMILES: CCCCSc1nnc2c(n1)OC(c1ccc(C)cc1)Nc1ccccc1-2] | ** | * | * | * | ** | * |  | ND |  |
| DG | 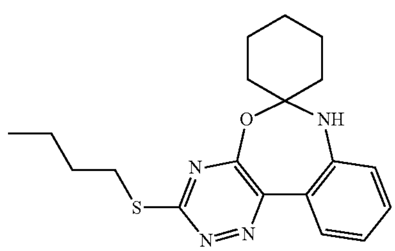 [SMILES: CCCCSc1nnc2c(n1)OC1(CCCCC1)Nc1ccccc1-2] | * | * | ** | * | * | * |  |  | ** |
| DH | 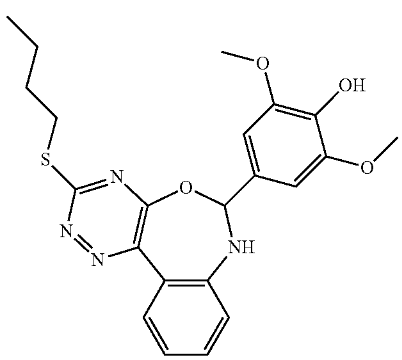 [SMILES: CCCCSc1nnc2c(n1)OC(c1cc(OC)c(O)c(OC)c1)Nc1ccccc1-2] | * | * | ** | * | * |  |  | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| DI | 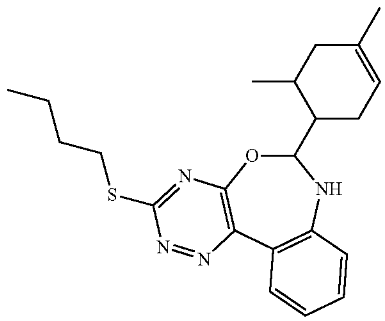 [SMILES: CCCCSc1nnc2c(n1)OC(C1CC=C(C)CC1C)Nc1ccccc1-2] | ** | * | ** | * | * | * |  |  | ** |
| DJ | 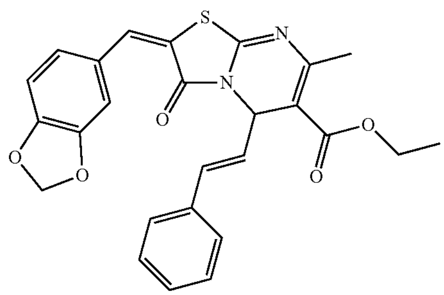 [SMILES: CCOC(=O)C1=C(C)N=c2s/c(=C/c3ccc4c(c3)OCO4)c(=O)n2C1/C=C/c1ccccc1] | * | ** | * | NT |  | NT |  | ND | ND |
| DK | 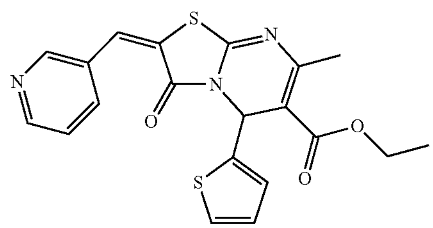 [SMILES: CCOC(=O)C1=C(C)N=c2s/c(=C/c3cccnc3)c(=O)n2C1c1cccs1] | * | * | ** | NT | * | NT | ** | ND | ND |
| DL | 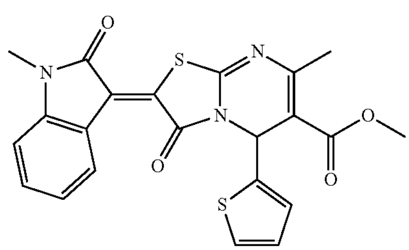 | * | * | * | * |  | * |  | ND |  |
| DM | 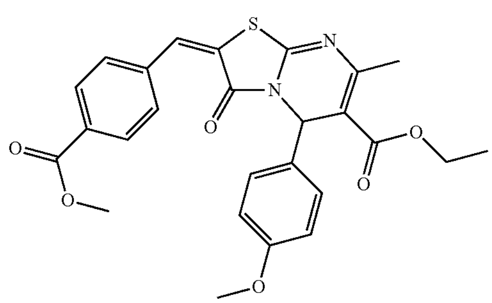 [SMILES: CCOC(=O)C1=C(C)N=c2s/c(=C/c3ccc(C(=O)OC)cc3)c(=O)n2C1c1ccc(OC)cc1] | * | * | *** | * | *** | * | ** | ND | ND |
| DN | 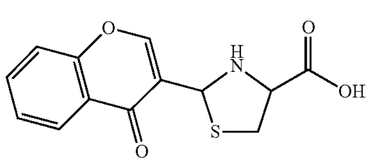 [SMILES: O=C(O)C1CSC(c2coc3ccccc3c2=O)N1] | * | * | ** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| DO | 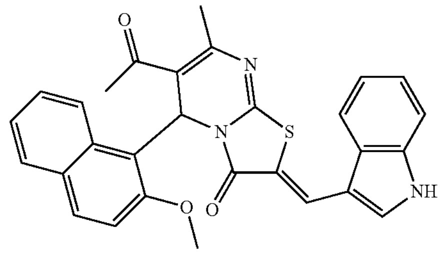 [SMILES: COc1ccc2ccccc2c1C1C(C(C)=O)=C(C)N=c2s/c(=C\c3c[nH]c4ccccc34)c(=O)n21] | * | * | ** | * | ** | * | ** | ND | * |
| DP | 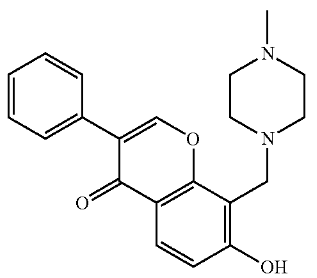 [SMILES: CN1CCN(Cc2c(O)ccc3c(=O)c(-c4ccccc4)coc23)CC1] | * | * | * | * | * | * | ** | ND | ND |
| DQ | 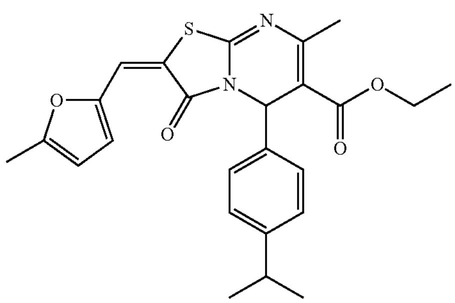 [SMILES: CCOC(=O)C1=C(C)N=c2s/c(=C/c3ccc(C)o3)c(=O)n2C1c1ccc(C(C)C)cc1] | ** | * | * | * | * | * | ** | ND | ND |
| DR | 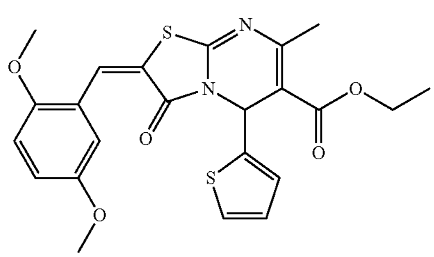 [SMILES: CCOC(=O)C1=C(C)N=c2s/c(=C/c3cc(OC)ccc3OC)c(=O)n2C1c1cccs1] |  | * | * | * | * | * | ** | ND | ND |
| DS | 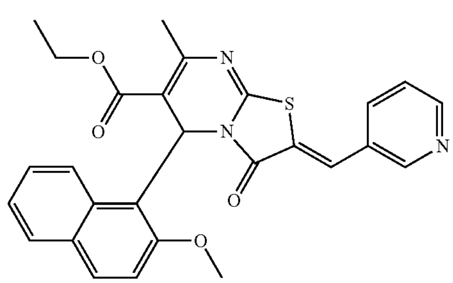 [SMILES: CCOC(=O)C1=C(C)N=c2s/c(=C\c3cccnc3)c(=O)n2C1c1c(OC)ccc2ccccc12] | *** | * | * | * | ** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| DT | 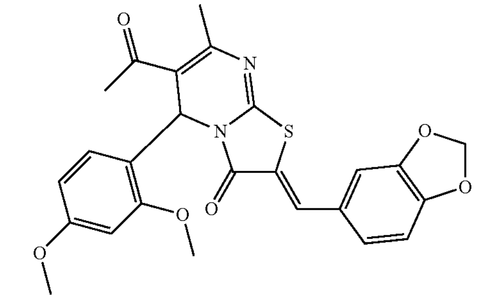 [SMILES: COc1ccc(C2C(C(C)=O)=C(C)N=c3s/c(=C\c4ccc5c(c4)OCO5)c(=O)n32)c(OC)c1] | *** | * | ** | * | ** | * | ** | ND | * |
| DU | 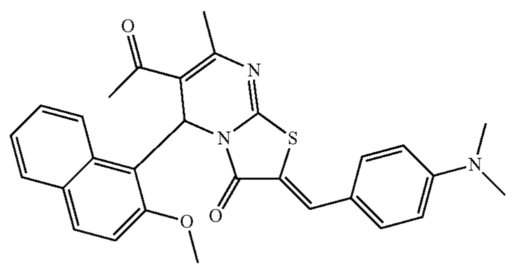 [SMILES: COc1ccc2ccccc2c1C1C(C(C)=O)=C(C)N=c2s/c(=C\c3ccc(N(C)C)cc3)c(=O)n21] | * | * | * | * | *** | * |  | ND |  |
| DV | 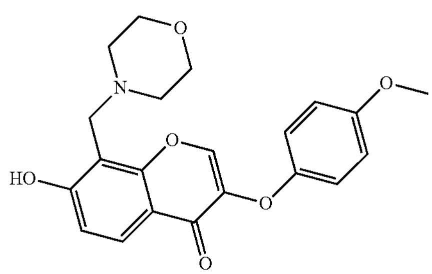 [SMILES: COc1ccc(Oc2coc3c(CN4CCOCC4)c(O)ccc3c2=O)cc1] | * | * | * | * | * |  |  | ND |  |
| DW | 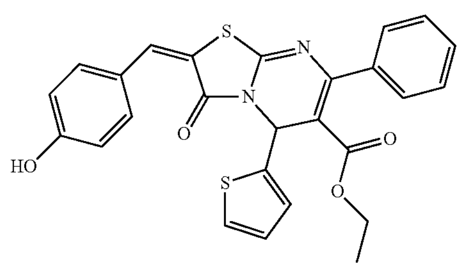 [SMILES: CCOC(=O)C1=C(c2ccccc2)N=c2s/c(=C/c3ccc(O)cc3)c(=O)n2C1c1cccs1] | * |  | ** | * |  |  |  | ND |  |
| DX | 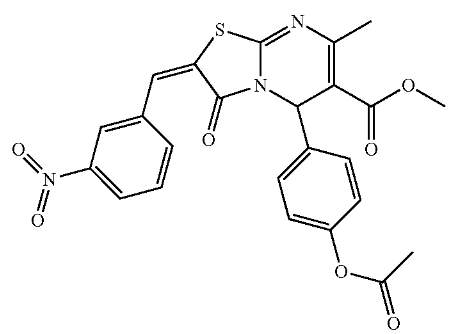 [SMILES: COC(=O)C1=C(C)N=c2s/c(=C/c3cccc([N+](=O)[O-])c3)c(=O)n2C1c1ccc(OC(C)=O)cc1] | * | * | * | * | * |  |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| DY | 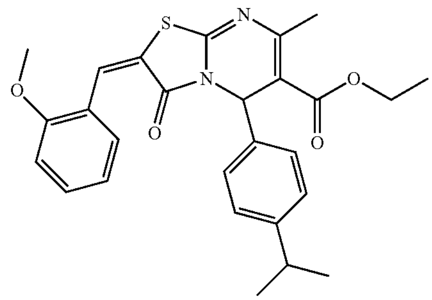 [SMILES: CCOC(=O)C1=C(C)N=c2s/c(=C/c3ccccc3OC)c(=O)n2C1c1ccc(C(C)C)cc1] | ** | * | ** | * |  |  |  | ND |  |
| DZ | 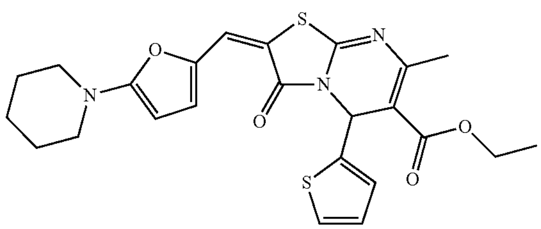 [SMILES: CCOC(=O)C1=C(C)N=c2s/c(=C/c3ccc(N4CCCCC4)o3)c(=O)n2C1c1cccs1] | ** | * | NT | * |  |  |  |  | ** |
| EA | 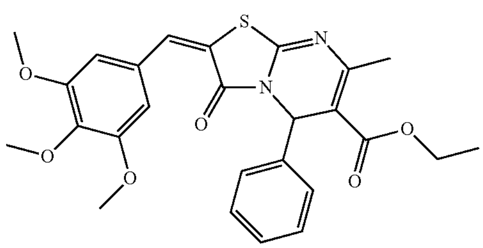 [SMILES: CCOC(=O)C1=C(C)N=c2s/c(=C/c3cc(OC)c(OC)c(OC)c3)c(=O)n2C1c1ccccc1] | * | * | * | NT | * | NT | ** | * | * |
| EB | 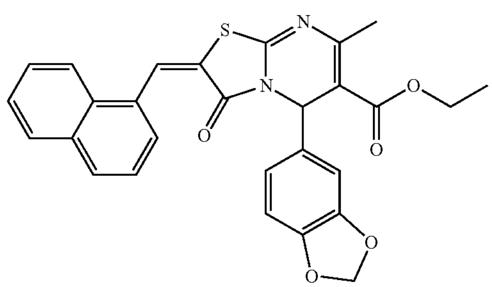 [SMILES: CCOC(=O)C1=C(C)N=c2s/c(=C/c3cccc4ccccc34)c(=O)n2C1c1ccc2c(c1)OCO2] | * | * |  | NT |  | NT | ** | * | ** |
| EC | 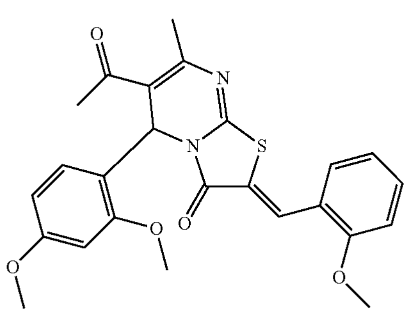 [SMILES: COc1ccc(C2C(C(C)=O)=C(C)N=c3s/c(=C\c4ccccc4OC)c(=O)n32)c(OC)c1] | * | * | ** | NT | * | NT |  |  | ND |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|----|
| ED | 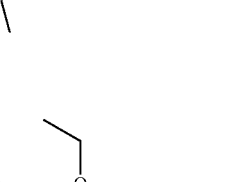 | NT | * | NT | * | NT | * |  |  | ** |
| EF | 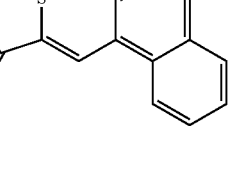 | NT |  | NT | * | NT | * |  | * | ** |
| EG | 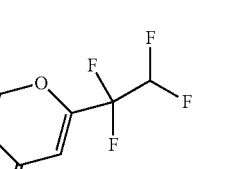 | NT | * | NT | ** | NT | * |  |  | * |
| EH | 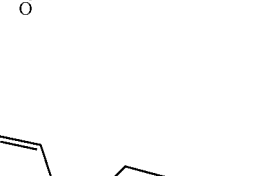 | NT | * | NT | * | NT |  |  | * | ** |
| EI | 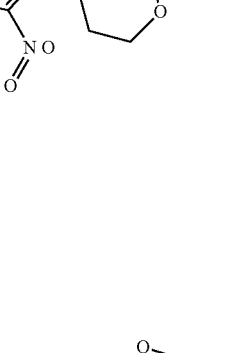 | * | * | * | NT |  | NT |  | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| EJ | 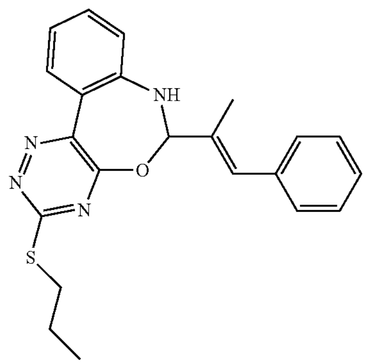 [SMILES: CCCSc1nnc2c(n1)OC(/C(C)=C/c1ccccc1)Nc1ccccc1-2] | * | * | * | NT | * | NT | ** | ND | ND |
| EK | 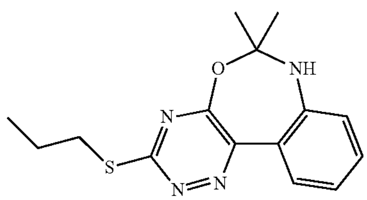 [SMILES: CCCSc1nnc2c(n1)OC(C)(C)Nc1ccccc1-2] | * | * |  | NT |  | NT |  | ND | * |
| EL | 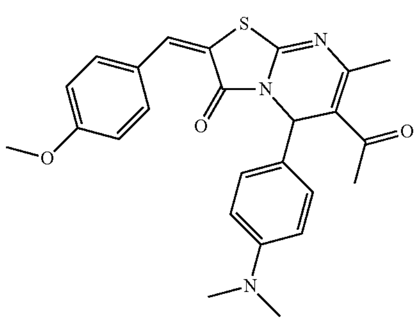 [SMILES: COc1ccc(/C=c2/sc3n(c2=O)C(c2ccc(N(C)C)cc2)C(C(C)=O)=C(C)N=3)cc1] | * | * | * | NT | * | NT | ** | ND | ND |
| EM | 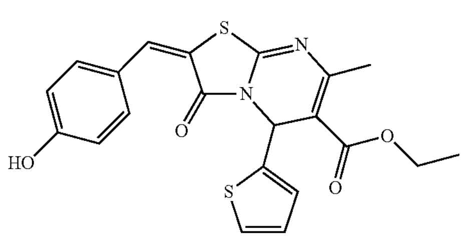 [SMILES: CCOC(=O)C1=C(C)N=c2s/c(=C/c3ccc(O)cc3)c(=O)n2C1c1cccs1] | NT |  |  | NT | * | NT | ** | ND | ND |
| EN | 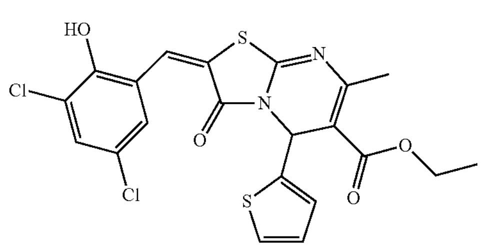 [SMILES: CCOC(=O)C1=C(C)N=c2s/c(=C/c3cc(Cl)cc(Cl)c3O)c(=O)n2C1c1cccs1] | * | * |  | NT |  | NT | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| EO | 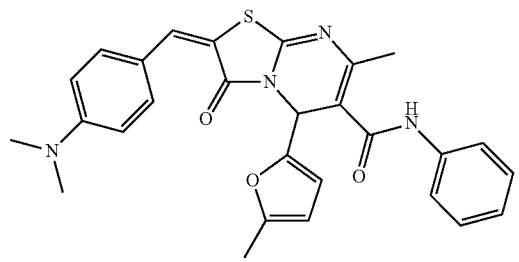 [SMILES: CC1=C(C(=O)Nc2ccccc2)C(c2ccc(C)o2)n2c(s/c(=C/c3ccc(N(C)C)cc3)c2=O)=N1] | ** | * | ** | * | ** | * |  | ND |  |
| EQ | 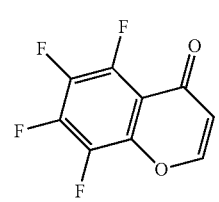 [SMILES: O=c1ccoc2c(F)c(F)c(F)c(F)c12] | * | * | ** | * | ** | * | ** | ND | ND |
| ER | 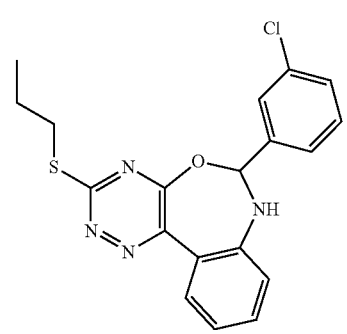 [SMILES: CCCSc1nnc2c(n1)OC(c1cccc(Cl)c1)Nc1ccccc1-2] | * | * | ** | * | ** | * |  | ND |  |
| ES | 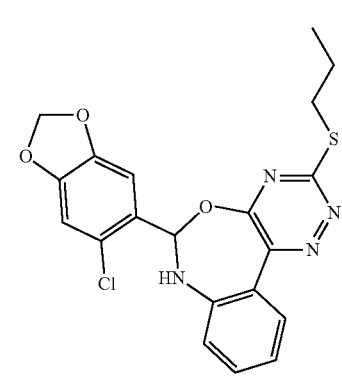 [SMILES: CCCSc1nnc2c(n1)OC(c1cc3c(cc1Cl)OCO3)Nc1ccccc1-2] | * | * | ** | * |  | * | ** | ND | D |
| ET | 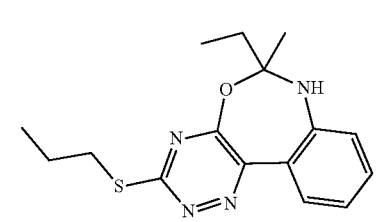 [SMILES: CCCSc1nnc2c(n1)OC(C)(CC)Nc1ccccc1-2] | * |  | *** | * | ** | * | ** | | |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| EU | 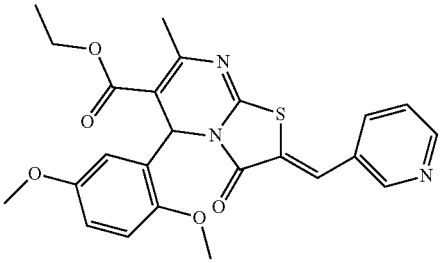 [SMILES: CCOC(=O)C1=C(C)N=c2s/c(=C\c3cccnc3)c(=O)n2C1c1cc(OC)ccc1OC] | * | * | * | * | * | * | ** | ND | ND |
| EV | 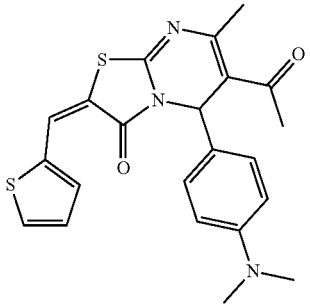 [SMILES: CC(=O)C1=C(C)N=c2s/c(=C/c3cccs3)c(=O)n2C1c1ccc(N(C)C)cc1] | * | * | *** | * | * | * | ** | ND | ND |
| EW | 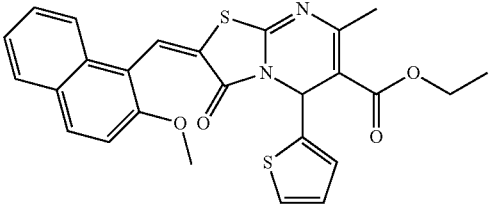 [SMILES: CCOC(=O)C1=C(C)N=c2s/c(=C/c3c(OC)ccc4ccccc34)c(=O)n2C1c1cccs1] | * | * | * | * | * |  |  | ND | ** |
| EX | 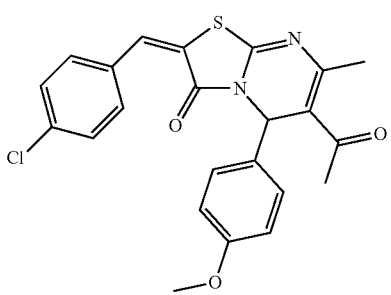 [SMILES: COc1ccc(C2C(C(C)=O)=C(C)N=c3s/c(=C/c4ccc(Cl)cc4)c(=O)n32)cc1] | *** | * | * | * | * |  | ** | ND | ND |
| EY | 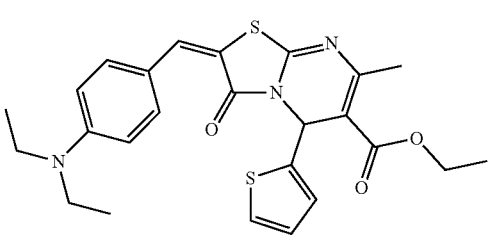 [SMILES: CCOC(=O)C1=C(C)N=c2s/c(=C/c3ccc(N(CC)CC)cc3)c(=O)n2C1c1cccs1] | ** | * | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| EZ | 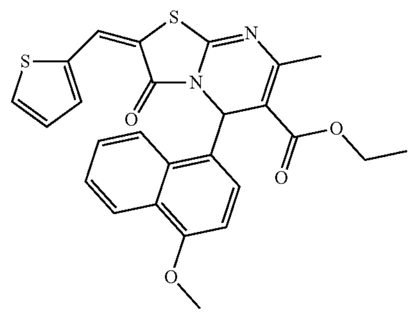 [SMILES: CCOC(=O)C1=C(C)N=c2s/c(=C/c3cccs3)c(=O)n2C1c1ccc(OC)c2ccccc12] | ** | * | * | * | ** | * | ** | ND | * |
| FA | 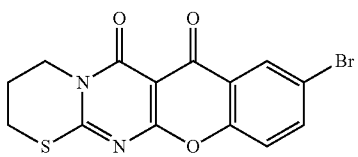 [SMILES: O=c1c2cc(Br)ccc2oc2nc3n(c(=O)c12)CCCS3] | ** | * | * | * | * | * | ** | ND | * |
| FB | 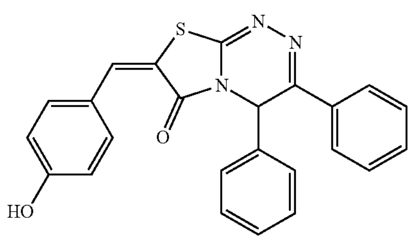 [SMILES: O=c1/c(=C\c2ccc(O)cc2)sc2n1C(c1ccccc1)C(c1ccccc1)=NN=2] | ** | * | * | * | * | * | ** | ND | * |
| FC | 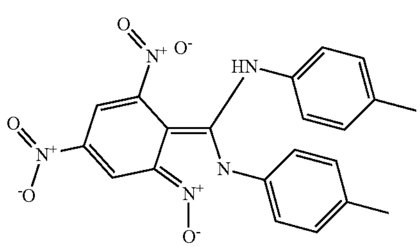 | NT | * | NT | * | NT | * | ** | * | * |
| FD | 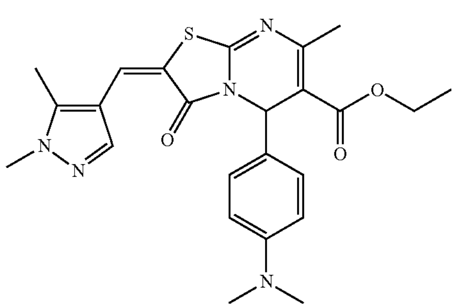 [SMILES: CCOC(=O)C1=C(C)N=c2s/c(=C/c3cnn(C)c3C)c(=O)n2C1c1ccc(N(C)C)cc1] | NT | * | NT | * | NT | * | ** | * | ** |
| FE | 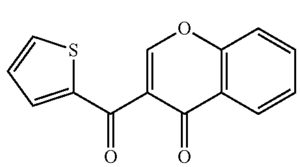 [SMILES: O=C(c1cccs1)c1coc2ccccc2c1=O] | NT | * | NT | ** | NT | * |  |  | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| FG | 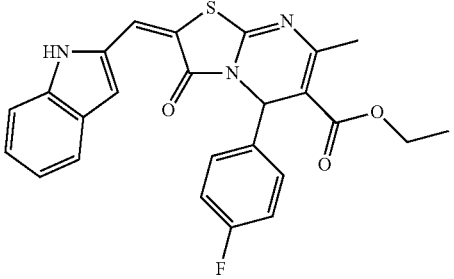 [SMILES: CCOC(=O)C1=C(C)N=c2s/c(=C/c3cc4ccccc4[nH]3)c(=O)n2C1c1ccc(F)cc1] | NT |  | NT | * | NT |  |  | * | ND |
| FH | 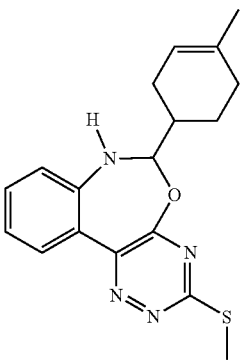 [SMILES: CSc1nnc2c(n1)OC(C1CC=C(C)CC1)Nc1ccccc1-2] | * | * | ** | * | ** | * |  | ND |  |
| FI | 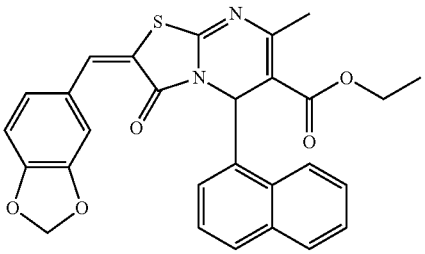 [SMILES: CCOC(=O)C1=C(C)N=c2s/c(=C/c3ccc4c(c3)OCO4)c(=O)n2C1c1cccc2ccccc12] | ** | * | * | * | * | * | ** | ND | ND |
| FJ | 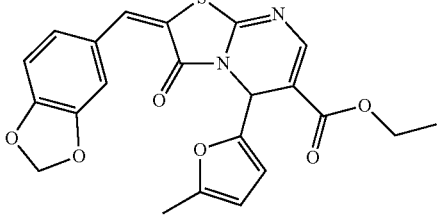 |  |  | * |  | ** | * |  | ND |  |
| FK | 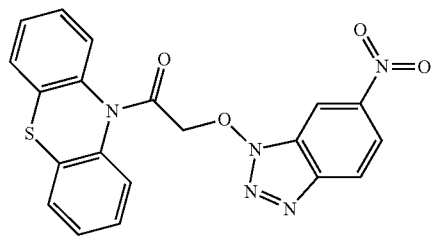 [SMILES: O=C(COn1nnc2ccc([N+](=O)[O-])cc21)N1c2ccccc2Sc2ccccc21] | * | * | *** | * | * | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| FL | 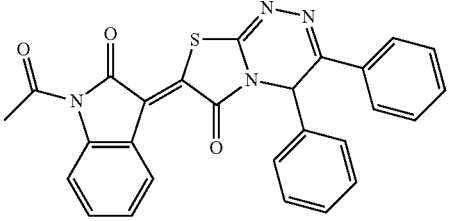 [SMILES: CC(=O)N1C(=O)/C(=c2\sc3n(c2=O)C(c2ccccc2)C(c2ccccc2)=NN=3)c2ccccc21] | ** | * | ** | * |  |  |  | ND |  |
| FM | 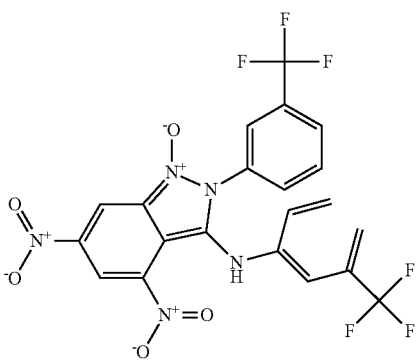 | *** | * | * | * | ** | * |  | ND |  |
| FN | 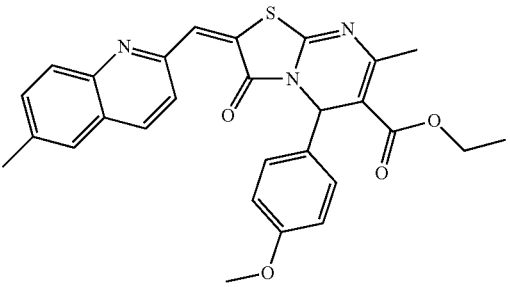 [SMILES: CCOC(=O)C1=C(C)N=c2s/c(=C/c3ccc4cc(C)ccc4n3)c(=O)n2C1c1ccc(OC)cc1] | * | *** | * |  |  | NT | ** | ND | * |
| FO | 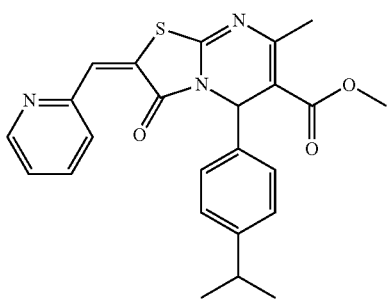 [SMILES: COC(=O)C1=C(C)N=c2s/c(=C/c3ccccn3)c(=O)n2C1c1ccc(C(C)C)cc1] | * | * | * |  | *** | * | ** | * | * |
| FP | 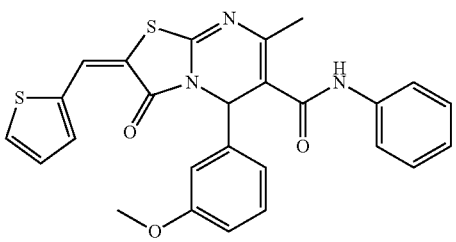 [SMILES: COc1cccc(C2C(C(=O)Nc3ccccc3)=C(C)N=c3s/c(=C/c4cccs4)c(=O)n32)c1] | * | * | * | * | ** | * |  |  | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| FQ | 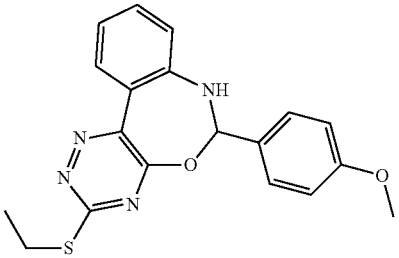 [SMILES: CCSc1nnc2c(n1)OC(c1ccc(OC)cc1)Nc1ccccc1-2] | * | * |  |  | * |  |  | ** | * |
| FR | 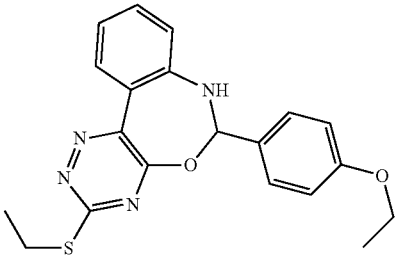 [SMILES: CCOc1ccc(C2Nc3ccccc3-c3nnc(SCC)nc3O2)cc1] | * | * | * | NT |  | NT |  | * | ** |
| FS | 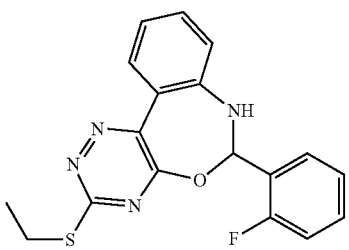 [SMILES: CCSc1nnc2c(n1)OC(c1ccccc1F)Nc1ccccc1-2] | NT | * | NT | ** | NT | * |  |  | ND |
| FT | 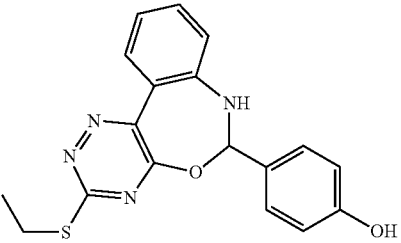 [SMILES: CCSc1nnc2c(n1)OC(c1ccc(O)cc1)Nc1ccccc1-2] | * | NT | ** | * | * | * |  | ND |  |
| FU | 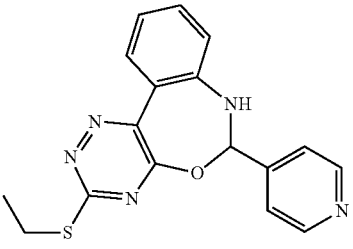 [SMILES: CCSc1nnc2c(n1)OC(c1ccncc1)Nc1ccccc1-2] |  |  | ** | * |  | * |  | ND |  |
| FV | 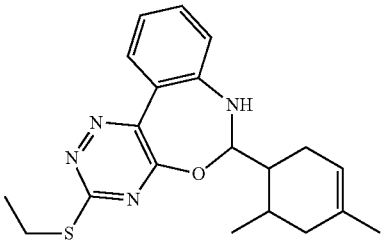 [SMILES: CCSc1nnc2c(n1)OC(C1CC=C(C)CC1C)Nc1ccccc1-2] | * | * | ** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| FW | 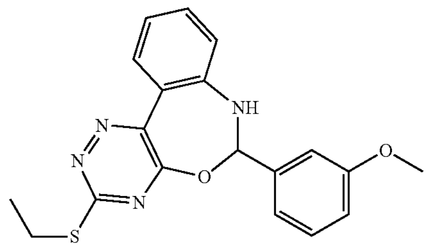 [SMILES: CCSc1nnc2c(n1)OC(c1cccc(OC)c1)Nc1ccccc1-2] | ** | * | ** | * | *** | * | ** | ND | ND |
| FX | 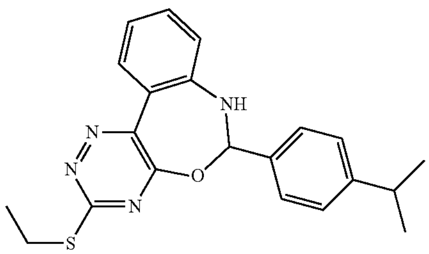 [SMILES: CCSc1nnc2c(n1)OC(c1ccc(C(C)C)cc1)Nc1ccccc1-2] | * | * | ** | * | ** | * |  | N |  |
| FY | 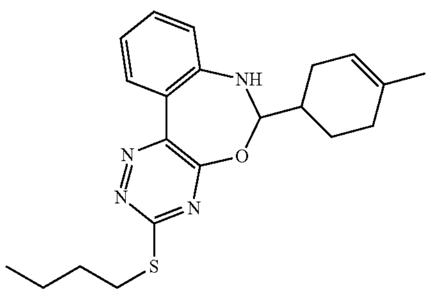 [SMILES: CCCCSc1nnc2c(n1)OC(C1CC=C(C)CC1)Nc1ccccc1-2] | ** | * | *** | * | ** | * |  |  | ND |
| FZ | 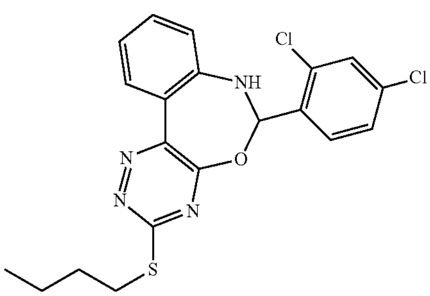 [SMILES: CCCCSc1nnc2c(n1)OC(c1ccc(Cl)cc1Cl)Nc1ccccc1-2] | * | * | ** | * | ** | * |  | ND |  |
| GA | 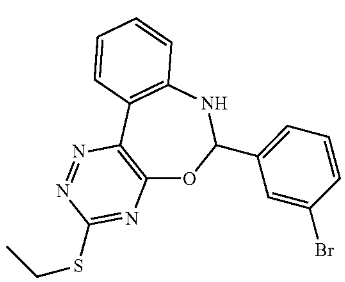 [SMILES: CCSc1nnc2c(n1)OC(c1cccc(Br)c1)Nc1ccccc1-2] | * | * | ** | * | * |  | ** | ND | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| GB | 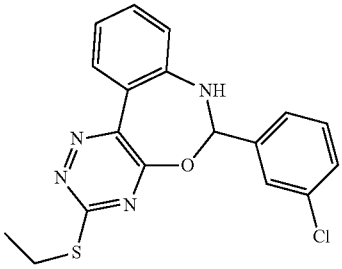 [SMILES: CCSc1nnc2c(n1)OC(c1cccc(Cl)c1)Nc1ccccc1-2] | ** | * | *** | * | ** | * | ** | ND | * |
| GC | 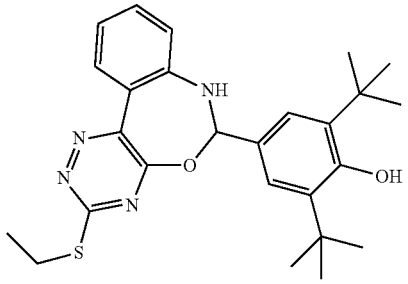 [SMILES: CCSc1nnc2c(n1)OC(c1cc(C(C)(C)C)c(O)c(C(C)(C)C)c1)Nc1ccccc1-2] | ** | * | ** | * | ** | * |  | ND |  |
| GD | 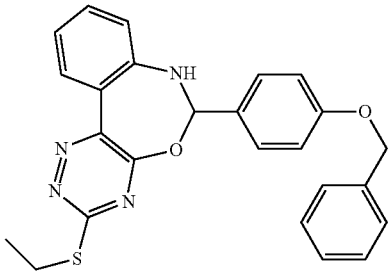 [SMILES: CCSc1nnc2c(n1)OC(c1ccc(OCc3ccccc3)cc1)Nc1ccccc1-2] | * | * | * | * | * | * | ** | ND | ND |
| GE | 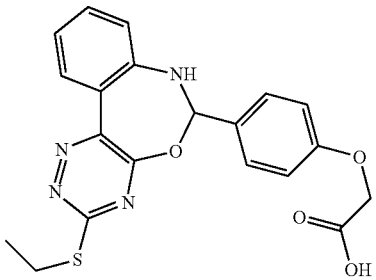 [SMILES: CCSc1nnc2c(n1)OC(c1ccc(OCC(=O)O)cc1)Nc1ccccc1-2] | * | * | * | * | * | * | ** | ND | ND |
| GF | 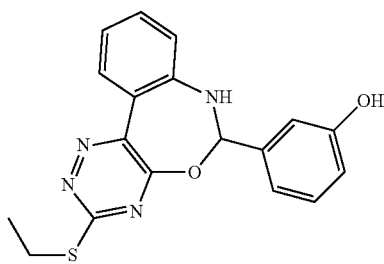 [SMILES: CCSc1nnc2c(n1)OC(c1cccc(O)c1)Nc1ccccc1-2] |  |  | *** | * | * | * | ** | ND | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| GG | 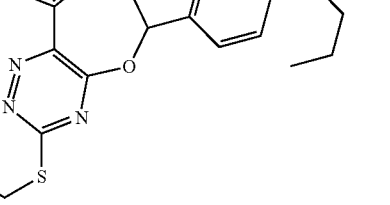 | * | * | * | * | ** | * | ** | ND | * |
| GH | 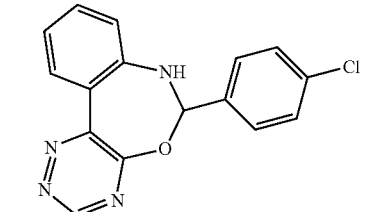 | * | * | * | * | * | * | ** | ND | ND |
| GI | 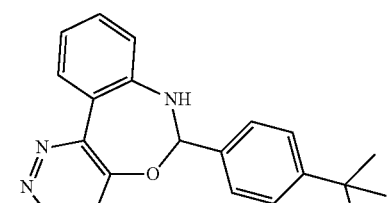 |  |  |  |  |  | * |  | ND |  |
| GJ | 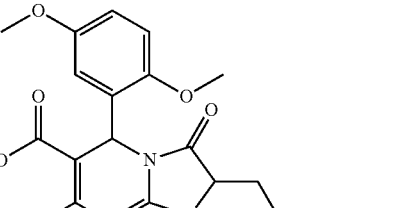 | ** | * | * | * | * |  |  | ND | ND |
| GK | 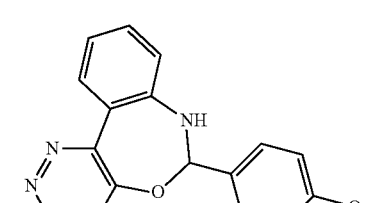 | ** | * | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| GL | 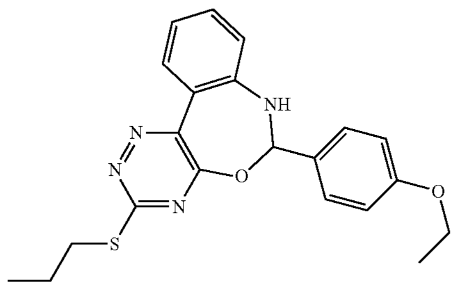 [SMILES: CCCSc1nnc2c(n1)OC(c1ccc(OCC)cc1)Nc1ccccc1-2] | ** | * | * | * | * | * | ** | ND | ND |
| GM | 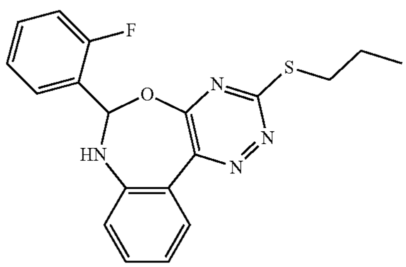 [SMILES: CCCSc1nnc2c(n1)OC(c1ccccc1F)Nc1ccccc1-2] | ** | * | * | * | * | * |  | ND | ND |
| GN | 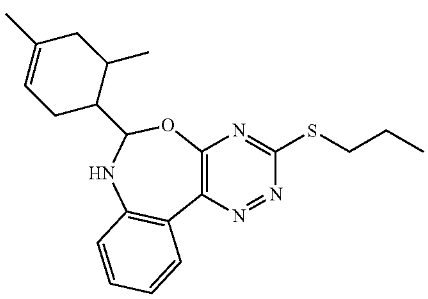 [SMILES: CCCSc1nnc2c(n1)OC(C1CC=C(C)CC1C)Nc1ccccc1-2] | ** | * | * | * | * | * | ** | ND | ND |
| GO | 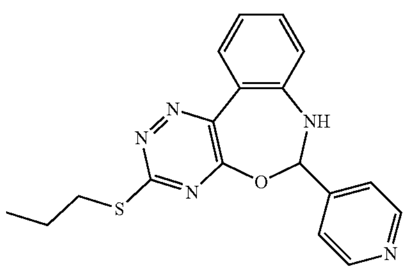 [SMILES: CCCSc1nnc2c(n1)OC(c1ccncc1)Nc1ccccc1-2] | ** | * | * | * | ** | * | ** | ND | * |
| GP | 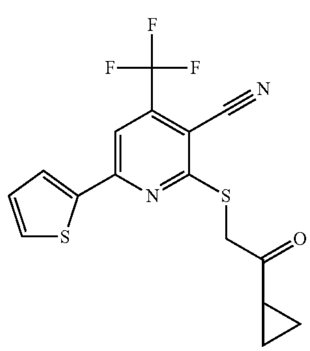 [SMILES: N#Cc1c(C(F)(F)F)cc(-c2cccs2)nc1SCC(=O)C1CC1] | NT | * | NT |  | NT |  |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| GQ | 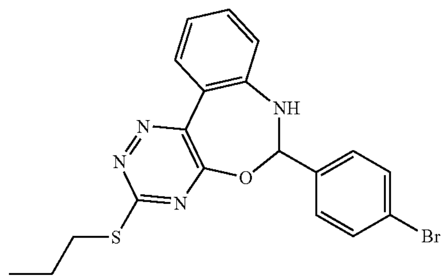 [SMILES: CCCSc1nnc2c(n1)OC(c1ccc(Br)cc1)Nc1ccccc1-2] | NT |  | NT | * | NT |  |  | * | ** |
| GR | 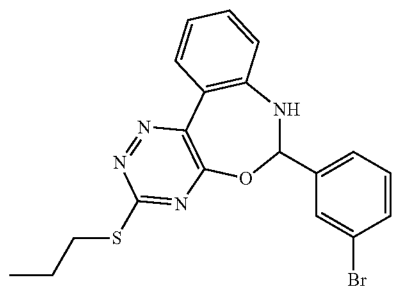 [SMILES: CCCSc1nnc2c(n1)OC(c1cccc(Br)c1)Nc1ccccc1-2] | NT | * | NT | * | NT | * | ** | * | ND |
| GS | 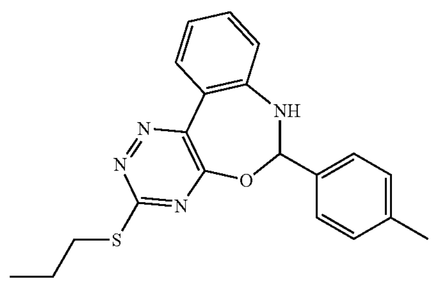 [SMILES: CCCSc1nnc2c(n1)OC(c1ccc(C)cc1)Nc1ccccc1-2] | NT | * | NT | * | NT | * |  | ** | ND |
| GT | 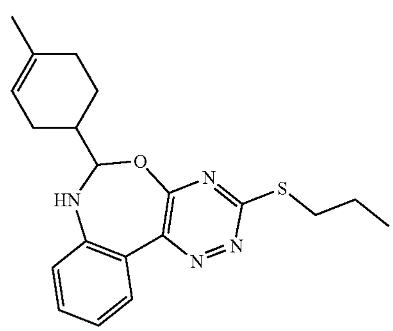 [SMILES: CCCSc1nnc2c(n1)OC(C1CC=C(C)CC1)Nc1ccccc1-2] | NT | * | NT |  | NT |  | ** | * | ND |
| GU | 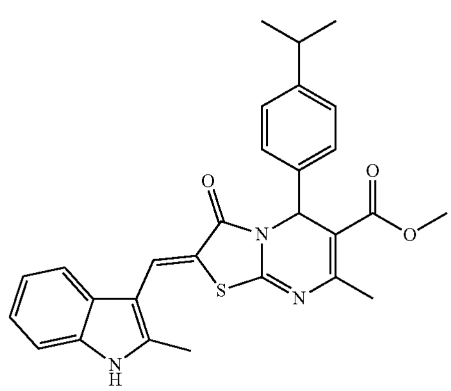 [SMILES: COC(=O)C1=C(C)N=c2s/c(=C\c3c(C)[nH]c4ccccc34)c(=O)n2C1c1ccc(C(C)C)cc1] | NT |  | NT | * | NT | * |  |  | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| GV | 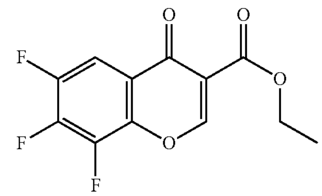 [SMILES: CCOC(=O)c1coc2c(F)c(F)c(F)cc2c1=O] | ** | * | * | * | * | * | ** | ND | ND |
| GW | 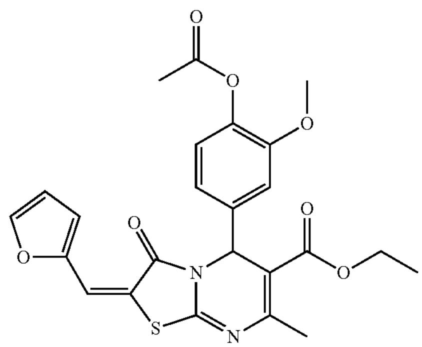 [SMILES: CCOC(=O)C1=C(C)N=c2s/c(=C/c3ccco3)c(=O)n2C1c1ccc(OC(C)=O)c(OC)c1] | *** | * | ** | * |  |  |  | ND |  |
| GX | 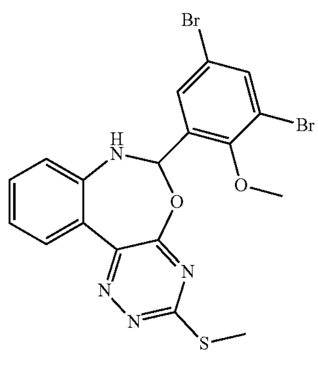 [SMILES: COc1c(Br)cc(Br)cc1C1Nc2ccccc2-c2nnc(SC)nc2O1] | ** | * | ** | * | * | * |  | ND |  |
| GY | 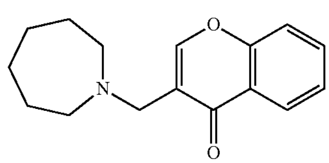 [SMILES: O=c1c(CN2CCCCCC2)coc2ccccc12] | ** | * | * | * | ** | * |  | ND |  |
| GZ | 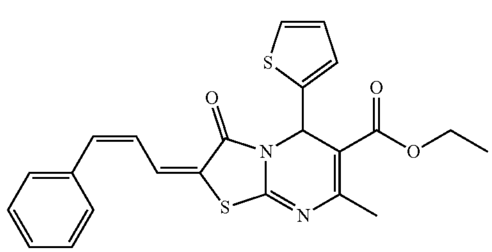 [SMILES: CCOC(=O)C1=C(C)N=c2s/c(=C/C=C\c3ccccc3)c(=O)n2C1c1cccs1] |  |  | ** | * |  |  |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| HA | 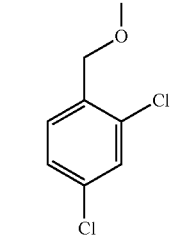 | *** | * | *** | * | *** | * |  | ND |  |
| HB | 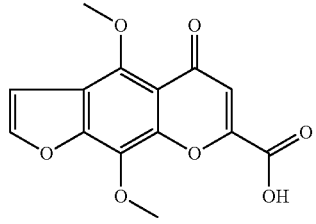 [SMILES: COc1c2occc2c(OC)c2c(=O)cc(C(=O)O)oc12] | * | * | ** | * | ** | * | ** | ND | * |
| HC | 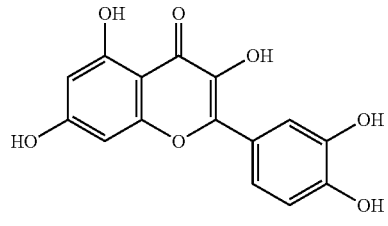 [SMILES: O=c1c(O)c(-c2ccc(O)c(O)c2)oc2cc(O)cc(O)c12] | * | * |  | * |  | NT |  | ND | ** |
| HD | 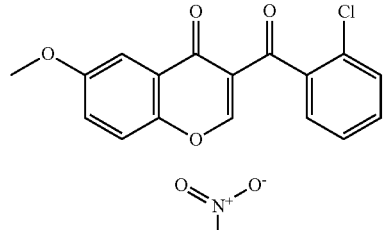 | * |  |  | * |  | * | ** | ND | * |
| HE | 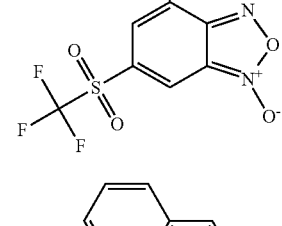 | * | * | ** | * | * | * |  |  | ** |
| HF | 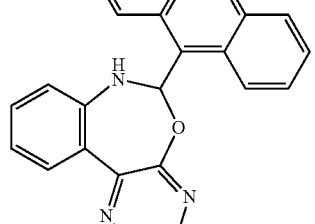 | * |  |  | * | * | * |  |  | ND |

199

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| HG | 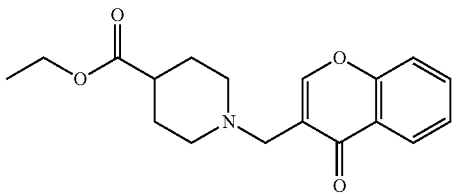 [SMILES: CCOC(=O)C1CCN(Cc2coc3ccccc3c2=O)CC1] | * | * | ** | * | * | * |  |  | ** |
| HH | 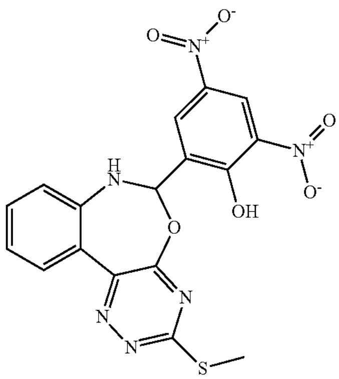 [SMILES: CSc1nnc2c(n1)OC(c1cc([N+](=O)[O-])cc([N+](=O)[O-])c1O)Nc1ccccc1-2] | * | * | ** | * | ** | * |  |  | ** |
| HI | 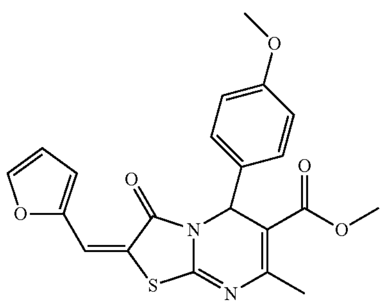 [SMILES: COC(=O)C1=C(C)N=c2s/c(=C/c3ccco3)c(=O)n2C1c1ccc(OC)cc1] | * | * | ** | * | ** | * |  |  | ** |
| HJ | 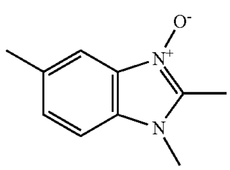 | NT | * |  |  | * | * |  |  | ** |
| HK | 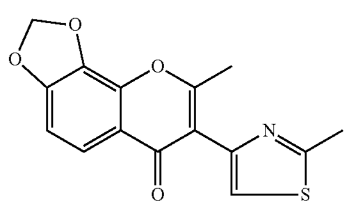 [SMILES: Cc1nc(-c2c(C)oc3c4c(ccc3c2=O)OCO4)cs1] | NT | * | NT |  | NT |  |  |  | * |
| HL | 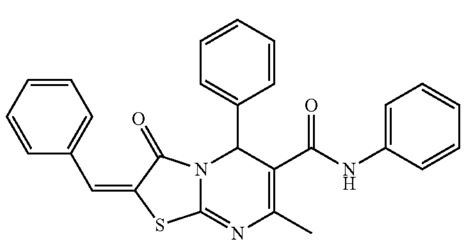 [SMILES: CC1=C(C(=O)Nc2ccccc2)C(c2ccccc2)n2c(s/c(=C/c3ccccc3)c2=O)=N1] | NT | * | NT | * | NT | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| HM | 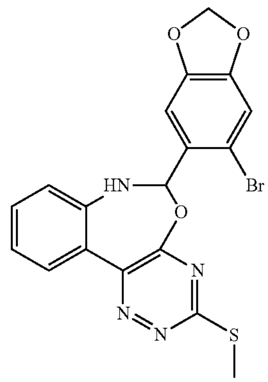 [SMILES: CSc1nnc2c(n1)OC(c1cc3c(cc1Br)OCO3)Nc1ccccc1-2] | * | NT |  |  | * | * |  | ND |  |
| HN | 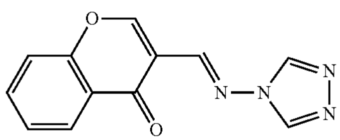 [SMILES: O=c1c(/C=N/n2cnnc2)coc2ccccc12] | * | NT |  |  | * |  |  | ND | ND |
| HO | 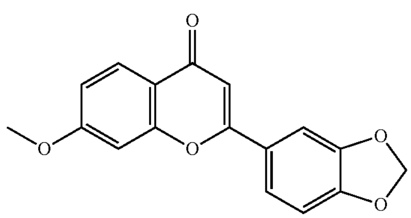 [SMILES: COc1ccc2c(=O)cc(-c3ccc4c(c3)OCO4)oc2c1] |  | NT |  | * | * |  |  | ND | ND |
| HP | 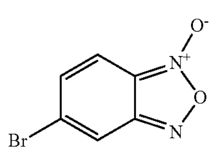 [SMILES: [O-][n+]1onc2cc(Br)ccc21] | * | NT | ** | * | * | * | ** | ND | * |
| HQ | 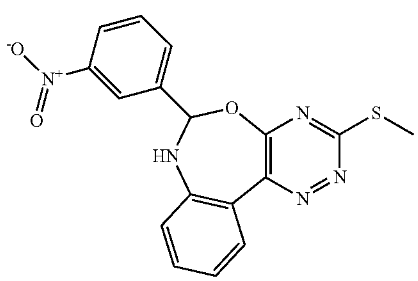 | NT | * | NT | ** | NT | * |  |  | ** |
| HR | 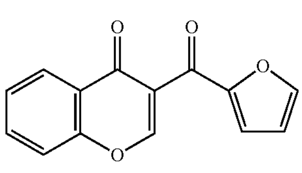 [SMILES: O=C(c1ccco1)c1coc2ccccc2c1=O] | NT | * | NT | * | NT | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| HS | 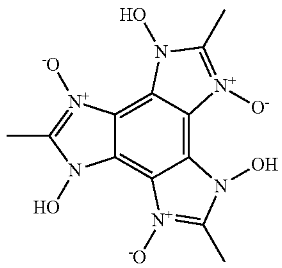 | * |  |  | NT |  | NT |  | ND | * |
| HT | 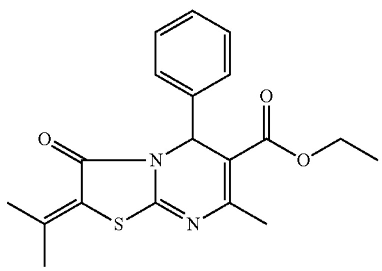 [SMILES: CCOC(=O)C1=C(C)N=c2sc(=C(C)C)c(=O)n2C1c1ccccc1] | * | * | * | NT |  | NT |  | ND | ** |
| HU | 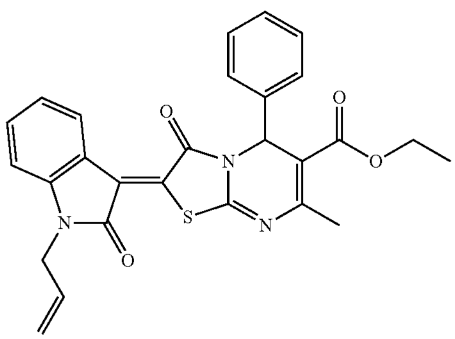 [SMILES: C=CCN1C(=O)/C(=c2\sc3n(c2=O)C(c2ccccc2)C(C(=O)OCC)=C(C)N=3)c2ccccc21] | * | * | * | * | *** | * |  | ND |  |
| HV | 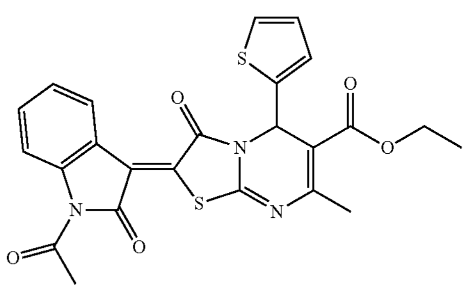 [SMILES: CCOC(=O)C1=C(C)N=c2s/c(=C3\C(=O)N(C(C)=O)c4ccccc43)c(=O)n2C1c1cccs1] | ** | * | *** | * | ** | * |  | ND |  |
| HW | 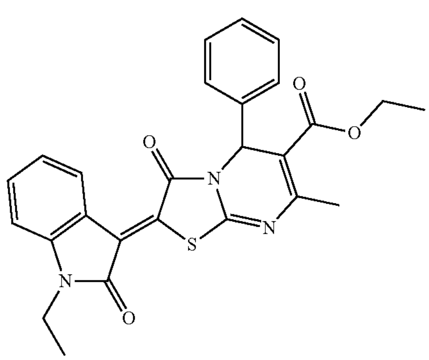 [SMILES: CCOC(=O)C1=C(C)N=c2s/c(=C3\C(=O)N(CC)c4ccccc43)c(=O)n2C1c1ccccc1] | *** | * | * | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| HX | 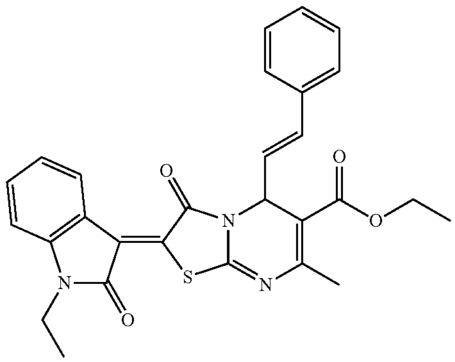 [SMILES: CCOC(=O)C1=C(C)N=c2s/c(=C3\C(=O)N(CC)c4ccccc43)c(=O)n2C1/C=C/c1ccccc1] | * | * | *** | * | ** | * |  | ND |  |
| HY | 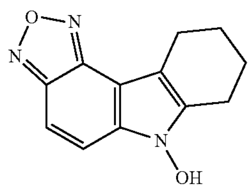 [SMILES: On1c2c(c3c4nonc4ccc31)CCCC2] | *** | * | *** | * | *** | * | ** | ND | * |
| HZ | 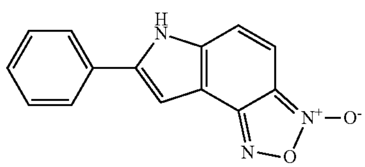 [SMILES: [O-][n+]1onc2c3cc(-c4ccccc4)[nH]c3ccc21] | ** | * | ** | * | ** | * |  | ND |  |
| IA | 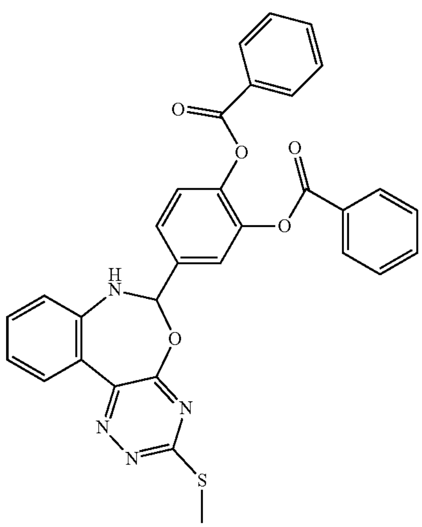 [SMILES: CSc1nnc2c(n1)OC(c1ccc(OC(=O)c3ccccc3)c(OC(=O)c3ccccc3)c1)Nc1ccccc1-2] | *** | * | *** | * | *** | * | ** | ND | * |
| IB | 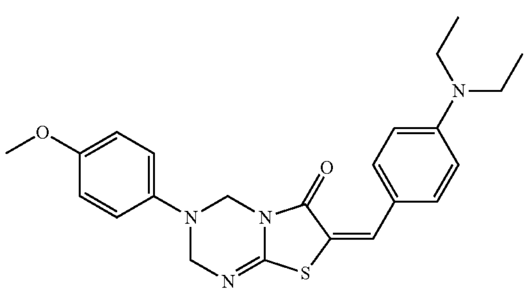 [SMILES: CCN(CC)c1ccc(/C=c2/sc3n(c2=O)CN(c2ccc(OC)cc2)CN=3)cc1] | ** | * | *** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| IC | 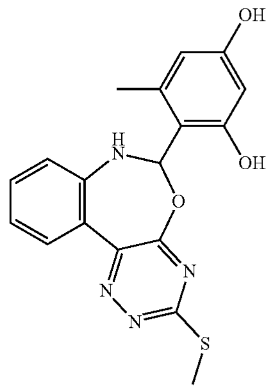 [SMILES: CSc1nnc2c(n1)OC(c1c(C)cc(O)cc1O)Nc1ccccc1-2] | ** | * | ** | * | *** | * | ** | ND | ND |
| ID | 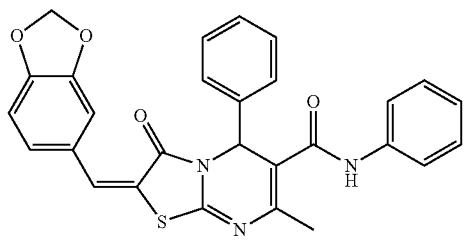 [SMILES: CC1=C(C(=O)Nc2ccccc2)C(c2ccccc2)n2c(s/c(=C/c3ccc4c(c3)OCO4)c2=O)=N1] | *** | * | *** | * | *** | * | ** | ND | * |
| IE | 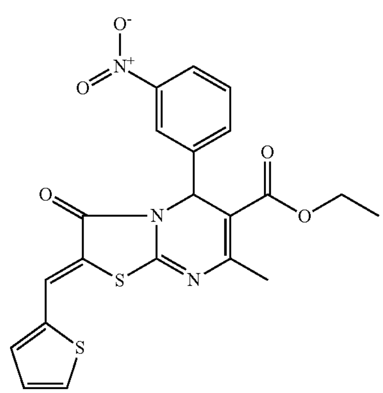 [SMILES: CCOC(=O)C1=C(C)N=c2s/c(=C\c3cccs3)c(=O)n2C1c1cccc([N+](=O)[O-])c1] | * | * | * | * | *** | * |  | ND |  |
| IF | 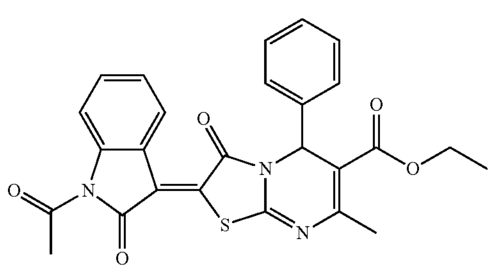 [SMILES: CCOC(=O)C1=C(C)N=c2s/c(=C3\C(=O)N(C(C)=O)c4ccccc43)c(=O)n2C1c1ccccc1] | * | * | *** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|----|
| IG | 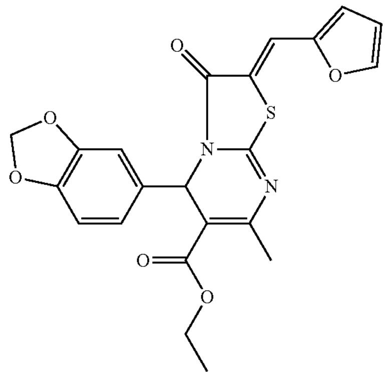 [SMILES: CCOC(=O)C1=C(C)N=c2s/c(=C\c3ccco3)c(=O)n2C1c1ccc2c(c1)OCO2] | * | * | ** | * | ** | * | ** | ND | ND |
| IH | 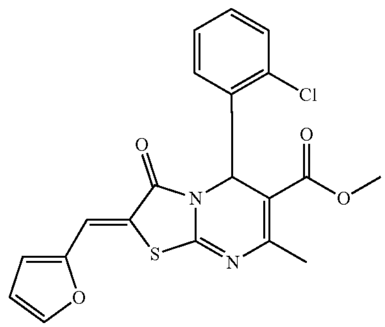 [SMILES: COC(=O)C1=C(C)N=c2s/c(=C\c3ccco3)c(=O)n2C1Cc1ccccc1Cl] | ** | * | *** | * | ** | * | ** | ND | * |
| II | 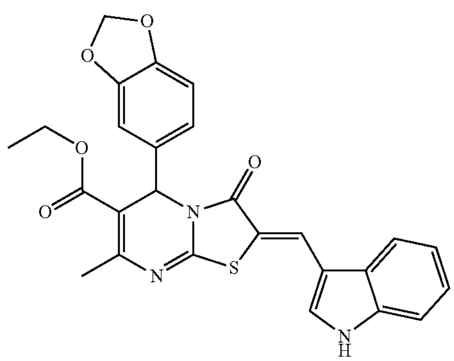 [SMILES: CCOC(=O)C1=C(C)N=c2s/c(=C\c3c[nH]c4ccccc34)c(=O)n2C1c1ccc2c(c1)OCO2] | * |  | *** | * | ** | * |  | ND |  |
| IJ | 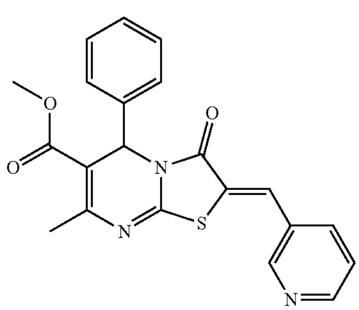 [SMILES: COC(=O)C1=C(C)N=c2s/c(=C\c3cccnc3)c(=O)n2C1c1ccccc1] | * |  | *** | * | *** | * | ** | ND | * |
| IK | 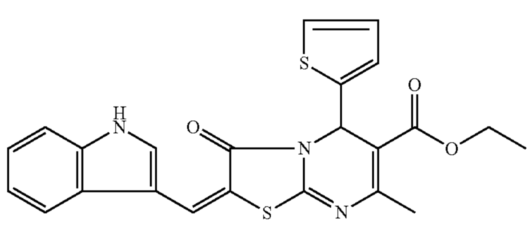 [SMILES: CCOC(=O)C1=C(C)N=c2s/c(=C/c3c[nH]c4ccccc34)c(=O)n2C1c1cccs1] | *** | * | ** | * | *** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| IL | 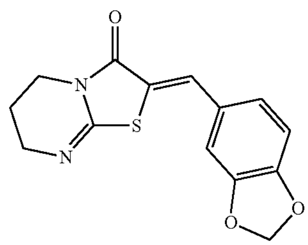 [SMILES: O=c1/c(=C/c2ccc3c(c2)OCO3)sc2n1CCCN=2] | * | * | *** | * | *** | * |  | ND |  |
| IM | 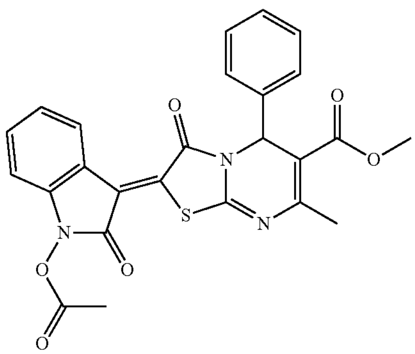 [SMILES: COC(=O)C1=C(C)N=c2s/c(=C3\C(=O)N(OC(C)=O)c4ccccc43)c(=O)n2C1c1ccccc1] | ** | * | ** | * | ** | * |  | ND |  |
| IN | 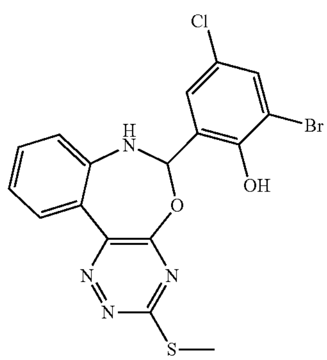 [SMILES: CSc1nnc2c(n1)OC(c1cc(Cl)cc(Br)c1O)Nc1ccccc1-2] | ** | * | * | * | ** | * | ** | ND | ND |
| IO | 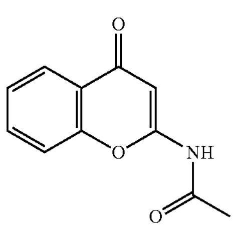 | * | * | * | * | * | * | ** | ND | ND |
| IP | 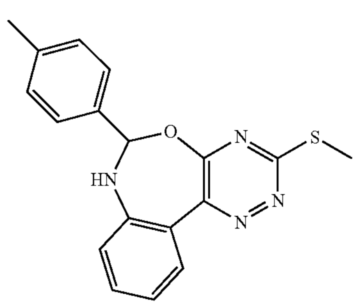 | * | * | * | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| IQ | 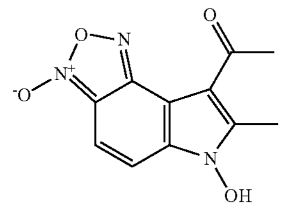 | *** | * | ** | * | *** | * | ** | ND | ND |
| IR | 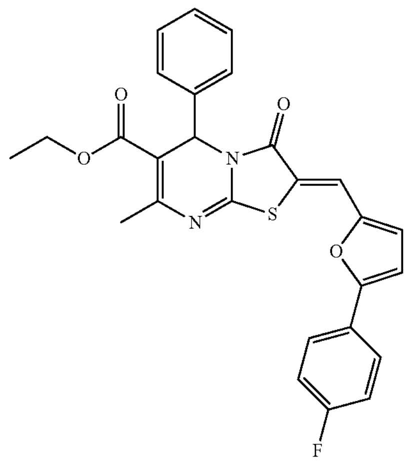 [SMILES: CCOC(=O)C1=C(C)N=c2s/c(=C\c3ccc(-c4ccc(F)cc4)o3)c(=O)n2C1c1ccccc1] | ** | * | ** | * |  |  |  | ND |  |
| IS | 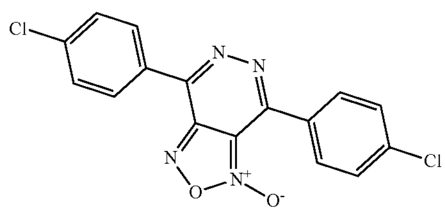 [SMILES: [O-][n+]1onc2c(-c3ccc(Cl)cc3)nnc(-c3ccc(Cl)cc3)c21] | ** | * | * | * |  |  |  | ND | * |
| IT | 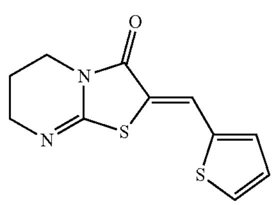 [SMILES: O=c1/c(=C/c2cccs2)sc2n1CCCN=2] | ** | * | * | * | ** | * | ** | ND | * |
| IU | 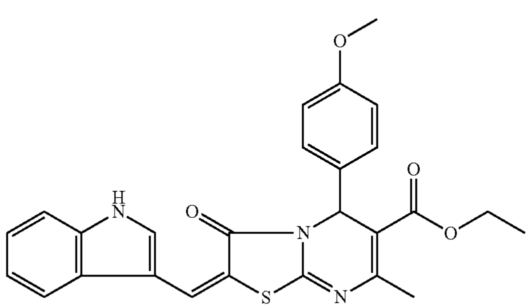 [SMILES: CCOC(=O)C1=C(C)N=c2s/c(=C/c3c[nH]c4ccccc34)c(=O)n2C1c1ccc(OC)cc1] |  | * | * | * | * |  |  | ND | ND |
| IV | 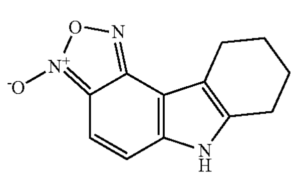 | * | * | * | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| IW | 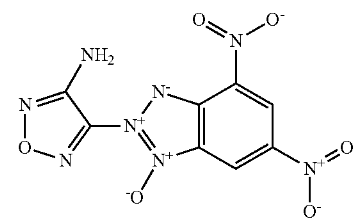 | *** | * | * | * | * | * | ** | ND | ND |
| IX | 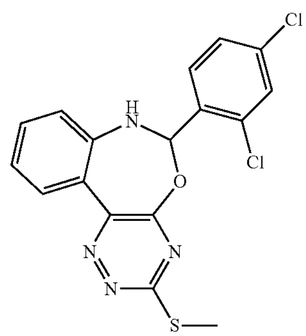 [SMILES: CSc1nnc2c(n1)OC(c1ccc(Cl)cc1Cl)Nc1ccccc1-2] |  |  | * | * | * | * | ** | ND | * |
| IY | 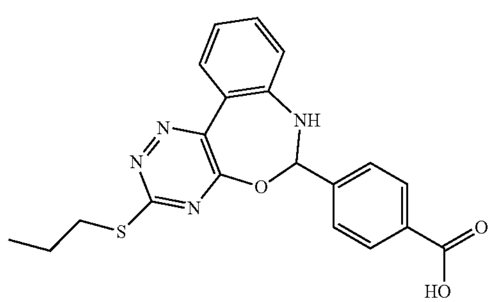 [SMILES: CCCSc1nnc2c(n1)OC(c1ccc(C(=O)O)cc1)Nc1ccccc1-2] | ** | * | * | * | * | * |  | ND |  |
| IZ | 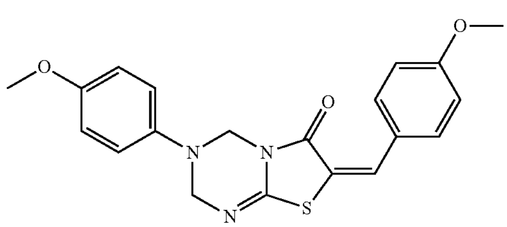 | ** | * | * | * | * | * | ** | ND | * |
| JA | 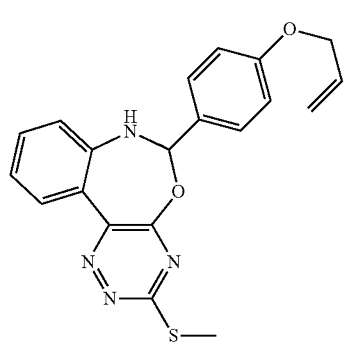 [SMILES: C=CCOc1ccc(C2(C)Nc3ccccc3-c3nnc(SC)nc3O2)cc1] | ** | * | * | * | ** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| JB | 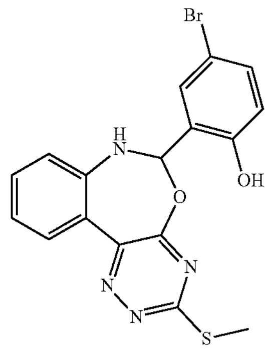 [SMILES: CSc1nnc2c(n1)OC(c1cc(Br)ccc1O)Nc1ccccc1-2] | * |  | ** | * | *** | * | ** | ND | ND |
| JD | 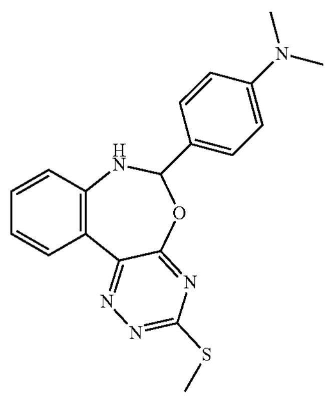 [SMILES: CSc1nnc2c(n1)OC(c1ccc(N(C)C)cc1)Nc1ccccc1-2] | ** | * | * | * | * | * | ** | ND | * |
| JE | 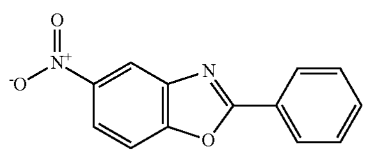 | NT | * | NT | * | NT | * |  |  | * |
| JF | 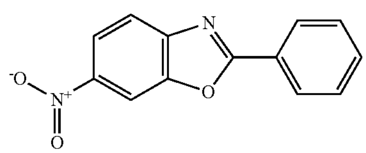 | NT |  | NT |  | NT | * |  | * | * |
| JG | 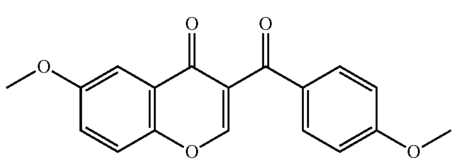 | NT | * | NT | * | NT |  |  | ** | ND |
| JH | 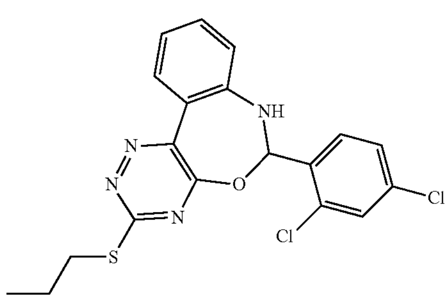 [SMILES: CCCSc1nnc2c(n1)OC(c1ccc(Cl)cc1Cl)Nc1ccccc1-2] | NT | * | NT | * | NT | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| JI | 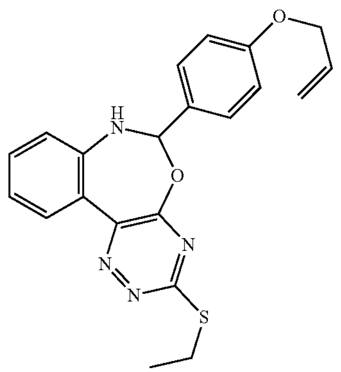 [SMILES: C=CCOc1ccc(C2Nc3ccccc3-c3nnc(SCC)nc3O2)cc1] | NT | * | NT | * | NT |  |  |  |  |
| JJ | 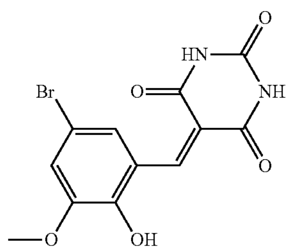 [SMILES: COc1cc(Br)cc(C=C2C(=O)NC(=O)NC2=O)c1O] |  |  | ** | * |  |  |  | ND |  |
| JK | 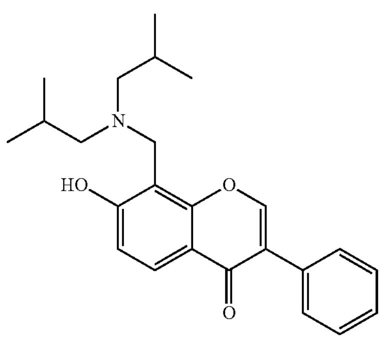 [SMILES: CC(C)CN(Cc1c(O)ccc2c(=O)c(-c3ccccc3)coc12)CC(C)C] |  |  | * | * | ** | * |  | ND |  |
| JL | 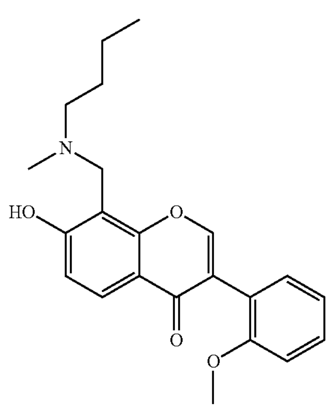 [SMILES: CCCCN(C)Cc1c(O)ccc2c(=O)c(-c3ccccc3OC)coc12] | * |  |  | * | *** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| JM | 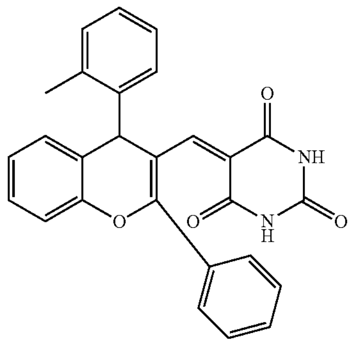 [SMILES: Cc1ccccc1C1C(C=C2C(=O)NC(=O)NC2=O)=C(c2ccccc2)Oc2ccccc21] | * | * | * | * | * | * |  | ND |  |
| JN | 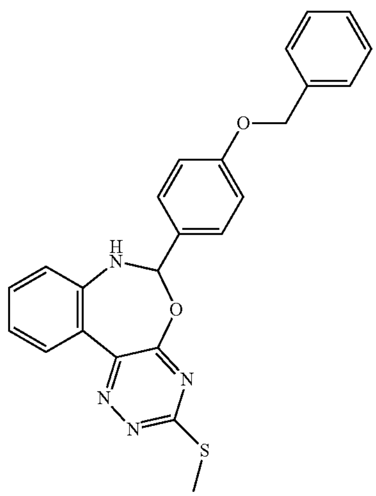 [SMILES: CSc1nnc2c(n1)OC(c1ccc(OCc3ccccc3)cc1)Nc1ccccc1-2] | * | *** | * | * | * | NT |  | ND |  |
| JO | 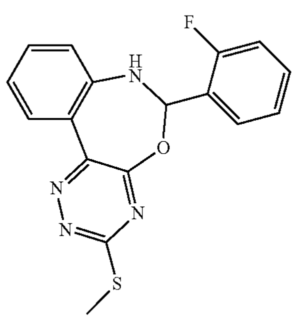 [SMILES: CSc1nnc2c(n1)OC(c1ccccc1F)Nc1ccccc1-2] |  | * | ** | * |  | NT |  | ND | ** |
| JP | 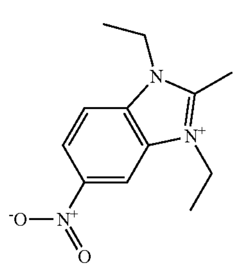 | * | * | ** | * | ** | * | ** | | |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| JQ | 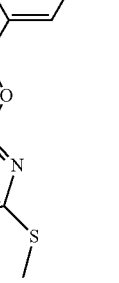 | * | * | ** | * | ** | * |  |  | ** |
| JR | 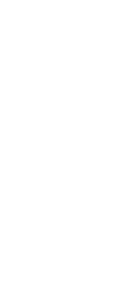 | * | * | * | * | * | * |  | ** | ND |
| JZ | 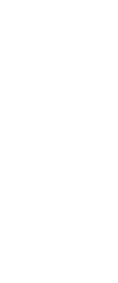 | * |  |  | * | * | * |  |  | ** |
| KA | 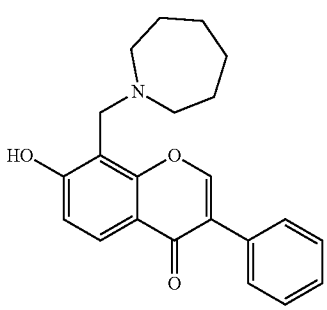 [SMILES: O=c1c(-c2ccccc2)coc2c(CN3CCCCCC3)c(O)ccc12] | * | * | NT | * | * | * |  |  | ** |
| KB | 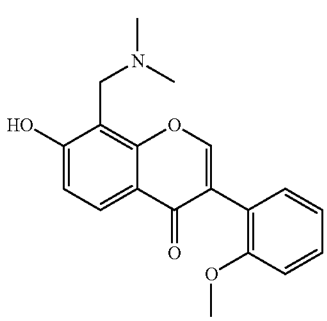 [SMILES: COc1ccccc1-c1coc2c(CN(C)C)c(O)ccc2c1=O] | *** | * | *** | * | * | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|----|
| KC | 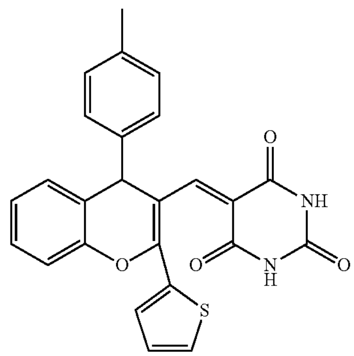 [SMILES: Cc1ccc(C2C(C=C3C(=O)NC(=O)NC3=O)=C(c3cccs3)Oc3ccccc32)cc1] | * | * | ** | * | * | * |  |  | ** |
| KD | 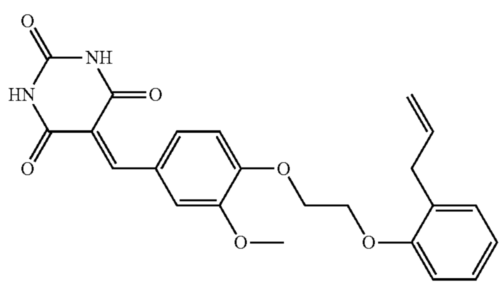 [SMILES: C=CCc1ccccc1OCCOc1ccc(C=C2C(=O)NC(=O)NC2=O)cc1OC] | ** | * | ** | NT | * | NT | ** | * | ** |
| KE | 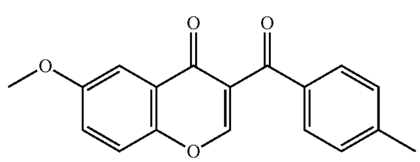 | * | * | * | NT |  | NT |  | ** | * |
| KF | 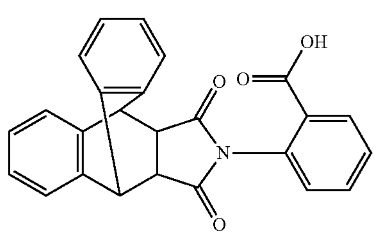 [SMILES: O=C(O)c1ccccc1N1C(=O)C2C3c4ccccc4C(c4ccccc43)C2C1=O] | NT | * | NT | * | NT |  |  |  |  |
| KG | 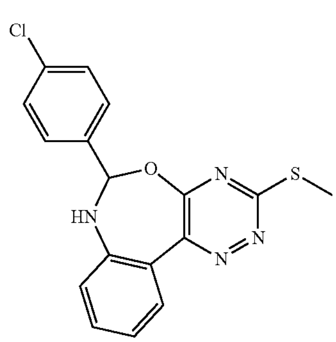 [SMILES: CSc1nnc2c(n1)OC(c1ccc(Cl)cc1)Nc1ccccc1-2] | * | NT | ** | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| KH | 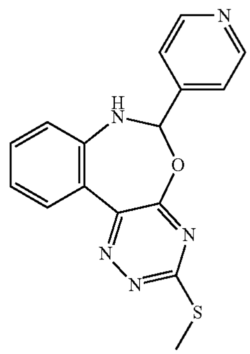 [SMILES: CSc1nnc2c(n1)OC(c1ccncc1)Nc1ccccc1-2] | * | NT | ** | * |  | * |  | ND |  |
| KI | 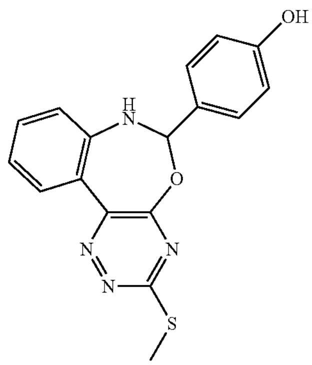 [SMILES: CSc1nnc2c(n1)OC(c1ccc(O)cc1)Nc1ccccc1-2] | * | NT | *** | * | * | * | ** | ND | ND |
| KJ | 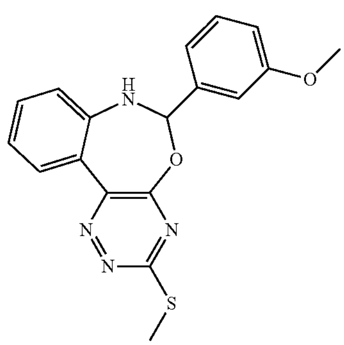 [SMILES: COc1cccc(C2Nc3ccccc3-c3nnc(SC)nc3O2)c1] | * | NT |  |  | * | * |  | ND | ND |
| KK | 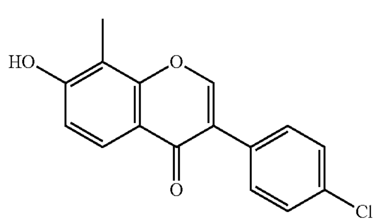 [SMILES: Cc1c(O)ccc2c(=O)c(-c3ccc(Cl)cc3)coc12] | * | * | * | NT | * | NT |  | ND |  |
| KL | 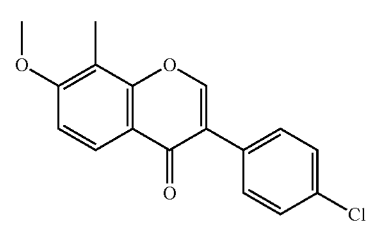 [SMILES: COc1ccc2c(=O)c(-c3ccc(Cl)cc3)coc2c1C] | ** | * | ** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| KM | 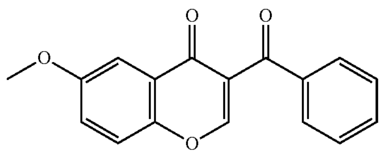 [SMILES: COc1ccc2occ(C(=O)c3ccccc3)c(=O)c2c1] | ** | * | ** | * |  |  | ** | ND | ND |
| KN | 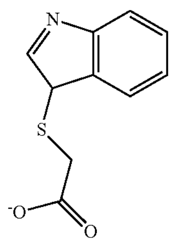 | * | * |  | * | ** | * |  | ND |  |
| KO | 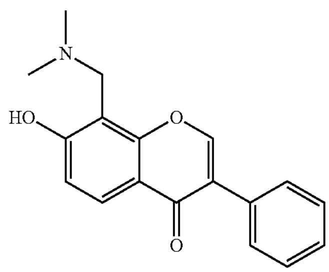 [SMILES: CN(C)Cc1c(O)ccc2c(=O)c(-c3ccccc3)coc12] | ** | * | * | * |  | * |  | ND |  |
| KP | 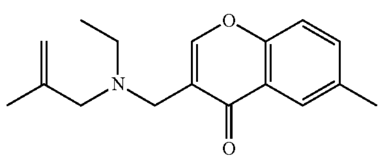 [SMILES: C=C(C)CN(CC)Cc1coc2ccc(C)cc2c1=O] | * | * | ** | * |  |  |  | ND |  |
| KQ | 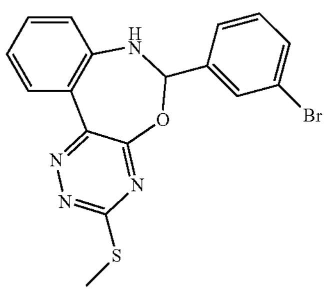 [SMILES: CSc1nnc2c(n1)OC(c1cccc(Br)c1)Nc1ccccc1-2] | * | * | ** | * | *** | * | ** | ND | * |
| KR | 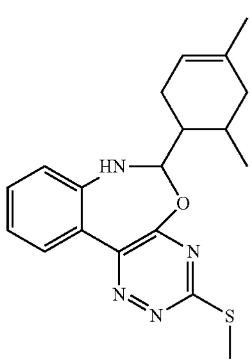 [SMILES: CSc1nnc2c(n1)OC(C1CC=C(C)CC1C)Nc1ccccc1-2] | * | * | * |  | *** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| KS | 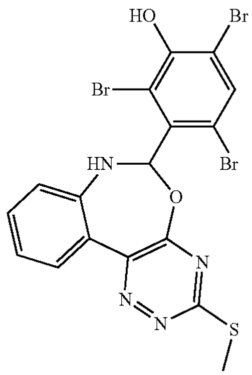 [SMILES: CSc1nnc2c(n1)OC(c1c(Br)cc(Br)c(O)c1Br)Nc1ccccc1-2] | * | * | ** | * | ** | * | ** | ND | * |
| KT | 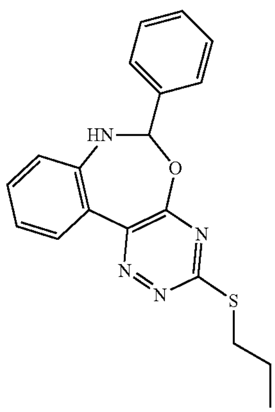 [SMILES: CCCSc1nnc2c(n1)OC(c1ccccc1)Nc1ccccc1-2] | ** | * | *** | * | *** | * | ** | ND | * |
| KU | 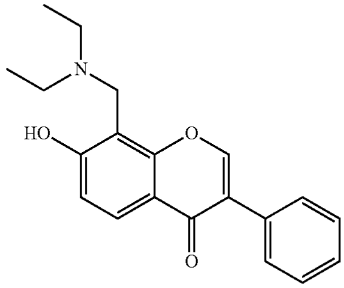 [SMILES: CCN(CC)Cc1c(O)ccc2c(=O)c(-c3ccccc3)coc12] | ** | * | *** | * | * |  |  | ND |  |
| KV | 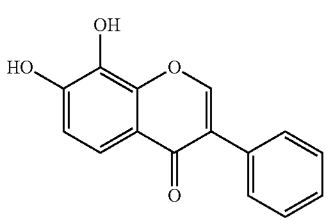 [SMILES: O=c1c(-c2ccccc2)coc2c(O)c(O)ccc12] | *** | * | *** | * | ** | * | ** | ND | * |
| KW | 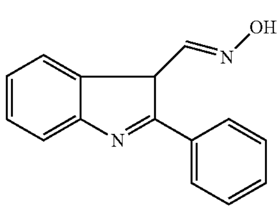 [SMILES: O/N=C/C1C(c2ccccc2)=Nc2ccccc21] | * | * | * | * | * | ** | ND | ND | |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| KX | 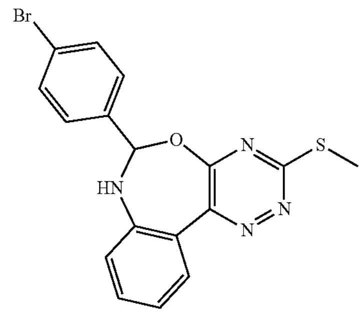 [SMILES: CSc1nnc2c(n1)OC(c1ccc(Br)cc1)Nc1ccccc1-2] | ** | * | * | ** | * | * | ** | ND | ND |
| KY | 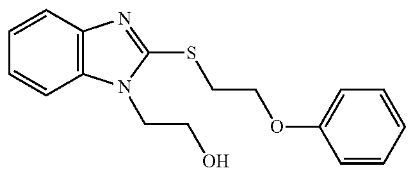 [SMILES: OCCn1c(SCCOc2ccccc2)nc2ccccc21] | *** | * | * |  |  | * |  | ND |  |
| KZ | 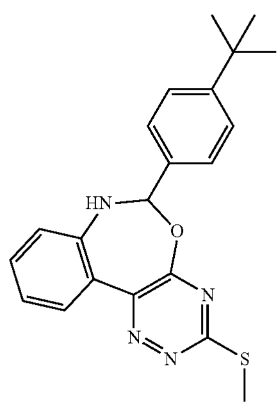 [SMILES: CSc1nnc2c(n1)OC(c1ccc(C(C)(C)C)cc1)Nc1ccccc1-2] |  |  | * | * | * |  |  | ND | ND |
| LA | 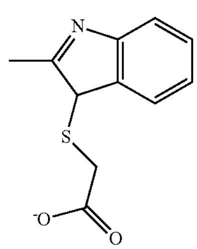 | *** | * | * | * | * | * | ** | ND | ND |
| LB | 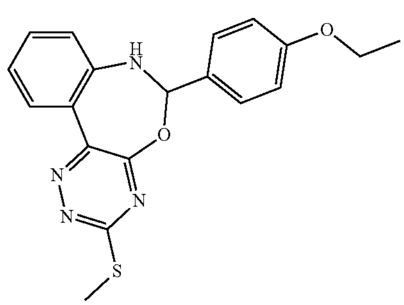 [SMILES: CCOc1ccc(C2Nc3ccccc3-c3nnc(SC)nc3O2)cc1] | ** | * | * | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| LC | 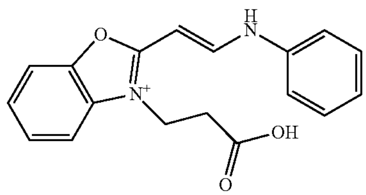 [SMILES: O=C(O)CC[n+]1c(/C=C/Nc2ccccc2)oc2ccccc21] | * | * | * | * | * | * | ** | ND | ND |
| LD | 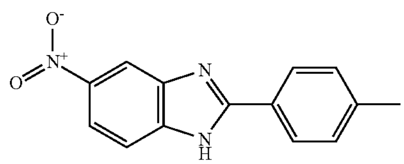 [SMILES: Cc1ccc(-c2nc3cc([N+](=O)[O-])ccc3[nH]2)cc1] | ** | * | * | * | * | * | ** | ND | * |
| LE | 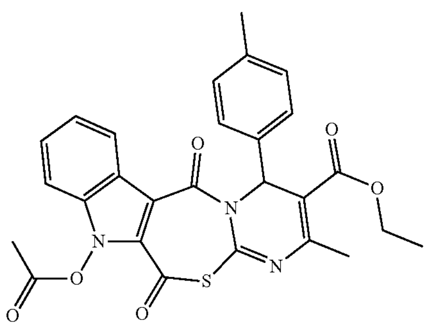 [SMILES: CCOC(=O)C1=C(C)N=C2SC(=O)c3c(c4ccccc4n3OC(C)=O)C(=O)N2C1c1ccc(C)cc1] | *** | * | * | * | * | * | ** | ND | ND |
| LF | 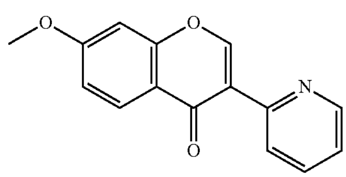 [SMILES: COc1ccc2c(=O)c(-c3ccccn3)coc2c1] | ** | * | * | * | * |  |  | ND | ND |
| LG | 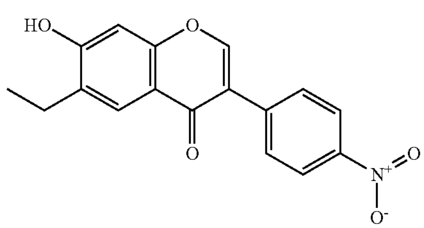 [SMILES: CCc1cc2c(=O)c(-c3ccc([N+](=O)[O-])cc3)coc2cc1O] | ** | * | * | * | ** | * | ** | ND | * |
| LH | 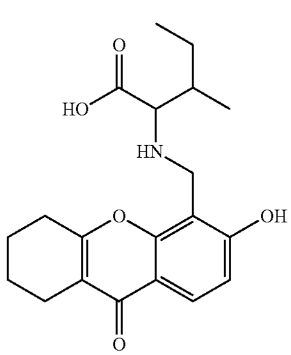 [SMILES: CCC(C)C(NCc1c(O)ccc2c(=O)c3c(oc12)CCCC3)C(=O)O] | * |  | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| LI | 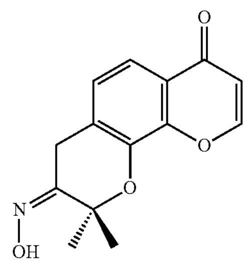 | *** | * | ** | * | *** | * | ** | ND | * |
| LJ | 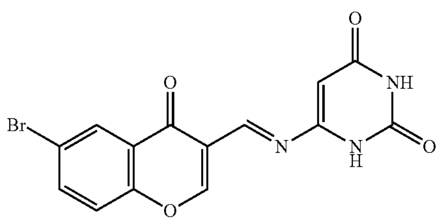 [SMILES: O=c1cc(/N=C/c2coc3ccc(Br)cc3c2=O)[nH]c(=O)[nH]1] | NT | * | NT | ** | NT | * | ** | * | ** |
| LK | 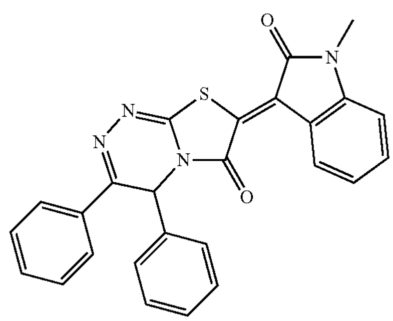 [SMILES: CN1C(=O)/C(=c2\sc3n(c2=O)C(c2ccccc2)C(c2ccccc2)=NN=3)c2ccccc21] | NT | * | NT | * | NT | * |  |  | * |
| LL | 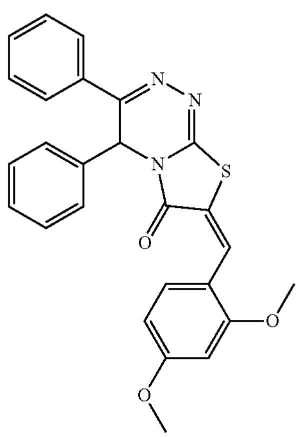 [SMILES: COc1ccc(/C=c2/sc3n(c2=O)C(c2ccccc2)C(c2ccccc2)=NN=3)c(OC)c1] | NT | * | NT | * | NT | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| LM | 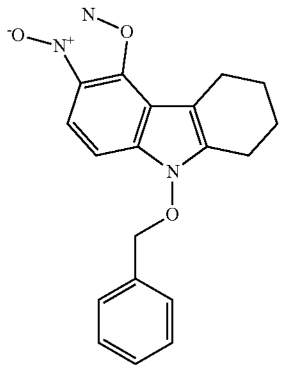 | NT |  | NT | * | NT | * |  |  | ND |
| LN | 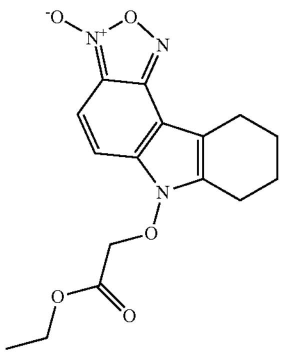 |  |  | ** | * | *** | * |  | ND |  |
| LO | 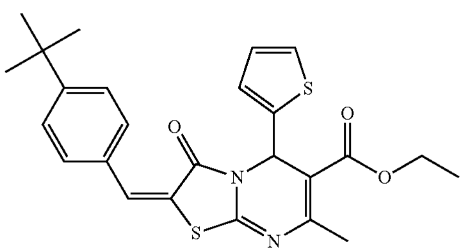 [SMILES: CCOC(=O)C1=C(C)N=c2s/c(=C/c3ccc(C(C)(C)C)cc3)c(=O)n2C1c1cccs1] | * | * | * | * | * |  |  | ND |  |
| LP | 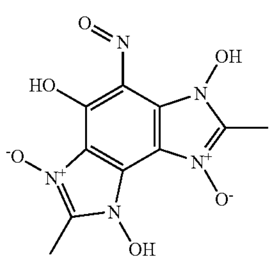 | * | * | *** | * | ** | * | ** | ND | * |
| LQ | 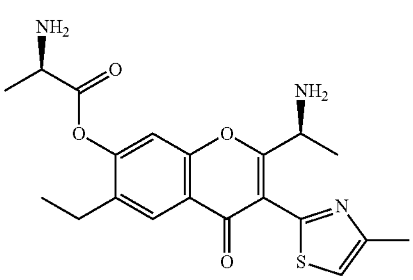 [SMILES: CCc1cc2c(=O)c(-c3nc(C)cs3)c([C@H](C)N)oc2cc1OC(=O)[C@@H](C)N] |  |  | * | * | * | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| LR | 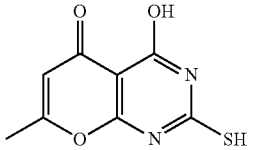 | ** | * | * | * | ** | * |  | ND |  |
| LS | 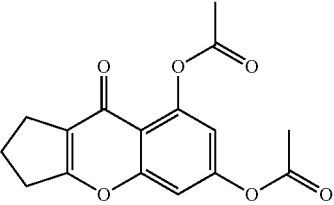 [SMILES: CC(=O)Oc1cc(OC(C)=O)c2c(=O)c3c(oc2c1)CCC3] | * |  | * |  | ** | * | ** | ND | * |
| LT | 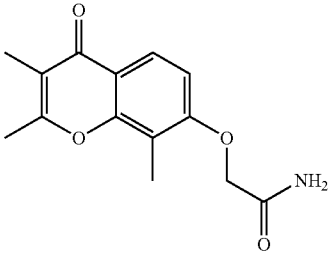 [SMILES: Cc1oc2c(C)c(OCC(N)=O)ccc2c(=O)c1C] | * |  | * |  |  |  |  | ND | ND |
| LU | 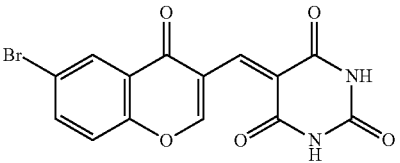 [SMILES: O=C1NC(=O)C(=Cc2coc3ccc(Br)cc3c2=O)C(=O)N1] | * | * |  | * |  | NT | ** | ND | ND |
| LV | 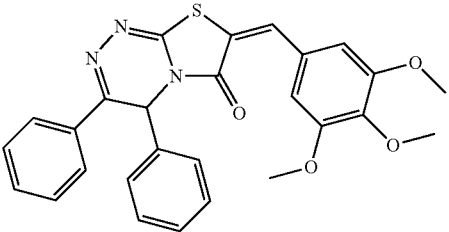 [SMILES: COc1cc(/C=c2/sc3n(c2=O)C(c2ccccc2)C(c2ccccc2)=NN=3)cc(OC)c1OC] | * | * | ** | * | * |  |  | ** | * |
| LW | 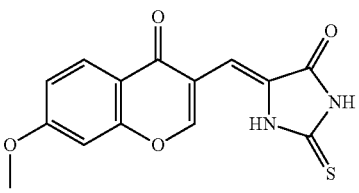 [SMILES: COc1ccc2c(=O)c(/C=C3\NC(=S)NC3=O)coc2c1] | * | * | NT | * | ** | * |  |  | ** |
| LX | 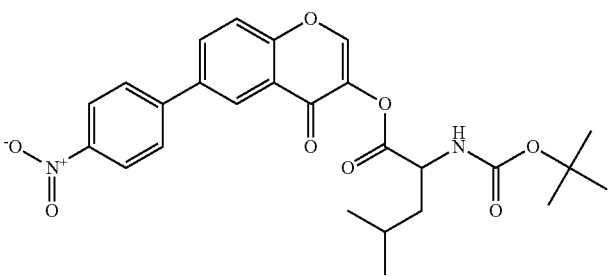 | * | * | NT | * | * | * |  |  | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| LY | 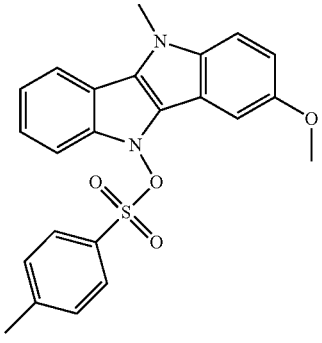 | * | * | ** | * | ** | * |  |  | ** |
| LZ | 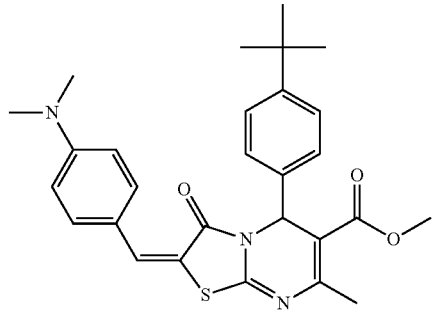 | * | * | NT | * | * | * |  |  | ** |
| MA | 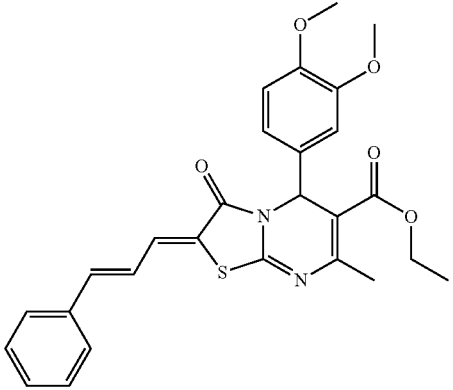 [SMILES: CCOC(=O)C1=C(C)N=c2s/c(=C\C=C\c3ccccc3)c(=O)n2C1c1ccc(OC)c(OC)c1] | * | * | ** | NT | * | NT | ** | * | * |
| MB | 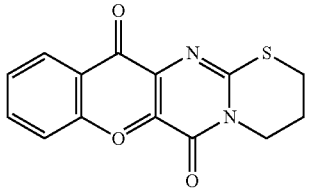 | * | * | * | NT |  | NT |  | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| MC | 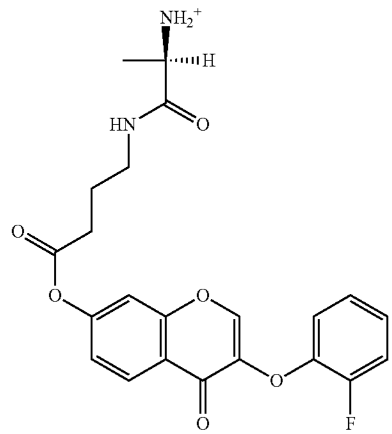 [SMILES: C[C@@H]([NH3+])C(=O)NCCCC(=O)Oc1ccc2c(=O)c(Oc3ccccc3F)coc2c1] | * | * |  |  | * | * | ** | * | * |
| MD | 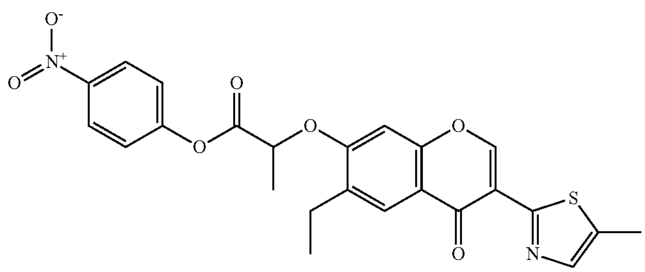 [SMILES: CCc1cc2c(=O)c(-c3ncc(C)s3)coc2cc1OC(C)C(=O)Oc1ccc([N+](=O)[O-])cc1] | NT | * | NT | * | NT |  |  | ** | * |
| ME | 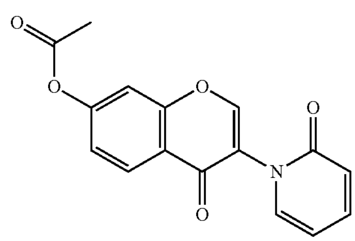 [SMILES: CC(=O)Oc1ccc2c(=O)c(-n3ccccc3=O)coc2c1] | NT | * | NT | * | NT |  |  | ** | * |
| MF | 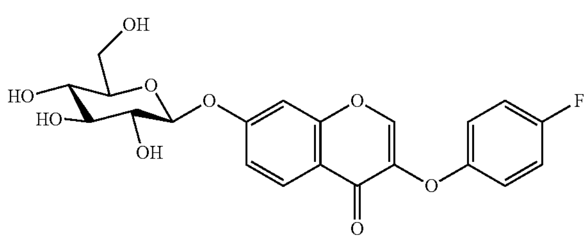 | NT | * | NT | * | NT | * |  | ** | ND |
| MG | 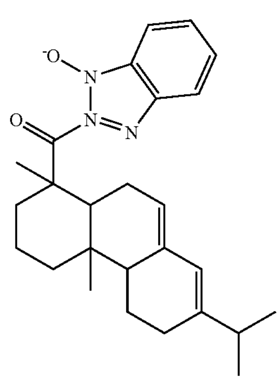 | NT | * | NT |  | NT |  |  |  | |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| MH | 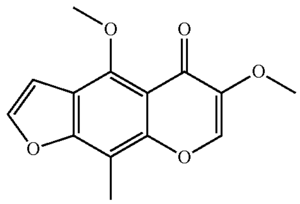 [SMILES: COc1coc2c(C)c3occc3c(OC)c2c1=O] | NT | * | NT | * | NT | * |  | ** | * |
| MI | 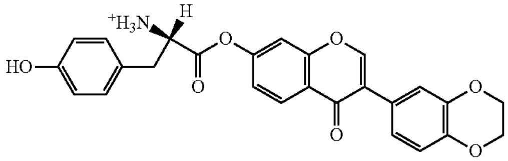 [SMILES: [NH3+][C@H](Cc1ccc(O)cc1)C(=O)Oc1ccc2c(=O)c(-c3ccc4c(c3)OCCO4)coc2c1] | * | NT | * | * | * | * |  | ND |  |
| MJ | 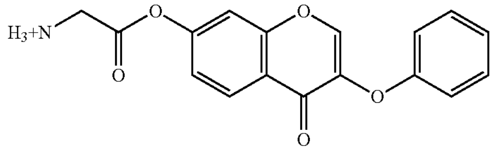 | * | NT | * | * | * | * | ** | ND | * |
| MK | 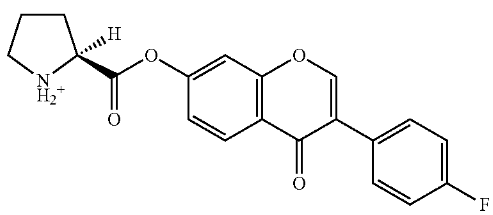 [SMILES: O=C(Oc1ccc2c(=O)c(-c3ccc(F)cc3)coc2c1)[C@@H]1CCC[NH2+]1] |  | NT |  | ** | * |  |  | ND | ND |
| ML | 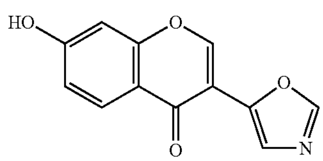 [SMILES: O=c1c(-c2cnco2)coc2cc(O)ccc12] | * | NT |  |  | * | * |  | ND | ** |
| MM | 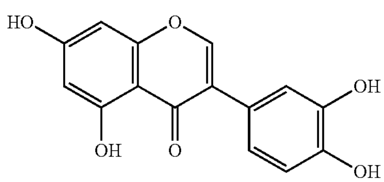 [SMILES: O=c1c(-c2ccc(O)c(O)c2)coc2cc(O)cc(O)c12] | * | NT |  | * | * | * |  | ND | ND |
| MN | 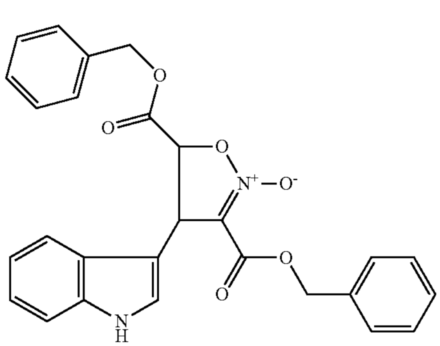 [SMILES: O=C(OCc1ccccc1)C1=[N+]([O-])OC(C(=O)OCc2ccccc2)C1c1c[nH]c2ccccc12] | NT | * | NT | ** | NT | * | ** | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| MO | 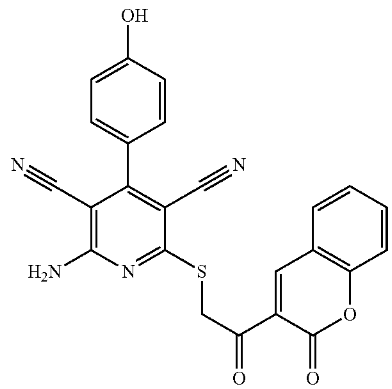 [SMILES: N#Cc1c(N)nc(SCC(=O)c2cc3ccccc3oc2=O)c(C#N)c1-c1ccc(O)cc1] | NT | * | NT | * | NT | * |  |  | ** |
| MP | 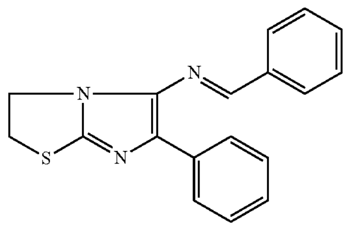 [SMILES: C(=N\c1c(-c2ccccc2)nc2n1CCS2)/c1ccccc1] | NT | * | NT | ** | NT | * |  |  | ** |
| MQ | 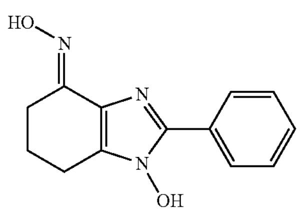 [SMILES: O/N=C1\CCCc2c1nc(-c1ccccc1)n2O] | NT | * | NT | *** | NT | * |  |  | ND |
| MR | 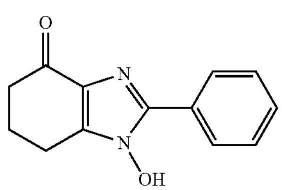 [SMILES: O=C1CCCc2c1nc(-c1ccccc1)n2O] | * |  |  | NT | * | NT |  | ND |  |
| MS | 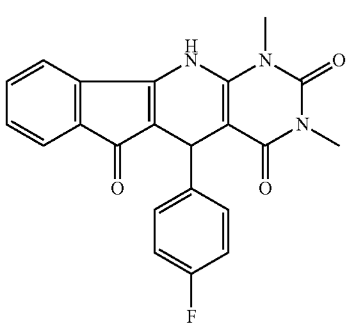 [SMILES: Cn1c2c(c(=O)n(C)c1=O)C(c1ccc(F)cc1)C1=C(N2)c2ccccc2C1=O] | NT | * | * | NT | * | NT | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| MT | 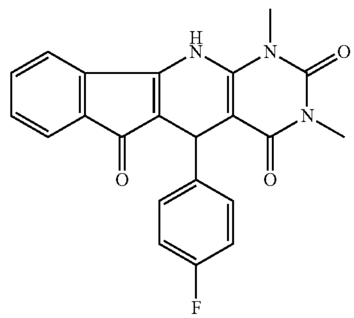 [SMILES: Cn1c2c(c(=O)n(C)c1=O)C(c1ccc(F)cc1)C1=C(N2)c2ccccc2C1=O] | * | * | ** | NT | * | NT | ** | ND | ND |
| MU | 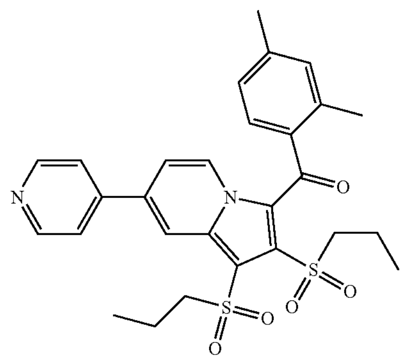 [SMILES: CCCS(=O)(=O)c1c(S(=O)(=O)CCC)c2cc(-c3ccncc3)ccn2c1C(=O)c1ccc(C)cc1C] |  |  | *** | * | ** | * | ** | ND | * |
| MV | 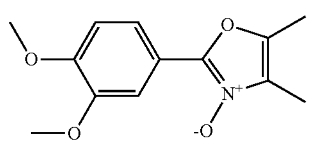 | * | * | ** | * | ** | * |  | ND |  |
| MX | 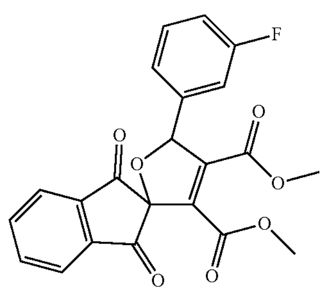 [SMILES: COC(=O)C1=C(C(=O)OC)C2(OC1c1cccc(F)c1)C(=O)c1ccccc1C2=O] | * | * | * | * | * |  | ** | ND | ND |
| MY | 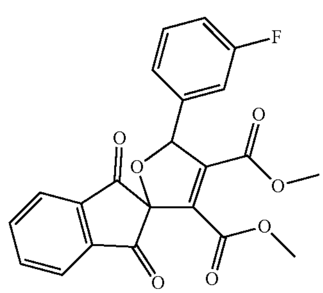 [SMILES: COC(=O)C1=C(C(=O)OC)C2(OC1c1cccc(F)c1)C(=O)c1ccccc1C2=O] |  | * | ** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| MZ | 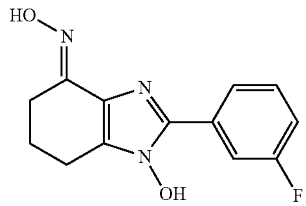 [SMILES: O/N=C1\CCCc2c1nc(-c1cccc(F)c1)n2O] | * | * | ** | * | *** | * | ** | ND | * |
| NA | 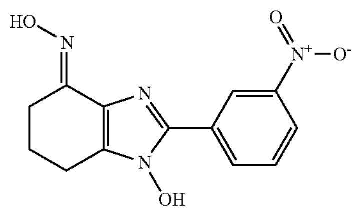 [SMILES: O=[N+]([O-])c1cccc(-c2nc3c(n2O)CCC/C3=N\O)c1] | * | * |  | * | ** | * | ** | ND | * |
| NB | 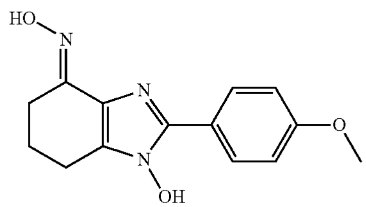 [SMILES: COc1ccc(-c2nc3c(n2O)CCC/C3=N\O)cc1] | * | ** | * | * |  |  | ** | ND | * |
| NC | 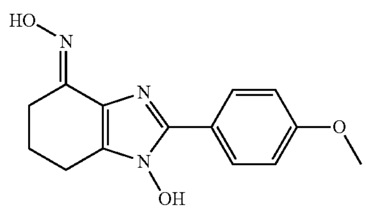 [SMILES: COc1ccc(-c2nc3c(n2O)CCC/C3=N\O)cc1] | * | * | *** | * | ** | * | ** | ND | * |
| ND | 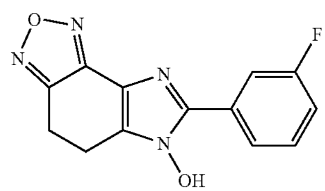 [SMILES: On1c(-c2cccc(F)c2)nc2c1CCc1nonc1-2] | * | * | *** | * | *** | * | ** | ND | ND |
| NE | 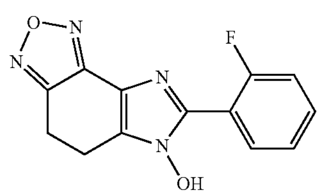 [SMILES: On1c(-c2ccccc2F)nc2c1CCc1nonc1-2] | ** | * | ** | * | ** | * |  | ND |  |
| NF | 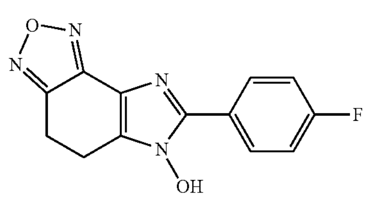 [SMILES: On1c(-c2ccc(F)cc2)nc2c1CCc1nonc1-2] | * | * | * |  | *** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| NG | 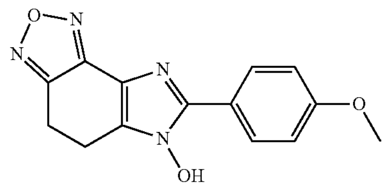 [SMILES: COc1ccc(-c2nc3c(n2O)CCc2nonc2-3)cc1] | ** | * | *** | * | ** | * |  | ND |  |
| NH | 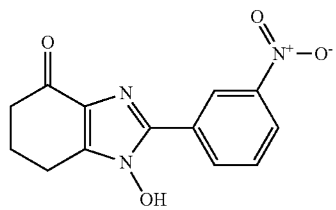 [SMILES: O=C1CCCc2c1nc(-c1cccc([N+](=O)[O-])c1)n2O] | ** | * | * | * | * | * | ** | ND | ND |
| NI | 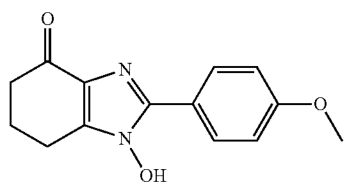 [SMILES: COc1ccc(-c2nc3c(n2O)CCCC3=O)cc1] | * | * | * | * | * | * | ** | ND | ND |
| NJ | 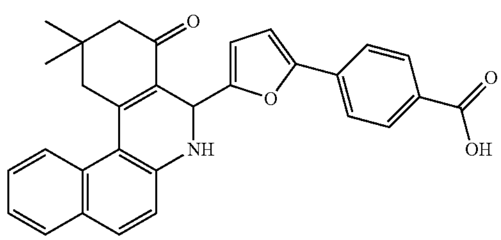 [SMILES: CC1(C)CC(=O)C2=C(C1)c1c(ccc3ccccc13)NC2c1ccc(-c2ccc(C(=O)O)cc2)o1] | * | * | * | * | ** | * | ** | ND | ND |
| NK | 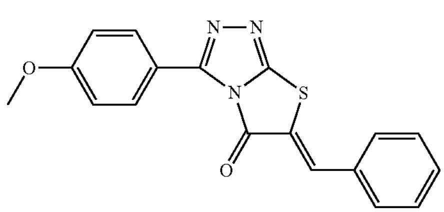 [SMILES: COc1ccc(-c2nnc3s/c(=C\c4ccccc4)c(=O)n23)cc1] | * | * | * | * | * | * | ** | ND | ND |
| NL | 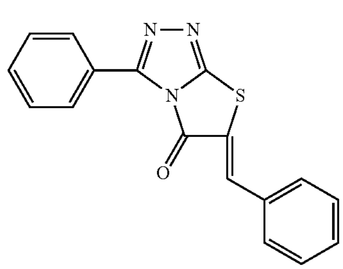 [SMILES: O=c1/c(=C/c2ccccc2)sc2nnc(-c3ccccc3)n12] | ** | * | * | * |  | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| NM | 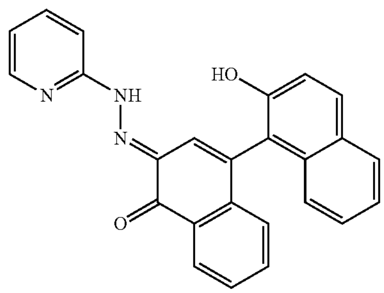 [SMILES: O=C1/C(=N/Nc2ccccn2)C=C(c2c(O)ccc3ccccc23)c2ccccc21] | * | * | * | ** | * | * |  | ND |  |
| NN | 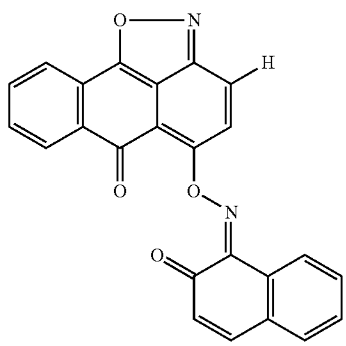 [SMILES: O=C1C=Cc2ccccc2/C1=N/Oc1ccc2noc3c2c1C(=O)c1ccccc1-3] | ** | * | * | * | * |  |  | ND | * |
| NO | 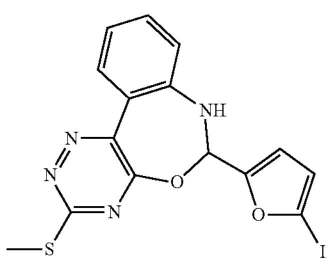 [SMILES: CSc1nnc2c(n1)OC(c1ccc(I)o1)Nc1ccccc1-2] | *** | * | * |  |  |  |  | ND | * |
| NP | 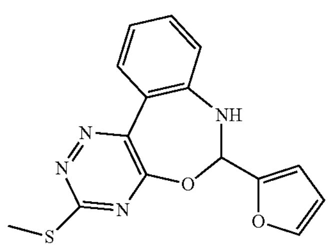 [SMILES: CSc1nnc2c(n1)OC(c1ccco1)Nc1ccccc1-2] | *** | * | * |  | * | * | ** | ND | ND |
| NQ | 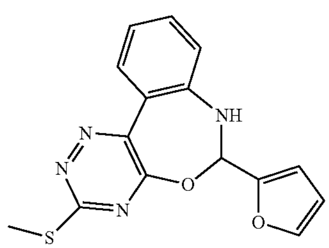 [SMILES: CSc1nnc2c(n1)OC(c1ccco1)Nc1ccccc1-2] | ** | * | * | * | * | * | ** | ND | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| NR | 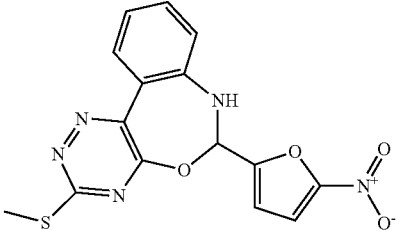 [SMILES: CSc1nnc2c(n1)OC(c1ccc([N+](=O)[O-])o1)Nc1ccccc1-2] | ** | * | * | * | ** | * | ** | ND | ND |
| NS | 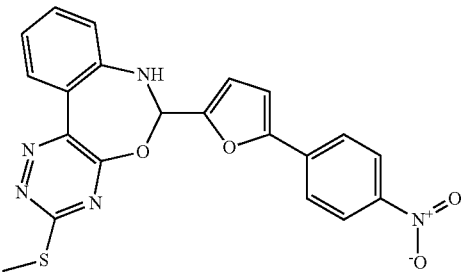 | ** | * | * | * | * | * | ** | ND | ND |
| NT | 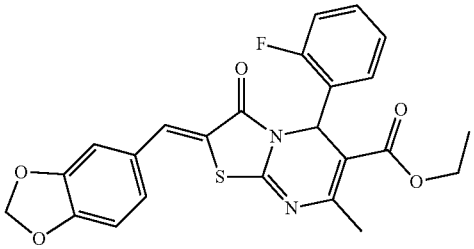 [SMILES: CCOC(=O)C1=C(C)N=c2s/c(=C\c3ccc4c(c3)OCO4)c(=O)n2C1c1ccccc1F] | ** | * | * | * | * | * | ** | ND | ND |
| NU | 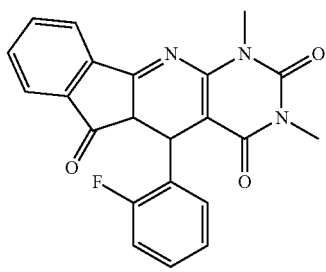 [SMILES: Cn1c2c(c(=O)n(C)c1=O)C(c1ccccc1F)C1C(=O)c3ccccc3C1=N2] | ** | * | * | * | * | * | ** | ND | ND |
| NV | 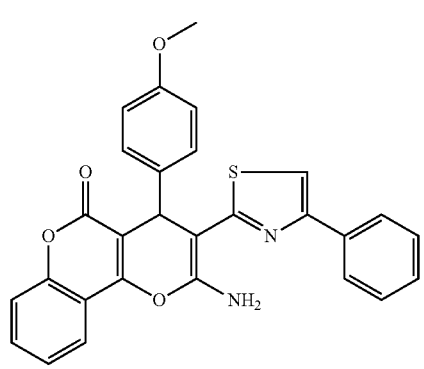 [SMILES: COc1ccc(C2C(c3nc(-c4ccccc4)cs3)=C(N)Oc3c2c(=O)oc2ccccc32)cc1] | * | * | * | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| NW | 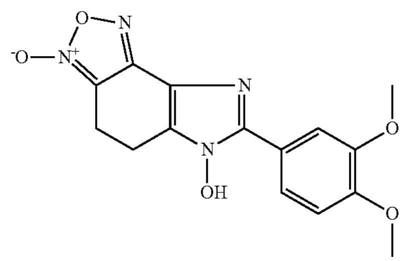 | ** | * | * | * | * | * | ** | ND | * |
| NX | 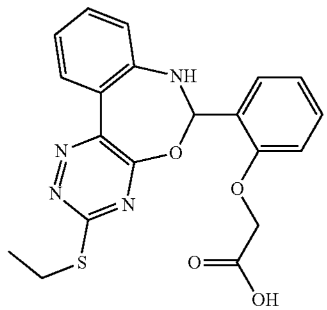 [SMILES: CCSc1nnc2c(n1)OC(c1ccccc1OCC(=O)O)Nc1ccccc1-2] |  |  | * | * | * | * |  | ND |  |
| NY | 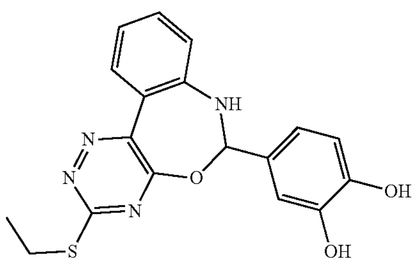 [SMILES: CCSc1nnc2c(n1)OC(c1ccc(O)c(O)c1)Nc1ccccc1-2] | ** | * | * | * | * | * | ** | ND | * |
| NZ | 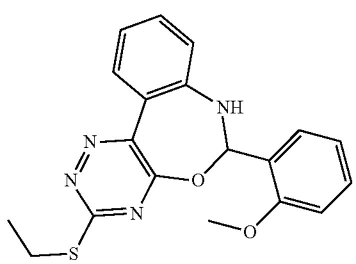 [SMILES: CCSc1nnc2c(n1)OC(c1ccccc1OC)Nc1ccccc1-2] | *** | * | * | * | *** | * | ** | ND | ND |
| OA | 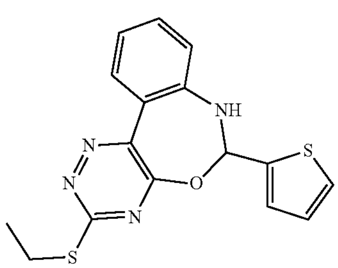 [SMILES: CCSc1nnc2c(n1)OC(c1cccs1)Nc1ccccc1-2] | * | * |  | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OB | 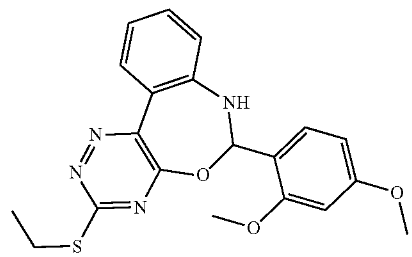 [SMILES: CCSc1nnc2c(n1)OC(c1ccc(OC)cc1OC)Nc1ccccc1-2] | *** | * | ** | * | ** | * |  | ND |  |
| OC | 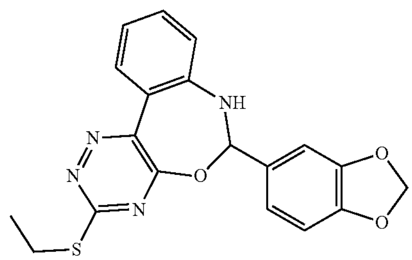 [SMILES: CCSc1nnc2c(n1)OC(c1ccc3c(c1)OCO3)Nc1ccccc1-2] | * |  | ** | * | ** | * | ** | ND | D |
| N£ OD | 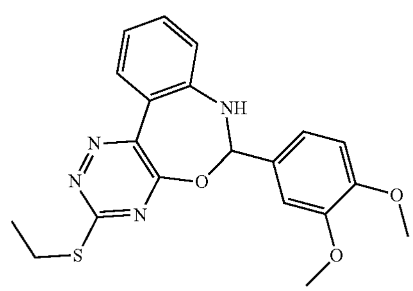 [SMILES: CCSc1nnc2c(n1)OC(c1ccc(OC)c(OC)c1)Nc1ccccc1-2] | * | * | ** | * | * |  | ** | ND | * |
| OE | 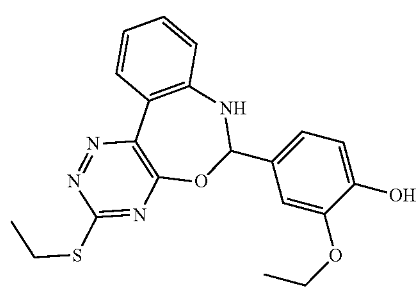 [SMILES: CCOc1cc(C2Nc3ccccc3-c3nnc(SCC)nc3O2)ccc1O] | *** | * | ** | * | *** | * | ** | ND | ND |
| OF | 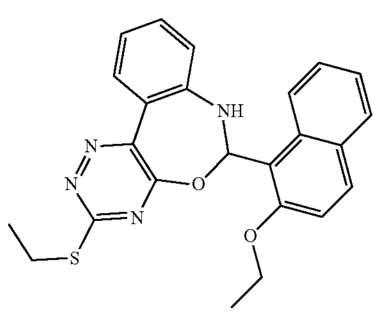 [SMILES: CCOc1ccc2ccccc2c1C1Nc2ccccc2-c2nnc(SCC)nc2O1] | NT | * | NT | * | NT | * |  | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OG | 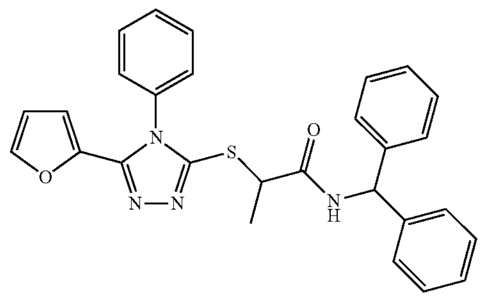 [SMILES: CC(Sc1nnc(-c2ccco2)n1-c1ccccc1)C(=O)NC(c1ccccc1)c1ccccc1] | NT | * | NT | * | NT | * | ** | * | ** |
| OH | 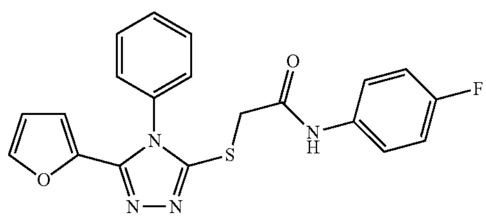 [SMILES: O=C(CSc1nnc(-c2ccco2)n1-c1ccccc1)Nc1ccc(F)cc1] | NT | * | NT | * | NT | * | ** | * | ** |
| OI | 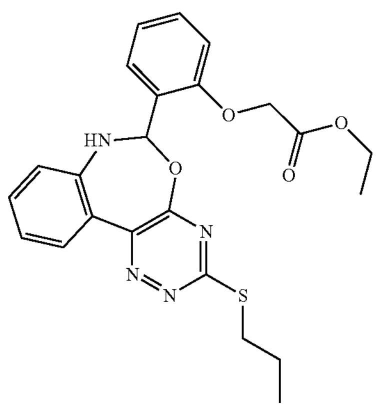 [SMILES: CCCSc1nnc2c(n1)OC(c1ccccc1OCC(=O)OCC)Nc1ccccc1-2] | NT | * | NT |  | NT |  |  |  | ND |
| OJ | 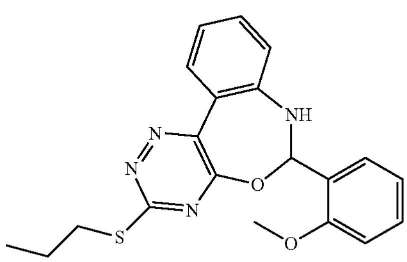 [SMILES: CCCSc1nnc2c(n1)OC(c1ccccc1OC)Nc1ccccc1-2] | NT | * | NT |  | NT |  | ** | * | ND |
| OK | 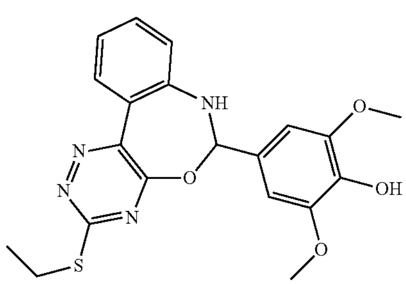 [SMILES: CCSc1nnc2c(n1)OC(c1cc(OC)c(O)c(OC)c1)Nc1ccccc1-2] | NT | * | NT | * | NT |  |  | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OL | 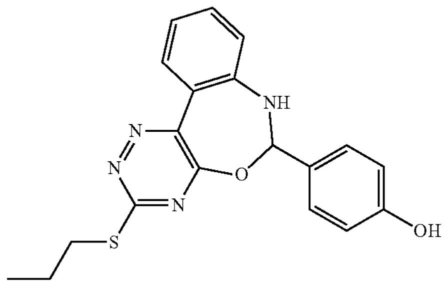 [SMILES: CCCSc1nnc2c(n1)OC(c1ccc(O)cc1)Nc1ccccc1-2] | NT | * | NT |  | NT | * |  |  | * |
| OM | 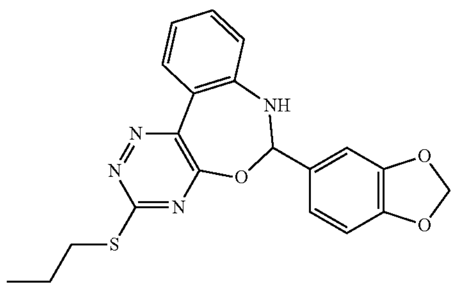 [SMILES: CCCSc1nnc2c(n1)OC(c1ccc3c(c1)OCO3)Nc1ccccc1-2] | NT | * | NT |  | NT | * | ** | * | ND |
| ON | 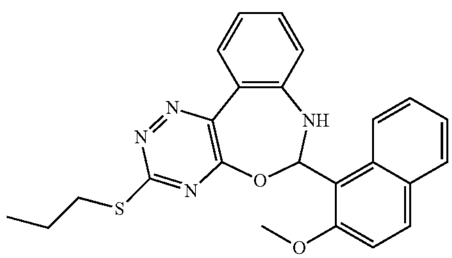 [SMILES: CCCSc1nnc2c(n1)OC(c1c(OC)ccc3ccccc13)Nc1ccccc1-2] |  |  | ** | * |  | * |  | ND |  |
| OO | 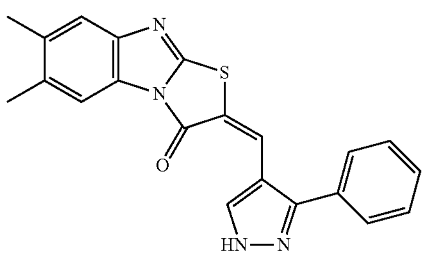 [SMILES: Cc1cc2nc3s/c(=C/c4c[nH]nc4-c4ccccc4)c(=O)n3c2cc1C] | * | * | ** | * | ** | * | ** | ND | * |
| OP | 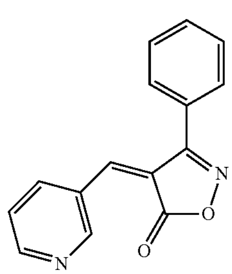 [SMILES: O=C1ON=C(c2ccccc2)/C1=C/c1cccnc1] | * | * | ** | * | ** | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OQ | 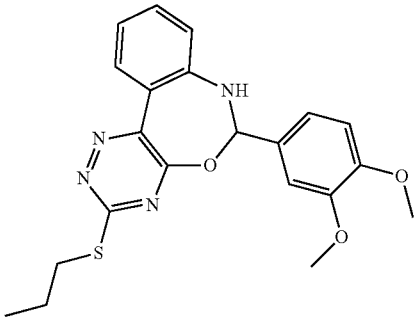 [SMILES: CCCSc1nnc2c(n1)OC(c1ccc(OC)c(OC)c1)Nc1ccccc1-2] | * |  | ** | * | ** | * | ** | ND | * |
| OR | 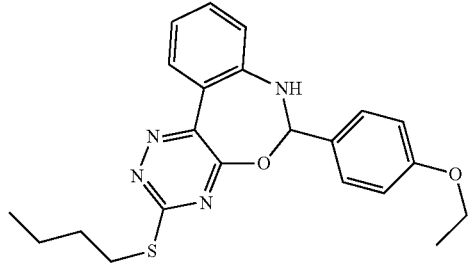 [SMILES: CCCCSc1nnc2c(n1)OC(c1ccc(OCC)cc1)Nc1ccccc1-2] | * | ** | * | * | * | * |  | ND |  |
| OS | 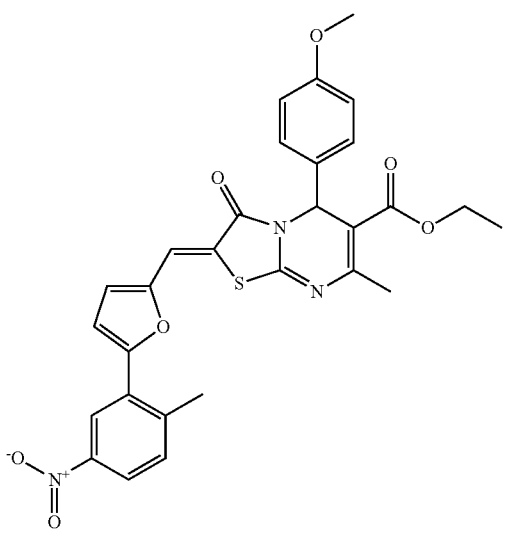 | * |  |  | * | * | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OT | 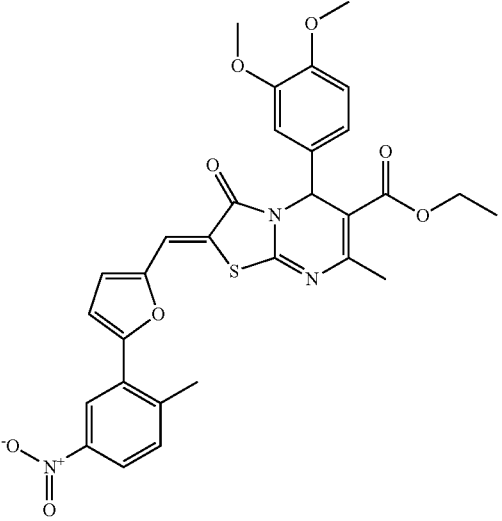 | * |  |  |  |  |  |  | ND | ** |
| OU | 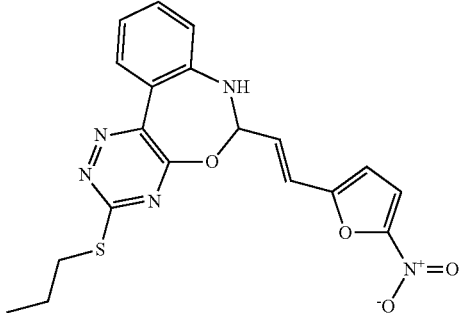 | ** | * |  |  | * |  | ** | ND | ND |
| OV | 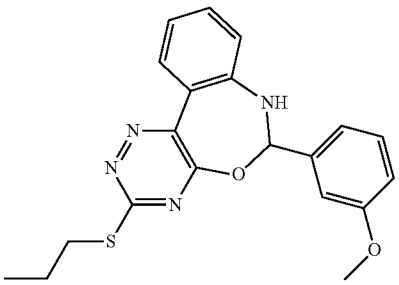 [SMILES: CCCSc1nnc2c(n1)OC(c1cccc(OC)c1)Nc1ccccc1-2] | * | * |  | ** | * | NT |  | ND |  |
| OW | 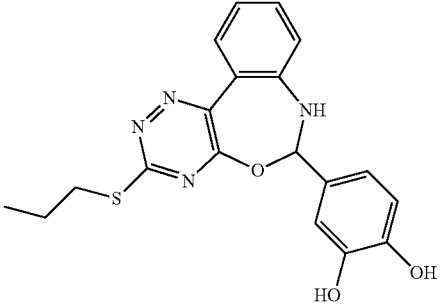 [SMILES: CCCSc1nnc2c(n1)OC(c1ccc(O)c(O)c1)Nc1ccccc1-2] | * | * | * | * | * |  |  | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| OX | 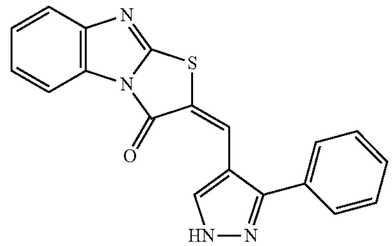 [SMILES: O=c1/c(=C\c2c[nH]nc2-c2ccccc2)sc2nc3ccccc3n12] | * | * | ** | * | * | * |  |  | * |
| OY | 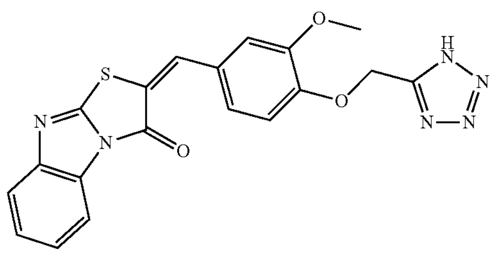 [SMILES: COc1cc(/C=c2/sc3nc4ccccc4n3c2=O)ccc1OCc1nnn[nH]1] | * | * | ** | * | * | * |  |  | ND |
| OZ | 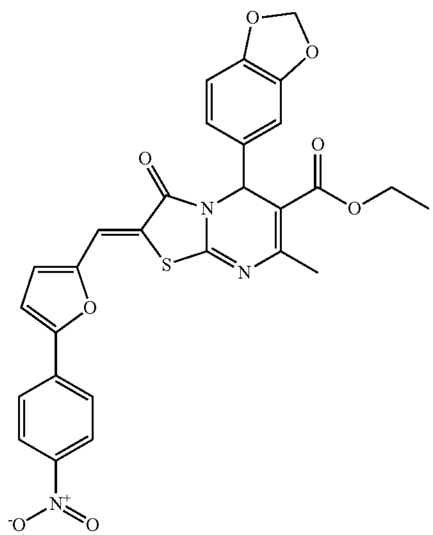 | * | * | ** | * | ** | * | ** | * | ** |
| PA | 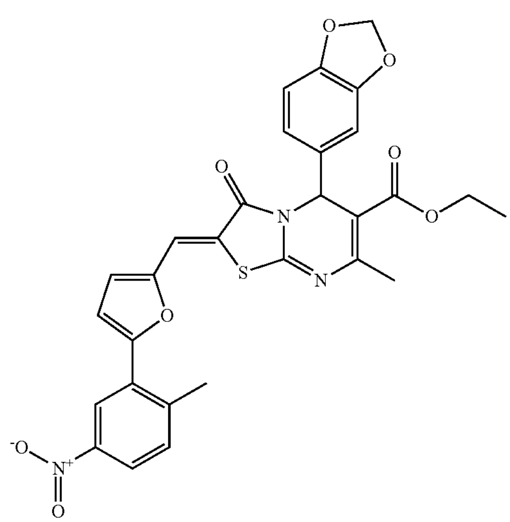 | * | * | *** | NT | * | NT |  |  | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| PB | 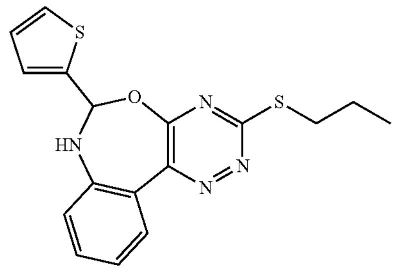 [SMILES: CCCSc1nnc2c(n1)OC(c1cccs1)Nc1ccccc1-2] | NT | * | NT | * | NT |  |  | ** | ND |
| PC | 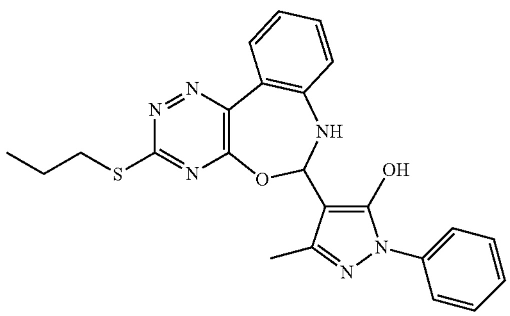 [SMILES: CCCSc1nnc2c(n1)OC(c1c(C)nn(-c3ccccc3)c1O)Nc1ccccc1-2] | NT |  | NT | * | NT | * | ** | * | ** |
| PD | |  | NT |  | * |  | * | ** | ND | ND |
| PD | | * | NT | ** | *** | ** | * | ** | ND | ** |
| PE | 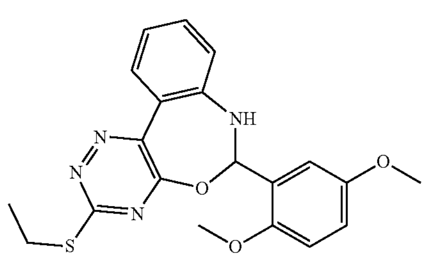 [SMILES: CCSc1nnc2c(n1)OC(c1cc(OC)ccc1OC)Nc1ccccc1-2] | * | NT |  |  | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| PF | 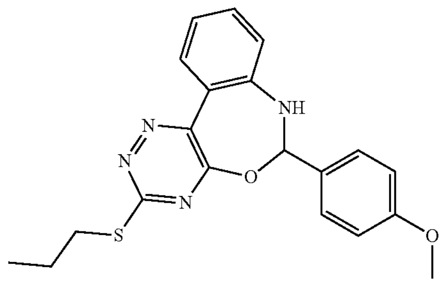 [SMILES: CCCSc1nnc2c(n1)OC(c1ccc(OC)cc1)Nc1ccccc1-2] |  | NT | * | * | * |  |  | ND | * |
| PG | 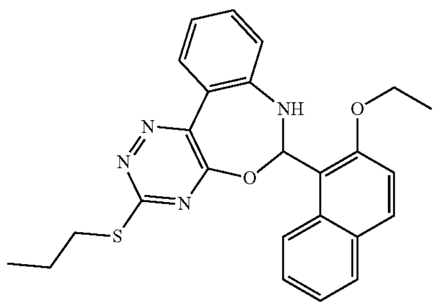 [SMILES: CCCSc1nnc2c(n1)OC(c1c(OCC)ccc3ccccc13)Nc1ccccc1-2] | * | NT | ** | * | * | * | ** | ND | ND |
| PH | 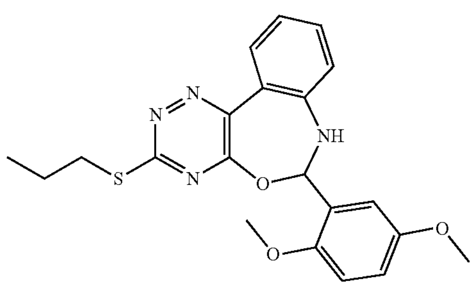 [SMILES: CCCSc1nnc2c(n1)OC(c1cc(OC)ccc1OC)Nc1ccccc1-2] | * | NT | ** | * | ** | * | ** | ND | ND |
| PI | 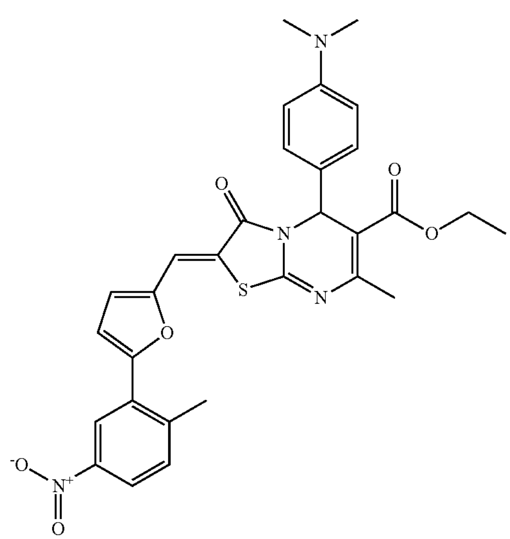 |  | NT | * | ** | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|----|
| PJ | 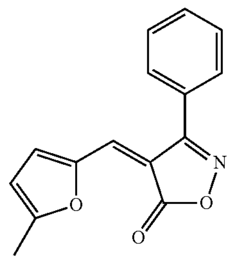 [SMILES: Cc1ccc(/C=C2\C(=O)ON=C2c2ccccc2)o1] | * | NT | ** | * |  |  |  | ND |  |
| PK | 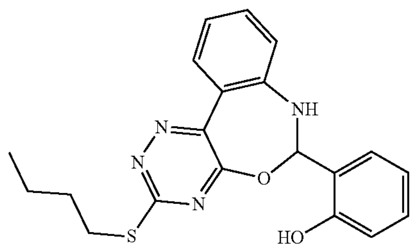 [SMILES: CCCCSc1nnc2c(n1)OC(c1ccccc1O)Nc1ccccc1-2] | NT | * | NT | ** | NT | * |  |  | ** |
| PL | 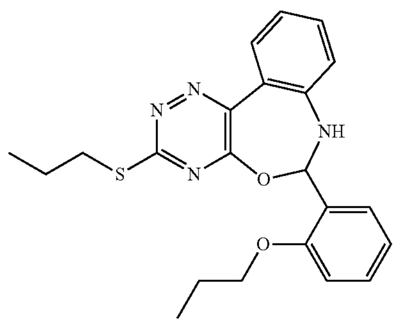 [SMILES: CCCOc1ccccc1C1Nc2ccccc2-c2nnc(SCCC)nc2O1] | NT | * | NT | ** | NT | * |  |  | ** |
| PM | 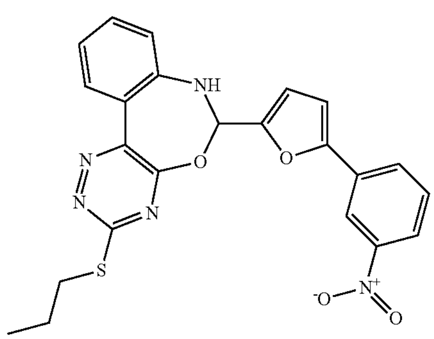 | NT | * | NT | ** | NT | * | ** | * | ** |
| PN | 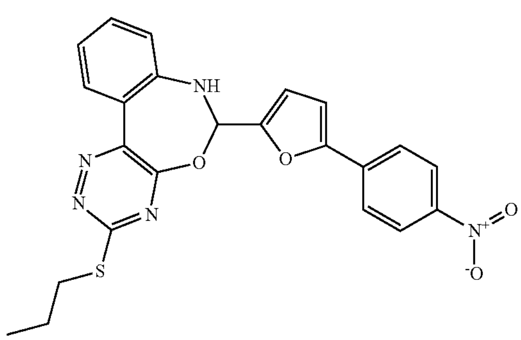 | NT | * | NT |  | NT |  |  |  | * |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|----|
| PO | 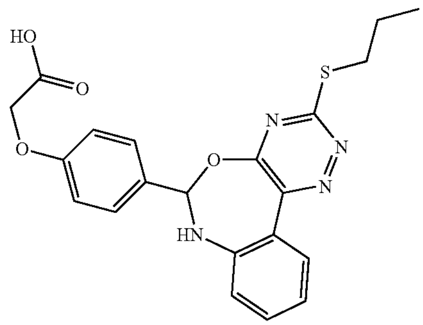 [SMILES: CCCSc1nnc2c(n1)OC(c1ccc(OCC(=O)O)cc1)Nc1ccccc1-2] | NT | * | NT | * | NT | * | ** | * | ND |
| PP | 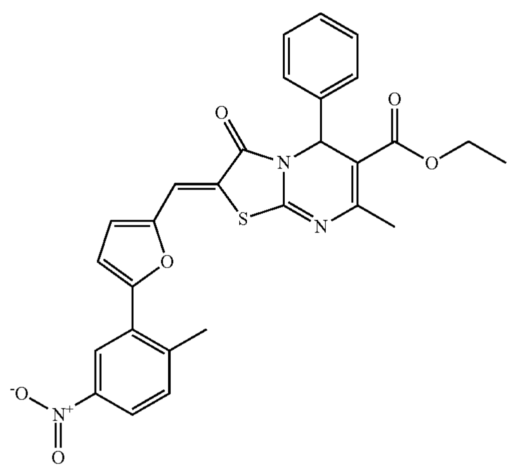 | *** | * | * | NT | * | NT | ** | ND | ND |
| PQ | 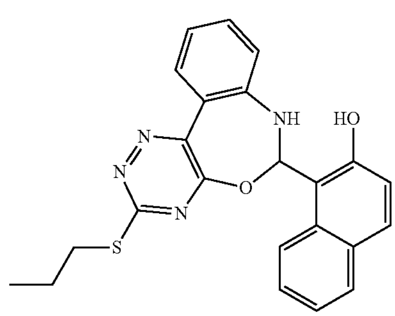 [SMILES: CCCSc1nnc2c(n1)OC(c1c(O)ccc3ccccc13)Nc1ccccc1-2] |  |  |  | NT |  | NT | ** | ND | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| PR | 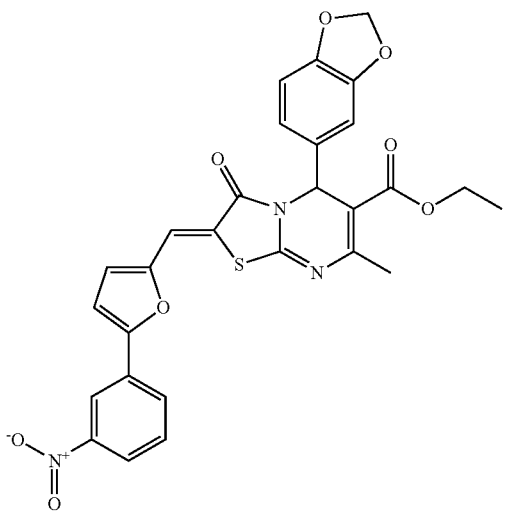 |  | * | * | NT | * | NT | ** | ND | ND |
| PS | 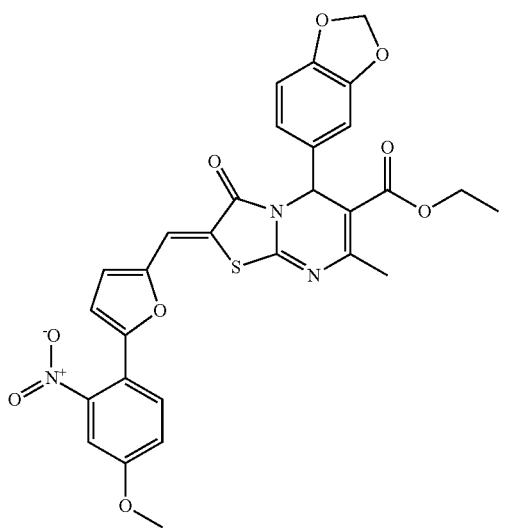 | * | * | ** | NT | * | NT |  | ND |  |
| PT | 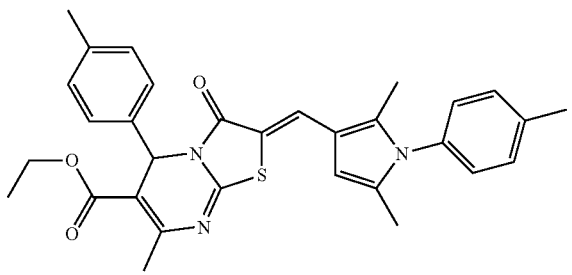 [SMILES: CCOC(=O)C1=C(C)N=c2s/c(=C\c3cc(C)n(-c4ccc(C)cc4)c3C)c(=O)n2C1c1ccc(C)cc1] | ** | * | ** | * | ** | * | ** | ND | ND |
| PU | 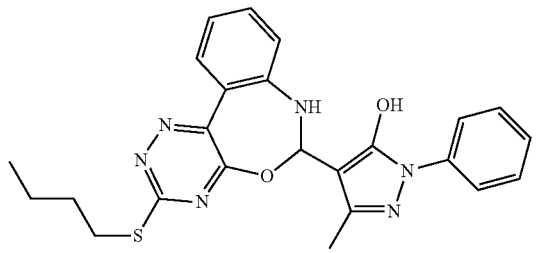 [SMILES: CCCCSc1nnc2c(n1)OC(c1c(C)nn(-c3ccccc3)c1O)Nc1ccccc1-2] | *** | * | *** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| PV | 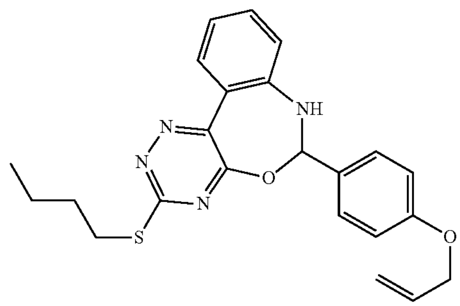 [SMILES: C=CCOc1ccc(C2Nc3ccccc3-c3nnc(SCCCC)nc3O2)cc1] | *** | * | *** | * | *** | * |  | ND |  |
| PW | 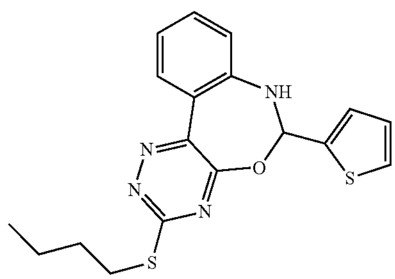 [SMILES: CCCCSc1nnc2c(n1)OC(c1cccs1)Nc1ccccc1-2] | ** | * | *** | * | *** | * | ** | ND | * |
| PX | 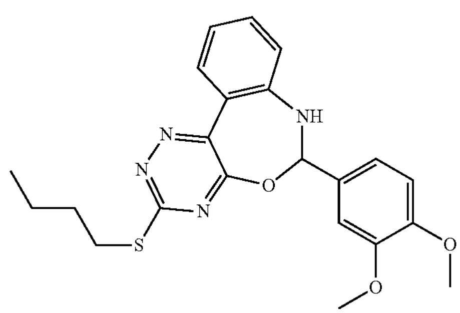 [SMILES: CCCCSc1nnc2c(n1)OC(c1ccc(OC)c(OC)c1)Nc1ccccc1-2] | * | * | ** | * | ** | * |  | ND |  |
| PY | 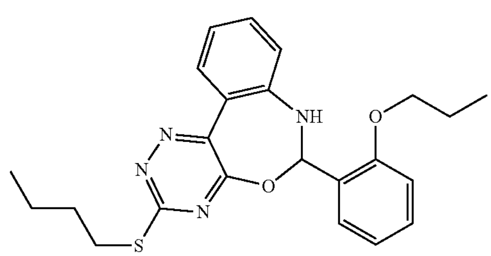 [SMILES: CCCCSc1nnc2c(n1)OC(c1ccccc1OCCC)Nc1ccccc1-2] | * | * | *** | * | ** | * |  | ND |  |
| PZ | 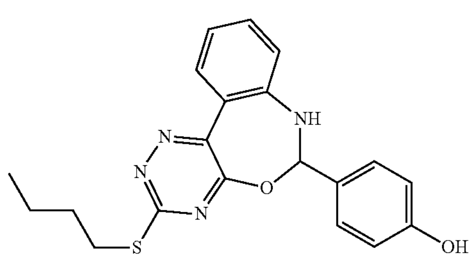 [SMILES: CCCCSc1nnc2c(n1)OC(c1ccc(O)cc1)Nc1ccccc1-2] | ** | * | ** | * | ** | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| QA | 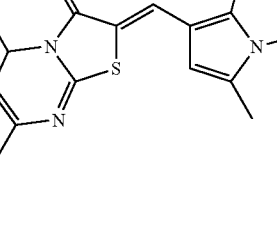 | * | * | ** | * |  |  |  | ND |  |
| QB | 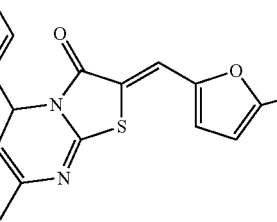 |  | * | *** | * | * |  | ** | ND | * |
| QC | 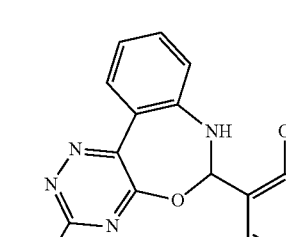 | * | * | *** | * | *** | * | ** | ND | ND |
| QD | 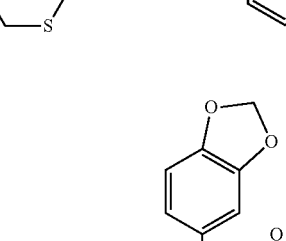 | ** | * | ** | * | ** | * | ** | ND | ND |
| QE | 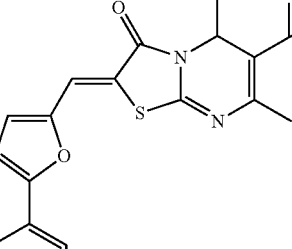 | * | * | *** | * | ** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|----|-----|
| QF | 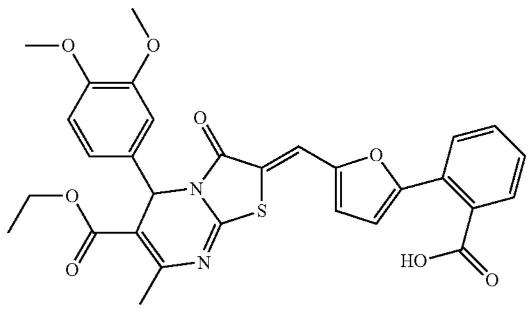 [SMILES: CCOC(=O)C1=C(C)N=c2s/c(=C\c3ccc(-c4ccccc4C(=O)O)o3)c(=O)n2C1c1ccc(OC)c(OC)c1] | * | * | *** | * | *** | * | ** | ND | ND |
| QG | 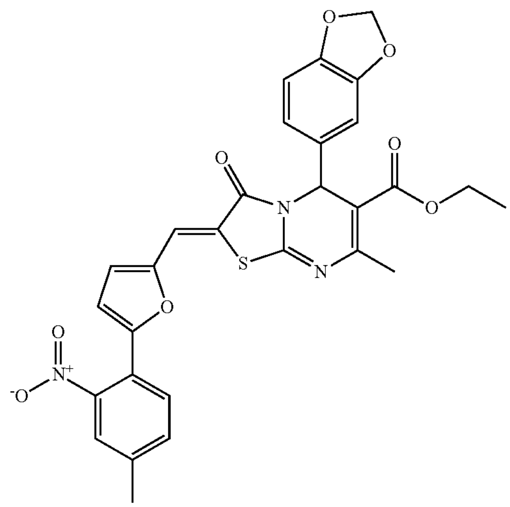 | ** | * | ** | * | ** | * |  | ND |  |
| QH | 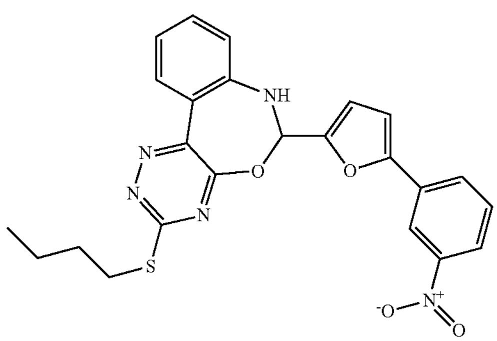 | *** | * | *** | * | *** | * | ** | ND | * |
| QI | 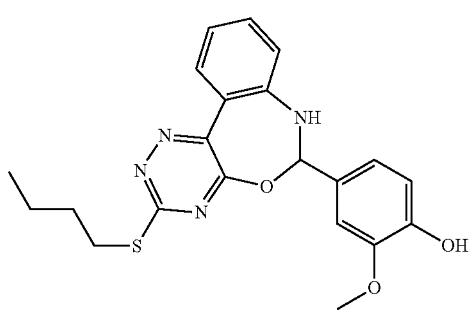 [SMILES: CCCCSc1nnc2c(n1)OC(c1ccc(O)c(OC)c1)Nc1ccccc1-2] | * | * | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| QJ | 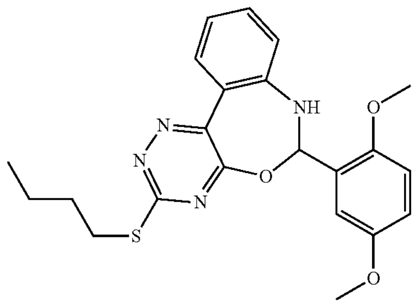 [SMILES: CCCCSc1nnc2c(n1)OC(c1cc(OC)ccc1OC)Nc1ccccc1-2] | ** | * | *** | * | * |  | ** | ND | * |
| QK | 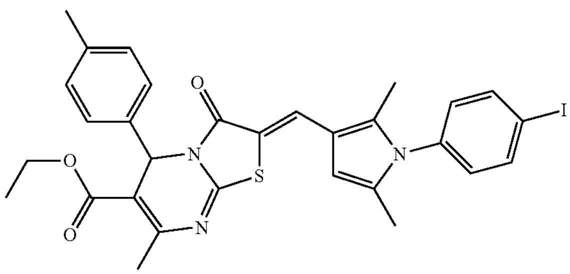 [SMILES: CCOC(=O)C1=C(C)N=c2s/c(=C\c3cc(C)n(-c4ccc(I)cc4)c3C)c(=O)n2C1c1ccc(C)cc1] | ** | * | ** | * | ** | * |  | ND |  |
| QL | 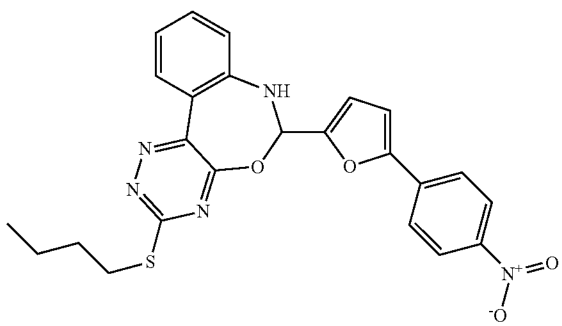 | * |  | * | * | ** | * | ** | ND | ND |
| QM | 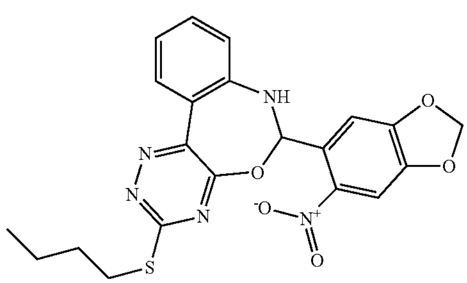 | * | * | * | * | * | * | ** | ND | ND |
| QN | 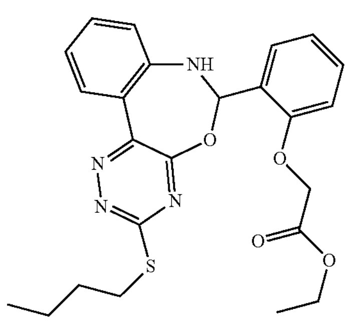 [SMILES: CCCCSc1nnc2c(n1)OC(c1ccccc1OCC(=O)OCC)Nc1ccccc1-2] | * | * | * | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| QO | 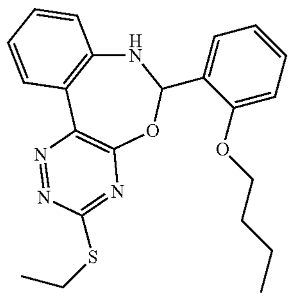 [SMILES: CCCCOc1ccccc1C1Nc2ccccc2-c2nnc(SCC)nc2O1] | * | * | * | * | ** | * | ** | ND | * |
| QP | 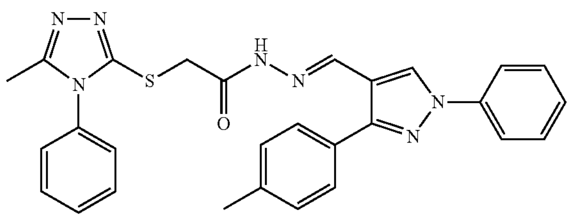 [SMILES: Cc1ccc(-c2nn(-c3ccccc3)cc2/C=N/NC(=O)CSc2nnc(C)n2-c2ccccc2)cc1] | *** | * | * | * | *** | * | ** | ND | * |
| QQ | 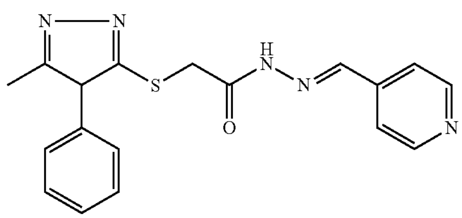 [SMILES: CC1=NN=C(SCC(=O)N/N=C/c2ccncc2)C1c1ccccc1] | * | * | * | * |  |  | ** | ND | ND |
| QR | 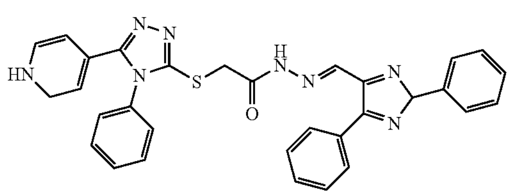 [SMILES: O=C(CSc1nnc(C2=CCNC=C2)n1-c1ccccc1)N/N=C/C1=NC(c2ccccc2)N=C1c1ccccc1] |  |  | * | * | * | * |  | ND | ND |
| QS | 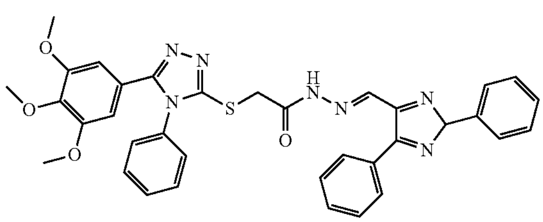 [SMILES: COc1cc(-c2nnc(SCC(=O)N/N=C/C3=NC(c4ccccc4)N=C3c3ccccc3)n2-c2ccccc2)cc(OC)c1OC] | * | * |  |  | * | * |  | ND | ND |
| QT | 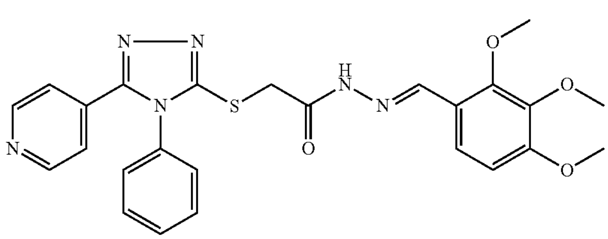 [SMILES: COc1ccc(/C=N/NC(=O)CSc2nnc(-c3ccncc3)n2-c2ccccc2)c(OC)c1OC] | ** | * | * | * |  | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| QU | 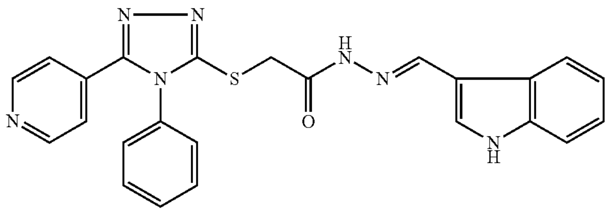 [SMILES: O=C(CSc1nnc(-c2ccncc2)n1-c1ccccc1)N/N=C/c1c[nH]c2ccccc12] |  |  | * | ** | * |  |  | ND | * |
| QV | 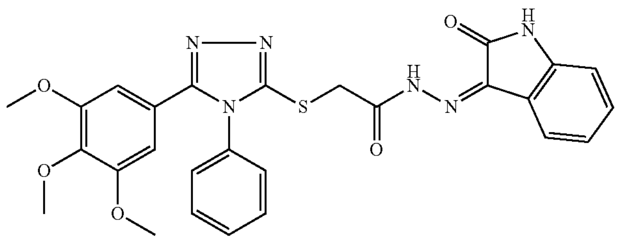 [SMILES: COc1cc(-c2nnc(SCC(=O)N/N=C3\C(=O)Nc4ccccc43)n2-c2ccccc2)cc(OC)c1OC] | ** | * | * |  |  |  |  | ND | * |
| QW | 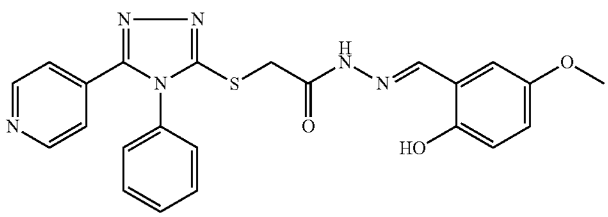 [SMILES: COc1ccc(O)c(/C=N/NC(=O)CSc2nnc(-c3ccncc3)n2-c2ccccc2)c1] | *** | * | * | * | * |  |  | ND | ND |
| QX | 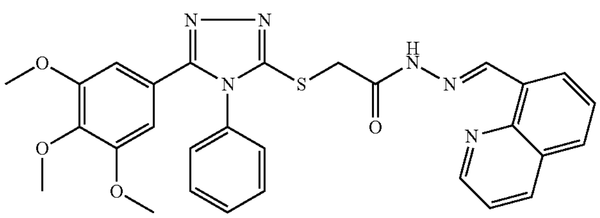 [SMILES: COc1cc(-c2nnc(SCC(=O)N/N=C/c3cccc4cccnc34)n2-c2ccccc2)cc(OC)c1OC] |  |  | * | * | * |  |  | ND | ND |
| QY | 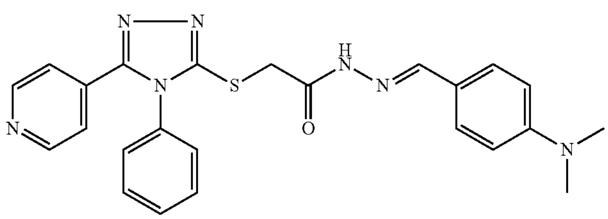 [SMILES: CN(C)c1ccc(/C=N/NC(=O)CSc2nnc(-c3ccncc3)n2-c2ccccc2)cc1] | ** | * | * | * | * |  |  | ND | ND |
| QZ | 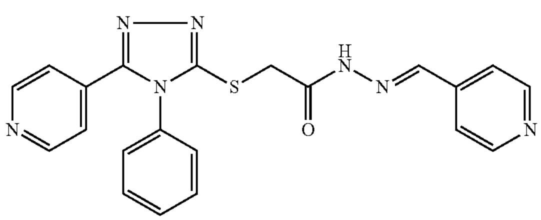 [SMILES: O=C(CSc1nnc(-c2ccncc2)n1-c1ccccc1)N/N=C/c1ccncc1] |  |  | * | * | * | * | ** | ND | ND |
| RA | 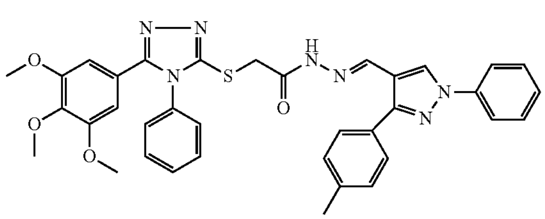 |  |  | * | * | * |  |  | ND | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| RB | 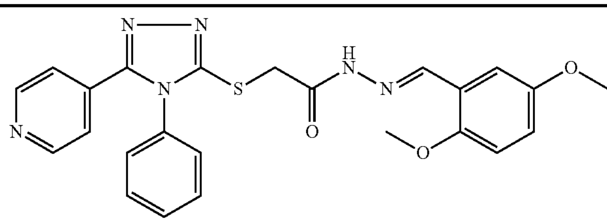 | ** | * | * | * | * | * | ** | ND | * |
| RC | 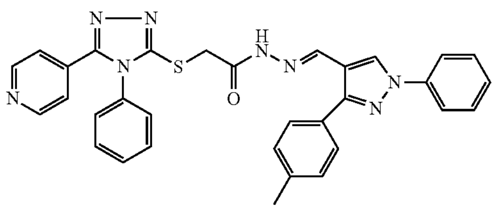 | ** | * | * | ** | * | * | ** | ND | ND |
| RD | 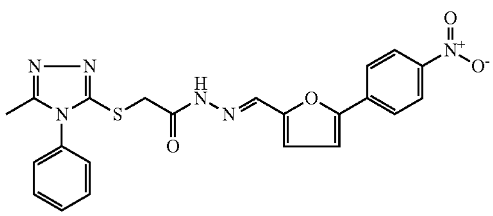 | NT |  | NT | * | NT | * |  | * | ND |
| RE | 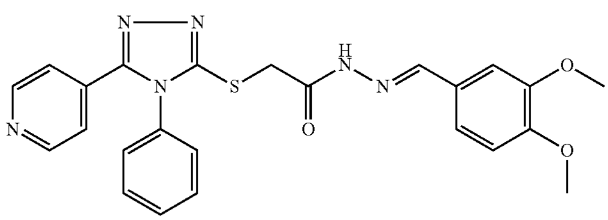 | NT | * | NT |  | NT | * | ** | * | ND |
| RF | 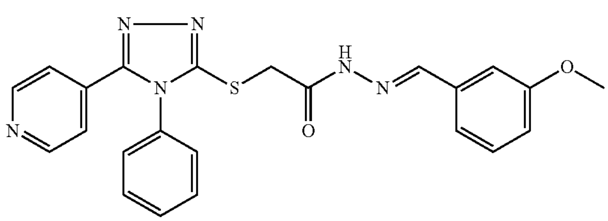 | NT |  | NT | * | NT |  |  | * | ** |
| RG | 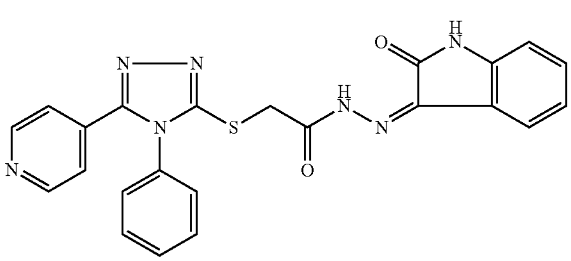 | NT | * | NT | * | NT |  |  | * | ** |
| RH | 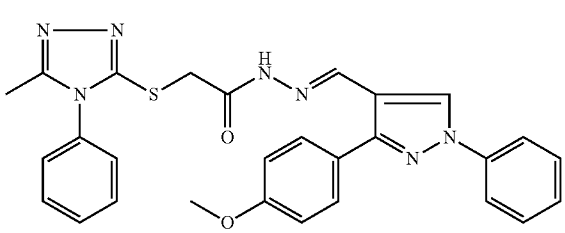 | NT | * | NT | * | NT |  |  | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| RI | 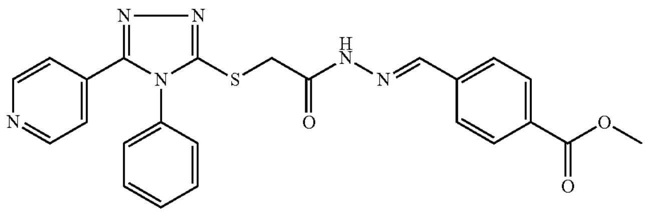 | NT | * | NT | * | NT | * | ** | * | ND |
| RJ | 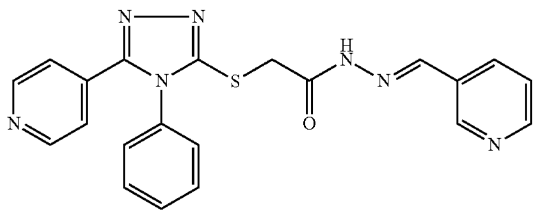 | NT |  | NT |  | NT | * | ** | * | ** |
| RK | 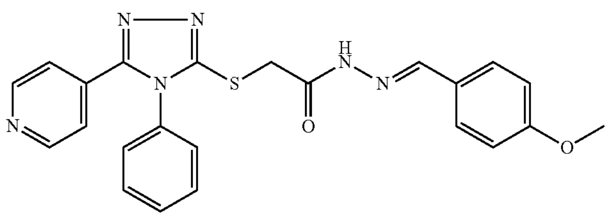 | NT | * | NT | * | NT |  | ** | * | ** |
| RL | 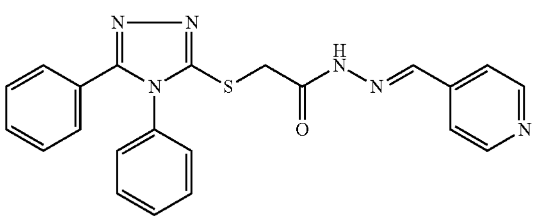 | NT |  | NT | * | NT |  |  | ** | ND |
| RM | 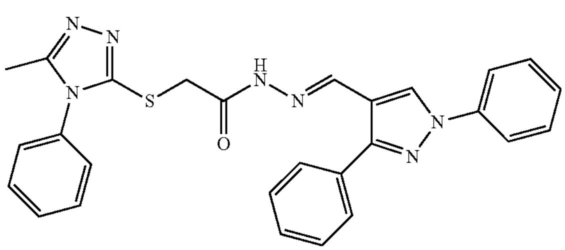 | NT | * | NT | * | NT | * | ** | * | ND |
| RN | 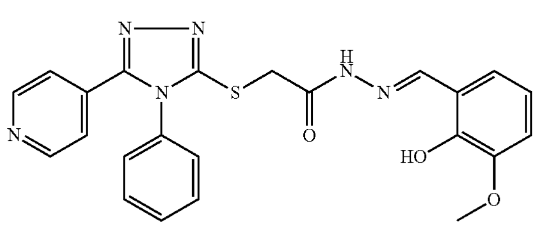 | NT | * | NT | * | NT |  |  | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| RO | 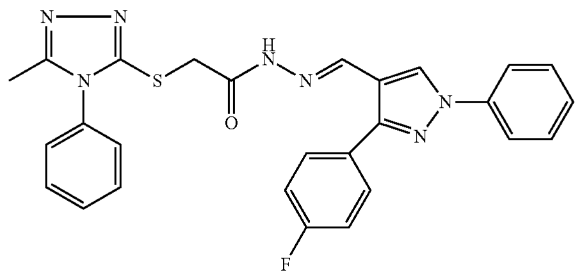 | NT | * | NT | * | NT |  |  | * | * |
| RP | 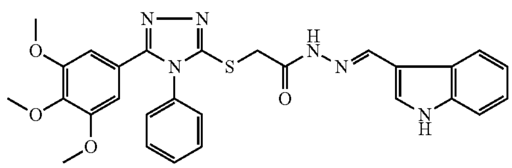 | NT |  | NT |  | NT | * |  | * | ** |
| RQ | 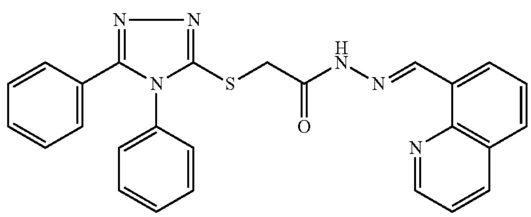 | NT | * | NT | * | NT | * | ** | * | ** |
| RS | 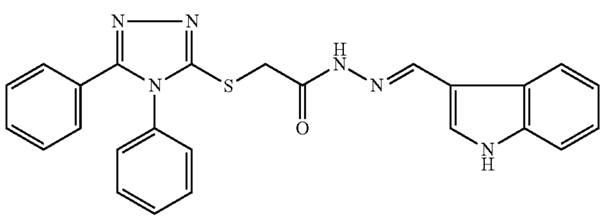 | * | * | *** | * | * | * |  | ND |  |
| RT | 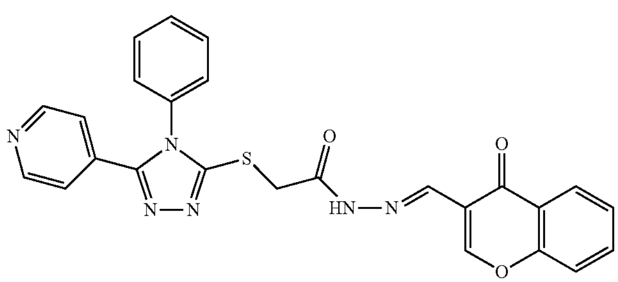 | * | * | * | * |  | * | ** | ND | * |
| RU | 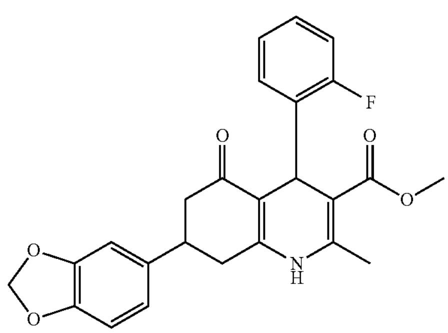 | * | * | * | ** | * |  |  | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| RV | 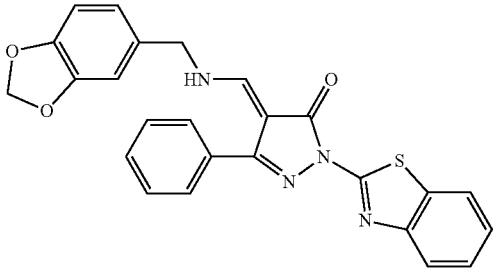 | * |  | *** | * | ** | * |  | ND |  |
| RW | 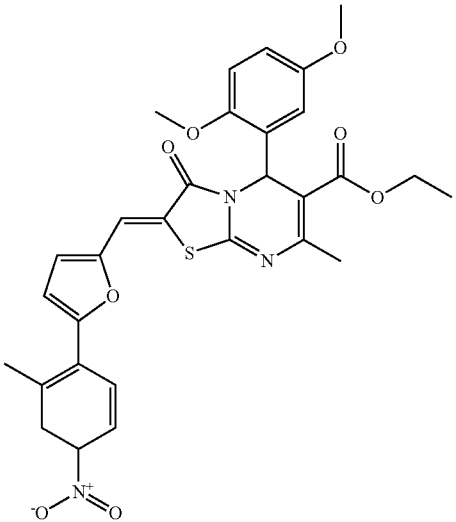 | * |  |  |  | *** | * |  | ND |  |
| RX | 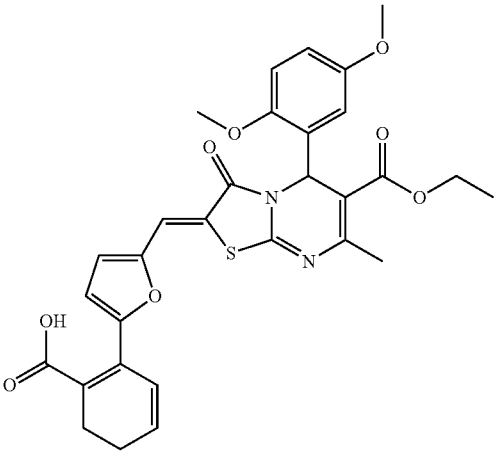 | * |  | * | * | *** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| RY | 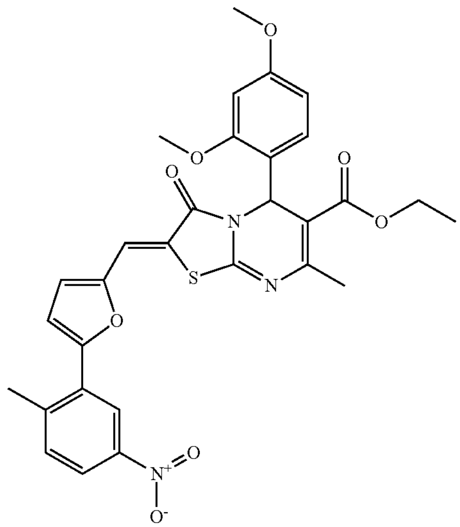 |  |  | ** | * | ** | * |  | ND |  |
| RZ | 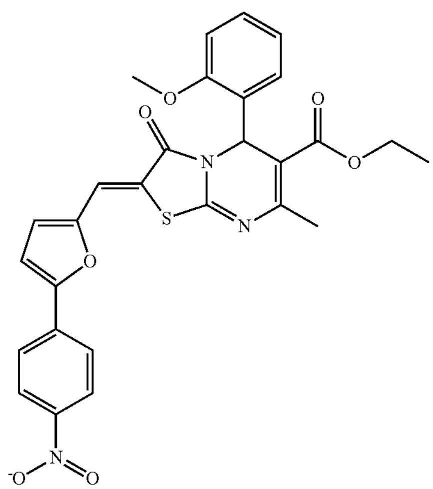 | * | * | ** | * | ** | * |  | ND |  |
| SA | 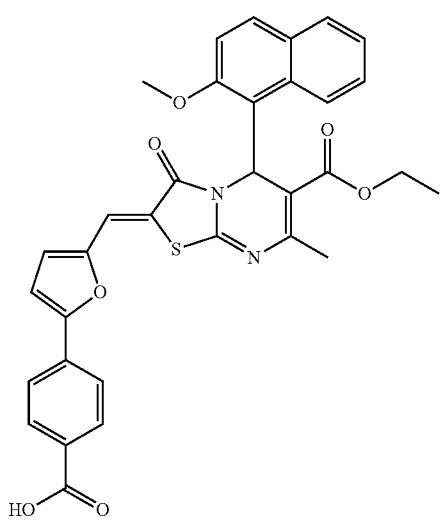 [SMILES: CCOC(=O)C1=C(C)N=c2s/c(=C\c3ccc(-c4ccc(C(=O)O)cc4)o3)c(=O)n2C1c1c(OC)ccc2ccccc12] | ** | * | ** | * | ** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SB | 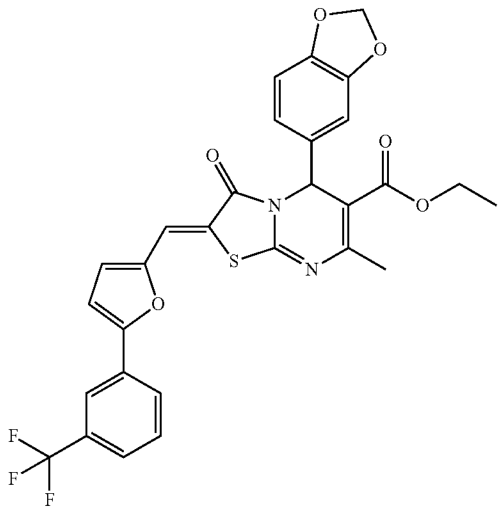 [SMILES: CCOC(=O)C1=C(C)N=c2s/c(=C\c3ccc(-c4cccc(C(F)(F)F)c4)o3)c(=O)n2C1c1ccc2c(c1)OCO2] | * |  |  | * | ** | * |  | ND |  |
| SC | 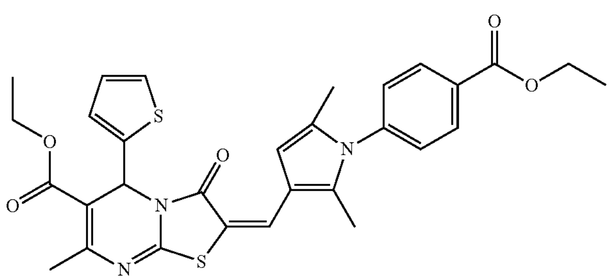 [SMILES: CCOC(=O)C1=C(C)N=c2s/c(=C/c3cc(C)n(-c4ccc(C(=O)OCC)cc4)c3C)c(=O)n2C1c1cccs1] | * | * |  | * | ** | * |  | ND |  |
| SD | 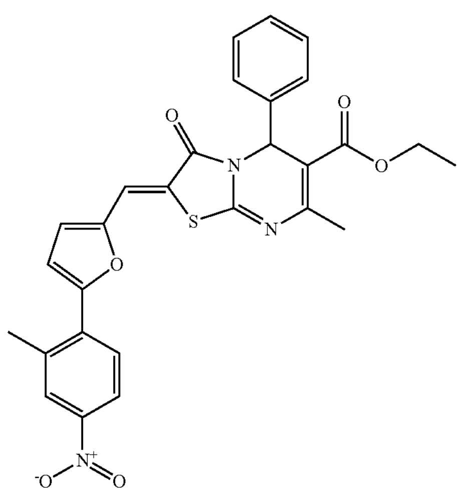 | * | * | * | *** | * | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SE | 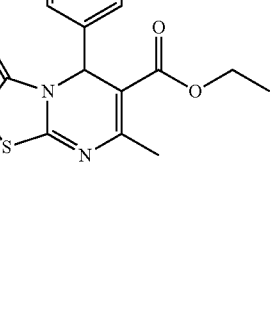 | * |  | ** | * | ** | * | ** | ND | ND |
| SF | 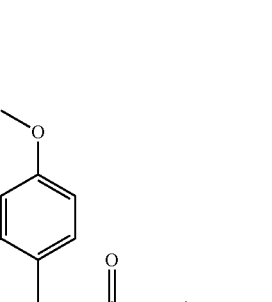 | *** | * | ** | * |  |  | ** | ND | ND |
| SG | 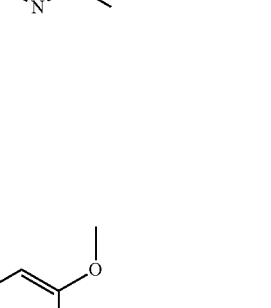 | * |  |  | * |  | NT |  | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SH | 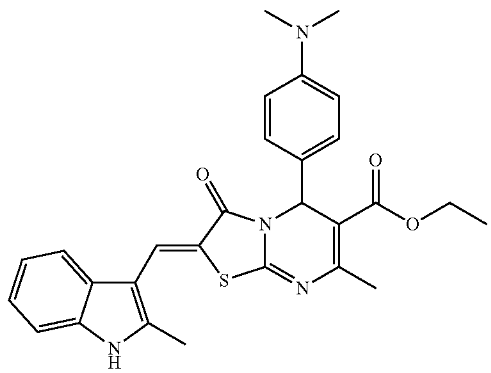 [SMILES: CCOC(=O)C1=C(C)N=c2s/c(=C\c3c(C)[nH]c4ccccc34)c(=O)n2C1c1ccc(N(C)C)cc1] |  |  | * |  |  | NT |  | ND | ND |
| SI | 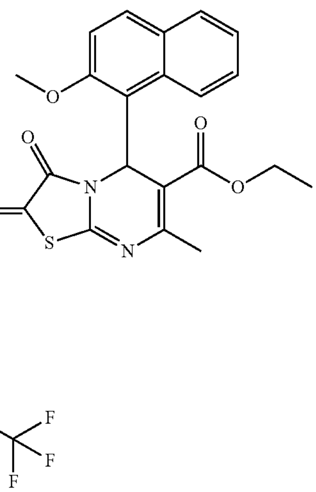 | * |  |  | *** | * | NT | ** | ND | ND |
| SJ | 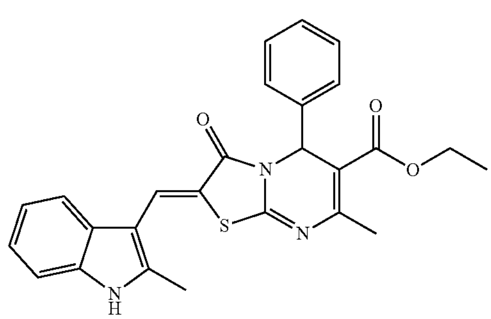 [SMILES: CCOC(=O)C1=C(C)N=c2s/c(=C\c3c(C)[nH]c4ccccc34)c(=O)n2C1c1ccccc1] | *** | * | * | * | * | * |  |  | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SK | 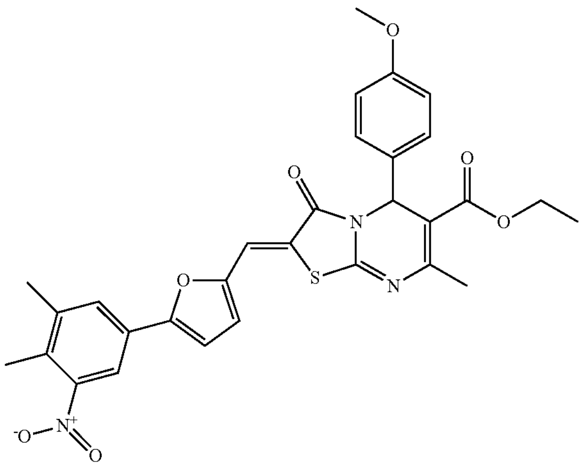 | * | * | ** | * | * | * |  |  | ND |
| SL | 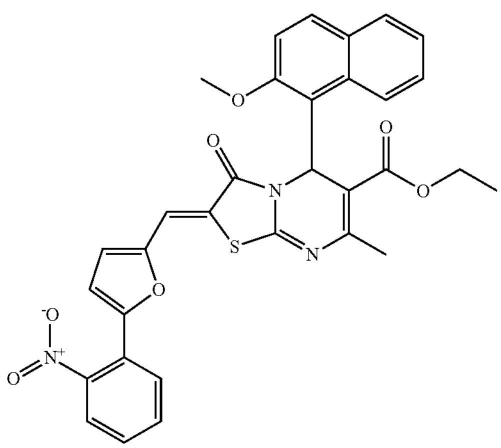 | * | * | ** | * | ** | * |  |  | ND |
| SM | 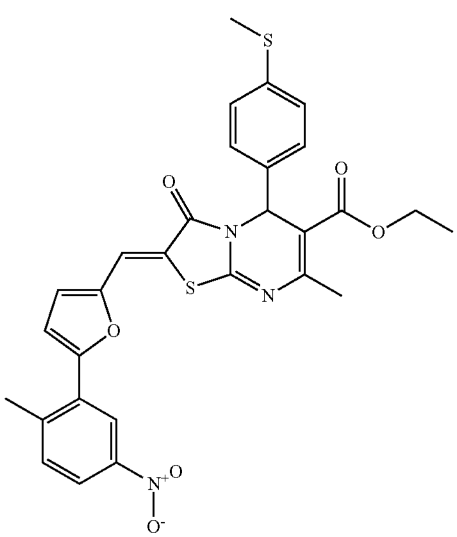 | * | * |  | NT |  | NT | ** | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SN | 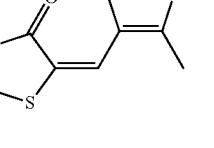 | * | * |  | NT |  | NT | ** | * | * |
| SO | 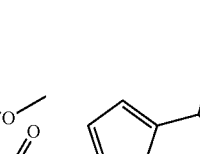 | * | * | * | NT |  | NT |  | ** | * |
| SP | 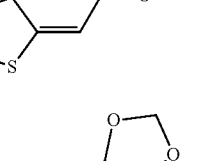 | * | NT |  |  | * |  |  | ND | ** |
| SQ | 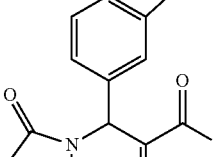 | * | NT |  |  | * | * |  | ND | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SR | 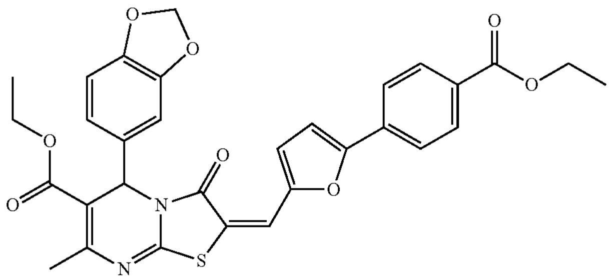 [SMILES: CCOC(=O)C1=C(C)N=c2s/c(=C/c3ccc(-c4ccc(C(=O)OCC)cc4)o3)c(=O)n2C1c1ccc2c(c1)OCO2] | * | NT | ** | * | ** | * | ** | ND | * |
| SS | 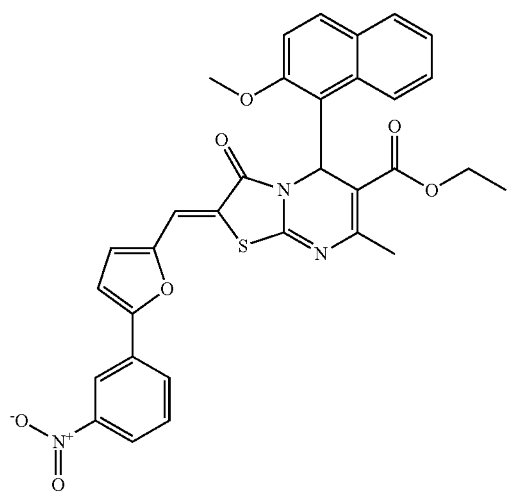 | * | NT | ** | * | ** | * | ** | ND | ND |
| ST | 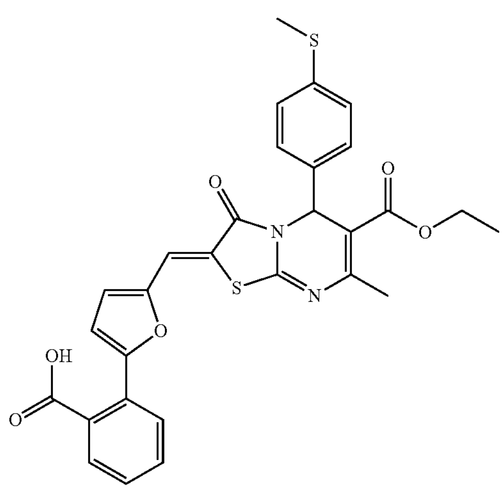 [SMILES: CCOC(=O)C1=C(C)N=c2s/c(=C\c3ccc(-c4ccccc4C(=O)O)o3)c(=O)n2C1c1ccc(SC)cc1] | * | NT | * | ** | * | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| SU | 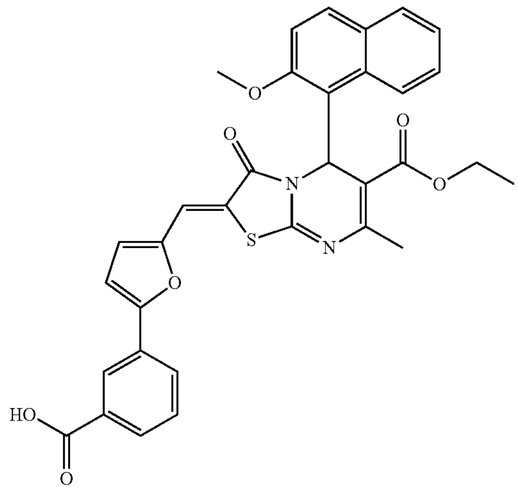 [SMILES: CCOC(=O)C1=C(C)N=c2s/c(=C\c3ccc(-c4cccc(C(=O)O)c4)o3)c(=O)n2C1c1c(OC)ccc2ccccc12] | * | NT | * | * | * | * |  | ND |  |
| SV | 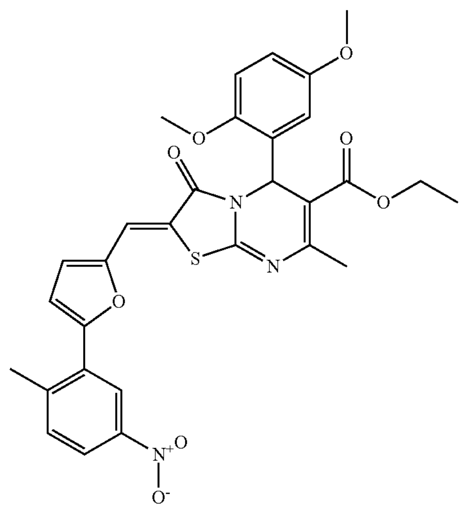 | NT |  | NT |  | NT | * |  |  | ** |
| SW | 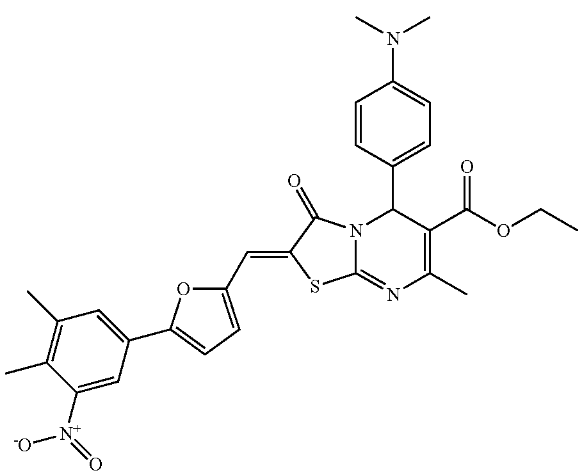 | NT | * | NT | * | NT |  |  | ** | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| SX | 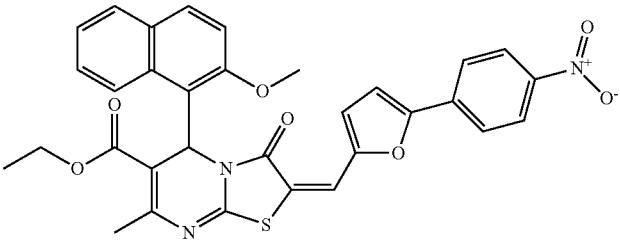 [SMILES: CCOC(=O)C1=C(C)N=c2s/c(=C/c3ccc(-c4ccc([N+](=O)[O-])cc4)o3)c(=O)n2C1c1c(OC)ccc2ccccc12] | * | * | * | NT |  | NT |  | ND | * |
| SY | 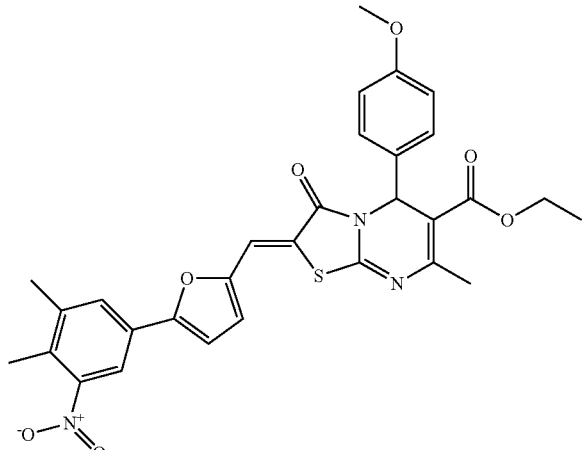 |  | * | ** | * | *** | * | ** | ND | ND |
| SZ | 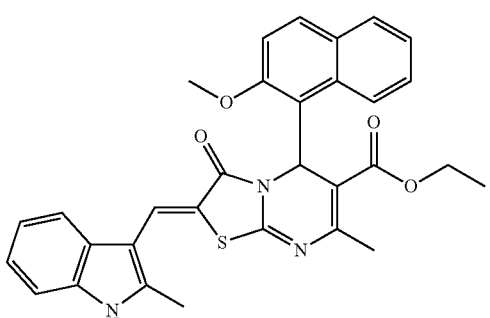 | ** | * | ** | * | ** | * | ** | ND | ND |
| TA | 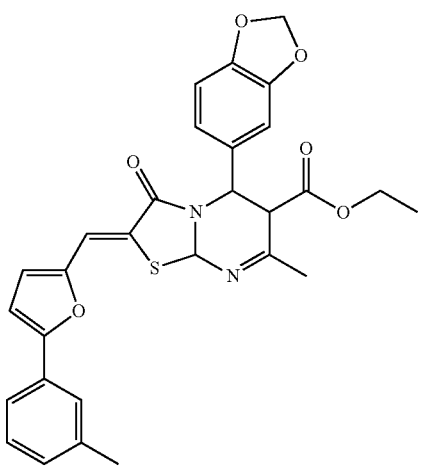 [SMILES: CCOC(=O)C1C(C)=NC2S/C(=C\c3ccc(-c4cccc(C)c4)o3)C(=O)N2C1c1ccc2c(c1)OCO2] | ** | * | *** | * | ** | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TB | 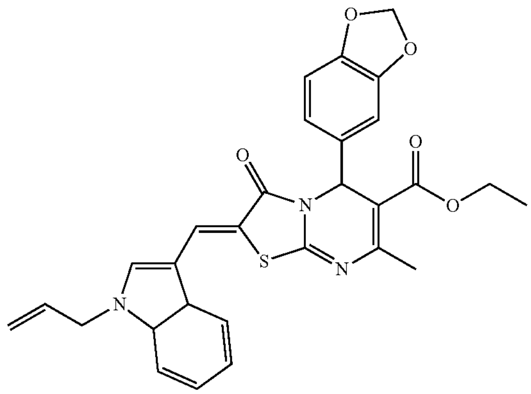 [SMILES: C=CCN1C=C(/C=c2\sc3n(c2=O)C(c2ccc4c(c2)OCO4)C(C(=O)OCC)=C(C)N=3)C2C=CC=CC21] | * | * | ** | * | ** | * |  | ND |  |
| TC | 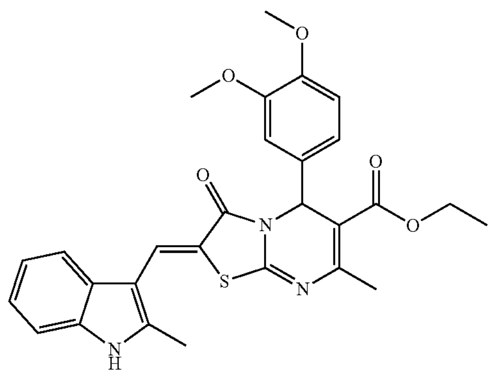 [SMILES: CCOC(=O)C1=C(C)N=c2s/c(=C\c3c(C)[nH]c4ccccc34)c(=O)n2C1c1ccc(OC)c(OC)c1] | *** | * | *** | * | *** | * | ** | ND | ND |
| TD | 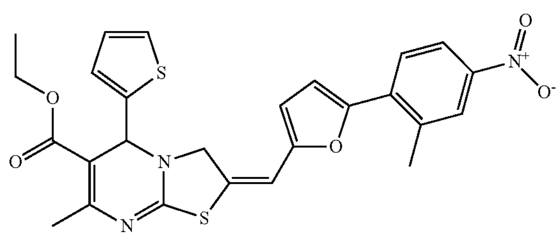 [SMILES: CCOC(=O)C1=C(C)N=C2S/C(=C/c3ccc(-c4ccc([N+](=O)[O-])cc4C)o3)CN2C1c1cccs1] | *** | * | *** | * | *** | * | ** | ND | * |
| TE | 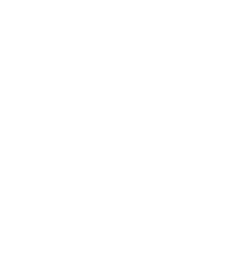 | * | * | *** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TF | 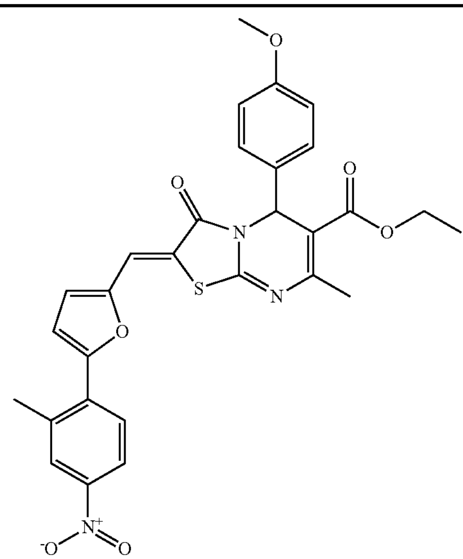 | * | * | ** | * | ** | * |  | ND |  |
| TG | 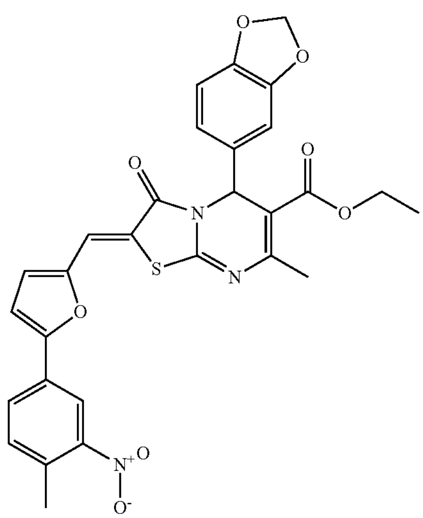 |  | * | ** | * |  |  |  | ND |  |
| TH | 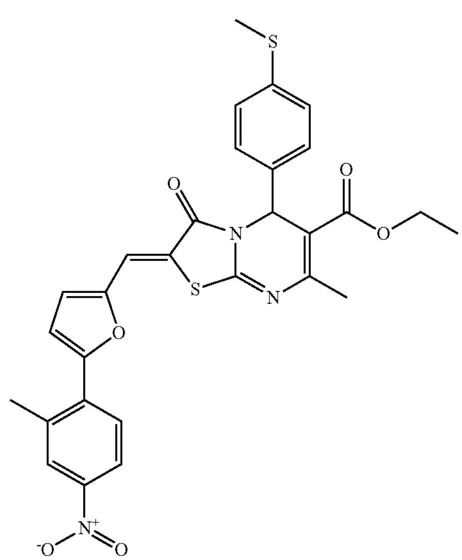 | * | * | ** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TI | 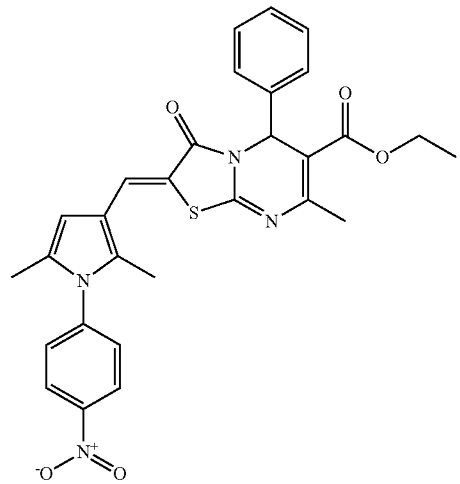 | * | * | *** | * |  |  | ** | ND | * |
| TJ | 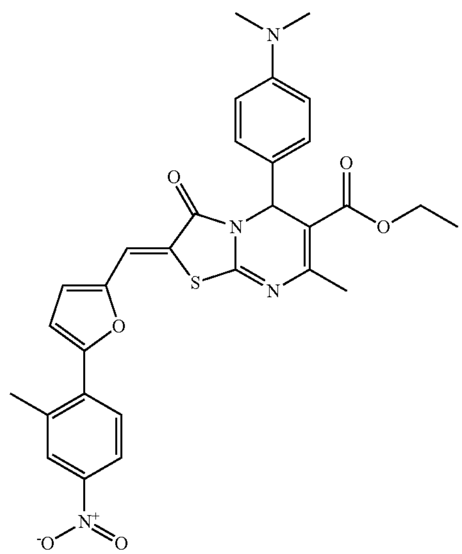 | * | * | * | * | ** | * |  | ND |  |
| TK | 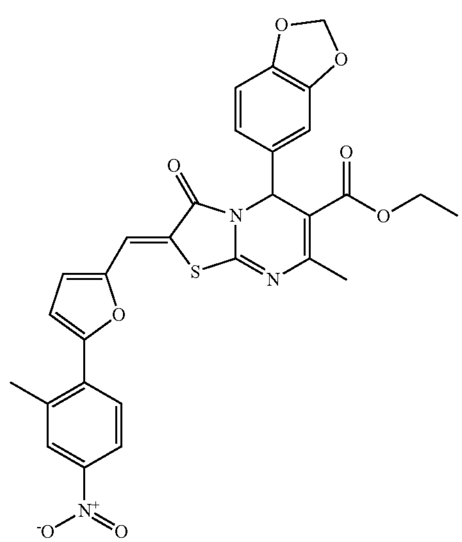 | ** | * | * |  |  | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TL | 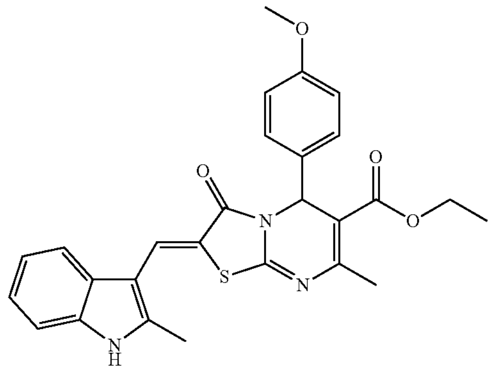 [SMILES: CCOC(=O)C1=C(C)N=c2s/c(=C\c3c(C)[nH]c4ccccc34)c(=O)n2C1c1ccc(OC)cc1] | * | * | ** | * | ** | * | ** | ND | ND |
| TM | 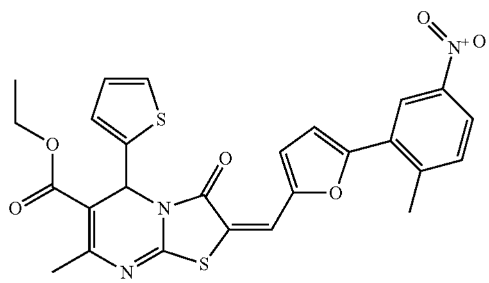 | * | * | * | * | *** | * | ** | ND | * |
| TN | 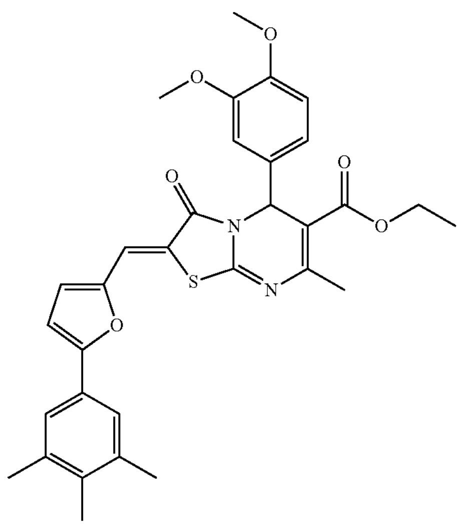 [SMILES: CCOC(=O)C1=C(C)N=c2s/c(=C\c3ccc(-c4cc(C)c(C)c(C)c4)o3)c(=O)n2C1c1ccc(OC)c(OC)c1] | * | * | * | * | ** | * | ** | ND | ND |
| TO | 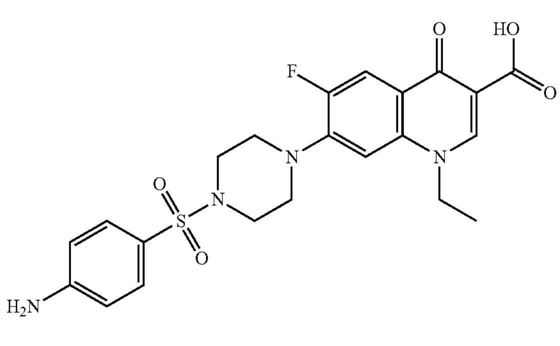 [SMILES: CCn1cc(C(=O)O)c(=O)c2cc(F)c(N3CCN(S(=O)(=O)c4ccc(N)cc4)CC3)cc21] | * | * | NT | * | * | * |  | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TP | 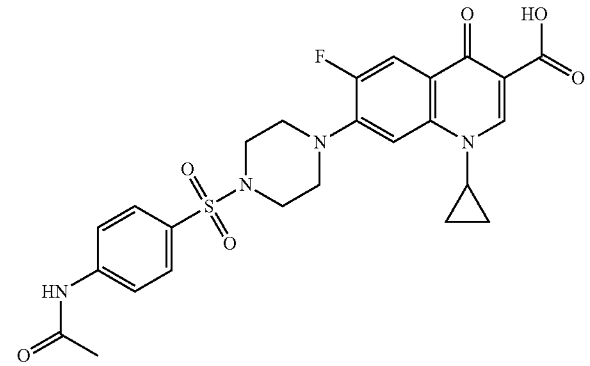 [SMILES: CC(=O)Nc1ccc(S(=O)(=O)N2CCN(c3cc4c(cc3F)c(=O)c(C(=O)O)cn4C3CC3)CC2)cc1] | *** | * | * | * | * |  | ** | ND | ND |
| TQ | 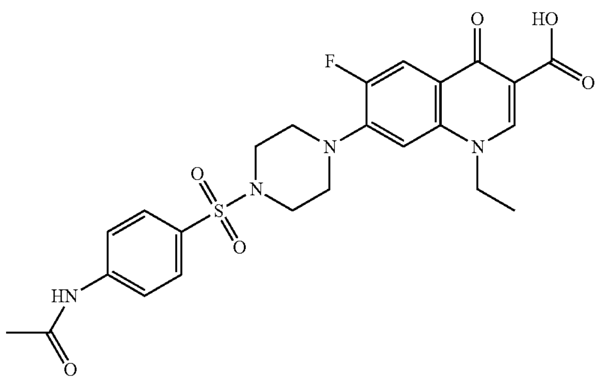 [SMILES: CCn1cc(C(=O)O)c(=O)c2cc(F)c(N3CCN(S(=O)(=O)c4ccc(NC(C)=O)cc4)CC3)cc21] | *** | * | * |  | * | * |  | ND | * |
| TR | 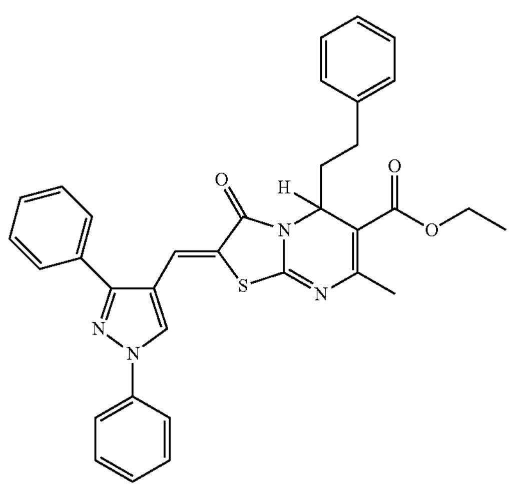 [SMILES: CCOC(=O)C1=C(C)N=c2s/c(=C\c3cn(-c4ccccc4)nc3-c3ccccc3)c(=O)n2C1CCc1ccccc1] | *** | * | * |  | * |  |  | ND | ND |
| TS | 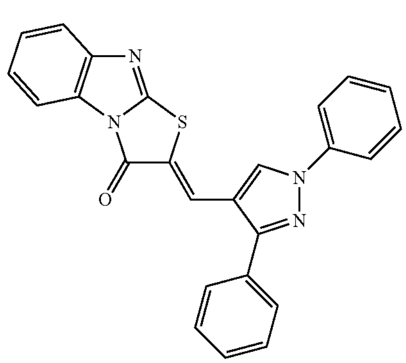 [SMILES: O=c1/c(=C/c2cn(-c3ccccc3)nc2-c2ccccc2)sc2nc3ccccc3n12] | *** | * | * |  | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TT | 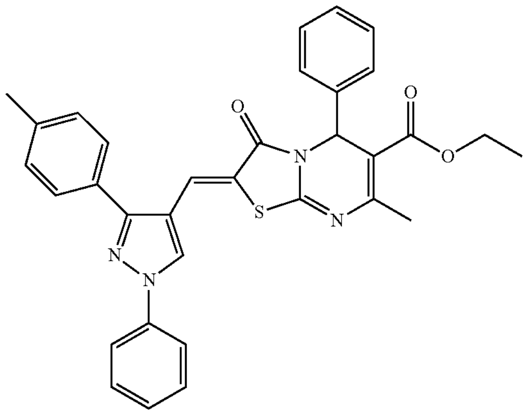 [SMILES: CCOC(=O)C1=C(C)N=c2s/c(=C\c3cn(-c4ccccc4)nc3-c3ccc(C)cc3)c(=O)n2C1c1ccccc1] | *** | * | * | * | * | * | ** | ND | ND |
| TU | 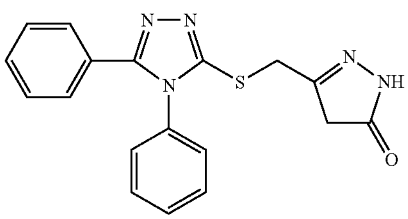 [SMILES: O=C1CC(CSc2nnc(-c3ccccc3)n2-c2ccccc2)=NN1] |  |  | * | * | * | * | ** | ND | * |
| TV | 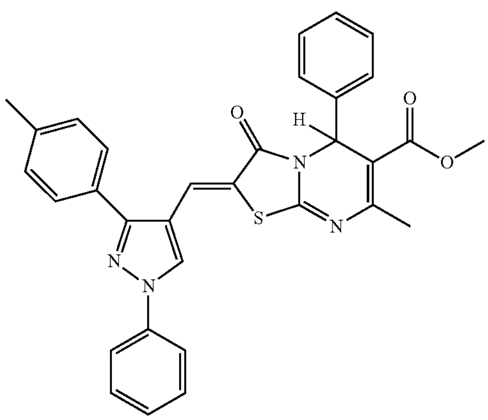 | *** | * | * | * | ** | * | ** | ND | * |
| TW | 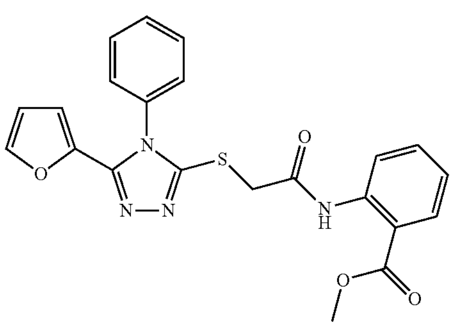 [SMILES: COC(=O)c1ccccc1NC(=O)CSc1nnc(-c2ccco2)n1-c1ccccc1] | *** | * | * | * | *** | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| TX | 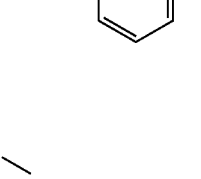 | * |  | * | * | *** | * | ** | ND | * |
| TY | 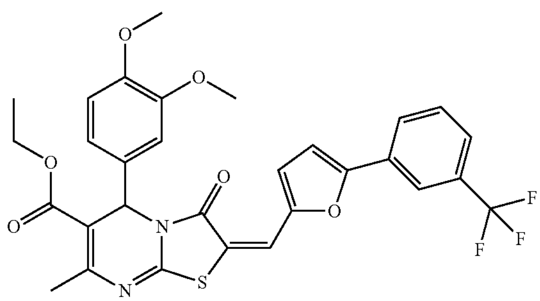 [SMILES: CCOC(=O)C1=C(C)N=c2s/c(=C/c3ccc(-c4cccc(C(F)(F)F)c4)o3)c(=O)n2C1c1ccc(OC)c(OC)c1] | *** | * | * | * | ** | * | ** | ND | ND |
| TZ | 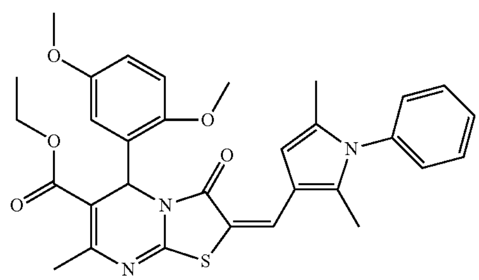 [SMILES: CCOC(=O)C1=C(C)N=c2s/c(=C/c3cc(C)n(-c4ccccc4)c3C)c(=O)n2C1c1cc(OC)ccc1OC] | *** | * | * | * | *** | * | ** | ND | ND |
| UA | 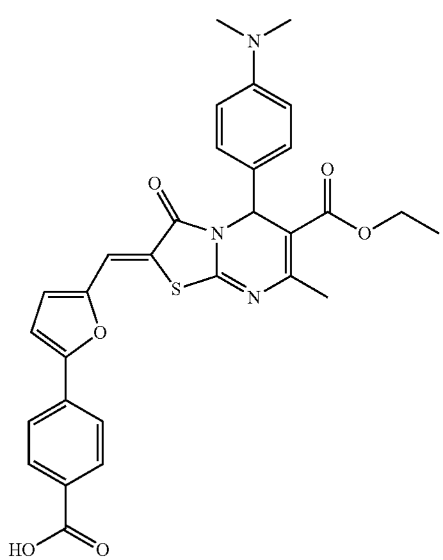 [SMILES: CCOC(=O)C1=C(C)N=c2s/c(=C\c3ccc(-c4ccc(C(=O)O)cc4)o3)c(=O)n2C1c1ccc(N(C)C)cc1] | *** | * | * | * | *** | * | ** | ND | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| UB | 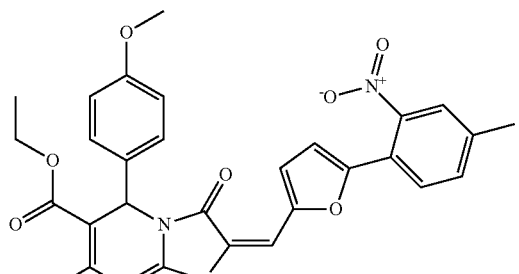 | NT | ** | NT | * | NT | * | ** | * | * |
| UC | 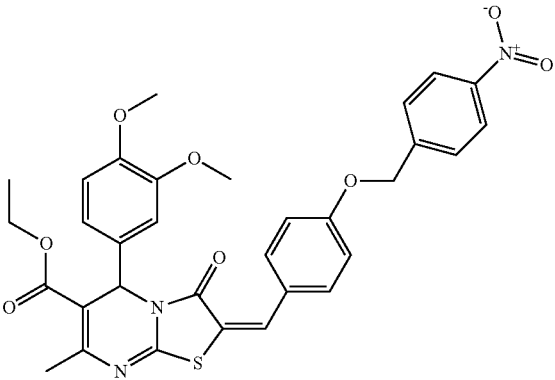 | NT |  | NT | * | NT | * |  |  |  |
| UD | 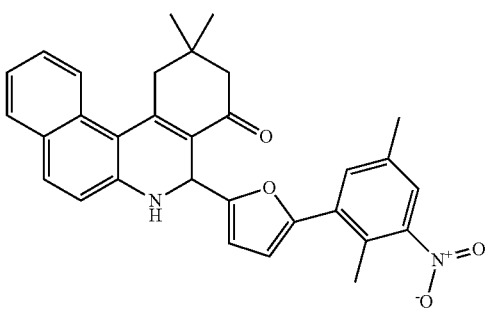 | NT |  | NT | * | NT | * |  | * | * |
| *£ UE | 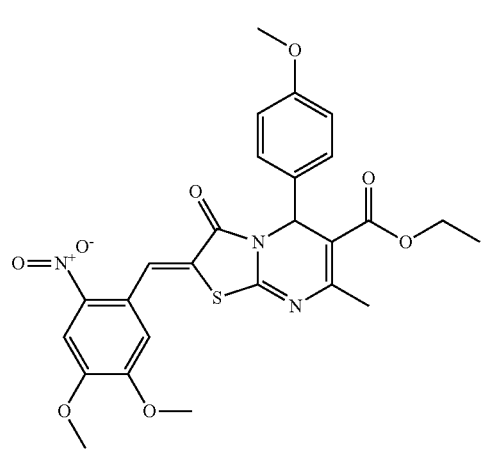 | * | * | ** | * |  |  |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| UF | 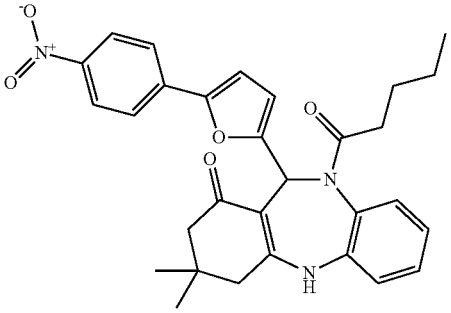 | * |  |  |  |  | * |  | ND |  |
| UG | 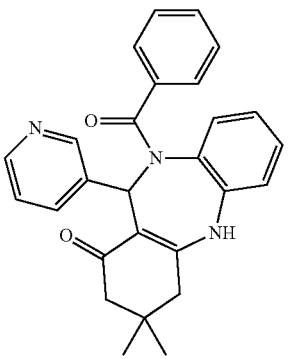 [SMILES: CC1(C)CC(=O)C2=C(C1)Nc1ccccc1N(C(=O)c1ccccc1)C2c1cccnc1] |  |  |  |  |  |  |  | ND |  |
| UH | 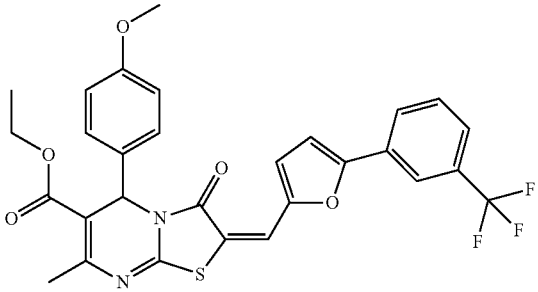 [SMILES: CCOC(=O)C1=C(C)N=c2s/c(=C/c3ccc(-c4cccc(C(F)(F)F)c4)o3)c(=O)n2C1c1ccc(OC)cc1] | * | * | * | * | * | * |  | ND |  |
| UI | 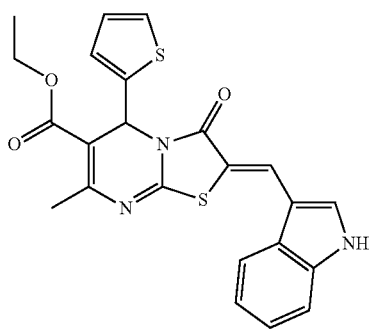 [SMILES: CCOC(=O)C1=C(C)N=c2s/c(=C\c3c[nH]c4ccccc34)c(=O)n2C1c1cccs1] |  |  | ** | * |  |  | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| UJ | 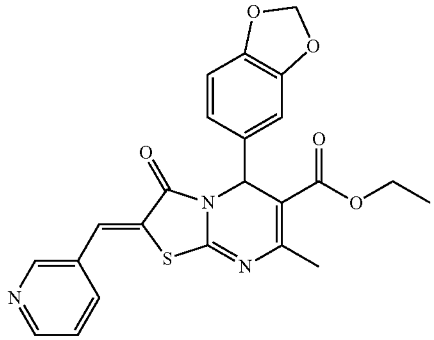 [SMILES: CCOC(=O)C1=C(C)N=c2s/c(=C\c3cccnc3)c(=O)n2C1c1ccc2c(c1)OCO2] |  |  | *** | * | ** | * | ** | ND | ND |
| UK | 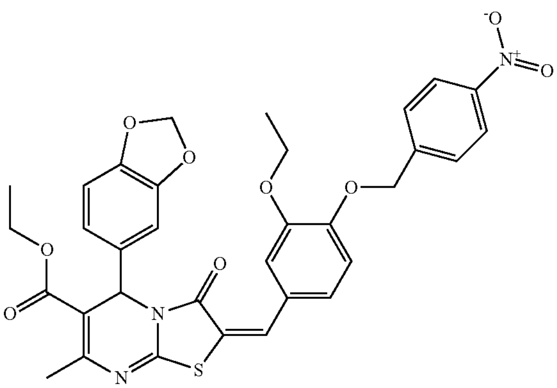 | * | * | * | * | * | * | ** | ND | * |
| UL | 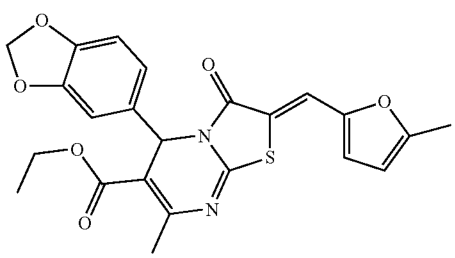 [SMILES: CCOC(=O)C1=C(C)N=c2s/c(=C\c3ccc(C)o3)c(=O)n2C1c1ccc2c(c1)OCO2] | * |  | * | ** | * |  |  | ND | * |
| UM | 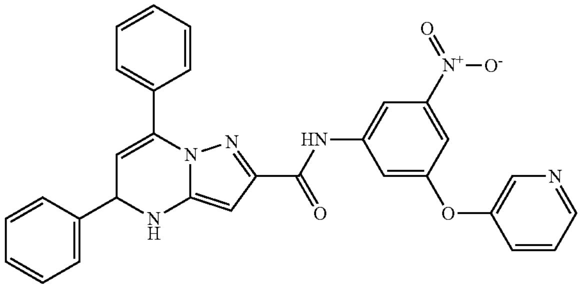 [SMILES: O=C(Nc1cc(Oc2cccnc2)cc([N+](=O)[O-])c1)c1cc2n(n1)C(c1ccccc1)=CC(c1ccccc1)N2] |  |  | ** | * |  | * |  | ND |  |
| UN | 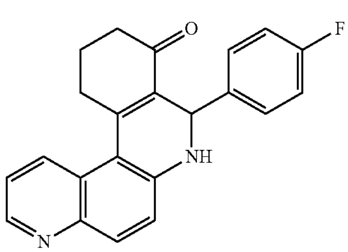 [SMILES: O=C1CCCC2=C1C(c1ccc(F)cc1)Nc1ccc3ncccc3c12] | * | * | ** | * |  |  | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| UO | 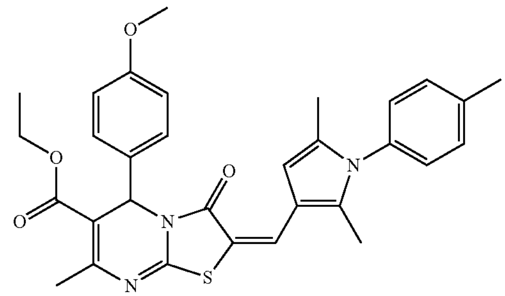 [SMILES: CCOC(=O)C1=C(C)N=c2s/c(=C/c3cc(C)n(-c4ccc(C)cc4)c3C)c(=O)n2C1c1ccc(OC)cc1] | * | * | * | * | * | * |  | ND |  |
| UP | 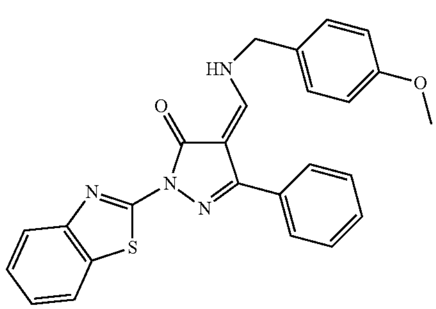 [SMILES: COc1ccc(CN/C=C2\C(=O)N(c3nc4ccccc4s3)N=C2c2ccccc2)cc1] | * | * |  | * | ** | * | ** | ND | ND |
| UQ | 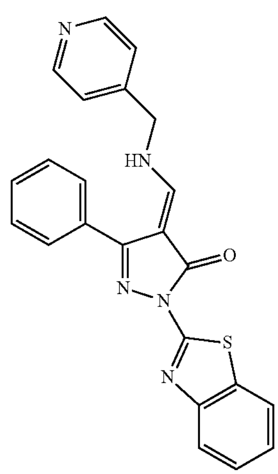 [SMILES: O=C1/C(=C/NCc2ccncc2)C(c2ccccc2)=NN1c1nc2ccccc2s1] | * |  |  | * | *** | * |  | D |  |
| UR | 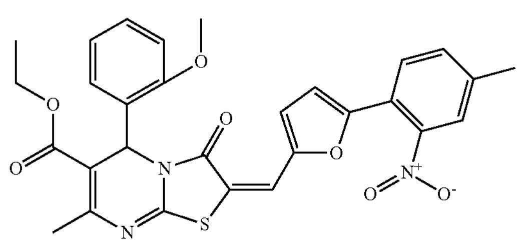 [SMILES: CCOC(=O)C1=C(C)N=c2s/c(=C/c3ccc(-c4ccc(C)cc4[N+](=O)[O-])o3)c(=O)n2C1c1ccccc1OC] | * | * | ** | * | ** | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| US | 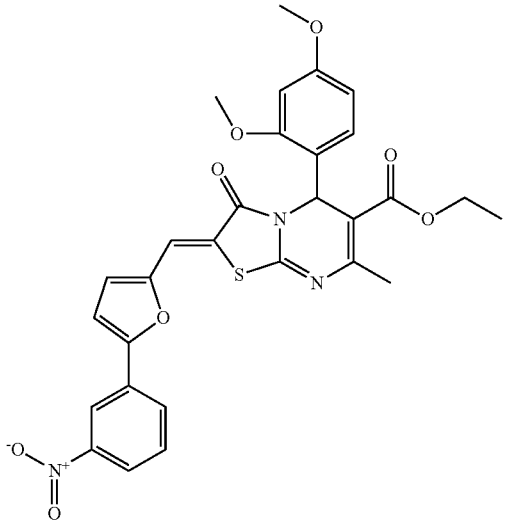 |  |  | ** | * | ** | * |  | ND |  |
| UT | 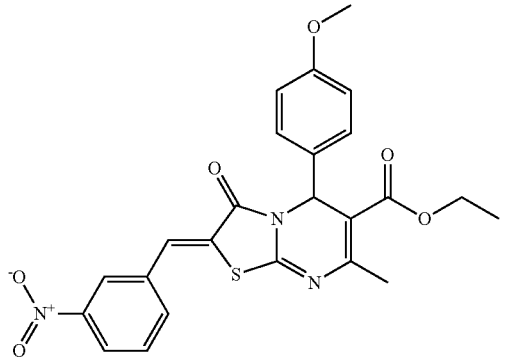 | * | * | * | * | ** | * | ** | ND | * |
| UU | 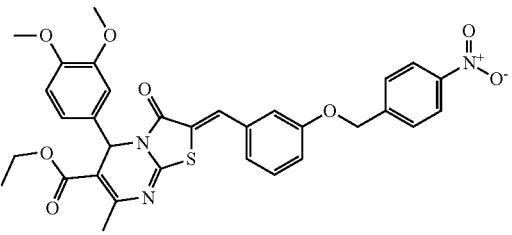 [SMILES: CCOC(=O)C1=C(C)N=c2s/c(=C\c3cccc(OCc4ccc([N+](=O)[O-])cc4)c3)c(=O)n2C1c1ccc(OC)c(OC)c1] | ** | * |  |  | ** | * | ** | ND | ND |
| UV | 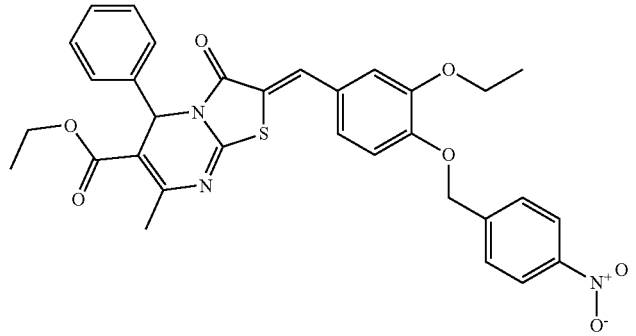 | * | * |  | *** | * | NT | ** | | |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| UW | 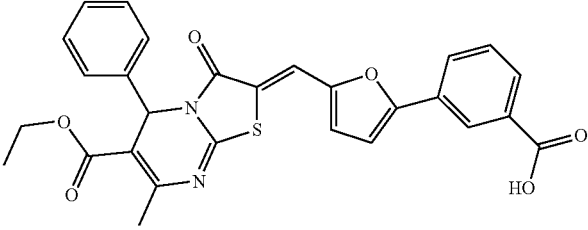 [SMILES: CCOC(=O)C1=C(C)N=c2s/c(=C\c3ccc(-c4cccc(C(=O)O)c4)o3)c(=O)n2C1c1ccccc1] | * | * |  |  |  | NT |  | ND |  |
| UX | 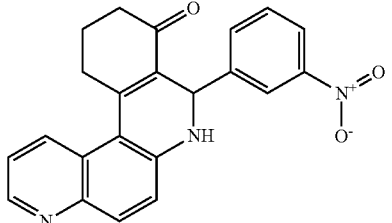 | * | * |  | * |  | NT | ** | ND | * |
| UY | 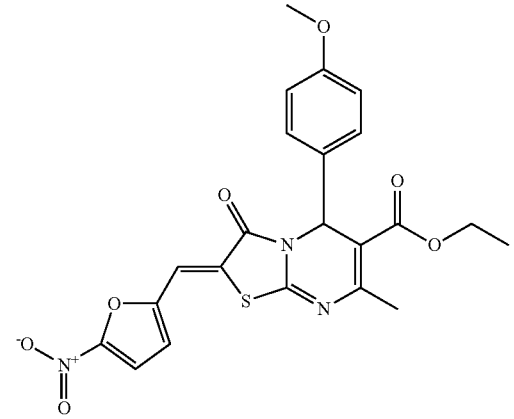 | * | * |  | * |  | NT |  | ND | ** |
| UZ | 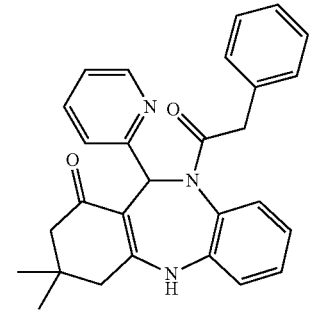 [SMILES: CC1(C)CC(=O)C2=C(C1)Nc1ccccc1N(C(=O)Cc1ccccc1)C2c1ccccn1] | * | * |  | ** | * | NT |  | ND |  |
| VA | 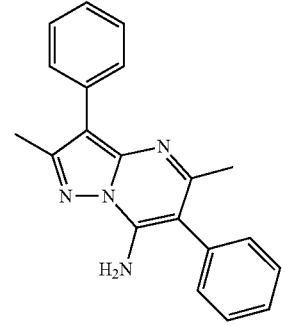 [SMILES: Cc1nc2c(-c3ccccc3)c(C)nn2c(N)c1-c1ccccc1] | * | * | ** | * | * | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VB | 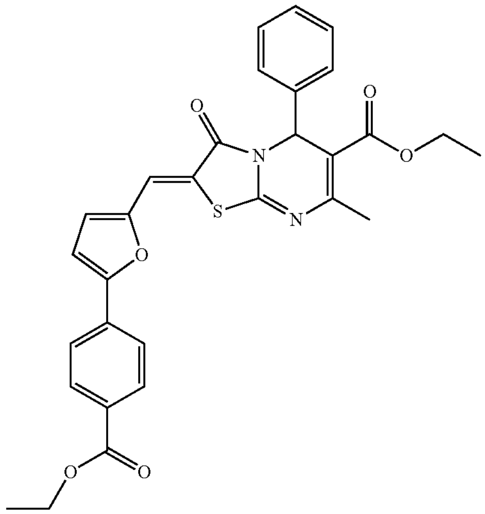 [SMILES: CCOC(=O)C1=C(C)N=c2s/c(=C\c3ccc(-c4ccc(C(=O)OCC)cc4)o3)c(=O)n2C1c1ccccc1] | * | * | ** | * | * | * |  |  | ** |
| VC | 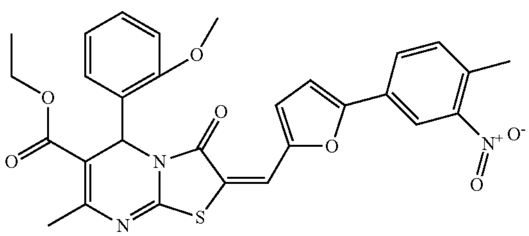 | * | * | ** | * | * | * |  |  | ** |
| VD | 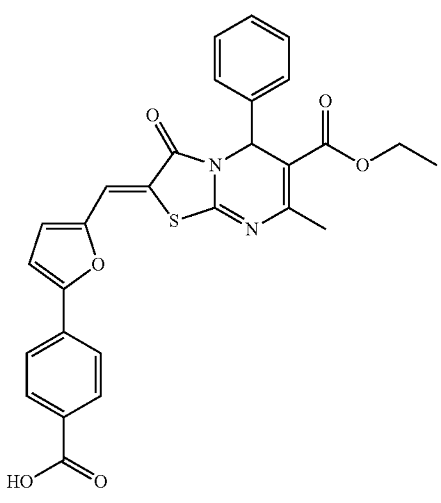 [SMILES: CCOC(=O)C1=C(C)N=c2s/c(=C\c3ccc(-c4ccc(C(=O)O)cc4)o3)c(=O)n2C1c1ccccc1] | NT | * | ** | * | * | * |  |  | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VE | 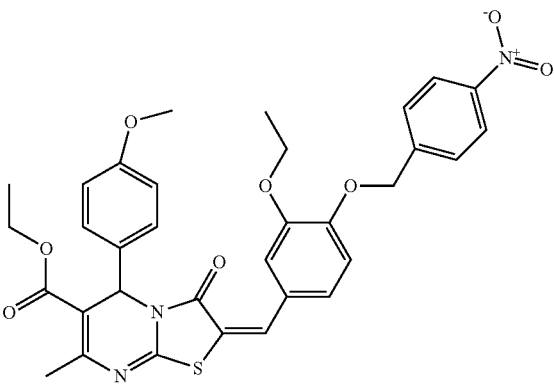 | * | * | * | NT | * | NT |  |  | * |
| VF | 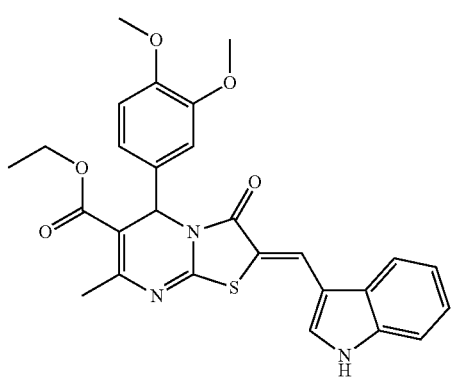 [SMILES: CCOC(=O)C1=C(C)N=c2s/c(=C\c3c[nH]c4ccccc34)c(=O)n2C1c1ccc(OC)c(OC)c1] | * | * | * | NT | * | NT |  |  | * |
| VG | 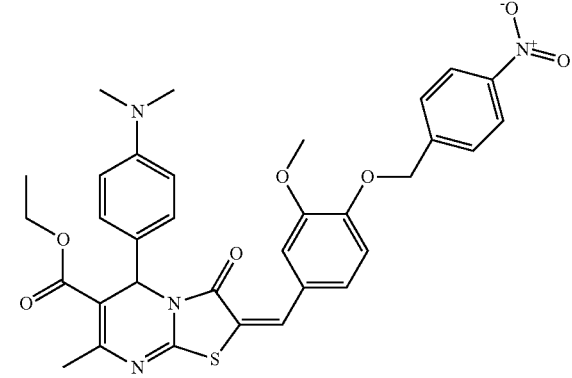 | * | * | ** | NT | * | NT | ** | * | D |
| VH | 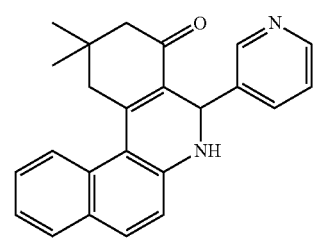 [SMILES: CC1(C)CC(=O)C2=C(C1)c1c(ccc3ccccc13)NC2c1cccnc1] | NT |  | NT |  | NT | * |  |  |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VI | 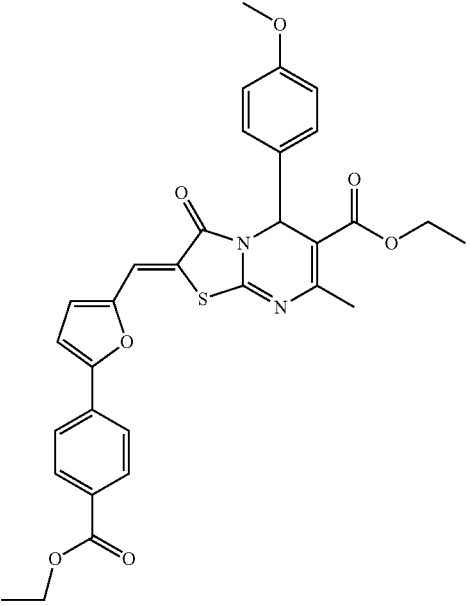 [SMILES: CCOC(=O)C1=C(C)N=c2s/c(=C\c3ccc(-c4ccc(C(=O)OCC)cc4)o3)c(=O)n2C1c1ccc(OC)cc1] | NT | * | NT | * | NT | * | ** | * | * |
| VJ | 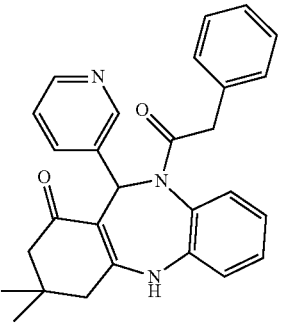 [SMILES: CC1(C)CC(=O)C2=C(C1)Nc1ccccc1N(C(=O)Cc1ccccc1)C2c1cccnc1] | NT | * | NT | ** | NT | * |  |  | ** |
| VK | 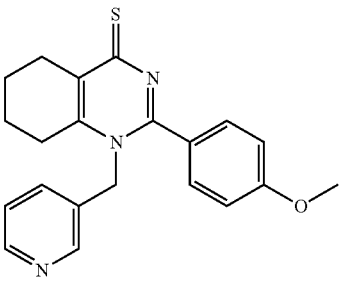 [SMILES: COc1ccc(-c2nc(=S)c3c(n2Cc2cccnc2)CCCC3)cc1] | NT | * | NT |  | NT |  |  |  | ** |
| VL | 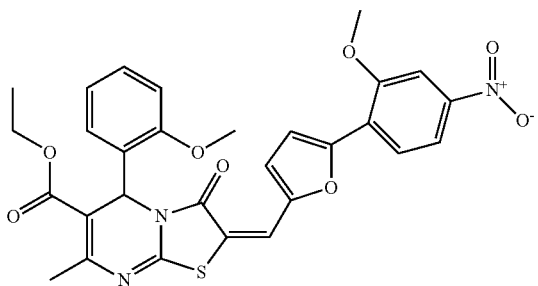 [SMILES: CCOC(=O)C1=C(C)N=c2s/c(=C/c3ccc(-c4ccc([N+](=O)[O-])cc4OC)o3)c(=O)n2C1c1ccccc1OC] | * | NT | * | ** | * | * |  | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VM | 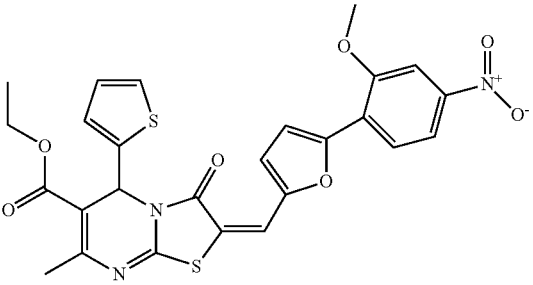 [SMILES: CCOC(=O)C1=C(C)N=c2s/c(=C/c3ccc(-c4ccc([N+](=O)[O-])cc4OC)o3)c(=O)n2C1c1cccs1] | * | NT | ** | * | * | * | ** | ND | * |
| VN | 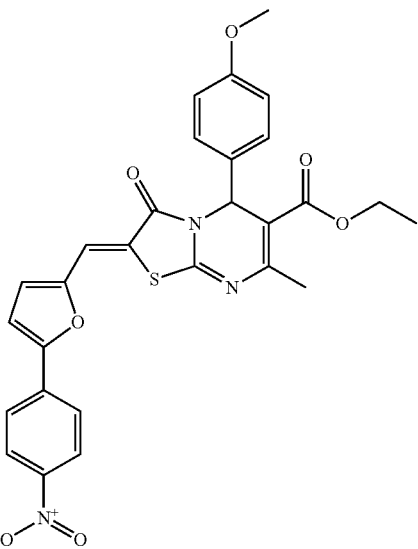 | ** | NT | * | ** | * | * | ** | ND | * |
| VO | 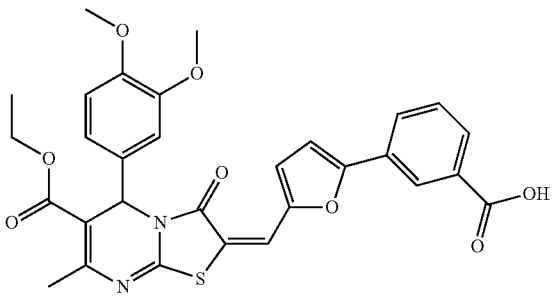 [SMILES: CCOC(=O)C1=C(C)N=c2s/c(=C/c3ccc(-c4cccc(C(=O)O)c4)o3)c(=O)n2C1c1ccc(OC)c(OC)c1] | NT | * | NT | *** | NT | * |  |  | * |
| VP | 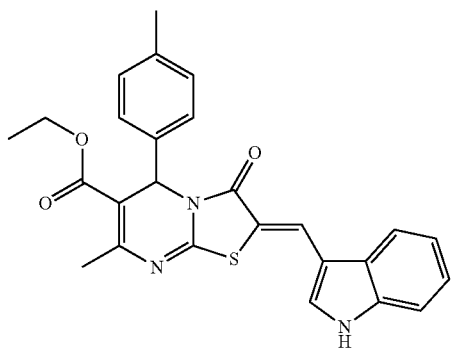 [SMILES: CCOC(=O)C1=C(C)N=c2s/c(=C\c3c[nH]c4ccccc34)c(=O)n2C1c1ccc(C)cc1] | * | * | * | NT | * | NT | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VQ | 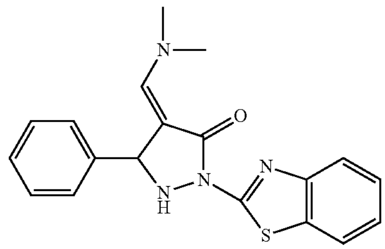 [SMILES: CN(C)/C=C1\C(=O)N(c2nc3ccccc3s2)NC1c1ccccc1] | * | ** | * | NT |  | NT |  | ND | ND |
| VR | 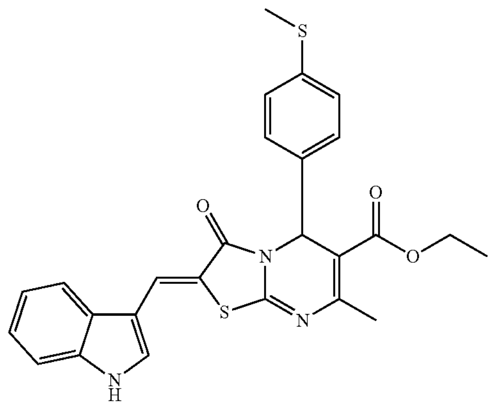 [SMILES: CCOC(=O)C1=C(C)N=c2s/c(=C\c3c[nH]c4ccccc34)c(=O)n2C1c1ccc(SC)cc1] | * | * |  | NT |  | NT | ** | ND | ND |
| VS | 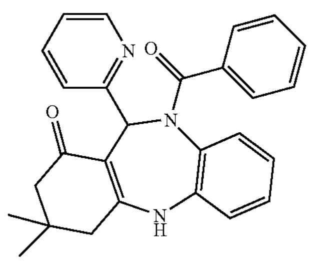 [SMILES: CC1(C)CC(=O)C2=C(C1)Nc1ccccc1N(C(=O)c1ccccc1)C2c1ccccn1] | ** | * | ** | * |  |  |  | ND |  |
| VT | 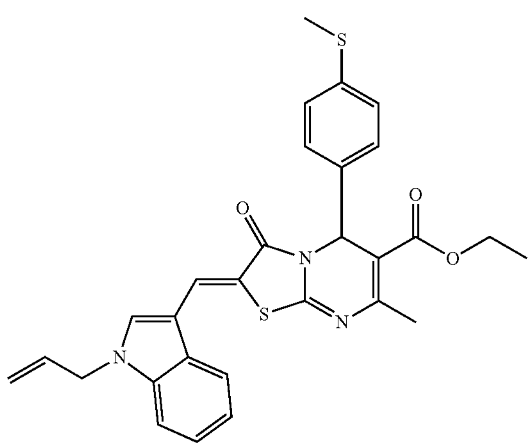 [SMILES: C=CCn1cc(/C=c2\sc3n(c2=O)C(c2ccc(SC)cc2)C(C(=O)OCC)=C(C)N=3)c2ccccc21] | * | * | ** | * | * | * | ** | ND | * |
| VU | 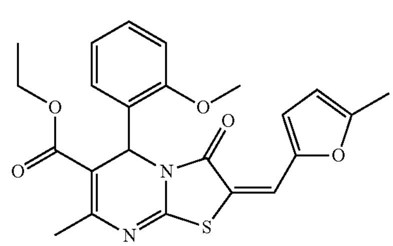 [SMILES: CCOC(=O)C1=C(C)N=c2s/c(=C/c3ccc(C)o3)c(=O)n2C1c1ccccc1OC] | * | * | * | * | * | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| VV | 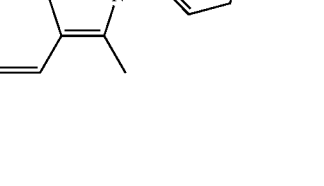 | * | * | ** | * |  | * | ** | ND | * |
| VW | 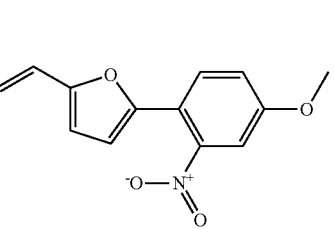 | * | * | ** | * | ** | * |  | ND |  |
| VX | 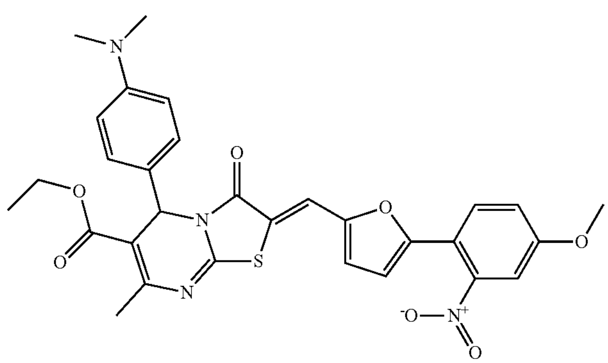 | * | * | * | * |  |  |  | ND |  |
| VY | 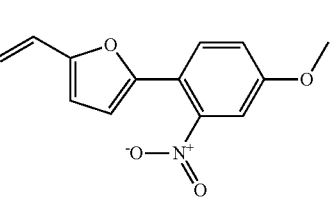 | ** | * | *** | * | ** | * | ** | ND | ND |
| VZ | 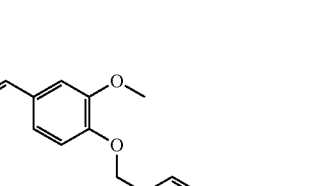 | ** | * | ** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| WA | 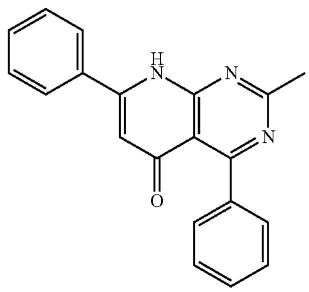 [SMILES: Cc1nc(-c2ccccc2)c2c(=O)cc(-c3ccccc3)[nH]c2n1] |  |  | *** | * | ** | * |  | D |  |
| N£ WB | | * |  | * | * | ** | * |  | ND |  |
| WC | 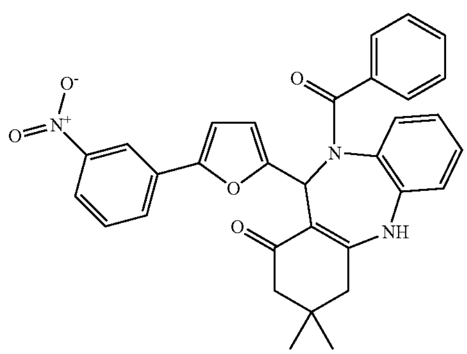 [SMILES: CC1(C)CC(=O)C2=C(C1)Nc1ccccc1N(C(=O)c1ccccc1)C2c1ccc(-c2cccc([N+](=O)[O-])c2)o1] | * | * | * |  |  |  |  | ND |  |
| WD | 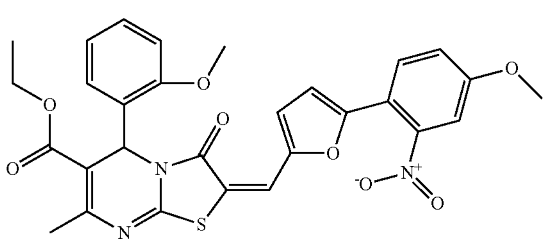 |  | * | ** | * | ** | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| WE | 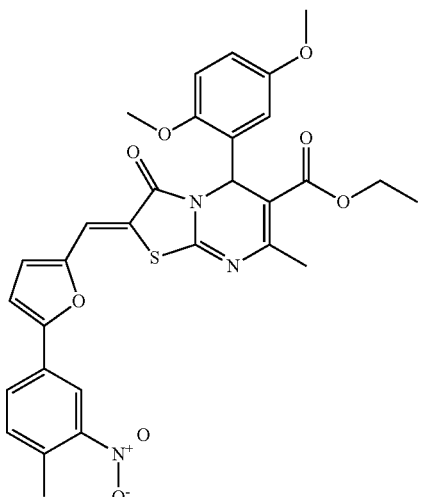 | * |  | * |  | *** | * | ** | ND | ND |
| WF | 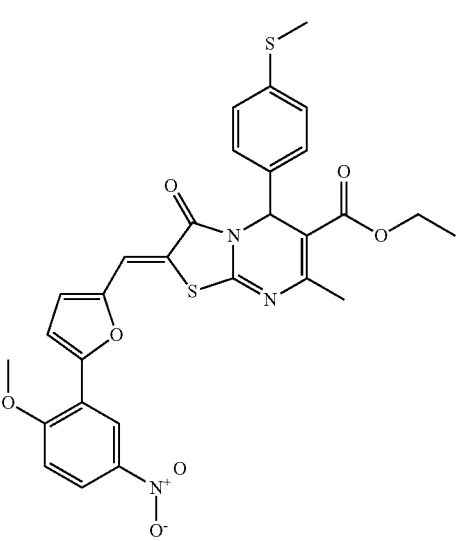 |  |  | * | * |  |  |  | ND |  |
| WG | 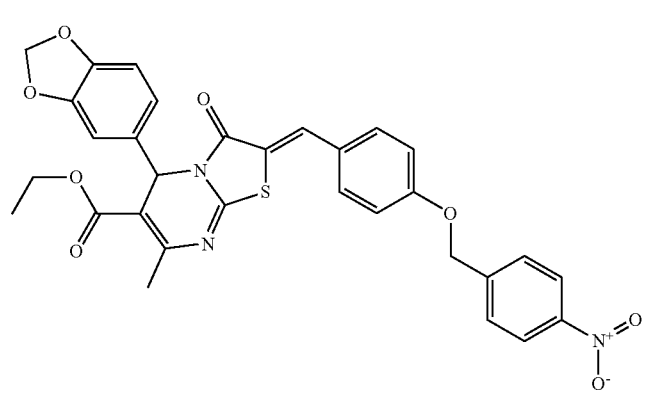 [SMILES: CCOC(=O)C1=C(C)N=c2s/c(=C\c3ccc(OCc4ccc([N+](=O)[O-])cc4)cc3)c(=O)n2C1c1ccc2c(c1)OCO2] | * | * | *** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| WH | 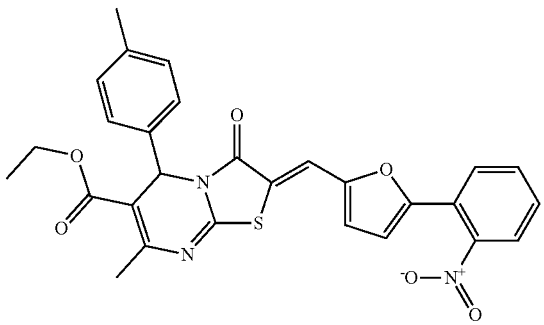 | * |  |  | * |  |  |  | ND |  |
| WI | 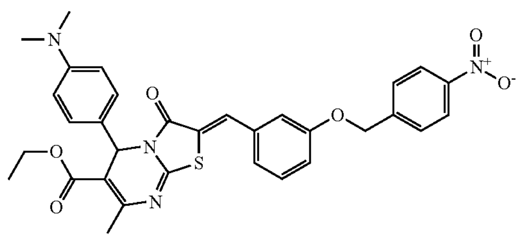 [SMILES: CCOC(=O)C1=C(C)N=c2s/c(=C\c3cccc(OCc4ccc([N+](=O)[O-])cc4)c3)c(=O)n2C1c1ccc(N(C)C)cc1] | * | * | * |  |  | * |  | ND |  |
| WJ | 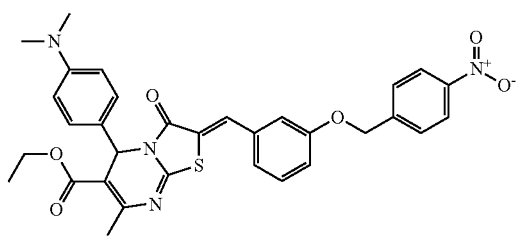 [SMILES: CCOC(=O)C1=C(C)N=c2s/c(=C\c3cccc(OCc4ccc([N+](=O)[O-])cc4)c3)c(=O)n2C1c1ccc(N(C)C)cc1] | * | * | ** | * | ** | * | ** | ND | * |
| WK | 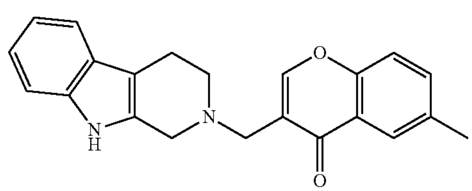 [SMILES: Cc1ccc2occ(CN3CCc4c([nH]c5ccccc45)C3)c(=O)c2c1] | *** | * | *** | * | *** | * | ** | ND | * |
| WL | 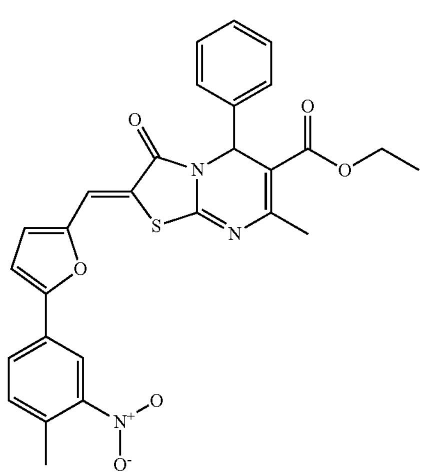 [SMILES: CCOC(=O)C1=C(C)N=c2s/c(=C\c3ccc(-c4ccc(C)c([NH+]([O-])O)c4)o3)c(=O)n2C1c1ccccc1] | ** | * | ** | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| WM | 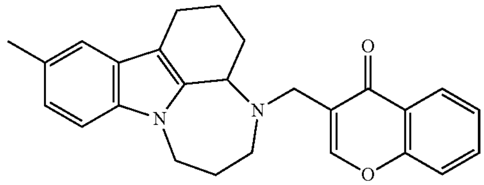 [SMILES: Cc1ccc2c(c1)c1c3n2CCCN(Cc2coc4ccccc4c2=O)C3CCC1] | ** | * | * | * |  |  | ** | ND | * |
| WN | 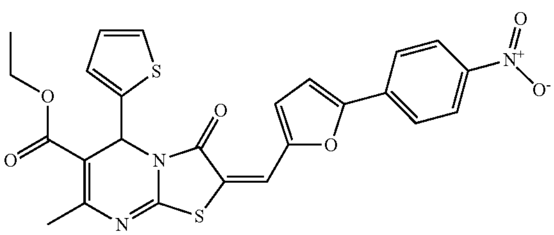 [SMILES: CCOC(=O)C1=C(C)N=c2s/c(=C/c3ccc(-c4ccc([N+](=O)[O-])cc4)o3)c(=O)n2C1c1cccs1] | ** | * | * | * | * | * | ** | ND | * |
| WO | 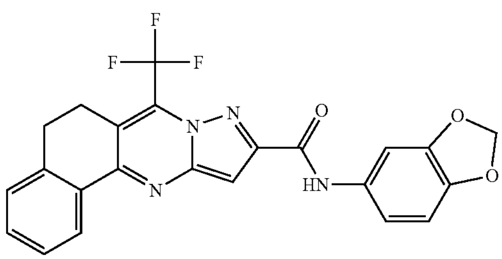 [SMILES: O=C(Nc1ccc2c(c1)OCO2)c1cc2nc3c(c(C(F)(F)F)n2n1)CCc1ccccc1-3] | ** | * | * |  |  | * |  | ND | ** |
| WP | 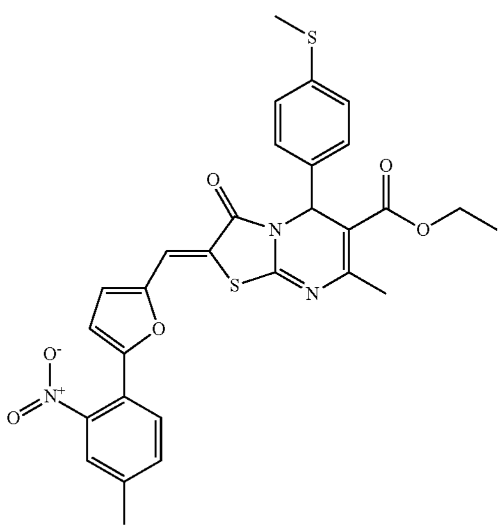 [SMILES: CCOC(=O)C1=C(C)N=c2s/c(=C\c3ccc(-c4ccc(C)cc4[N+](=O)[O-])o3)c(=O)n2C1c1ccc(SC)cc1] | ** | * | * | * |  |  | ** | ND | * |
| WQ | 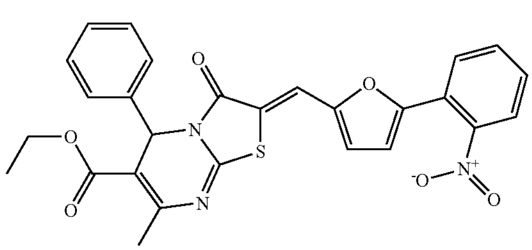 | ** | * | * | * | * | * |  | ND | ND |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| WR | 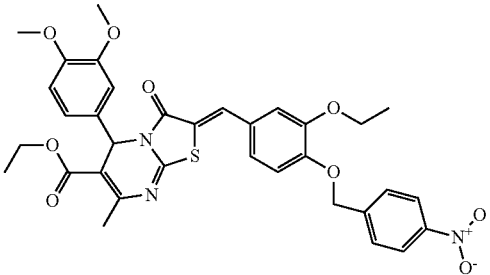 [SMILES: CCOC(=O)C1=C(C)N=c2s/c(=C\c3ccc(OCc4ccc([NH+]([O-])O)cc4)c(OCC)c3)c(=O)n2C1c1ccc(OC)c(OC)c1] | * | * | * | * | ** | * | ** | ND | ND |
| WS | 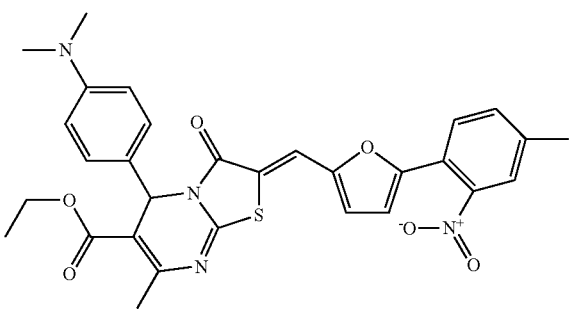 | *** | * | * | * | * | * | ** | ND | ND |
| WT | 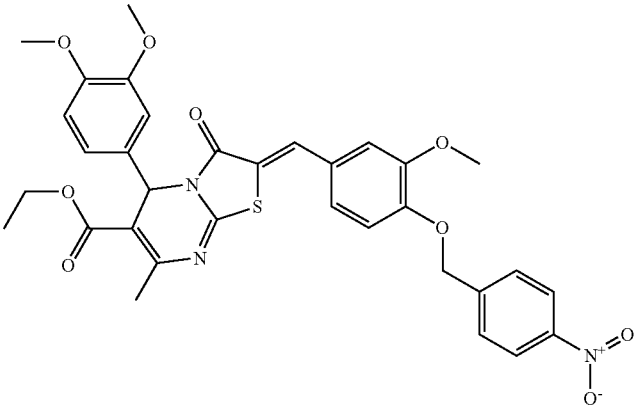 [SMILES: CCOC(=O)C1=C(C)N=c2s/c(=C\c3ccc(OCc4ccc([N+](=O)[O-])cc4)c(OC)c3)c(=O)n2C1c1ccc(OC)c(OC)c1] |  |  | * | * | * | * |  | ND |  |
| WU | 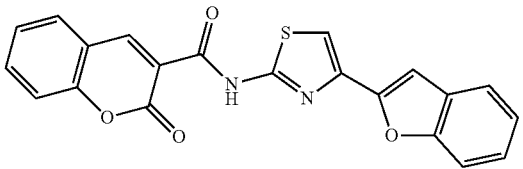 [SMILES: O=C(Nc1nc(-c2cc3ccccc3o2)cs1)c1cc2ccccc2oc1=O] | ** | * | * | * | ** | * | ** | ND | * |
| WV | 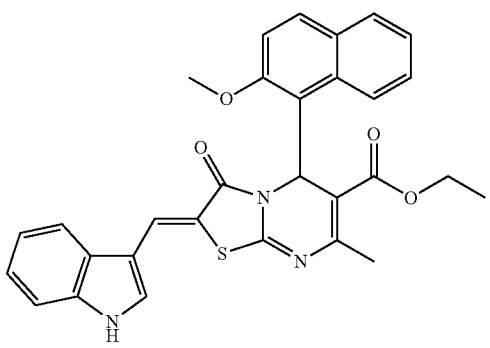 [SMILES: CCOC(=O)C1=C(C)N=c2s/c(=C\c3c[nH]c4ccccc34)c(=O)n2C1c1c(OC)ccc2ccccc12] | *** | * | * | * | *** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| WW | 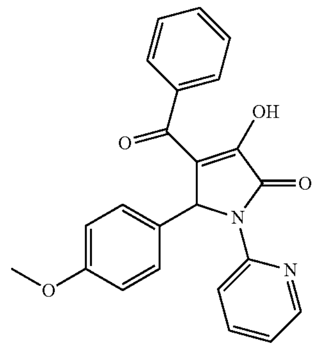 [SMILES: COc1ccc(C2C(C(=O)c3ccccc3)=C(O)C(=O)N2c2ccccn2)cc1] | *** | * | * | * | *** | * | ** | ND | * |
| WX | 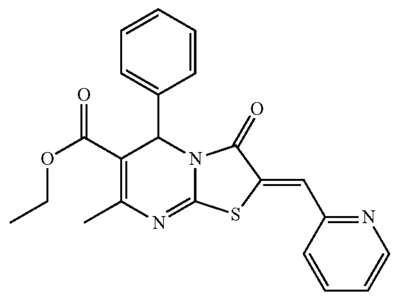 [SMILES: CCOC(=O)C1=C(C)N=c2s/c(=C\c3ccccn3)c(=O)n2C1c1ccccc1] | * |  | * | * | ** | * | ** | ND | * |
| WY | 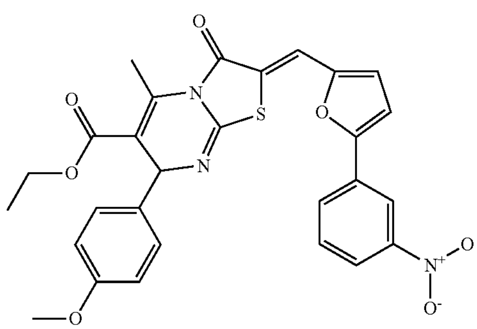 [SMILES: CCOC(=O)C1=C(C)n2c(s/c(=C\c3ccc(-c4cccc([NH+]([O-])O)c4)o3)c2=O)=NC1c1ccc(OC)cc1] | *** | * | * | * | *** | * |  | ND |  |
| WZ | 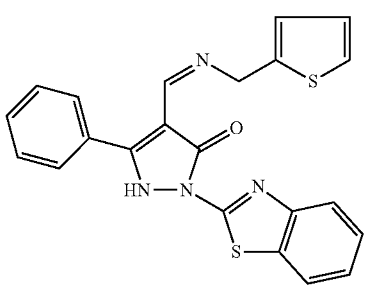 [SMILES: O=c1c(/C=N\Cc2cccs2)c(-c2ccccc2)[nH]n1-c1nc2ccccc2s1] | *** | * | * | * | *** | * | ** | ND | ND |
| XA | 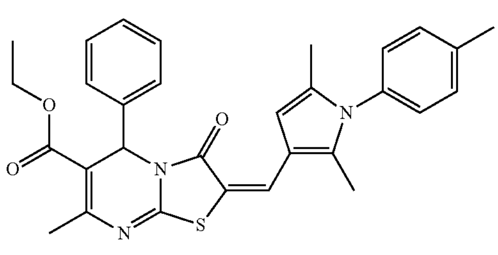 [SMILES: CCOC(=O)C1=C(C)N=c2s/c(=C/c3cc(C)n(-c4ccc(C)cc4)c3C)c(=O)n2C1c1ccccc1] | *** | * | * | * | *** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XB | 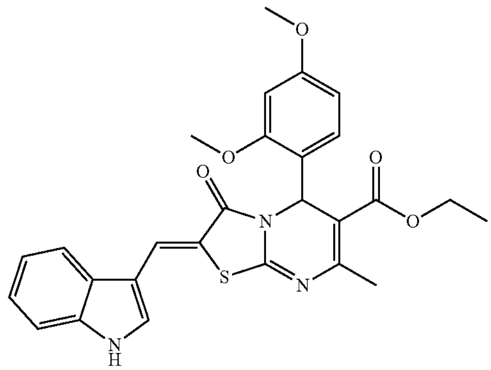 [SMILES: CCOC(=O)C1=C(C)N=c2s/c(=C\c3c[nH]c4ccccc34)c(=O)n2C1c1ccc(OC)cc1OC] | *** | * | * | * | *** | * | ** | ND | * |
| XC | 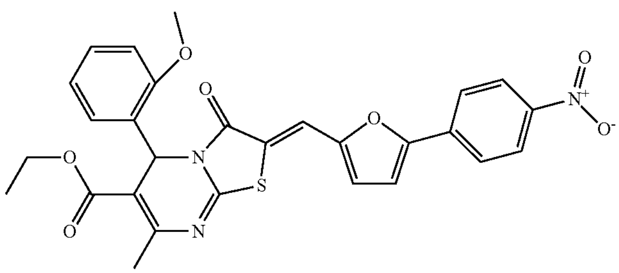 [SMILES: CCOC(=O)C1=C(C)N=c2s/c(=C\c3ccc(-c4ccc([N+](=O)[O-])cc4)o3)c(=O)n2C1c1ccccc1OC] | *** | * | * | * | *** | * | ** | ND | ND |
| XD | 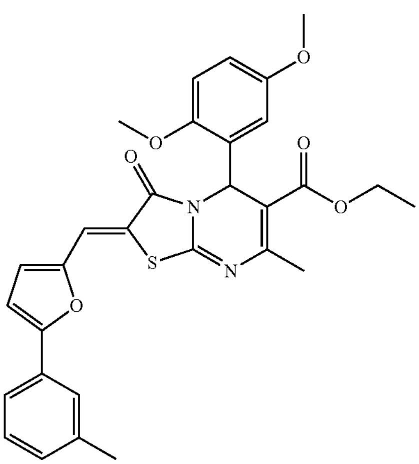 [SMILES: CCOC(=O)C1=C(C)N=c2s/c(=C\c3ccc(-c4cccc(C)c4)o3)c(=O)n2C1c1cc(OC)ccc1OC] |  | * | * | * | * | * | ** | ND | ND |
| XE | 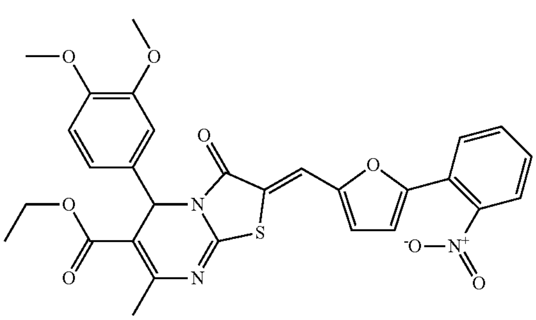 | *** | * | ** | * | * |  | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XF | 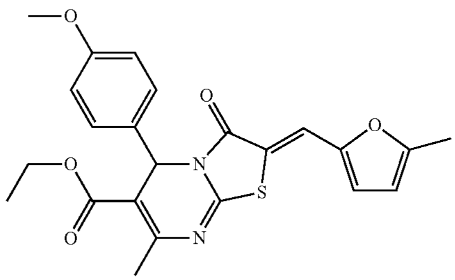 [SMILES: CCOC(=O)C1=C(C)N=c2s/c(=C\c3ccc(C)o3)c(=O)n2C1c1ccc(OC)cc1] | NT | * | NT | * | NT |  |  | * | ND |
| XG | 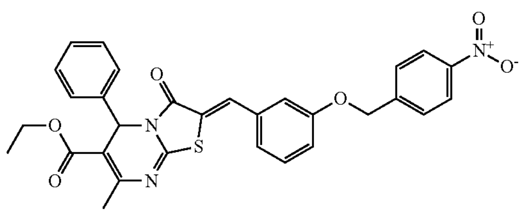 [SMILES: CCOC(=O)C1=C(C)N=c2s/c(=C\c3cccc(OCc4ccc([N+](=O)[O-])cc4)c3)c(=O)n2C1c1ccccc1] | NT | * | NT | ** | NT | * | ** | * | * |
| XH | 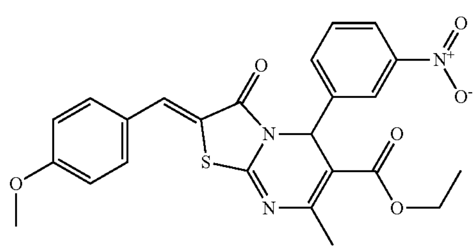 [SMILES: CCOC(=O)C1=C(C)N=c2s/c(=C\c3ccc(OC)cc3)c(=O)n2C1c1cccc([N+](=O)[O-])c1] | NT | * | NT | ** | NT | * |  |  | ** |
| XI | 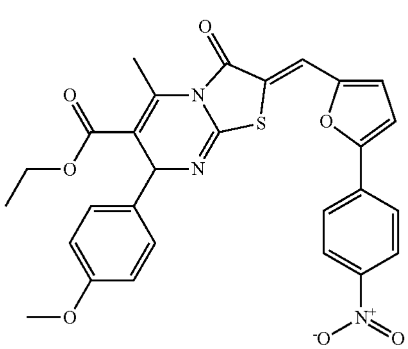 | NT |  | NT |  | NT | * |  | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XG | 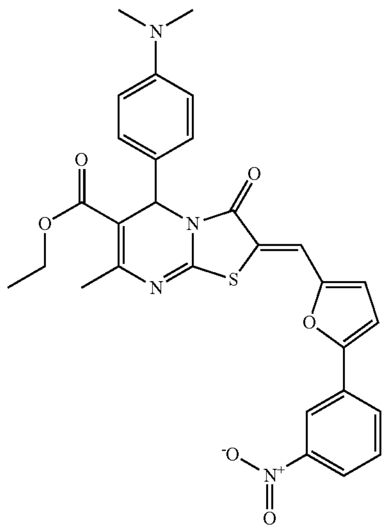 | NT | * | NT | ** | NT | * |  |  | * |
| XH | 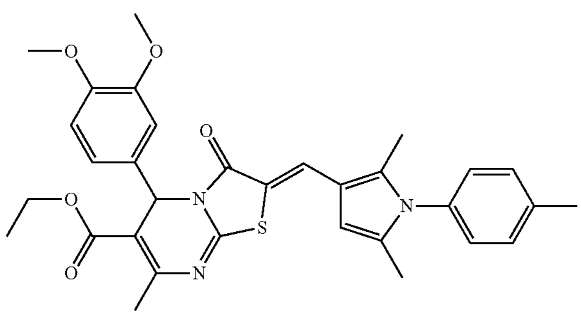 [SMILES: CCOC(=O)C1=C(C)N=c2s/c(=C\c3cc(C)n(-c4ccc(C)cc4)c3C)c(=O)n2C1c1ccc(OC)c(OC)c1] | NT | * | NT | * | NT | * | ** | * | D |
| XI | 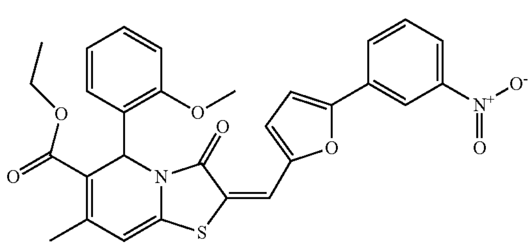 [SMILES: CCOC(=O)C1=C(C)C=c2s/c(=C/c3ccc(-c4cccc([N+](=O)[O-])c4)o3)c(=O)n2C1c1ccccc1OC] | NT | * | NT | * | NT | * |  |  | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XJ | 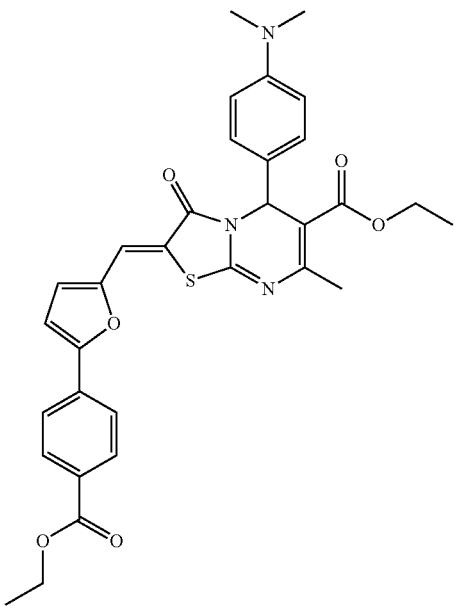 [SMILES: CCOC(=O)C1=C(C)N=c2s/c(=C\c3ccc(-c4ccc(C(=O)OCC)cc4)o3)c(=O)n2C1c1ccc(N(C)C)cc1] | NT | * | NT |  | NT | * |  |  | ** |
| XK | 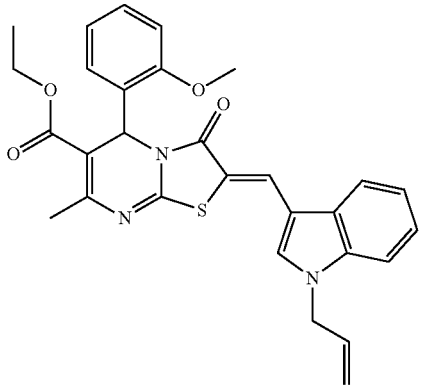 [SMILES: C=CCn1cc(/C=c2\sc3n(c2=O)C(c2ccccc2OC)C(C(=O)OCC)=C(C)N=3)c2ccccc21] | NT | * | NT | * | NT | * | ** | * | * |
| XL | 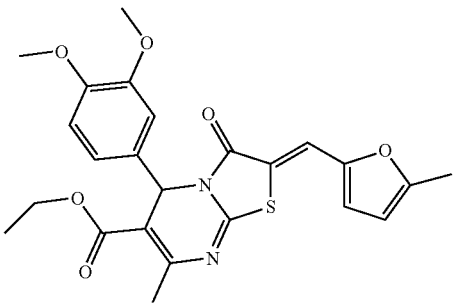 [SMILES: CCOC(=O)C1=C(C)N=c2s/c(=C\c3ccc(C)o3)c(=O)n2C1c1ccc(OC)c(OC)c1] |  |  |  |  |  |  | ** | ND | * |
| XM | 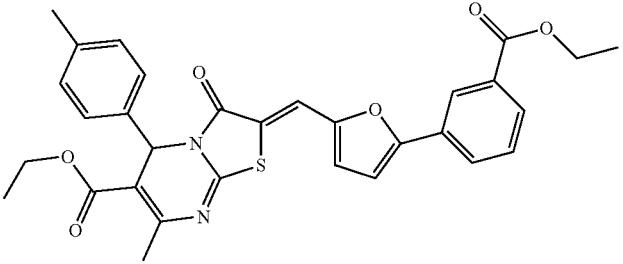 [SMILES: CCOC(=O)C1=C(C)N=c2s/c(=C\c3ccc(-c4cccc(C(=O)OCC)c4)o3)c(=O)n2C1c1ccc(C)cc1] | * | * |  | * | * | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XN | 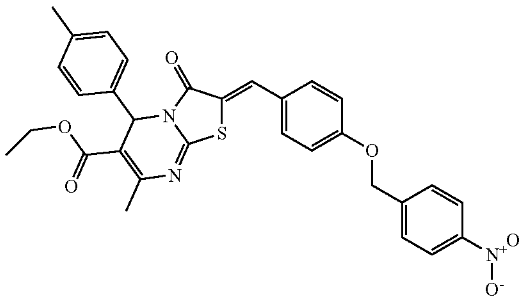 |  |  | * | * | * | * | ** | ND | ND |
| XO | 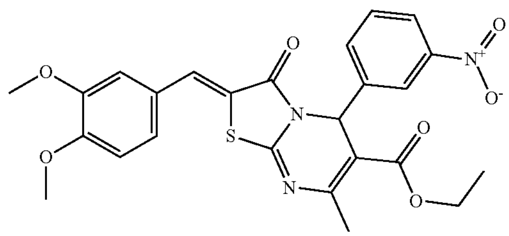 [SMILES: CCOC(=O)C1=C(C)N=c2s/c(=C\c3ccc(OC)c(OC)c3)c(=O)n2C1c1cccc([N+](=O)[O-])c1] | * | * | * | *** | * | * |  | ND |  |
| XP | 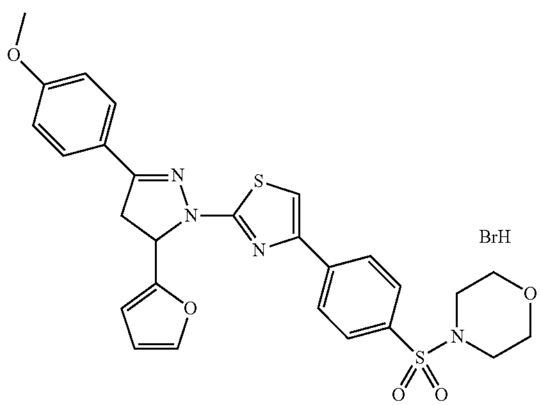 [SMILES: COc1ccc(C2=NN(c3nc(-c4ccc(S(=O)(=O)N5CCOCC5)cc4)cs3)C(c3ccco3)C2)cc1 ; Br] | * |  |  | * |  |  | ** | ND | ND |
| XQ | 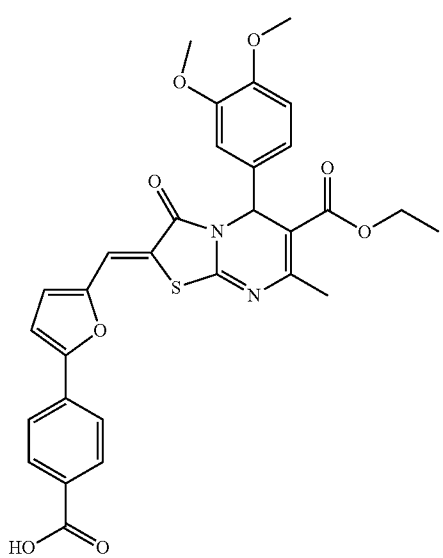 [SMILES: CCOC(=O)C1=C(C)N=c2s/c(=C\c3ccc(-c4ccc(C(=O)O)cc4)o3)c(=O)n2C1c1ccc(OC)c(OC)c1] | * |  | ** | * |  |  | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XR | 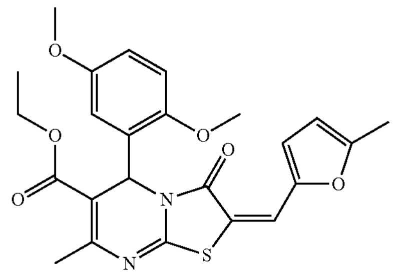 [SMILES: CCOC(=O)C1=C(C)N=c2s/c(=C/c3ccc(C)o3)c(=O)n2C1c1cc(OC)ccc1OC] |  | * | ** | * | ** | * |  | ND |  |
| XS | 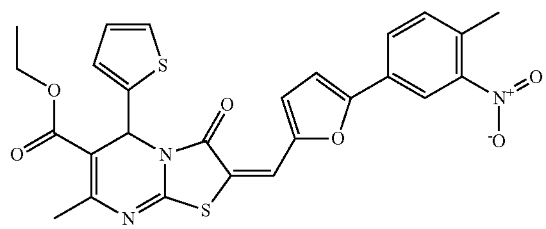 | * |  |  | * | ** | * |  | ND |  |
| XT | 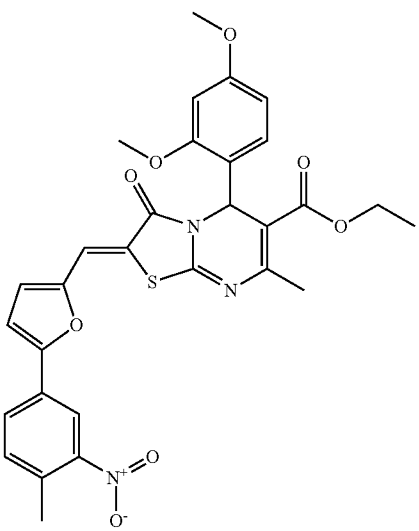 [SMILES: CCOC(=O)C1=C(C)N=c2s/c(=C\c3ccc(-c4ccc(C)c([N+](=O)[O-])c4)o3)c(=O)n2C1c1ccc(OC)cc1OC] | * |  |  | * | ** | * |  | ND |  |
| XU | 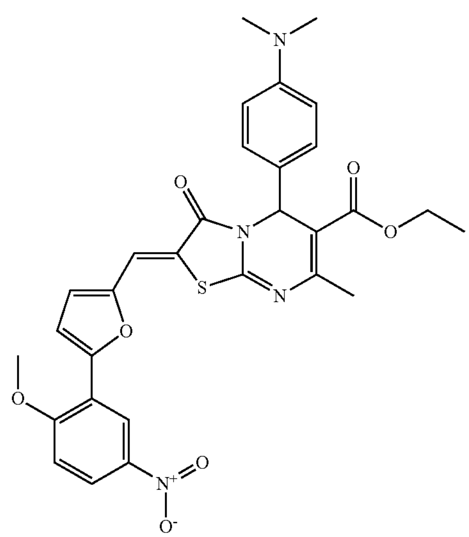 [SMILES: CCOC(=O)C1=C(C)N=c2s/c(=C\c3ccc(-c4cc([N+](=O)[O-])ccc4OC)o3)c(=O)n2C1c1ccc(N(C)C)cc1] | * | * | ** | * | ** | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| XV | 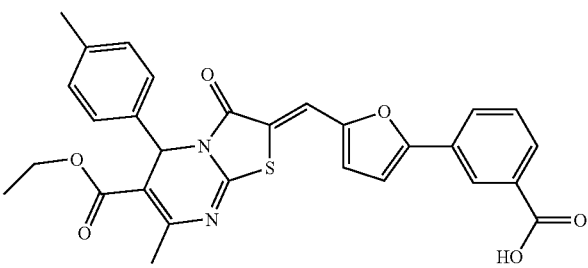 [SMILES: CCOC(=O)C1=C(C)N=c2s/c(=C\c3ccc(-c4cccc(C(=O)O)c4)o3)c(=O)n2C1c1ccc(C)cc1] |  |  | * | * | ** | * | ** | ND | * |
| XW | 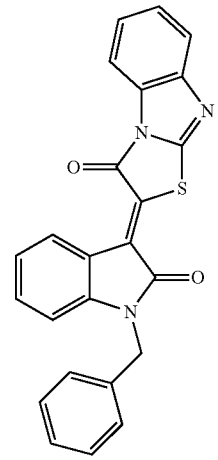 [SMILES: O=C1/C(=c2\sc3nc4ccccc4n3c2=O)c2ccccc2N1Cc1ccccc1] | * |  |  | * |  |  | ** | ND | ND |
| XY | 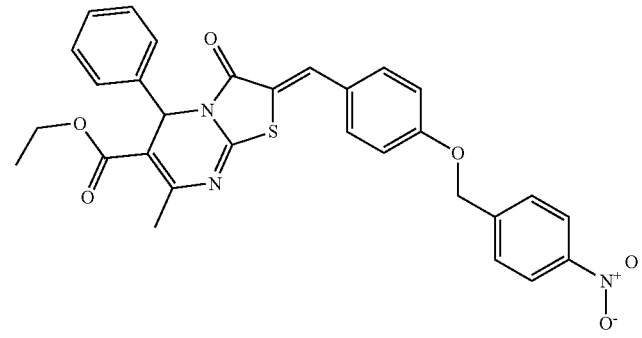 | * | * |  | * | ** | * |  | ND |  |
| XZ | 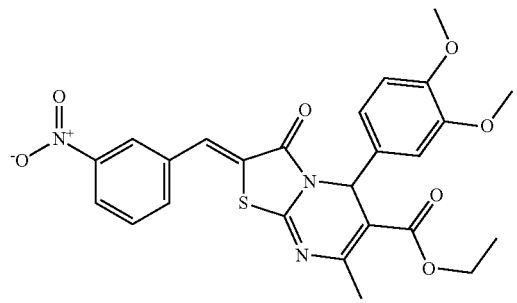 | * | * |  | *** | * | NT |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YA | 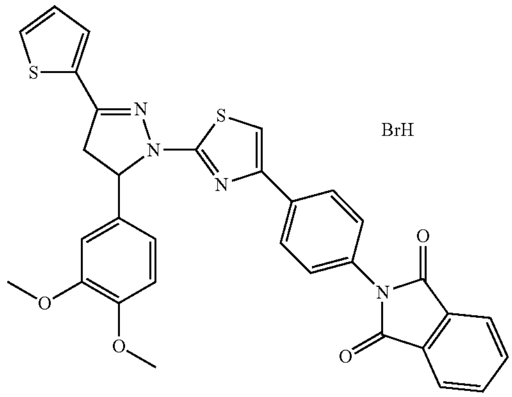 [SMILES: COc1ccc(C2CC(c3cccs3)=NN2c2nc(-c3ccc(N4C(=O)c5ccccc5C4=O)cc3)cs2)cc1OC ; Br] |  |  | ** | * | * | * |  |  | * |
| YB | 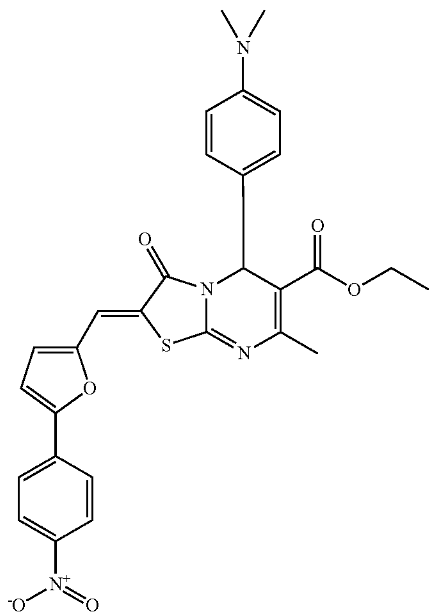 | * | * | ** | * | * | * |  |  |  |
| YC | 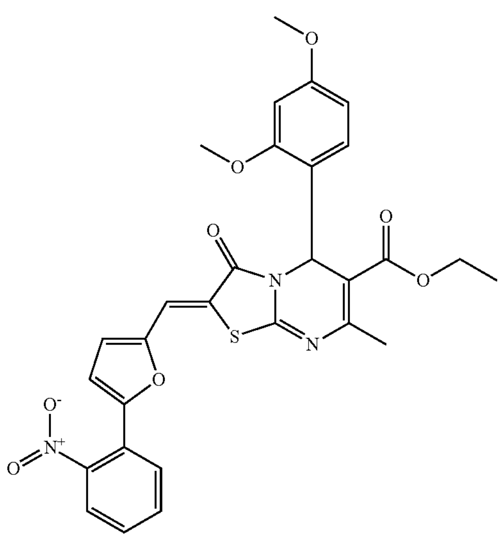 [SMILES: CCOC(=O)C1=C(C)N=c2s/c(=C\c3ccc(-c4ccccc4[N+](=O)[O-])o3)c(=O)n2C1c1ccc(OC)cc1OC] | * | * | ** | * | * |  |  |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YD | 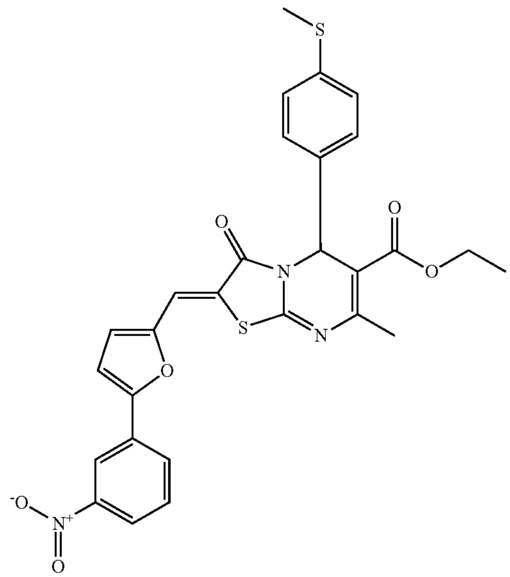 | ** | * | *** | NT | * | NT |  |  | ** |
| YE | 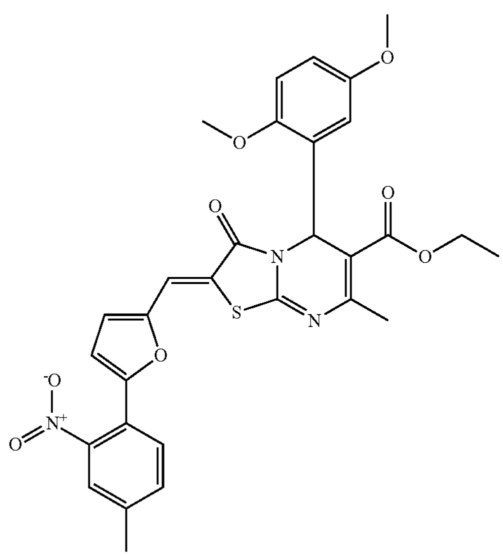 | ** | * | ** | NT | * | NT | ** | * | * |
| YF | 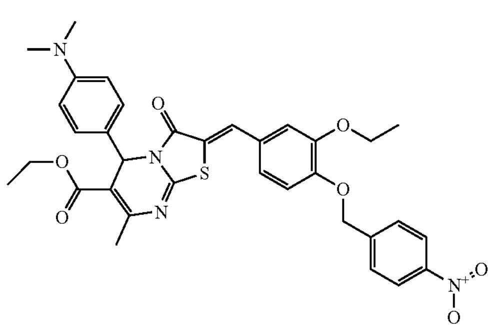 | NT | * | NT | * | NT | * |  |  |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YG | 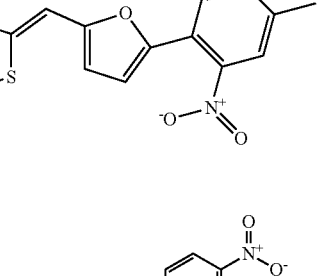 | NT | * | NT |  | NT | * |  |  | * |
| YH | 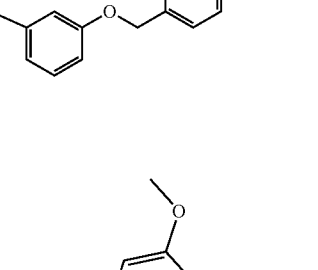 | NT | * | NT | * | NT | * |  |  | ** |
| YI | 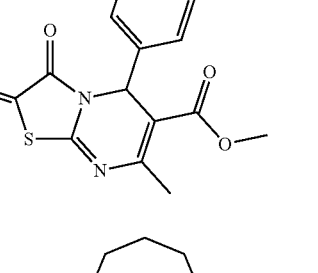 | NT | * | NT | * | NT | * |  |  | ** |
| YJ | 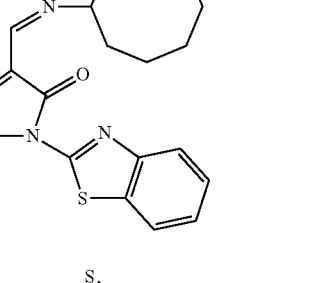 | * | NT | * | ** | * | * |  | ND |  |
| YK | 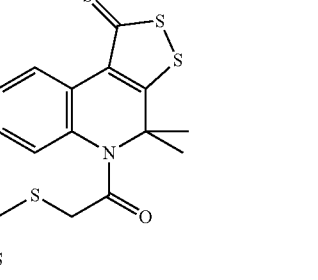 | * | NT | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YL | 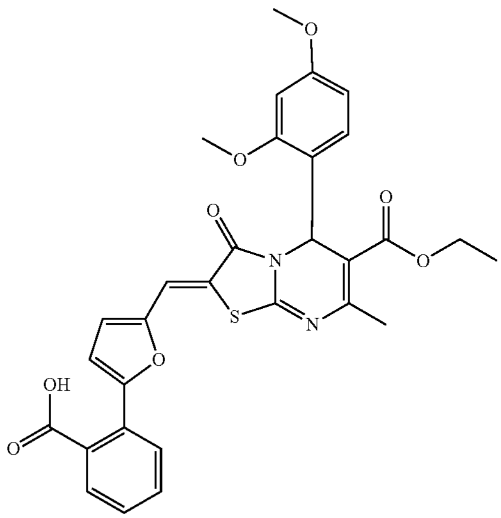 [SMILES: CCOC(=O)C1=C(C)N=c2s/c(=C\c3ccc(-c4ccccc4C(=O)O)o3)c(=O)n2C1c1ccc(OC)cc1OC] | * | NT | * | ** | * | * |  | ND |  |
| YM | 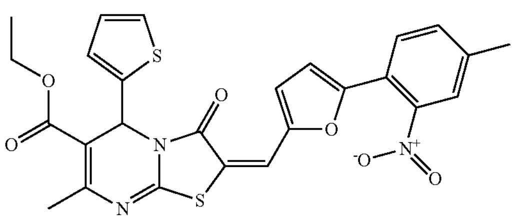 | * | NT |  |  | * | * | ** | ND | * |
| YN | 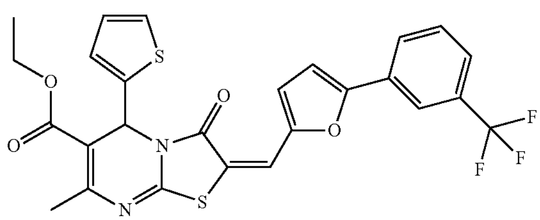 [SMILES: CCOC(=O)C1=C(C)N=c2s/c(=C/c3ccc(-c4cccc(C(F)(F)F)c4)o3)c(=O)n2C1c1cccs1] | * | NT | * | ** | * |  |  | ND | ** |
| YO | 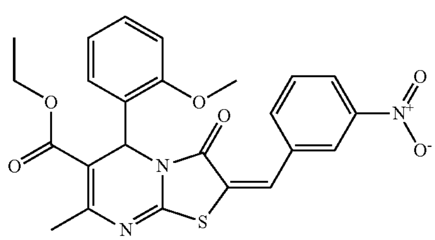 [SMILES: CCOC(=O)C1=C(C)N=c2s/c(=C/c3cccc([N+](=O)[O-])c3)c(=O)n2C1c1ccccc1OC] | NT | * | NT | * | NT | * |  |  | ND |
| YP | 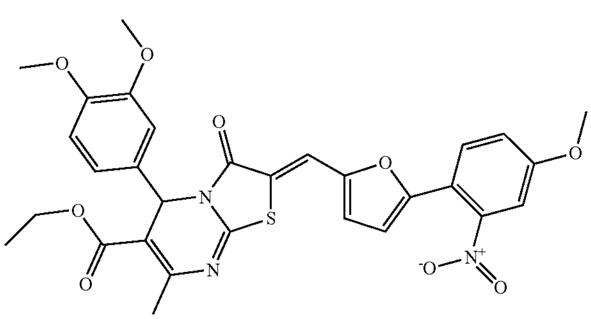 | NT | * | NT | * | NT | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YQ | 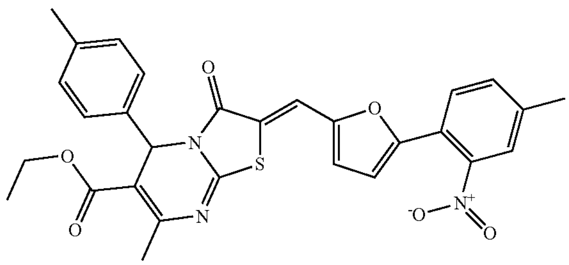 | NT | * | NT | ** | NT | * |  |  | ** |
| YR | 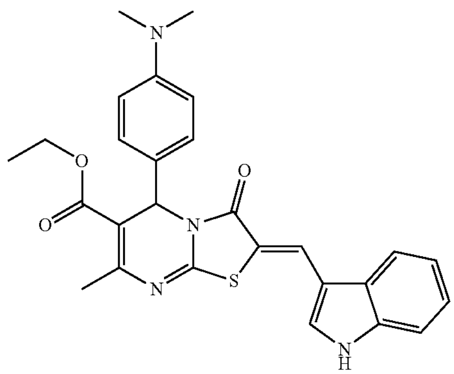 [SMILES: CCOC(=O)C1=C(C)N=c2s/c(=C\c3c[nH]c4ccccc34)c(=O)n2C1c1ccc(N(C)C)cc1] | * |  |  | NT | * | NT |  | ND | ND |
| YS | 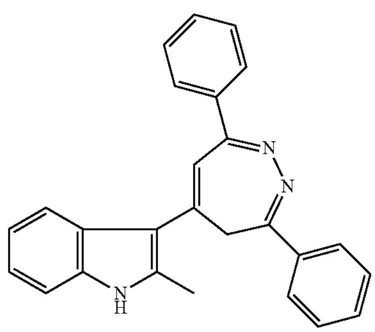 [SMILES: Cc1[nH]c2ccccc2c1C1=CC(c2ccccc2)=NN=C(c2ccccc2)C1] | * |  | ** | * | * | * | ** | ND | * |
| YT | 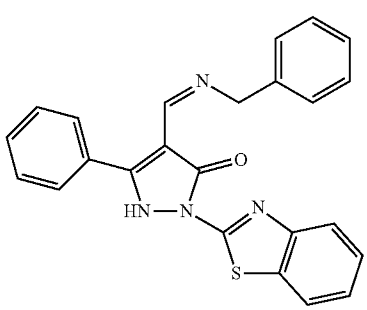 [SMILES: O=c1c(/C=N\Cc2ccccc2)c(-c2ccccc2)[nH]n1-c1nc2ccccc2s1] |  | * | ** | * | *** | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YU | 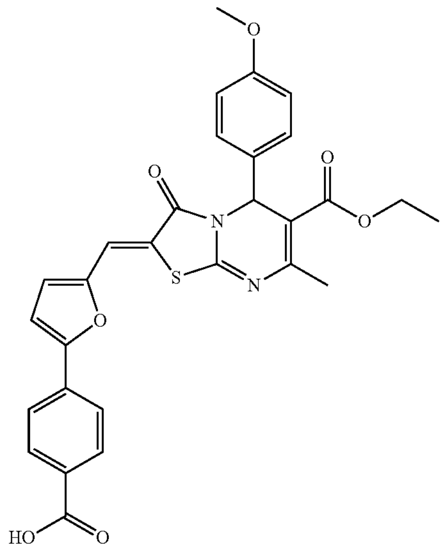 [SMILES: CCOC(=O)C1=C(C)N=c2s/c(=C\c3ccc(-c4ccc(C(=O)O)cc4)o3)c(=O)n2C1c1ccc(OC)cc1] |  |  | ** | * |  |  |  | ND |  |
| YV | 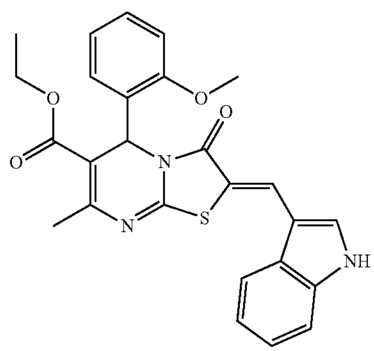 [SMILES: CCOC(=O)C1=C(C)N=c2s/c(=C\c3c[nH]c4ccccc34)c(=O)n2C1c1ccccc1OC] | ** | * | *** | * | *** | * |  | ND |  |
| YW | 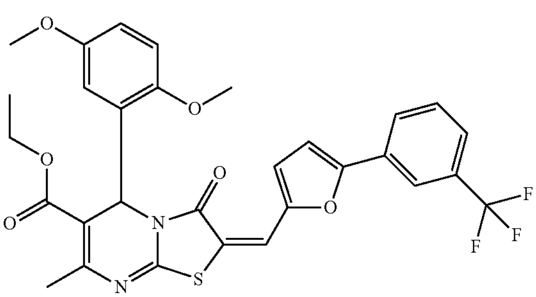 [SMILES: CCOC(=O)C1=C(C)N=c2s/c(=C/c3ccc(-c4cccc(C(F)(F)F)c4)o3)c(=O)n2C1c1cc(OC)ccc1OC] | * | * | * | * | * | * |  | ND |  |
| YX | 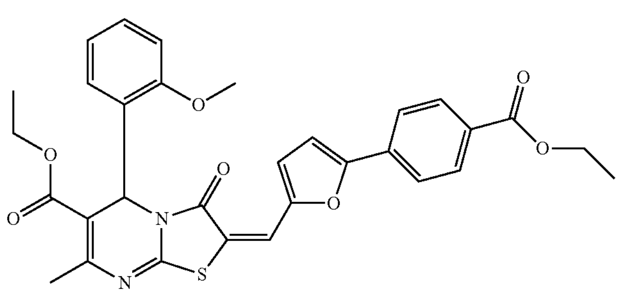 [SMILES: CCOC(=O)C1=C(C)N=c2s/c(=C/c3ccc(-c4ccc(C(=O)OCC)cc4)o3)c(=O)n2C1c1ccccc1OC] | ** | * | ** | * |  |  |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| YY | 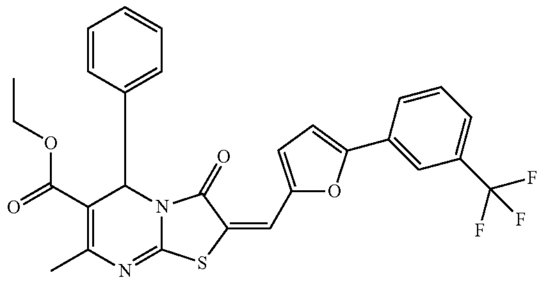 [SMILES: CCOC(=O)C1=C(C)N=c2s/c(=C/c3ccc(-c4cccc(C(F)(F)F)c4)o3)c(=O)n2C1c1ccccc1] | ** | * | ** | * | ** | * |  | ND |  |
| YZ | 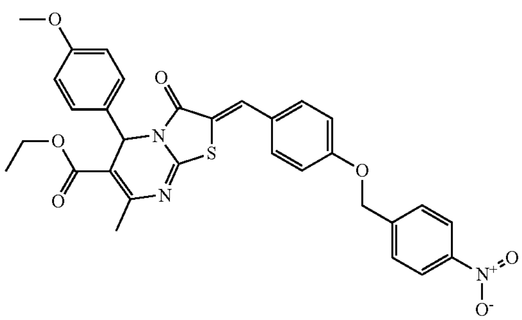 [SMILES: CCOC(=O)C1=C(C)N=c2s/c(=C\c3ccc(OCc4ccc([N+](=O)[O-])cc4)cc3)c(=O)n2C1c1ccc(OC)cc1] |  |  | *** | * | *** | * | ** | ND | * |
| ZA | 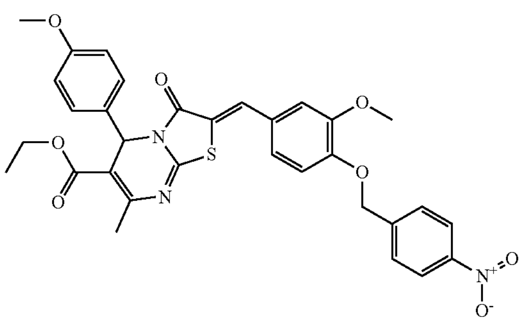 [SMILES: CCOC(=O)C1=C(C)N=c2s/c(=C\c3ccc(OCc4ccc([N+](=O)[O-])cc4)c(OC)c3)c(=O)n2C1c1ccc(OC)cc1] | ** | * | ** | * | ** | * |  | ND |  |
| ZB | 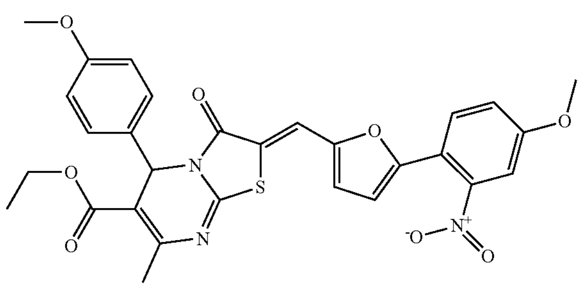 | * | * | *** | * | ** | * | ** | ND | ND |
| ZC | 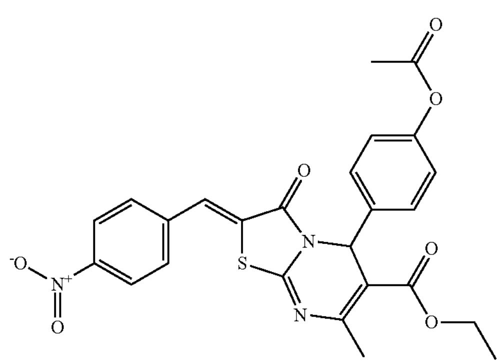 |  | * | * | * |  | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ZD | 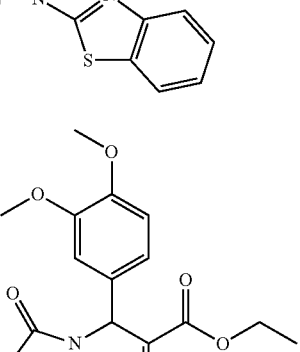 | * | * | * | * | * | * | ** | ND | ND |
| ZE | 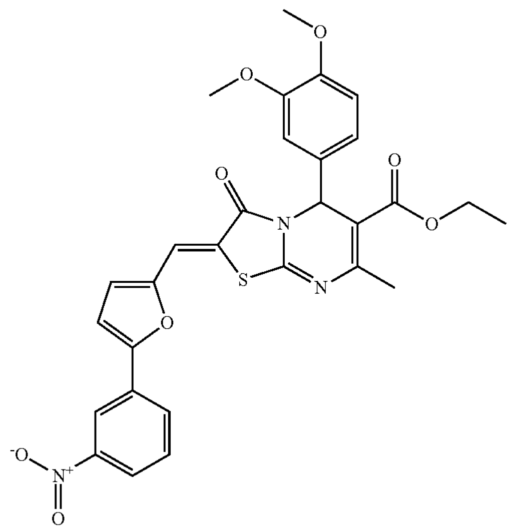 |  |  | *** | * | * | * | ** | ND | ND |
| ZF | 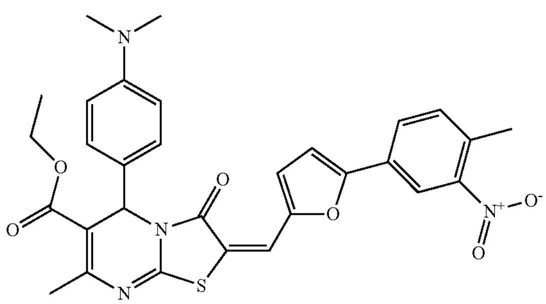 [SMILES: CCOC(=O)C1=C(C)N=c2s/c(=C/c3ccc(-c4ccc(C)c([N+](=O)[O-])c4)o3)c(=O)n2C1c1ccc(N(C)C)cc1] | * |  | ** | * | *** | * | ** | ND | * |
| ZG | 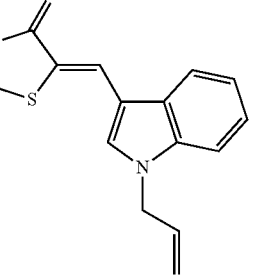 |  |  | ** | * | * | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| ZH | 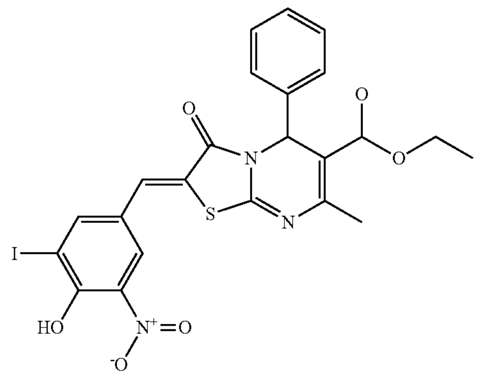 | ** | * | * | ** | * | * |  | ND | * |
| ZI | 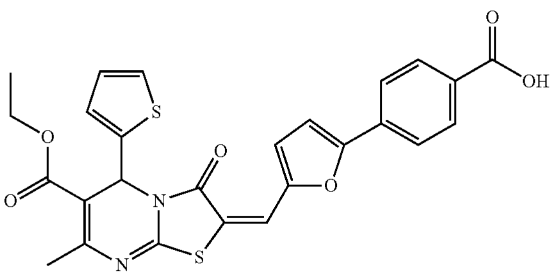 [SMILES: CCOC(=O)C1=C(C)N=c2s/c(=C/c3ccc(-c4ccc(C(=O)O)cc4)o3)c(=O)n2C1c1cccs1] | *** | * | * | * | *** | * | ** | ND | ND |
| ZJ | 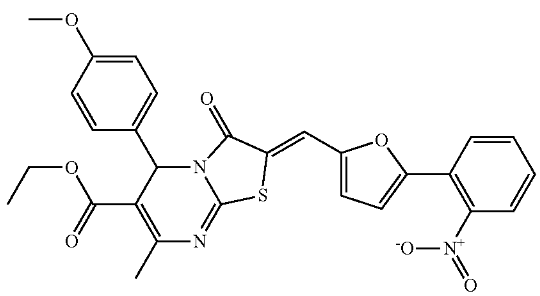 | *** | * | ** | * | *** | * | ** | ND | * |
| ZK | 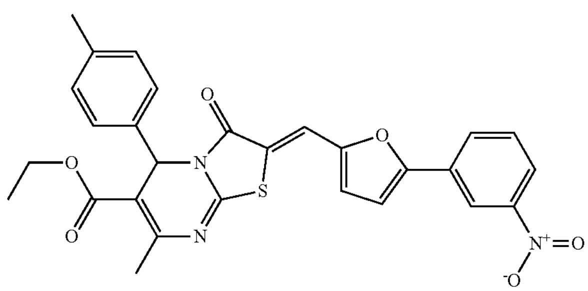 | NT | * | NT | * | NT | * | ** | * | ND |
| ZL | 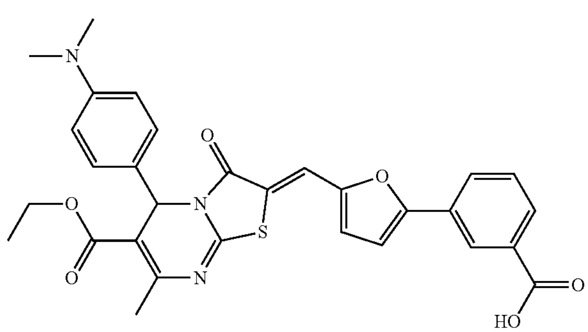 [SMILES: CCOC(=O)C1=C(C)N=c2s/c(=C\c3ccc(-c4cccc(C(=O)O)c4)o3)c(=O)n2C1c1ccc(N(C)C)cc1] | NT | * | NT | * | NT | * | ** | * | ND |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ZM | 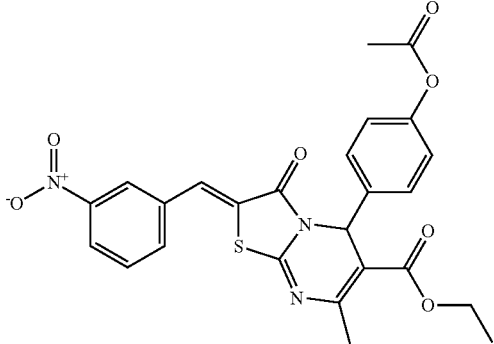 | NT | * | NT |  | NT |  | ** | * | ND |
| ZN | 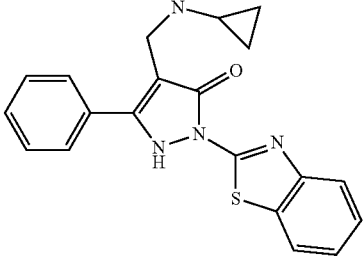 [SMILES: O=c1c(CNC2CC2)c(-c2ccccc2)[nH]n1-c1nc2ccccc2s1] | NT | * | NT | ** | NT | * | ** | * | ND |
| ZO | 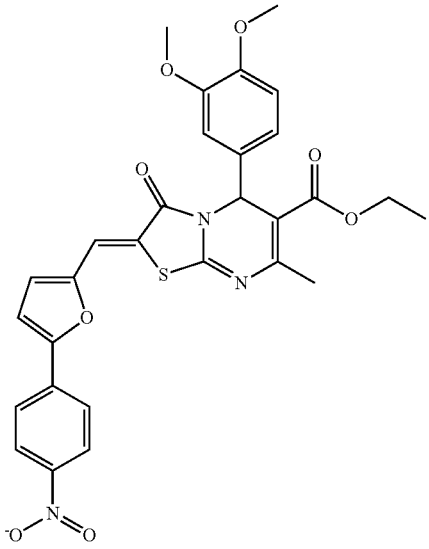 | NT | * | NT | * | NT | * | ** | * | ** |
| ZP | 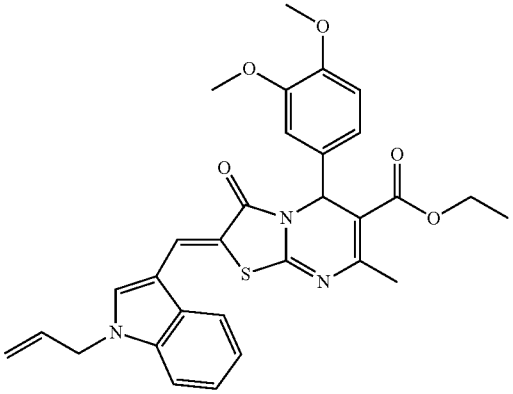 [SMILES: C=CCn1cc(/C=c2\sc3n(c2=O)C(c2ccc(OC)c(OC)c2)C(C(=O)OCC)=C(C)N=3)c2ccccc21] | NT | * | NT |  | NT | * |  |  | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ZQ | 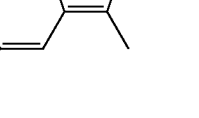 | NT |  | NT | * | NT | * |  | * | ND |
| ZR | 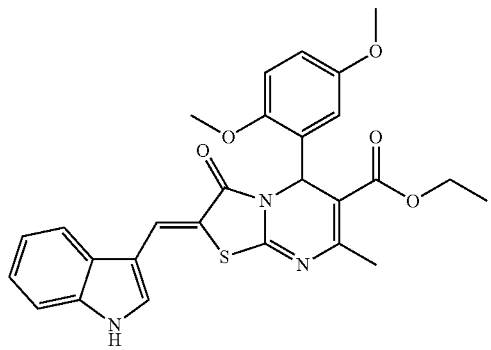 [SMILES: CCOC(=O)C1=C(C)N=c2s/c(=C\c3c[nH]c4ccccc34)c(=O)n2C1c1cc(OC)ccc1OC] | NT | * | NT | * | NT | * |  |  | ** |
| ZS | 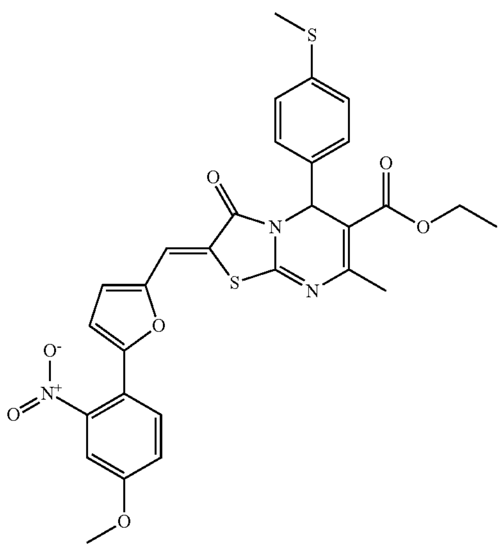 [SMILES: CCOC(=O)C1=C(C)N=c2s/c(=C\c3ccc(-c4ccc(OC)cc4[N+](=O)[O-])o3)c(=O)n2C1c1ccc(SC)cc1] | *** | * | * | * | ** | * |  | N |  |
| ZT | 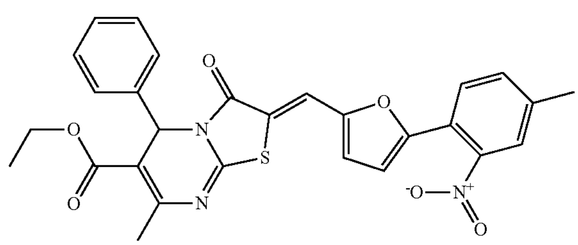 | * |  |  | * |  |  |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ZU | 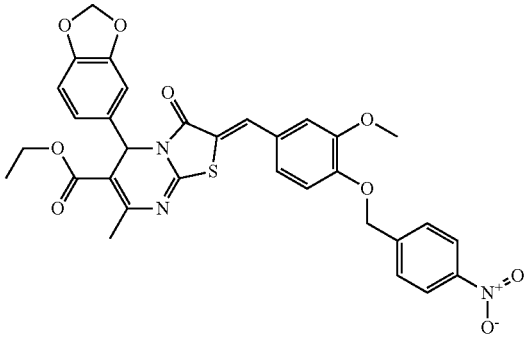 [SMILES: CCOC(=O)C1=C(C)N=c2s/c(=C\c3ccc(OCc4ccc([N+](=O)[O-])cc4)c(OC)c3)c(=O)n2C1c1ccc2c(c1)OCO2] | ** | * | * | * | * | * |  | ND |  |
| AAA | 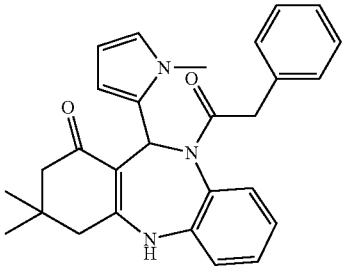 [SMILES: Cn1cccc1C1C2=C(CC(C)(C)CC2=O)Nc2ccccc2N1C(=O)Cc1ccccc1] | * | * | ** | * | ** | * | ** | ND | * |
| AAB | 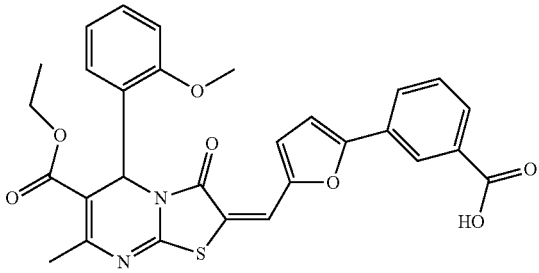 [SMILES: CCOC(=O)C1=C(C)N=c2s/c(=C/c3ccc(-c4cccc(C(=O)O)c4)o3)c(=O)n2C1c1ccccc1OC] | * | * | * | * | *** | * | ** | ND | ND |
| AAC | 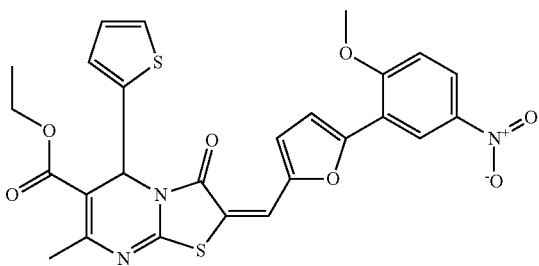 |  |  | ** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAD | 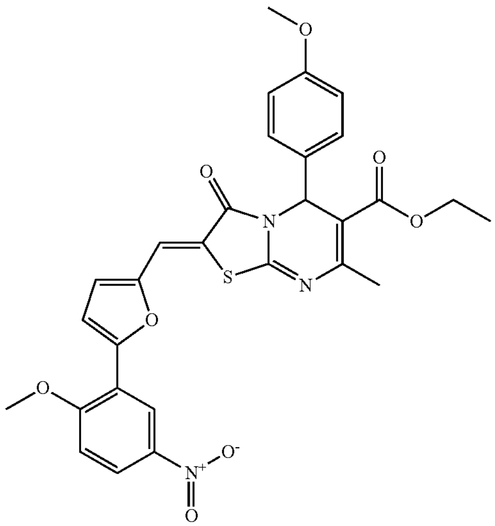 [SMILES: CCOC(=O)C1=C(C)N=c2s/c(=C\c3ccc(-c4cc([N+](=O)[O-])ccc4OC)o3)c(=O)n2C1c1ccc(OC)cc1] | * | * |  | * | ** | * | ** | ND | * |
| AAE | 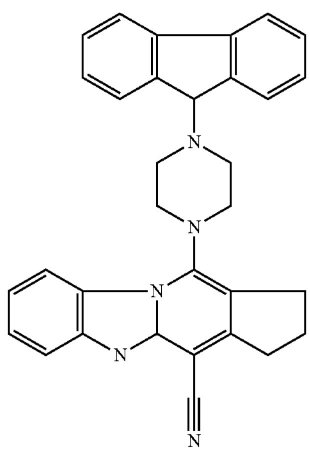 [SMILES: N#CC1=C2CCCC2=C(N2CCN(C3c4ccccc4-c4ccccc43)CC2)N2c3ccccc3NC12] | * |  | ** | * | ** | * |  | ND |  |
| AAF | 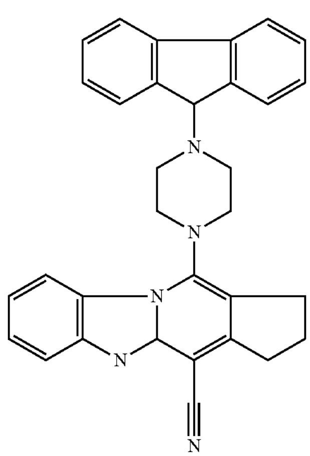 [SMILES: N#CC1=C2CCCC2=C(N2CCN(C3c4ccccc4-c4ccccc43)CC2)N2c3ccccc3NC12] |  | * | * | * | * | * | ** | ND | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAG | 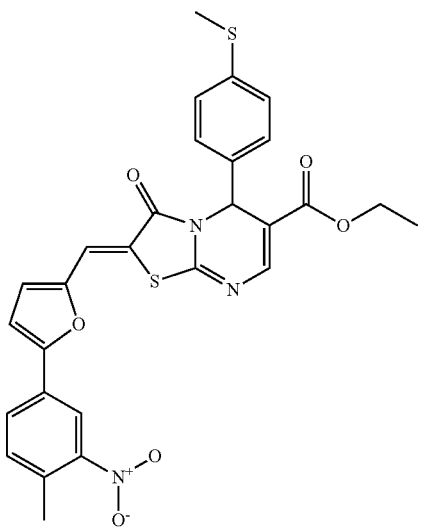 [SMILES: CCOC(=O)C1=CN=c2s/c(=C\c3ccc(-c4ccc(C)c([NH+]([O-])O)c4)o3)c(=O)n2C1c1ccc(SC)cc1] | * | * |  | * | ** | * |  | ND |  |
| AAH | 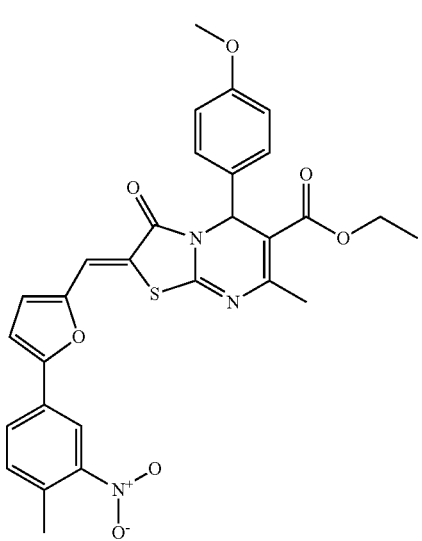 [SMILES: CCOC(=O)C1=C(C)N=c2s/c(=C\c3ccc(-c4ccc(C)c([NH+]([O-])O)c4)o3)c(=O)n2C1c1ccc(OC)cc1] | * |  | ** | * | ** | * |  | ND |  |
| AAI | 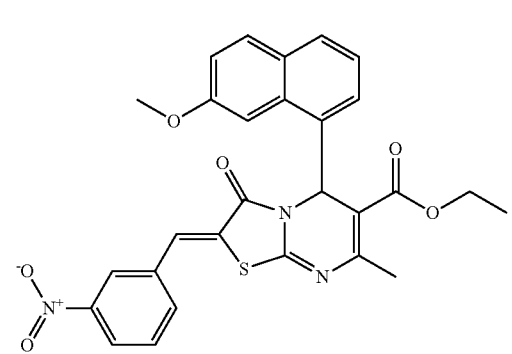 | * |  |  | * |  | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAJ | 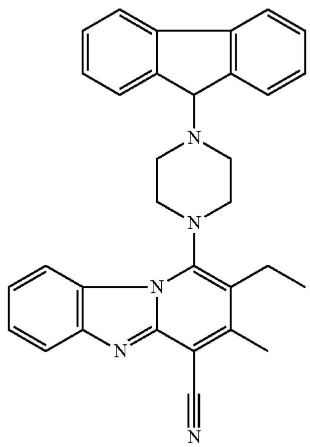 [SMILES: CCc1c(C)c(C#N)c2nc3ccccc3n2c1N1CCN(C2c3ccccc3-c3ccccc32)CC1] | * | * |  | ** | * | NT | ** | ND | ND |
| AAK | 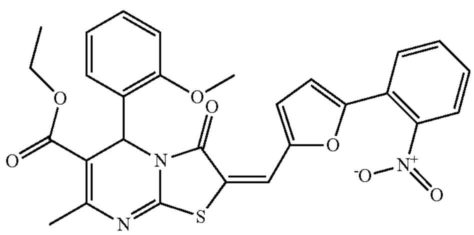 | * | * |  | * |  | NT |  | ND | * |
| AAL | 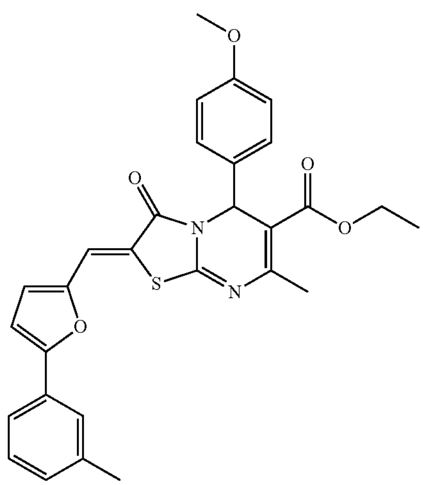 [SMILES: CCOC(=O)C1=C(C)N=c2s/c(=C\c3ccc(-c4cccc(C)c4)o3)c(=O)n2C1c1ccc(OC)cc1] | * | * | ** | * | ** | * | ** | ND | ND |
| AAM | 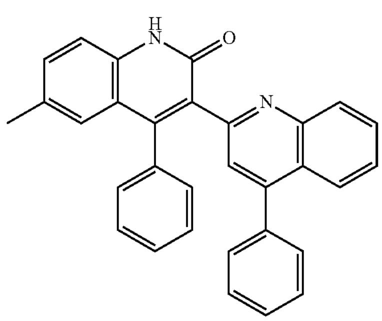 [SMILES: Cc1ccc2[nH]c(=O)c(-c3cc(-c4ccccc4)c4ccccc4n3)c(-c3ccccc3)c2c1] | * |  | * | *** | * |  |  | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAN | 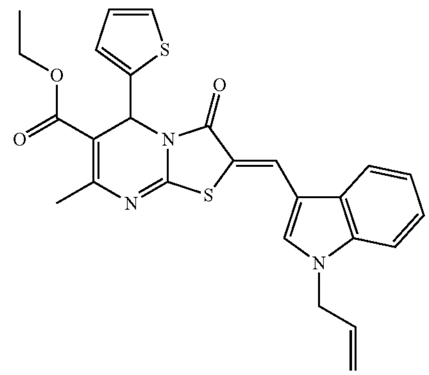 [SMILES: C=CCn1cc(/C=c2\sc3n(c2=O)C(c2cccs2)C(C(=O)OCC)=C(C)N=3)c2ccccc21] | * | * | ** | * | * | * |  |  | ND |
| AAO | 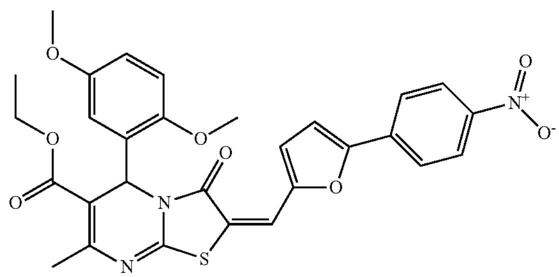 [SMILES: CCOC(=O)C1=C(C)N=c2s/c(=C/c3ccc(-c4ccc([N+](=O)[O-])cc4)o3)c(=O)n2C1c1cc(OC)ccc1OC] | * | * | ** | * | * | * | ** | * | * |
| AAP | 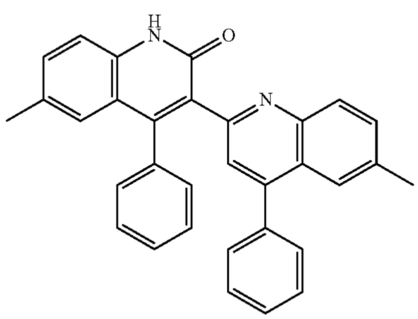 | * | * | ** | * | * | * | ** | * | * |
| AAQ | 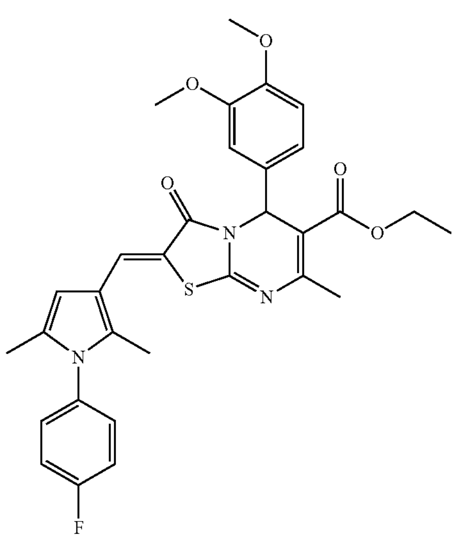 [SMILES: CCOC(=O)C1=C(C)N=c2s/c(=C\c3cc(C)n(-c4ccc(F)cc4)c3C)c(=O)n2C1c1ccc(OC)c(OC)c1] | * |  |  | * | ** | * |  |  | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAR | 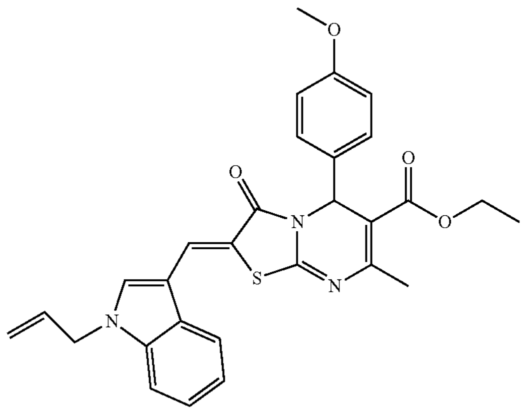 [SMILES: C=CCn1cc(/C=c2\sc3n(c2=O)C(c2ccc(OC)cc2)C(C(=O)OCC)=C(C)N=3)c2ccccc21] | * | * | ** | * | * | * |  |  | ** |
| AAS | 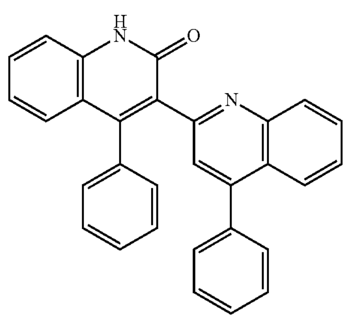 [SMILES: O=c1[nH]c2ccccc2c(-c2ccccc2)c1-c1cc(-c2ccccc2)c2ccccc2n1] | * | * |  |  | * | * |  | ** | * |
| AAT | 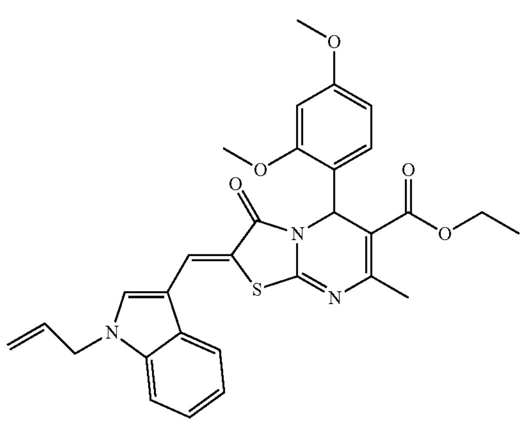 [SMILES: C=CCn1cc(/C=c2\sc3n(c2=O)C(c2ccc(OC)cc2OC)C(C(=O)OCC)=C(C)N=3)c2ccccc21] | * | * |  | * | * |  |  | ** | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AAU | 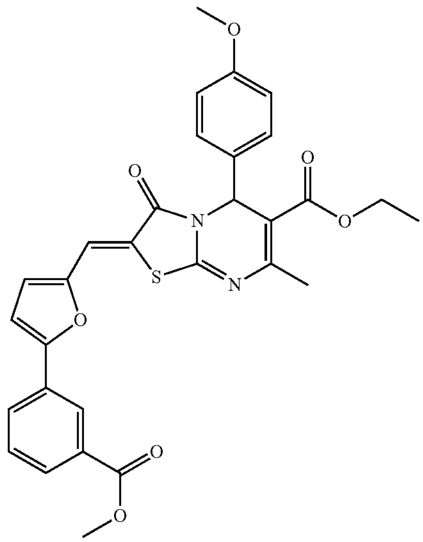 [SMILES: CCOC(=O)C1=C(C)N=c2s/c(=C\c3ccc(-c4cccc(C(=O)OC)c4)o3)c(=O)n2C1c1ccc(OC)cc1] | * | NT | * | * | * | * | ** | ND | * |
| AAV | 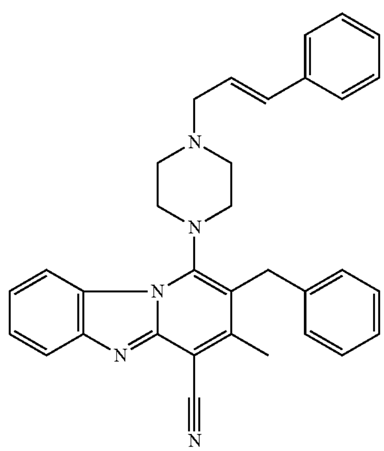 [SMILES: Cc1c(Cc2ccccc2)c(N2CCN(C/C=C/c3ccccc3)CC2)n2c(nc3ccccc32)c1C#N] | * | NT | *** | * | * | * |  | ND | ** |
| AAW | 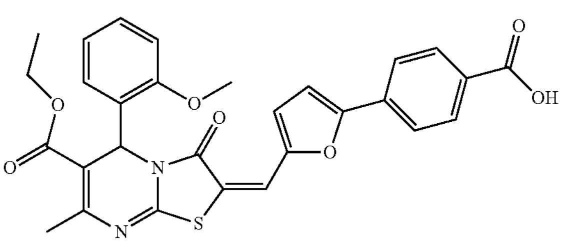 [SMILES: CCOC(=O)C1=C(C)N=c2s/c(=C/c3ccc(-c4ccc(C(=O)O)cc4)o3)c(=O)n2C1c1ccccc1OC] | * | NT | * | *** | * |  |  | ND | ND |
| AAX | 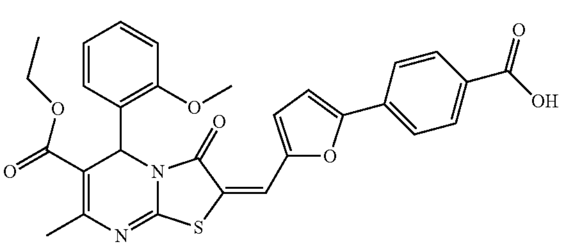 [SMILES: CCOC(=O)C1=C(C)N=c2s/c(=C/c3ccc(-c4ccc(C(=O)O)cc4)o3)c(=O)n2C1c1ccccc1OC] | * | NT |  | *** | * |  |  | ND | ** |

TABLE 5-continued
| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| AAZ | 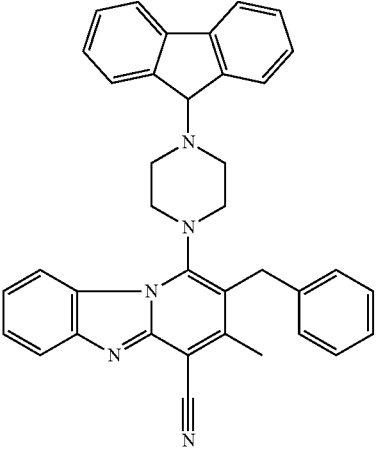 [SMILES: Cc1c(Cc2ccccc2)c(N2CCN(C3c4ccccc4-c4ccccc43)CC2)n2c(nc3ccccc32)c1C#N] | * | NT | ** | * | * | * | ** | ND | ND |
| ABA | 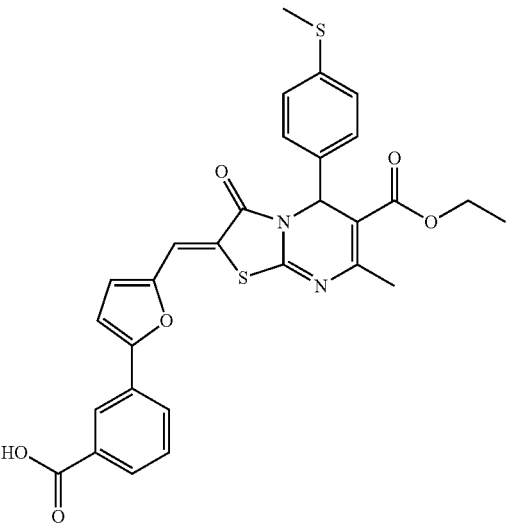 [SMILES: CCOC(=O)C1=C(C)N=c2s/c(=C\c3ccc(-c4cccc(C(=O)O)c4)o3)c(=O)n2C1c1ccc(SC)cc1] | * | NT |  |  | ** | * |  | ND |  |
| ABB | 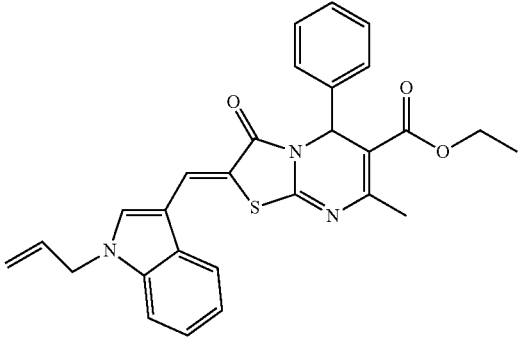 [SMILES: C=CCn1cc(/C=c2\sc3n(c2=O)C(c2ccccc2)C(C(=O)OCC)=C(C)N=3)c2ccccc21] | * | NT | * | *** | * | * |  | ND | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ABC | 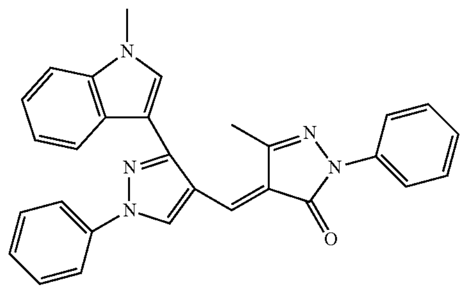 [SMILES: CC1=NN(c2ccccc2)C(=O)/C1=C/c1cn(-c2ccccc2)nc1-c1cn(C)c2ccccc12] | NT | * | NT | * | NT | * |  |  | ** |
| ABD | 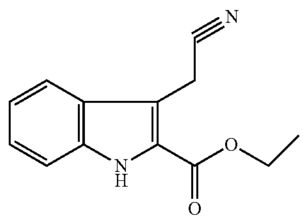 [SMILES: CCOC(=O)c1[nH]c2ccccc2c1CC#N] | NT | * | NT | * | NT | * | ** | * | ND |
| ABE | 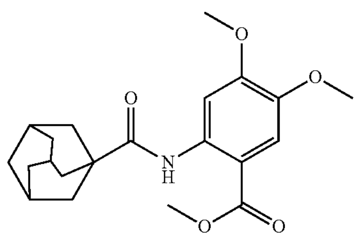 [SMILES: COC(=O)c1cc(OC)c(OC)cc1NC(=O)C12CC3CC(CC(C3)C1)C2] | NT | * | NT | ** | NT | * | ** | * | ** |
| ABF | 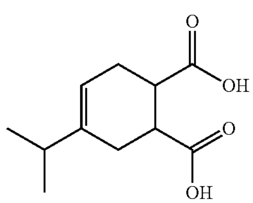 | NT | * | NT | * | NT | * |  |  | ND |
| ABG | 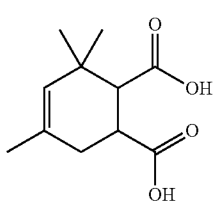 | NT | * | NT |  | NT | * | ** | * | ND |
| ABH | 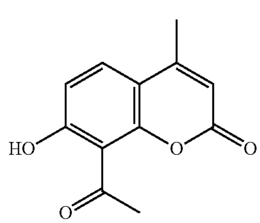 [SMILES: CC(=O)c1c(O)ccc2c(C)cc(=O)oc12] | NT | * | NT | * | NT | * |  |  | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ABI | 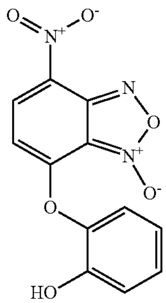 [SMILES: O=[N+]([O-])c1ccc(Oc2ccccc2O)c2c1no[n+]2[O-]] | * | ** | * | NT | * | NT |  | ND |  |
| ABJ | 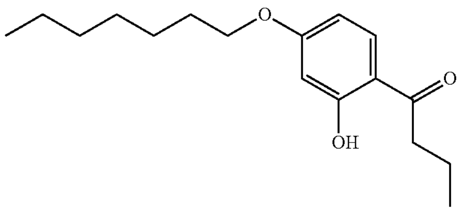 [SMILES: CCCCCCCOc1ccc(C(=O)CCC)c(O)c1] | ** | * | *** | * |  | * | ** | ND | * |
| ABK | 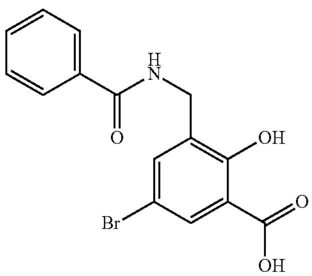 [SMILES: O=C(NCc1cc(Br)cc(C(=O)O)c1O)c1ccccc1] | ** | * | *** | * |  |  |  | ND |  |
| ABL | 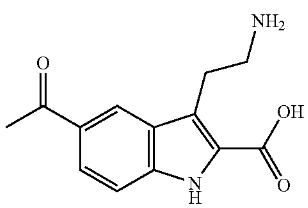 [SMILES: CC(=O)c1ccc2[nH]c(C(=O)O)c(CCN)c2c1] | ** | * | ** | * | ** | * |  | ND |  |
| ABN | 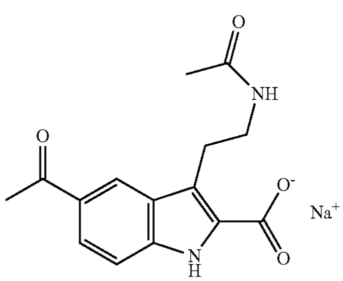 [SMILES: CC(=O)NCCc1c(C(=O)[O-])[nH]c2ccc(C(C)=O)cc12 ; [Na+]] | ** | * | ** | * | ** | * |  | ND |  |
| ABO | 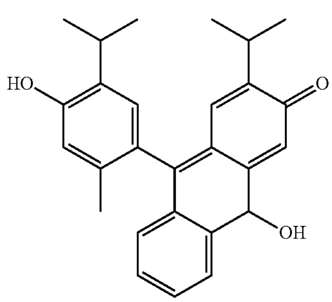 [SMILES: Cc1cc(O)c(C(C)C)cc1C1=C2C=C(C(C)C)C(=O)C=C2C(O)c2ccccc21] | * | * | ** | * |  | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ABP | 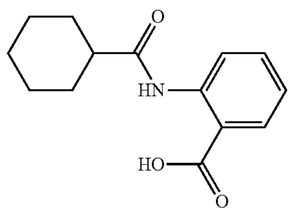 [SMILES: O=C(O)c1ccccc1NC(=O)C1CCCCC1] | * | * | *** | * | ** | * |  | ND |  |
| ABQ | 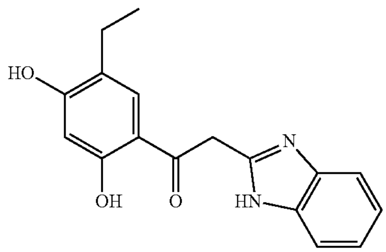 [SMILES: CCc1cc(C(=O)Cc2nc3ccccc3[nH]2)c(O)cc1O] | * | * | ** | * | ** | * |  | ND |  |
| ABR | 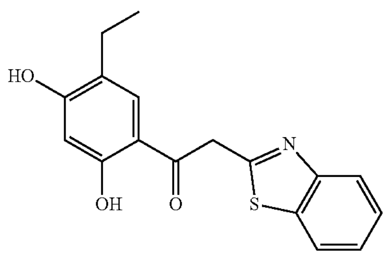 [SMILES: CCc1cc(C(=O)Cc2nc3ccccc3s2)c(O)cc1O] | * | * | *** | * | ** | * |  | ND |  |
| ABS | 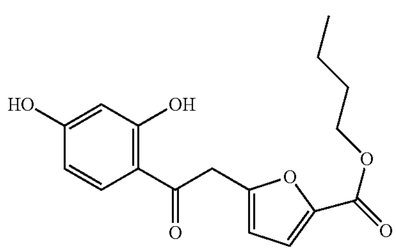 [SMILES: CCCCOC(=O)c1ccc(CC(=O)c2ccc(O)cc2O)o1] | * | * | *** | * | ** | * |  | ND |  |
| ABT | 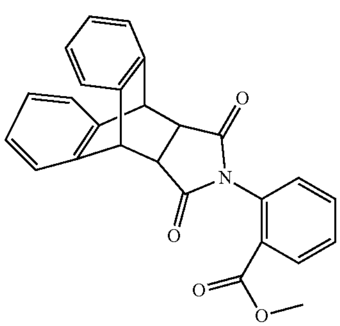 [SMILES: COC(=O)c1ccccc1N1C(=O)C2C3c4ccccc4C(c4ccccc43)C2C1=O] | ** | * | ** | * | ** | * | ** | ND | * |
| ABU | 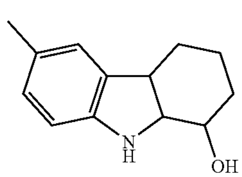 | * | * | ** | * | *** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ABV | 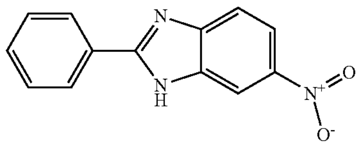 [SMILES: O=[N+]([O-])c1ccc2nc(-c3ccccc3)[nH]c2c1] | * | * |  |  | * | * |  | ND |  |
| ABW | 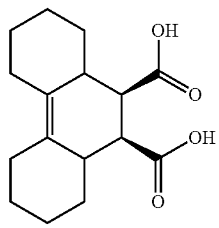 [SMILES: O=C(O)[C@@H]1C2CCCCC2=C2CCCCC2[C@@H]1C(=O)O] | * | * | * | * | * | * |  | ND |  |
| ABX | 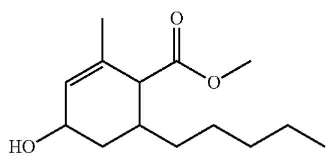 [SMILES: CCCCCC1CC(O)C=C(C)C1C(=O)OC] | * | * | * | * |  |  |  | ND |  |
| ABY | 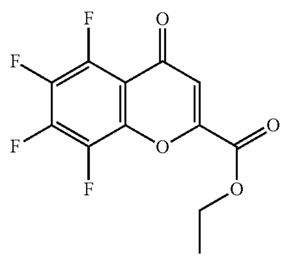 [SMILES: CCOC(=O)c1cc(=O)c2c(F)c(F)c(F)c(F)c2o1] | ** | * | * | * | * | * |  | ND |  |
| ABZ | 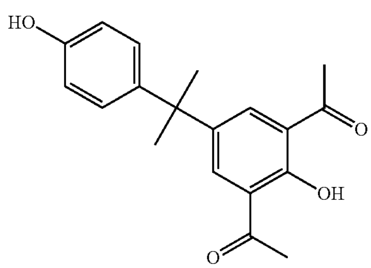 [SMILES: CC(=O)c1cc(C(C)(C)c2ccc(O)cc2)cc(C(C)=O)c1O] | ** | * | * |  |  | * |  | ND | * |
| ACA | 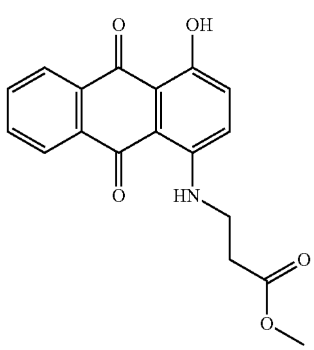 [SMILES: COC(=O)CCNc1ccc(O)c2c1C(=O)c1ccccc1C2=O] | *** | * |  |  | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ACB | 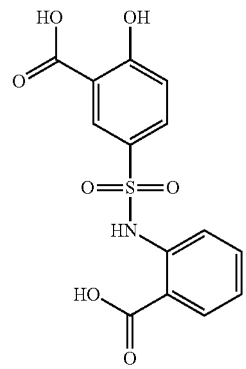 [SMILES: O=C(O)c1cc(S(=O)(=O)Nc2ccccc2C(=O)O)ccc1O] | * | * | * | * | * | * | ** | ND | ND |
| ACC | 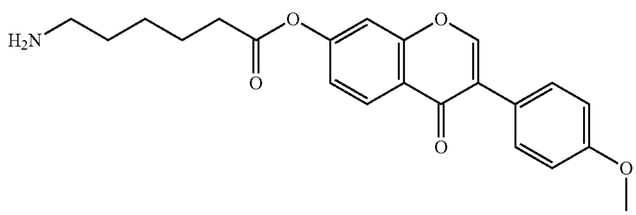 [SMILES: COc1ccc(-c2coc3cc(OC(=O)CCCCCN)ccc3c2=O)cc1] | *** | * | ** | * | ** | * | ** | ND | ND |
| ACD | 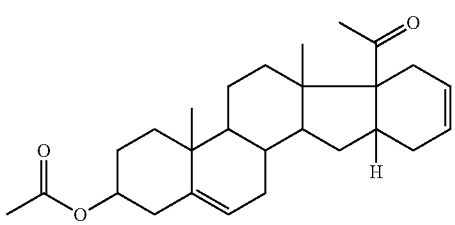 [SMILES: CC(=O)OC1CCC2(C)C(=CCC3C2CCC2(C)C3CC3CC=CCC32C(C)=O)C1] | *** | * | * | * | * | * | ** | ND | * |
| ACE | 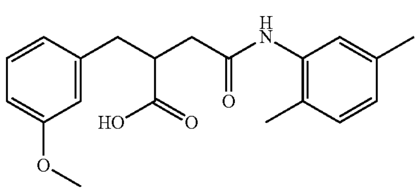 [SMILES: COc1cccc(CC(CC(=O)Nc2cc(C)ccc2C)C(=O)O)c1] | ** | * | * | * | * | * | ** | ND | ND |
| ACF | 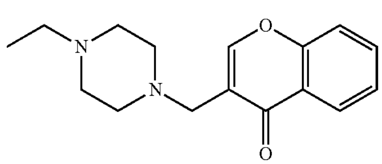 [SMILES: CCN1CCN(Cc2coc3ccccc3c2=O)CC1] | *** | * | * | * | *** | * | ** | ND | * |
| ACG | 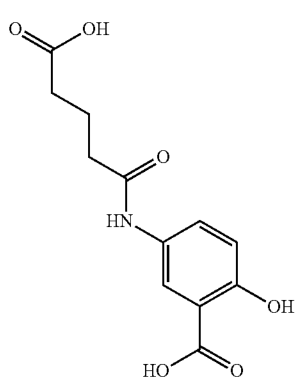 [SMILES: O=C(O)CCCC(=O)Nc1ccc(O)c(C(=O)O)c1] | *** | * | * | * | ** | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ACH | 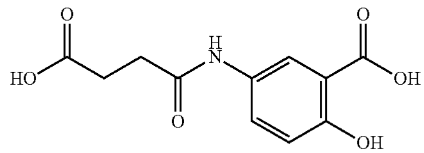 [SMILES: O=C(O)CCC(=O)Nc1ccc(O)c(C(=O)O)c1] | * |  | *** | * | *** | * | ** | ND | ND |
| ACI | 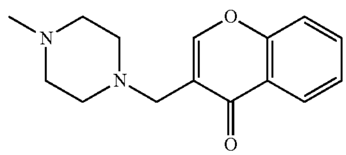 [SMILES: CN1CCN(Cc2coc3ccccc3c2=O)CC1] | NT | * | NT |  | NT | * | ** | * | ** |
| ACJ | 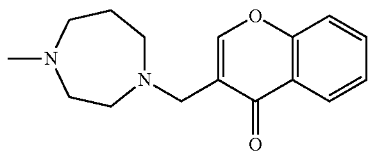 [SMILES: CN1CCCN(Cc2coc3ccccc3c2=O)CC1] | NT | * | NT | ** | NT | * | ** | * | ND |
| ACK | 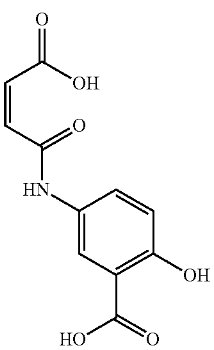 [SMILES: O=C(O)/C=C\C(=O)Nc1ccc(O)c(C(=O)O)c1] | NT | * | NT | * | NT | * | ** | * | ND |
| ACL | 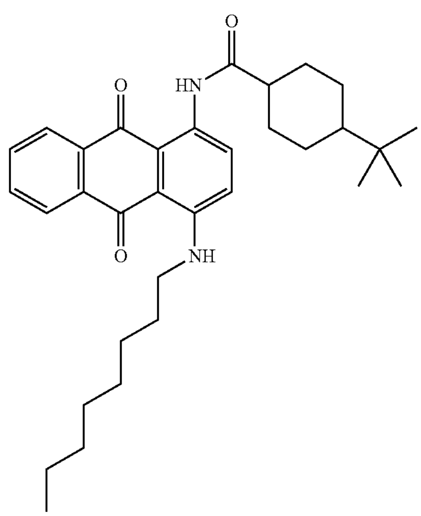 [SMILES: CCCCCCCCNc1ccc(NC(=O)C2CCC(C(C)(C)C)CC2)c2c1C(=O)c1ccccc1C2=O] | NT | * | NT | * | NT | * | ** | * | ND |
| ACM | 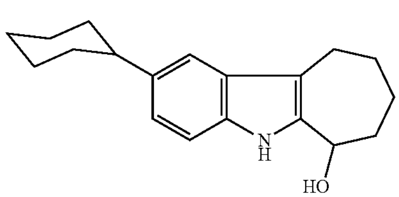 [SMILES: OC1CCCCc2c1[nH]c1ccc(C3CCCCC3)cc21] | * | * | * | * | * | * |  | ND |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ACN | 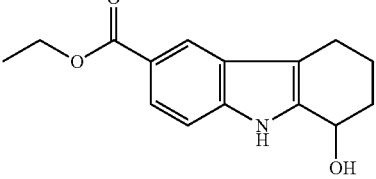 | NT | * | NT | * | NT |  |  | * | ** |
| ACO | 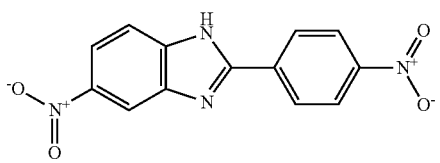 | NT | * | NT | * | NT | * | ** | * | ** |
| ACP | 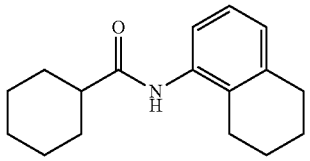 [SMILES: O=C(Nc1cccc2c1CCCC2)C1CCCCC1] | NT | * | NT | * | NT |  |  |  |  |
| ACQ | 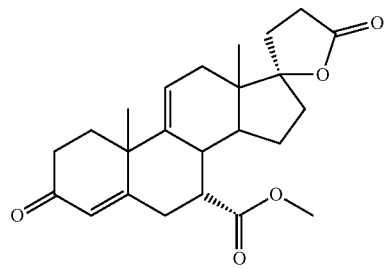 | NT |  | NT | * | NT |  |  |  |  |
| ACR | 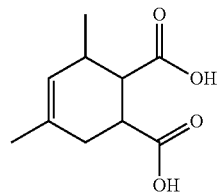 | NT | * | NT | * | NT | * |  |  | ** |
| ACS | 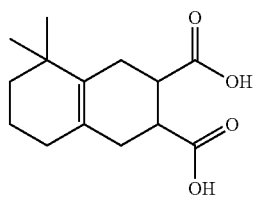 [SMILES: CC1(C)CCCC2=C1CC(C(=O)O)C(C(=O)O)C2] | ** | * | ** | * | ** | * |  | ND |  |
| ACT | 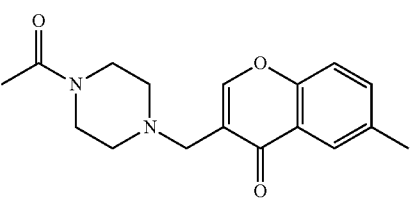 [SMILES: CC(=O)N1CCN(Cc2coc3ccc(C)cc3c2=O)CC1] |  |  | ** | * | * |  |  | ND |  |
| ACU | 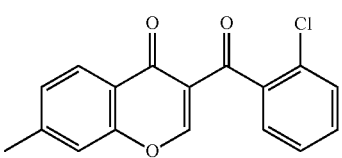 [SMILES: Cc1ccc2c(=O)c(C(=O)c3ccccc3Cl)coc2c1] |  |  | ** | * | * | * |  | ND |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ACV | 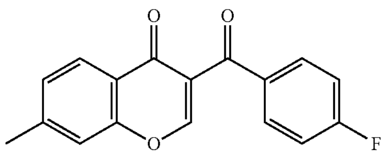 [SMILES: Cc1ccc2c(=O)c(C(=O)c3ccc(F)cc3)coc2c1] | *** | * | * |  | *** | * |  | ND |  |
| ACW | 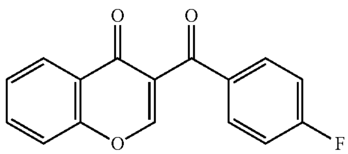 [SMILES: O=C(c1ccc(F)cc1)c1coc2ccccc2c1=O] |  |  | * |  |  |  |  | ND | * |
| ACX | 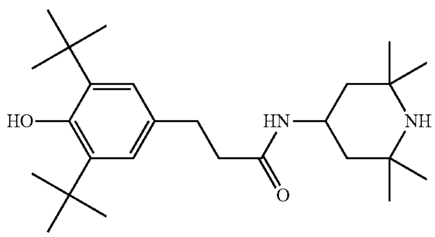 [SMILES: CC1(C)CC(NC(=O)CCc2cc(C(C)(C)C)c(O)c(C(C)(C)C)c2)CC(C)(C)N1] | * |  |  |  |  |  |  | ND | * |
| ACY | 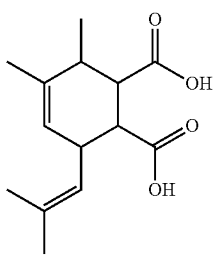 [SMILES: CC(C)=CC1C=C(C)C(C)C(C(=O)O)C1C(=O)O] |  |  | * | * |  |  | ** | ND | ND |
| ACZ | 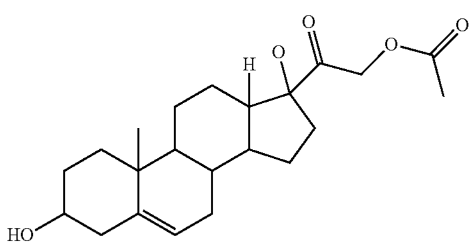 [SMILES: CC(=O)OCC(=O)C1(O)CCC2C3CC=C4CC(O)CCC4(C)C3CCC21] |  |  | * | * | * | * | ** | ND | * |
| ADA | 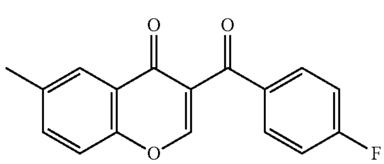 [SMILES: Cc1ccc2occ(C(=O)c3ccc(F)cc3)c(=O)c2c1] |  | * | * | *** | * | * |  | ND | ND |
| ADB | 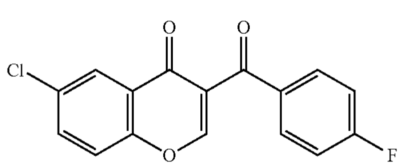 [SMILES: O=C(c1ccc(F)cc1)c1coc2ccc(Cl)cc2c1=O] | * |  |  | * |  | * | ** | ND | ND |
| ADC | 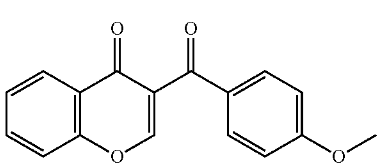 [SMILES: COc1ccc(C(=O)c2coc3ccccc3c2=O)cc1] |  | * |  |  |  | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ADD | 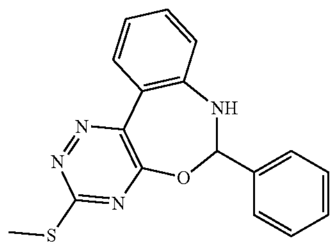 [SMILES: CSc1nnc2c(n1)OC(c1ccccc1)Nc1ccccc1-2] | * | * |  | * |  | * |  | ND |  |
| ADE | 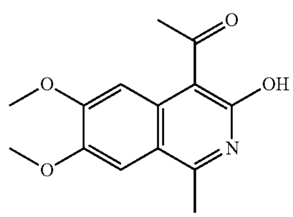 [SMILES: COc1cc2c(C)nc(O)c(C(C)=O)c2cc1OC] | * |  | ** | * | ** | * | ** | ND | * |
| ADF | 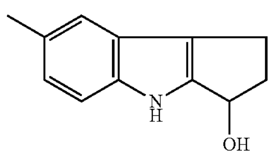 | * |  |  | * | ** | * |  | ND |  |
| ADG | 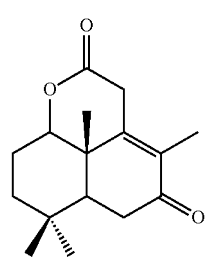 | * | * | ** | * | ** | * |  | ND |  |
| ADH | 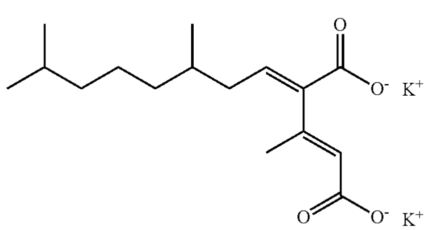 [SMILES: CC(=C\C(=O)[O-])/C(=C\CC(C)CCCC(C)C)C(=O)[O-] ; [K+] ; [K+]] |  |  | ** | * | ** | * | ** | ND | ND |
| ADI | 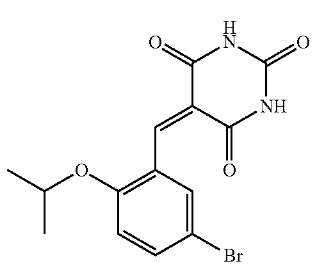 [SMILES: CC(C)Oc1ccc(Br)cc1C=C1C(=O)NC(=O)NC1=O] | * |  | * | * | * | * | ** | ND | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ADJ | 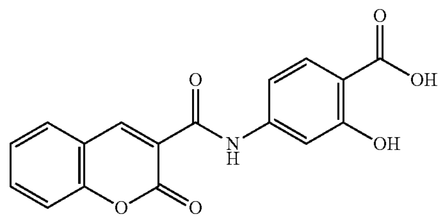 [SMILES: O=C(O)c1ccc(NC(=O)c2cc3ccccc3oc2=O)cc1O] | * |  |  | * | ** | * |  | ND |  |
| ADK | 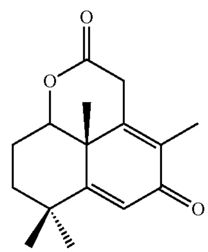 | * |  |  | * | ** | * |  | ND |  |
| ADL | 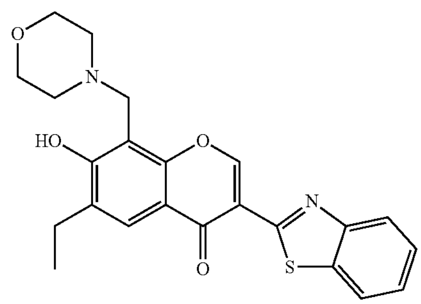 [SMILES: CCc1cc2c(=O)c(-c3nc4ccccc4s3)coc2c(CN2CCOCC2)c1O] | * | * | ** | * | ** | * |  | ND |  |
| ADM | 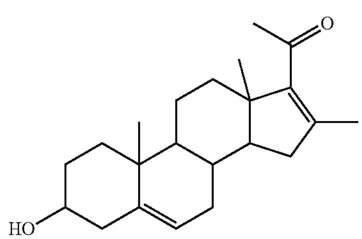 [SMILES: CC(=O)C1=C(C)CC2C3CC=C4CC(O)CCC4(C)C3CCC12C] | * |  |  | * | ** | * | ** | ND | * |
| ADN | 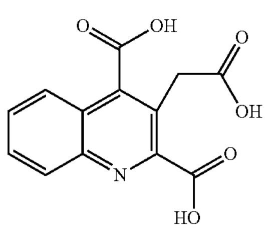 [SMILES: O=C(O)Cc1c(C(=O)O)nc2ccccc2c1C(=O)O] |  |  | ** | * | ** | * | ** | ND | * |
| ADO | 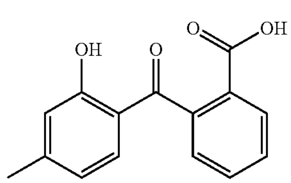 [SMILES: Cc1ccc(C(=O)c2ccccc2C(=O)O)c(O)c1] | * |  | ** | * | ** | * | ** | ND | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ADP | 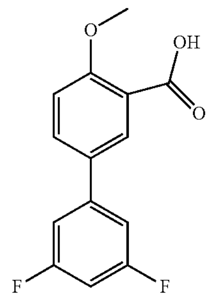 [SMILES: COc1ccc(-c2cc(F)cc(F)c2)cc1C(=O)O] | * |  |  |  |  | * |  | ND | * |
| ADQ | 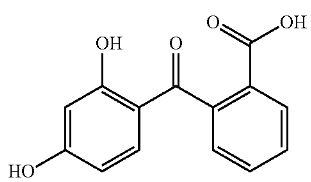 [SMILES: O=C(O)c1ccccc1C(=O)c1ccc(O)cc1O] |  |  |  | * | ** | * | ** | ND | ND |
| ADR | 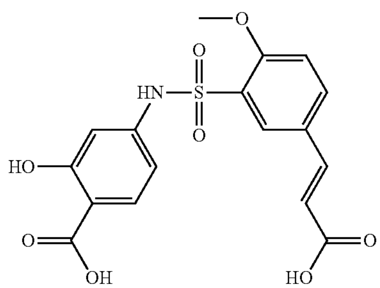 [SMILES: COc1ccc(/C=C/C(=O)O)cc1S(=O)(=O)Nc1ccc(C(=O)O)c(O)c1] | * | * |  |  |  | NT |  | ND |  |
| ADS | 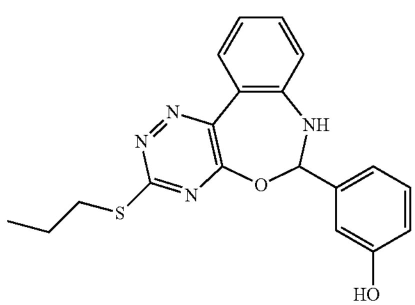 [SMILES: CCCSc1nnc2c(n1)OC(c1cccc(O)c1)Nc1ccccc1-2] | * | * |  |  | * | ** | * |  |  |
| ADT | 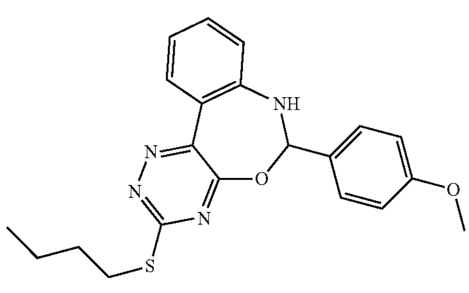 [SMILES: CCCCSc1nnc2c(n1)OC(c1ccc(OC)cc1)Nc1ccccc1-2] | * | * | ** | * | * | * | * |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ADU | 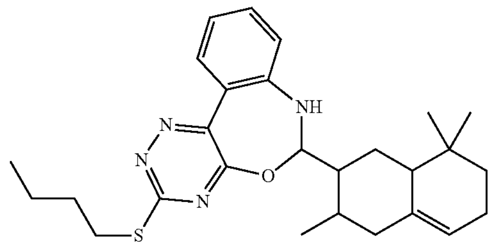 [SMILES: CCCCSc1nnc2c(n1)OC(C1CC3C(=CCCC3(C)C)CC1C)Nc1ccccc1-2] | * | NT | * | * | * | ** | * | * | ** |
| ADV | 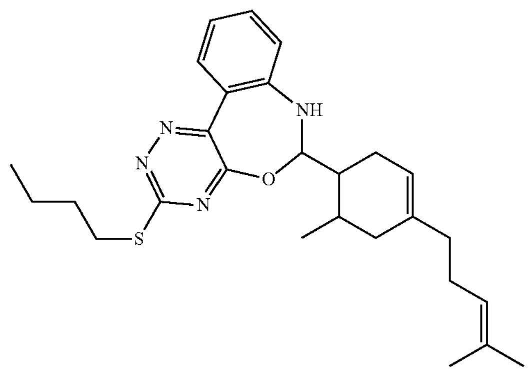 [SMILES: CCCCSc1nnc2c(n1)OC(C1CC=C(CCC=C(C)C)CC1C)Nc1ccccc1-2] | * | NT |  |  | * | * | * | * | ND |
| ADW | 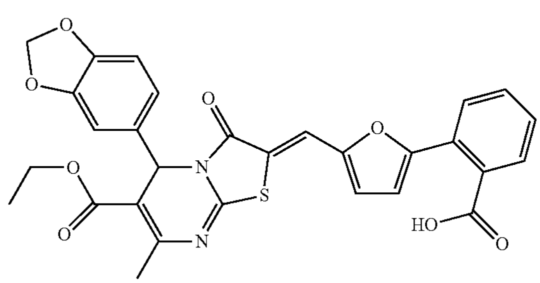 [SMILES: CCOC(=O)C1=C(C)N=c2s/c(=C\c3ccc(-c4ccccc4C(=O)O)o3)c(=O)n2C1c1ccc2c(c1)OCO2] | * | NT | ** | * | * | * | * | * | ND |
| ADX | 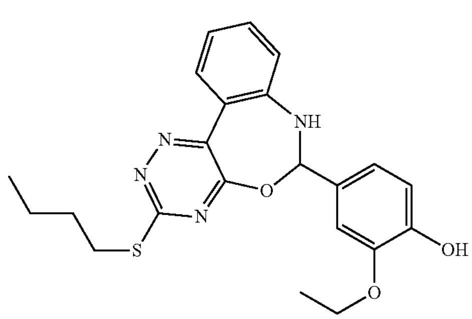 [SMILES: CCCCSc1nnc2c(n1)OC(c1ccc(O)c(OCC)c1)Nc1ccccc1-2] | NT | * | NT | * | NT | * | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ADY | 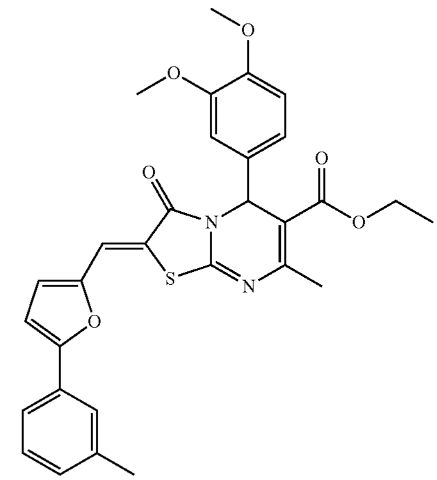 [SMILES: CCOC(=O)C1=C(C)N=c2s/c(=C\c3ccc(-c4cccc(C)c4)o3)c(=O)n2C1c1ccc(OC)c(OC)c1] | NT | * | NT | * | NT | * | * |  |  |
| ADZ | 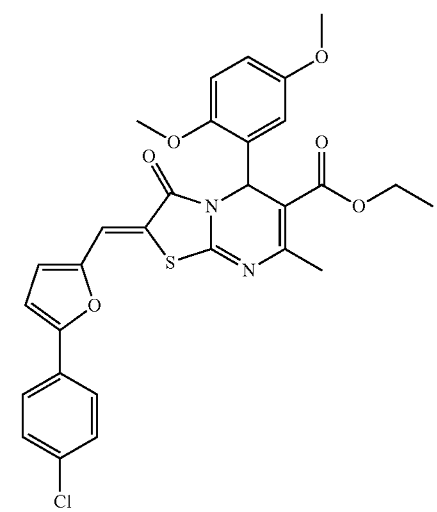 [SMILES: CCOC(=O)C1=C(C)N=c2s/c(=C\c3ccc(-c4ccc(Cl)cc4)o3)c(=O)n2C1c1cc(OC)ccc1OC] | NT | * | NT |  | NT |  | * |  |  |
| AEA | 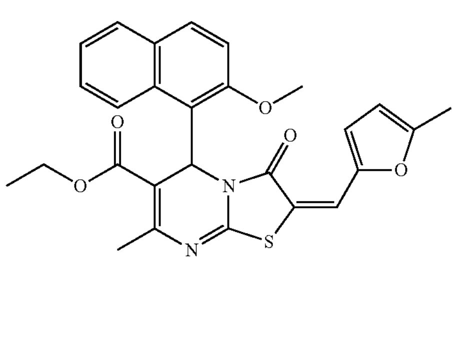 [SMILES: CCOC(=O)C1=C(C)N=c2s/c(=C/c3ccc(C)o3)c(=O)n2C1c1c(OC)ccc2ccccc12] | ** | * | *** | * | *** | * | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AEB | 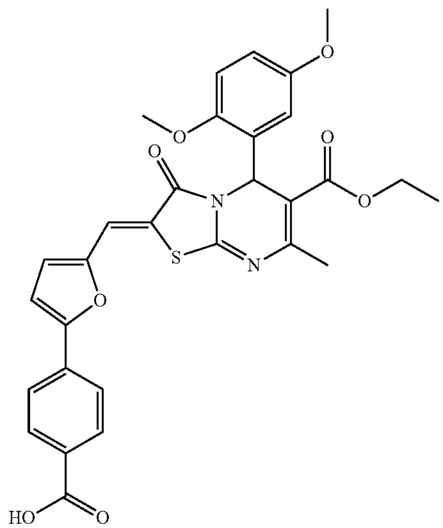 [SMILES: CCOC(=O)C1=C(C)N=c2s/c(=C\c3ccc(-c4ccc(C(=O)O)cc4)o3)c(=O)n2C1c1cc(OC)ccc1OC] | ** | * | ** | * |  | * | * | * | ** |
| AEC | 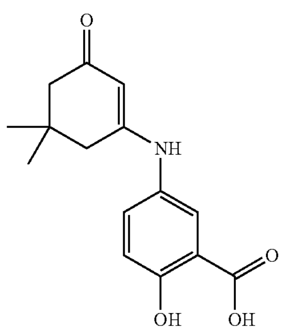 [SMILES: CC1(C)CC(=O)C=C(Nc2ccc(O)c(C(=O)O)c2)C1] | * | * | *** | * |  |  | * | * | ** |
| AED | 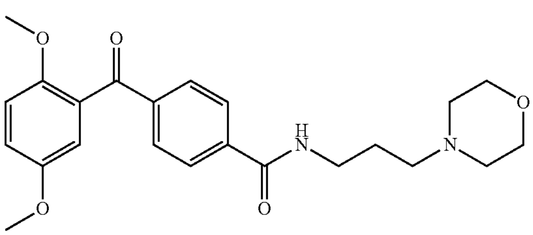 [SMILES: COc1ccc(OC)c(C(=O)c2ccc(C(=O)NCCCN3CCOCC3)cc2)c1] |  | * | *** | * | ** | * | * | * | ** |
| AEF | 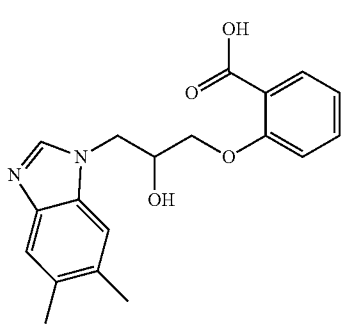 [SMILES: Cc1cc2ncn(CC(O)COc3ccccc3C(=O)O)c2cc1C] | ** | * | ** | * | ** | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| EG | 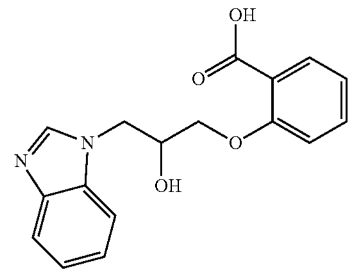 [SMILES: O=C(O)c1ccccc1OCC(O)Cn1cnc2ccccc21] | ** | * | * |  | * | * | * | * | ** |
| AEH | 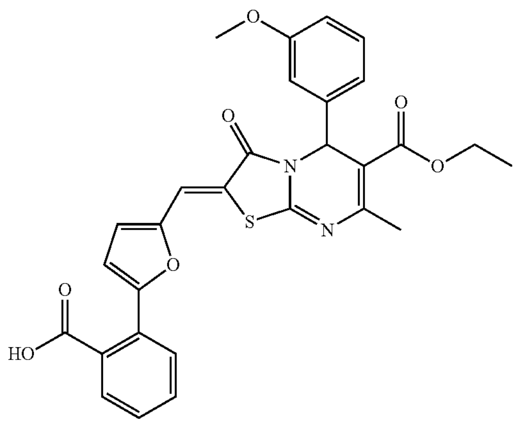 [SMILES: CCOC(=O)C1=C(C)N=c2s/c(=C\c3ccc(-c4ccccc4C(=O)O)o3)c(=O)n2C1c1cccc(OC)c1] | ** | * | *** | * | ** | * | * | * | ** |
| AEI | 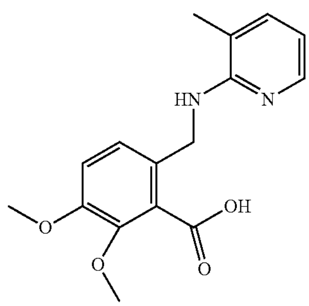 [SMILES: COc1ccc(CNc2ncccc2C)c(C(=O)O)c1OC] | * | * | * | * | * | * | * | * | * |
| AEJ | 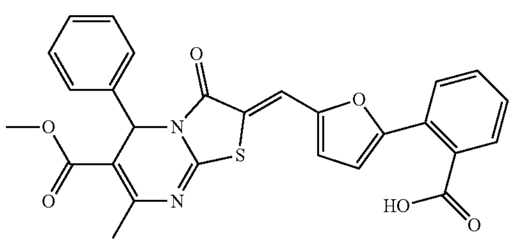 [SMILES: COC(=O)C1=C(C)N=c2s/c(=C\c3ccc(-c4ccccc4C(=O)O)o3)c(=O)n2C1c1ccccc1] | ** | * | * |  |  | *** | * | * | * |
| AEK | 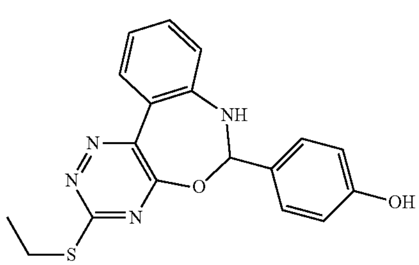 [SMILES: CCSc1nnc2c(n1)OC(c1ccc(O)cc1)Nc1ccccc1-2] | *** | * | * |  | * | ** | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AEL | 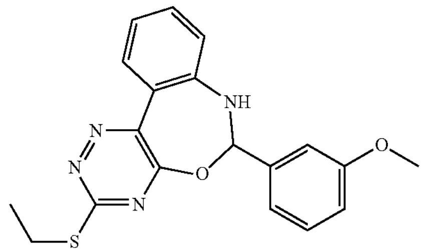 [SMILES: CCSc1nnc2c(n1)OC(c1cccc(OC)c1)Nc1ccccc1-2] | NT | * | NT | * | NT | * | * | * | ND |
| AEM | 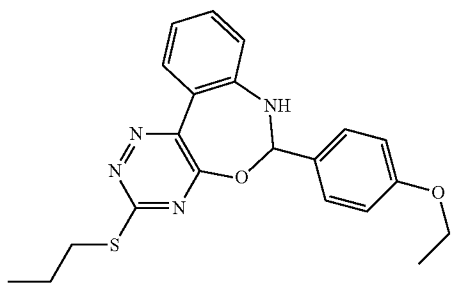 [SMILES: CCCSc1nnc2c(n1)OC(c1ccc(OCC)cc1)Nc1ccccc1-2] | NT | * | NT | * | NT | ** | * | * | ** |
| EN | 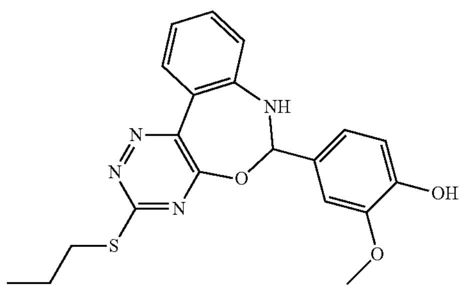 [SMILES: CCCSc1nnc2c(n1)OC(c1ccc(O)c(OC)c1)Nc1ccccc1-2] | NT | * | NT | * | NT | * | * | ** | ND |
| AEO | 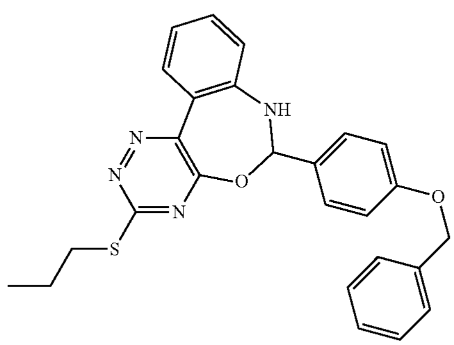 [SMILES: CCCSc1nnc2c(n1)OC(c1ccc(OCc3ccccc3)cc1)Nc1ccccc1-2] | NT | * | NT | * | NT | * | * | * | ** |
| AEQ | 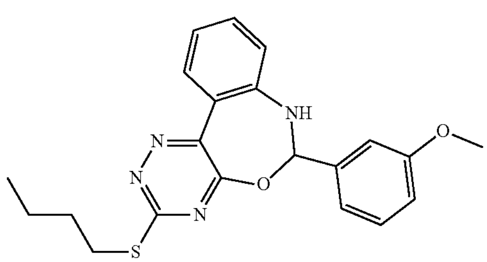 [SMILES: CCCCSc1nnc2c(n1)OC(c1cccc(OC)c1)Nc1ccccc1-2] | NT | * | NT | * | NT | * | * |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AER | 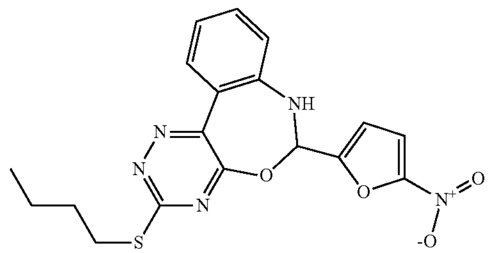 | NT | * | NT | * | NT | * | * |  |  |
| AES | 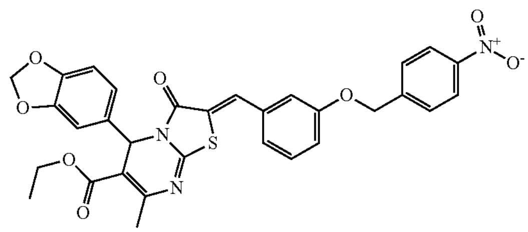 [SMILES: CCOC(=O)C1=C(C)N=c2s/c(=C\c3cccc(OCc4ccc([N+](=O)[O-])cc4)c3)c(=O)n2C1c1ccc2c(c1)OCO2] | * | * | *** | * | *** | * | * | * | ** |
| AET | 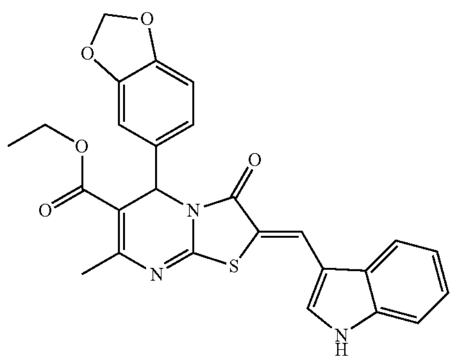 [SMILES: CCOC(=O)C1=C(C)N=c2s/c(=C\c3c[nH]c4ccccc34)c(=O)n2C1c1ccc2c(c1)OCO2] | NT | * | NT | * | NT | * | * | * | ** |
| EU | 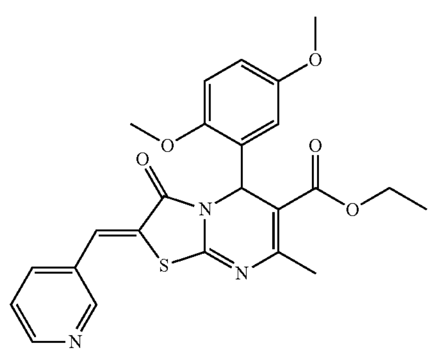 [SMILES: CCOC(=O)C1=C(C)N=c2s/c(=C\c3cccnc3)c(=O)n2C1c1cc(OC)ccc1OC] | NT | * | NT | * | NT | * | * |  |  |
| AEV | 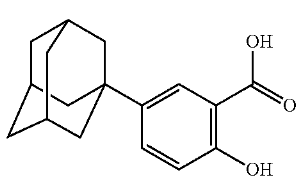 [SMILES: O=C(O)c1cc(C23CC4CC(CC(C4)C2)C3)ccc1O] | * |  |  |  |  | * | * | * | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AEW | 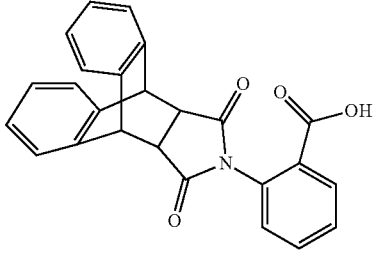 [SMILES: O=C(O)c1ccccc1N1C(=O)C2C3c4ccccc4C(c4ccccc43)C2C1=O] |  |  | ** | * | ** | * | * | * | * |
| EX | 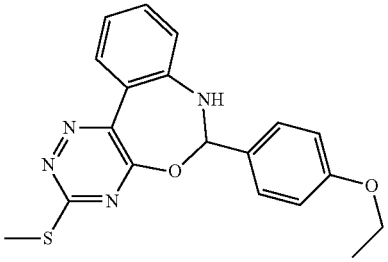 [SMILES: CCOc1ccc(C2Nc3ccccc3-c3nnc(SC)nc3O2)cc1] | * |  |  |  |  | * | * | * | ND |
| AEY | 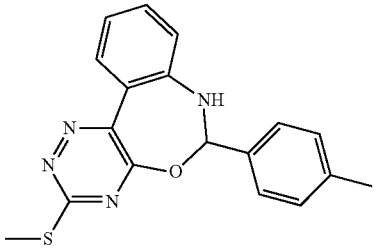 |  |  |  |  |  |  | * | * | ** |
| AEZ | 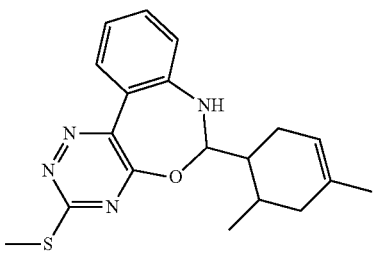 | * | ** | * | * | * | * | * | * | ** |
| AFA | 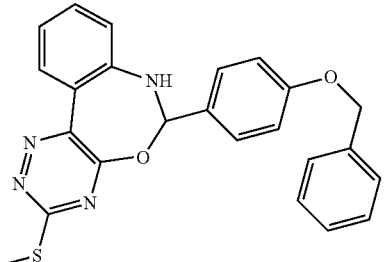 |  |  | ** | * |  |  | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| FB | 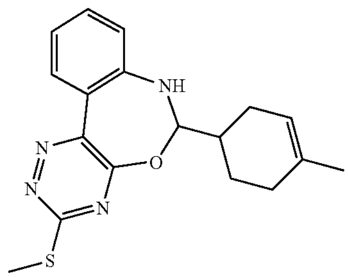 | * |  |  | * |  |  | * | * | ** |
| AFC | 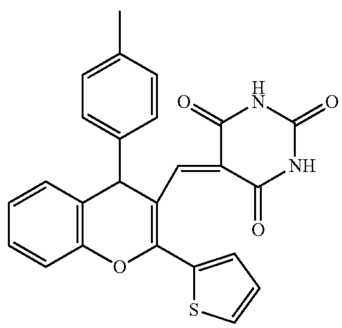 [SMILES: Cc1ccc(C2C(C=C3C(=O)NC(=O)NC3=O)=C(c3cccs3)Oc3ccccc32)cc1] |  |  | ** | * | ** | * | * | * | ** |
| AFD | 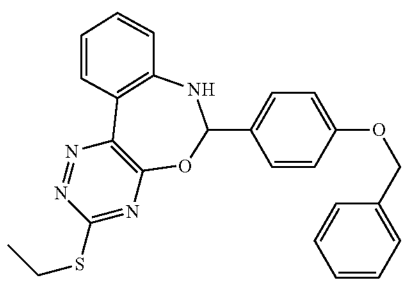 [SMILES: CCSc1nnc2c(n1)OC(c1ccc(OCc3ccccc3)cc1)Nc1ccccc1-2] | *** | * | *** | * | ** | * | * | * | ** |
| AFE | 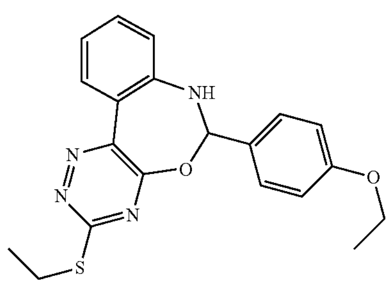 [SMILES: CCOc1ccc(C2Nc3ccccc3-c3nnc(SCC)nc3O2)cc1] | ** | * | ** | * | ** | * | * | * | ** |
| AFG | 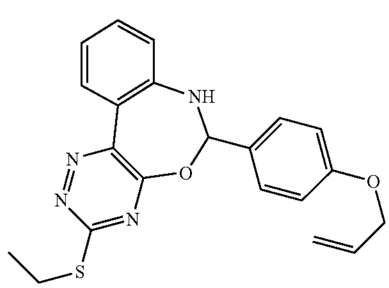 [SMILES: C=CCOc1ccc(C2Nc3ccccc3-c3nnc(SCC)nc3O2)cc1] | * |  |  | * | ** | * | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AFH | 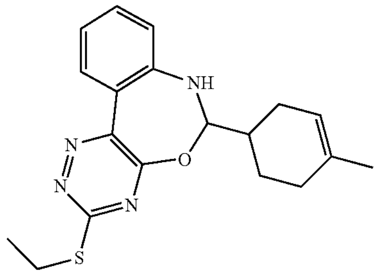 [SMILES: CCSc1nnc2c(n1)OC(C1CC=C(C)CC1)Nc1ccccc1-2] | * | * | ** | * | ** | * | * | * | ND |
| AFI | 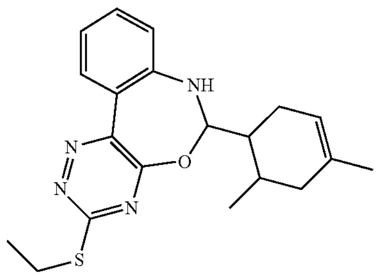 [SMILES: CCSc1nnc2c(n1)OC(C1CC=C(C)CC1C)Nc1ccccc1-2] | * |  | * |  |  | * | * | * | ** |
| AFJ | 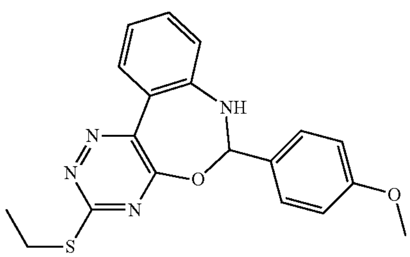 [SMILES: CCSc1nnc2c(n1)OC(c1ccc(OC)cc1)Nc1ccccc1-2] | * | * |  |  | * | ** | * | ** | * |
| AFK | 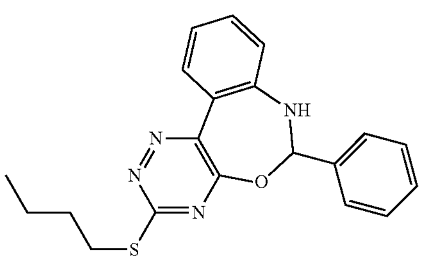 [SMILES: CCCCSc1nnc2c(n1)OC(c1ccccc1)Nc1ccccc1-2] | * | * | ** | * | * | ** | * |  |  |
| AFL | 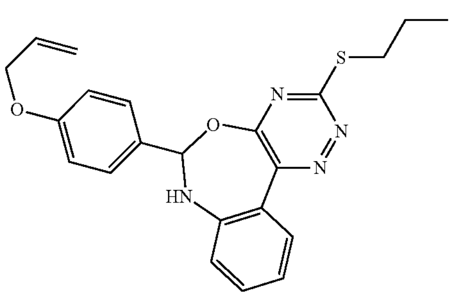 [SMILES: C=CCOc1ccc(C2Nc3ccccc3-c3nnc(SCCC)nc3O2)cc1] | ** | * | ** | * | ** | * | * | ** | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AFM | 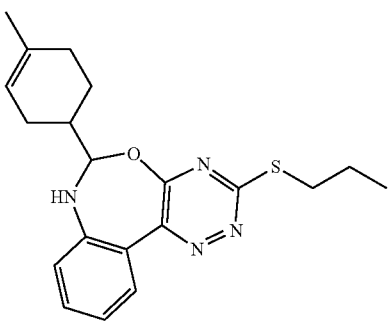 [SMILES: CCCSc1nnc2c(n1)OC(C1CC=C(C)CC1)Nc1ccccc1-2] | NT | * | *** | * | ** | * | * |  |  |
| AFN | 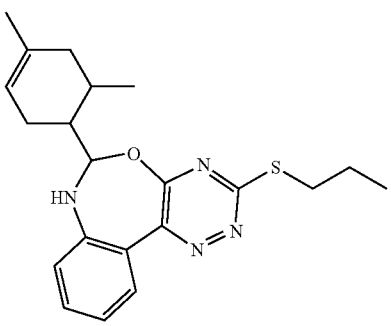 [SMILES: CCCSc1nnc2c(n1)OC(C1CC=C(C)CC1C)Nc1ccccc1-2] | * | * | * | NT | * | NT | * | ** | * |
| AFO | 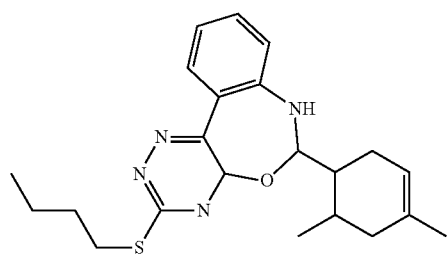 [SMILES: CCCCSC1=NN=C2c3ccccc3NC(C3CC=C(C)CC3C)OC2N1] | NT | * | NT | * | NT | *** | * | ** | ND |
| AFP | 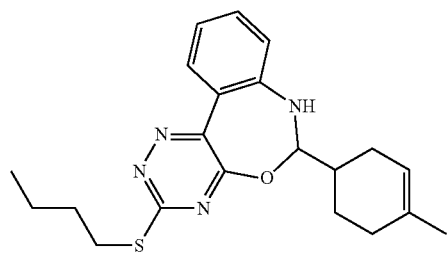 [SMILES: CCCCSc1nnc2c(n1)OC(C1CC=C(C)CC1)Nc1ccccc1-2] | NT | * | NT | * | NT | * | * |  |  |
| AFQ | 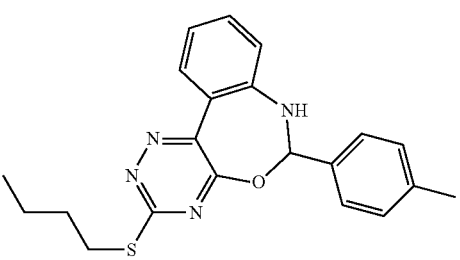 [SMILES: CCCCSc1nnc2c(n1)OC(c1ccc(C)cc1)Nc1ccccc1-2] | NT | * |  | * | NT | * | * |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AFR | 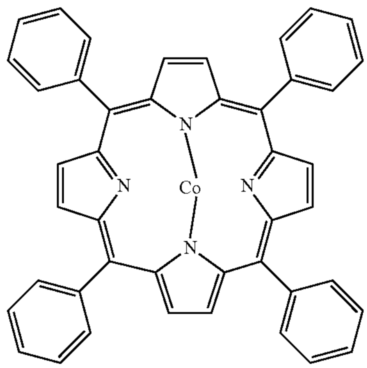 | * | NT | * | *** | * | *** | * | * | * |
| AFS | 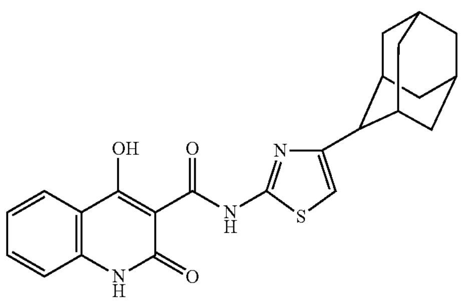 [SMILES: O=C(Nc1nc(C2C3CC4CC(C3)CC2C4)cs1)c1c(O)c2ccccc2[nH]c1=O] |  | NT | * |  |  | ** | * | * | * |
| AFT | 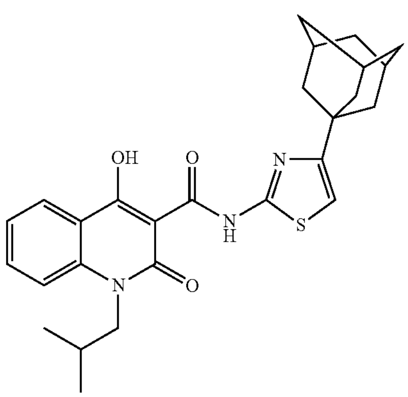 [SMILES: CC(C)Cn1c(=O)c(C(=O)Nc2nc(C34CC5CC(CC(C5)C3)C4)cs2)c(O)c2ccccc21] | * | NT | * | * | * | * | * | * | * |
| AFU | 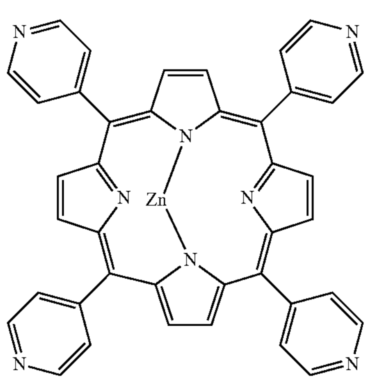 | * | * | * | NT | * | NT | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AFV | 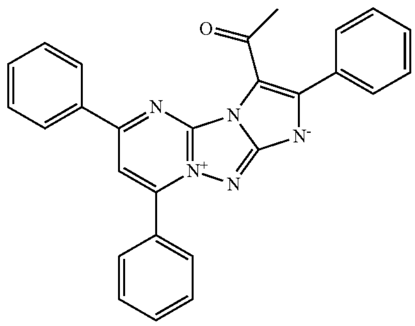 [SMILES: CC(=O)c1c(-c2ccccc2)[n-]c2n[n+]3c(-c4ccccc4)cc(-c4ccccc4)nc3n12] | ** | * | ** | * |  | * | * | * | ** |
| AFW | 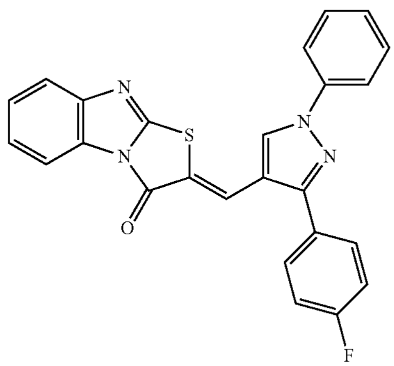 [SMILES: O=c1/c(=C/c2cn(-c3ccccc3)nc2-c2ccc(F)cc2)sc2nc3ccccc3n12] | ** | * | ** | * | ** | * | * | * | |
| *£ AFX | 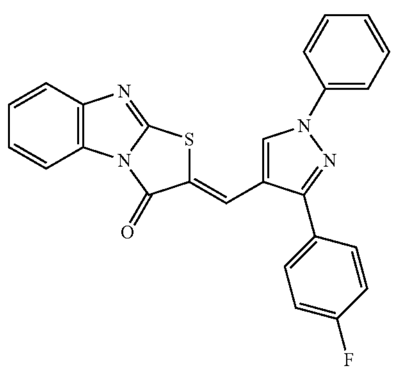 [SMILES: O=c1/c(=C/c2cn(-c3ccccc3)nc2-c2ccc(F)cc2)sc2nc3ccccc3n12] | ** | * | *** | * | ** | * | * | * | ** |
| AFY | 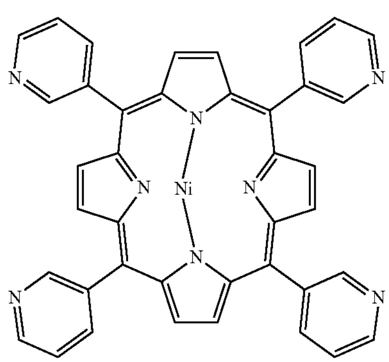 | * | * | * | * | ** | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AFZ | 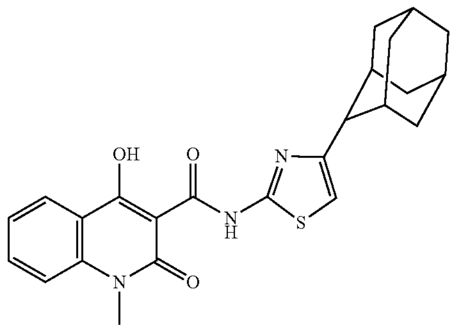 [SMILES: Cn1c(=O)c(C(=O)Nc2nc(C3C4CC5CC(C4)CC3C5)cs2)c(O)c2ccccc21] | * | * | ** | * |  | * | * | * | ** |
| AGA | 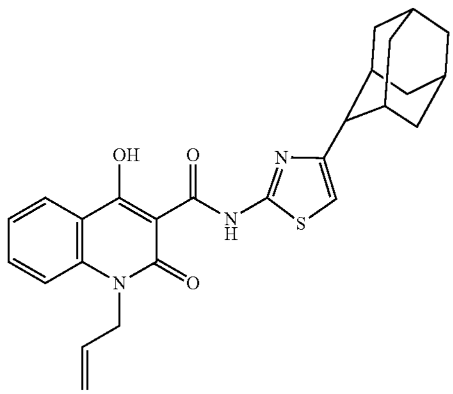 [SMILES: C=CCn1c(=O)c(C(=O)Nc2nc(C3C4CC5CC(C4)CC3C5)cs2)c(O)c2ccccc21] | * | * | * | * | * | * | * | * | ND |
| AGB | 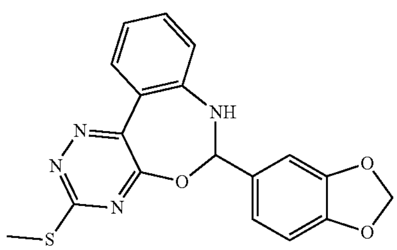 [SMILES: CSc1nnc2c(n1)OC(c1ccc3c(c1)OCO3)Nc1ccccc1-2] | *** | * | * |  | * | *** | * | * | * |
| AGC | 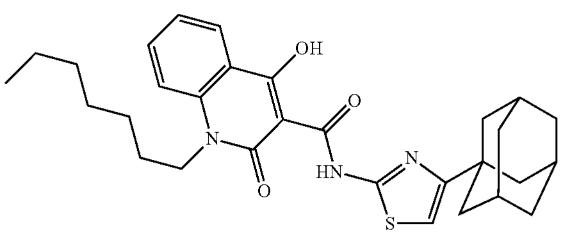 [SMILES: CCCCCCCn1c(=O)c(C(=O)Nc2nc(C34CC5CC(CC(C5)C3)C4)cs2)c(O)c2ccccc21] | ** | * | * |  | * | *** | * | * | * |
| AGD | 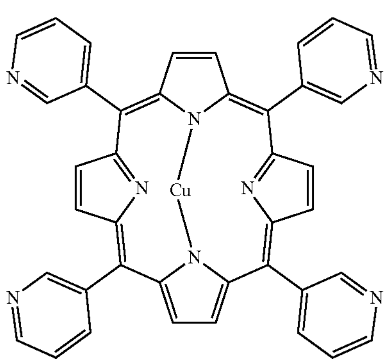 | ** | * | * | * | * | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AGE | 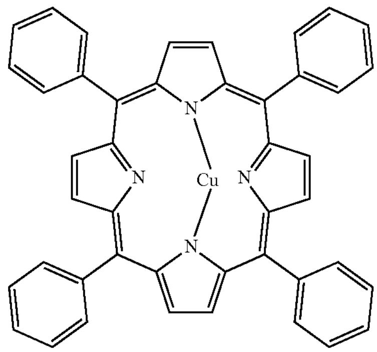 | NT |  | NT |  | NT | *** | * | * | ** |
| AGF | 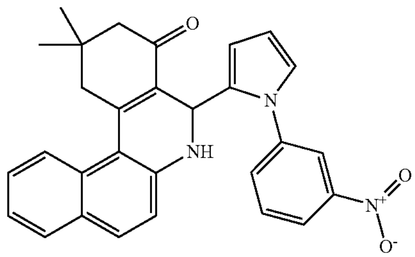 [SMILES: CC1(C)CC(=O)C2=C(C1)c1c(ccc3ccccc13)NC2c1cccn1-c1cccc([N+](=O)[O-])c1] | NT | * | NT | * | NT | * | * | * | ** |
| AGG | 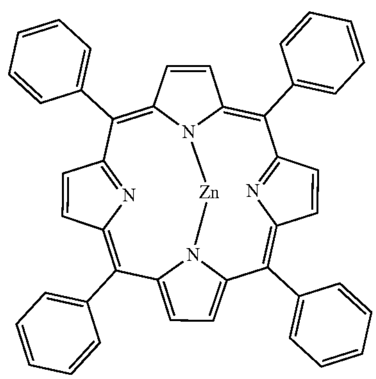 | NT | * | NT |  | NT |  | * | * | ** |
| AGH | 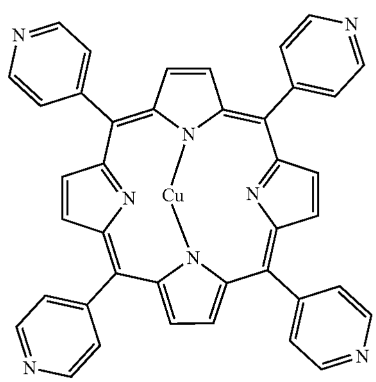 | NT | * | NT | * | NT | ** | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AGI | 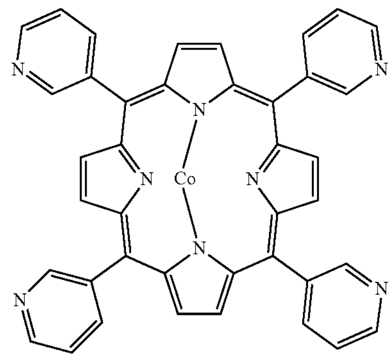 | NT | * | NT | * | NT | * | * | * | ** |
| AGJ | 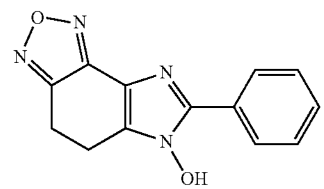 [SMILES: On1c(-c2ccccc2)nc2c1CCc1nonc1-2] | ** | * | *** | * | ** | * | * | * | ** |
| AGK | 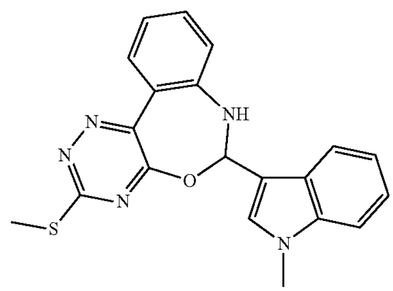 [SMILES: CSc1nnc2c(n1)OC(c1cn(C)c3ccccc13)Nc1ccccc1-2] | NT | * | NT | ** | NT | * | * |  |  |
| AGL | 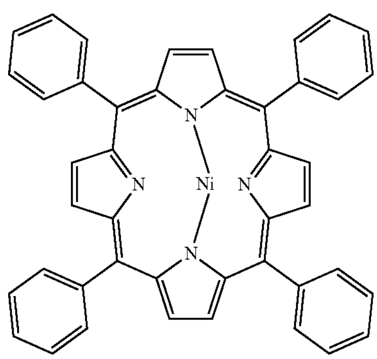 | NT | * | NT | * | NT | * | * | * | ** |
| AGM | 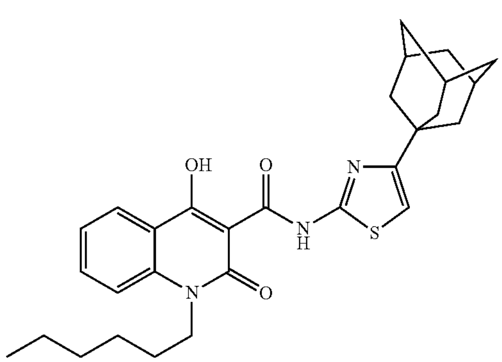 [SMILES: CCCCCCn1c(=O)c(C(=O)Nc2nc(C34CC5CC(CC(C5)C3)C4)cs2)c(O)c2ccccc21] | NT | * | NT | * | NT | ** | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AGN | 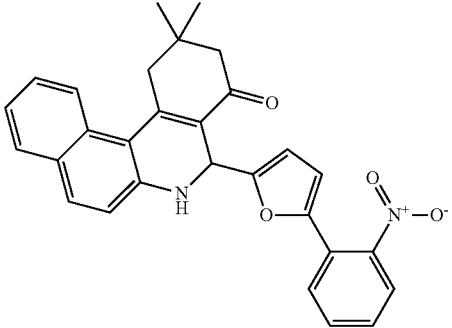 [SMILES: CC1(C)CC(=O)C2=C(C1)c1c(ccc3ccccc13)NC2c1ccc(-c2ccccc2[N+](=O)[O-])o1] | * |  |  | * |  |  | * | * | * |
| AGO | 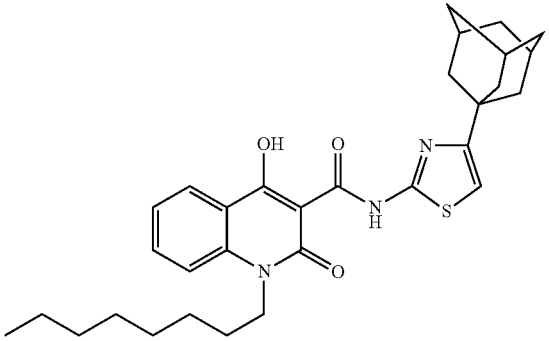 [SMILES: CCCCCCCCn1c(=O)c(C(=O)Nc2nc(C34CC5CC(CC(C5)C3)C4)cs2)c(O)c2ccccc21] |  |  | ** | * | ** | * | * | * | * |
| AGP | 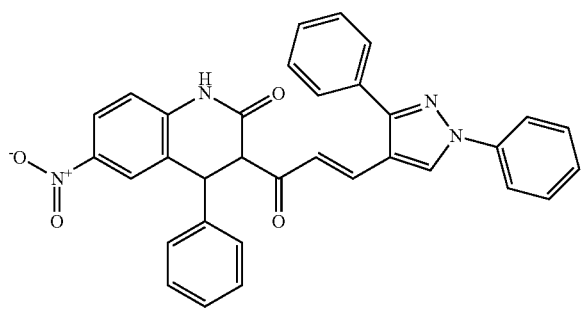 |  |  | * |  |  |  | * | * | ** |
| AGQ | 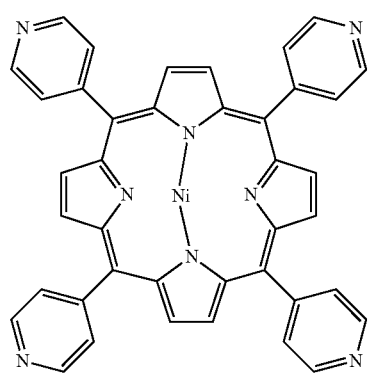 |  |  | ** | * | ** | * | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AGR | 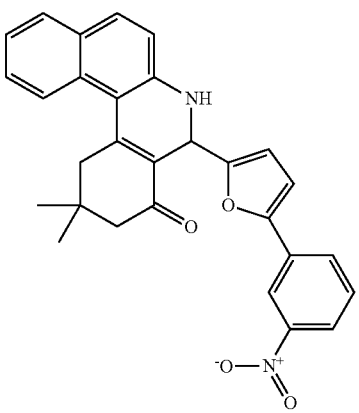 | * | * | ** | * |  |  | * | * | ND |
| AGS | 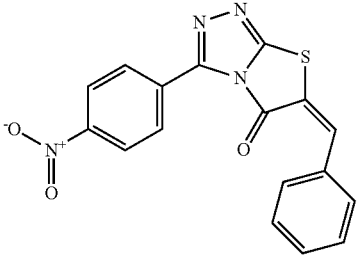 | * | * |  | * |  |  | * | * | ** |
| AGT | 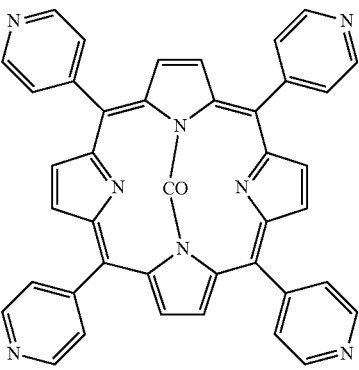 [SMILES: O=c1n2c3ccc2c(-c2ccncc2)c2nc(c(-c4ccncc4)c4ccc(c(-c5ccncc5)c5nc(c3-c3ccncc3)C=C5)n14)C=C2] | * | * | ** | * | ** | * | * | * | * |
| AGU | 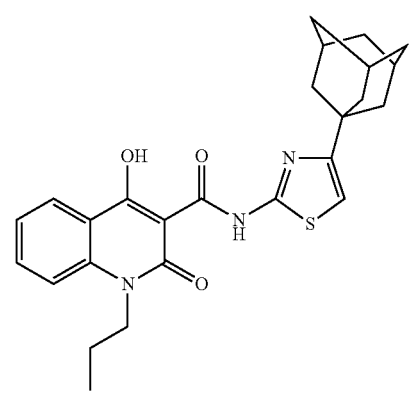 [SMILES: CCCn1c(=O)c(C(=O)Nc2nc(C34CC5CC(CC(C5)C3)C4)cs2)c(O)c2ccccc21] |  |  | ** | * | ** | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AGV | 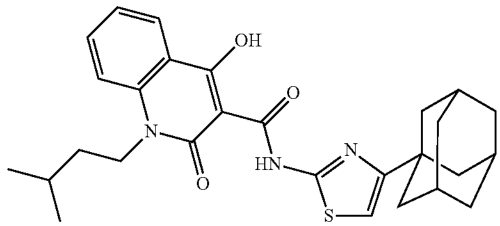 [SMILES: CC(C)CCn1c(=O)c(C(=O)Nc2nc(C34CC5CC(CC(C5)C3)C4)cs2)c(O)c2ccccc21] | * | * |  | * |  | ** | * | * | ** |
| AGW | 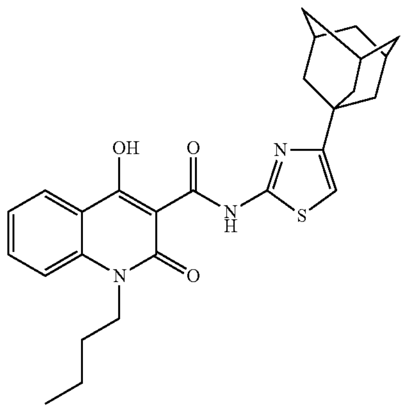 [SMILES: CCCCn1c(=O)c(C(=O)Nc2nc(C34CC5CC(CC(C5)C3)C4)cs2)c(O)c2ccccc21] | * | * |  |  |  | NT | * | * | * |
| AGX | 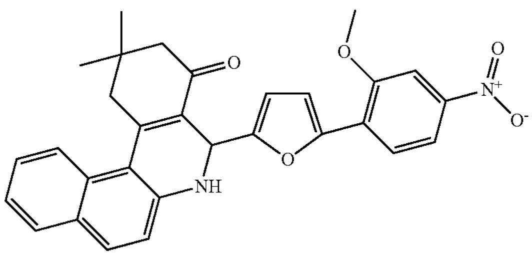 [SMILES: COc1cc([N+](=O)[O-])ccc1-c1ccc(C2Nc3ccc4ccccc4c3C3=C2C(=O)CC(C)(C)C3)o1] | NT |  | NT |  | NT | *** | * |  |  |
| AGY | 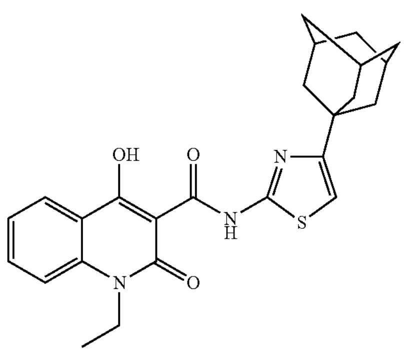 [SMILES: CCn1c(=O)c(C(=O)Nc2nc(C34CC5CC(CC(C5)C3)C4)cs2)c(O)c2ccccc21] | NT | * | NT | ** | NT | * | * | ** | * |
| AGZ | 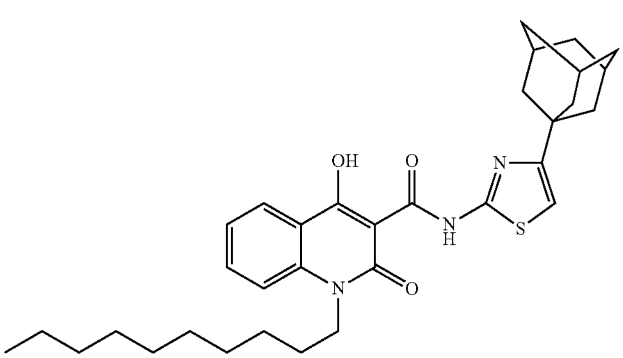 [SMILES: CCCCCCCCCCn1c(=O)c(C(=O)Nc2nc(C34CC5CC(CC(C5)C3)C4)cs2)c(O)c2ccccc21] | NT | * | NT | * | NT | * | * |  |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AHA | 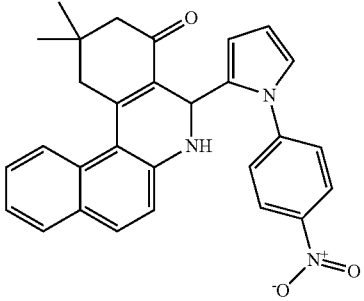 | NT | * | NT | ** | NT | * | * |  |  |
| AHB | 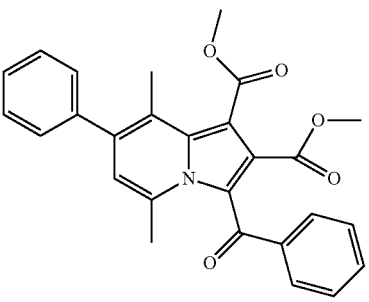 [SMILES: COC(=O)c1c(C(=O)OC)c2c(C)c(-c3ccccc3)cc(C)n2c1C(=O)c1ccccc1] | * | NT | * | ** | * | * | * | * | ** |
| AHC | 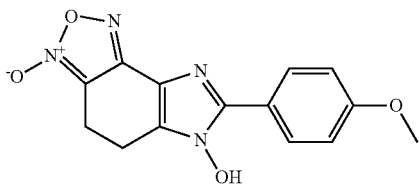 | NT | * | NT | ** | NT | * | * | * | * |
| AHD | 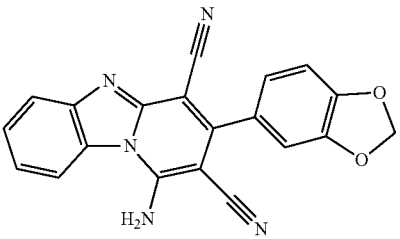 [SMILES: N#Cc1c(-c2ccc3c(c2)OCO3)c(C#N)c2nc3ccccc3n2c1N] | NT | * | NT | * | NT | * | * | ** | * |
| AHE | 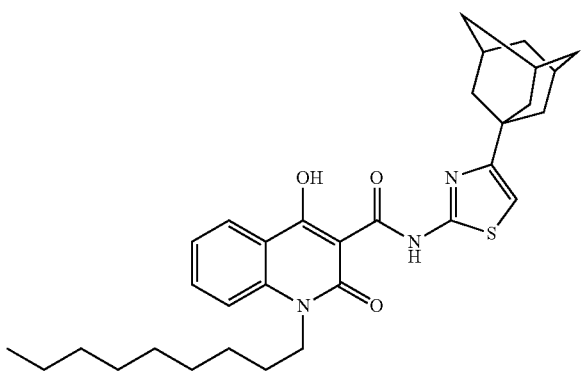 [SMILES: CCCCCCCCCn1c(=O)c(C(=O)Nc2nc(C34CC5CC(CC(C5)C3)C4)cs2)c(O)c2ccccc21] | *** | * | *** | * | ** | * | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AHF | 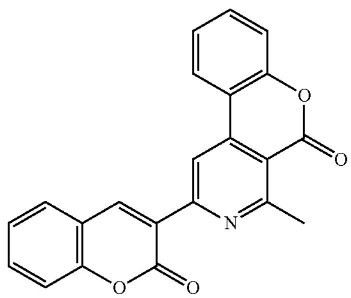 [SMILES: Cc1nc(-c2cc3ccccc3oc2=O)cc2c1c(=O)oc1ccccc12] | *** | * | ** | * | ** | * | * | * | ** |
| AHG | 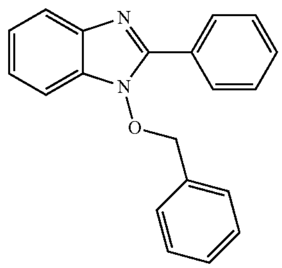 [SMILES: c1ccc(COn2c(-c3ccccc3)nc3ccccc32)cc1] | ** | * | ** | * | ** | * | * | * | ** |
| AHH | 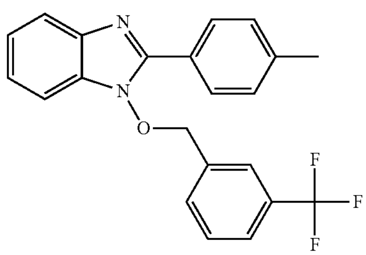 | * | * | *** | * | ** | * | * | * | ** |
| AHI | 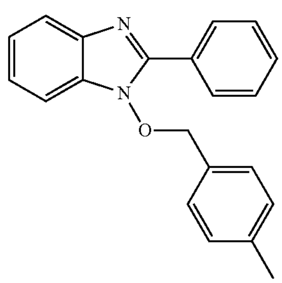 [SMILES: Cc1ccc(COn2c(-c3ccccc3)nc3ccccc32)cc1] | * | * | * | * | *** | * | * | * | ND |
| AHJ | 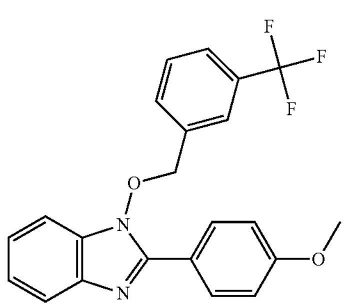 [SMILES: COc1ccc(-c2nc3ccccc3n2OCc2cccc(C(F)(F)F)c2)cc1] | ** | * | ** | * | *** | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| HK | 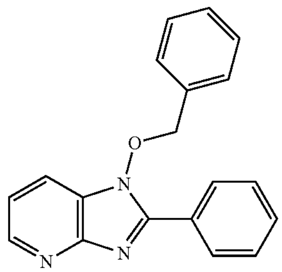 [SMILES: c1ccc(COn2c(-c3ccccc3)nc3ncccc32)cc1] |  |  | * |  |  | *** | * | * | ** |
| AHL | 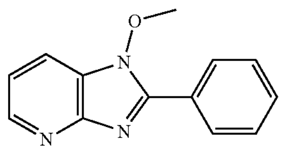 [SMILES: COn1c(-c2ccccc2)nc2ncccc21] | NT | * | NT | * | NT | * | * | * | ND |
| AHM | 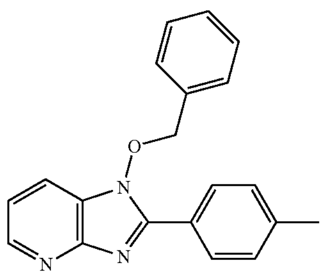 [SMILES: Cc1ccc(-c2nc3ncccc3n2OCc2ccccc2)cc1] | NT | * | NT | * | NT | * | * | * | ND |
| AHN | 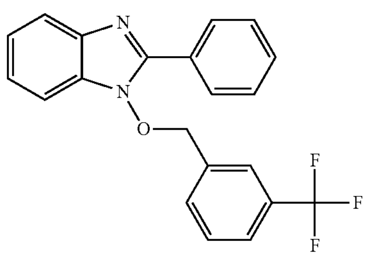 [SMILES: FC(F)(F)c1cccc(COn2c(-c3ccccc3)nc3ccccc32)c1] | NT |  | NT |  | NT | *** | * | * | ND |
| AHO | 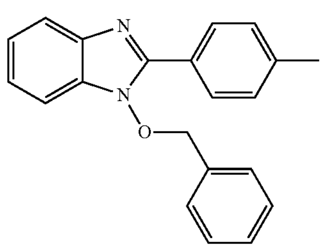 [SMILES: Cc1ccc(-c2nc3ccccc3n2OCc2ccccc2)cc1] | NT | * | NT | * | NT | * | * | * | ND |
| AHP | 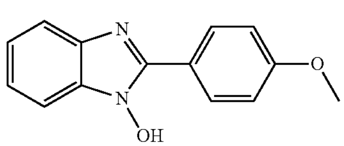 [SMILES: COc1ccc(-c2nc3ccccc3n2O)cc1] | NT | * | NT | * | NT | ** | * |  |  |
| AHQ | 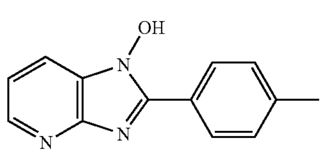 [SMILES: Cc1ccc(-c2nc3ncccc3n2O)cc1] | ** | * | * | * | * | * | * | * | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AHR | 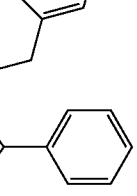 | * | * | * | * | * | * | * | * | * |
| AHS | 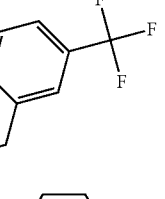 | * |  |  | * |  |  | * | * | * |
| AHT | 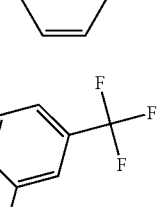 | * |  |  | * | ** | * | * | * | ** |
| AHU | 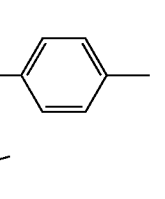 | * |  |  | * | ** | * | * | * | ND |
| AHV | 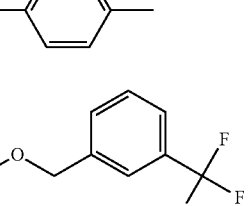 | * |  |  | * | ** | * | * | * | ** |
| AHW | 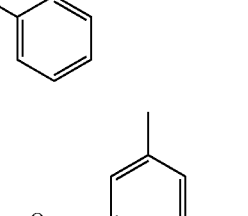 |  |  |  | * |  |  | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AHX | 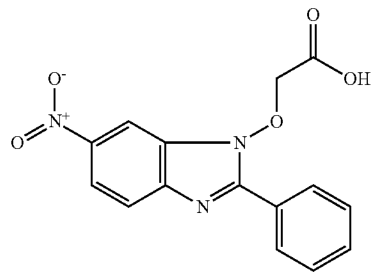 [SMILES: O=C(O)COn1c(-c2ccccc2)nc2ccc([N+](=O)[O-])cc21] | * | * |  | * |  | NT | * | * | ND |
| AHY | 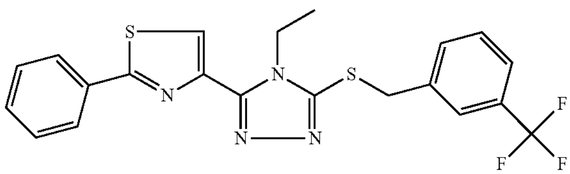 [SMILES: CCn1c(SCc2cccc(C(F)(F)F)c2)nnc1-c1csc(-c2ccccc2)n1] | * | * |  |  | * | *** | * |  |  |
| AHZ | 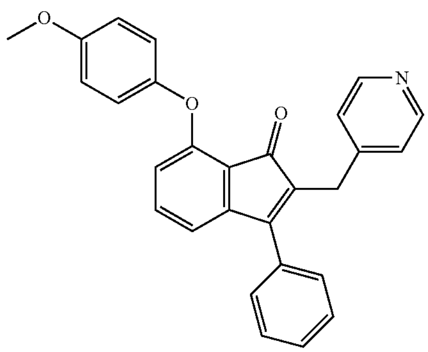 [SMILES: COc1ccc(Oc2cccc3c2C(=O)C(Cc2ccncc2)=C3c2ccccc2)cc1] | * | * | ** | NT | * | NT | * | ** | ND |
| AIA | 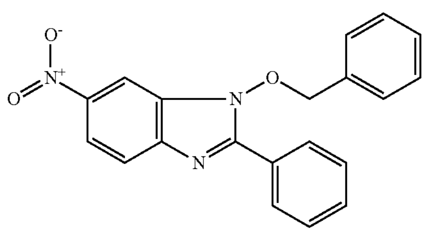 [SMILES: O=[N+]([O-])c1ccc2nc(-c3ccccc3)n(OCc3ccccc3)c2c1] | NT |  | NT |  | NT | * | * | ** | ND |
| AIB | 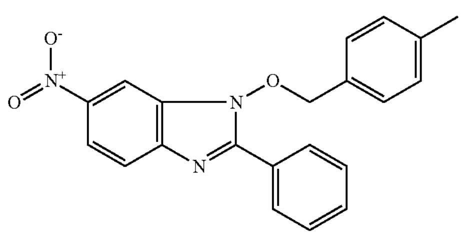 [SMILES: Cc1ccc(COn2c(-c3ccccc3)nc3ccc([N+](=O)[O-])cc32)cc1] | ** | * | *** | * | ** | * | * | * | ** |
| AIC | 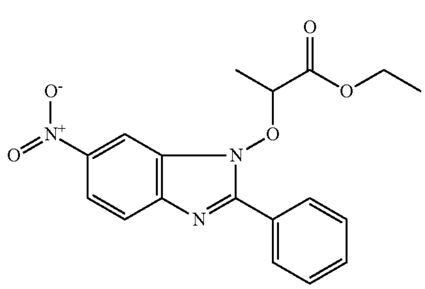 [SMILES: CCOC(=O)C(C)On1c(-c2ccccc2)nc2ccc([N+](=O)[O-])cc21] |  | * | * | * |  | * | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AID | 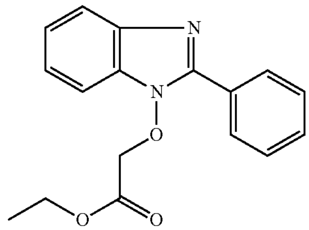 [SMILES: CCOC(=O)COn1c(-c2ccccc2)nc2ccccc21] | ** | * | ** | * | *** | * | * | * | ND |
| AIE | 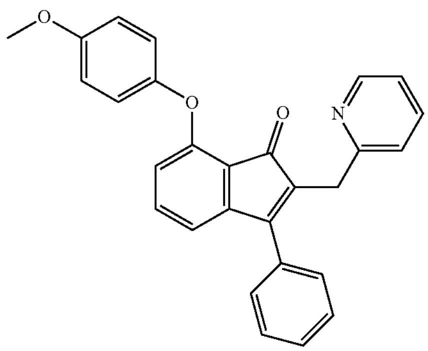 [SMILES: COc1ccc(Oc2cccc3c2C(=O)C(Cc2ccccn2)=C3c2ccccc2)cc1] | ** | * | * | * | * | * | * | * | * |
| AIF | 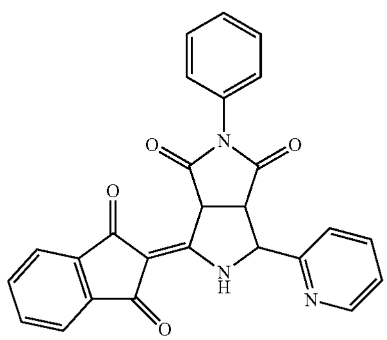 [SMILES: O=C1C(=C2NC(c3ccccn3)C3C(=O)N(c4ccccc4)C(=O)C23)C(=O)c2ccccc21] | *** | * | * | * | *** | * | * | * | ND |
| AIG | 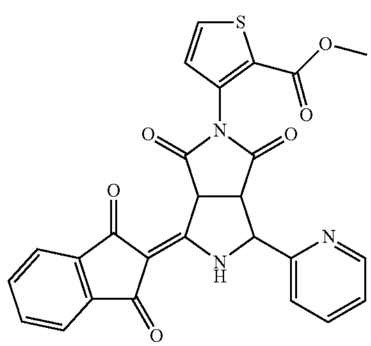 [SMILES: COC(=O)c1sccc1N1C(=O)C2C(=C3C(=O)c4ccccc4C3=O)NC(c3ccccn3)C2C1=O] |  |  | * | * | * | * | * | * | ND |
| AIH | 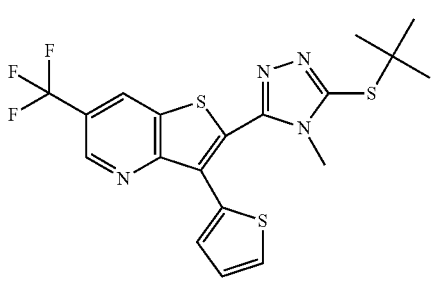 [SMILES: Cn1c(SC(C)(C)C)nnc1-c1sc2cc(C(F)(F)F)cnc2c1-c1cccs1] | NT | * | NT | * | NT | * | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AII | 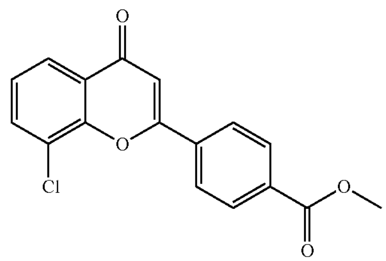 [SMILES: COC(=O)c1ccc(-c2cc(=O)c3cccc(Cl)c3o2)cc1] | NT | * | NT | ** | NT | * | * | * | ND |
| AIJ | 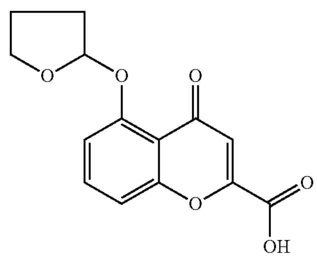 [SMILES: O=C(O)c1cc(=O)c2c(OC3CCCO3)cccc2o1] | NT | * | NT | * | NT | * | * | ** | ND |
| AIK | 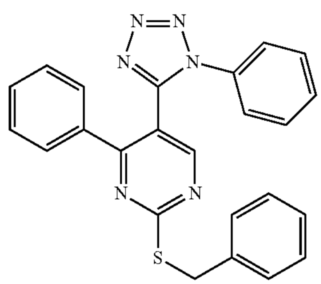 [SMILES: c1ccc(CSc2ncc(-c3nnnn3-c3ccccc3)c(-c3ccccc3)n2)cc1] | * |  | * |  | ** | * | * | * | ND |
| AIL | 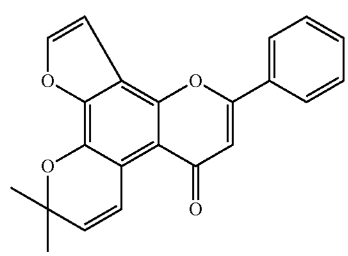 [SMILES: CC1(C)C=Cc2c(c3occc3c3oc(-c4ccccc4)cc(=O)c23)O1] |  | * | * | ** | * | *** | * | * | * |
| AIM | 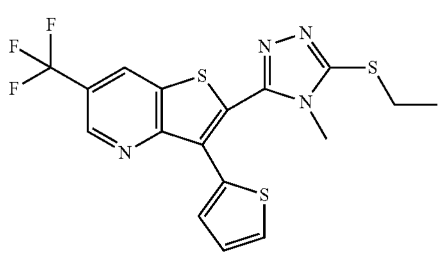 [SMILES: CCSc1nnc(-c2sc3cc(C(F)(F)F)cnc3c2-c2cccs2)n1C] | * | * | ** | * | ** | * | * | * | ** |
| AIN | 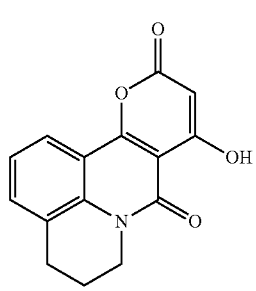 [SMILES: O=c1cc(O)c2c(=O)n3c4c(cccc4c2o1)CCC3] | ** | * | ** | * | ** | * | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AIO | 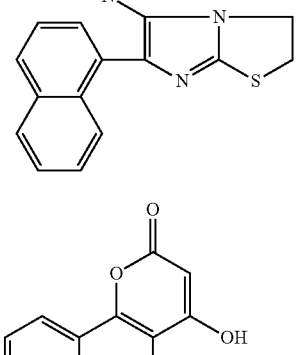 | * | * |  |  |  |  | * | * | ** |
| AIP | 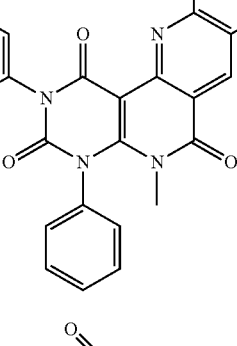 | * |  |  | * | ** | * | * | * | ND |
| AIQ | 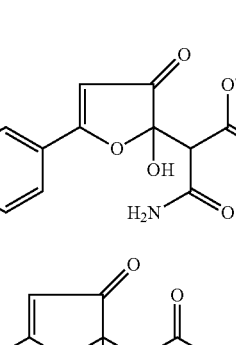 | * |  |  |  |  | ** | * | * | ND |
| AIR | 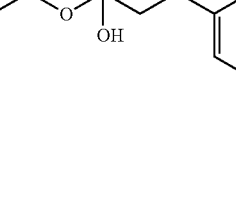 | ** | * | ** | * | ** | * | * |  |  |
| AIS | 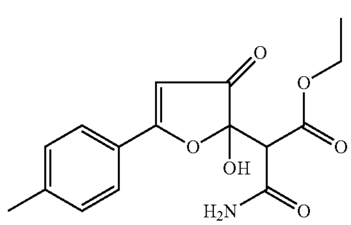 [SMILES: CCOC(=O)C(C(N)=O)C1(O)OC(c2ccc(C)cc2)=CC1=O] | * | * | ** | * | ** | * | * |  |  |
| AIT | 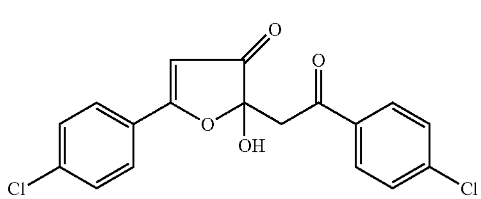 [SMILES: O=C(CC1(O)OC(c2ccc(Cl)cc2)=CC1=O)c1ccc(Cl)cc1] | * | * | NT | * | * | * | * |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AIU | 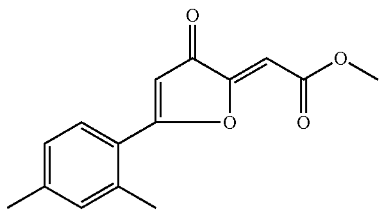 | * | * | ** | NT | * | NT | * | * | * |
| AIV | 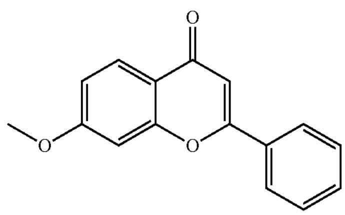 [SMILES: COc1ccc2c(=O)cc(-c3ccccc3)oc2c1] | NT | * | NT | * | NT | ** | * |  |  |
| AIW | 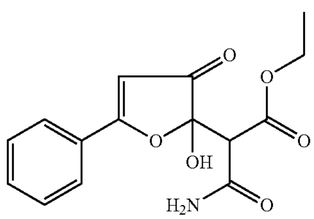 [SMILES: CCOC(=O)C(C(N)=O)C1(O)OC(c2ccccc2)=CC1=O] | * | NT | * | * |  | * | * | * | ** |
| AIX | 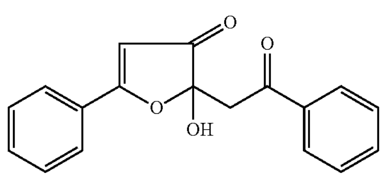 [SMILES: O=C(CC1(O)OC(c2ccccc2)=CC1=O)c1ccccc1] | ** | * | ** | * | ** | * | * | * | ** |
| AIY | 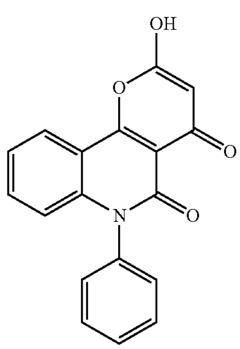 [SMILES: O=c1cc(O)oc2c1c(=O)n(-c1ccccc1)c1ccccc21] | ** | * | ** | * | *** | * | * | * | ** |
| AIZ | 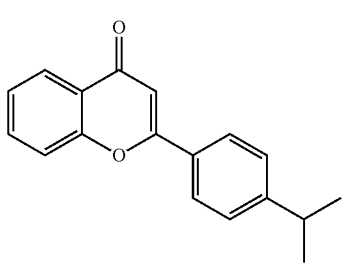 [SMILES: CC(C)c1ccc(-c2cc(=O)c3ccccc3o2)cc1] | * | * | *** | * | *** | * | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AJA | 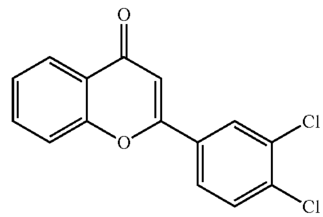 [SMILES: O=c1cc(-c2ccc(Cl)c(Cl)c2)oc2ccccc12] | * | * | ** | * | ** | * | * | * | ND |
| AJB | 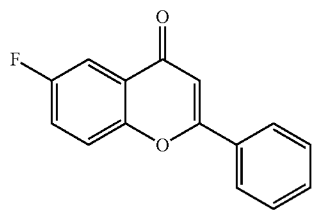 [SMILES: O=c1cc(-c2ccccc2)oc2ccc(F)cc12] | * | * | *** | * | ** | * | * | * | ND |
| AJD | 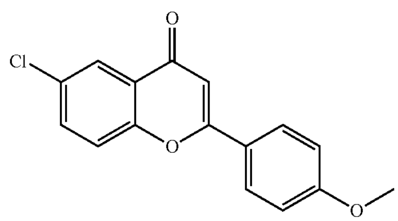 [SMILES: COc1ccc(-c2cc(=O)c3cc(Cl)ccc3o2)cc1] |  |  | * | * | ** | * | * | * | * |
| AJE | 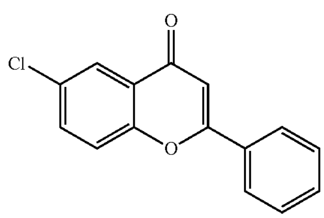 [SMILES: O=c1cc(-c2ccccc2)oc2ccc(Cl)cc12] | NT | * | NT | ** | NT | * | * | * | ND |
| AJF | 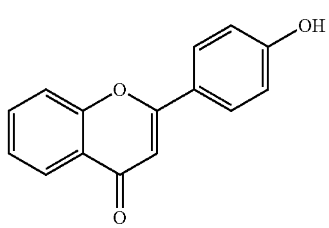 [SMILES: O=c1cc(-c2ccc(O)cc2)oc2ccccc12] | NT | * | NT | * | NT | * | * | * | * |
| AJG | 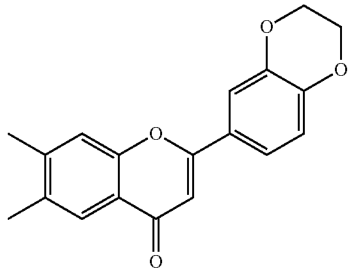 [SMILES: Cc1cc2oc(-c3ccc4c(c3)OCCO4)cc(=O)c2cc1C] | NT | * | NT | * | NT | *** | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AJH | 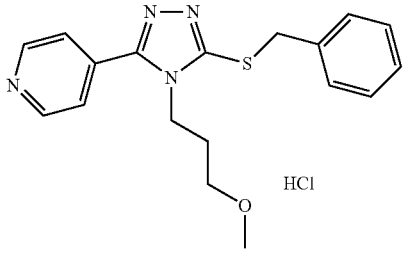 [SMILES: COCCCn1c(SCc2ccccc2)nnc1-c1ccncc1 ; Cl] |  | * | *** | * | ** | * | * | * | ** |
| AJI | 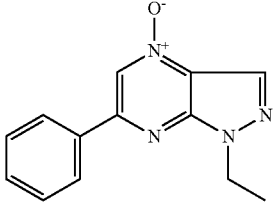 [SMILES: CCn1ncc2c1nc(-c1ccccc1)c[n+]2[O-]] |  |  | * | * | * | ** | * | * | * |
| AJJ | 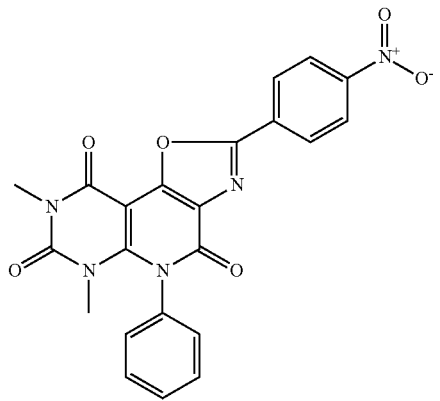 [SMILES: Cn1c(=O)c2c3oc(-c4ccc([N+](=O)[O-])cc4)nc3c(=O)n(-c3ccccc3)c2n(C)c1=O] |  |  | * | ** | * | * | * | * | * |
| AJK | 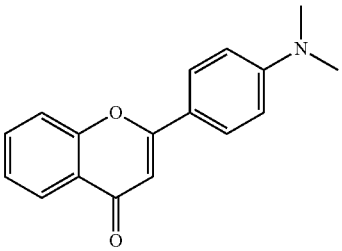 [SMILES: CN(C)c1ccc(-c2cc(=O)c3ccccc3o2)cc1] | *** | * | ** | * | ** | * | * | * | ND |
| AJL | 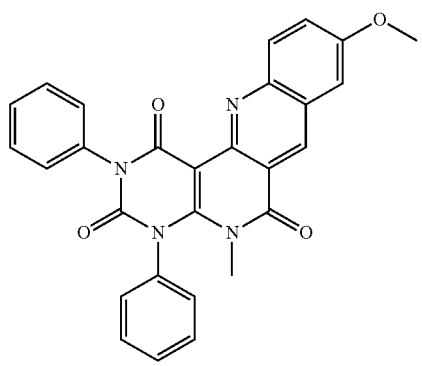 [SMILES: COc1ccc2nc3c(cc2c1)c(=O)n(C)c1c3c(=O)n(-c2ccccc2)c(=O)n1-c1ccccc1] | * |  |  | * | ** | * | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AJM | 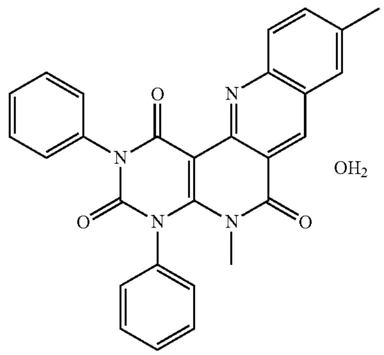 | * |  |  |  |  | *** | * | * | ND |
| AJN | 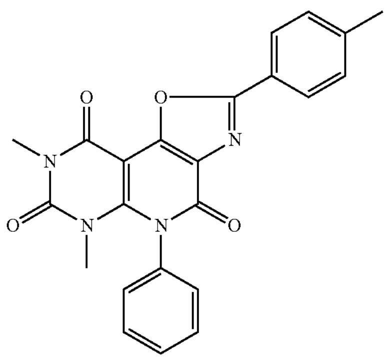 [SMILES: Cc1ccc(-c2nc3c(=O)n(-c4ccccc4)c4c(c(=O)n(C)c(=O)n4C)c3o2)cc1] | * | * |  |  |  | NT | * | * | ** |
| AJO | 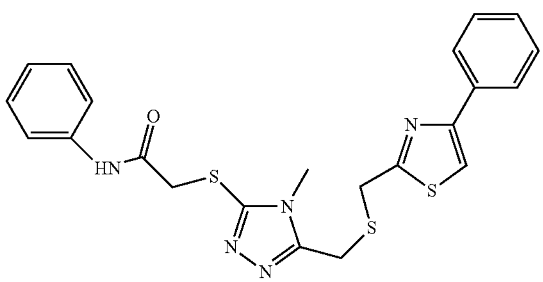 [SMILES: Cn1c(CSCc2nc(-c3ccccc3)cs2)nnc1SCC(=O)Nc1ccccc1] | * | NT | ** | * | ** | NT | * | * | ** |
| AJP | 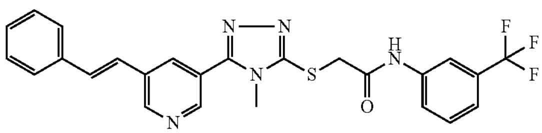 [SMILES: Cn1c(SCC(=O)Nc2cccc(C(F)(F)F)c2)nnc1-c1cncc(/C=C/c2ccccc2)c1] | * | * |  | * | ** | NT | * | * | * |
| AJQ | 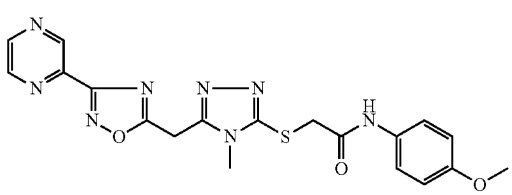 [SMILES: COc1ccc(NC(=O)CSc2nnc(Cc3nc(-c4cnccn4)no3)n2C)cc1] | NT | * | NT | * | NT | * | * | * | * |
| AJR | 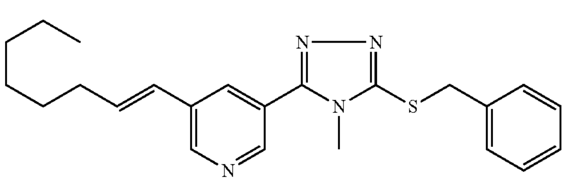 [SMILES: CCCCCC/C=C/c1cncc(-c2nnc(SCc3ccccc3)n2C)c1] | NT | * | NT |  | NT | * | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AJZ | 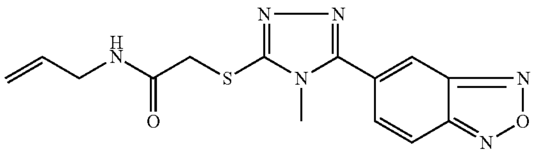 [SMILES: C=CCNC(=O)CSc1nnc(-c2ccc3nonc3c2)n1C] | * | * |  | NT |  | NT | * | * | ** |
| AKA | 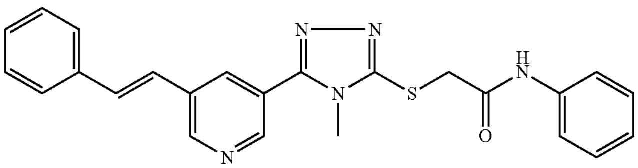 [SMILES: Cn1c(SCC(=O)Nc2ccccc2)nnc1-c1cncc(/C=C/c2ccccc2)c1] | ** | * | ** | * |  | * | * | * | ** |
| AKB | 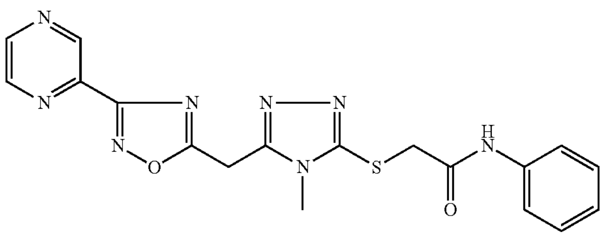 [SMILES: Cn1c(Cc2nc(-c3cnccn3)no2)nnc1SCC(=O)Nc1ccccc1] |  |  | * |  |  | * | * | * | ** |
| AKC | 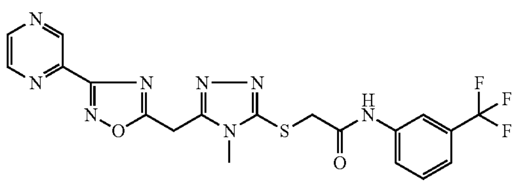 [SMILES: Cn1c(Cc2nc(-c3cnccn3)no2)nnc1SCC(=O)Nc1cccc(C(F)(F)F)c1] | ** | * |  |  | * | * | * | * | ND |
| AKD | 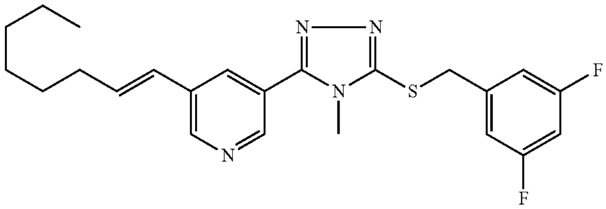 [SMILES: CCCCCC/C=C/c1cncc(-c2nnc(SCc3cc(F)cc(F)c3)n2C)c1] | ** | * | * | * | * | * | * | * | ND |
| AKE | 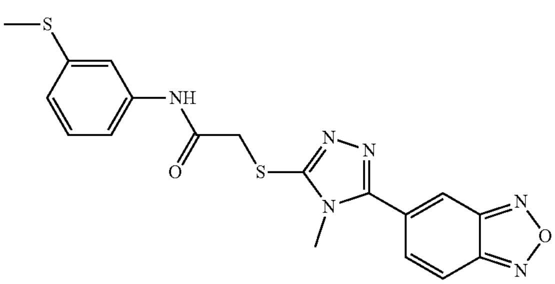 [SMILES: CSc1cccc(NC(=O)CSc2nnc(-c3ccc4nonc4c3)n2C)c1] | *** | * | * |  | * | *** | * | * | ** |
| AKF | 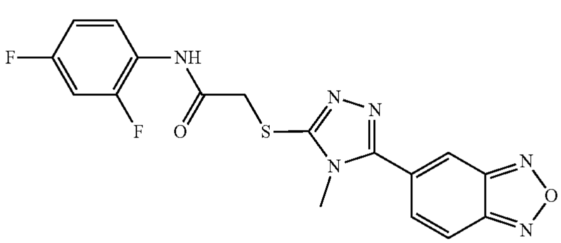 [SMILES: Cn1c(SCC(=O)Nc2ccc(F)cc2F)nnc1-c1ccc2nonc2c1] | *** | * | * |  | * | *** | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AKG | 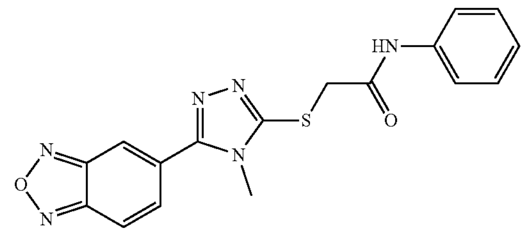 [SMILES: Cn1c(SCC(=O)Nc2ccccc2)nnc1-c1ccc2nonc2c1] | *** | * | * | * |  |  | * | * | ND |
| AKH | 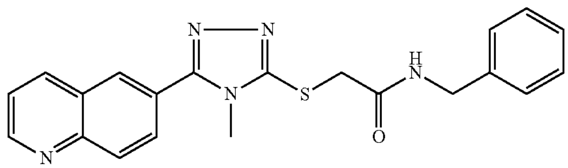 [SMILES: Cn1c(SCC(=O)NCc2ccccc2)nnc1-c1ccc2ncccc2c1] | NT | * | NT | * | NT | *** | * | * | ** |
| AKI | 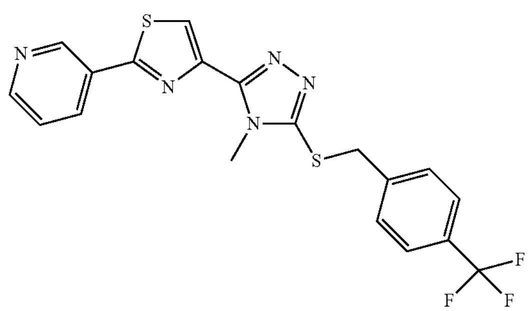 [SMILES: Cn1c(SCc2ccc(C(F)(F)F)cc2)nnc1-c1csc(-c2cccnc2)n1] | * | * |  |  |  | * | * | * | ** |
| AKJ | 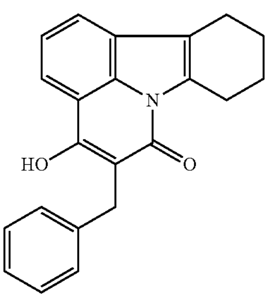 [SMILES: O=c1c(Cc2ccccc2)c(O)c2cccc3c4c(n1c23)CCCC4] | * | NT |  |  | * | * | * | * | ND |
| AKK | 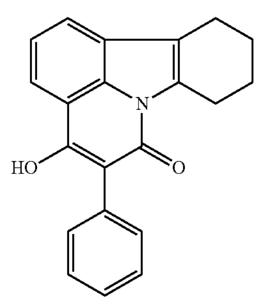 [SMILES: O=c1c(-c2ccccc2)c(O)c2cccc3c4c(n1c23)CCCC4] | * | NT |  |  | * | ** | * | * | ** |
| AKL | 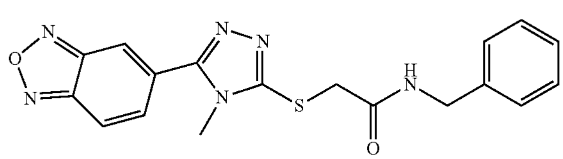 [SMILES: Cn1c(SCC(=O)NCc2ccccc2)nnc1-c1ccc2nonc2c1] | NT | * | NT | ** | NT | * | * | * | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AKM | 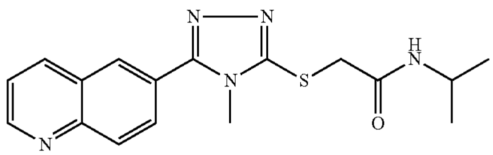 [SMILES: CC(C)NC(=O)CSc1nnc(-c2ccc3ncccc3c2)n1C] | NT | * | NT | * | NT | * | * |  |  |
| AKN | 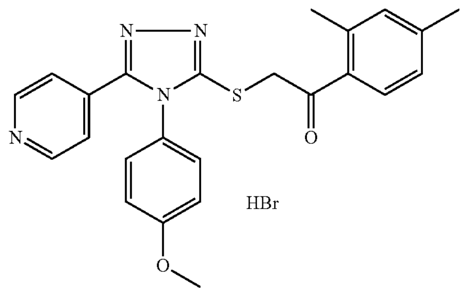 [SMILES: COc1ccc(-n2c(SCC(=O)c3ccc(C)cc3C)nnc2-c2ccncc2)cc1 ; Br] | NT |  | NT |  | NT | * | * | ** | * |
| AKO | 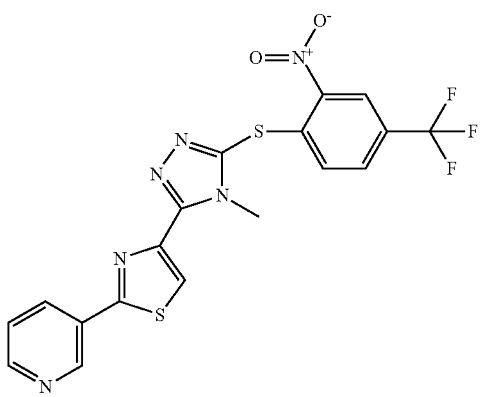 [SMILES: Cn1c(Sc2ccc(C(F)(F)F)cc2[N+](=O)[O-])nnc1-c1csc(-c2cccnc2)n1] | * | * | ** | * |  | * | * | * | ** |
| AKP | 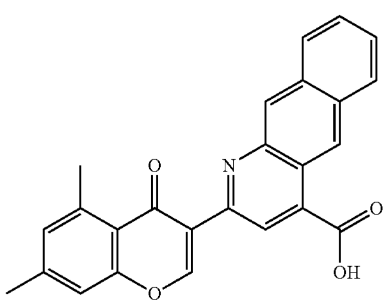 [SMILES: Cc1cc(C)c2c(=O)c(-c3cc(C(=O)O)c4cc5ccccc5cc4n3)coc2c1] | * | NT |  |  |  | * | * | * | ND |
| AKQ | 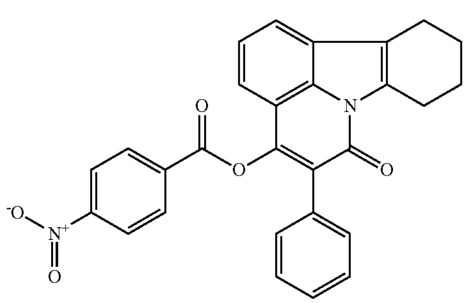 | NT |  | NT |  | NT | * | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AKR | 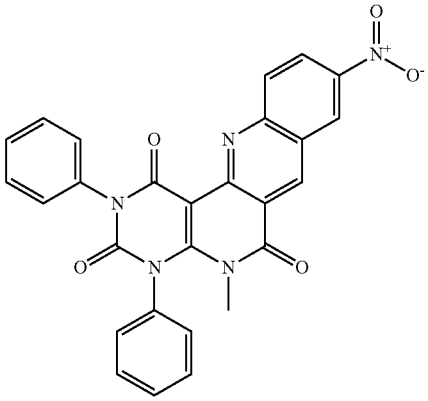 [SMILES: Cn1c(=O)c2cc3cc([N+](=O)[O-])ccc3nc2c2c(=O)n(-c3ccccc3)c(=O)n(-c3ccccc3)c21] | * | * | ** | * | ** | * | * | * | * |
| AKS | 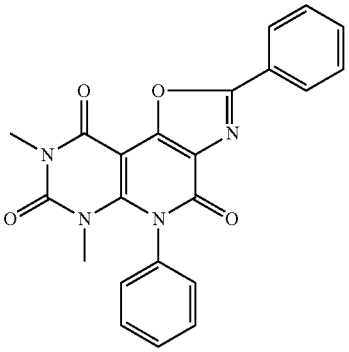 [SMILES: Cn1c(=O)c2c3oc(-c4ccccc4)nc3c(=O)n(-c3ccccc3)c2n(C)c1=O] | * | * | ** | * |  |  | * | * | ** |
| AKT | 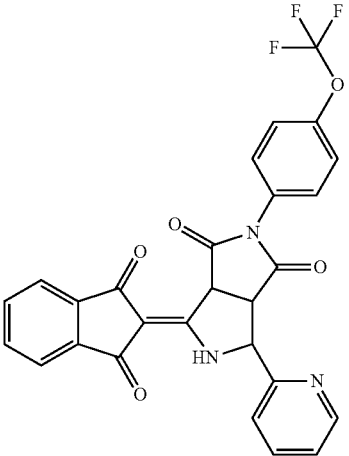 [SMILES: O=C1C(=C2NC(c3ccccn3)C3C(=O)N(c4ccc(OC(F)(F)F)cc4)C(=O)C23)C(=O)c2ccccc21] |  |  | * | * | * | * | * | * | ** |
| AKU | 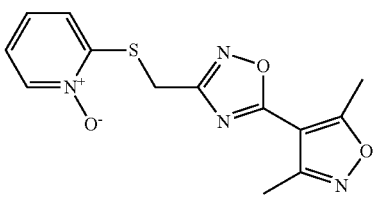 [SMILES: Cc1noc(C)c1-c1nc(CSc2cccc[n+]2[O-])no1] | NT |  | NT | * | NT | *** | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|----|----|-----|
| AKV | 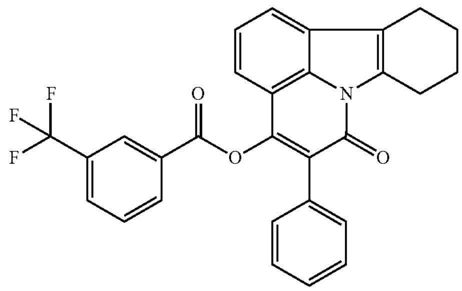 [SMILES: O=C(Oc1c(-c2ccccc2)c(=O)n2c3c(c4cccc1c42)CCCC3)c1cccc(C(F)(F)F)c1] | NT |  | NT |  | NT | ** | * | ** | * |
| AKW | 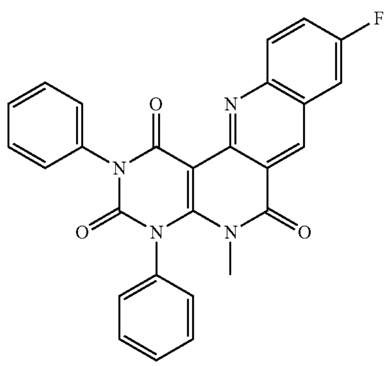 [SMILES: Cn1c(=O)c2cc3cc(F)ccc3nc2c2c(=O)n(-c3ccccc3)c(=O)n(-c3ccccc3)c21] | NT | * | NT | * | NT | * | * |  |  |
| AKX | 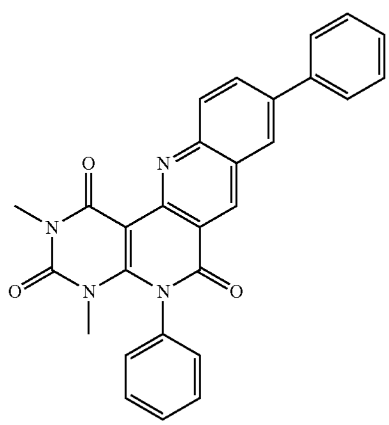 [SMILES: Cn1c(=O)c2c3nc4ccc(-c5ccccc5)cc4cc3c(=O)n(-c3ccccc3)c2n(C)c1=O] | NT | * | NT | * | NT | *** | * |  |  |
| AKY | 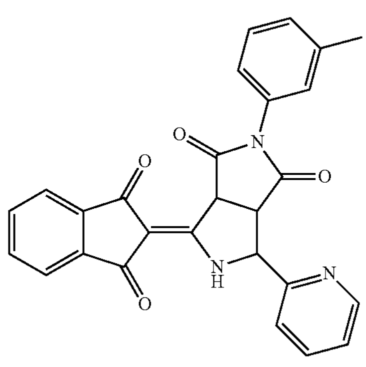 [SMILES: Cc1cccc(N2C(=O)C3C(=C4C(=O)c5ccccc5C4=O)NC(c4ccccn4)C3C2=O)c1] | * | * | ** | * | ** | * | * |  |  |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AKZ | 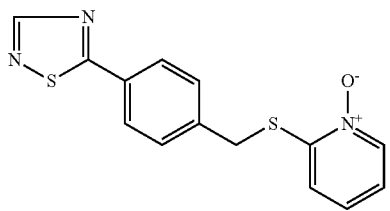 [SMILES: [O-][n+]1ccccc1SCc1ccc(-c2ncns2)cc1] | NT |  | NT |  | NT | ** | * |  |  |
| ALA | 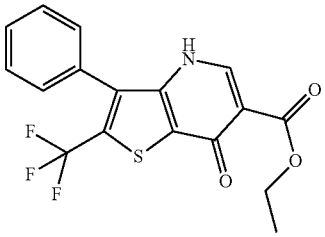 [SMILES: CCOC(=O)c1c[nH]c2c(-c3ccccc3)c(C(F)(F)F)sc2c1=O] | NT | * | NT | * | NT | * | * | * | ** |
| ALB | 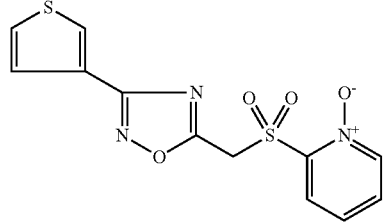 [SMILES: O=S(=O)(Cc1nc(-c2ccsc2)no1)c1cccc[n+]1[O-]] | * | NT | ** | * | * | * | * | * | ND |
| ALC | 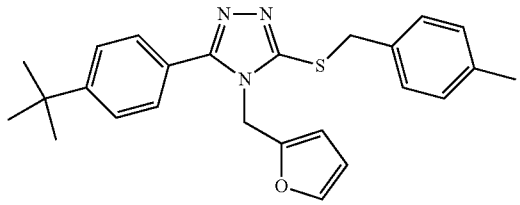 [SMILES: Cc1ccc(CSc2nnc(-c3ccc(C(C)(C)C)cc3)n2Cc2ccco2)cc1] |  |  | ** | * | *** | * | * | * | ** |
| ALD | 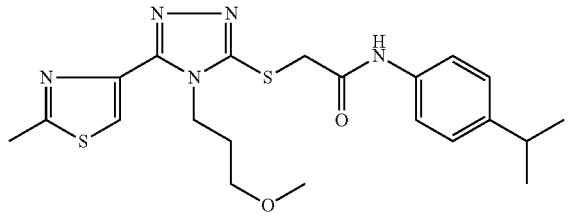 [SMILES: COCCCn1c(SCC(=O)Nc2ccc(C(C)C)cc2)nnc1-c1csc(C)n1] | * |  |  | NT | ** | NT | * | * | ND |
| ALE | 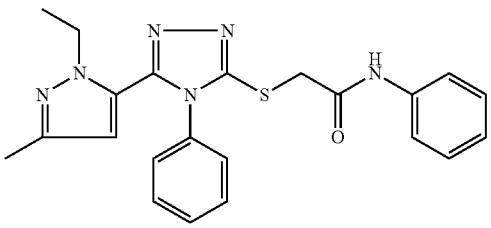 [SMILES: CCn1nc(C)cc1-c1nnc(SCC(=O)Nc2ccccc2)n1-c1ccccc1] | * | * | ** | * | ** | * | * | * | ** |
| ALF | 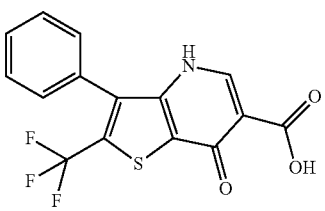 [SMILES: O=C(O)c1c[nH]c2c(-c3ccccc3)c(C(F)(F)F)sc2c1=O] | * | ** | * | ** | * | *** | * | * | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ALG | 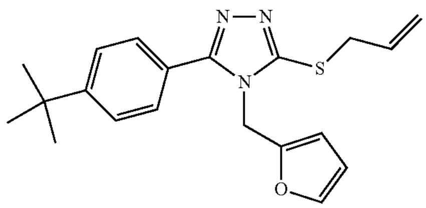 [SMILES: C=CCSc1nnc(-c2ccc(C(C)(C)C)cc2)n1Cc1ccco1] | * | *** | * | ** | * | *** | * | * | * |
| ALH | 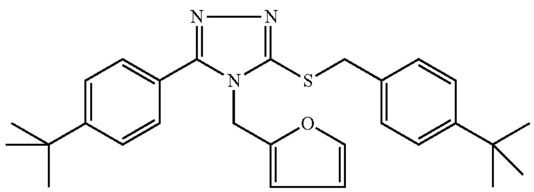 [SMILES: CC(C)(C)c1ccc(CSc2nnc(-c3ccc(C(C)(C)C)cc3)n2Cc2ccco2)cc1] | | * | ** | * | * | * | * | * | * |
| ALI | 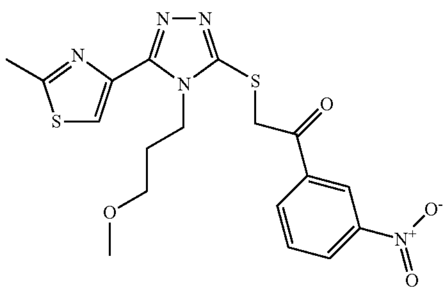 [SMILES: COCCCn1c(SCC(=O)c2cccc([N+](=O)[O-])c2)nnc1-c1csc(C)n1] |  |  | * | * | * | * | * | * | ** |
| ALJ | 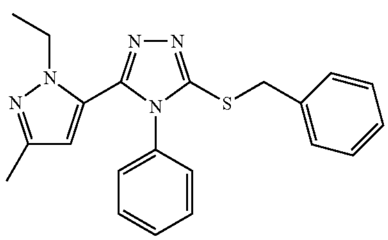 [SMILES: CCn1nc(C)cc1-c1nnc(SCc2ccccc2)n1-c1ccccc1] | * |  | * | * | *** | * | * | * | ** |
| ALK | 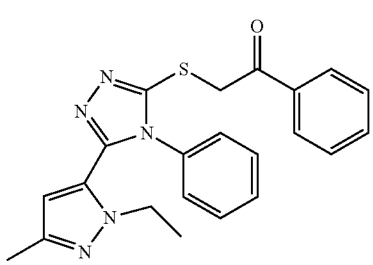 [SMILES: CCn1nc(C)cc1-c1nnc(SCC(=O)c2ccccc2)n1-c1ccccc1] | * | NT | * | ** | * | *** | * | * | ** |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ALL | 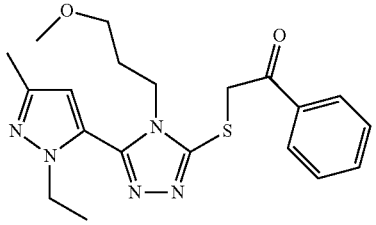 [SMILES: CCn1nc(C)cc1-c1nnc(SCC(=O)c2ccccc2)n1CCCOC] | ** | * | * | *** | * | *** | * | * | * |
| ALM | 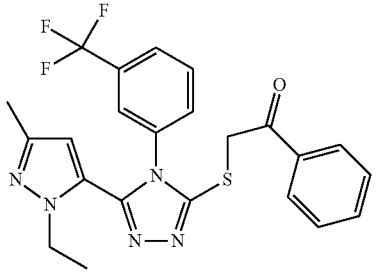 [SMILES: CCn1nc(C)cc1-c1nnc(SCC(=O)c2ccccc2)n1-c1cccc(C(F)(F)F)c1] | * |  | ** | * | ** | * | * | * | ** |
| ALN | 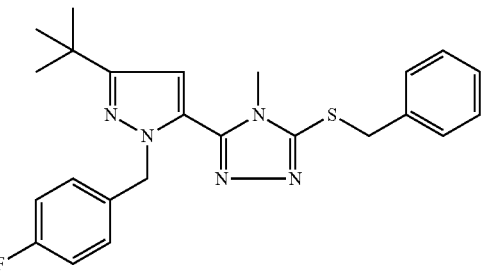 | NT | * | NT | ** | NT | * | * |  |  |
| ALO | 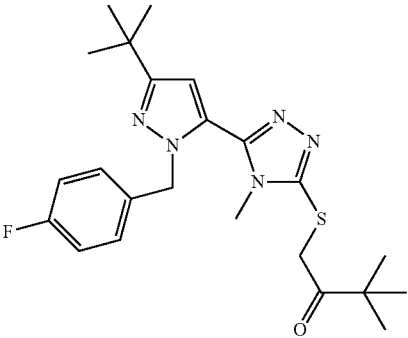 [SMILES: Cn1c(SCC(=O)C(C)(C)C)nnc1-c1cc(C(C)(C)C)nn1Cc1ccc(F)cc1] | *** | * | * | * | * | *** | * | * | * |
| ALP | 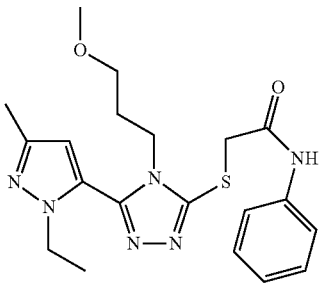 [SMILES: CCn1nc(C)cc1-c1nnc(SCC(=O)Nc2ccccc2)n1CCCOC] |  |  | * | * | * | * | * | * | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ALQ | 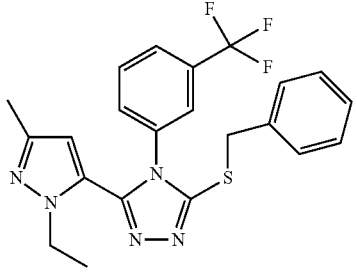 [SMILES: CCn1nc(C)cc1-c1nnc(SCc2ccccc2)n1-c1cccc(C(F)(F)F)c1] | * | * | * | * | * | * | * | * | * |
| ALR | 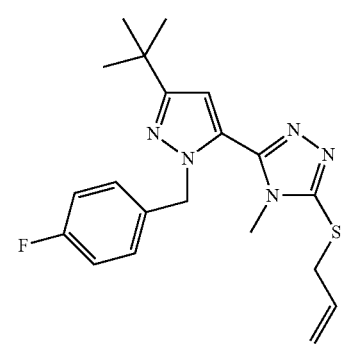 [SMILES: C=CCSc1nnc(-c2cc(C(C)(C)C)nn2Cc2ccc(F)cc2)n1C] | NT | * | NT | ** | NT | * | * | * | * |
| ALS | 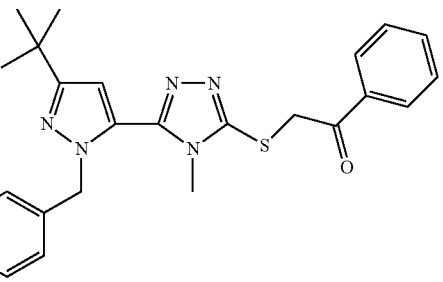 | * | * | * | NT | * | NT | * | * | ** |
| ALT | 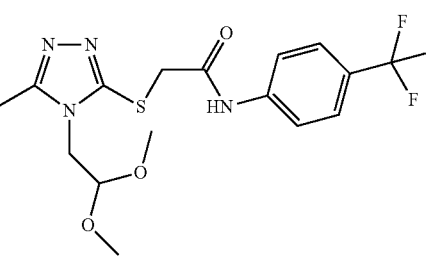 | * | *** | * |  |  | NT | * | * | ** |
| ALU | 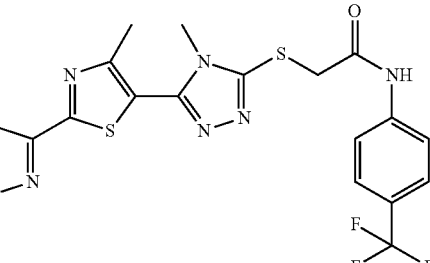 | * | * |  |  | * | * | * | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ALV | 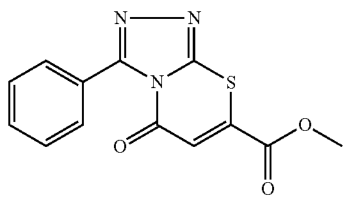 [SMILES: COC(=O)c1cc(=O)n2c(-c3ccccc3)nnc2s1] | * |  | * |  | * | *** | * | ** | ND |
| ALW | 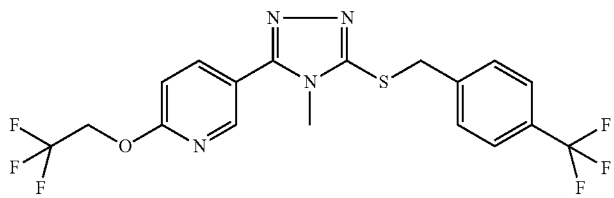 [SMILES: Cn1c(SCc2ccc(C(F)(F)F)cc2)nnc1-c1ccc(OCC(F)(F)F)nc1] | ** | * | * | * | * | * | * | ** | ND |
| ALX | 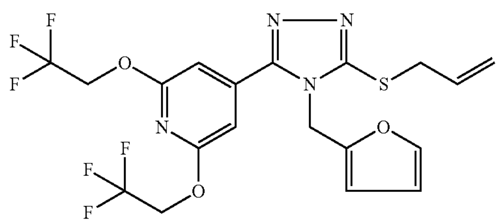 [SMILES: C=CCSc1nnc(-c2cc(OCC(F)(F)F)nc(OCC(F)(F)F)c2)n1Cc1ccco1] | * |  | * | * | ** | * | * | ** | * |
| ALY | 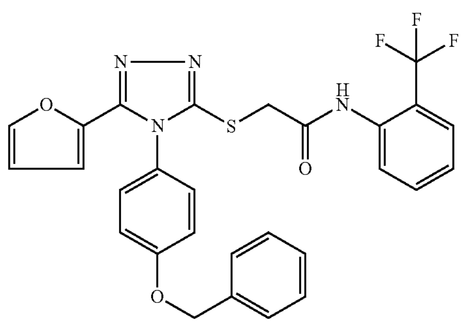 [SMILES: O=C(CSc1nnc(-c2ccco2)n1-c1ccc(OCc2ccccc2)cc1)Nc1ccccc1C(F)(F)F] | NT |  | * | * | ** | * | * |  |  |
| ALZ | 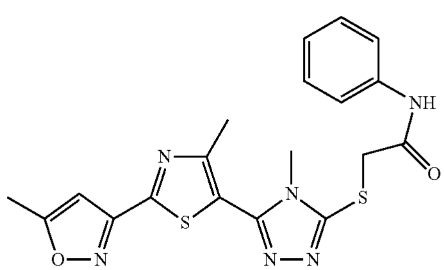 [SMILES: Cc1cc(-c2nc(C)c(-c3nnc(SCC(=O)Nc4ccccc4)n3C)s2)no1] | NT | * | *** | * | ** | * | * |  |  |
| AMA | 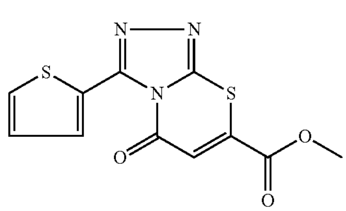 [SMILES: COC(=O)c1cc(=O)n2c(-c3cccs3)nnc2s1] | * | * | * | NT | ** | NT | * | ** | * |

TABLE 5-continued
| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AMB | 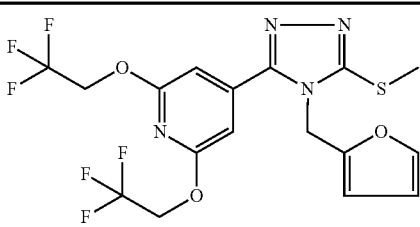 |  | * | * | * | * |  | * |  |  |
| AMC | 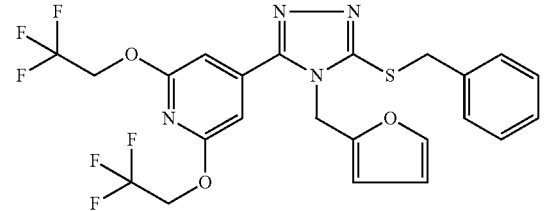 [SMILES: FC(F)(F)COc1cc(-c2nnc(SCc3ccccc3)n2Cc2ccco2)cc(OCC(F)(F)F)n1] | * | * |  |  |  |  | * |  |  |
| AMD | 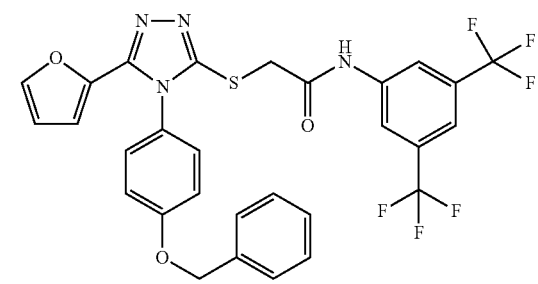 [SMILES: O=C(CSc1nnc(-c2ccco2)n1-c1ccc(OCc2ccccc2)cc1)Nc1cc(C(F)(F)F)cc(C(F)(F)F)c1] | ** | * | ** | * | ** | * | * | ** | * |
| AME | 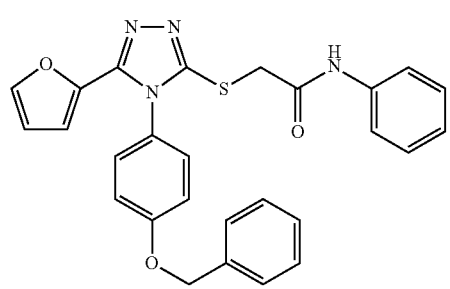 [SMILES: O=C(CSc1nnc(-c2ccco2)n1-c1ccc(OCc2ccccc2)cc1)Nc1ccccc1] | ** | * | * | * | ** | * | * | ** | * |
| AMF | 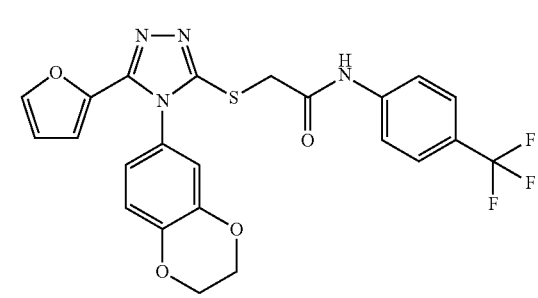 [SMILES: O=C(CSc1nnc(-c2ccco2)n1-c1ccc2c(c1)OCCO2)Nc1ccc(C(F)(F)F)cc1] | * | * | * | * | * | * | * |  |  |
| AMG | 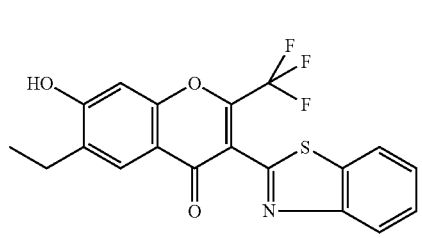 [SMILES: CCc1cc2c(=O)c(-c3nc4ccccc4s3)c(C(F)(F)F)oc2cc1O] | * | * | * | * | * | * | * | ** | ND |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AMH | 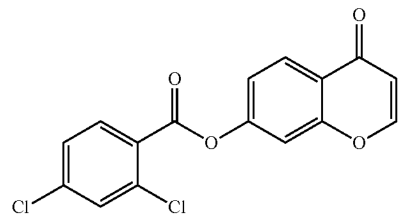 [SMILES: O=C(Oc1ccc2c(=O)ccoc2c1)c1ccc(Cl)cc1Cl] | * | * | * | NT | ** | NT | * |  |  |
| AMI | 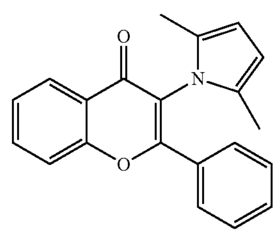 [SMILES: Cc1ccc(C)n1-c1c(-c2ccccc2)oc2ccccc2c1=O] | ** | * | ** | * | ** | * | * |  |  |
| AMJ | 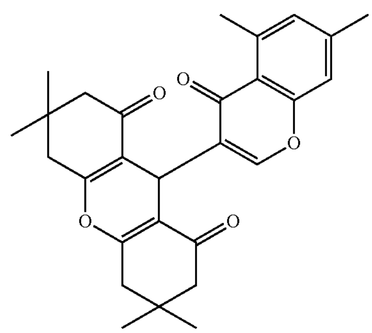 | * | * | ** | * | * | *** | * | ** | ND |
| AMK | 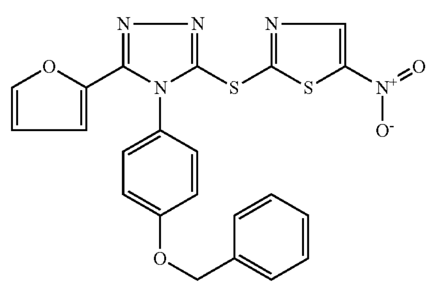 [SMILES: O=[N+]([O-])c1cnc(Sc2nnc(-c3ccco3)n2-c2ccc(OCc3ccccc3)cc2)s1] | NT |  | NT | * | NT | * | * |  |  |
| AML | 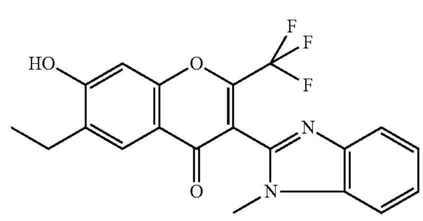 [SMILES: CCc1cc2c(=O)c(-c3nc4ccccc4n3C)c(C(F)(F)F)oc2cc1O] | ** | * | ** | * | *** | * | * | ** | ND |
| AMM | 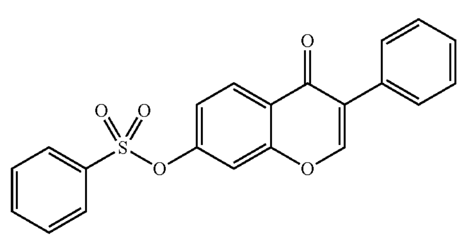 [SMILES: O=c1c(-c2ccccc2)coc2cc(OS(=O)(=O)c3ccccc3)ccc12] |  |  | * | * | * | ** | * | ** | ND |

TABLE 5-continued

| ID | STRUCTURE | MarA IGEN | MarA Lance | SoxS IGEN | SoxS Lance | Rob IGEN | Rob Lance | OD | CV | Luc |
|----|-----------|-----------|------------|-----------|------------|----------|-----------|-----|-----|-----|
| AMN | 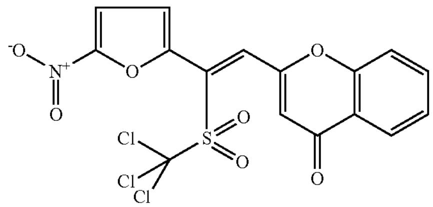 | NT | * | NT | ** | NT | * | * | * | * |
| AMO | 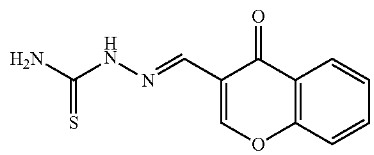 [SMILES: NC(=S)N/N=C/c1coc2ccccc2c1=O] | * | * | ** | * | * | ** | * |  |  |
| AMP | 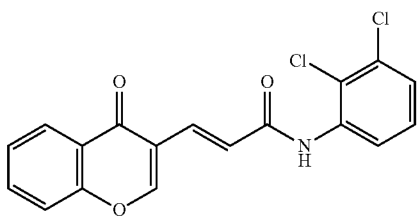 [SMILES: O=C(/C=C/c1coc2ccccc2c1=O)Nc1cccc(Cl)c1Cl] | ** | * | * | * | * | ** | * | ** | ND |
| AMQ | 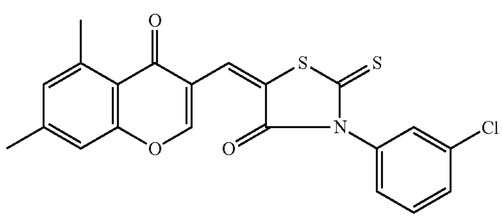 [SMILES: Cc1cc(C)c2c(=O)c(/C=C3/SC(=S)N(c4cccc(Cl)c4)C3=O)coc2c1] | * | * |  |  | ** | * | * | ** | ND |
| AMR | 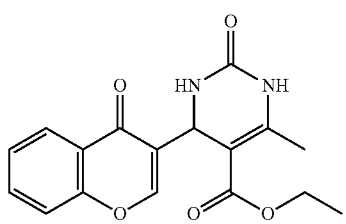 [SMILES: CCOC(=O)C1=C(C)NC(=O)NC1c1coc2ccccc2c1=O] | * | * | * | NT | ** | NT | * | * | * |
| AMS | 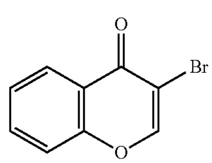 [SMILES: O=c1c(Br)coc2ccccc12] | * |  | * | * | * |  | * | ** | ND |
| AMT | 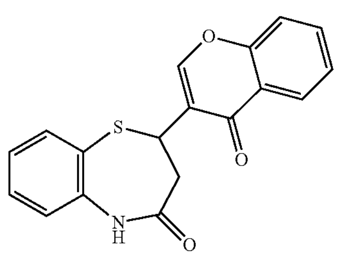 [SMILES: O=C1CC(c2coc3ccccc3c2=O)Sc2ccccc2N1] | * | * |  |  |  |  | * | * | ** |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| AMU | 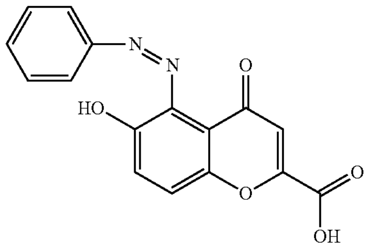 [SMILES: O=C(O)c1cc(=O)c2c(/N=N\c3ccccc3)c(O)ccc2o1] | * | * | * | * | *** | * | * |  |  |
| AMV | 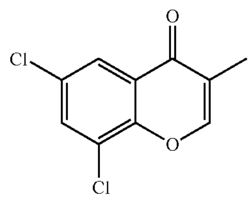 | * | * | ** | * | ** | * | * | * | * |
| AMX | 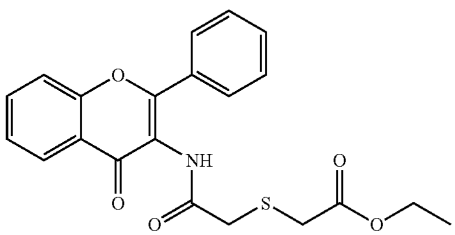 [SMILES: CCOC(=O)CSCC(=O)Nc1c(-c2ccccc2)oc2ccccc2c1=O] | * | NT |  | * | * | *** | * |  |  |
| AMY | 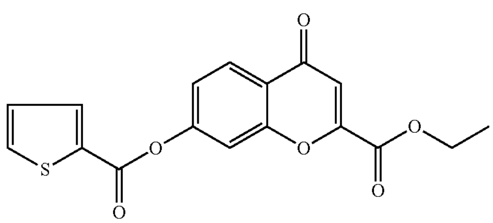 [SMILES: CCOC(=O)c1cc(=O)c2ccc(OC(=O)c3cccs3)cc2o1] |  | * | *** | * |  | * | * |  |  |
| AMZ | 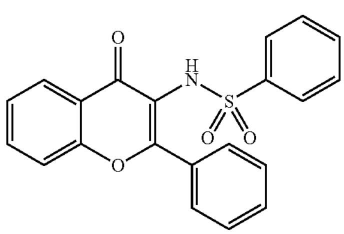 [SMILES: O=c1c(NS(=O)(=O)c2ccccc2)c(-c2ccccc2)oc2ccccc12] | *** | * | * | * | * | * | * | ** | ND |
| ANA | 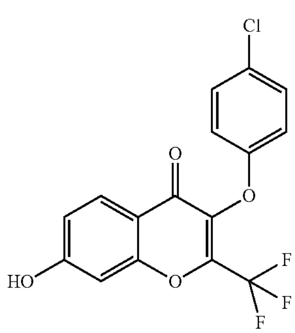 [SMILES: O=c1c(Oc2ccc(Cl)cc2)c(C(F)(F)F)oc2cc(O)ccc12] | *** | * | ** | * | *** | * | * |  |  |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ANB | 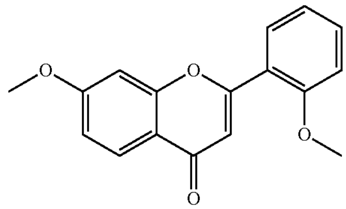 | ** | * | * | * | * | ** | * |  |  |
| ANC | 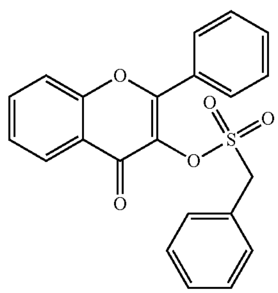 [SMILES: O=c1c(OS(=O)(=O)Cc2ccccc2)c(-c2ccccc2)oc2ccccc12] | NT | * | NT | ** | * | ** | * |  |  |
| AND | 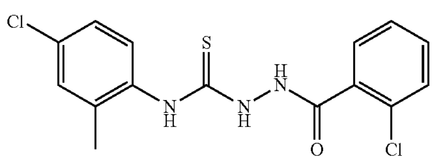 [SMILES: Cc1cc(Cl)ccc1NC(=S)NNC(=O)c1ccccc1Cl] | * | NT | * | *** | * | *** | * |  |  |
| ANE | 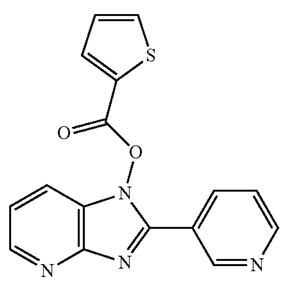 [SMILES: O=C(On1c(-c2cccnc2)nc2ncccc21)c1cccs1] | *** | * | *** | * | ** | * | * |  |  |
| ANF | 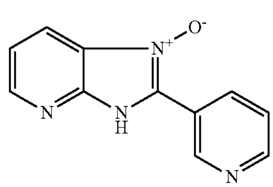 [SMILES: [O-][n+]1c(-c2cccnc2)[nH]c2ncccc21] | * | * | * | * |  | * | * |  |  |
| ANG | 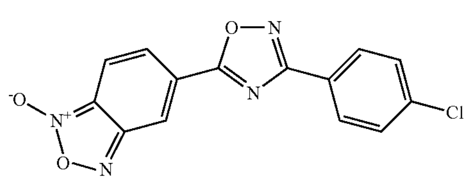 | ** | * | ** | * | ** | * | * |  |  |
| ANH | 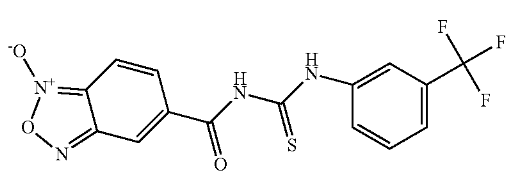 | * |  |  | *** | * | NT | * | ** | * |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ANI | 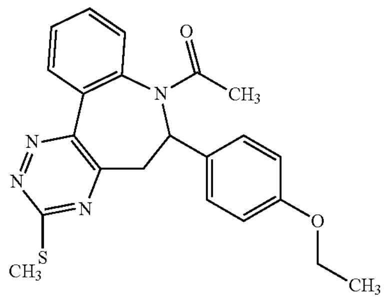 | NT | NT | NT | NT | NT | NT | NT | NT | NT |
| ANJ | 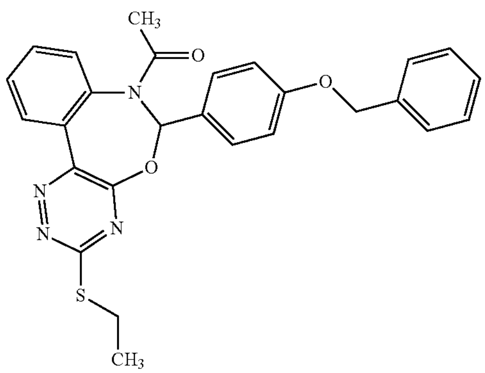 [SMILES: CCSc1nnc2c(n1)OC(c1ccc(OCc3ccccc3)cc1)N(C(C)=O)c1ccccc1-2] | NT | NT | NT | NT | NT | NT | NT | NT | NT |
| ANK | 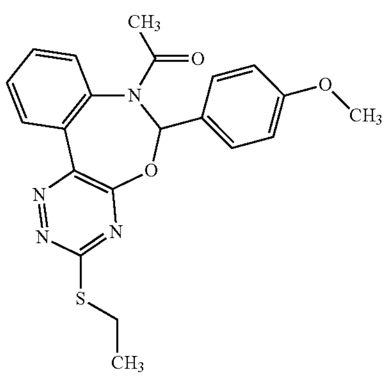 [SMILES: CCSc1nnc2c(n1)OC(c1ccc(OC)cc1)N(C(C)=O)c1ccccc1-2] | NT | NT | NT | NT | NT | NT | NT | NT | NT |
| ANL | 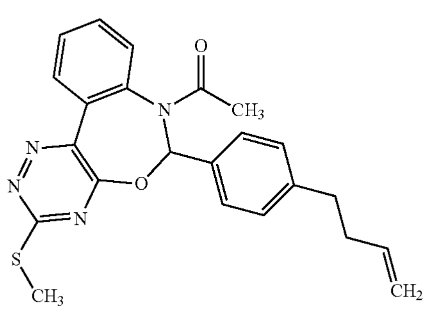 [SMILES: C=CCCc1ccc(C2Oc3nc(SC)nnc3-c3ccccc3N2C(C)=O)cc1] | NT | NT | NT | NT | NT | NT | NT | NT | |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ANM | 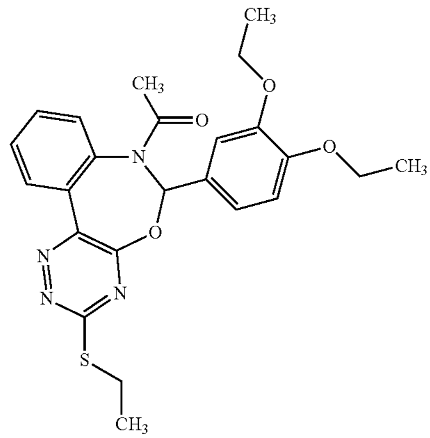 [SMILES: CCOc1ccc(C2Oc3nc(SCC)nnc3-c3ccccc3N2C(C)=O)cc1OCC] | NT | NT | NT | NT | NT | NT | NT | NT | NT |
| ANN | 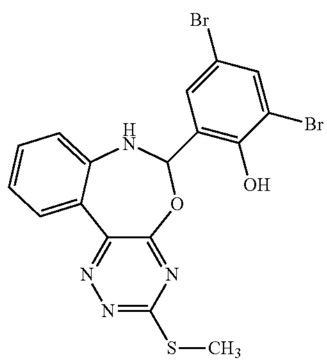 [SMILES: CSc1nnc2c(n1)OC(c1cc(Br)cc(Br)c1O)Nc1ccccc1-2] | NT | NT | NT | NT | NT | NT | NT | NT | NT |
| ANO | 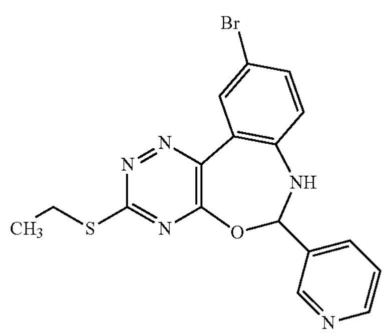 [SMILES: CCSc1nnc2c(n1)OC(c1cccnc1)Nc1ccc(Br)cc1-2] | NT | NT | NT | NT | NT | NT | NT | NT | NT |
| ANP | 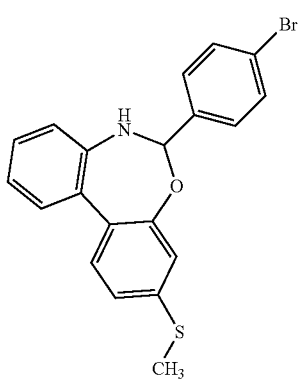 [SMILES: CSc1ccc2c(c1)OC(c1ccc(Br)cc1)Nc1ccccc1-2] | NT | * | NT | NT | * | NT | NT | NT | NT |

TABLE 5-continued

| ID | STRUCTURE | MarA IGEN | MarA Lance | SoxS IGEN | SoxS Lance | Rob IGEN | Rob Lance | OD | CV | Luc |
|---|---|---|---|---|---|---|---|---|---|---|
| ANQ | 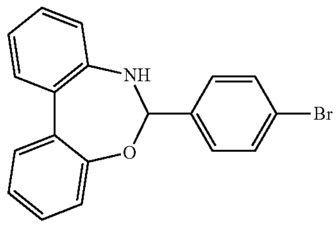 [SMILES: Brc1ccc(C2Nc3ccccc3-c3ccccc3O2)cc1] | NT | * | NT | NT | * | NT | NT | NT | NT |
| ANR | 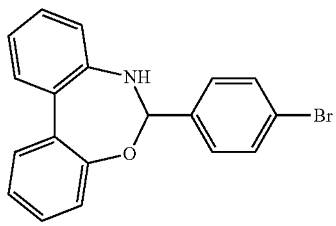 [SMILES: Brc1ccc(C2Nc3ccccc3-c3ccccc3O2)cc1] | NT | * | NT | NT | * | NT | NT | NT | NT |
| ANS | 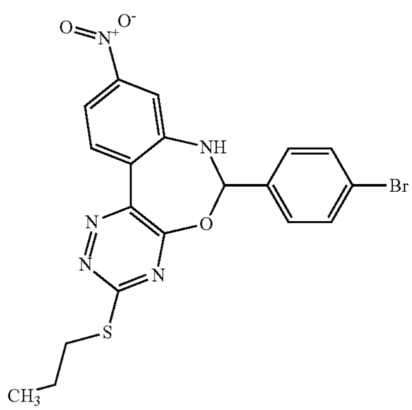 | NT | * | NT | NT | * | NT | NT | NT | NT |
| ANT | 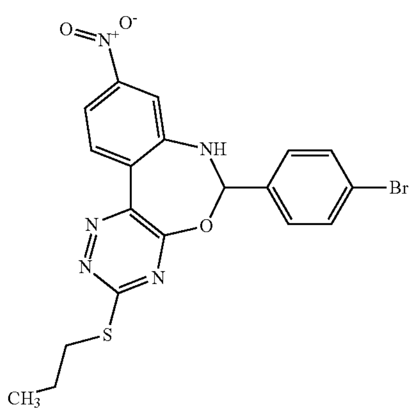 | NT | * | NT | NT | * | NT | NT | NT | NT |

Example 9

Luciferase Assay

The luciferase assay is used to determine if any of the compounds tested reduce the luminescent signal. This indicates that the test compounds affect regulation of micF, which in turn is regulated by Mar.

Materials

The bacteria used were *E. coli* AG112 KmicF-Luc. The negative control Bacteria were *E. coli* AG112. The test compounds were prepared in a 10 mg/mL DMSO stock solution.

Methods

Preparation of Inoculum

Inoculum (or "Starter Inoculum") was started the night before the day of the experiment by adding either a colony or stab of a glycerol stock to 2 mL of LB Broth. The Starter Inoculum was then placed in a 37° C. shaker incubator and allowed to grow overnight.

The following day, the Starter Inoculum was removed from the shaker and added to fresh LB Broth. For each plate to be assayed, 6 mL of LB broth was prepared, with 5-10 μL of Starter Inoculum being added per mL of added LB to form the "Test Inoculum". Typically, four plates of test compounds were assayed. In this typical example, 6 mL of LB Broth was used for each plate, or 24 mL of LB, followed by the addition of 5 μL/mL of Starter Inoculum, or 120 μL of Starter Inoculum to form the Test Inoculum.

Following preparation of the Test Inoculum, the Test Inoculum was placed in a 37 degree Celsius shaker and incubated for about 4 hours. The Test Inoculum was monitored for bacterial growth by taking OD readings at 535 nm on a spectrophotometer. The Test inoculum should be removed when the OD reaches between 0.6 and 1.5.

Preparation of Controls

Positive and negative controls were created by adding 2 uL DMSO to 198 uL LB Broth. At least 4 of each control were generated. Typically, there were 8 of each. 50 uL of diluted DMSO was added to 50 uL LB Broth in the assay plates.

Preparation of Compounds

The compounds were screened at 25 ug/mL. Two identical plates of each compound were set up: 1 clear plate for growth (or "Clear Plate"), 1 white plate for luminescence (or "White Plate"). Next, 2 μL of each compound was taken from the daughter plate (containing 10 mg/mL stock) and added to 198 μL of LB Broth. The sample was then mixed. Next, 25 μL of the diluted test compound was added to 25 μL of LB Broth in all of the assay plates. The concentration of the compound at this stage was 50 μg/mL.

Preparation of Plate

50 μL of the Test Inoculum was added to each well of the plates, except for the negative controls. Half of the negative controls received 50 μL of AG112, while the other half of the negative controls received 50 μL LB Broth. The final concentration of the test compound was 25 μg/mL.

The Clear Plates were placed in the plate reader and read at $OD_{535}$. This was the "Initial" growth read. The plates were then incubated plates for 5 hours at 37 degrees Celsius. After 5 hours, the plates were removed from the incubator. The Clear Plates were placed in the plate reader and read at $OD_{535}$. This was the "Final" growth read.

100 μL of Promega Steady-Glo reagent was added to each well (including all controls) in the White Plates. The plates, covered with aluminum foil, were then shaken on a plate shaker set at 10000 rpm for 10 min. The plates were then placed in plate reader and read on luminescence for 1 sec per well. This was the LUMINESCENT read.

Data Analysis

To determine whether the test compound inhibited growth, the Initial growth read was subtracted from the Final growth read. This was the Subtracted Growth. The same calculation was performed for the positive controls. The results for the positive controls were averaged. The % Inhibition of Growth was determined using the following formula:

100−(100*Subtracted growth of sample/Average growth of Pos Controls)

To determine whether compound inhibits Luciferase, use the following equation:

100−(100*Luminescence for Compound/Average Luminescence of Pos Controls)

ND indicates that a particular test compound did not appear to decrease the lumninesce of in this particular assay. * indicates that the luminescence was decreased somewhat and ** indicates that the luminescence was decreased a substantial amount. The results from this assay are also shown in Table 5.

Example 10

Synthesis of Various Benzimidazole Compounds

Scheme 1: Synthesis of (6-Nitro-benzoimidazol-1-yloxy)-acetic acid (6)

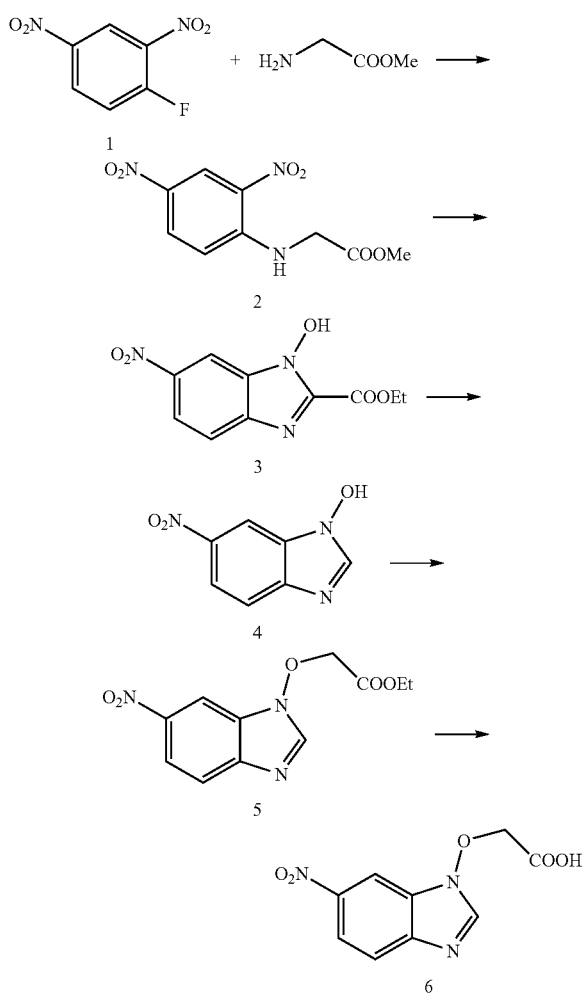

(2,4-Dinitro-phenylamino)-acetic acid methyl ester (2)

A mixture of 1-fluoro-2,4-dinitrobenzene (1) (15 g, 0.81 mmol), glycine methyl ester hydrochloride (11.5 g, 0.92 mmol), $K_2CO_3$ (22.3 g, 0.162 mmol) and methanol (300 mL) was heated at 60° C. for 30 minutes. After cooling in an ice bath, the resulting yellow precipitate was collected by filtration, washed with water and methanol and dried in vacuo. Yield 10.5 g (51%).

1-Hydroxy-6-nitro-1H-benzoimidazole-2-carboxylic acid ethyl ester (3)

A solution of (2,4-Dinitro-phenylamino)-acetic acid methyl ester (2) (3 g, 11.8 mmol) in ethanol (100 mL) was heated to 70° C. After addition of 2.4 mL (24.2 mmol) of piperidine, the solution was refluxed at 70° C. After 2 hours, the solvent was removed in vacuo and the resulting residue was dissolved in water (100 mL). Acidification of the solution with HCl yielded a yellow precipitate, which was collected by filtration, washed with water and ethanol and dried in vacuo. Yield 1.9 g, (63%) of yellow solid.

6-Nitro-benzoimidazol-1-ol hydrochloride (4)

A mixture of 1-hydroxy-6-nitro-1H-benzoimidazole-2-carboxylic acid ethyl ester (3) (5 g, 20 mmol) and concentrated HCl (100 mL) was refluxed for 3 hours. After cooling the mixture to room temperature, the resulting solid was collected by filtration. Yield 1.9 g (44%) of the HCl salt.

6-Nitro-benzoimidazol-1-yloxy)-acetic acid ethyl ester (5)

To a mixture of 6-nitro-benzoimidazol-1-ol hydrochloride (4) (2 g, 9.3 mmol) and $K_2CO_3$ (2.56 g, 19 mmol) in DMF (60 mL) was added ethyl bromoacetate (3.1 g, 19 mmol) with stirring at room temperature. After 4 hours, the reaction mixture was poured into water. The resulting solid was collected by filtration, washed with water and ethanol and dried in vacuo. Yield 1.2 g (49%).

(6-Nitro-benzoimidazol-1-yloxy)-acetic acid (6)

A mixture of 6-nitro-benzoimidazol-1-yloxy)-acetic acid ethyl ester (5) (250 mg, 0.94 mmol), THF (5 mL), water (1 mL) and concentrated HCl (1 mL) was heated to reflux for 2 hours. The reaction mixture was evaporated and the crude residue was purified by HPLC (21.2×250 mm Phenomenex Luna C18(2) column; flow rate=20 mL/min; linear gradient 0-100% B over 30 minutes; A Buffer=water with 0.1% TFA, B Buffer=acetonitrile with 0.1% TFA). HPLC solvents removed in vacuo to yield yellow solid. Yield 65 mg (29%).

Synthesis of 2-aryl-benzimidazoles

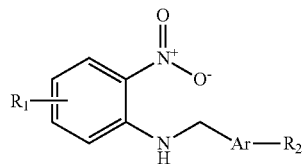

$R_1$=$NO_2$, F, Cl, Br, $NH_2$, NHAc, COMe, COPh, $CF_3$, COOH, OMe, CN, $CONH_2$, $^tBu$, COOR, etc.
$R_2$=substituted or unsubstituted phenyl, substituted or unsubstituted heterocycle (5 or 6 membered rings etc.)

To a solution of $R_1$-substituted-2-nitrofluorobenzene in DMF or DMSO, was added 2 equiv of $NaHCO_3$. Ca. 1.5-2 equivalents of the corresponding substituted benzylamine (e.g., $R_2$=—H, -Me, —$NH_2$, —Cl, —OMe, —C(=NH)$NH_2$ etc.) was added slowly to the reaction mixture with vigorous stirring. The reaction was monitored by HPLC/TLC and upon complete consumption of the starting material, the reaction mixture was poured into ice water and the precipitate was filtered, washed with excess water and air-dried. In some cases, upon pouring the reaction mixture in water, treatment with 10% dilute HCl (aq.) was needed to wash away excess salts and any base. The material thus obtained is usually pure, and can be used for the next step without any further purification. Yields are between 50-95%. Purity of each of the compounds was confirmed using $^1H$ NMR spectroscopy, HPLC, and MS.

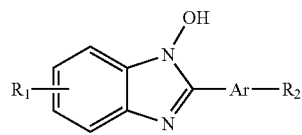

$R_1$=$NO_2$, F, Cl, Br, $NH_2$, NHAc, COMe, COPh, $CF_3$, COOH, OMe, CN, $CONH_2$, $^tBu$, COOR, etc.
$R_2$=substituted or unsubstituted phenyl, substituted or unsubstituted heterocycle (5 or 6 membered rings etc.)

A solution/suspension of the substituted nitro compound (from the previous step) in methanol or THF or methanol/DMF was warmed to 50° C., treated with an excess base (NaH, $CH_3O^-Na^+$, aq. NaOH, etc.) and stirred. HPLC monitoring of the reaction mixture indicated the completion (10 min-12 h depending upon the substituent) of the reaction. The reaction mixture was poured over ice, treated with dil. HCl to acidic pH, and the resulting precipitate was filtered, washed thoroughly with dil HCl, and finally with water. In cases, where the product was water soluble, the reaction mixture was quenched with ice-water, evaporated to dryness, and the product was purified via extraction, washing, or if necessary, via chromatography. All the compounds were characterized using HPLC, MS, and $^1H$ NMR spectroscopy. Yields: 30-90%

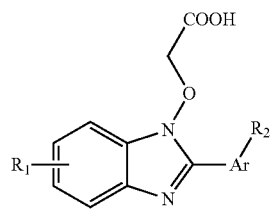

$R_1$=$NO_2$, F, Cl, Br, $NH_2$, NHAc, COMe, COPh, $CF_3$, COOH, OMe, CN, $CONH_2$, $^tBu$, COOR, etc.
$R_2$=substituted or unsubstituted phenyl, substituted or unsubstituted heterocycle (5 or 6 membered rings etc.)

To a DMF solution of the benzimidazole-N-hydroxide (from the previous step) 1.5-2 equiv of anhydrous $Na_2CO_3$ was added, followed by the addition of 1.2-1.8 equiv of bromo-acetic acid. The reaction mixture was stirred at room temperature and monitored via HPLC/MS. Upon completion of the reaction, the reaction mixture was poured over ice and treated with dil. HCl to an acidic pH. In most cases the product crashed out of the solution, which was filtered, washed thoroughly with dil. HCl, and water and air dried. The product thus obtained is usually pure, but when needed, it could be recrystallized from DMF/ether or methanol/ether or dichloromethane/hexane solvent systems. In cases, where the product is water soluble, the quenched reaction mixture was concentrated to a volume where the product started to crash out. The final product was purified via chromatography in such cases or in cases that the crude material is impure. The final product was characterized using HPLC, MS, $^1H$ NMR spectroscopy, and in some representative cases, using CHN analyses and $^{13}C$ NMR spectroscopy as well.

Scheme 2

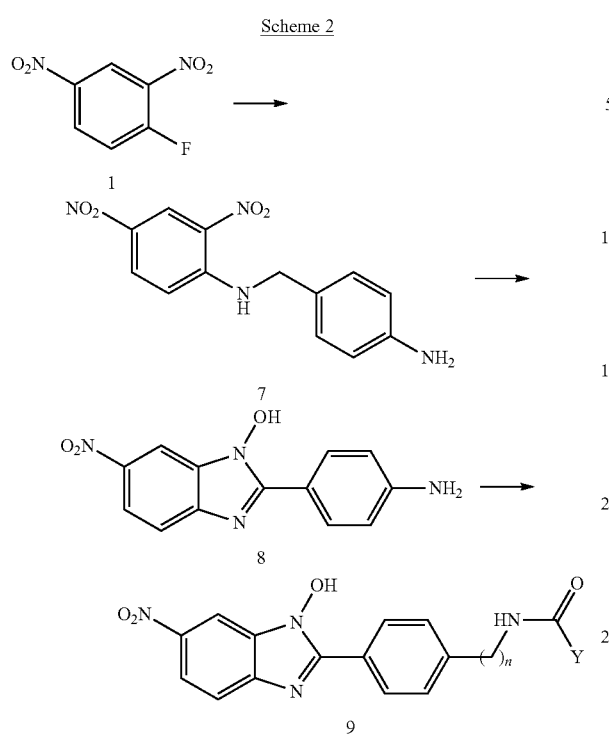

Y = substituted or unsubstituted phenyl, substituted or unsubstituted heterocycle (5 or 6 membered rings), etc.

Preparation of N-(4-aminobenzyl)-2,4-dinitroaniline (7)

To a solution of 4-aminobenzylamine (25.5 mL, 225 mmol) and powdered NaHCO$_3$ (94.5 g, 1125 mmol) in anhydrous DMF (300 mL) was added 2,4-dinitrofluorbenzene (1) (18.8 mL, 150 mmol) dropwise at room temperature. After 2 hours, the solution was slowly diluted with water (1000 mL) to precipitate the product, which was collected on a fritted funnel while rinsing with water until the eluent was colorless. The solid was further dried under high vacuum to afford 43.0 g as a bright orange solid in 99% yield.

Preparation of 6-nitro-2-(4-aminophenyl)-1-hydroxybenzimidazole (8)

To a solution of N-(4-aminobenzyl)-2,4-dinitroaniline (7) (21.6 g, 74.9 mmol) in anhydrous EtOH (300 mL) and anhydrous DMF (75 mL) was slowly added sodium methoxide (30% w/w) (69.1 g, 375 mmol) at room temperature under argon atmosphere, followed by heating to 60° C. for 2 hours. After cooling to ambient termperature, the solution was diluted with water (700 mL) and then acidified with saturated citric acid. The resulting precipitate was collected on a sintered funnel while rinsing with water. The crude product was recrystallized in hot EtOH to afford 18.1 g as a brown solid in 90% yield.

General procedure for the preparation of N-acyl-6-nitro-2-(4-aminophenyl)-1-hydroxybenzimidazoles (9)

To a solution of 6-nitro-2-(4-aminophenyl)-1-hydroxybenzimidazole (8) (270 mg, 1.00 mmol) in anhydrous pyridine (2.0 mL) was added acid chlorides[a] (2.5 mmol) or the in situ mixed anhydrides at room temperature. (The mixed anhydride was prepared by adding trimethylacetyl chloride (2.5 mmol) dropwise to a solution of the carboxylic acid (2.55 mmol) in anhydrous pyridine at 0° C. After 1 hour, 6-nitro-2-(-4-aminophenyl)-1-hydroxybenzimidazole was added in one portion.) After stirring for 2-3 hours at room temperature, the solution was diluted with 3M NaOH (6.0 mL) and stirred for another hour. The deep amber solution was diluted with water (100 mL) and then acidified with saturated citric acid. The resulting precipitate was collected on a sintered funnel while rinsing with water. The crude product was further purified by either prepatory HPLC or by recrystallization in hot ethanol or a mixture of hot ethanol and chloroform.

Scheme 3

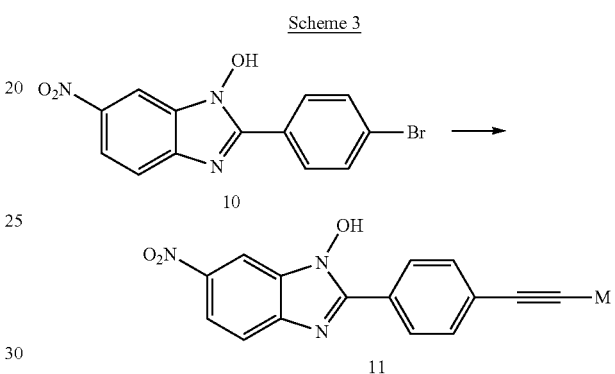

M = substituted or unsubstituted phenyl, substituted or unsubstituted heterocycle (5 or 6 membered rings), etc

Preparation of 6-nitro-2-(4-phenylethynyl-phenyl)-1-hydroxybenzimidazoles (11)

A solution of 6-nitro-2-(4-bromophenyl)-1-hydroxybenzimidazole (10) (334 mg, 1 mmol) in DMF (2 mL) and Et$_3$N (1 mL) was degassed with argon for 30 minutes. Phenylacetylene (408 mg, 4 mmol), CuI (38 mg, 0.2 mmol), and Pd(PPh$_3$)$_4$ (116 mg, 0.1 mmol) were added. Degassing was continued for another 5 minutes and the reaction vial was placed in a sand bath preheated to 100° C. overnight. The reaction was cooled and diluted with 50 mL of water and the pH was adjusted to pH 4 with 10% aqueous HCl. The solids were filtered and triturated successively with 1,2-dichloroethane and warm methanol. The resultant yellow solid was further purifed by passing through a silica gel flash column eluting with EtOAc:Hexanes (1:1). Fractions containing the product were pooled and evaporated to provide 27 mg of a yellow solid.

Scheme 4

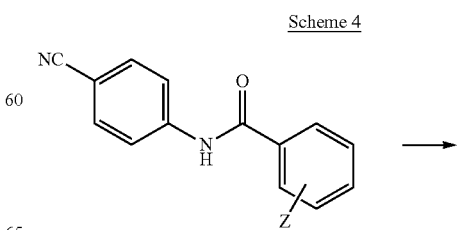

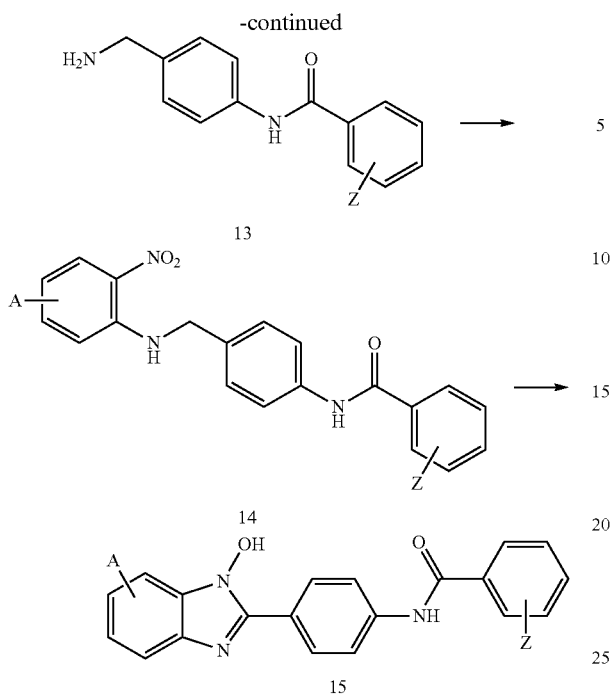

A = F, CF₃, CN, COOH, alkylamine, COCH₃, H, etc.
Z = F, alkylamine, etc.

Preparation of 4-phenylamidobenzylamine (13)

In a pressure reaction, 4-dimethylaminophenylamidobenzonitrile (12) (26 g, 98 mmol) was dissolved in anhydrous THF (940 mL), and the solution was purged with argon for 2-3 minutes, followed by the addition of 11 mL of uniformly suspended catalyst (Raney® nickel 2400, suspension in water). After addition of a small amount of methanol to the suspension, the reactor was pressurized at 55 psi H₂ while stirring vigorously for 2.5 hours. The reaction mixture was filtered over a bed of diatomaceous earth (e.g. Celite®), and washed 3×100 mL of anhydrous THF. The combined filtrates were evaporated to dryness, and further dried under high vacuum to afford 25.1 g of white solid.

Preparation of 4-[(2-nitro-phenylamino)-methyl]-phenylbenzamide (14)

To a solution of 4-phenylamidobenzylamine (13) (225 mmol) and powdered NaHCO₃ (1125 mmol) in anhydrous DMF (300 mL) was added substituted 4-nitrofluorbenzene (150 mmol) dropwise at room temperature. After 2 h, the solution was slowly diluted with water (1000 mL) to precipitate the product, which was collected on a fritted funnel while rinsing with water until the eluent was colorless. The solid was further dried under high vacuum to afford the product.

Preparation of 4-(benzimidazol-2-yl)-phenylbenzamide (15)

To a solution of 4-[(2-nitro-phenylamino)-methyl]-phenylbenzamide (14) (74.9 mmol) in anhydrous EtOH and anhydrous DMF (75 mL) was slowly added sodium methoxide (30% w/w) (375 mmol) at room temperature under argon atmosphere, followed by heating to 60° C. for 2 h. After cooling to ambient termperature, the solution was diluted with water (700 mL) and then acidified with saturated citric acid. The resulting precipitate was collected on a sintered funnel while rinsing with water. The crude product was recrystallized in hot EtOH.

Scheme 5

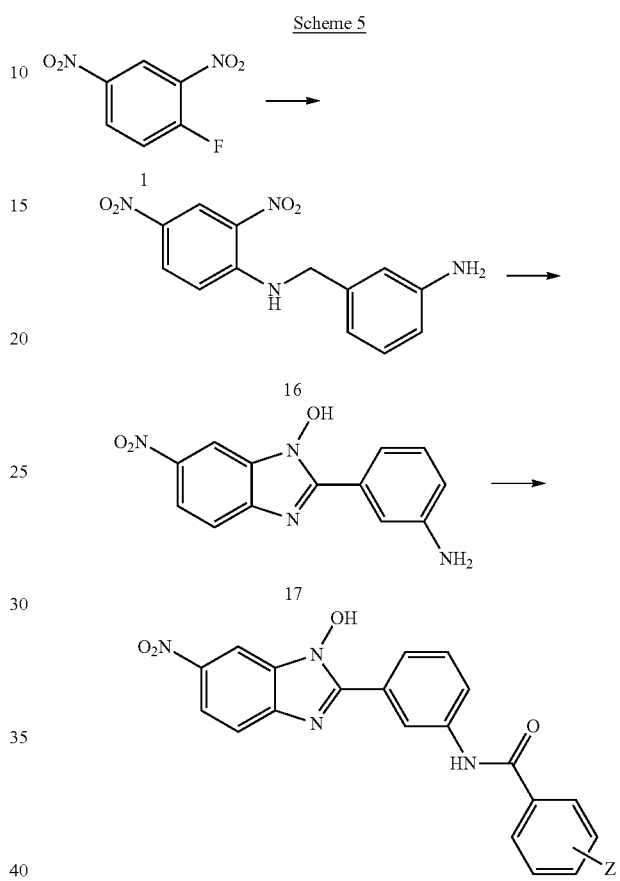

Z = F, alkylamine, etc.

Preparation of 3-aminobenzyldinitrophenylamine (16)

To a solution of 3-aminobenzylamine (225 mmol) and powdered NaHCO₃ (1125 mmol) in anhydrous DMF (300 mL) was added 2,4-dinitrofluorbenzene (1) (18.8 mL, 150 mmol) dropwise at room temperature. After 2 hours, the solution was slowly diluted with water (1000 mL) to precipitate the product, which was collected on a fritted funnel while rinsing with water until the eluent was colorless. The solid was further dried under high vacuum.

Preparation of 3-aminonitrobenzoimidazolol (17)

To a solution of 3-aminobenzyldinitrophenylamine (16) (74.9 mmol) in anhydrous EtOH (300 mL) and anhydrous DMF (75 mL) was slowly added sodium methoxide (30% w/w) (375 mmol) at room temperature under argon atmosphere, followed by heating to 60° C. for 2 h. After cooling to ambient termperature, the solution was diluted with water (700 mL) and then acidified with saturated citric acid. The resulting precipitate was collected on a sintered funnel while rinsing with water. The crude product was recrystallized in hot EtOH.

Preparation of 4-(benzoimidazolyl)phenylbenzamide (18)

To a solution of 3-aminonitrobenzoimidazolol (17) (1.00 mmol) in anhydrous pyridine (2.0 mL) was added acid chlorides[a] (2.5 mmol) or the in situ mixed anhydrides at room temperature. (The mixed anhydride was prepated by adding trimethylacetyl chloride (2.5 mmol) dropwise to a solution of the carboxylic acid (2.55 mmol) in anhydrous pyridine at 0° C., After 1 hour, 6-nitro-2-(-4-aminophenyl)-1-hydroxybenzimidazole was added in one portion.) After stirring for 2-3 h at room temperature, the solution was diluted with 3M NaOH (6.0 mL) and stirred for another 1 h. The deep amber solution was diluted with water (100 mL) and then acidified with saturated citric acid. The resulting precipitate was collected on a sintered funnel while rinsing with water. The crude product was further purified by either prepatory HPLC or by recrystallization in hot ethanol or a mixture of hot ethanol and chloroform.

Example 11

SoxS Gel Shift Assay of Test Compounds

The test compounds were diluted in DMSO to the required concentration and added to the appropriate wells. Protein (SoxS) was added to the wells in EMSA buffer at a concentration that was determined to cause a 50% shift of the DNA. The plates were then covered, mixed and shaked for 30 minutes at room temperature to allow for compound-protein binding.

Ten µl of DNA mix (2.4 µl 5×EMSA buffer, 0.2 µl poly (dIdC), 1 µl $^{33}$P-DNA probe, 7.4 µl dH$_2$O per reaction) was then added to each well. The final DNA concentrations were approximately 1 nM. The samples were then mixed for 15 minutes at room temperature which allowed protein-DNA complexes to form.

Electrophoresis was started at approximately 110V and the gels were pre-run for 10-15 minutes. Five µl of gel loading buffer was then added to each sample and mixed. Fifteen µl of each sample was then loaded onto gel. The gel was electrophoresed at 110V for approximately 2 hours or until the bromophenol blue marker approached the bottom of the gel. The gel was then transfered to Whatman filter paper, covered, and dried at 80° C. for approximately 30 minutes. Autoradiography film was exposed to the gel overnight and developed.

The probe alone well showed a single DNA species (unbound) of an apparent low molecular weight. Controls containing protein showed approximately 50% of the DNA at a shifted or bound position (apparent higher mwt) and 50% at the same position as the probe alone (free DNA). Samples containing test compounds showed ratios of bands between these two controls. A compound that completely inhibited protein-DNA binding appeared to be similar to that of the probe alone. Table 6 shows the results of this assay. Compounds which showed superior inhibition of DNA binding are indicated by "*," compounds which showed very good or good inhibition of DNA binding are indicated by "" or "*" respectively. Compounds which showed some inhibition of DNA binding are indicated by "-."

TABLE 6

| ID | STRUCTURE | SoxS Gel Shift |
|---|---|---|
| ANI | 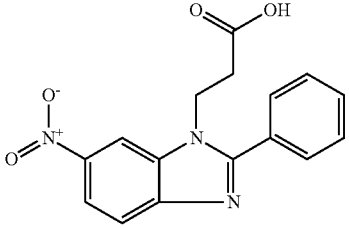 [SMILES: O=C(O)CCn1c(-c2ccccc2)nc2ccc([N+](=O)[O-])cc21] | — |
| ANJ | 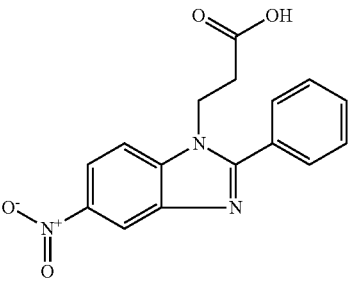 [SMILES: O=C(O)CCn1c(-c2ccccc2)nc2cc([N+](=O)[O-])ccc21] | — |

TABLE 6-continued
| ID | STRUCTURE | SoxS Gel Shift |
|----|-----------|----------------|
| ANK | 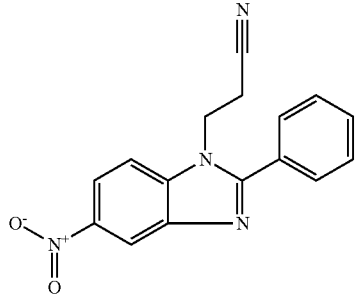 [SMILES: N#CCCn1c(-c2ccccc2)nc2cc([N+](=O)[O-])ccc21] | — |
| ANL | 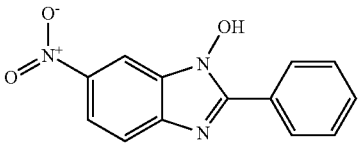 [SMILES: O=[N+]([O-])c1ccc2nc(-c3ccccc3)n(O)c2c1] | *** |
| ANM | 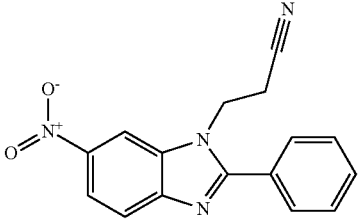 [SMILES: N#CCCn1c(-c2ccccc2)nc2ccc([N+](=O)[O-])cc21] | — |
| ANN | 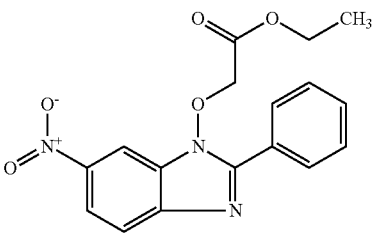 [SMILES: CCOC(=O)COn1c(-c2ccccc2)nc2ccc([N+](=O)[O-])cc21] | — |
| ANO | 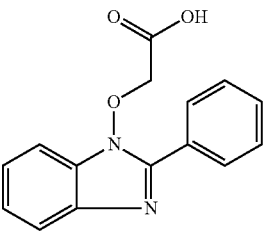 [SMILES: O=C(O)COn1c(-c2ccccc2)nc2ccccc21] | * |
| ANP | 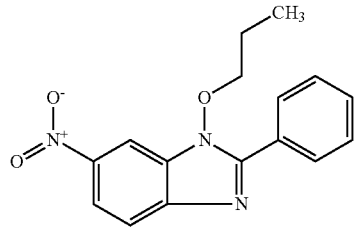 [SMILES: CCCOn1c(-c2ccccc2)nc2ccc([N+](=O)[O-])cc21] | — |

TABLE 6-continued

| ID | STRUCTURE | SoxS Gel Shift |
|---|---|---|
| ANQ | 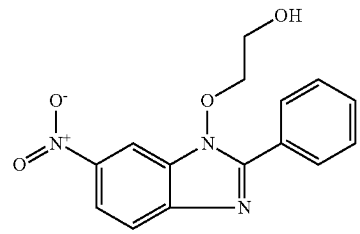 [SMILES: O=[N+]([O-])c1ccc2nc(-c3ccccc3)n(OCCO)c2c1] | * |
| ANR | 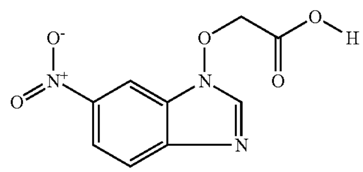 [SMILES: O=C(O)COn1cnc2ccc([N+](=O)[O-])cc21] | — |
| ANS | 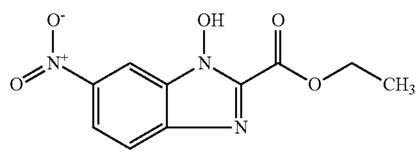 [SMILES: CCOC(=O)c1nc2ccc([N+](=O)[O-])cc2n1O] | — |
| ANT | 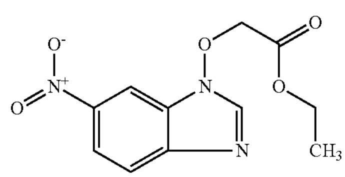 [SMILES: CCOC(=O)COn1cnc2ccc([N+](=O)[O-])cc21] | ** |
| ANU | 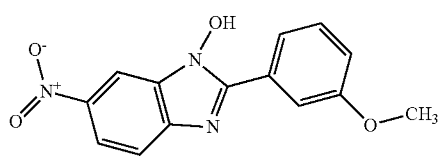 [SMILES: COc1cccc(-c2nc3ccc([N+](=O)[O-])cc3n2O)c1] | — |
| ANV | 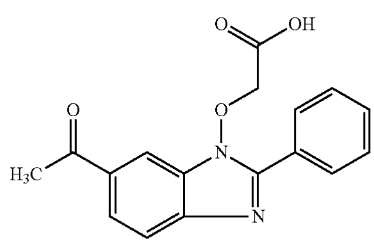 [SMILES: CC(=O)c1ccc2nc(-c3ccccc3)n(OCC(=O)O)c2c1] | * |
| ANW | 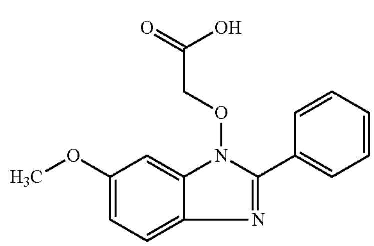 [SMILES: COc1ccc2nc(-c3ccccc3)n(OCC(=O)O)c2c1] | — |

TABLE 6-continued

| ID | STRUCTURE | SoxS Gel Shift |
|---|---|---|
| ANX | 2-(6-carboxy-2-phenyl-1H-benzimidazol-1-yloxy)acetic acid | — |
| ANY | 2-(6-benzoyl-2-phenyl-1H-benzimidazol-1-yloxy)acetic acid | — |
| ANZ | 2-(6-cyano-2-phenyl-1H-benzimidazol-1-yloxy)acetic acid | — |
| AOA | 2-(2-phenyl-6-(trifluoromethyl)-1H-benzimidazol-1-yloxy)acetic acid | — |
| AOB | 2-(6-fluoro-2-phenyl-1H-benzimidazol-1-yloxy)acetic acid | — |
| AOC | 2-(6-(methoxycarbonyl)-2-phenyl-1H-benzimidazol-1-yloxy)acetic acid | — |
| AOD | 1-hydroxy-2-phenyl-1H-benzimidazole | — |

TABLE 6-continued

| ID | STRUCTURE | SoxS Gel Shift |
|---|---|---|
| AOE | 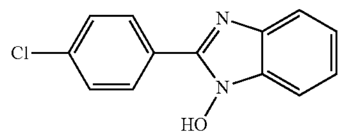 [SMILES: On1c(-c2ccc(Cl)cc2)nc2ccccc21] | * |
| AOF | 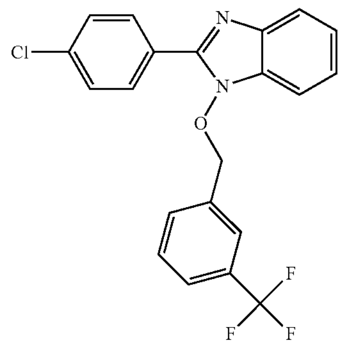 [SMILES: FC(F)(F)c1cccc(COn2c(-c3ccc(Cl)cc3)nc3ccccc32)c1] | — |
| AOG | 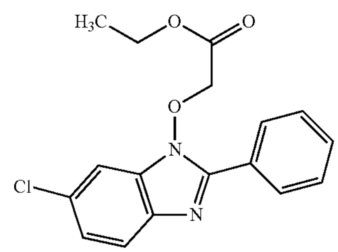 [SMILES: CCOC(=O)COn1c(-c2ccccc2)nc2ccc(Cl)cc21] | — |
| AOH | 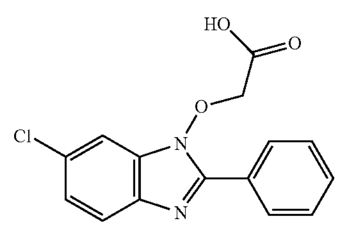 [SMILES: O=C(O)COn1c(-c2ccccc2)nc2ccc(Cl)cc21] | — |
| AOI | 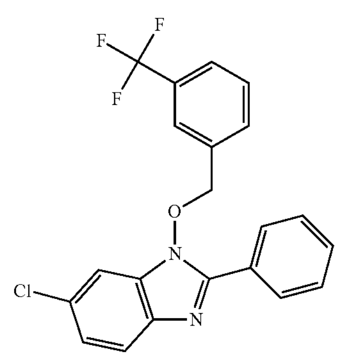 [SMILES: FC(F)(F)c1cccc(COn2c(-c3ccccc3)nc3ccc(Cl)cc32)c1] | — |
| AOJ | 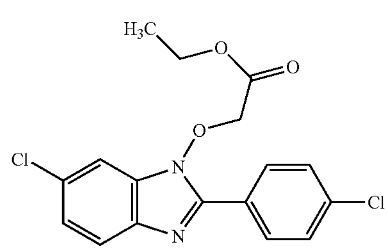 [SMILES: CCOC(=O)COn1c(-c2ccc(Cl)cc2)nc2ccc(Cl)cc21] | * |

TABLE 6-continued
| ID | STRUCTURE | SoxS Gel Shift |
|---|---|---|
| AOK | 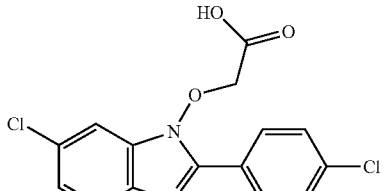 | — |
| AOL | 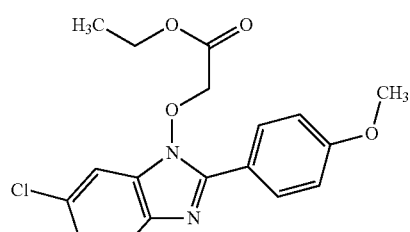 | — |
| AOM | 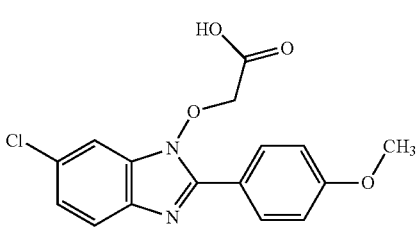 [SMILES: COc1ccc(-c2nc3ccc(Cl)cc3n2OCC(=O)O)cc1] | — |
| AON | 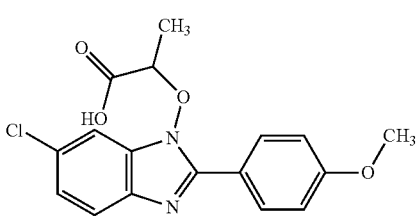 [SMILES: COc1ccc(-c2nc3ccc(Cl)cc3n2OC(C)C(=O)O)cc1] | * |
| AOO | 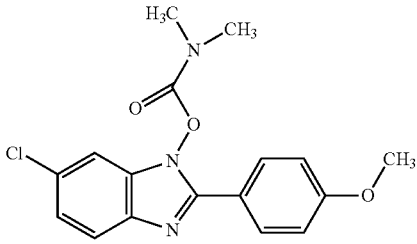 [SMILES: COc1ccc(-c2nc3ccc(Cl)cc3n2OC(=O)N(C)C)cc1] | * |
| AOP | 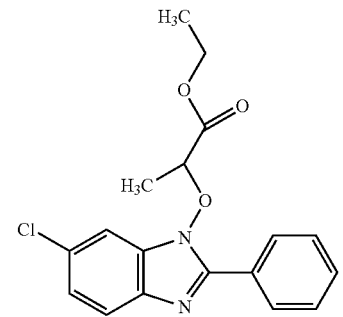 [SMILES: CCOC(=O)C(C)On1c(-c2ccccc2)nc2ccc(Cl)cc21] | * |

TABLE 6-continued
| ID | STRUCTURE | SoxS Gel Shift |
|---|---|---|
| AOQ | 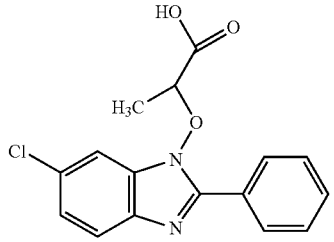 [SMILES: CC(On1c(-c2ccccc2)nc2ccc(Cl)cc21)C(=O)O] | — |
| AOR | 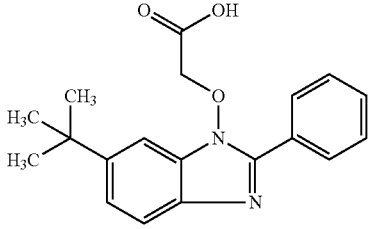 [SMILES: CC(C)(C)c1ccc2nc(-c3ccccc3)n(OCC(=O)O)c2c1] | — |
| AOS | 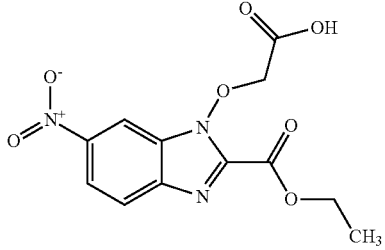 [SMILES: CCOC(=O)c1nc2ccc([N+](=O)[O-])cc2n1OCC(=O)O] | * |
| AOT | 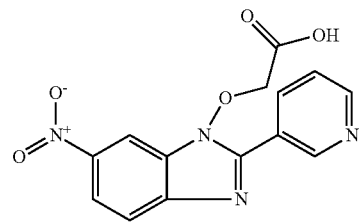 [SMILES: O=C(O)COn1c(-c2cccnc2)nc2ccc([N+](=O)[O-])cc21] | — |
| AOU | 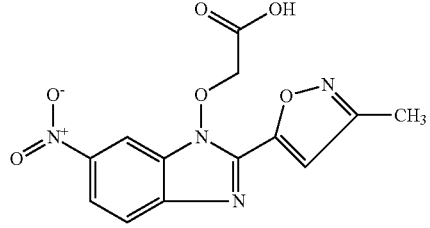 [SMILES: Cc1cc(-c2nc3ccc([N+](=O)[O-])cc3n2OCC(=O)O)on1] | *** |
| AOV | 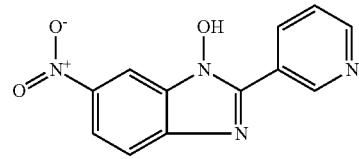 [SMILES: O=[N+]([O-])c1ccc2nc(-c3cccnc3)n(O)c2c1] | — |
| AOW | 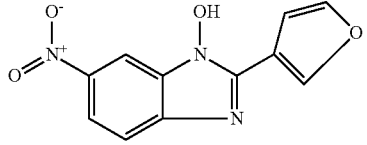 [SMILES: O=[N+]([O-])c1ccc2nc(-c3ccoc3)n(O)c2c1] | *** |

TABLE 6-continued
| ID | STRUCTURE | SoxS Gel Shift |
|---|---|---|
| AOX | 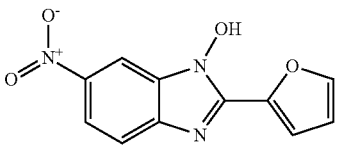 | *** |
| AOY | 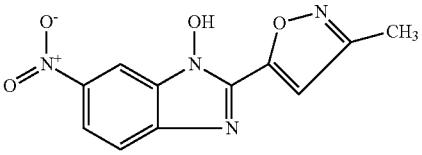 [SMILES: Cc1cc(-c2nc3ccc([N+](=O)[O-])cc3n2O)on1] | *** |
| AOZ | 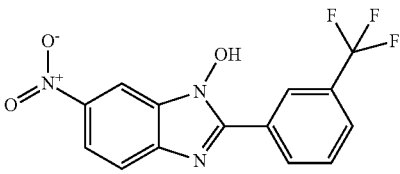 [SMILES: O=[N+]([O-])c1ccc2nc(-c3cccc(C(F)(F)F)c3)n(O)c2c1] | * |
| APA | 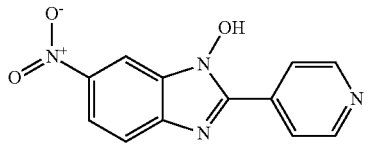 [SMILES: O=[N+]([O-])c1ccc2nc(-c3ccncc3)n(O)c2c1] | — |
| APB | 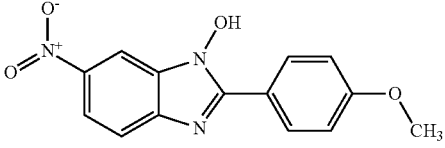 | — |
| APC | 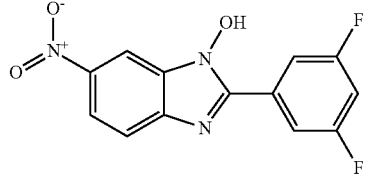 [SMILES: O=[N+]([O-])c1ccc2nc(-c3cc(F)cc(F)c3)n(O)c2c1] | — |
| APD | 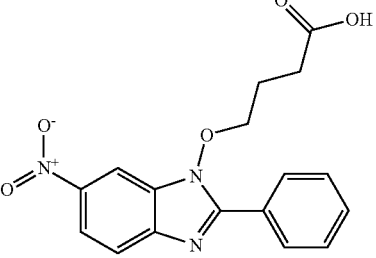 | * |
| APE | 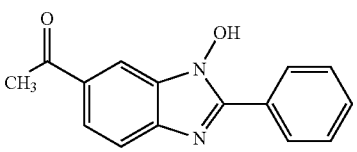 [SMILES: CC(=O)c1ccc2nc(-c3ccccc3)n(O)c2c1] | — |
| APF | 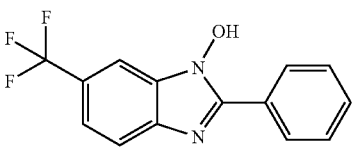 [SMILES: On1c(-c2ccccc2)nc2ccc(C(F)(F)F)cc21] | — |

TABLE 6-continued

| ID | STRUCTURE | SoxS Gel Shift |
|---|---|---|
| APG | 6-fluoro-1-hydroxy-2-phenyl-1H-benzimidazole | — |
| APH | 6-methoxy-1-hydroxy-2-phenyl-1H-benzimidazole | — |
| API | 1-hydroxy-2-phenyl-1H-benzimidazole-6-carboxylic acid | — |
| APJ | 1-hydroxy-2-phenyl-1H-benzimidazole-6-carboxamide | ** |
| APK | N-(1-hydroxy-2-phenyl-1H-benzimidazol-6-yl)acetamide | — |
| APL | 1-hydroxy-2-phenyl-1H-benzimidazole-6-carbonitrile | — |
| APM | 1-(cyanomethoxy)-6-nitro-2-phenyl-1H-benzimidazole | — |
| APN | 1-(2-aminoethoxy)-6-nitro-2-phenyl-1H-benzimidazole | * |
| APO | 6-(dimethylamino)-1-hydroxy-2-phenyl-1H-benzimidazole | — |

TABLE 6-continued

| ID | STRUCTURE | SoxS Gel Shift |
|---|---|---|
| APP | 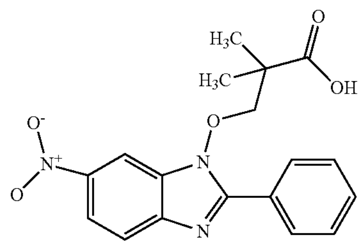 [SMILES: CC(C)(COn1c(-c2ccccc2)nc2ccc([NH+]([O-])O)cc21)C(=O)O] | — |
| APQ | 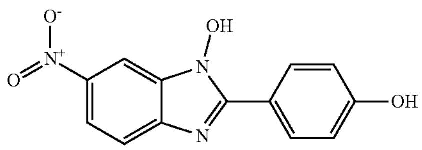 [SMILES: O=[N+]([O-])c1ccc2nc(-c3ccc(O)cc3)n(O)c2c1] | ** |
| APR | 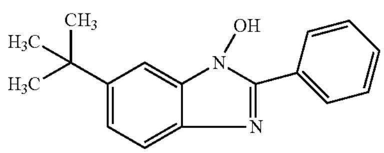 [SMILES: CC(C)(C)c1ccc2nc(-c3ccccc3)n(O)c2c1] | — |
| APS | 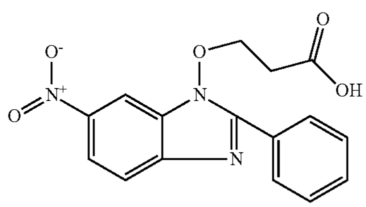 [SMILES: O=C(O)CCOn1c(-c2ccccc2)nc2ccc([N+](=O)[O-])cc21] | — |
| APT | 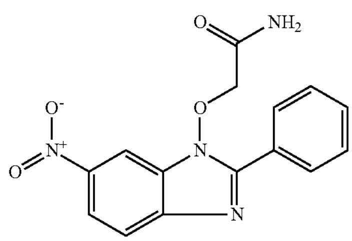 [SMILES: NC(=O)COn1c(-c2ccccc2)nc2ccc([N+](=O)[O-])cc21] | ** |
| APU | 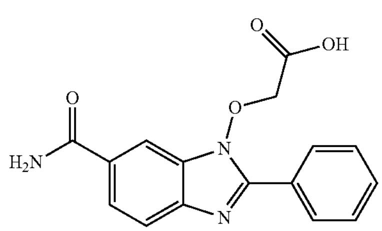 [SMILES: NC(=O)c1ccc2nc(-c3ccccc3)n(OCC(=O)O)c2c1] | — |
| APV | 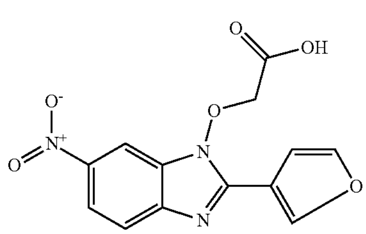 [SMILES: O=C(O)COn1c(-c2ccoc2)nc2ccc([N+](=O)[O-])cc21] | *** |

TABLE 6-continued

| ID | STRUCTURE | SoxS Gel Shift |
|---|---|---|
| APW | 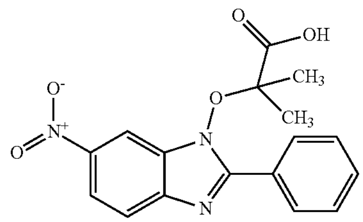 [SMILES: CC(C)(On1c(-c2ccccc2)nc2ccc([N+](=O)[O-])cc21)C(=O)O] | — |
| APX | 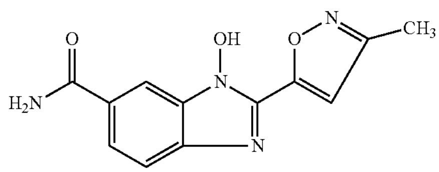 [SMILES: Cc1cc(-c2nc3ccc(C(N)=O)cc3n2O)on1] | * |
| APY | 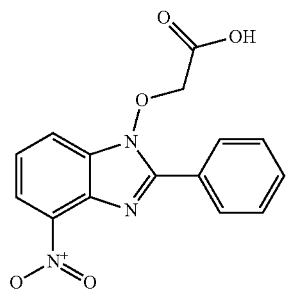 | ** |
| APZ | 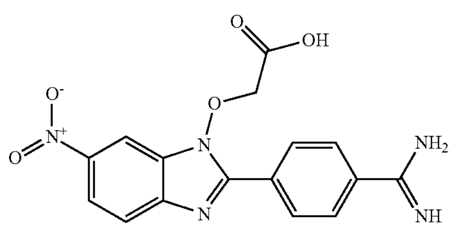 [SMILES: N=C(N)c1ccc(-c2nc3ccc([N+](=O)[O-])cc3n2OCC(=O)O)cc1] | — |
| AQA | 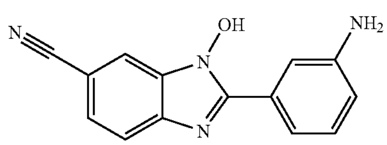 [SMILES: N#Cc1ccc2nc(-c3cccc(N)c3)n(O)c2c1] | — |
| AQB | 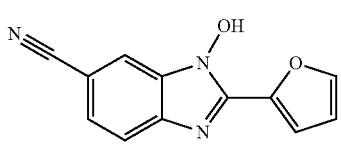 [SMILES: N#Cc1ccc2nc(-c3ccco3)n(O)c2c1] | — |
| AQC | 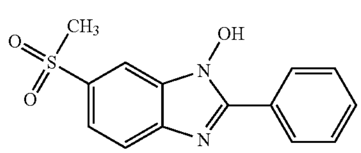 [SMILES: CS(=O)(=O)c1ccc2nc(-c3ccccc3)n(O)c2c1] | — |
| AQD | 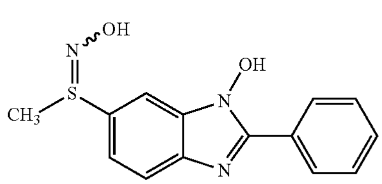 [SMILES: CS(=NO)c1ccc2nc(-c3ccccc3)n(O)c2c1] | — |

TABLE 6-continued

| ID | STRUCTURE | SoxS Gel Shift |
|---|---|---|
| AQE | (structure) | — |
| AQF | (structure) | ** |
| AQG | (structure) | * |
| AQH | (structure) | — |
| AQI | (structure) | — |
| AQJ | (structure) | *** |
| AQK | (structure) | — |
| AQL | (structure) | *** |
| AQM | (structure) | — |

TABLE 6-continued

| ID | STRUCTURE | SoxS Gel Shift |
|---|---|---|
| AQN | 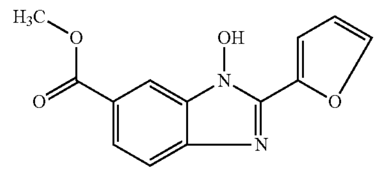 [SMILES: COC(=O)c1ccc2nc(-c3ccco3)n(O)c2c1] | — |
| AQO | 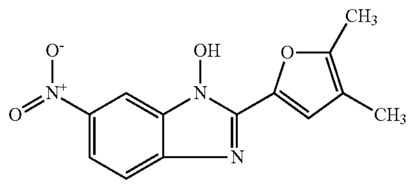 [SMILES: Cc1cc(-c2nc3ccc([N+](=O)[O-])cc3n2O)oc1C] | — |
| AQP | 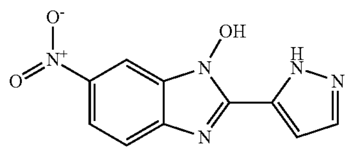 [SMILES: O=[N+]([O-])c1ccc2nc(-c3ccn[nH]3)n(O)c2c1] | — |
| AQQ | 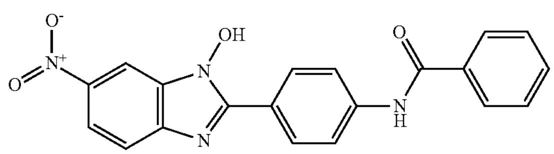 [SMILES: O=C(Nc1ccc(-c2nc3ccc([N+](=O)[O-])cc3n2O)cc1)c1ccccc1] | *** |
| AQR | 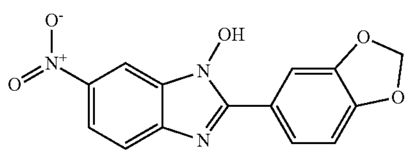 [SMILES: O=[N+]([O-])c1ccc2nc(-c3ccc4c(c3)OCO4)n(O)c2c1] | — |
| AQS | 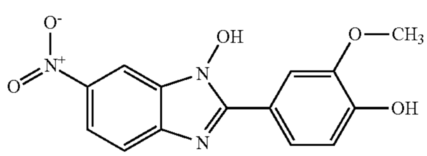 [SMILES: COc1cc(-c2nc3ccc([N+](=O)[O-])cc3n2O)ccc1O] | — |
| AQT | 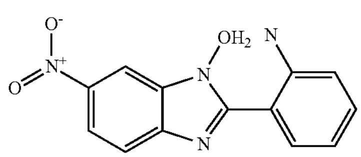 | — |
| AQU | 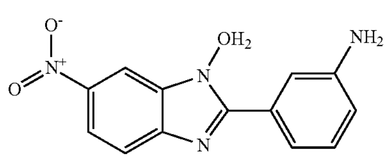 [SMILES: Nc1cccc(-c2nc3ccc([N+](=O)[O-])cc3n2O)c1] | ** |
| AQV | 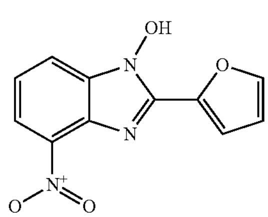 | *** |

TABLE 6-continued

| ID | STRUCTURE | SoxS Gel Shift |
|---|---|---|
| AQW | 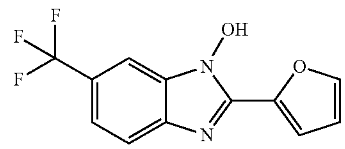 [SMILES: On1c(-c2ccco2)nc2ccc(C(F)(F)F)cc21] | — |
| AQX | 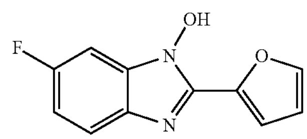 [SMILES: On1c(-c2ccco2)nc2ccc(F)cc21] | — |
| AQY | 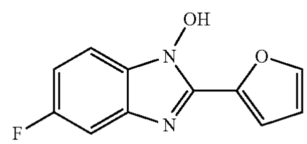 [SMILES: On1c(-c2ccco2)nc2cc(F)ccc21] | — |
| AQZ | 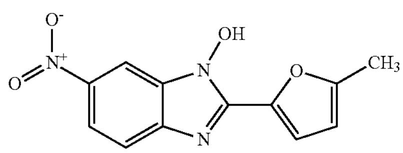 [SMILES: Cc1ccc(-c2nc3ccc([N+](=O)[O-])cc3n2O)o1] | ** |
| ARA | 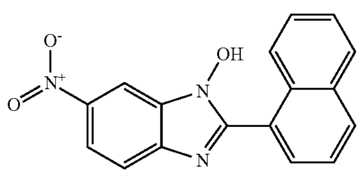 [SMILES: O=[N+]([O-])c1ccc2nc(-c3cccc4ccccc34)n(O)c2c1] | — |
| ARB | 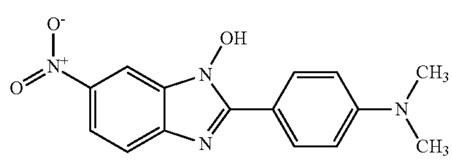 | *** |
| ARC | 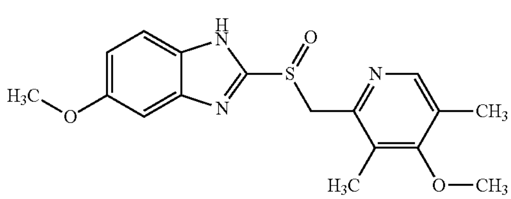 | — |
| ARD | 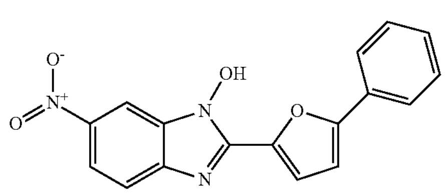 [SMILES: O=[N+]([O-])c1ccc2nc(-c3ccc(-c4ccccc4)o3)n(O)c2c1] | *** |
| ARE | 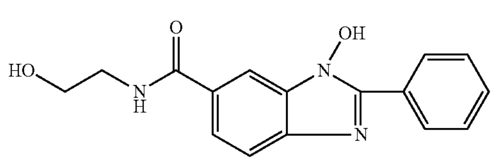 [SMILES: O=C(NCCO)c1ccc2nc(-c3ccccc3)n(O)c2c1] | — |

TABLE 6-continued

| ID | STRUCTURE | SoxS Gel Shift |
|---|---|---|
| ARF | 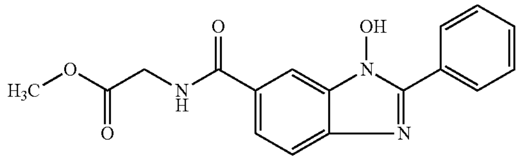 [SMILES: COC(=O)CNC(=O)c1ccc2nc(-c3ccccc3)n(O)c2c1] | — |
| ARG | 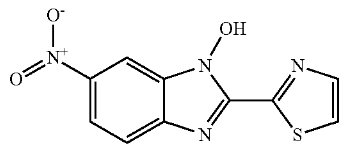 [SMILES: O=[N+]([O-])c1ccc2nc(-c3nccs3)n(O)c2c1] | — |
| ARH | 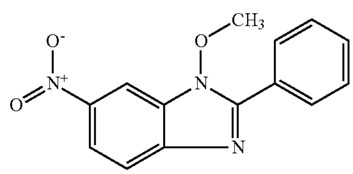 [SMILES: COn1c(-c2ccccc2)nc2ccc([N+](=O)[O-])cc21] | — |
| ARI | 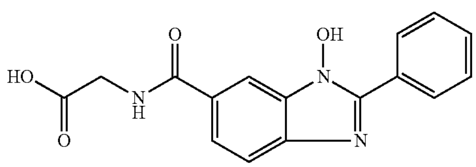 [SMILES: O=C(O)CNC(=O)c1ccc2nc(-c3ccccc3)n(O)c2c1] | — |
| ARJ | 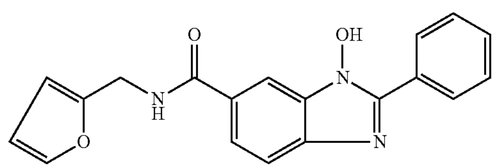 [SMILES: O=C(NCc1ccco1)c1ccc2nc(-c3ccccc3)n(O)c2c1] | — |
| ARK | 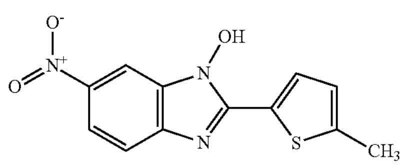 [SMILES: Cc1ccc(-c2nc3ccc([N+](=O)[O-])cc3n2O)s1] | — |
| ARL | 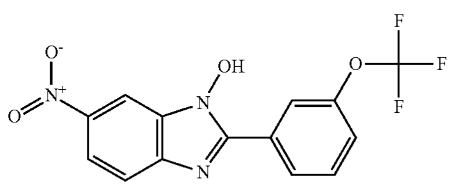 [SMILES: O=[N+]([O-])c1ccc2nc(-c3cccc(OC(F)(F)F)c3)n(O)c2c1] | — |
| ARM | 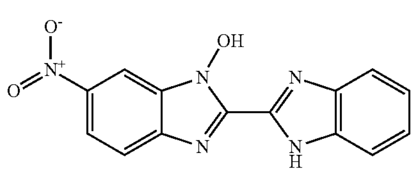 [SMILES: O=[N+]([O-])c1ccc2nc(-c3nc4ccccc4[nH]3)n(O)c2c1] | — |

TABLE 6-continued

| ID | STRUCTURE | SoxS Gel Shift |
|----|-----------|----------------|
| ARN | 6-nitro-1-hydroxy-2-[2-(trifluoromethoxy)phenyl]benzimidazole | — |
| ARO | 6-nitro-1-hydroxy-2-[1-(carboxymethyl)benzimidazol-2-yl]benzimidazole | *** |
| ARP | 6-nitro-1-hydroxy-2-(2-methoxyphenyl)benzimidazole | — |
| ARQ | 6-nitro-1-hydroxy-2-(3,4-dimethoxyphenyl)benzimidazole | — |
| ART | 6-(N-furfurylsulfamoyl)-1-hydroxy-2-phenylbenzimidazole | — |
| ARU | 6-nitro-1-hydroxy-2-(3-acetamidophenyl)benzimidazole | — |
| ARV | 6-nitro-1-hydroxy-2-(3-carboxyphenyl)benzimidazole | *** |

TABLE 6-continued
| ID | STRUCTURE | SoxS Gel Shift |
|---|---|---|
| ARW | 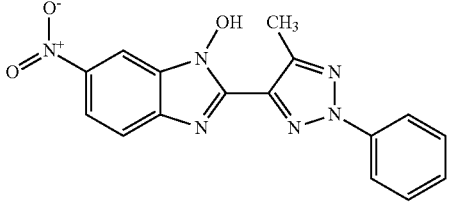 [SMILES: Cc1nn(-c2ccccc2)nc1-c1nc2ccc([N+](=O)[O-])cc2n1O] | — |
| ARX | 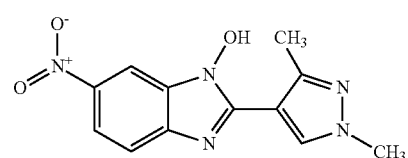 | — |
| ARY | 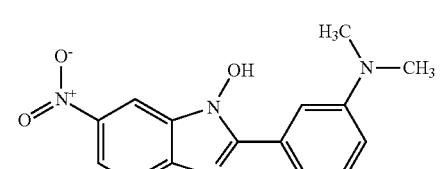 | — |
| ARZ | 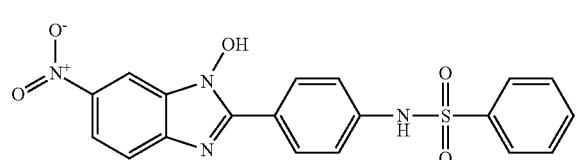 | NT |
| ASA | 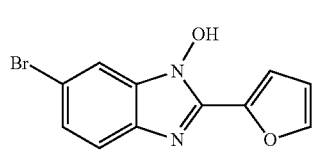 [SMILES: On1c(-c2ccco2)nc2ccc(Br)cc21] | NT |
| ASB | 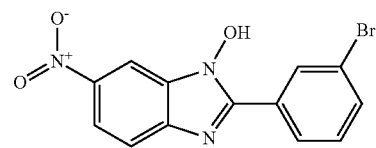 [SMILES: O=[N+]([O-])c1ccc2nc(-c3cccc(Br)c3)n(O)c2c1] | NT |
| ASC | 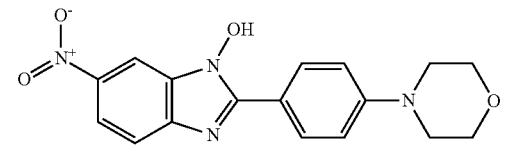 [SMILES: O=[N+]([O-])c1ccc2nc(-c3ccc(N4CCOCC4)cc3)n(O)c2c1] | NT |
| ASD | 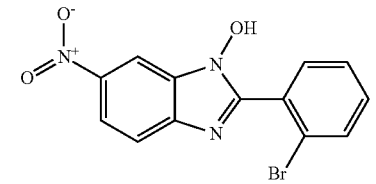 [SMILES: O=[N+]([O-])c1ccc2nc(-c3ccccc3Br)n(O)c2c1] | NT |
| ASE | 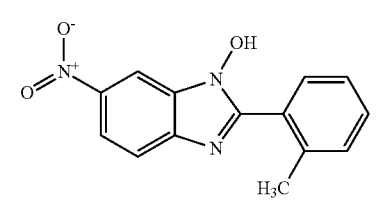 [SMILES: Cc1ccccc1-c1nc2ccc([N+](=O)[O-])cc2n1O] | NT |

TABLE 6-continued

| ID | STRUCTURE | SoxS Gel Shift |
|---|---|---|
| ASF | 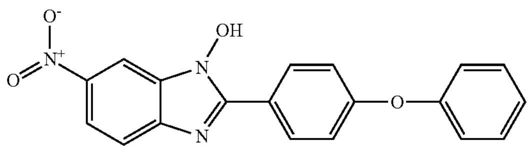 [SMILES: O=[N+]([O-])c1ccc2nc(-c3ccc(Oc4ccccc4)cc3)n(O)c2c1] | NT |
| ASG | 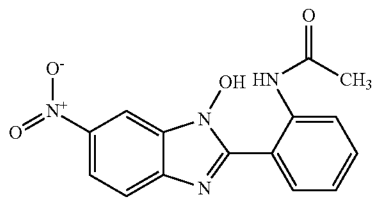 [SMILES: CC(=O)Nc1ccccc1-c1nc2ccc([N+](=O)[O-])cc2n1O] | * |
| ASH | 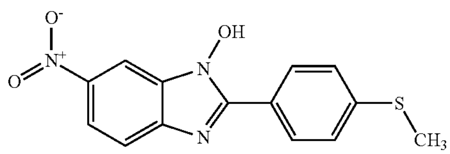 [SMILES: CSc1ccc(-c2nc3ccc([N+](=O)[O-])cc3n2O)cc1] | NT |
| ASI | 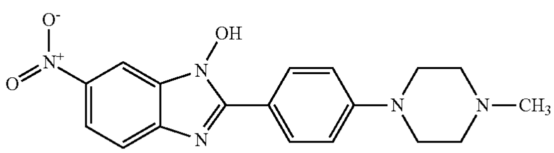 [SMILES: CN1CCN(c2ccc(-c3nc4ccc([N+](=O)[O-])cc4n3O)cc2)CC1] | NT |
| ASJ | 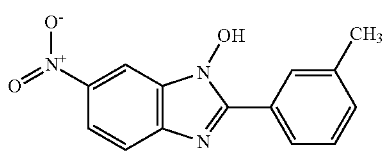 [SMILES: Cc1cccc(-c2nc3ccc([N+](=O)[O-])cc3n2O)c1] | NT |
| ASK | 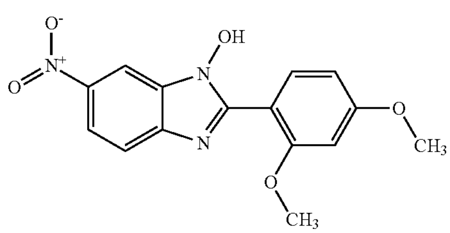 [SMILES: COc1ccc(-c2nc3ccc([N+](=O)[O-])cc3n2O)c(OC)c1] | NT |
| ASL | 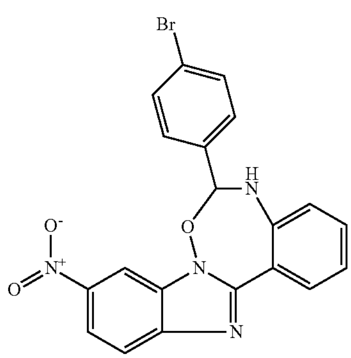 [SMILES: O=[N+]([O-])c1ccc2nc3n(c2c1)OC(c1ccc(Br)cc1)Nc1ccccc1-3] | NT |

587
588
TABLE 6-continued
| ID | STRUCTURE | SoxS Gel Shift |
|---|---|---|
| ASM | 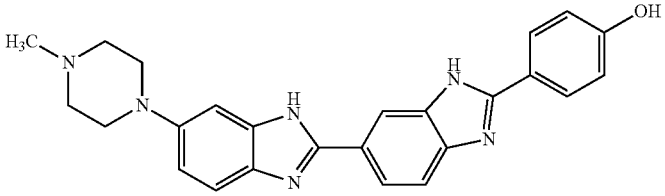 [SMILES: CN1CCN(c2ccc3nc(-c4ccc5nc(-c6ccc(O)cc6)[nH]c5c4)[nH]c3c2)CC1] | — |
| ASN | 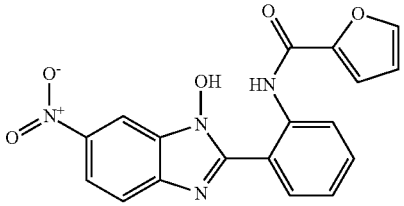 [SMILES: O=C(Nc1ccccc1-c1nc2ccc([N+](=O)[O-])cc2n1O)c1ccco1] | *** |
| ASO | 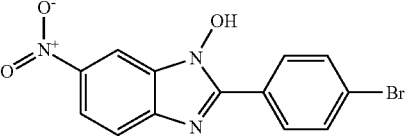 [SMILES: O=[N+]([O-])c1ccc2nc(-c3ccc(Br)cc3)n(O)c2c1] | NT |
| ASP | 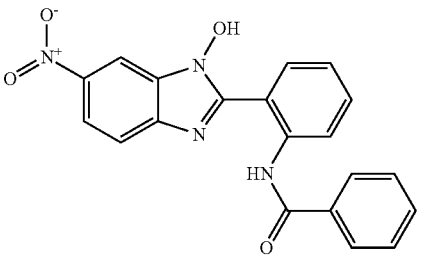 [SMILES: O=C(Nc1ccccc1-c1nc2ccc([N+](=O)[O-])cc2n1O)c1ccccc1] | ** |
| ASQ | 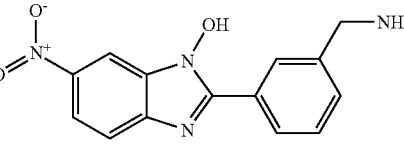 | NT |
| ASR | 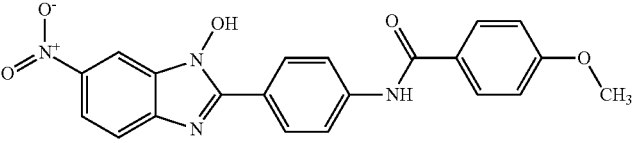 | NT |
| ASS | 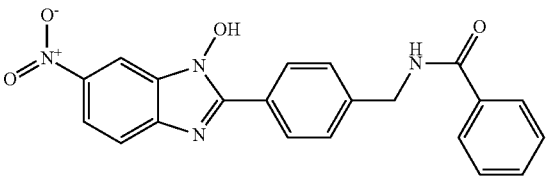 [SMILES: O=C(NCc1ccc(-c2nc3ccc([N+](=O)[O-])cc3n2O)cc1)c1ccccc1] | NT |
| AST | 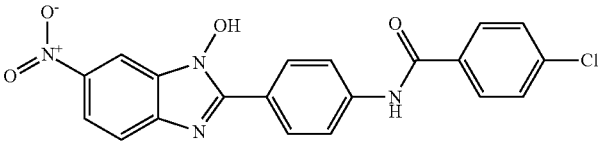 [SMILES: O=C(Nc1ccc(-c2nc3ccc([N+](=O)[O-])cc3n2O)cc1)c1ccc(Cl)cc1] | NT |

TABLE 6-continued

| ID | STRUCTURE | SoxS Gel Shift |
|---|---|---|
| ASU | 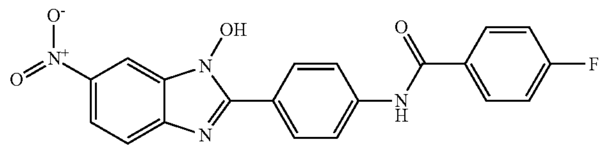 [SMILES: O=C(Nc1ccc(-c2nc3ccc([N+](=O)[O-])cc3n2O)cc1)c1ccc(F)cc1] | NT |
| ASV | 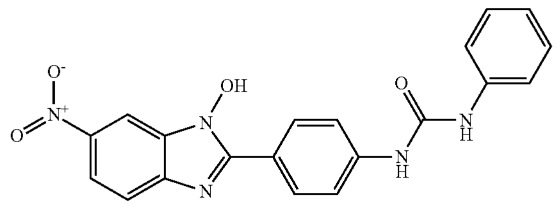 [SMILES: O=C(Nc1ccccc1)Nc1ccc(-c2nc3ccc([N+](=O)[O-])cc3n2O)cc1] | NT |
| ASW | 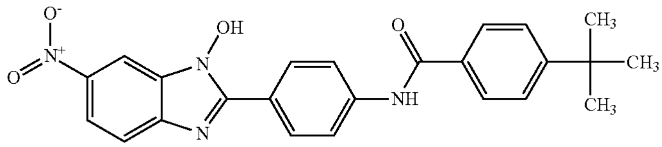 [SMILES: CC(C)(C)c1ccc(C(=O)Nc2ccc(-c3nc4ccc([N+](=O)[O-])cc4n3O)cc2)cc1] | NT |
| ASX | 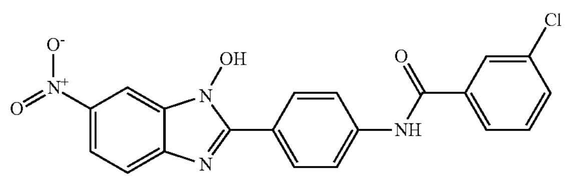 [SMILES: O=C(Nc1ccc(-c2nc3ccc([N+](=O)[O-])cc3n2O)cc1)c1cccc(Cl)c1] | NT |
| ASY | 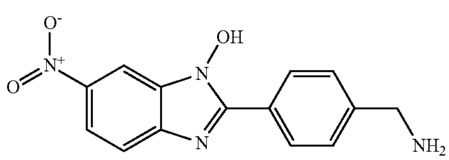 | NT |
| ASZ | 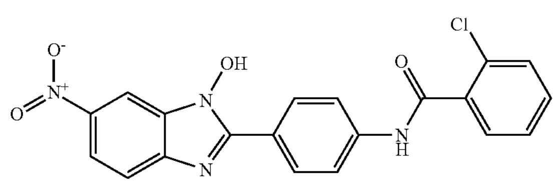 [SMILES: O=C(Nc1ccc(-c2nc3ccc([N+](=O)[O-])cc3n2O)cc1)c1ccccc1Cl] | NT |
| ATA | 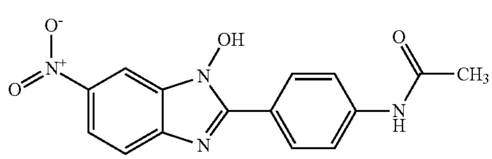 [SMILES: CC(=O)Nc1ccc(-c2nc3ccc([N+](=O)[O-])cc3n2O)cc1] | NT |
| ATB | 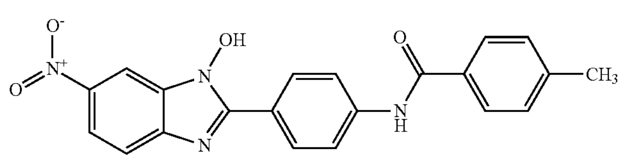 [SMILES: Cc1ccc(C(=O)Nc2ccc(-c3nc4ccc([N+](=O)[O-])cc4n3O)cc2)cc1] | NT |
| ATC | 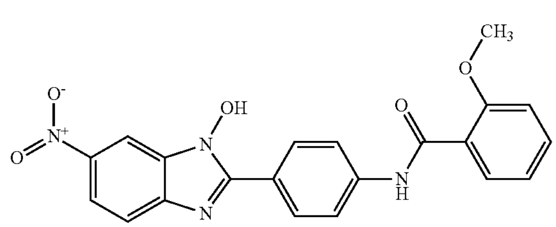 [SMILES: COc1ccccc1C(=O)Nc1ccc(-c2nc3ccc([N+](=O)[O-])cc3n2O)cc1] | NT |

TABLE 6-continued

| ID | STRUCTURE | SoxS Gel Shift |
|---|---|---|
| ATD | 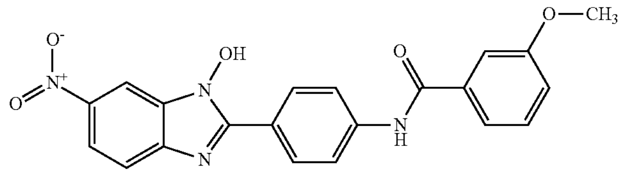 [SMILES: COc1cccc(C(=O)Nc2ccc(-c3nc4ccc([N+](=O)[O-])cc4n3O)cc2)c1] | NT |
| ATE | 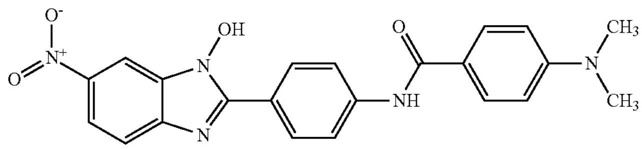 [SMILES: CN(C)c1ccc(C(=O)Nc2ccc(-c3nc4ccc([N+](=O)[O-])cc4n3O)cc2)cc1] | NT |
| ATF | 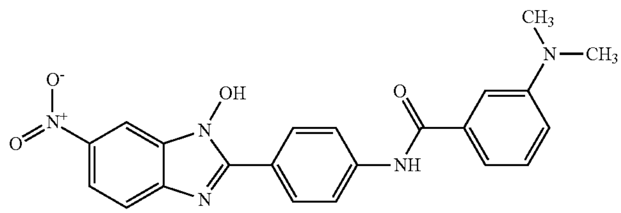 [SMILES: CN(C)c1cccc(C(=O)Nc2ccc(-c3nc4ccc([N+](=O)[O-])cc4n3O)cc2)c1] | NT |
| ATG | 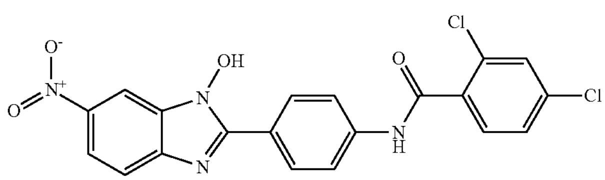 [SMILES: O=C(Nc1ccc(-c2nc3ccc([N+](=O)[O-])cc3n2O)cc1)c1ccc(Cl)cc1Cl] | NT |
| ATH | 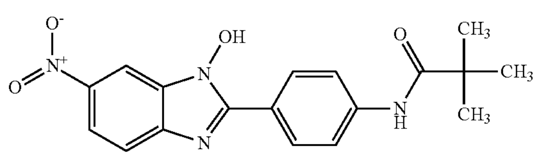 [SMILES: CC(C)(C)C(=O)Nc1ccc(-c2nc3ccc([N+](=O)[O-])cc3n2O)cc1] | NT |
| ATI | 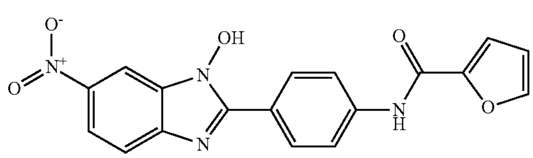 [SMILES: O=C(Nc1ccc(-c2nc3ccc([N+](=O)[O-])cc3n2O)cc1)c1ccco1] | NT |
| ATJ | 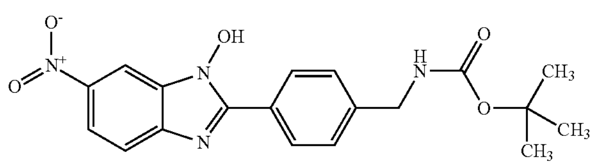 [SMILES: CC(C)(C)OC(=O)NCc1ccc(-c2nc3ccc([N+](=O)[O-])cc3n2O)cc1] | NT |
| ATK | 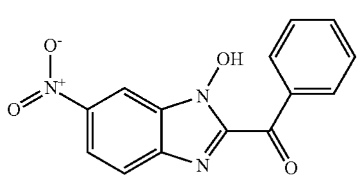 [SMILES: O=C(c1ccccc1)c1nc2ccc([N+](=O)[O-])cc2n1O] | NT |

TABLE 6-continued

| ID | STRUCTURE | SoxS Gel Shift |
|---|---|---|
| ATL | 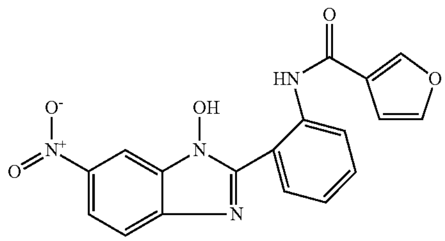 [SMILES: O=C(Nc1ccccc1-c1nc2ccc([N+](=O)[O-])cc2n1O)c1ccoc1] | NT |
| ATM | 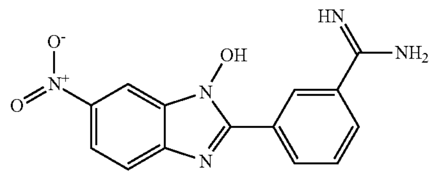 | NT |
| ATN | 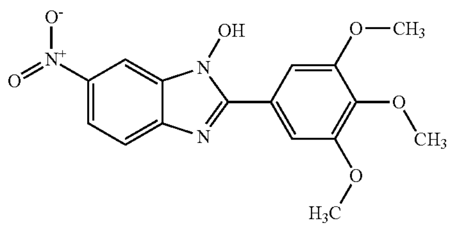 [SMILES: COc1cc(-c2nc3ccc([N+](=O)[O-])cc3n2O)cc(OC)c1OC] | NT |
| ATO | 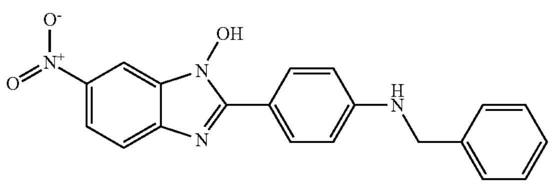 [SMILES: O=[N+]([O-])c1ccc2nc(-c3ccc(NCc4ccccc4)cc3)n(O)c2c1] | NT |
| ATP | 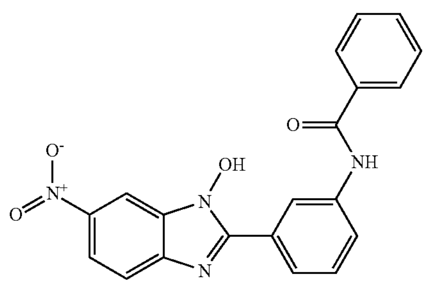 [SMILES: O=C(Nc1cccc(-c2nc3ccc([N+](=O)[O-])cc3n2O)c1)c1ccccc1] | NT |
| ATQ | 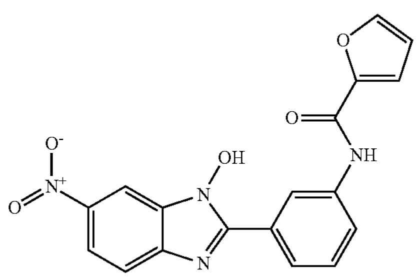 [SMILES: O=C(Nc1cccc(-c2nc3ccc([N+](=O)[O-])cc3n2O)c1)c1ccco1] | NT |
| ATR | 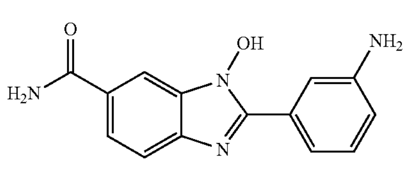 [SMILES: NC(=O)c1ccc2nc(-c3cccc(N)c3)n(O)c2c1] | NT |

TABLE 6-continued

| ID | STRUCTURE | SoxS Gel Shift |
|---|---|---|
| ATS | 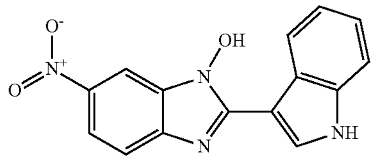 [SMILES: O=[N+]([O-])c1ccc2nc(-c3c[nH]c4ccccc34)n(O)c2c1] | NT |
| ATT | 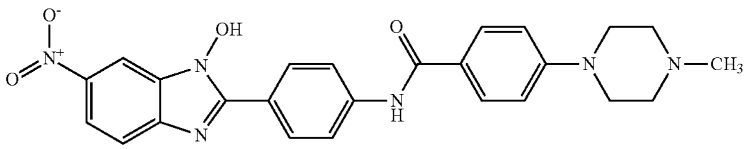 [SMILES: CN1CCN(c2ccc(C(=O)Nc3ccc(-c4nc5ccc([N+](=O)[O-])cc5n4O)cc3)cc2)CC1] | NT |
| ATU | 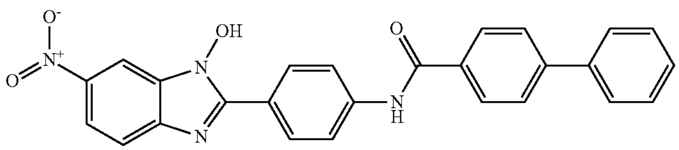 [SMILES: O=C(Nc1ccc(-c2nc3ccc([N+](=O)[O-])cc3n2O)cc1)c1ccc(-c2ccccc2)cc1] | NT |
| ATV | 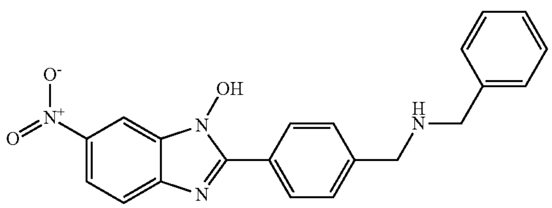 [SMILES: O=[N+]([O-])c1ccc2nc(-c3ccc(CNCc4ccccc4)cc3)n(O)c2c1] | NT |
| ATW | 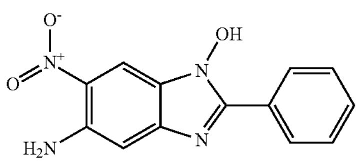 [SMILES: Nc1cc2nc(-c3ccccc3)n(O)c2cc1[N+](=O)[O-]] | NT |
| ATX | 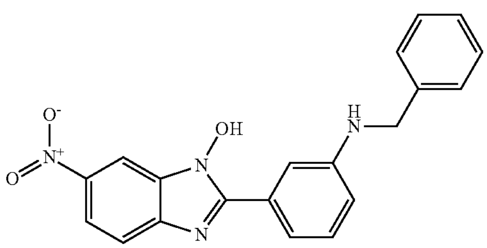 [SMILES: O=[N+]([O-])c1ccc2nc(-c3cccc(NCc4ccccc4)c3)n(O)c2c1] | NT |
| ATY | 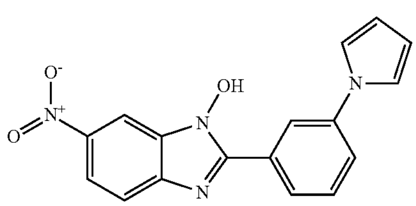 [SMILES: O=[N+]([O-])c1ccc2nc(-c3cccc(-n4cccc4)c3)n(O)c2c1] | NT |
| ATZ | 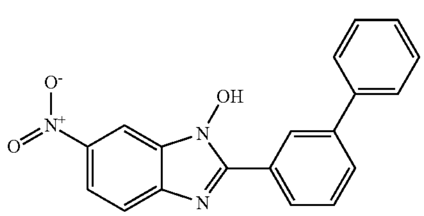 [SMILES: O=[N+]([O-])c1ccc2nc(-c3cccc(-c4ccccc4)c3)n(O)c2c1] | NT |

TABLE 6-continued

| ID | STRUCTURE | SoxS Gel Shift |
|---|---|---|
| AUA | 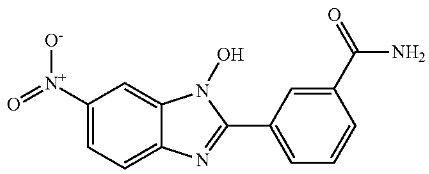 [SMILES: NC(=O)c1cccc(-c2nc3ccc([N+](=O)[O-])cc3n2O)c1] | NT |
| AUB | 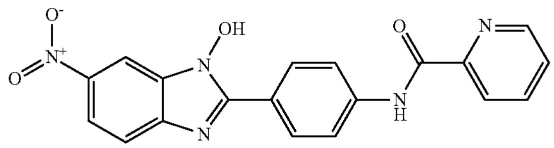 [SMILES: O=C(Nc1ccc(-c2nc3ccc([N+](=O)[O-])cc3n2O)cc1)c1ccccn1] | NT |
| AUC | 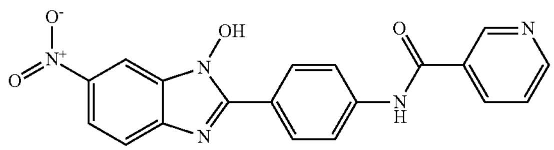 | NT |
| AUD | 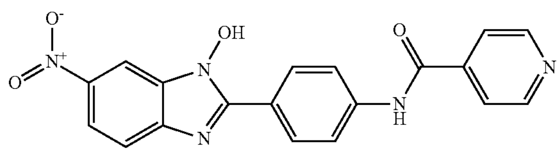 [SMILES: O=C(Nc1ccc(-c2nc3ccc([N+](=O)[O-])cc3n2O)cc1)c1ccncc1] | NT |
| AUE | 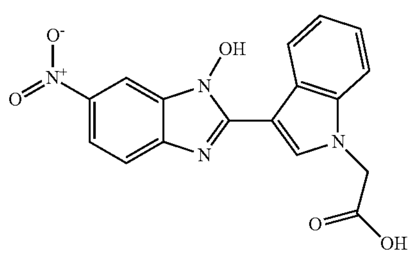 [SMILES: O=C(O)Cn1cc(-c2nc3ccc([N+](=O)[O-])cc3n2O)c2ccccc21] | NT |
| AUF | 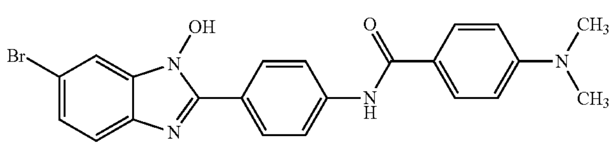 [SMILES: CN(C)c1ccc(C(=O)Nc2ccc(-c3nc4ccc(Br)cc4n3O)cc2)cc1] | NT |
| AUG | 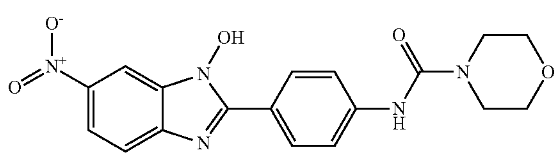 [SMILES: O=C(Nc1ccc(-c2nc3ccc([N+](=O)[O-])cc3n2O)cc1)N1CCOCC1] | NT |
| AUH | 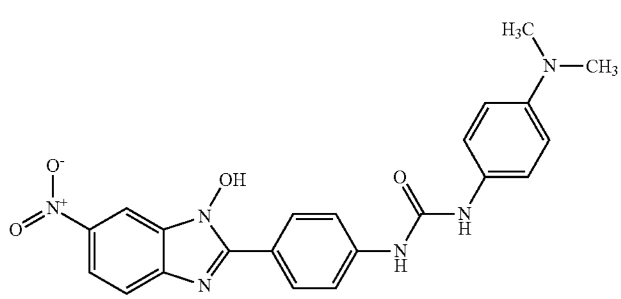 [SMILES: CN(C)c1ccc(NC(=O)Nc2ccc(-c3nc4ccc([N+](=O)[O-])cc4n3O)cc2)cc1] | NT |

TABLE 6-continued

| ID | STRUCTURE | SoxS Gel Shift |
|---|---|---|
| AUI | [structure: 6-nitro-1-hydroxy-benzimidazole linked to phenyl-NHC(O)-phenyl-OCF3] | NT |
| AUJ | [structure: 6-nitro-1-hydroxy-benzimidazole linked to phenyl-NHC(O)-cyclohexyl] | NT |

Example 12

Development of Luminescence Assays

A quantitative chemiluminescence-based assay is being used to measure the DNA binding activity of various MarA (AraC) family members. With this technique, a biotinylated double-stranded DNA molecule (2 nM) is incubated with a MarA (AraC) protein (20 nM) fused to 6-histidine (6-His) residues in a streptavidin coated 96-well microtiter (white) plate (Pierce Biotechnology, Rockford, Ill.). Unbound DNA and protein are removed by washing and a primary monoclonal anti-6His antibody is subsequently added. A second washing is performed and a secondary HRP-conjugated antibody is then added to the mixture. Excess antibody is removed by a third wash step and a chemiluminescence substrate (Cell Signaling Technology, Beverly, Mass.) is added to the plate. Luminescence is read immediately using a Victor V plate reader (PerkinElmer Life Sciences, Wellesley, Mass.). Compounds that inhibit the binding of the protein to the DNA result in a loss of protein from the plate at the first wash step and are identified by a reduced luminescence signal. The concentration of compound necessary to reduce signal by 50% ($EC_{50}/IC_{50}$) can be calculated using serial dilutions of the inhibitory compounds. Also, single trancription factor modulators that affect different transcription factors have been identified as shown below:

TABLE 7

Activity of selected trancription factor modulators against disparate MarA (AraC) family members.

| Host-Protein | % Identity to MarA | $EC_{50}$ (µM) | | | | |
|---|---|---|---|---|---|---|
| | | ARD | ASX | ASU | ATB | ATE |
| E. coli | | | | | | |
| MarA | 100 | 11.7 | | | | 1.2 |
| SoxS | 42 | 8.3 | 4.9 | 3 | 2.7 | 0.82 |
| Rob | 51 | 28 | 3.4 | 4.7 | 7.4 | 1.3 |
| S. typhimurium | | | | | | |
| Rma | 38 | 17 | 3.5 | 4.9 | | 1.8 |
| SlyA* | ND | 11.9 | 21.7 | 51 | | 14.3 |
| P. mirabilis | | | | | | |
| PqrA | 40 | 13.6 | | | | 1.4 |

TABLE 7-continued

Activity of selected trancription factor modulators against disparate MarA (AraC) family members.

| Host-Protein | % Identity to MarA | $EC_{50}$ (µM) | | | | |
|---|---|---|---|---|---|---|
| | | ARD | ASX | ASU | ATB | ATE |
| P. aeruginosa | | | | | | |
| ExsA | 24 | 15.6 | 2.5 | 4 | 4 | 1.9 |

*SlyA is a MarR protein and is included as a control, to illustrate preferential binding to MarA family members.

$EC_{50}$'s for other compounds of the invention for SoxS were also determined. Compounds ANU, AOW, AOX, APJ, AQQ, AQV, ARB, ASS, and AST was found to have $EC_{50}$'s higher than that of ARD.

Example 13

In Vivo Activity of Mar Inhibitors in Pyelonephritis Model of Infection

Groups of female CD1 mice (n=6) were diuresed and infected with E. coli UPEC strain C189 via intravesicular inoculation. Subsequently, mice were dosed with a Trancription factor modulator (25 mg/kg), a control compound, e.g., SXT (Qualitest Pharmaceuticals, Huntsville, Ala.), or vehicle alone (0 mg/kg), via an oral route of administration at the time of infection and once a day for 4 days thereafter, to maintain a constant level of drug in the mice. After a 5-day period of infection and prior to sacrifice via $CO_2/O_2$ asphyxiation, a urine sample was taken by gentle compression of the abdomen. Following asphyxiation, the bladder and kidneys were removed aseptically. Urine volumes and individual organ weights were recorded, the organs were suspended in sterile PBS containing 0.025% Triton X-100, and then homogenized. Serial 10-fold dilutions of the urine samples and homogenates were plated onto McConkey agar plates to determine CFU/ml of urine or CFU/gram of organ.

Efficacy in these experiments were defined as a $\geq$2-log decrease in CFU/ml of urine or CFU/g organ. These values are in accord with previous experiments investigating the treatment of UTI in mice. In Table 8, the results of the example are shown. Compounds which caused a decrease in the CFU/g of kidney tissue are indicated with a *. Compounds which showed no decrease in CFU/g of kidney issue are indicated with a -. All of the compounds tested in this assay were previously determined to have at least some in vitro SoxS activity.

TABLE 8

| Compound | Efficacy | Compound | Efficacy |
|---|---|---|---|
| AQK | * | AQU | - |
| AQZ | * | ASN | - |
| ARB | * | ASQ | - |
| ARD | * | AST | - |
| ARO | * | ASU | - |
| ARV | * | ATB | - |
| ASR | * | ATE | - |
| ATH | * | | |
| ARY | * | | |
| ASK | * | | |

Example 14

In Vitro Activity of Mar Inhibitors Against LcrF (VirF) from *Y. pseudotuberculosis*

The MarA (AraC) family member LcrF (VirF) was cloned, expressed and purified from *Y. pseudotuberculosis*. The purifed protein was used to develop a cell-free system to monitor DNA-protein interactions in vitro. The activities of Mar inhibitors were surveyed agains LcrF to identify inhibitory activity and % cytotoxicity in whole cell assays at 50 μg/mL. The results of the example are shown in Table 9. Compounds which showed superior inhibition of DNA binding are indicated by "*," and compounds which showed very good or good inhibition of DNA binding are indicated by "" or "*" respectively. Compounds which showed a minimum cytotoxicity in whole cell assays at 50 μg/mL are indicated by "***," and compounds which showed some cytotoxicity or a high cytotoxicity are indicated by "*" or "*" respectively. Table 10 gives $EC_{50}$ data for selected transcription factor modulaters against LrcF (VirF) from *Y. pseudotuberculosis*.

TABLE 10

Activity of selected trancription factor modulators against MarA (AraC) family member LrcF (VirF) from *Y. pseudotuberculosis*.

| Compound | $EC_{50}$ (μM) | Compound | $EC_{50}$ (μM) | Compound | $EC_{50}$ (μM) |
|---|---|---|---|---|---|
| ASR | 18.3 | BBS | 29 | BBP | 7.1 |
| ASU | 17.7 | BBW | >57.3 | BCK | 0.8 |
| ATB | 15.5 | BBT | 27.5 | BCL | 5.1 |
| ATE | 36.5 | BBV | >57.9 | BCO | 2.2 |

TABLE 9

| ID | MOLECULAR STRUCTURE | EC50 for VirF (μm) | % cytotoxicity in Whole cell assay at 50 μg/ml |
|---|---|---|---|
| ASU | 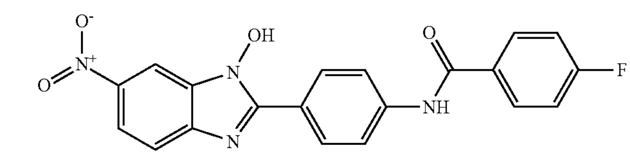 [SMILES: O=C(Nc1ccc(-c2nc3ccc([N+](=O)[O-])cc3n2O)cc1)c1ccc(F)cc1]  | *** | — |
| ATE | 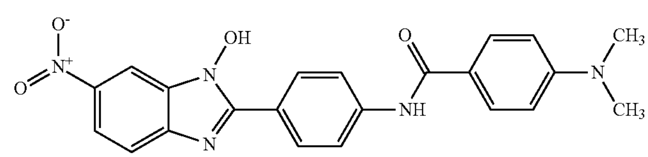 [SMILES: CN(C)c1ccc(C(=O)Nc2ccc(-c3nc4ccc([N+](=O)[O-])cc4n3O)cc2)cc1]  | ** | * |
| BAA | 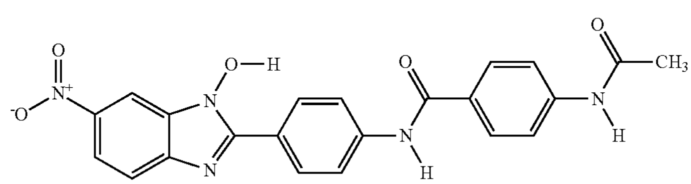  | * | — |
| BAA | 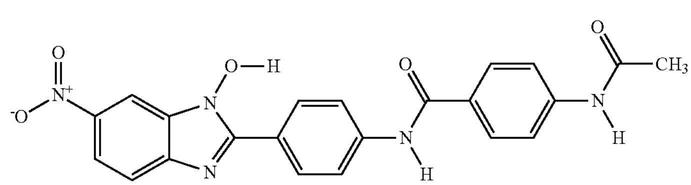  | * | — |
| BAB | 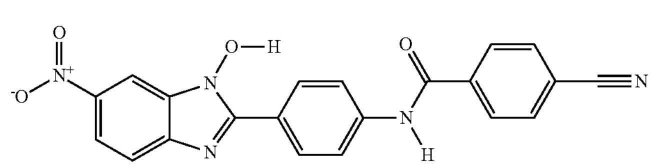  | ** | *** |

TABLE 9-continued

| ID | MOLECULAR STRUCTURE | EC50 for VirF (µm) | % cytotoxicity in Whole cell assay at 50 µg/ml |
|---|---|---|---|
| BAC | 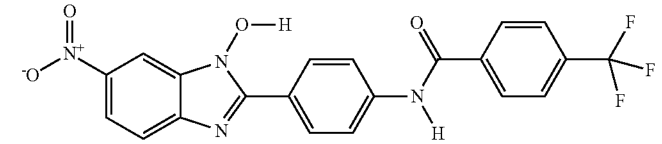 | * | — |
| BAD | 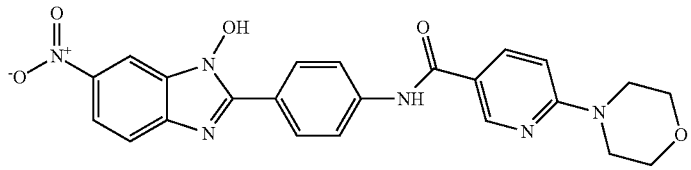 | * | — |
| BAE | 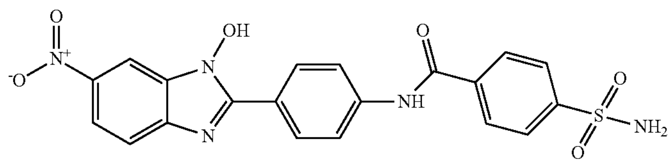 | * | — |
| BAF | 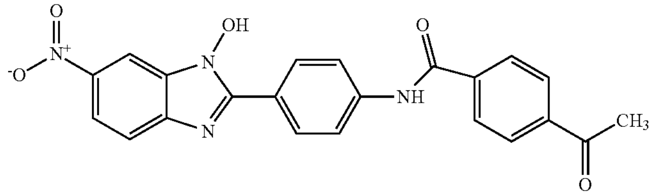 |  | * |
| BAG | 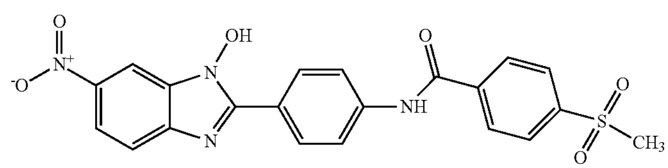 | * | — |
| BAH | 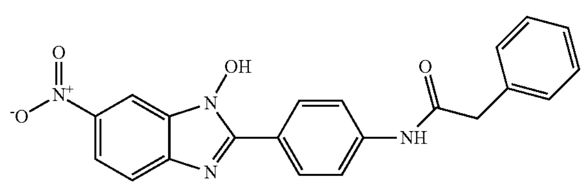 | * | — |
| BAI | 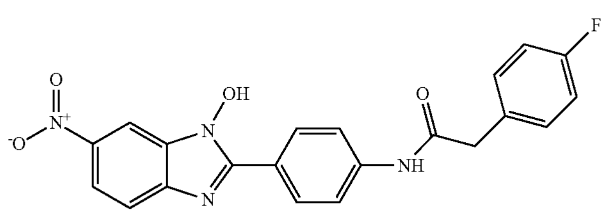 | * | — |
| BAJ | 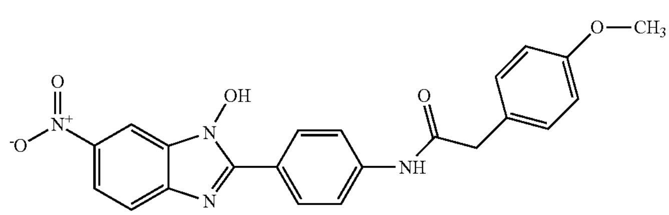 | ** | — |

TABLE 9-continued

| ID | MOLECULAR STRUCTURE | EC50 for VirF (μm) | % cytotoxicity in Whole cell assay at 50 μg/ml |
|---|---|---|---|
| BAK | 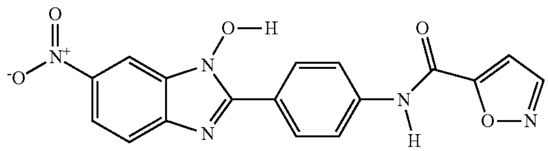 | ** | * |
| BAL | 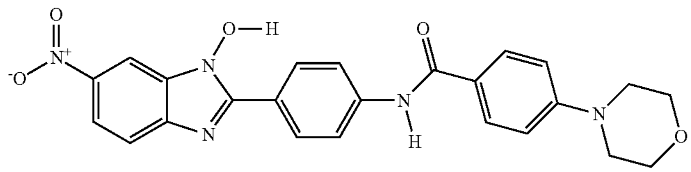 | * | — |
| BAM | 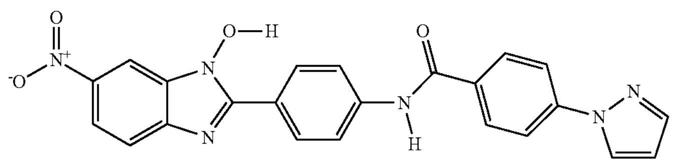 | * | — |
| BAN | 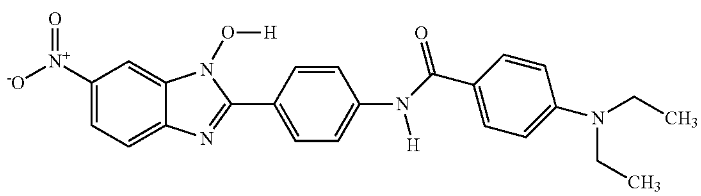 | * | — |
| BAO | 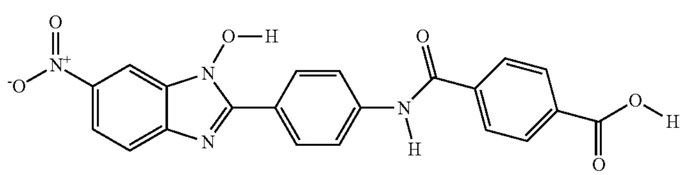 | * | — |
| BAP | 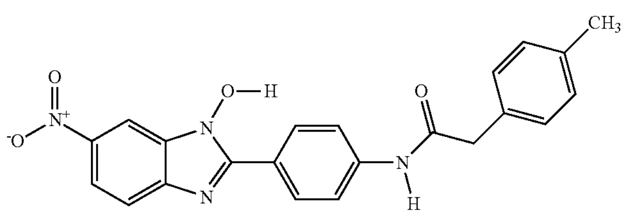 | * | — |
| BAQ | 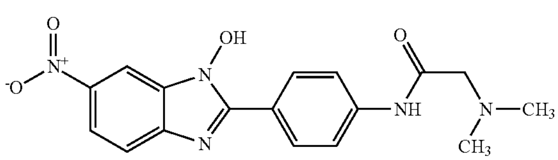 | * | — |
| BAR | 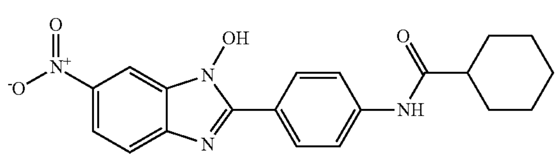 | * | — |

TABLE 9-continued

| ID | MOLECULAR STRUCTURE | EC50 for VirF (μm) | % cytotoxicity in Whole cell assay at 50 μg/ml |
|----|---------------------|--------------------|------------------------------------------------|
| BAS | 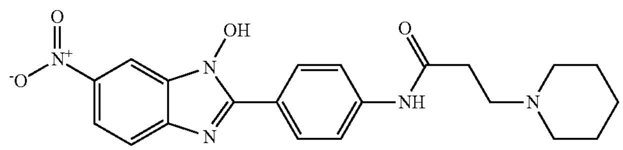 | * | — |
| BAT | 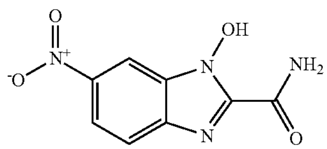 | * | — |
| BAU | 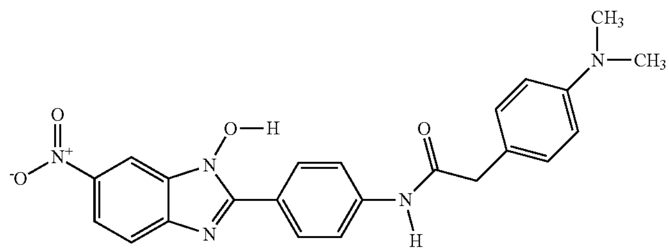 | * | * |
| BAV | 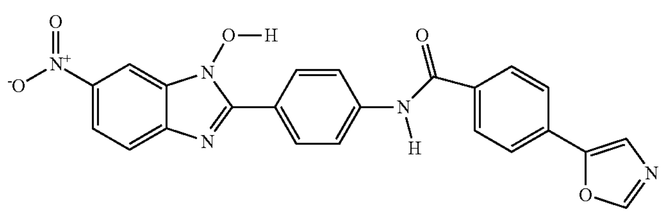 |  |  |
| BAW | 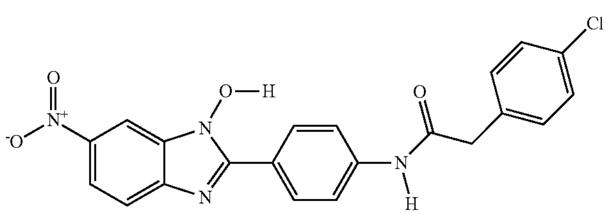 | * | — |
| BAX | 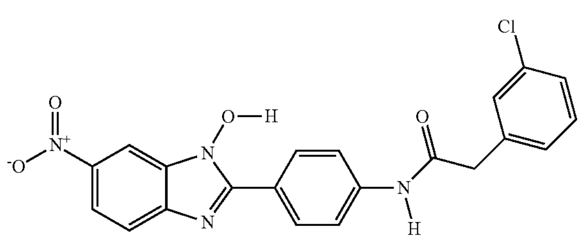 | * | — |
| BAY | 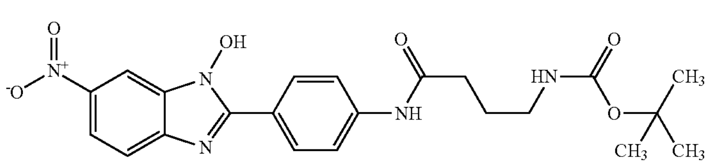 | * | — |

TABLE 9-continued

| ID | MOLECULAR STRUCTURE | EC50 for VirF (μm) | % cytotoxicity in Whole cell assay at 50 μg/ml |
|---|---|---|---|
| BAZ | 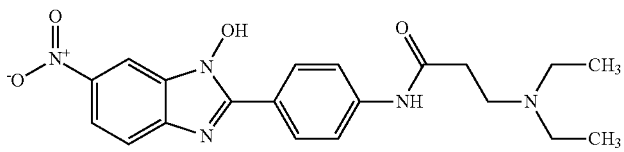 | * | — |
| BBA | (Chiral) | * | — |
| BBB | 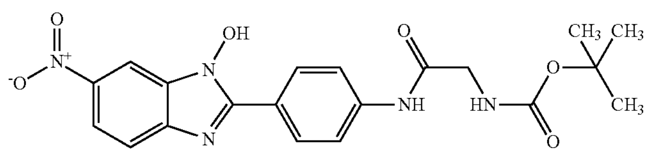 | * | — |
| BBC | (Chiral) | * | — |
| BBD | 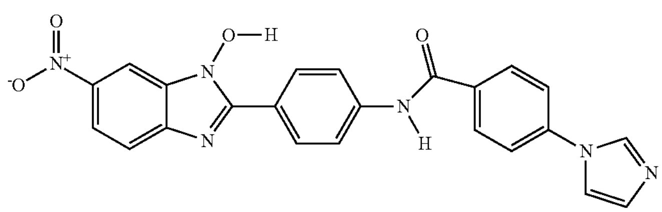 | * | ** |
| BBE | 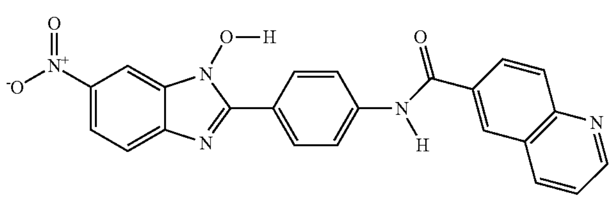 | * | — |
| BBF | 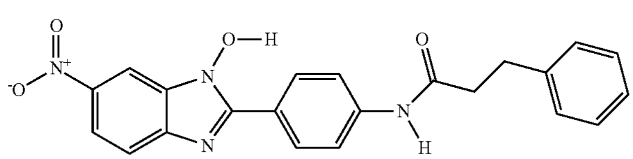 | * | — |
| BBG | 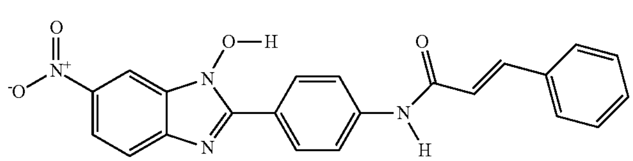 | ** | — |

TABLE 9-continued

| ID | MOLECULAR STRUCTURE | EC50 for VirF (µm) | % cytotoxicity in Whole cell assay at 50 µg/ml |
|---|---|---|---|
| BBH | 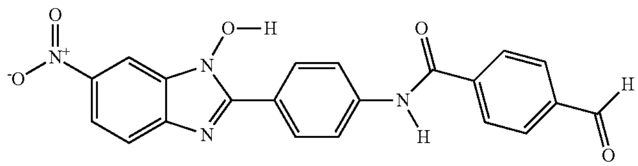 | ** | — |
| BBI | 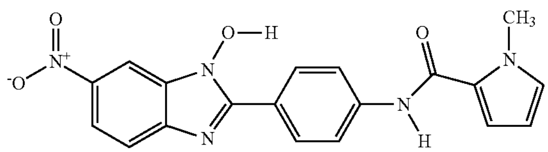 | ** | — |
| BBJ | 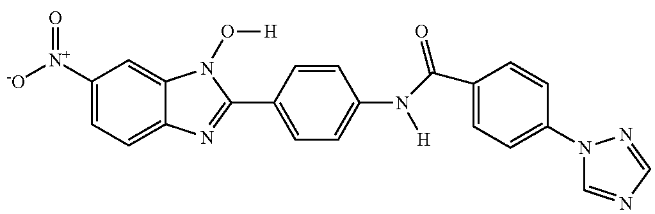 |  |  |
| BBK | 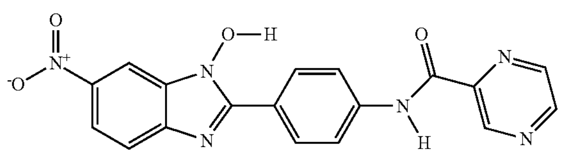 | * | — |
| BBL | 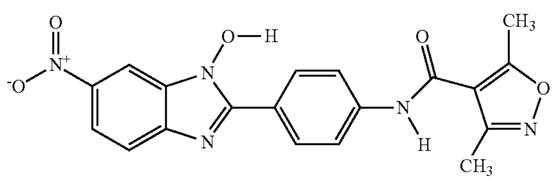 | * | — |
| BBM | 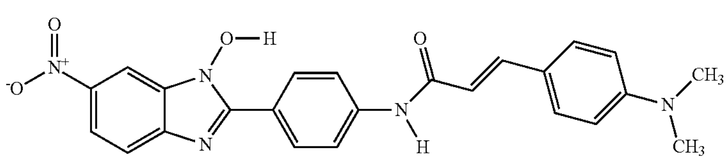 | ** | * |
| BBN | 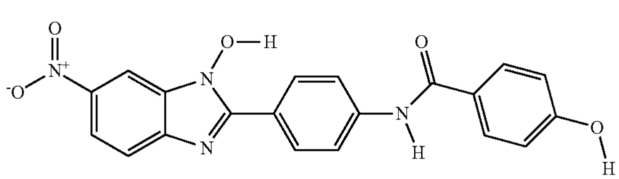 | * | — |
| BBO | 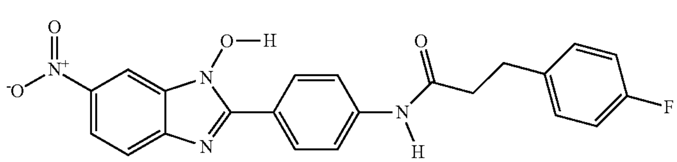 | * | — |

TABLE 9-continued

| ID | MOLECULAR STRUCTURE | EC50 for VirF (μm) | % cytotoxicity in Whole cell assay at 50 μg/ml |
|---|---|---|---|
| BBP | 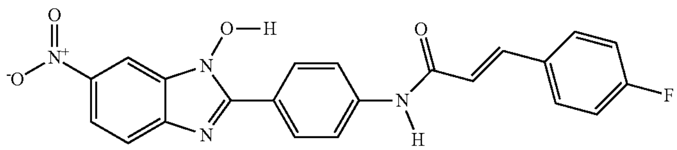 | * | * |
| BBQ | 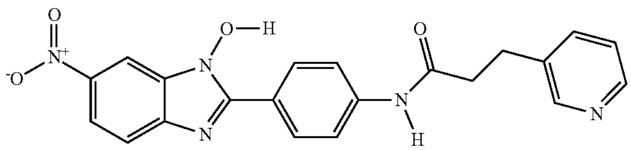 | * | — |
| BBR | 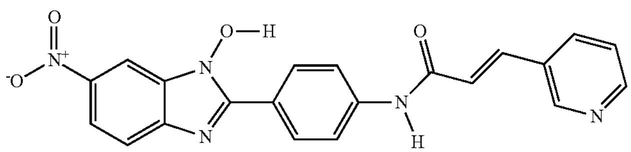 | * | — |
| BBS | 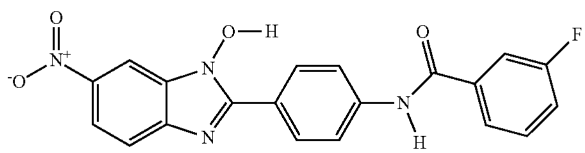 |  |  |
| BBT | 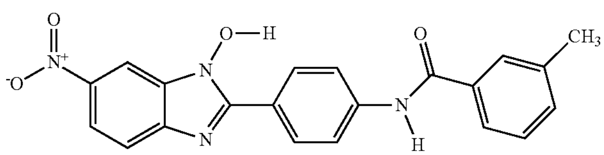 | ** | * |
| BBU | 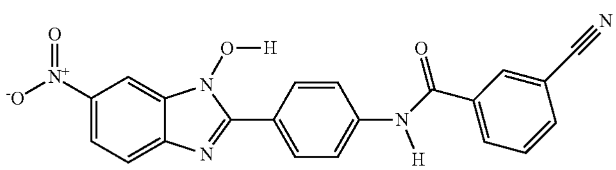 | * | — |
| BBV | 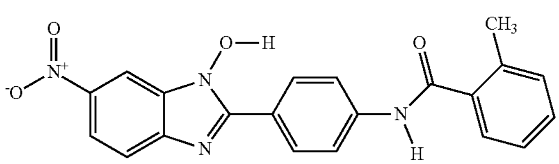 | * | — |
| BBW | 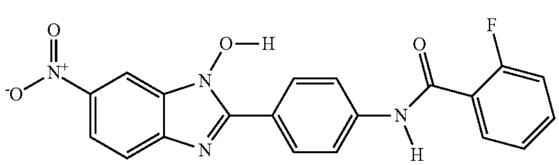 | * | — |
| BBX | 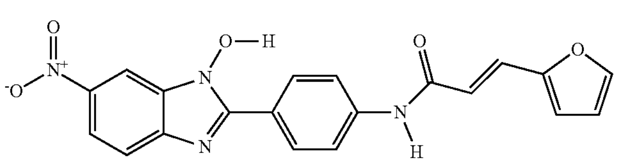 | ** | — |

TABLE 9-continued

| ID | MOLECULAR STRUCTURE | EC50 for VirF (μm) | % cytotoxicity in Whole cell assay at 50 μg/ml |
|---|---|---|---|
| BBX | 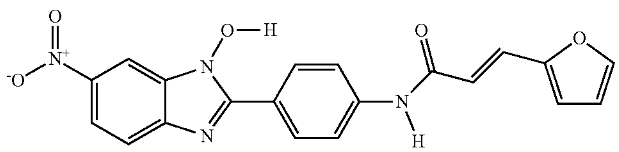 | ** | — |
| BBY | 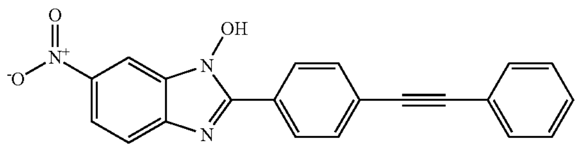 | * | — |
| BBZ | 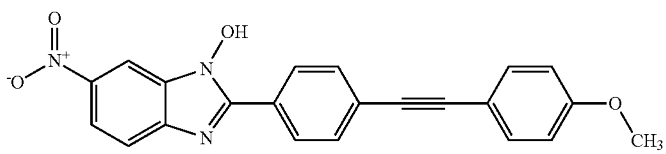 | * | ** |
| BCA | 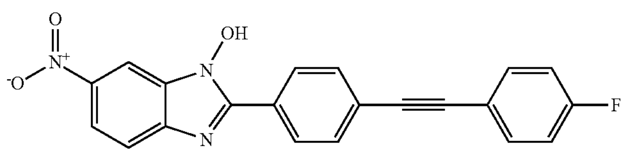 | * | — |
| BCB | 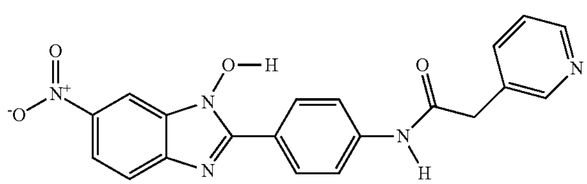 | * | — |
| BCC | 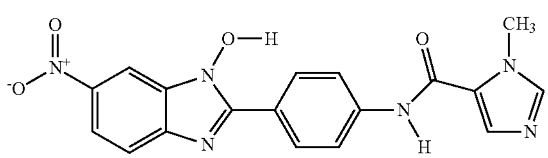 | * | — |
| BCD | 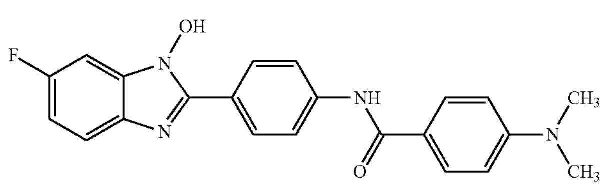 [SMILES: CN(C)c1ccc(C(=O)Nc2ccc(-c3nc4ccc(F)cc4n3O)cc2)cc1] | * | — |
| BCE | 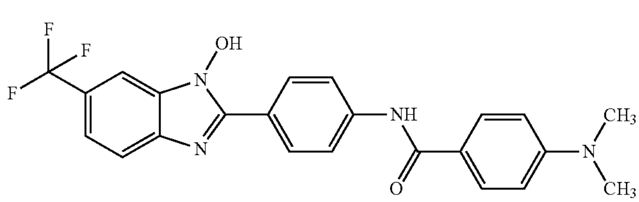 [SMILES: CN(C)c1ccc(C(=O)Nc2ccc(-c3nc4ccc(C(F)(F)F)cc4n3O)cc2)cc1] | * | — |

TABLE 9-continued

| ID | MOLECULAR STRUCTURE | EC50 for VirF (μm) | % cytotoxicity in Whole cell assay at 50 μg/ml |
|---|---|---|---|
| BCF | 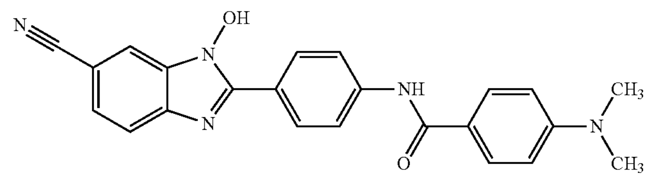 [SMILES: CN(C)c1ccc(C(=O)Nc2ccc(-c3nc4ccc(C#N)cc4n3O)cc2)cc1] | ** | — |
| BCG | 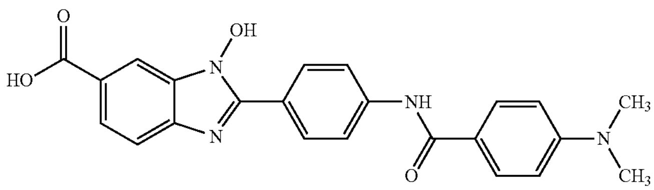 [SMILES: CN(C)c1ccc(C(=O)Nc2ccc(-c3nc4ccc(C(=O)O)cc4n3O)cc2)cc1] | * | — |
| BCH | 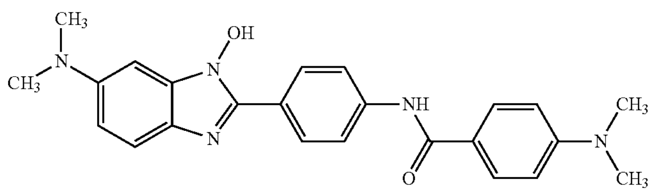 | ** | — |
| BCI | 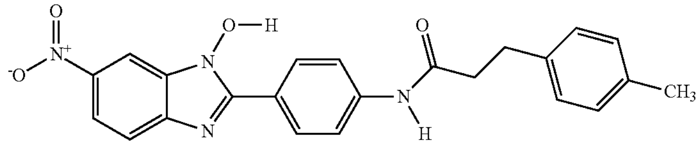 | * | — |
| BCJ | 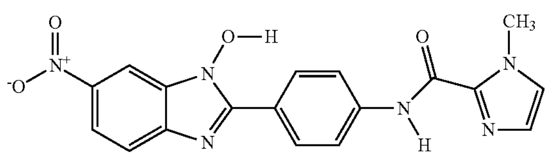 | * | — |
| BCK | 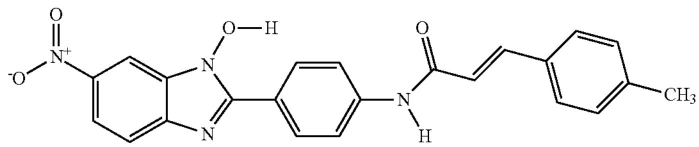 | *** | — |
| BCL | 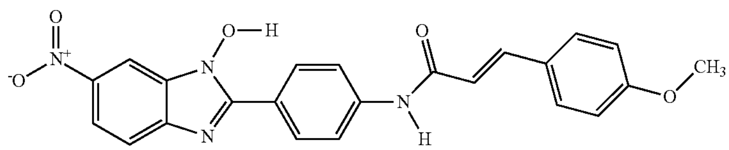 | *** | — |
| BCM | 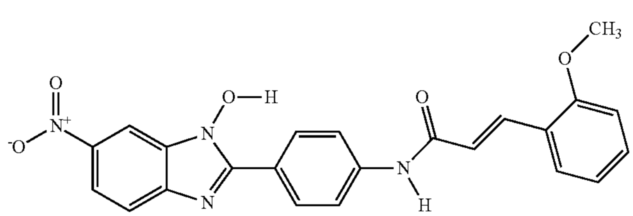 | ** | — |

TABLE 9-continued

| ID | MOLECULAR STRUCTURE | EC50 for VirF (μm) | % cytotoxicity in Whole cell assay at 50 μg/ml |
|---|---|---|---|
| BCN | 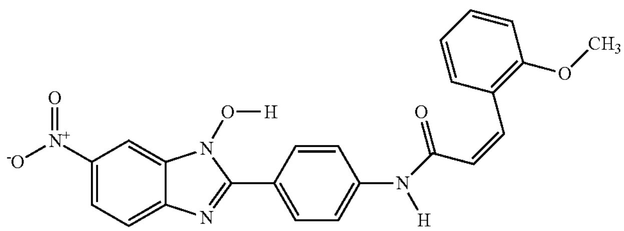 | ** | — |
| BCO | 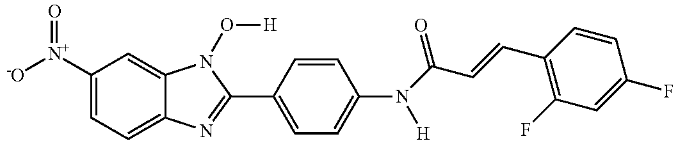 | *** | — |
| BCP | 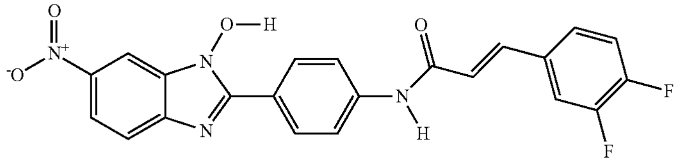 | ** | — |
| BCQ | 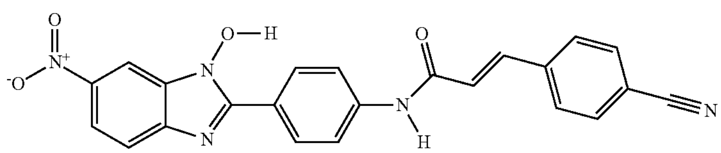 | ** | — |
| BCR | 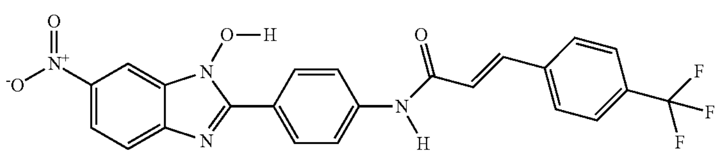 | *** | — |
| BCS | 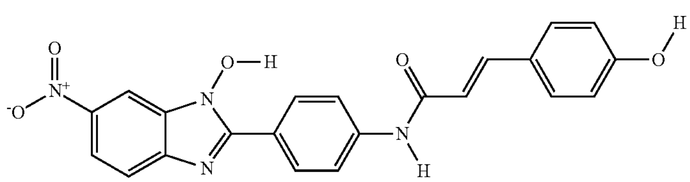 | * | — |
| BCT | 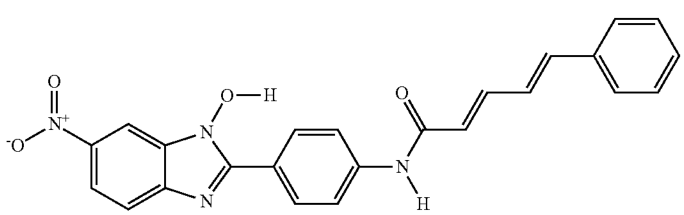 | ** | — |

TABLE 9-continued

| ID | MOLECULAR STRUCTURE | EC50 for VirF (μm) | % cytotoxicity in Whole cell assay at 50 μg/ml |
|---|---|---|---|
| BCU | 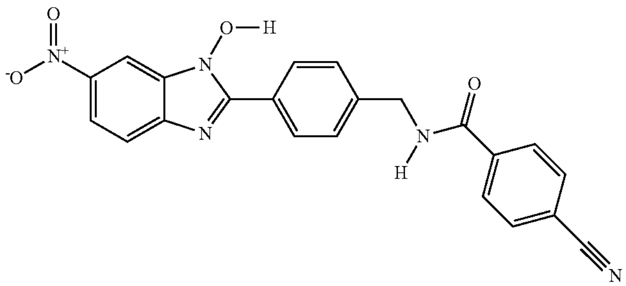 | * | — |
| BCV | 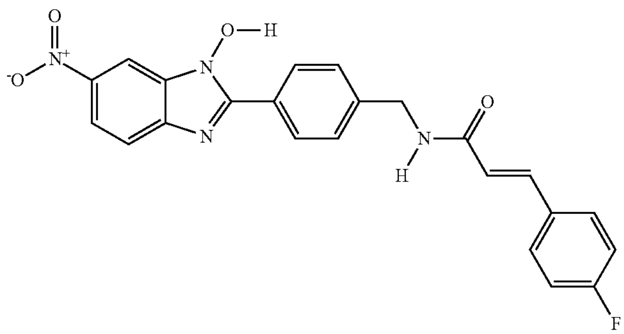 | ** | — |
| BCW | 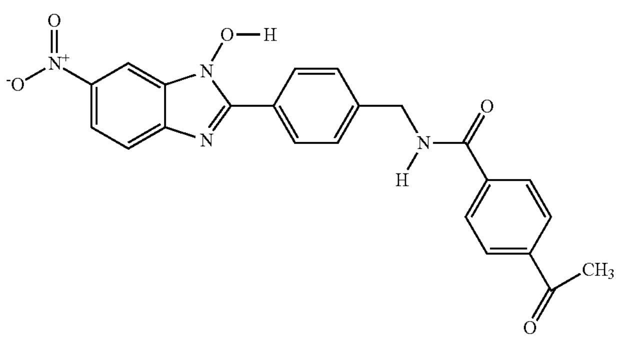 | * | — |
| BCX | 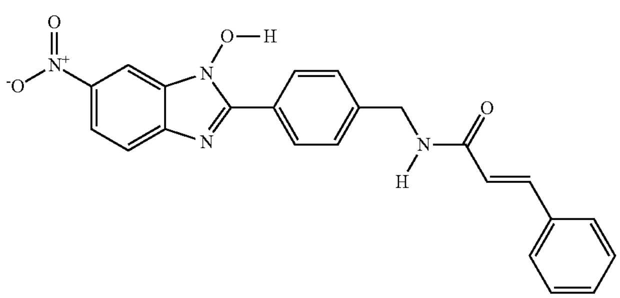 | * | — |
| BCY | 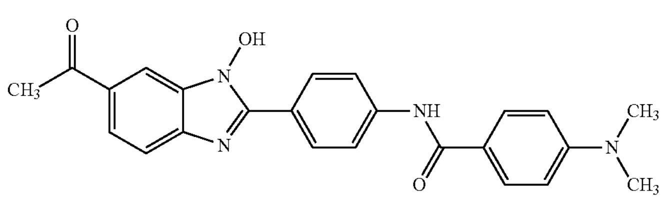 [SMILES: CC(=O)c1ccc2nc(-c3ccc(NC(=O)c4ccc(N(C)C)cc4)cc3)n(O)c2c1] | * | — |

TABLE 9-continued

| ID | MOLECULAR STRUCTURE | EC50 for VirF (μm) | % cytotoxicity in Whole cell assay at 50 μg/ml |
|----|---------------------|--------------------|-----------------------------------------------|
| BCZ | [structure: 6-nitro-1-hydroxy-benzimidazole linked to phenyl-NHC(O)-4-fluorophenyl] | * | — |
| BDA | [structure: 1-hydroxybenzimidazole-2-yl-phenyl-NHC(O)-4-(N,N-dimethylamino)phenyl] | * | — |
| BDB | [structure: 5-cyano-1-hydroxybenzimidazole-2-yl-phenyl-NHC(O)-4-(N,N-dimethylamino)phenyl] | ** | — |
| BDC | [structure: 5-methyl-1-hydroxybenzimidazole-2-yl-phenyl-NHC(O)-4-(N,N-dimethylamino)phenyl] | * | — |
| BDD | [structure: 5-carboxy-1-hydroxybenzimidazole-2-yl-phenyl-NHC(O)-4-(N,N-dimethylamino)phenyl] | * | — |
| BDE | [structure: 6-(N,N-dimethylamino)-1-hydroxybenzimidazole-2-yl-phenyl-NHC(O)-4-fluorophenyl] | * | — |

Example 15

Activity of Mar Inhibitors in Whole Cell Systems

Type III secretion, the process whereby cytotoxic proteins (Yops) are sectreted from a bacterium into a host cell, in pathogenic *Yersinia* spp. is regulated by LcrF. Wild type *Y. pseudotuberculosis* are toxic toward J774 tissue culture cells whereas bacteria bearing a mutation in either yopJ (a Yop that inhibits eukaryotic signaling pathways) or lcrF. The cytotoxicity of wild type *Y. pseudotuberculosis* was exploited in order to screen compounds for their ability to penetrate the intact bacterial cell and prevent type III secretion by binding to an inactivating LcrF function.

The CytoTox 96® assay kit from Promega was used for this assay. Briefly, J774 macrophages were plated out at $2 \times 10^4$ cells per well in 96-well plates on the day prior to infection. *Yersinia pseudotuberculosis* were grown overnight at 26° C. in 2×YT media and then diluted 1:25 or 1:40 the following morning into 2×YT supplemented with 20 mM $MgCl_2$ and 20 mM sodium oxalate. The cultures were grown for a further 90 min at 26° C. and then shifted to 37° C. for 90 minutes. The temperature shift and the sodium oxalate, which chelates calcium, lead to induction of LcrF expression. Later experiments also included the YPIIIpIB1ΔJ (YopJ mutant) and YPIIIpIB1ΔLcrF (LcrF mutant). YPIIIpIB1ΔJ is a YopJ deletion mutant and any cytotoxicity that is unrelated to YopJ (i.e. lps-mediated) will be seen with this strain. The OD600 was measured and the culture adjusted to an OD600 of 1.0. This should correspond to approximately $1.25\times10^9$ cells/mL. Dilutions were prepared in DMEM (the J774 culture media) at different multiplicity of infections (MOIs), assuming J774 cell density of $2\times10^4$. *Yersinia pseudotuberculosis* were added in 10 μl aliquots and cells were incubated at 37° C. either in a chamber with a $CO_2$ generating system, or later, in a tissue culture incubator with 5% $CO_2$ for 2 h. Gentamicin was then added to a final concentration of 50 μg/ml and the incubations were continued either for a further 2-3 h or overnight. Controls were included for media alone, target cell spontaneous lysis, target cell maximum lysis and effector cell spontaneous lysis. For maximum lysis, triton X-100 was added to a final concentration of 0.8% 45 minutes prior to termination of the experiment. Supernatants containing released LDH were harvested following centrifugation at 1,000 rpm for 5 minutes. Supernatants were either frozen overnight or assayed immediately. 50 μl of supernatant was mixed with 50 μl fresh assay buffer and incubated in the dark for 30 minutes 50 μl of stop solution was added to each well and the plates were read at 490 nm. The results of this assay are shown in Table 9 and Table 11. Compounds which showed a minimum cytotoxicity in whole cell assays at 50 μg/mL are indicated by "*," and compounds which showed some cytotoxicity or high cytotoxicity are indicated by "" or "*" respectively.

TABLE 11

Activity of select Mar Inhibitors in an Assay that Measures Type III sectretion of *Yersinia pseudotuberculosis*.

| Compound | % Cytotoxicity |
|---|---|
| AQQ | * |
| ASR | ** |
| ASU | * |
| ATB | ** |
| BAB | *** |
| BAF | *** |

Example 16

Investigation of Toxicity of Select Mar Inhibitors In Vivo

The in vivo toxicity of Mar inhibitors ATB, BAB, BAF, BBP and BBS were investigated in repeat dose experiments. Mice were given two subcutaneous doses (25 mg/Kg) of a Mar inhibitor on day 1 and a single dose of the compound on days 2-5. No overt signs of toxicity for any of the compounds were noted indicating that the Mar inhibitors are generally well tolerated.

Example 17

Development of a Murine Model of *Yersina* spp. to Measure Compound Efficacy An in-frame and non-polar deletion in lcrF was contructed to measure the effect of LcrF on the virulence of *Y. pseudotuberculosis*. Following infection with ~150 colony forming units (CFU), the LcrF mutant exhibited a >2-log decrease in its ability to colonize the murine lung. When analyzed in a lethal infection model, the 50% lethal dose of wild type *Y. pseudotuberculosis* was ~5-10 CFU whereas the LD50 was >2,220 CFU for the mutant organism.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

TABLE 12

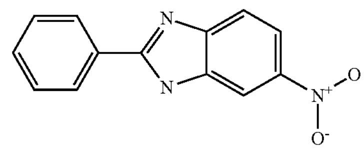 [SMILES: [O-][NH+](O)c1ccc2nc(-c3ccccc3)[nH]c2c1]

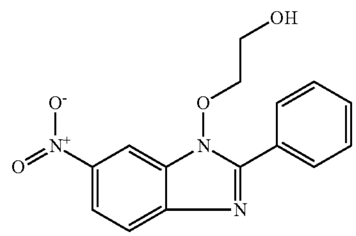 [SMILES: O=[N+]([O-])c1ccc2nc(-c3ccccc3)n(OCCO)c2c1]

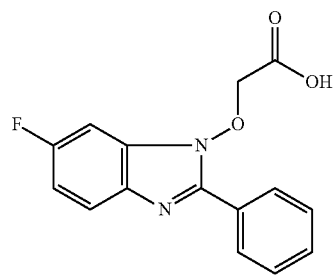 [SMILES: O=C(O)COn1c(-c2ccccc2)nc2ccc(F)cc21]

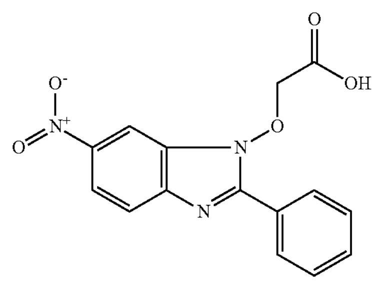 [SMILES: O=C(O)COn1c(-c2ccccc2)nc2ccc([N+](=O)[O-])cc21]

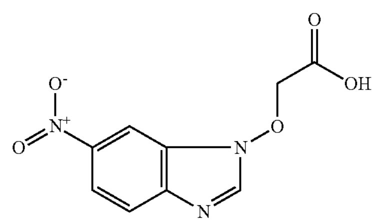 [SMILES: O=C(O)COn1cnc2ccc([N+](=O)[O-])cc21]

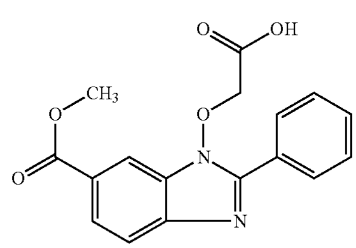 [SMILES: COC(=O)c1ccc2nc(-c3ccccc3)n(OCC(=O)O)c2c1]

TABLE 12-continued
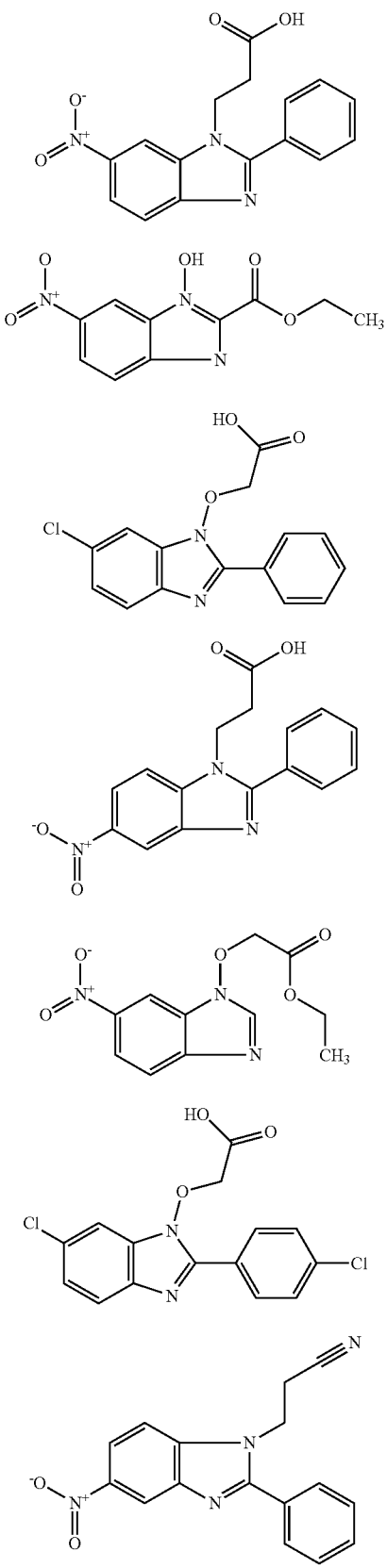
TABLE 12-continued
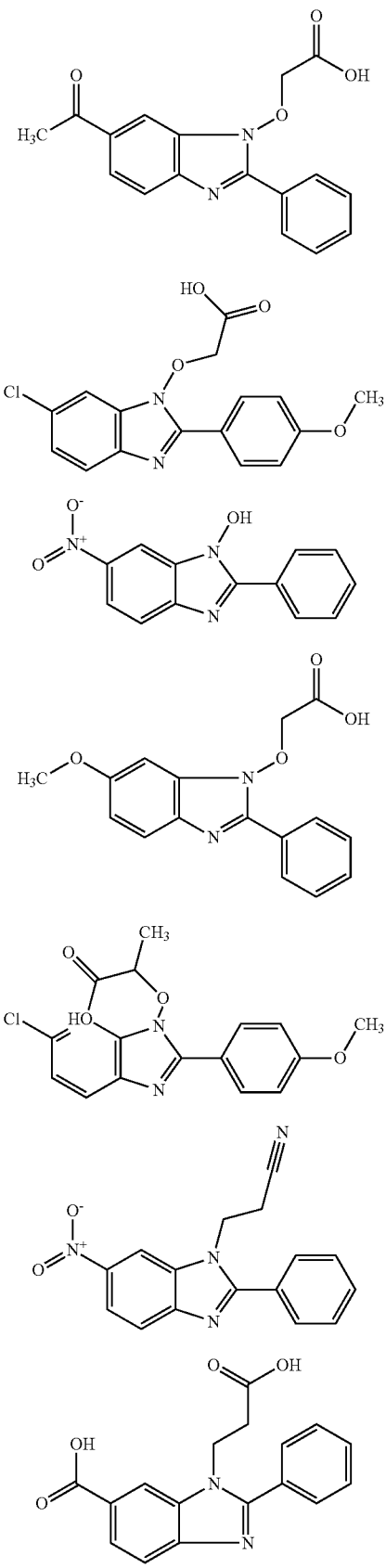

TABLE 12-continued
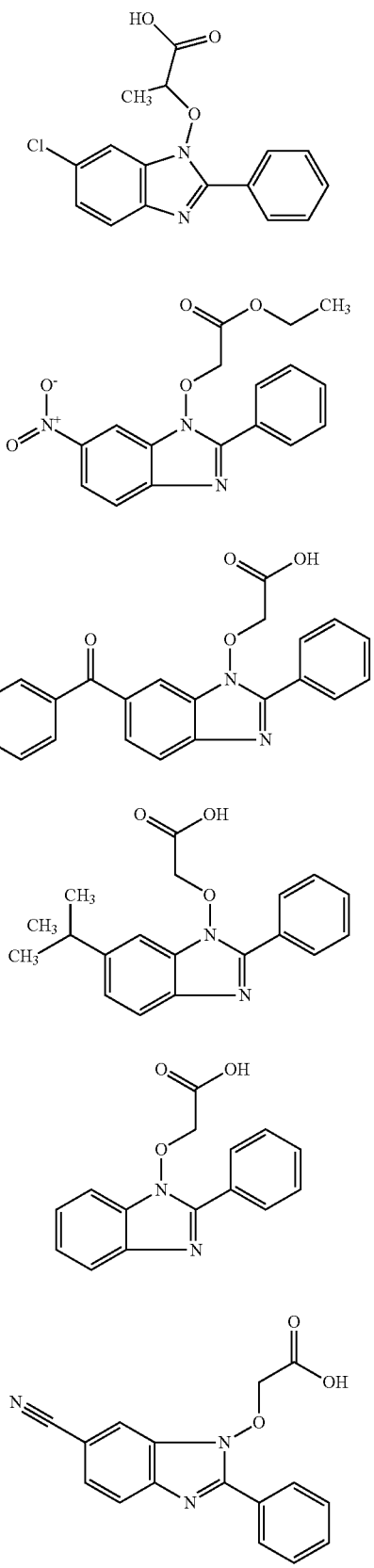
TABLE 12-continued
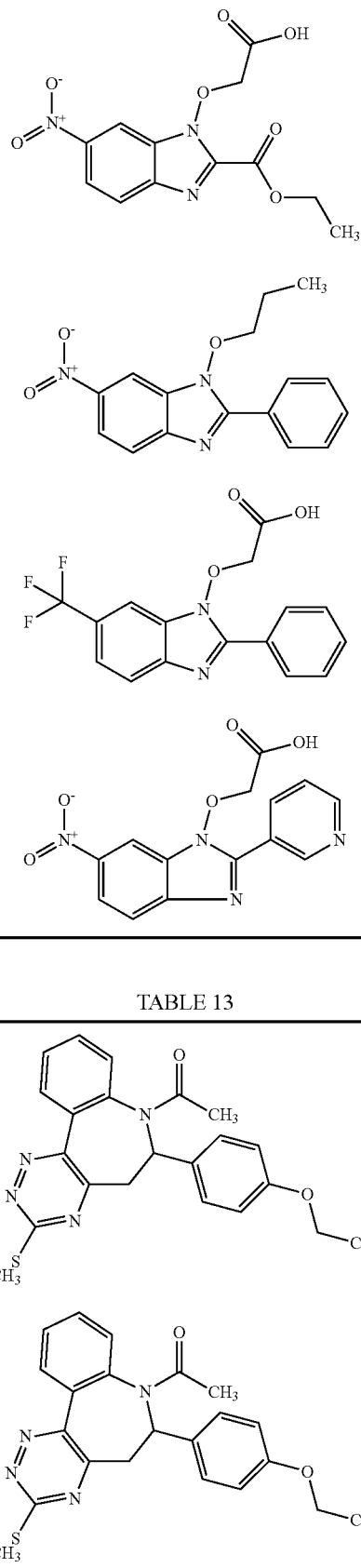
TABLE 13

TABLE 13-continued
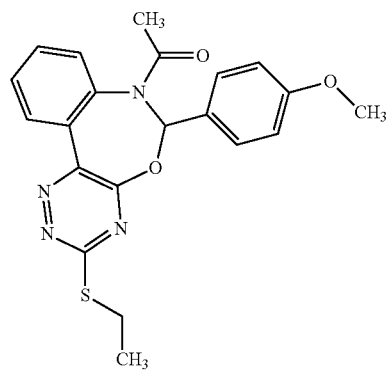 [SMILES: CCSc1nnc2c(n1)OC(c1ccc(OC)cc1)N(C(C)=O)c1ccccc1-2]
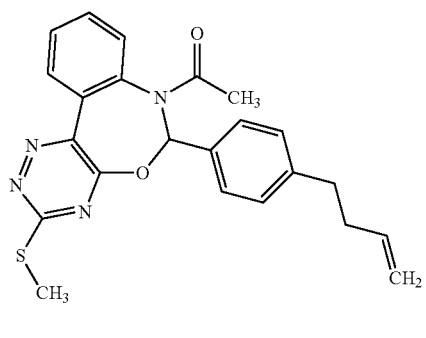 [SMILES: C=CCCc1ccc(C2Oc3nc(SC)nnc3-c3ccccc3N2C(C)=O)cc1]
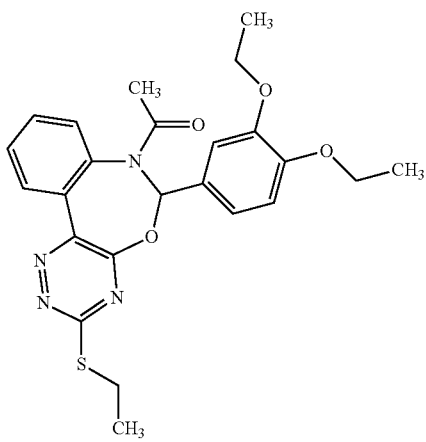 [SMILES: CCOc1ccc(C2Oc3nc(SCC)nnc3-c3ccccc3N2C(C)=O)cc1OCC]
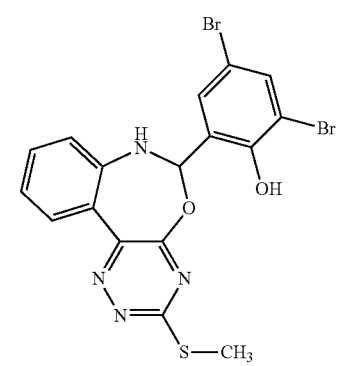 [SMILES: CSc1nnc2c(n1)OC(c1cc(Br)cc(Br)c1O)Nc1ccccc1-2]
TABLE 13-continued
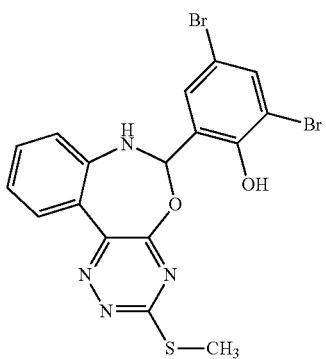 [SMILES: CSc1nnc2c(n1)OC(c1cc(Br)cc(Br)c1O)Nc1ccccc1-2]
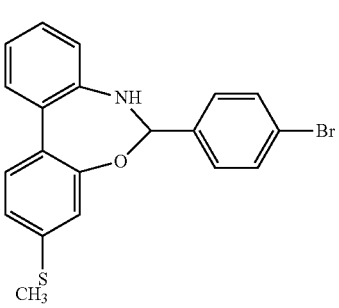 [SMILES: CSc1ccc2c(c1)OC(c1ccc(Br)cc1)Nc1ccccc1-2]
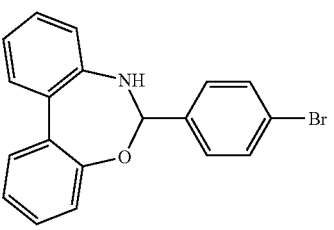 [SMILES: Brc1ccc(C2Nc3ccccc3-c3ccccc3O2)cc1]
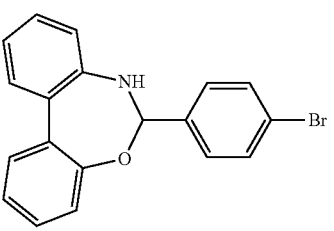 [SMILES: Brc1ccc(C2Nc3ccccc3-c3ccccc3O2)cc1]

TABLE 13-continued

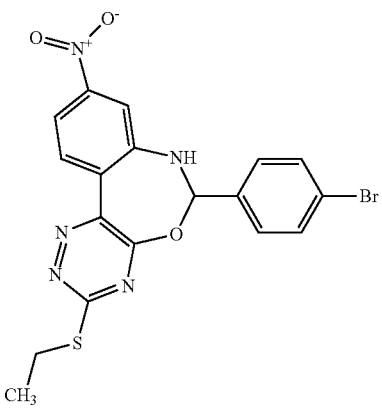 [SMILES: CCSc1nnc2c(n1)OC(c1ccc(Br)cc1)Nc1cc([N+](=O)[O-])ccc1-2]

TABLE 13-continued

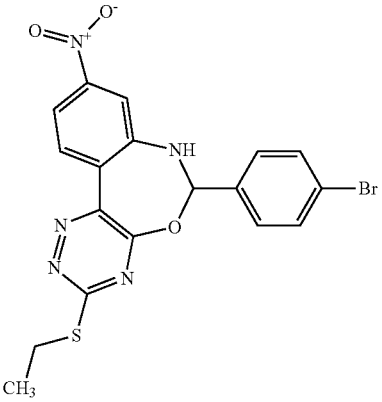 [SMILES: CCSc1nnc2c(n1)OC(c1ccc(Br)cc1)Nc1cc([N+](=O)[O-])ccc1-2]

The invention claimed is:

1. A pharmaceutical composition comprising a pharmaceutically acceptable carrier and a transcription factor modulating compound, or a pharmaceutically acceptable salt thereof, wherein said compound is of the following formula

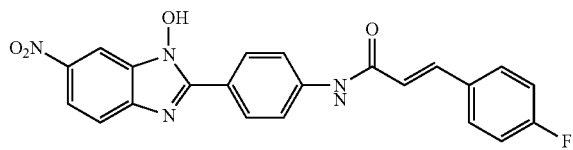

2. A compound of the formula:

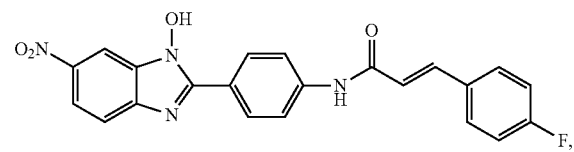 [SMILES: O=C(/C=C/c1ccc(F)cc1)Nc1ccc(-c2nc3ccc([N+](=O)[O-])cc3n2O)cc1]

or a pharmaceutically acceptable salt thereof.

3. The pharmaceutical composition of claim 1, further comprising an antibiotic.

* * * * *

UNITED STATES PATENT AND TRADEMARK OFFICE
CERTIFICATE OF CORRECTION

| | | |
|---|---|---|
| PATENT NO. | : 8,436,031 B2 | Page 1 of 1 |
| APPLICATION NO. | : 12/462405 | |
| DATED | : May 7, 2013 | |
| INVENTOR(S) | : Kim | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

Signed and Sealed this
Eleventh Day of February, 2014

Michelle K. Lee
*Deputy Director of the United States Patent and Trademark Office*